(12) United States Patent
Hubbell et al.

(10) Patent No.: US 11,253,579 B2
(45) Date of Patent: Feb. 22, 2022

(54) COMPOSITIONS AND METHODS FOR INDUCING IMMUNE TOLERANCE

(71) Applicants: The University of Chicago, Chicago, IL (US); Anokion SA, Ecublens (CH)

(72) Inventors: Jeffrey A. Hubbell, Chicago, IL (US); David Scott Wilson, Chicago, IL (US); Kristen Marie Lorentz, Cambridge, MA (US); Stephan Kontos, Cambridge, MA (US)

(73) Assignees: The University of Chicago, Chicago, IL (US); Anokion SA, Ecublens (CH)

( * ) Notice: Subject to any disclaimer, the term of this patent is extended or adjusted under 35 U.S.C. 154(b) by 0 days.

(21) Appl. No.: 16/622,732

(22) PCT Filed: Jun. 14, 2018

(86) PCT No.: PCT/US2018/037631
§ 371 (c)(1),
(2) Date: Dec. 13, 2019

(87) PCT Pub. No.: WO2018/232176
PCT Pub. Date: Dec. 20, 2018

(65) Prior Publication Data
US 2020/0101146 A1    Apr. 2, 2020

Related U.S. Application Data

(60) Provisional application No. 62/521,270, filed on Jun. 16, 2017.

(51) Int. Cl.
*A61K 39/008* (2006.01)
*A61K 39/35* (2006.01)
*A61K 39/00* (2006.01)

(52) U.S. Cl.
CPC ........ *A61K 39/0008* (2013.01); *A61K 39/001* (2013.01); *A61K 39/35* (2013.01); *A61K 2039/6087* (2013.01); *A61K 2039/6093* (2013.01); *A61K 2039/627* (2013.01)

(58) Field of Classification Search
CPC .. A61K 39/0008; A61K 39/001; A61K 39/35; A61K 2039/6087; A61K 2039/6093; A61K 2039/627
USPC .................................................... 424/185.1
See application file for complete search history.

(56) References Cited

U.S. PATENT DOCUMENTS

| | | |
|---|---|---|
| 4,671,958 A | 6/1987 | Rodwell et al. |
| 4,741,900 A | 5/1988 | Alvarez et al. |
| 4,859,449 A | 8/1989 | Mattes |
| 4,867,973 A | 9/1989 | Goers et al. |
| 4,950,738 A | 8/1990 | King et al. |
| 5,086,002 A | 2/1992 | Hillyard et al. |
| 5,140,104 A | 8/1992 | Coughlin et al. |
| 5,156,840 A | 10/1992 | Goers et al. |
| 5,162,512 A | 11/1992 | King et al. |
| 5,227,165 A | 7/1993 | Domb et al. |
| 5,227,293 A | 7/1993 | Stengelin et al. |
| 5,346,696 A | 9/1994 | Kim et al. |
| 5,358,857 A | 10/1994 | Stengelin et al. |
| 5,470,570 A | 11/1995 | Taylor et al. |
| 5,487,890 A | 1/1996 | Taylor et al. |
| 5,681,571 A | 10/1997 | Holmgren et al. |
| 5,698,679 A | 12/1997 | Nemazee et al. |
| 5,718,915 A | 2/1998 | Virtanen et al. |
| 5,879,679 A | 3/1999 | Taylor et al. |
| 5,885,808 A | 3/1999 | Spooner et al. |
| 5,886,143 A | 3/1999 | Theodore et al. |
| 5,948,639 A | 9/1999 | Gimeno et al. |
| 5,985,826 A | 11/1999 | Theodore et al. |
| 5,994,104 A | 11/1999 | Anderson et al. |
| 5,997,861 A | 12/1999 | Virtanen et al. |
| 6,022,564 A | 2/2000 | Takechi et al. |
| 6,090,925 A | 7/2000 | Woiszwillo et al. |
| 6,120,770 A | 9/2000 | Adams et al. |
| 6,153,203 A | 11/2000 | Holmgren et al. |
| 6,217,869 B1 | 4/2001 | Meyer et al. |
| 6,224,794 B1 | 5/2001 | Amsden et al. |

(Continued)

FOREIGN PATENT DOCUMENTS

| | | |
|---|---|---|
| CN | 1289256 A | 3/2001 |
| CN | 1756560 A | 4/2006 |

(Continued)

OTHER PUBLICATIONS

Moss et al. "Glossary of Class Names of Organic Compounds and Reactive Intermediates Based on Structure", Pure & Appl. Chem., vol. 67, Nos. 819, pp. 1307-1375, 1995 (Year: 1995).*
Benaglia et al. "Searching for More Effective Agents and Conditions for the RAFT Polymerization of MMA: Influence of Dithioester Substituents, Solvent, and Temperature" Macromolecules 2005, 38, 3129-3140 (Year: 2005).*
Boyer et al. "Bioapplications of RAFT Polymerization". Chem. Rev. 2009, 109, 5402-5436 (Year: 2009).*
Cheremisinoff. Condensed Encyclopedia of Polymer Engineering Terms, Butterworth-Heinemann, 2001, pp. 39-81. (Year: 2001).*
Calvaresi and Hergenrother. "Glucose conjugation for the specific targeting and treatment of cancer"; Chem Sci. Jun. 2013 ; 4(6): 2319-2333 (Year: 2013).*

(Continued)

*Primary Examiner* — Yevgeny Valenrod
(74) *Attorney, Agent, or Firm* — Knobbe, Martens, Olsen & Bear, LLP

(57) ABSTRACT

Several embodiments provided in the present disclosure relate to compositions that carry an antigen to which tolerance is desired, the antigen being coupled, bound, or otherwise joined to a targeting moiety, the targeting moiety configured to direct the composition to the liver of a subject. In several embodiments, the antigen in coupled to the targeting moiety by way of a polymeric linker. In several embodiments, the polymeric linker is configured to liberate the antigen in vivo. Methods of using the compositions to reduce and/or prevent unwanted immune responses against an antigen of interest are also provided.

18 Claims, 53 Drawing Sheets
Specification includes a Sequence Listing.

(56) References Cited

U.S. PATENT DOCUMENTS

| | | |
|---|---|---|
| 6,264,950 B1 | 7/2001 | Staerz |
| 6,322,796 B1 | 11/2001 | Holmgren et al. |
| 6,365,163 B1 | 4/2002 | Holmgren et al. |
| 6,379,699 B1 | 4/2002 | Virtanen et al. |
| 6,488,927 B2 | 12/2002 | Muzykantov et al. |
| 6,512,103 B1 | 1/2003 | Dairaghi et al. |
| 6,562,347 B1 | 5/2003 | Kwak et al. |
| 6,703,488 B1 | 3/2004 | Burton et al. |
| 6,737,057 B1 | 5/2004 | Zaghouani et al. |
| 6,814,964 B2 | 11/2004 | Virtanen et al. |
| 6,905,688 B2 | 6/2005 | Rosen et al. |
| 6,953,675 B2 | 10/2005 | Leung et al. |
| 7,041,287 B2 | 5/2006 | Muzykantov et al. |
| 7,132,475 B2 | 11/2006 | Hubbel et al. |
| 7,144,569 B1 | 12/2006 | Anderson et al. |
| 7,148,329 B1 | 12/2006 | Figdor et al. |
| 7,172,760 B2 | 2/2007 | Muzykantov et al. |
| 7,175,988 B2 | 2/2007 | Roschke et al. |
| 7,192,582 B2 | 3/2007 | Hudson et al. |
| 7,285,642 B2 | 10/2007 | Figdor et al. |
| 7,420,040 B2 | 9/2008 | Young et al. |
| 7,420,041 B2 | 9/2008 | Young et al. |
| 7,541,180 B2 | 6/2009 | Valiante |
| 7,585,508 B1 | 9/2009 | Prendergast |
| 7,612,180 B2 | 11/2009 | Goldenberg et al. |
| 7,704,943 B2 | 4/2010 | Griffin et al. |
| 7,704,964 B2 | 4/2010 | Delcayre et al. |
| 7,786,267 B2 | 8/2010 | Zurawski et al. |
| 7,811,809 B2 | 10/2010 | Heyduk et al. |
| 7,837,997 B2 | 11/2010 | Muzykantov et al. |
| 7,884,190 B2 | 2/2011 | Cohen et al. |
| 7,888,460 B2 | 2/2011 | Anderson et al. |
| 7,892,743 B2 | 2/2011 | Owen et al. |
| 7,932,294 B2 | 4/2011 | Satyam |
| 7,994,283 B2 | 8/2011 | Valiante et al. |
| 8,007,805 B2 | 8/2011 | George et al. |
| 8,021,689 B2 | 9/2011 | Reddy et al. |
| 8,057,798 B2 | 11/2011 | Zurawski et al. |
| 8,058,400 B2 | 11/2011 | Figdor et al. |
| 8,058,406 B2 | 11/2011 | Mi et al. |
| 8,105,599 B2 | 1/2012 | Figdor et al. |
| 8,236,934 B2 | 8/2012 | Banchereau et al. |
| 8,252,902 B2 | 8/2012 | Barbas et al. |
| 8,273,357 B2 | 9/2012 | Hacohen et al. |
| 8,277,812 B2 | 10/2012 | Iannacone et al. |
| 8,318,912 B2 | 11/2012 | Simon |
| 8,323,696 B2 | 12/2012 | Hubbel et al. |
| 8,329,144 B2 | 12/2012 | Anderson et al. |
| 8,333,973 B2 | 12/2012 | Muzykantov et al. |
| 8,343,497 B2 | 1/2013 | Shi et al. |
| 8,343,498 B2 | 1/2013 | Alexis et al. |
| 8,425,910 B2 | 4/2013 | Mi et al. |
| 8,449,888 B2 | 5/2013 | Zurawski et al. |
| 8,507,237 B2 | 8/2013 | Hermet et al. |
| 8,518,410 B2 | 8/2013 | Zurawski et al. |
| 8,551,476 B2 | 10/2013 | Mi et al. |
| 8,562,998 B2 | 10/2013 | Shi et al. |
| 8,580,253 B2 | 11/2013 | Rubin-Bejerano et al. |
| 8,586,052 B2 | 11/2013 | Zurawski et al. |
| 8,591,905 B2 | 11/2013 | von Andrian et al. |
| 8,592,364 B2 | 11/2013 | Swartz et al. |
| 8,613,903 B2 | 12/2013 | Goldenberg et al. |
| 8,617,823 B2 | 12/2013 | Rubin-Bejerano et al. |
| 8,637,028 B2 | 1/2014 | Alexis et al. |
| 8,673,293 B2 | 3/2014 | Martin et al. |
| 8,685,408 B2 | 4/2014 | Tartour et al. |
| 8,722,047 B2 | 5/2014 | Goldenberg et al. |
| 8,728,481 B2 | 5/2014 | Banchereau et al. |
| 8,859,629 B2 * | 10/2014 | van Delft ............ C07C 269/06 514/729 |
| 8,889,140 B2 | 11/2014 | Lee et al. |
| 8,906,381 B2 | 12/2014 | Iannacone et al. |
| 8,932,595 B2 | 1/2015 | Iannacone et al. |
| 8,961,991 B2 | 2/2015 | Zurawski et al. |
| 8,992,917 B2 | 3/2015 | Goldenberg et al. |
| 9,005,903 B2 | 4/2015 | Rubin-Bejerano et al. |
| 9,066,984 B2 | 6/2015 | Mi et al. |
| 9,102,730 B2 | 8/2015 | Zurawski et al. |
| 9,102,734 B2 | 8/2015 | Zurawski et al. |
| 9,187,561 B2 | 11/2015 | Goldenberg et al. |
| 9,216,156 B2 | 12/2015 | Fleury et al. |
| 9,233,072 B2 | 1/2016 | Alexis et al. |
| 9,234,040 B2 | 1/2016 | Zurawski et al. |
| 9,260,692 B2 | 2/2016 | Martin et al. |
| 9,308,280 B2 | 4/2016 | Shi et al. |
| 9,326,939 B2 | 5/2016 | Paulson et al. |
| 9,416,186 B2 | 8/2016 | Zurawski et al. |
| 9,439,859 B2 | 9/2016 | Alexis et al. |
| 9,453,074 B2 | 9/2016 | Oh et al. |
| 9,457,047 B2 | 10/2016 | Rubin-Bejerano et al. |
| 9,474,717 B2 | 10/2016 | von Andrian et al. |
| 9,517,257 B2 | 12/2016 | Hubbell et al. |
| 9,518,087 B2 | 12/2016 | Hubbell et al. |
| 9,522,183 B2 | 12/2016 | Paulson et al. |
| 9,539,210 B2 | 1/2017 | von Andrian et al. |
| 9,561,272 B2 | 2/2017 | Thomas et al. |
| 9,688,991 B2 | 6/2017 | Levy et al. |
| 9,751,945 B2 | 9/2017 | Ploegh et al. |
| 9,814,780 B2 | 11/2017 | Hubbell et al. |
| 9,850,296 B2 | 12/2017 | Hubbell et al. |
| 9,878,048 B2 | 1/2018 | Hubbell et al. |
| 9,901,645 B2 | 2/2018 | Hubbell et al. |
| 9,901,646 B2 | 2/2018 | Hubbell et al. |
| 10,046,056 B2 | 8/2018 | Hubbell et al. |
| 10,800,838 B2 | 10/2020 | Hubbell et al. |
| 10,821,157 B2 * | 11/2020 | Hubbell ............... A61P 37/02 |
| 10,919,963 B2 | 2/2021 | Hubbell et al. |
| 10,940,209 B2 | 3/2021 | Hubbell et al. |
| 10,946,079 B2 * | 3/2021 | Hubbell ............ A61K 39/0002 |
| 10,953,101 B2 * | 3/2021 | Hubbell ............ A61K 39/385 |
| 2002/0004037 A1 | 1/2002 | Koteliansky et al. |
| 2002/0038002 A1 | 3/2002 | Zaghouani |
| 2002/0081298 A1 | 6/2002 | Zaghouani |
| 2002/0103343 A1 | 8/2002 | Taylor et al. |
| 2002/0187131 A1 | 12/2002 | Hawiger et al. |
| 2002/0193572 A1 | 12/2002 | Leung et al. |
| 2003/0022826 A1 | 1/2003 | Haynes |
| 2003/0082643 A1 | 5/2003 | Hudson et al. |
| 2003/0103967 A1 | 5/2003 | Zaghouani |
| 2003/0104045 A1 | 6/2003 | Virtanen et al. |
| 2003/0175921 A1 | 9/2003 | Barbas et al. |
| 2003/0190676 A1 | 10/2003 | Barbas et al. |
| 2003/0211078 A1 | 11/2003 | Heavner |
| 2004/0052815 A1 | 3/2004 | Lycke |
| 2004/0077843 A1 | 4/2004 | Burton et al. |
| 2004/0146948 A1 | 7/2004 | Britton et al. |
| 2004/0147721 A1 | 7/2004 | Valiante |
| 2004/0185057 A1 | 9/2004 | Kirkby et al. |
| 2004/0197314 A1 | 10/2004 | Delcayre et al. |
| 2004/0258688 A1 | 12/2004 | Hawiger et al. |
| 2005/0031628 A1 | 2/2005 | George et al. |
| 2005/0053579 A1 | 3/2005 | Galipeau et al. |
| 2005/0113297 A1 | 5/2005 | Francois et al. |
| 2005/0118168 A1 | 6/2005 | Figdor et al. |
| 2005/0201973 A1 | 9/2005 | Virtanen et al. |
| 2005/0203022 A1 | 9/2005 | Gotwals et al. |
| 2005/0220804 A1 | 10/2005 | Figdor et al. |
| 2005/0250936 A1 | 11/2005 | Oppermann et al. |
| 2006/0034864 A1 | 2/2006 | Zaghouani |
| 2006/0127929 A1 | 6/2006 | Swager et al. |
| 2006/0153881 A1 | 7/2006 | Narum et al. |
| 2006/0173168 A1 | 8/2006 | Carlock et al. |
| 2006/0178299 A1 | 8/2006 | Anderson et al. |
| 2006/0257412 A1 | 11/2006 | Bowdish et al. |
| 2006/0280679 A1 | 12/2006 | Bowdish et al. |
| 2007/0059794 A1 | 3/2007 | Ideno et al. |
| 2007/0111222 A1 | 5/2007 | Chasin et al. |
| 2007/0122409 A1 | 5/2007 | Zaghouani |
| 2007/0190615 A1 | 8/2007 | Cohen et al. |
| 2007/0218053 A1 | 9/2007 | Zaghouani |
| 2008/0031899 A1 | 2/2008 | Reddy et al. |
| 2008/0131428 A1 | 6/2008 | Young et al. |
| 2008/0160041 A1 | 7/2008 | Figdor et al. |
| 2008/0175971 A1 | 7/2008 | Anderson et al. |

(56) References Cited

U.S. PATENT DOCUMENTS

| | | |
|---|---|---|
| 2008/0178299 A1 | 7/2008 | Merkle et al. |
| 2008/0206262 A1 | 8/2008 | Banchereau et al. |
| 2008/0213267 A1 | 9/2008 | Young et al. |
| 2008/0227707 A1 | 9/2008 | Carlock et al. |
| 2008/0233143 A1 | 9/2008 | Jackson et al. |
| 2008/0241170 A1 | 10/2008 | Zurawski et al. |
| 2008/0254044 A1 | 10/2008 | Zurawski |
| 2008/0261262 A1 | 10/2008 | Godfrin |
| 2008/0274092 A1 | 11/2008 | Godfrin et al. |
| 2008/0305104 A1 | 12/2008 | Young et al. |
| 2008/0318852 A1 | 12/2008 | Anderson et al. |
| 2009/0004218 A1 | 1/2009 | Hacohen et al. |
| 2009/0017039 A1 | 1/2009 | Mi et al. |
| 2009/0123467 A1 | 5/2009 | Bedi et al. |
| 2009/0130104 A1 | 5/2009 | Muzykantov et al. |
| 2009/0142263 A1 | 6/2009 | Young et al. |
| 2009/0149656 A1 | 6/2009 | Singaram et al. |
| 2009/0181011 A1 | 7/2009 | Zaghouani |
| 2009/0191118 A1 | 7/2009 | Young et al. |
| 2009/0202622 A1 | 8/2009 | Fleury et al. |
| 2009/0269285 A1 | 10/2009 | Anderson et al. |
| 2009/0280132 A1 | 11/2009 | Zaghouani |
| 2009/0317381 A1 | 12/2009 | Plaut et al. |
| 2009/0324538 A1 | 12/2009 | Wong et al. |
| 2010/0003266 A1 | 1/2010 | Simon |
| 2010/0003338 A1 | 1/2010 | Hubbell et al. |
| 2010/0015131 A1 | 1/2010 | Mi et al. |
| 2010/0055189 A1 | 3/2010 | Hubbell et al. |
| 2010/0092425 A1 | 4/2010 | Von Andrian et al. |
| 2010/0098718 A1 | 4/2010 | Valiante |
| 2010/0129392 A1 | 5/2010 | Shi et al. |
| 2010/0129439 A1 | 5/2010 | Alexis et al. |
| 2010/0129820 A1 | 5/2010 | Kool et al. |
| 2010/0222407 A1 | 9/2010 | Segura et al. |
| 2010/0233251 A1 | 9/2010 | Von Andrian et al. |
| 2010/0239575 A1 | 9/2010 | Banchereau et al. |
| 2010/0285015 A1 | 11/2010 | Muzykantov et al. |
| 2010/0291080 A1 | 11/2010 | Lee et al. |
| 2010/0291082 A1 | 11/2010 | Zurawski |
| 2010/0297114 A1 | 11/2010 | Zurawski |
| 2010/0310612 A1 | 12/2010 | DuFour et al. |
| 2010/0316620 A1 | 12/2010 | Bourgeaux et al. |
| 2010/0322929 A1 | 12/2010 | Zurawski et al. |
| 2010/0330115 A1 | 12/2010 | Zurawski et al. |
| 2011/0014171 A1 | 1/2011 | Bourgeaux et al. |
| 2011/0033426 A1 | 2/2011 | Martin et al. |
| 2011/0044912 A2 | 2/2011 | Anderson et al. |
| 2011/0045049 A1 | 2/2011 | Rubin-Bejerano et al. |
| 2011/0064709 A1 | 3/2011 | Miller et al. |
| 2011/0064754 A1 | 3/2011 | Taylor et al. |
| 2011/0082075 A1 | 4/2011 | Prendergast |
| 2011/0091493 A1 | 4/2011 | Mohamadzadeh et al. |
| 2011/0105379 A1 | 5/2011 | Shulman et al. |
| 2011/0123536 A1 | 5/2011 | Chermann et al. |
| 2011/0143994 A1 | 6/2011 | Lycke |
| 2011/0177532 A1 | 7/2011 | Rubin-Bejerano et al. |
| 2011/0200632 A1 | 8/2011 | Jackson et al. |
| 2011/0206759 A1 | 8/2011 | Swartz et al. |
| 2011/0268804 A1 | 11/2011 | Shi et al. |
| 2011/0268805 A1 | 11/2011 | Alexis et al. |
| 2011/0293644 A1 | 12/2011 | Anderson et al. |
| 2011/0311542 A1 | 12/2011 | Mi et al. |
| 2012/0004643 A1 | 1/2012 | Zurawski et al. |
| 2012/0009140 A1 | 1/2012 | Godfrin et al. |
| 2012/0014960 A1 | 1/2012 | Mi et al. |
| 2012/0027808 A1 | 2/2012 | Iannacone |
| 2012/0039989 A1 | 2/2012 | Hubbel et al. |
| 2012/0058180 A1 | 3/2012 | Kren et al. |
| 2012/0076831 A1 | 3/2012 | Miller et al. |
| 2012/0087890 A1 | 4/2012 | Iannacone et al. |
| 2012/0107301 A1 | 5/2012 | Bowdish et al. |
| 2012/0121570 A1 | 5/2012 | Godfrin |
| 2012/0121592 A1 | 5/2012 | Oh et al. |
| 2012/0128635 A1 | 5/2012 | Gregory et al. |
| 2012/0129210 A1 | 5/2012 | Bourgeaux et al. |
| 2012/0178139 A1 | 7/2012 | Hubbel et al. |
| 2012/0207745 A1 | 8/2012 | Godfrin et al. |
| 2012/0237513 A1 | 9/2012 | Zurawski et al. |
| 2012/0276095 A1 | 11/2012 | Langermann et al. |
| 2012/0282281 A1 | 11/2012 | Banchereau et al. |
| 2013/0004427 A1 | 1/2013 | El-Sayed et al. |
| 2013/0022634 A1 | 1/2013 | Lycke |
| 2013/0053543 A1 | 2/2013 | Davis et al. |
| 2013/0059299 A1 | 3/2013 | Parr et al. |
| 2013/0071413 A1 | 3/2013 | Simon |
| 2013/0078216 A1 | 3/2013 | Dunlevy et al. |
| 2013/0078267 A1 | 3/2013 | Anderson et al. |
| 2013/0101463 A1 | 4/2013 | Mambrini et al. |
| 2013/0115230 A1 | 5/2013 | Simon |
| 2013/0129790 A1 | 5/2013 | Alexis et al. |
| 2013/0164364 A1 | 6/2013 | Paulson et al. |
| 2013/0171074 A1 | 7/2013 | Barbas et al. |
| 2013/0171233 A1 | 7/2013 | Paulson et al. |
| 2013/0236533 A1 | 9/2013 | Von Andrian et al. |
| 2013/0287810 A1 | 10/2013 | Mohamadzadeh et al. |
| 2013/0287857 A1 | 10/2013 | Von Andrian et al. |
| 2013/0295120 A1 | 11/2013 | Zurawski et al. |
| 2013/0318648 A1 | 11/2013 | Anderson et al. |
| 2013/0323786 A1 | 12/2013 | Mi et al. |
| 2013/0336991 A1 | 12/2013 | Mi et al. |
| 2014/0037736 A1 | 2/2014 | Shi et al. |
| 2014/0079728 A1 | 3/2014 | Jackson et al. |
| 2014/0127198 A1 | 5/2014 | Zurawski et al. |
| 2014/0127301 A1 | 5/2014 | Alexis et al. |
| 2014/0134168 A1 | 5/2014 | Zurawski et al. |
| 2014/0199315 A1 | 7/2014 | Mi et al. |
| 2014/0205630 A1 | 7/2014 | Tartour |
| 2014/0212445 A1 | 7/2014 | Martin et al. |
| 2014/0227268 A1 | 8/2014 | Banchereau et al. |
| 2014/0234344 A1 | 8/2014 | Banchereau et al. |
| 2014/0308238 A1 | 10/2014 | Rubin-Bejerano et al. |
| 2014/0314865 A1 | 10/2014 | Von Andrian et al. |
| 2014/0377291 A1 | 12/2014 | Fischbach et al. |
| 2015/0104478 A1 | 4/2015 | Lee et al. |
| 2015/0166659 A1 | 6/2015 | Goldenberg et al. |
| 2015/0191730 A1 | 7/2015 | Levy et al. |
| 2015/0250862 A1 | 9/2015 | Cantor et al. |
| 2015/0299329 A1 | 10/2015 | Zurawski et al. |
| 2015/0307545 A1 | 10/2015 | Jackson et al. |
| 2016/0015821 A1 | 1/2016 | Hubbell et al. |
| 2016/0022792 A1 | 1/2016 | Zurawski et al. |
| 2016/0024212 A1 | 1/2016 | Goldenberg et al. |
| 2016/0031988 A1 | 2/2016 | Zurawski et al. |
| 2016/0058792 A1 | 3/2016 | Quintana et al. |
| 2016/0060324 A1 | 3/2016 | Paulson et al. |
| 2016/0060358 A1 | 3/2016 | Hay |
| 2016/0083468 A1 | 3/2016 | Mi et al. |
| 2016/0108096 A1 | 4/2016 | Thompson et al. |
| 2016/0243248 A1 | 8/2016 | Hubbell et al. |
| 2016/0346384 A1 | 12/2016 | Porcelli et al. |
| 2016/0354453 A1 | 12/2016 | Hubbell et al. |
| 2016/0375126 A1 | 12/2016 | Oh et al. |
| 2017/0007708 A1 | 1/2017 | Hubbell et al. |
| 2017/0020926 A1 | 1/2017 | Mata-Fink et al. |
| 2017/0066825 A1 | 3/2017 | Hubbell et al. |
| 2017/0066828 A1 | 3/2017 | Goldenberg et al. |
| 2017/0121379 A1 | 5/2017 | Zhang et al. |
| 2017/0137513 A1 | 5/2017 | Vallera et al. |
| 2017/0252417 A1 | 9/2017 | Irvine et al. |
| 2017/0296636 A9 | 10/2017 | Hubbell et al. |
| 2017/0320933 A1 | 11/2017 | Mannie |
| 2017/0326213 A1 | 11/2017 | Jajosky et al. |
| 2018/0000916 A1 | 1/2018 | Zurawski et al. |
| 2018/0094071 A1 | 4/2018 | Zurawski et al. |
| 2018/0100011 A1 | 4/2018 | Hubbell et al. |
| 2018/0104284 A1 | 4/2018 | Wallecha et al. |
| 2018/0117171 A1 | 5/2018 | Mooney et al. |
| 2018/0271986 A1 | 9/2018 | Hubbell et al. |
| 2018/0303951 A1 | 10/2018 | Hubbell et al. |
| 2019/0382479 A1 | 12/2019 | Hubbell et al. |
| 2020/0101169 A1 | 4/2020 | Hubbell et al. |
| 2020/0121762 A1 | 4/2020 | Hubbell et al. |

(56) References Cited

U.S. PATENT DOCUMENTS

| | | | |
|---|---|---|---|
| 2020/0129601 A1 | 4/2020 | Hubbell et al. | |
| 2020/0129625 A1 | 4/2020 | Hubbell et al. | |
| 2020/0129629 A1 | 4/2020 | Hubbell et al. | |

FOREIGN PATENT DOCUMENTS

| | | |
|---|---|---|
| CN | 101443351 A | 5/2009 |
| CN | 101750244 A | 6/2010 |
| CN | 102791293 A | 11/2012 |
| CN | 103282380 A | 9/2013 |
| CN | 103547272 A | 1/2014 |
| EP | 0119650 | 9/1984 |
| EP | 0175617 | 10/1991 |
| EP | 0088695 | 6/1992 |
| EP | 0173629 | 6/1992 |
| EP | 0480041 | 6/1993 |
| EP | 0308208 | 12/1993 |
| EP | 0251455 | 5/1994 |
| EP | 0294294 | 5/1995 |
| EP | 0789715 | 8/1997 |
| EP | 0808366 | 11/1997 |
| EP | 0722340 | 4/1998 |
| EP | 0505357 | 3/1999 |
| EP | 0602290 | 8/1999 |
| EP | 0978564 | 2/2000 |
| EP | 1012308 | 6/2000 |
| EP | 630407 | 8/2000 |
| EP | 1046651 | 10/2000 |
| EP | 1093464 | 4/2001 |
| EP | 1301541 | 4/2003 |
| EP | 0743856 | 7/2003 |
| EP | 1370588 | 12/2003 |
| EP | 1409009 | 4/2004 |
| EP | 1292621 | 9/2006 |
| EP | 1838734 | 10/2007 |
| EP | 1853313 | 11/2007 |
| EP | 1028978 | 1/2008 |
| EP | 1086137 | 6/2008 |
| EP | 1938836 | 7/2008 |
| EP | 1440156 | 8/2008 |
| EP | 1619208 | 10/2008 |
| EP | 1996700 | 12/2008 |
| EP | 1996701 | 12/2008 |
| EP | 1045861 | 3/2009 |
| EP | 2125012 | 12/2009 |
| EP | 2178896 | 4/2010 |
| EP | 1516881 | 6/2010 |
| EP | 2238986 | 10/2010 |
| EP | 2315779 | 5/2011 |
| EP | 1417229 | 6/2011 |
| EP | 2344185 | 7/2011 |
| EP | 2344187 | 7/2011 |
| EP | 2394657 | 12/2011 |
| EP | 2394661 | 12/2011 |
| EP | 2406290 | 1/2012 |
| EP | 2428226 | 3/2012 |
| EP | 2478917 | 7/2012 |
| EP | 2066294 | 10/2012 |
| EP | 2527363 | 11/2012 |
| EP | 2598120 | 6/2013 |
| EP | 2618817 | 7/2013 |
| EP | 2620157 | 7/2013 |
| EP | 2630967 | 8/2013 |
| EP | 1904104 | 9/2013 |
| EP | 1991564 | 9/2013 |
| EP | 2115129 | 11/2013 |
| EP | 2684889 | 1/2014 |
| EP | 1443963 | 5/2014 |
| EP | 1664270 | 5/2014 |
| EP | 2115002 | 8/2014 |
| EP | 1605974 | 11/2014 |
| EP | 1850832 | 12/2014 |
| EP | 2114985 | 12/2014 |
| EP | 2283358 | 4/2015 |
| EP | 2213742 | 1/2016 |
| EP | 2982695 | 2/2016 |
| EP | 2983791 | 2/2016 |
| EP | 2989123 | 3/2016 |
| EP | 2346528 | 4/2016 |
| EP | 2406286 | 5/2016 |
| EP | 2205273 | 9/2016 |
| EP | 3091034 | 11/2016 |
| EP | 2406288 | 12/2016 |
| EP | 2406289 | 2/2017 |
| EP | 2217269 | 4/2017 |
| EP | 2344186 | 4/2017 |
| EP | 2630966 | 4/2017 |
| JP | S5742852 A | 3/1982 |
| JP | S59173762 A | 10/1984 |
| JP | 2003-519619 | 6/2003 |
| JP | 2004-526452 | 9/2004 |
| JP | 2007-510915 | 4/2007 |
| JP | 2007-312776 | 12/2007 |
| JP | 2009-505049 | 2/2009 |
| JP | 2009-060894 | 3/2009 |
| JP | 2009-149664 | 7/2009 |
| JP | 2013-516967 | 5/2013 |
| JP | 2018-072431 | 8/2018 |
| WO | WO 1991/008770 | 6/1991 |
| WO | WO 1992/05801 | 4/1992 |
| WO | WO 1992/22310 | 12/1992 |
| WO | WO 1995/06737 | 3/1995 |
| WO | WO 1995/22977 | 8/1995 |
| WO | WO 1996/023882 | 8/1996 |
| WO | WO 1996/040245 | 12/1996 |
| WO | WO 1998/06737 | 2/1998 |
| WO | WO 1999/036437 | 7/1999 |
| WO | WO 1999/38536 | 8/1999 |
| WO | WO 2000/074717 | 12/2000 |
| WO | WO 2001/022995 | 4/2001 |
| WO | WO 2001/025793 | 4/2001 |
| WO | WO 2002/004522 | 1/2002 |
| WO | WO 2002/072799 A | 9/2002 |
| WO | WO 2002/083262 A | 10/2002 |
| WO | WO 2003/064464 | 8/2003 |
| WO | WO 2003/066820 | 8/2003 |
| WO | WO 2003/104273 | 12/2003 |
| WO | WO 2004/034966 A2 | 4/2004 |
| WO | WO 2004/035619 | 4/2004 |
| WO | WO 2004/045520 | 6/2004 |
| WO | WO 2004/098645 | 11/2004 |
| WO | WO 2005/045436 A | 5/2005 |
| WO | WO 2005/105129 | 11/2005 |
| WO | WO 2006/002382 | 1/2006 |
| WO | WO 2006/016247 | 2/2006 |
| WO | WO 2006/093524 | 9/2006 |
| WO | WO 2007/008300 | 1/2007 |
| WO | WO 2007/017556 A | 2/2007 |
| WO | WO 2007/097934 | 8/2007 |
| WO | WO 2007/098254 | 8/2007 |
| WO | WO 2007/099387 | 9/2007 |
| WO | WO 2007/099446 | 9/2007 |
| WO | WO 2007/101698 | 9/2007 |
| WO | WO 2007/150020 | 12/2007 |
| WO | WO 2008/063849 | 5/2008 |
| WO | WO 2009/019317 | 2/2009 |
| WO | WO 2009/056332 | 5/2009 |
| WO | WO 2009/078796 | 6/2009 |
| WO | WO 2009/086552 | 7/2009 |
| WO | WO 2009/120893 A2 | 10/2009 |
| WO | WO 2010/045518 | 4/2010 |
| WO | WO 2010/060155 | 6/2010 |
| WO | WO 2010/076517 | 7/2010 |
| WO | WO 2010/085509 | 7/2010 |
| WO | WO 2011/012715 | 2/2011 |
| WO | WO 2011/051346 | 5/2011 |
| WO | WO 2011/086143 | 7/2011 |
| WO | WO 2011/092715 | 8/2011 |
| WO | WO 2011/112482 A2 | 9/2011 |
| WO | WO 2012/021512 | 2/2012 |
| WO | WO 2012/057671 | 5/2012 |
| WO | WO 2012/083185 | 6/2012 |
| WO | WO 2012/112690 | 8/2012 |
| WO | WO 2012/167088 | 12/2012 |

(56) References Cited

FOREIGN PATENT DOCUMENTS

| | | |
|---|---|---|
| WO | WO 2013/121296 | 8/2013 |
| WO | WO 2013/160865 | 10/2013 |
| WO | WO 2014/011465 | 1/2014 |
| WO | WO 2014/023709 | 2/2014 |
| WO | WO 2014/052545 | 4/2014 |
| WO | WO 2014/135528 | 9/2014 |
| WO | WO 2014/169255 | 10/2014 |
| WO | WO 2015/140648 | 9/2015 |
| WO | WO 2015/157595 | 10/2015 |
| WO | WO 2015/171863 | 11/2015 |
| WO | WO 2015/175957 | 11/2015 |
| WO | WO 2016/022971 | 2/2016 |
| WO | WO 2016/044655 | 3/2016 |
| WO | WO 2016/044661 | 3/2016 |
| WO | WO 2016/070050 | 5/2016 |
| WO | WO 2016/210447 | 12/2016 |
| WO | WO 2017/015141 | 1/2017 |
| WO | WO 2017/023779 | 2/2017 |
| WO | WO 2017/025889 | 2/2017 |
| WO | WO 2017/041053 | 3/2017 |
| WO | WO2017/044308 | 3/2017 |
| WO | WO 2017/046652 | 3/2017 |
| WO | WO 2017/058996 | 4/2017 |
| WO | WO 2017/066484 | 4/2017 |
| WO | WO 2017/109134 | 6/2017 |
| WO | WO 2017/112899 | 6/2017 |
| WO | WO 2017/139498 | 8/2017 |
| WO | WO 2017/139787 | 8/2017 |
| WO | WO 2017/192785 | 11/2017 |
| WO | WO 2017/192786 | 11/2017 |
| WO | WO 2018/232176 | 12/2018 |
| WO | WO 2019/098682 | 5/2019 |
| WO | WO 2019/191079 | 10/2019 |
| WO | WO 2019/0215590 | 11/2019 |
| WO | WO 2021/053589 | 3/2021 |

OTHER PUBLICATIONS

Karim et al. "Hepatic expression and cellular distribution of the glucose transporter family"; World J Gastroenterol Dec. 14, 2012; 18(46): 6771-6781 (Year: 2012).*

Wang et al. in "Diagnostic imaging and therapeutic application of nanoparticles targeting the liver"; J. Mater. Chem. B, 2015, 3, 939. (Year: 2015).*

Klebe. "Optimization of Lead Structures", Drug Design, Springer-Verlag Berlin Heidelberg 2013, pp. 153-171. (Year: 2013).*

Amagai, et al, "Desmoglein as a target in skin disease and beyond", J Invest Dermatol, Mar. 2012; in 23 pages.

Baker, et al. "Hybrid Insulin Peptides are Autoantigens in Type 1 Diabetes", Diabetes, Sep. 2019, vol. 68, pp. 1830-1840.

Caja et al., "Antibodies in celiac disease: implications beyond diagnostics," Cellular & Molecular Immunology (2011) 8, 103-109.

Clements et al., "The Crystal Structure of Myelin Oligodendrocyte Glycoprotein, a key autoantigen in multiple sclerosis," Proc. Natl. Acad. Sci. (PNAS) vol. 100: 11059-11064 (Sep. 2003).

https://en.wikipedia.org/wiki/Reteplase accessed Apr. 13, 2020, printed Apr. 23, 2020 in 2 pages.

https://en.wikipedia.org/wiki/Tenecteplase, accessed Apr. 13, 2020, printed Apr. 23, 2020 in 4 pages.

Lobst et al., "Selective Sugar Binding to the Carbohydrate Recognition Domains of the Rat Hepatic and Macrophage Asialoglycoprotein Receptors." The Journal of Biological Chemistry, vol. 271, No. 12, Issue Mar. 22, 1996, 6686-6693.

Martini, S., Nielsen, M., Peters, B. et al. The Immune Epitope Database and Analysis Resource Program 2003-2018: reflections and outlook. Immunogenetics 72, 57-76 (2020).

Mitea, C. et al., "A Universal Approach to Eliminate Antigenic Properties of Alpha-Gliadin Peptides in Celiac Disease." PLoS One, vol. 5, Issue 12, e15637, pp. 1-9, Dec. 2010.

Nakayama, et al., "Determining Antigen Specificity of Human Islet Infiltrating T Cells in Type 1 Diabetes", Frontiers in Immunology, Mar. 8, 2019, vol. 10, pp. 1-7.

Sigma-Aldrich, "RAFT Agents," available online at https://www.sigmaaldrich.com/materials-science/material-science-products.html?TablePage=103936134, 4 pages (accessed on Sep. 21, 2020) (Year: 2020).

Stern et al., "Promoting Tolerance to Proteolipid protein-induced experimental autoimmune encephalomyelitis through targeting dendritic cells," Proc. Natl. Acad. Sci. (PNAS) vol. 107: 17280-17285, (Oct. 2010).

Wilcock, H. et al. "End Group Removal and Modification of RAFT polymers," Polymer Chemistry, vol. 1, Jan. 1, 2010, pp. 149-157.

Wilson, D.B., "Kent et al. Replying to: D.B. Wilson", Nature, 438, 2005.

"EPFL School of Life Sciences—Annual Report SV 2011," 156 Pages (Dec. 31, 2011 ).

"SubName: Full=Phosphate ABC Transporter, Inner Membrane Subunit PstC;", XP002717162, Retrieved From EBI Accession No. UNIPROT:C7QKI6, Database Accession No. C7QKI6 (Oct. 13, 2009).

"SubName: Full=Putative Integron Gene Cassette Protein; Flags: Fragment;", XP002717159, Retrieved From EBI Accession No. UNIPROT:BOBIT0, Database Accession No. B0BIT0 (Feb. 26, 2008).

"SubName: Full=Putative Transcriptional Regulator, ArsR Family;", XP002717163, Retrieved From EBI Accession No. UNIPROT:D2RZT2, Database Accession No. D2RZT2 (Mar. 2, 2010).

"SubName: Full=Putative Uncharacterized Protein;", XP002717158, Retrieved From EBI Accession No. UNIPROT: C0NJE0, Database Accession No. CONJEO (May 5, 2009).

"SubName: Full=Putative Uncharacterized Protein;", XP002717160, Retrieved From EBI Accession No. UNIPROT:B9PUP0, Database Accession No. B9PUP0 (Mar. 24, 2009).

"SubName: Full=Uncharacterized Protein;", XP002717157, Retrieved From EBI Accession No. UNIPROT:B5E9K2 Database Accession No. B5E9K2 (Oct. 14, 2008).

Ahmed et al., "Carbohydrate-based materials for targeted delivery of drugs and genes to the liver." Nanomedicine (Lond.) (205) 10(14), 2263-2288.

Albert et al., "Immature dendritic cells phagocytose apoptotic cells Via vl35 and CD36, and cross-present antigens to cytotoxic T lymphocytes," Journal of Experimental Medicine, vol. 188(7): 1359-1368 (Oct. 5, 1998).

Andre et al., "Determination of modulation of ligand properties of synthetic complex-type biantennary N-glycans by introduction of bisecting GlcNAc in silico, in vitro and in vivo" Eur. J. Biochem. 2004;271(1):118-134.

Arnaboldi et al., "Suppression of Th 1 and Th17, but not Th2, responses in a CD8+ T cell-mediated model of oral tolerance," Mucosal Immunology, vol. 2(5):427-438 (Sep. 2009).

Bailon et al., "Rational design of a potent, long-lasting form of interferon: A 40 kDa branched polyethylene glycol-conjugated interferon-2a for the treatment of hepatitis C," Bioconjugate Chemistry, vol. 12(2):195-202 (2001).

Bielekova et al., "Expansion and Functional Relevance of High-Avidity Myelin-Specific CD4 T Cells in Multiple Sclerosis," J Immunol 2004; 172:3893-3904.

Bigbee et al., "Binding specificities of eight monoclonal antibodies to human glycophorin A—studies with McM, and MkEn(UK) variant human erythrocytes and M- and MNv-type chimpanzee erythrocytes," Dec. 1, 1984, J. Immunol., 133(6): 3149-3155 (1984).

Blancher et al., "Reactivity of anti-glycophorin monoclonal antibodies (Mabs) in tests with red cells of non-human primates," Jan. 1, 1997, Transfus Clin Biol 4, 81-85 (1997).

Brack et al., "Tumor-ta rgeting properties of novel antibodies specific to the large isoform of tenascin-C," Clinic Cancer Research, vol. 12(10):3200-3208 (May 15, 2006).

Bursch et al., "Langerhans cells are not required for the COB T cell response to epidermal self-antigens," Journal of Immunology, vol. 182(8):4657-4664 (Apr. 15, 2009).

Cao et al., "Molecular Beacon Aptamers for Protein Monitoring in Real-Time and in Homogeneous Solutions," Current Proteomics, 2:31-401, (2005).

(56) References Cited

OTHER PUBLICATIONS

Chasis et al., "Signal Transduction by Glycophorin A: Role of Extracellula Rand Cytoplasmic Domains in a Modulatable Process", The Journal of Cell Biology, 107:1351-1357, (Oct. 1988).

Chiarantini et al., "Red Blood Cells as DeliveRy System for Recombinant HSV-1 Glycoprotein B: Immunogenicity and Protection in Mice," Vaccine, 15(3):276-280, (1997).

Ciccocioppo, R. et al, "The immune recognition of gluten in coeliac disease", British Society for Immunology, Clinical and Experimental Immunology, Feb. 1, 2005, pp. 408-416.

Coulstock et al., "Liver-targeting of interferon-alpha with tissue-specific domain antibodies" PLoS One, Public Library of Science, US, vol. 8, No. 2, Jan. 1, 2013.

Craig et al., "Processing of C3b-Opsonized Immune Complexes Bound to Non-Complement Receptor 1 Sites on Red Cells: Phagocytosis, Transfer and Associations with CR1," J. Immunol.

Crispe et al., "Cellular and molecular mechanisms of liver tolerance," Immunol Rev., 213: 101-118 (2006).

Dane et al., "Isolation of cell specific peptide ligands using fluorescent bacterial display libraries-" Journal of Immunological Methods, vol. 309(1-2):120-129, (Jan. 2006).

Darrah et al., "IL-10 production differentially influences the magnitude, quality, and protective capacity of Th1 responses depending on the vaccine platform," Journal of Experimental Medicine, vol. 207(7):1421-1433 (2010).

Dennis et al.,"Albumin Binding as a General Strategy forImproving the Pha rmacokinetics of Proteins-" Journal of Biological Chemistry, vol. 277(38):35035-35043 (Sep. 20, 2002).

Devalapally et al., "Poly(ethylene oxide)-modified Poly(beta-amino ester) Nanoparticles as a pH-sensitive System for Tumor-targeted Delivery of Hydrophobic Drugs: Part 3. Therapeutic Efficacy and Safety Studies in Ovarian CanceRXenog Raft Model," Cancer Chemotherapy Pharmacology, 59:477-484, (2007).

Dhalluin et al.,"Structural and biophysical characterization of the 40 kDa PEG-interferon-2a and its individual positional isomers," Bioconjugate Chemistry, vol. 16(3):504-517 (2005).

Di Lorenzo et al., "Translational Mini-Review Series on Type 1 Diabetes: Systemic analysis of T cell epitopes in autoimmune diabetes," 2007, Clin Exp Immunol, vol. 148: 1-146.

Dienst et al., "Specific occlusion of mu rine and human tumor vasculature by VCAM-1-ta rgeted recombinant fusion proteins," Journal ofThe National Cancer Institute, vol. 97(10):733-747, (2005).

Dieterich et al., "Identification of Tissue Transglutaminase as the Autoantigen of Celiac Disease," Nature Medicine vol. 3 p. 797-801 (1997).

Dominguez-Soto, et al., "The DC-SIGN-related lectin LSECtin mediates antigen capture and pathogen binding by human myeloid cells" www.bloodjournal.org. Immunobiology, Jun. 15, 2007, vol. 109, No. 12, pp. 5337-5345.

Dornmair Klaus et al: "T-cell-mediated autoimmunity: Novel techniques to characterize autoreactive T-cell receptors", American Journal of Pathology, vol. 163, No. 4, Oct. 2003 (Oct. 2003), pp. 1215-1226, ISSN: 0002-9440.

Ducan, R. Development of HPMA copolymer-anticancer conjugates: Clinical experience and lessons learnt. Advanced Drug Delivery Reviews 61 (2009) pp. 1131-1148.

Ferguson et al., "Armed response: How dying cells influence T-cell functions," Immunology Review, vol. 241 (1 ):77-88 (May 2011 ).

Fife et al.,"Insulin-induced remission in new-onset NOD mice is maintained by the PD-1-PD-L 1 pathway," The Journal of Experimental Medicine, vol. 203(12):2737-2747, (Nov. 27, 2006).

Fishburn,"The pharmacology of PEGylation: balancing PD with PK to generate novel therapeutics," Journal of Pharmaceutical Sciences vol. 97(10):4167-4183 (Oct. 10, 2008).

Folgori A et al: "A general strategy to identify mimotopes of pathological antigens using only random peptide libraries and huamn sera", EMBO (European Molecular Biology Organization) Journal, vol. 13, No. 9, May 1, 1994 (May 1, 1994), pp. 2236-2243, ISSN: 0261-4189.

Fonsatti et al.,"Targeting cancer vasculature via endoglin/CD105: A novel antibody-based diagnostic and therapeutic strategy in solid tumours," Cardiovascular Research, vol. 86(1):12-19, (2010).

Gadaleta et al.,"Trans-arterial chemoembolization as a therapy for liver tumours: New clinical developments and suggestions for combination with angiogenesis inhibitors," Critical Reviews in Oncology/Hematology, vol. 80:40-53 (2011).

Gao et al., "In situ growth of a stoichiometric PEG-like conjugate at a protein's N-terminus with significantly improved pharmacokinetics-" Proceedings of the National Academy Sciences vol. 106(36):15231-15236 (Sep. 8, 2009).

Geng et al., "Site-directed conjugation of "clicked" glycopolymers for form glycoprotein mimics: binding to mammalian lectin and induction of immunological function." J Am Chem Soc. Dec. 12, 2007;129(49):15156-63.

Getts et al., "Have We Overestimated the Benefit of Human(ized) Antibodies?" Landes Bioscience, 2(6):682-694, (Nov./Dec. 2010).

Getz et al., "Protease-Resistant Peptide Ligands From a Knottin Scaffold Library," ACS Chemical Biology, 8 Pages, (May 26, 2011).

Godsel et al., "Prevention of autoimmune myocarditis through the induction of antigen-specific peripheral immune tolerance-" Circulation vol. 103(12):1709-1714 (2001).

Gorovits et al., "Proposed mechanism of off-target toxicity for antibody-drug conjugates driven by mannose receptor uptake," Cancer Immunol Immunother (2013) 62:217-233.

Gorzelany et al., "Protein replacement therapies for rare diseases: a breeze for regulatory approval?" Science Translational Medicine 5, 178fs10 (2013).

Granoff et al., "A Novel Mimetic Antigen Eliciting Protective Antibody to Neisseria meningitidis" J Immunol 2001; 167:6487-6496.

Green et al.,"Immunogenic and tolerogenic cell death," National Review of Immunology vol. 9(5):353-363, (May 2009).

Grimm et al., "Memory of tolerance and induction of regulatory T cells by erythrocyte-targeted antigens." Scientific Reports, 5:159907.

Gupta et al., "Expression, purification, and characterization of an anti-RBCFab-p24 fusion protein for hemagglutination-based rapid detection of antibodies to HIV in whole blood." Protein Expression and Purification 26 (2002) 162-170.

Gurwitz, "Peptide Mimetics: Fast-Forward Look" Drug Development Research 78:231-235, Year 2017.

Hackel et al., "Picomolar affinity fibronectin domains engineered utilizing loop length diversity, recursive mutagenesis, and loop shuffling,"Journal of Molecular Biolology, vol. 381(5):1238-1252, (Sep. 19, 2008).

Hall et al., "Identification of peptide ligands facilitating nanopa rticle attachment toerythrocytes," Biotechnology Progess, vol. 23(3):749-754 (2007).

Hasselberg et al., "ADP-ribosylation controls the outcome of tolerance or enhanced priming following mucosal immunization" The Journal of Immunology, Aug. 24, 2016.

Holz et al., "CD8+ T cell tolerance following antigen recognition on hepatocytes," Journal of Autoimmunity, vol. 34 (1):15-22 (2010).

Huang et al., "Characterization of poly(ethylene glycol) and PEGylated products by LC/MS with postcolumn addition of amines," Analytical Chemistry, vol. 81(2):567-577 (Jan. 15, 2009).

Huang et al.,"Tumor infarction in mice by antibody-directed targeting of tissue factor to tumor vasculature," Science, vol. 275(5299):547-550 (Jan. 24, 1997).

Ichikawa et al., "Hepatic stellate cells function as regulatory bystanders," Journal of Immunology, vol. 186 (10):5549-5555 (May 15, 2011).

"Integer", Meriam-Webster, available online at https://www.merriam-webster.com/dictionary/integer, 12 pages (2019) (Year: 2019).

International Search Report and Written Opinion from corresponding PCT Application No. PCT/IB2013/000684, 12 pages, dated Jul. 9, 2013.

International Search Report and Written Opinion from corresponding PCT Application No. PCT/US2011/047078, 13 pages, dated May 1, 2012.

International Search Report for Application No. PCT/EP2014/054161 dated May 26, 2014.

(56) References Cited

OTHER PUBLICATIONS

Immunogenic, Definition of Immunogenic by Merriam-Webster, https://www.merriam-webster.com/dictionary/immunogenic[May 10, 2019 11:59:27 AM], retrieved on May 10, 2019, in 9 pages.
Janeway et al., "The complement system and innate immunity," Immunology: the Immune System in Health and Disease, 5th Edition. New York: Garland Science (2001).
Janeway et al., Immuno Biology, 8th Edtition, Garland Science (2012).
Jewett et al., "Cu-free click cycloaddition reactions in chemical biology," Chem Soc Rev. Apr. 2010; 39(4): 1272-1279.
Jones et al., "Localization of Pectic Galactan in Tomato Cell Walls Using a Monoclonal Antibody Specific to (1->4)-β-D-Galactan" Plant Physiol. 1997; 113:1405-1412.
Mamidyala, et al., "Glycomimetic Ligands for the Human Asialoglycoprotein Receptor", Journal of the American Chemical Society, Jan. 24, 2012, vol. 134, p. 1978-1981.
Julyan et al "Preliminary clinical study of the distribution of HPMA copolymers bearing doxorubicin and galactosamine" Journal of Controlled Release 57 (1999) pp. 281-290.
Keefe et al.,"Aptamers as therapeutics," Nature Reviews Drug Discovery, vol. 9(7):537-550 (2010).
Kenrick et al., "Bacterial Display Enables Efficient and Quantitative Peptide Affinity Maturation," Protein Engineering Design & Selection, vol. 23(1 ):9-17 (2010).
Khandelwal et al., "Assessment of survival of aging erythrocyte in circulation and attendant changes in size and CD147 expression by a novel two step biotinylation method," Experimental Gerontology, vol. 41(9):855-861 (Aug. 4, 2006).
Kim et al "Imaging and therapy of liver fibrosis using bioreducible polyethylenimine/siRNA complexes conjugated with N-acetylglucosamine as a targeting moiety" Biomaterials 34:6504-6514 (2013).
Kim et al., "Specific Binding of Glucose-derivatized Polymers to the Asialoglycoprotein Receptor of Mouse Primary Hepatocytes." The Journal of Biological Chemistry, vol. 276, No. 38, pp. 35312-35319, Sep. 21, 2001.
Kina et al.,"The Monoclonal Antibody TER-119 Recognizes a Molecule Associated with Glycophorin A and Specifically Marks the Late Stages of Murine Erythroid Lineage," British Journal of Haematolgy, vol. 109:280-287 (2000).
King et al. "Antibody responses to bee melittin (Api m 4) and hornet antigen 5 (Dol m 5) in mice treated with the dominant T-cell Epitope peptides" Journal of Allergy and Clinical Immunology, vol. 101, Issue 3, Mar. 1998, pp. 397-403.
Kontos et al., "Engineering antigens for in situ erythrocyte binding induces T-cell deletion," Proceeding of the National Academy Sciences, Dec. 17, 2012, vol. 110, No. 1, p. E60-E68.
Kontos et al., "Improving Protein Pharmacokinetics by Engineering Erythrocyte Affinity," Molecular Pharmaceutics, 2010, vol. 7, No. 6, p. 2141-2147.
Kontos, "Engineering Erythrocyte Affinity for Improved Pharmacokinetics and Immune Tolerogenesis", Thesis, 106 Pages (Jun. 23, 2011).
Kontos, et al., "Engineering antigen-specific immunological tolerance", www.sciencedirect.com, Current Opinion in Immunology, Jul. 8, 2015, 35:80-88.
Kopecek et al. "HPMA copolymers: Origins, early developments, present, and future." Advanced Drug Delivery Reviews 62, (2010) pp. 122-149.
Krebber et al., "Reliable Cloning of Functional Antibody Variable domains from Hybridomas and Spleen Cell Repertoires Employing a Reengineered Phage Display System," Journal of Immunological Methods, vol. 201 :35-55 (1997).
La Rosa, et al., "The Innate Immune System in Allograft Rejection and Tolerance," J. Immunol., 2007, 178:7503-7509.
Langer et al., "Optimization of the Preparation Process for Human Serum Albumin (HSA) Nanoparticles," International Journal of Pharmaceutics, 257:169-180, (2003).
Lee et al., "Aptamers as Molecular Recognition Elements for Electrical Nanobiosensors," Analytical and Bioanalytical Chemistry, 390:1023-1032, (2008).
Lee et al., "Signaling pathways downstream of pattern—recognition receptors and their cross talk," Annual Review of Biochemistry, vol. 76:447-480 (Feb. 28, 2007).
Lehrman et al., "The Binding of Fucose-containing Glycoproteins by Hepatic Lectins" The Journal of Biological Chemistry Jun. 5, 1986; 261, 7426-7432.
Lepenies et al., "Targeting C-type lectin receptors with multivalent carbohydrate ligands." Adv. Drug Deliv. Rev. (2013).
Li et al., "Targeting self- and foreign antigens to dendritic cells via DC-ASGPR generates IL-10pproducing suppressive CD4+ T cells," Jan. 2, 2012, Journal of Experimental Medicine 209, 109-121 (2012).
Liu et al. "Hapten may play an important role in food allergen-related intestinal immune inflammation," North American Journal of Medical Sciences, vol. 3. No. 3. (Mar. 2011).
Liu et al., "Immune tolerance after delivery of dying cells to dendritic cells in situ," Journal of Experimental Medicine, vol. 196(8): 1091-1097 (Oct. 21, 2002).
Liu et al.,"Functional Nucleic Acid Sensors", Chemical Reviews, 109(5):1948-1998, (May 2009).
Loma et al., "Multiple Sclerosis: Pathogenesis and Treatment" Department of Neurology, Curr. NeuropharmacOLOGY, 9:409-416, Year 2011.
Lorentz et al., "Engineered binding to erythrocytes induces immunological tolerance to *E. coli* asparaginase." Sci. Adv. 2015.
Luo et al., "ECDI-fixed allogeneic splenocytes induce donor-specific tolerance for long-term survival of islet transplants via two distinct mechanisms," Proceedings of National Academy of Science, vol. 105(38):14527-14532 (Sep. 23, 2008).
Lutolf et al.,"Synthesis and Physicochemical Characterization of End-Linked Poly(ethylene glycol)-co-peptide Hydrogels Formed by Michael-Type Addition," Biomacromolecules, 4:713-722, (Feb. 1, 2003).
Lutolf et al.,"Systematic modulation of Michael-type reactivity of thiols through the use of charged amino acids," Bioconjugate Chemistry vol. 12(6):1051-1056 (2001).
Lutterotti, A. et al., "Antigen-Specific Tolerance by Autologous Myelin Peptide-Coupled Cells: A Phase 1 Trial in Multiple Sclerosis," Science Translational Medicine 5, 188ra75-188ra75 (2013).
Magnani et al., "Red blood cells as an antigen-delivery system," Biotechnol Appl Biochem. Oct. 1992;16(2):188-94.
Maluccio et al., "Transcatheter arterial embolization with only particles for the treatment of unresectable hepatocellular carcinoma-" Journal of Vascular and interventional Radiology, vol. 19(6):862-869 (2008).
Mamidyala, S. et al., "Glycomimetic ligands for the human asialoglycoprotein receptor" J. Am Chem. Soc. Feb. 1, 2012, 134(4), pp. 1978-1981.
Maynard et al., "Antibody engineering," Annual Review of Biomedical Engineering, vol. 2:339-376 (2000).
Meager et al., "Anti-cytokine autoantibodies in autoimmunity: preponderance of neutralizing autoantibodies against interferon-alpha, interferon-omega and interleukin-12 in patients with thymoma and or myasthenia gravis" Clinical and Experimental Immunology, Wiley-Blackwell Publishing Ltd, GB, vol. 132, No. 1, Apr. 1, 2003.
Medina et al., "Targeting hepatic cancer cells with pegylated dendrimers displaying N-acetylgalactosamine and SP94 peptide ligands" Advanced Healthcare Materials, vol. 2, Issue 10, pp. 1337-1350, Oct. 2013.
Meyer et al. Metformin and Insulin in Type 1 Diabetes; Diabetes Care 26:1655-1656, Year: 2003.
Miller et al.,"Antigen-specific tolerance strategies for the prevention and treatment of autoimmune disease," Nature Reviews Immunology 7(9):665-677, (Sep. 2007).
Moghimi et al.,"Stealth liposomes and long circulating nanoparticles: critical issues in pharmacokinetics, opsonization and protein-binding properties," Progress in Lipid Research, vol. 42(6):463-478 (2003).
Mohandas et al.,"Red cell membrane: past, present, and future," Blood, vol. 112(10):3939-3948(Nov. 15, 2008).

(56) References Cited

OTHER PUBLICATIONS

Moreau et al, "PEPOP: Computational design of immunogenic peptides" BioMed Central, Jan. 30, 2008, 15 pages.
Mueller,"Mechanisms maintaining peripheral tolerance," Nature Immunology, vol. 11(1 ):21-27 (Jan. 2010).
Murphy, "Antigen Recognition by B-Cell and T-cell Receptors," 2012, Janeway's Immuno Biology, 8th Edition, Chapter 4, Garland Science Taylor & Francis Goup, London and New York.
Murray et al.,"The Mouse Immune Response to Carrier Erythrocyte Entrapped Antigens," Vaccine, 24:6129-6139, (2006).
Muzykantov, "Drug Delivery by Red Blood Cells: Vascular Carriers Designed by Mother Nature", Expert Opinion Drug Delivery, 7(4 ):403-427, (Apr. 2010).
Nardin et al., "How are immune complexes bound to the primate erythrocyte complement receptor transferred to acceptor phagocytic cells," Mol. Immunol.
Nishikawa et al. "Galactosylated proteins are recognized by the liver according to the surface density of galactose moieties" The American journal of physiology Jun. 1995; 268(5 Pt 1):G849-56, Abstract.
O'Neil et al., "Extracellular matrix binding mixed micelles for drug delivery applications," Journal of Control Release, vol. 137(2):146-151, (Mar. 27, 2009).
Parmeggiani et al., "Designed armadillo repeat proteins as general peptide-binding scaffolds: consensus design and computational optimization of the hydrophobic core," Journal of Molecular Biology, vol. 376(5):1282-1304 (2008).
Pasut et al.,"PEG conjugates in clinical development or use as anticancer agents: An overview," Advanced Drug Delivery Reviews, vol. 61(13):1177-1188 (2009).
Qin et al., "Galactosylated N-2-Hydroxypropyl Methacrylamide-b-N-3-Guanidinopropyl Methacrylamide Block Copolymers as Hepatocyte-Targeting Gene Carriers," Bioconjugate Chem. 22:1503-1512 (2011).
Qin, et al., Preparation and bioactivity of anti-hum red blood cell ScFvand CSFV E@ bifunctional fusion protein, Chin J. Biotech Jan. 25, 2010: 26(1): 28-34, Chinese Journal of Biotechnology (2010).
Rajpal, Arvind, et al. "A general method for greatly improving the affinity of antibodies by using combinatorial libraries", PNAS, www.pnas.org/cgi/doi/10.1073/pnas.0503543102, vol. 102 No. 24, pp. 8466-8471, Jun. 14, 2005.
Reddy et al., "Exploiting lymphatic transport and complement activation in nanoparticle vaccines," Nature Biotechnology, vol. 25(10):1159-1164 (Oct. 2007).
Reddy et al., "In vivo targeting of dendritic cells in lymph nodes with poly(propylene sulfide) nanoparticles," Journal of Controlled Release, vol. 112(1):26-34, (Mar. 10, 2006).
Reinagel et al., "The Primate Erythrocyte Complement Receptor (CR1) as a Priveleged Site: Binding of Immunoglobulin G to Erythrocyte CR1 Does Not Target Erythrocytes for Phagocytosis," 1997, Blood, vol. 89: p. 1068-1077.
Rice et al., "Directed evolution of a biterminal bacterial display scaffold enhances the display of diverse peptides", Protein Engineering, Design & Selection, vol. 21(7):435-442 (2008).
Rigopoulou et al., "Asialoglycoprotein receptor (ASGPR) as target autoantigen in liver autoimmunity: Lost and found," Autoimmunity Reviews, 12 (2012) 260-269.
Rockey et al., "Synthesis and radiolabeling of chelator-RNA aptamerbioconjugates with copper-64 for targeted molecular imaging-" Bioorganic& Medicinal Chemistry, vol. 19(13):4080-4090 (2011).
Ruoslahti et al., "Targeting of drugs and nanoparticles to tumors," Journal of Cell Biology, vol. 188(6):759-768 (2010).
Rybak et al., "The extra-domain A of fibronectin is a vascular marker of solid tumors and metastases," Cancer Research, vol. 67(22):10948-10957 (2007).
Saibeni et al., "Antibodies to tissue-type plasminogen activator (t-PA) in patients with inflammatory bowel disease: high prevalence, interactions with functional domains of t-PA and possible implications in thrombosis," J. Thrombosis and Haemostasis, 4:1510-1516 (2006).
Saint-Lu, N. et al., "Targeting the allergen to oral dendritic cells with mucoadhesive chitosan particles enhances tolerance induction," Allergy, vol. 64(7):1003-1013 (2009).
Sakaguchi et al., "Regulatory T Cells and Immune Tolerance," Cell 133, May 30, 2008, 775-787.
Sampson, "Aptamersand SELEX: the technology," World Patent Information, vol. (25):123-129 (2003).
Savla et al., "Tumor targeted quantum dot-mucin 1 aptamer-doxorubicin conjugate for imaging and treatment of cancer," Journal of Controlled Release, vol. 153(1):16-22, Feb. 20, 2011.
Schliemann et al., "In vivo biotinylation of the vasculature in B-cell lymphoma identifies BST-2 as a target for antibody-based therapy," Vascular Blood, vol. 115(3):736-744 (Jan. 21, 2010).
Sehon et al., "Conversion of Antigens to Tolerogenic Derivatives by Conjugation with Monomethoxypolyethylene Glycol", The Pharmacology and Toxicology of Proteins, pp. 205-219 (1987).
Sehon et al., The Pharmacology and Toxicology of Proteins, Proceedings of Cetus-UCLA Symposium Held at Lake Tahoe, Ca, Feb. 21-28, 1987, Alan r. Liss, Inc.—New York.
Seamons et al. Immune Tolerance to Myelin Proteins (Immunologic Research 2003; 28/3:201-221).
Seymour et al., "Hepatic Drug Targeting: Phase I evaluation of polymer-bound doxorubicin" Journal of Clinical Oncology, vol. 20, No. 6, Mar. 15, 2002, pp. 1668-1676.
Seymour et al., "N-(2-Hydroxypropyl)methacrylamide copolymers targeted to the hepatocyte galactose-receptor: pharmacokinetics in DBA2 mice." Br. J. Cancer (1991) 63, pp. 859-866.
Shan et al., "Structural Basis for Gluten Intolerance in Celiac Sprue," Science, 297, 2275 (2002).
Shen "A galactosamine-mediated drug delivery carrier for targeted liver cancer therapy" Pharmacological Research 64 (2011) 410-419.
Sheridan "Fresh from the biologic pipeline-2009," Nature Biotechnology, vol. 28(4):307-310 (Apr. 2010).
Silverman et al., "Engineered cystine-knot peptides that bind $v\beta3$ integrin with antibody-like affinities," Journal of Molecular Biology, vol. 382(4):1064-1075 (Jan. 30, 2009).
Sørensen et al., "Role of sialic acid for platelet life span: exposure of $\beta$-galactose results in the rapid clearance of platelets from the circulation by asialoglycoprotein receptor-expressing liver macrophages and hepatocytes." Blood, Aug. 20, 2009. vol. 114, No. 8.
Spitzer et al., "ScFv-Mediated in Vivo Targeting of DAF to Erythrocytes Inhibits Lysis by Complement," Molecular Immunology, vol. 40:911-919 (Oct. 30, 2003).
St. Clair et al., "New Reagents on the Horizon for Immune Tolerance," Sep. 20, 2006, Annu. Rev. Med. 2007. 58:329-46.
Staud et al., "Liver uptake and hepato-biliary transfer of galactosylated proteins in rats are determined by the extent of galactosylation" Biochimica et Biophysica Acta May 1999; 1427(2):183-192, Abstract.
Steiner et al., "Efficient selection of DARPins with sub-nanomolar affinities using SRP phage display," Journal of Molecular Biology, vol. 382(5):1211-1227 (2008).
Sun, et al, "Comparison between Ovalbumin and Ovalbumin Peptide 323-339 Responses in Allergic Mice: Humoral and Celluler Aspects," Scandinavian Journal of Immunology, vol. 71: 329-335 (Jan. 2010).
Supplementary European Search Report from corresponding PCT Application No. PCT/US2011047078, 21 Pages, dated Jan. 22, 2014.
Taneja et al., "Lessons from animal models for human autoimmune diseases," Sep. 1, 2001, Nature Immunology, vol. 2, No. 9, 781-784 (Sep. 2001).
Taylor et al., "Anti-glycophorin single-chain Fv fusion to low-affinity mutant erythropoietin improves red blood cell-lineage specificity", Protein Engineering, Design & Selection, vol. 23, No. 4 pp. 251-260, 2010.
Thijssen et al., "Galectin-1 is essential in tumor angiogenesis and is a target for antiangiogenesis therapy-", Proceeding of the Natinol Academy Sciences, vol. 103(43):15975-15980 (2006).
Teitelbaum et al., Immunomodulation of experimental autoimmune encephalomyelitis by oral administration of copolymer 1. Pro. Natl. Acad. Sci. USA vol. 96, pp. 3842-3847, Mar. 1999.

(56) References Cited

OTHER PUBLICATIONS

Thomson et al., "Antigen-presenting cell function in the tolerogenic liver environment," National Reviews Immunology, vol. 10(11):753-766 (Nov. 2010).
Tobio et al., "Stealth PLA-PEG Nanoparticles as Protein Carriers for Nasal Administration," Pharmaceutical Research, 15(2):270-275, (1998).
Trahtenherts, A. et al, "An internalizing antibody specific for the human asialoglycoprotein receptor" Hybridoma, vol. 28, No. 4, Aug. 1, 2009.
Tye-Din, et al. "Comprehensive, Quantitive Mapping of T Cell Epitopes in Gluten in Celiac Disease", www.ScienceTranslationalMedicine.org, Jul. 21, 2010, vol. 2 Issue 41, in 14 pages.
Turley et al., "Prospects for Antigen-Specific Tolerance Based Therapies for the Treatment of Multiple Selerosis," Results and Problems in Cell Differentiation, 51 :217-235, (2010).
Updike et al., "Infusion of red blood cell-loaded asparaginase in monkey: Immunologic, metabolic, and toxicologic consequences," 1983, J Lab Clin Med, vol. 101(5): p. 679-691.
Van Der Vlies et al., "Synthesis of pyridyl disulfide-functionalized nanopa rticles for conjugating thiol-containing small molecules, peptides, and proteins," Bioconjugate Chemistry, vol. 21(4):653-662 (2010).
Velluto et al., "PEG-b-PPS Diblock Copolymer Aggregates for Hydrophobic Drug Solubilization and Release: Cyclosporin A as an Example," Molecular Pharmaceutics, 11 Pages, (May 2, 2008).
Vogl et al., "Review on transarterial chemoembolization in hepatocellular carcinoma: Palliative, combined, neoadjuvant, bridging, and symptomatic indications," European Journal Radiology, vol. 72(3):505-516 (2009).
Walker et al., "Anti-serum albumin domain antibodies in the development of highly potent, efficacious and long-acting interferon," Protein Engineering Design & Selection, vol. 23(4):271-278 (2010).
Wan, "Regulatory T cells: immune suppression and beyond," May 1, 2010, Cell Mol Immunol. May 2010; 7(3):204-210.
Wang et al., "Synthesis and Micellization of Thermoresponsive Galactose-Based Diblock Copolymers," J Polymer Sci. 49:3280-3290 (2011).
Weisser et al., "Applications of single-chain variable fragment antibodies in therapeutics and diagnostics," Biotechnology Advances, vol. 27(4):502-520 (2009).
Wilson et al., "Rapid Whole Blood Assay For HIV-1 Seropositivity Using An Fab-Peptide Conjugate," Journal of Immunological Methods, vol. 138:111-119 (1991).
Wu, Herren, "Simultaneous Humanization and Affinity Optimization of Monoclonal Antibodies", Methods in Molecular Biology, vo. 207: Recombinant Antibodies for Cancer Therapy: Methods and Protocols, Tolowa, NJ, pp. 197-212, Jan. 1, 2003.
Yamazaki et al., "CD8+ CD205+ splenic dendritic cells are specialized to induce Foxp3+ regulatory T cells," Journal of Immunology, vol. 181(10):6923-6933 (2008).
Yeste Ada et al: "Antigen Microarrays for the Study of Autoimmune Diseases", Clinical Chemistry, vol. 59, No. 7, Jul. 2013 (Jul. 2013), pp. 1036-1044, ISSN: 0009-9147(print).
Yoo et al., "N-Acetylgalactosamino dendrons as clearing agents to enhance liver targeting of model antibody-fusion protein." Bioconjugate Chemistry, vol. 24, No. 12, Dec. 18, 2013, pp. 2088-2103.
Zaitsev et al., "Targeting of a Mutant Plasminogen Activator to Circulating Red Blood Cells for Prophylactic Fibrinolysis", The Journal of Pharmacology and Experimental Therapeutics, 332(3):1022-1031 and 976 (Nov. 30, 2009).
Zhao, X. et al "Construction and characterization of an anti-asialoglycoprotein receptor single-chain variable-fragment-targeted melittin" Biotechnology and Applied Biochemistry, Nov.-Dec. 2011; 58(6): pp. 405-411.
Zhong et al., "Ligand-directed Reduction-Sensitive Shell-Sheddable Biodegradable Micelles Actively Deliver Doxorubicin into the Nuclei of Target Cancer Cells," Biomacromalecules 14:3723-3730 (2013).
Kravtzoff et al., "Tolerance Evaluation of L-asparaginase loaded in red blood cells," 1996, Eur J Clin Pharmacol, vol. 51: 221-225.
Moad et al., "Mechanism and Kinetics of Dithiobenzoate-Mediated RAFT Polymerization—Status of the Dilemma." Macromolecular Journals Chem. Phys. 2014, 215: 9-26.

\* cited by examiner

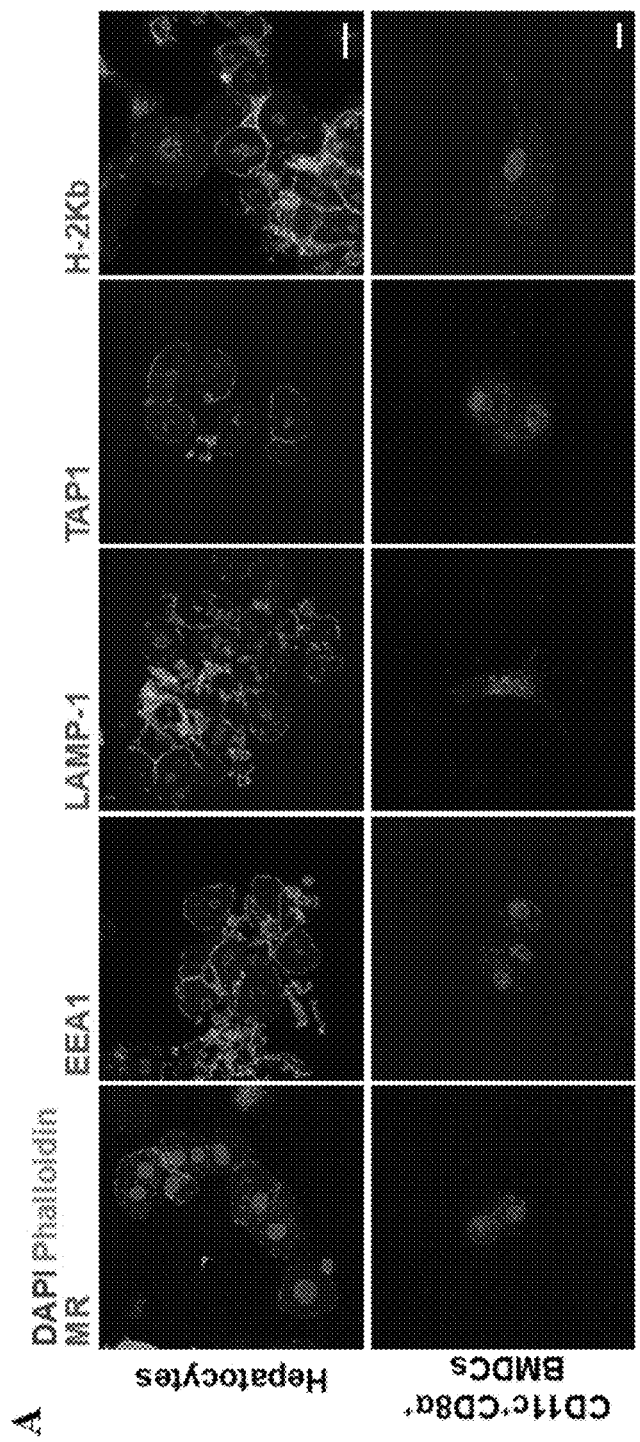
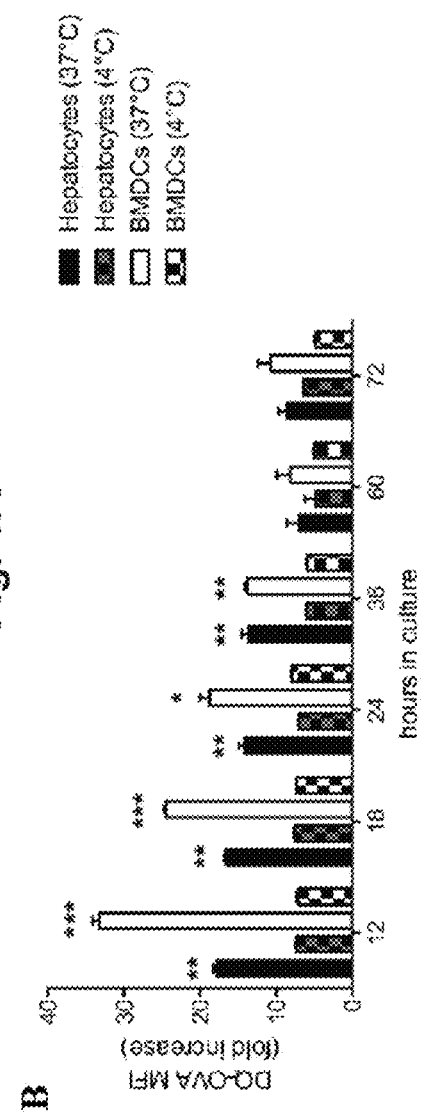
Fig. 1A
Fig. 1B

Fig. 3A-C

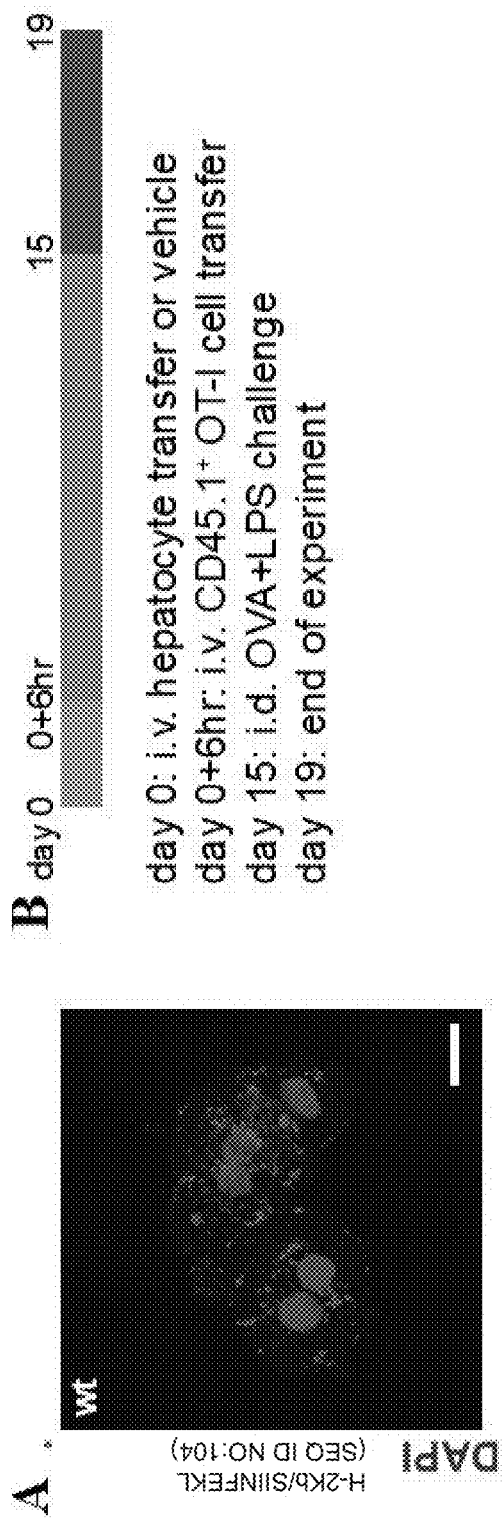

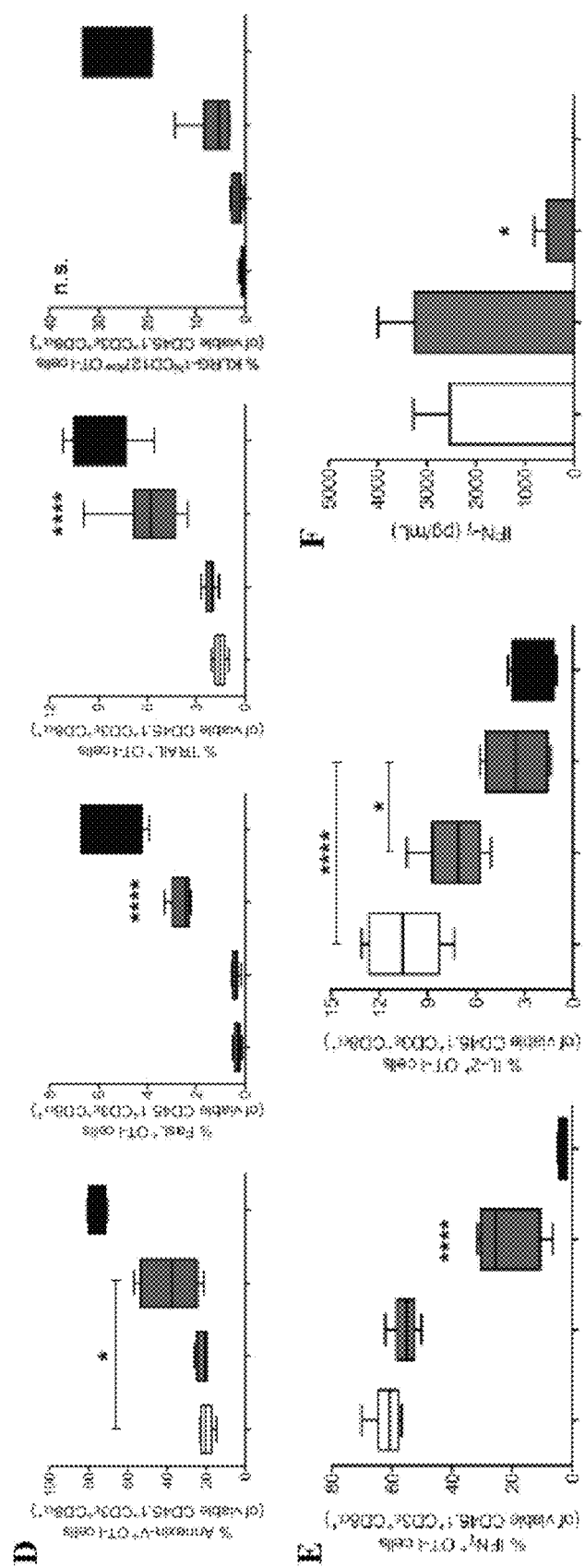
Fig. 5D-F.

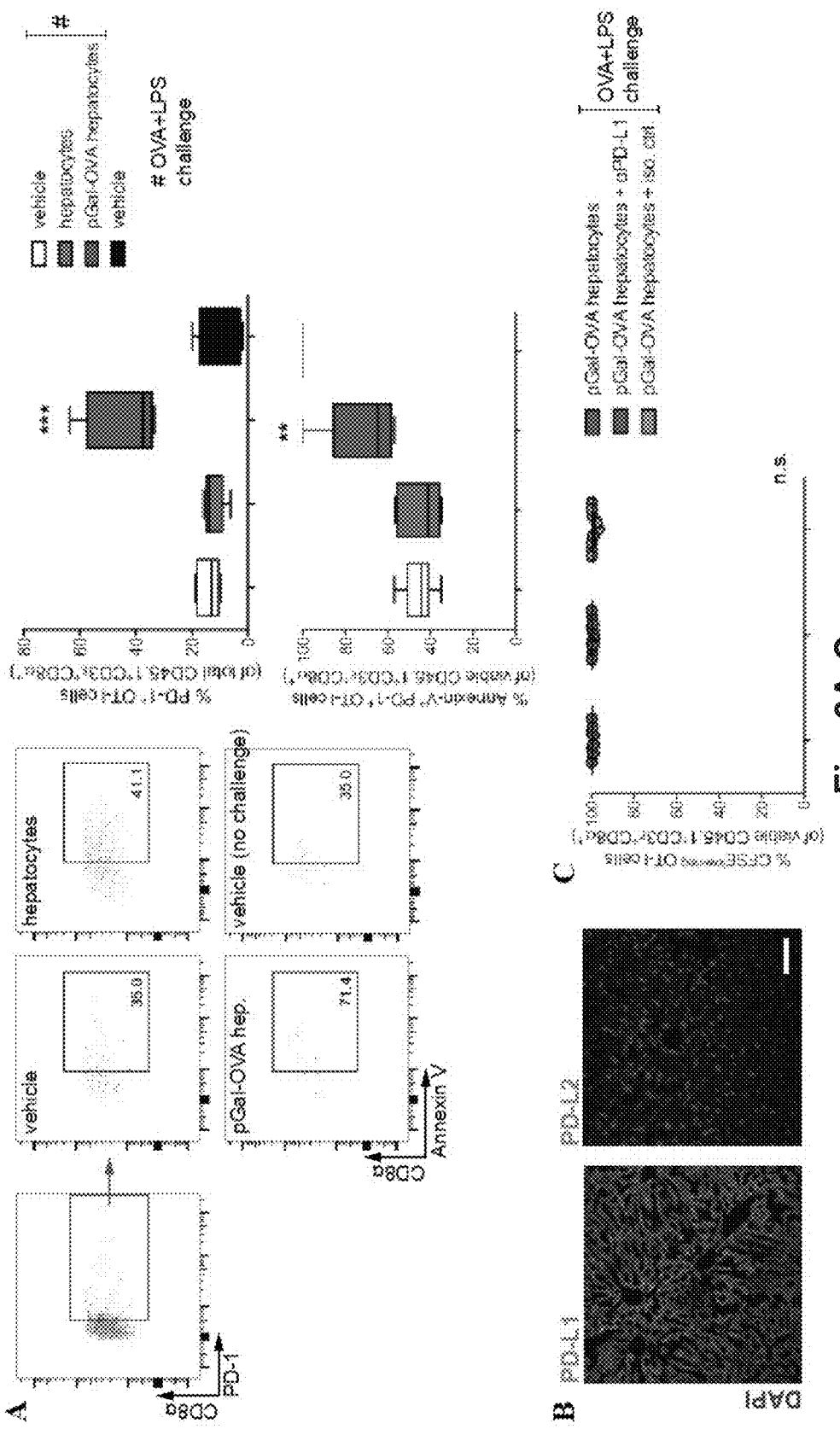
Fig. 6A-C

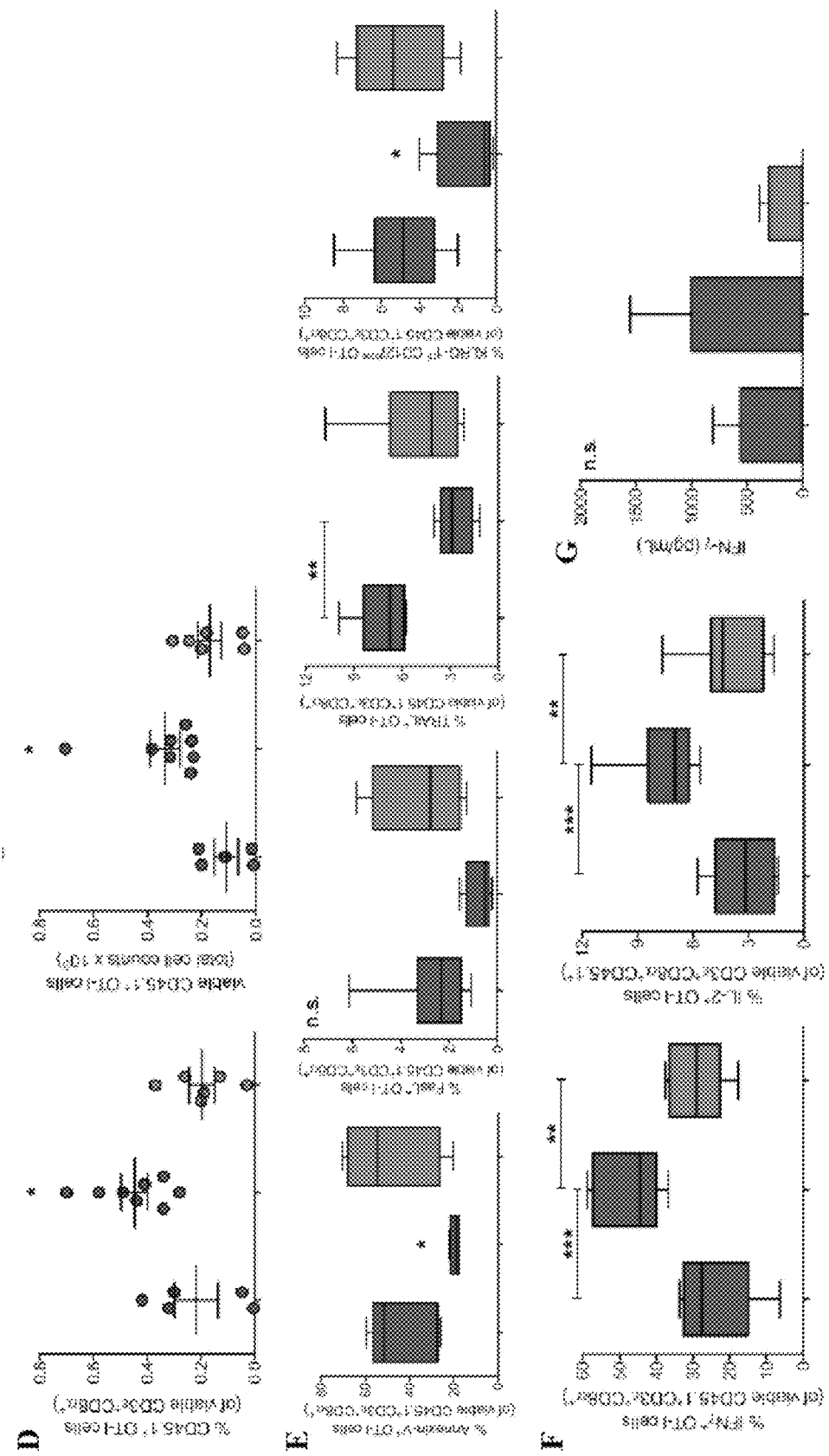
Fig. 6D-F

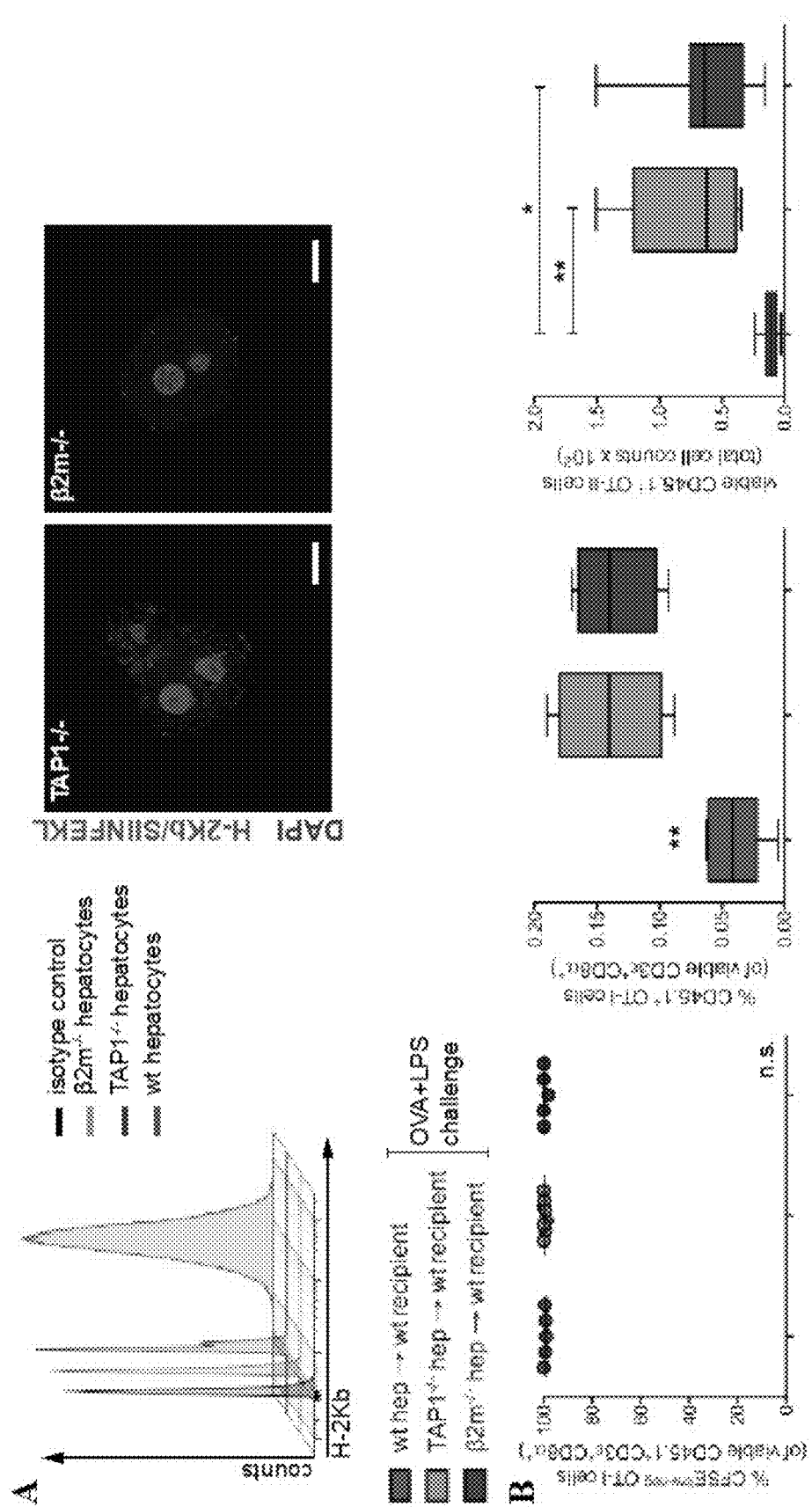
Fig. 7A-B

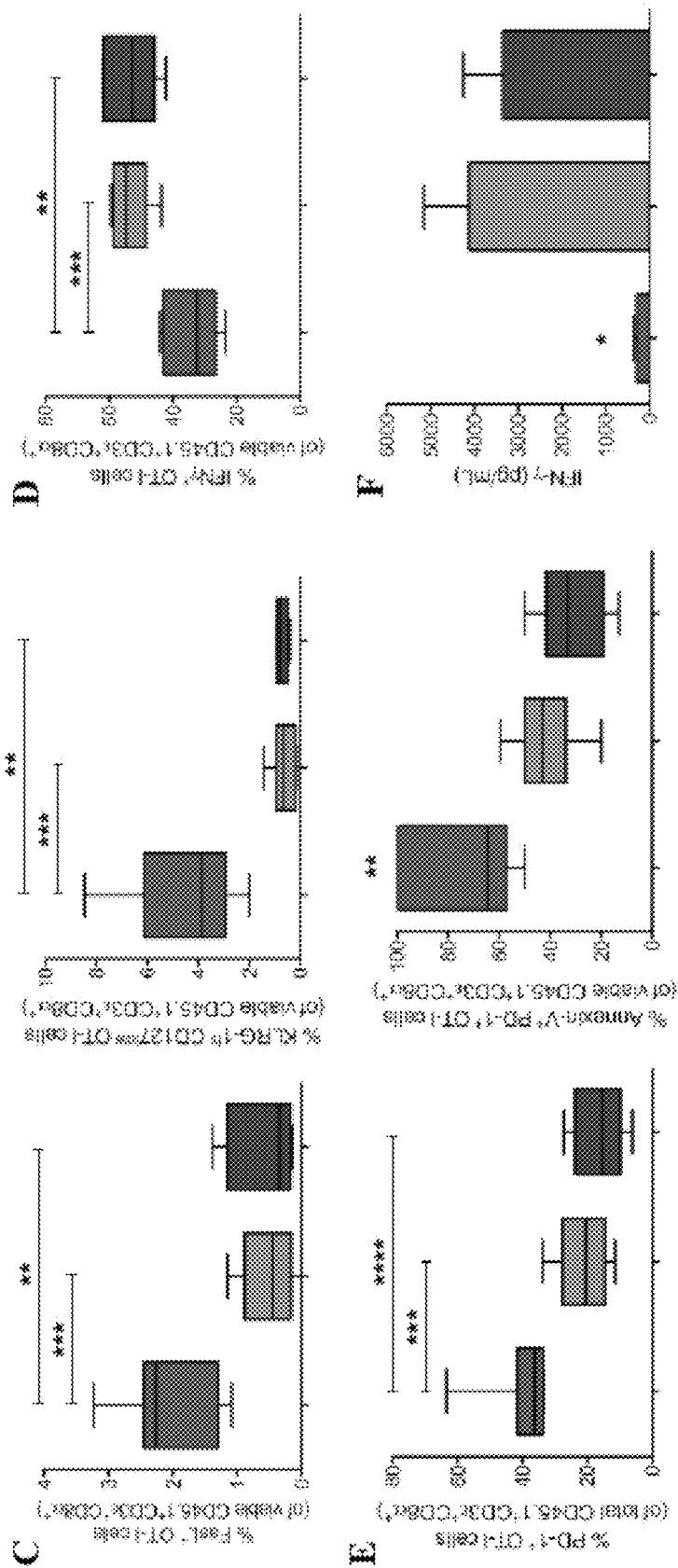
Fig. 7C-E

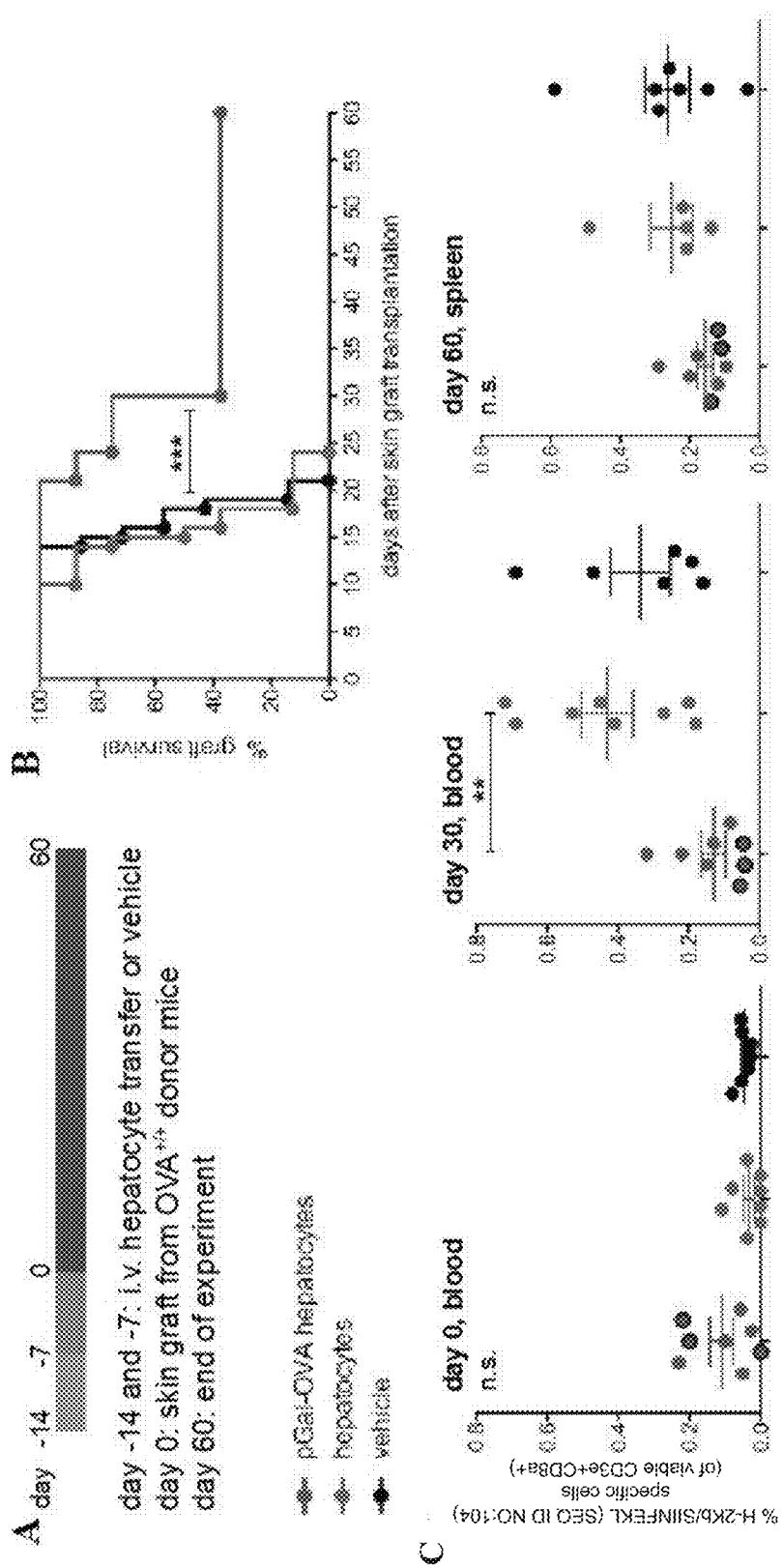
Fig. 8A-C

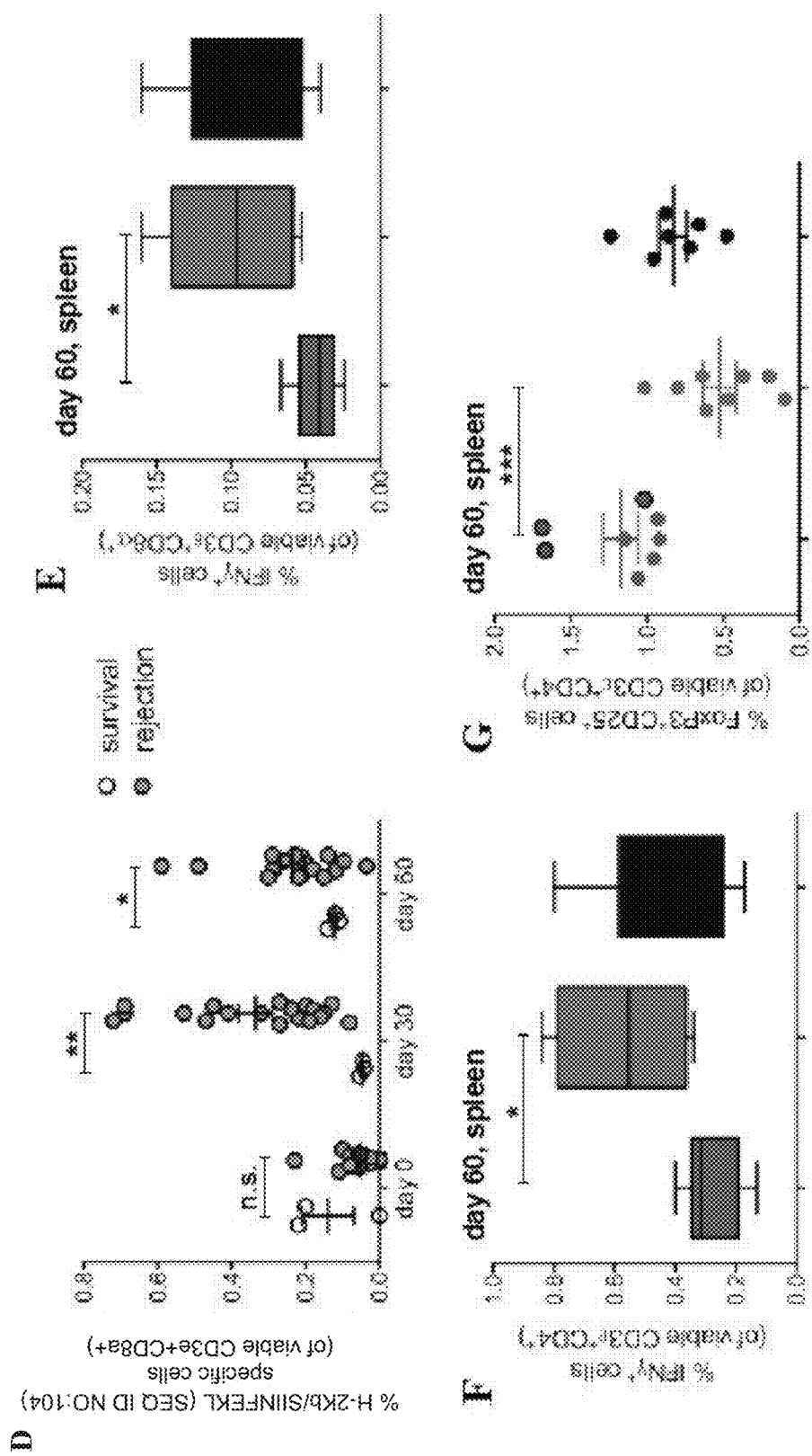
Fig. 8D-G

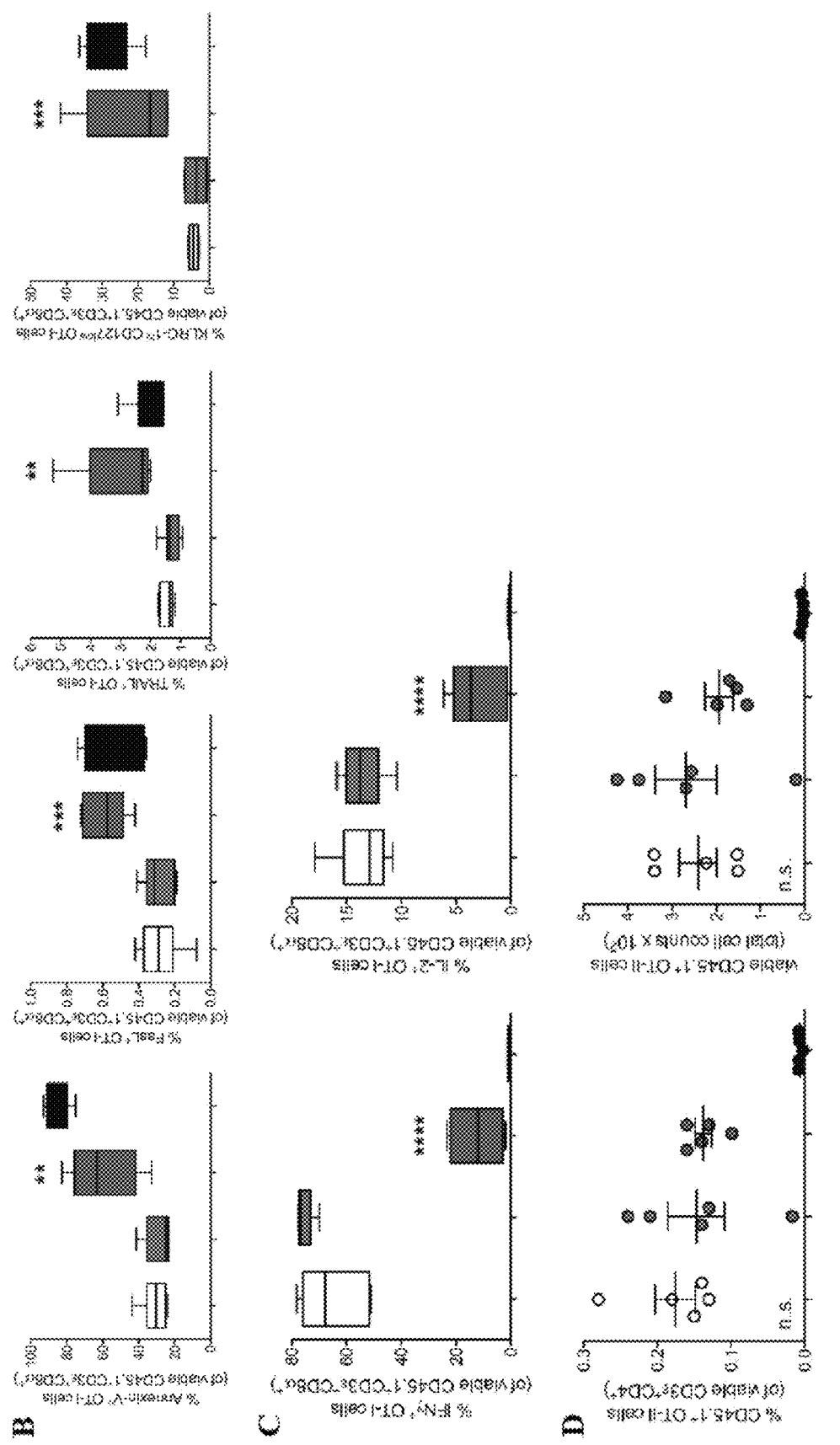
Fig. 9B-D

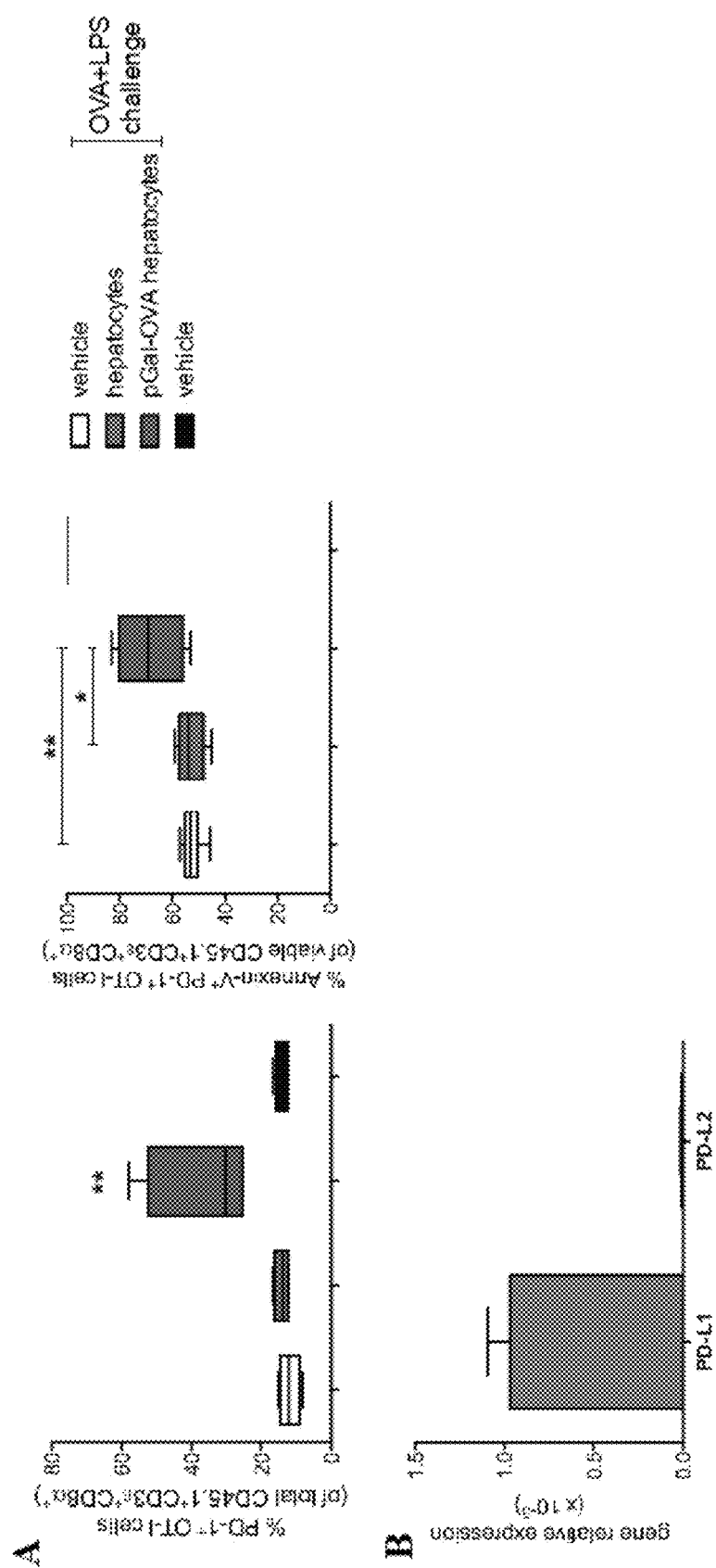
Fig. 10A-B

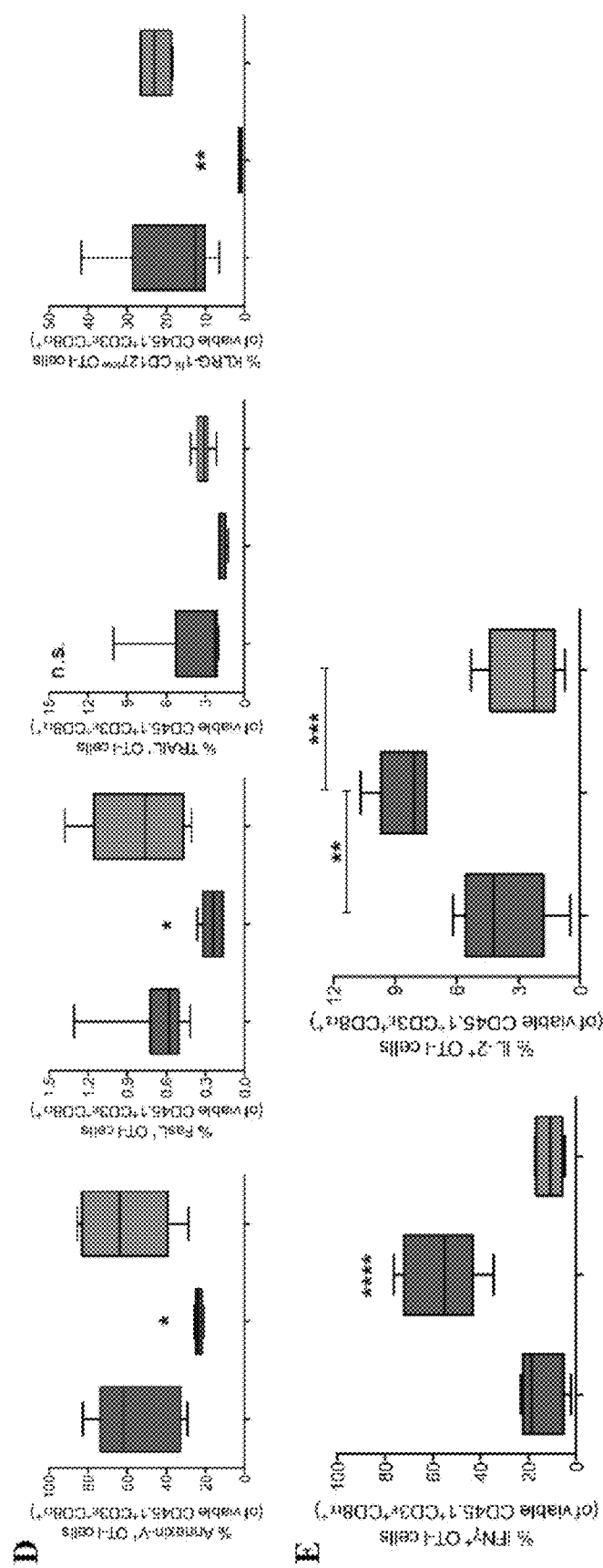
Fig. 10D-E

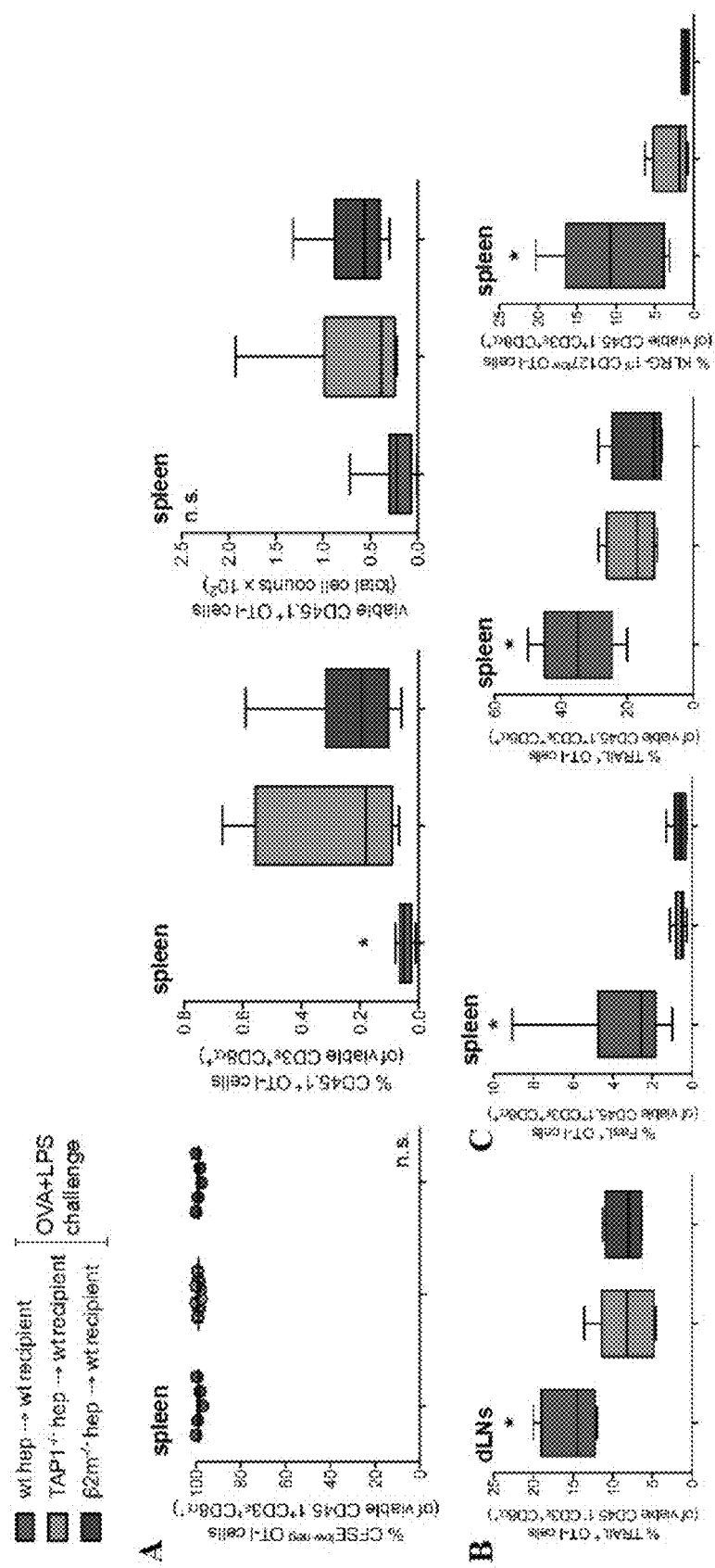
Fig. 11A-C

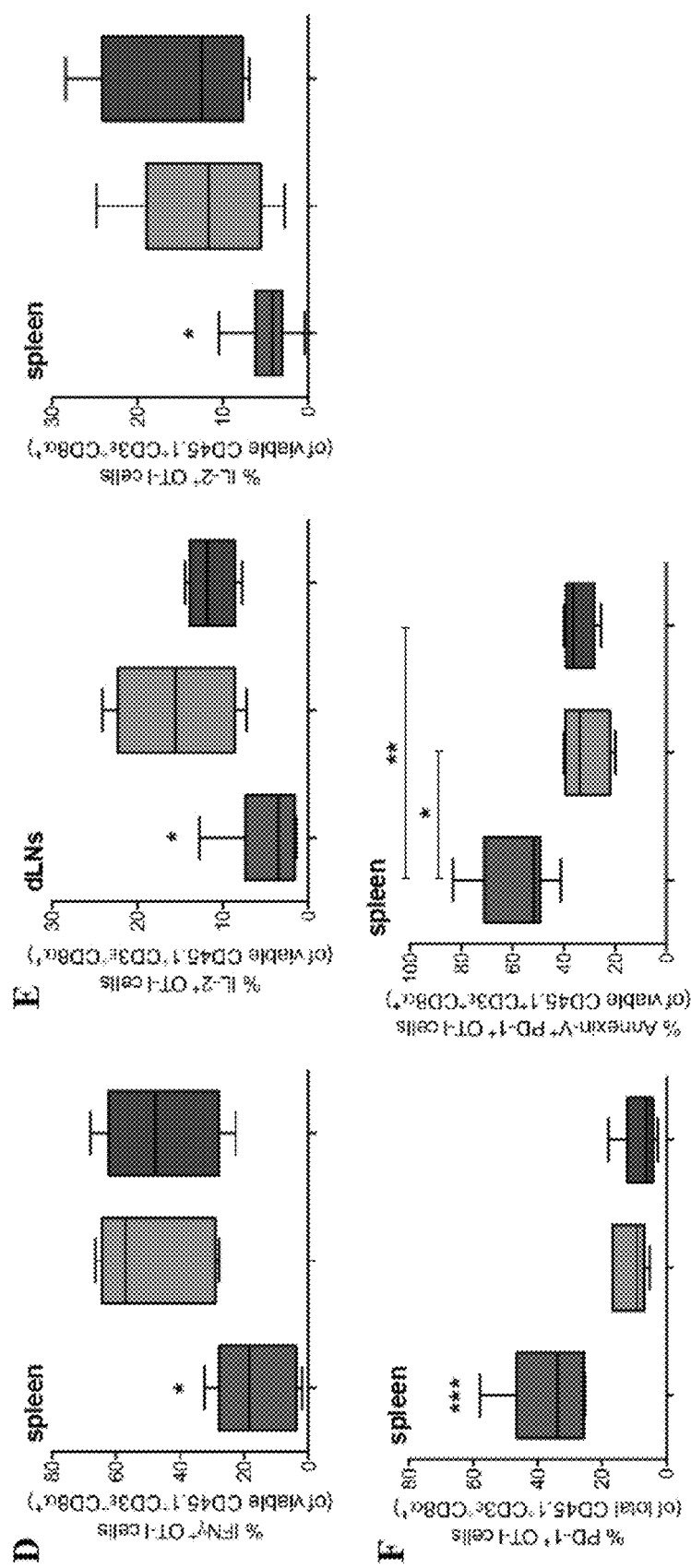
Fig. 11D-F

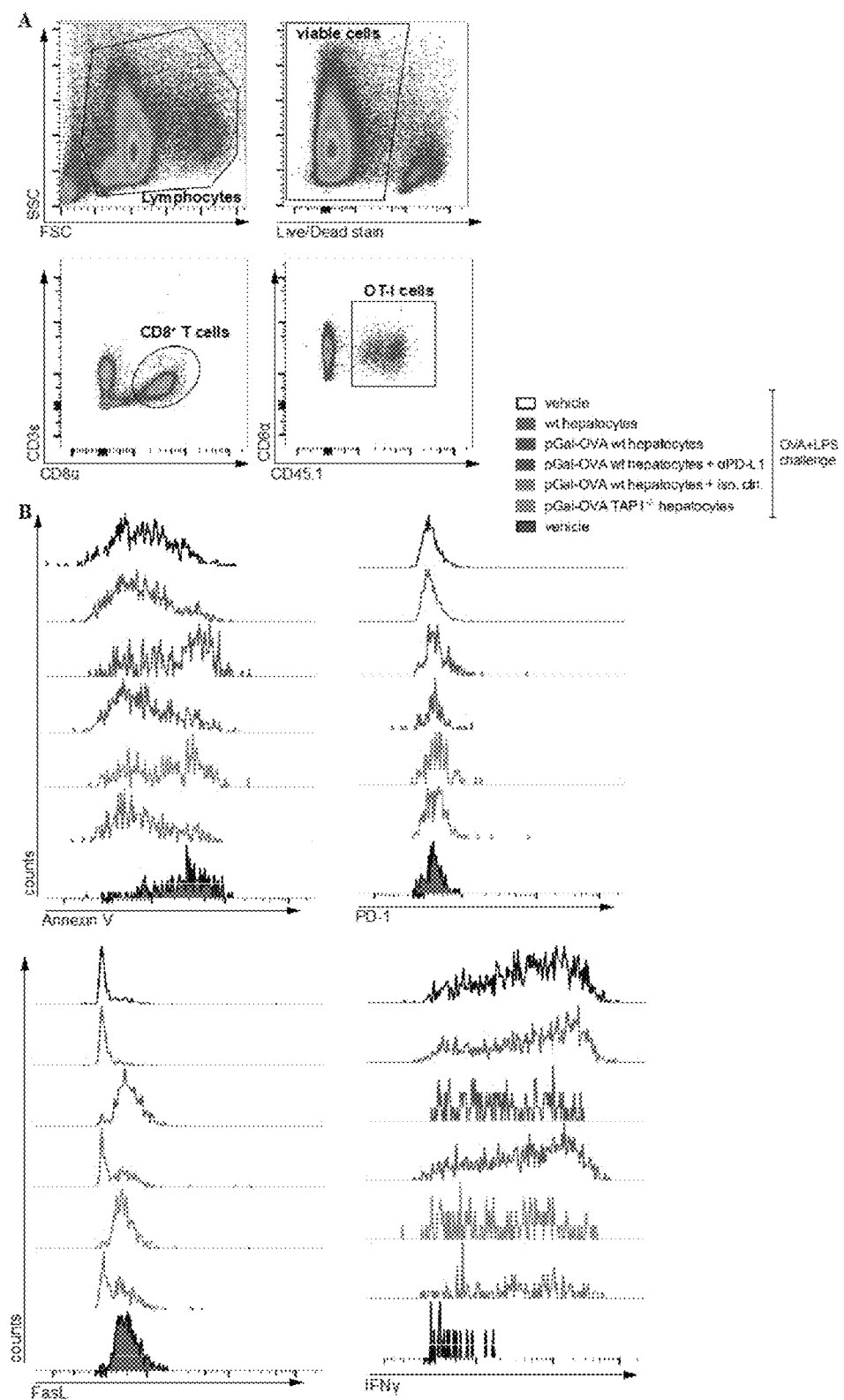
Fig. 12A-B

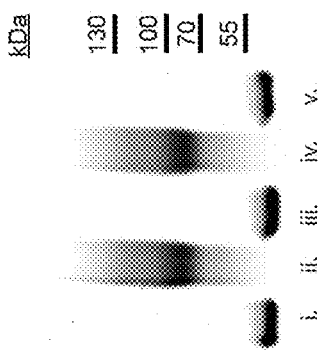
Fig. 13B
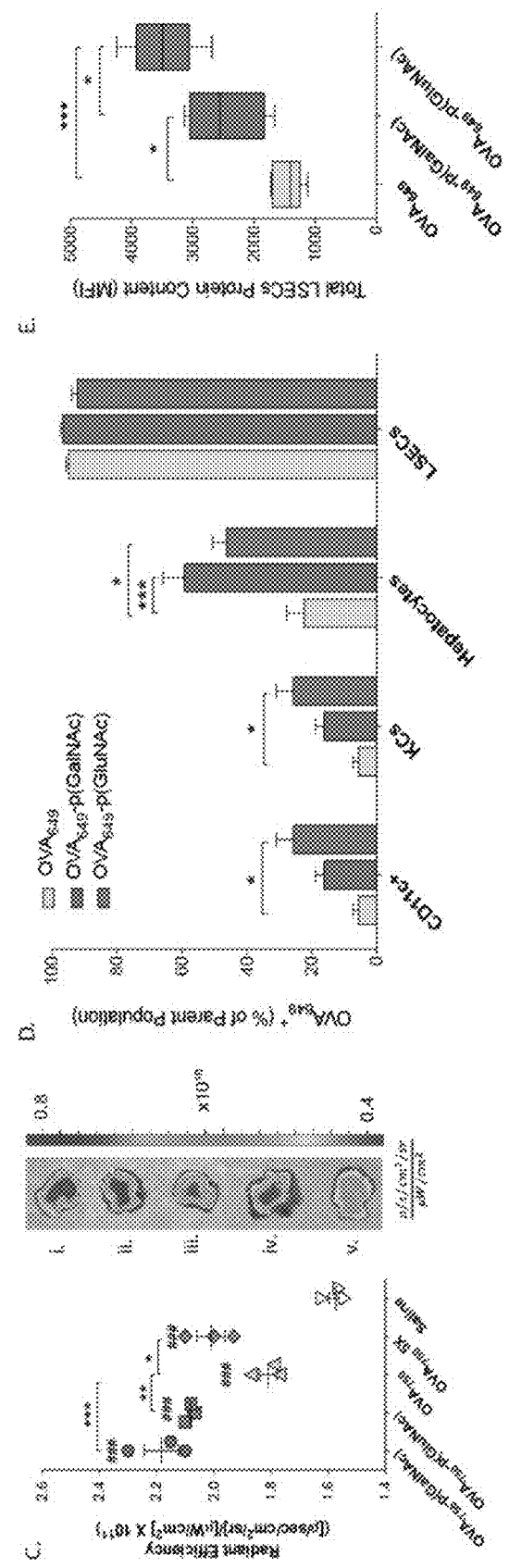
Fig. 13C-E

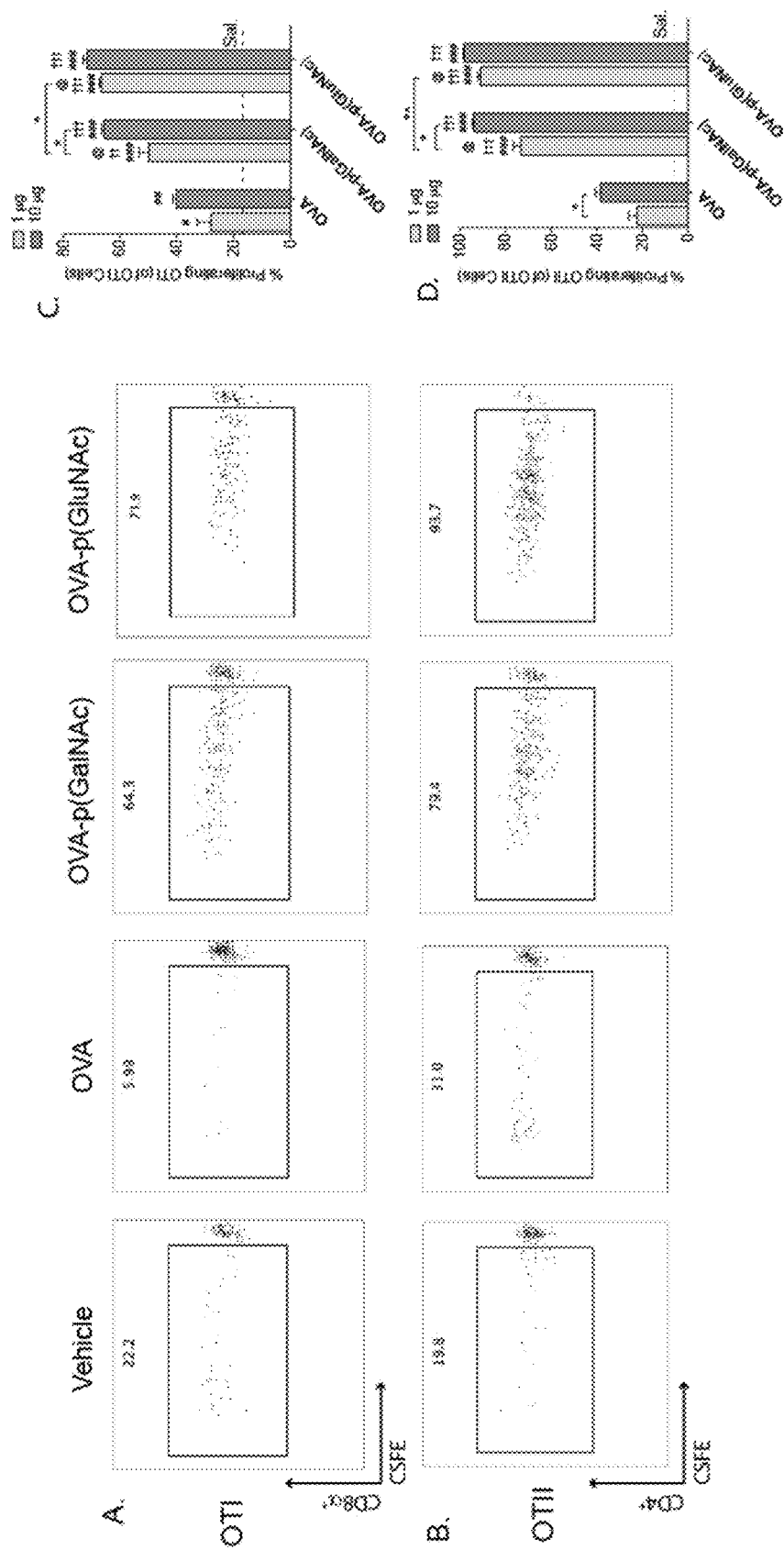
Fig. 14A-D

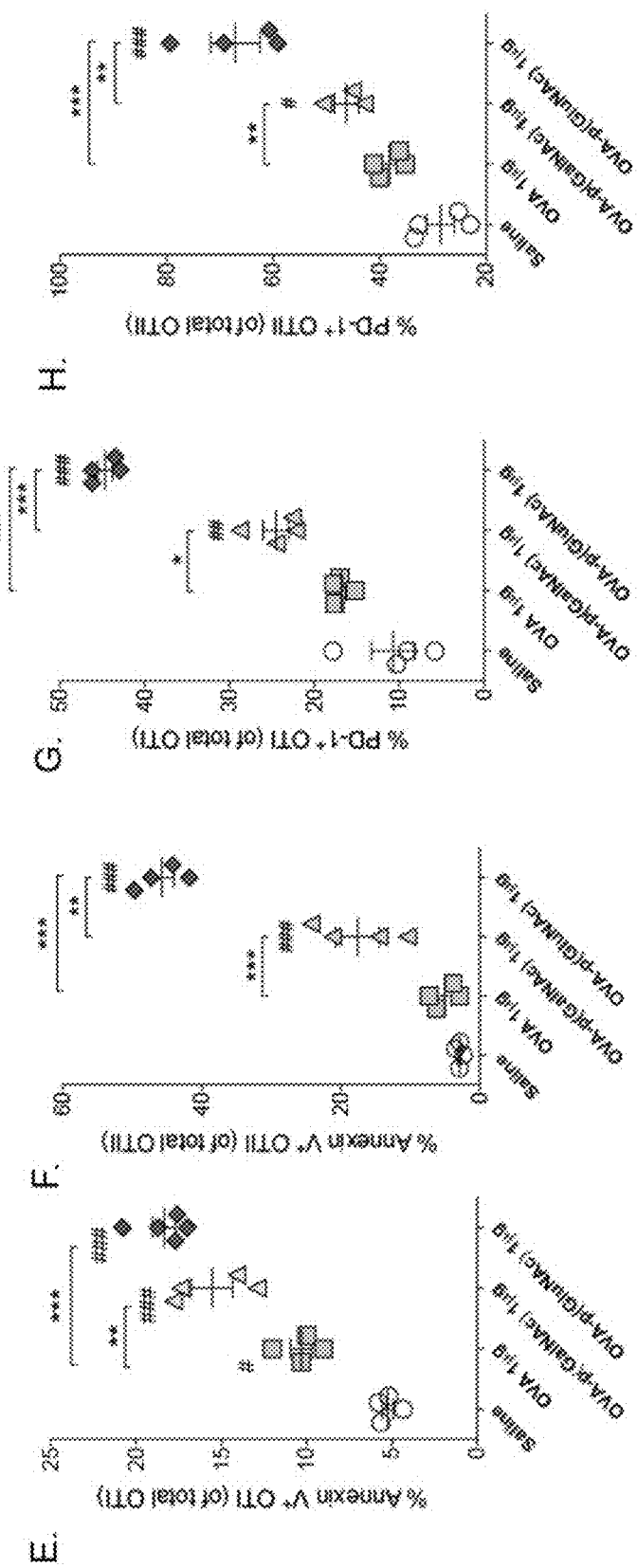
Fig. 14E-H

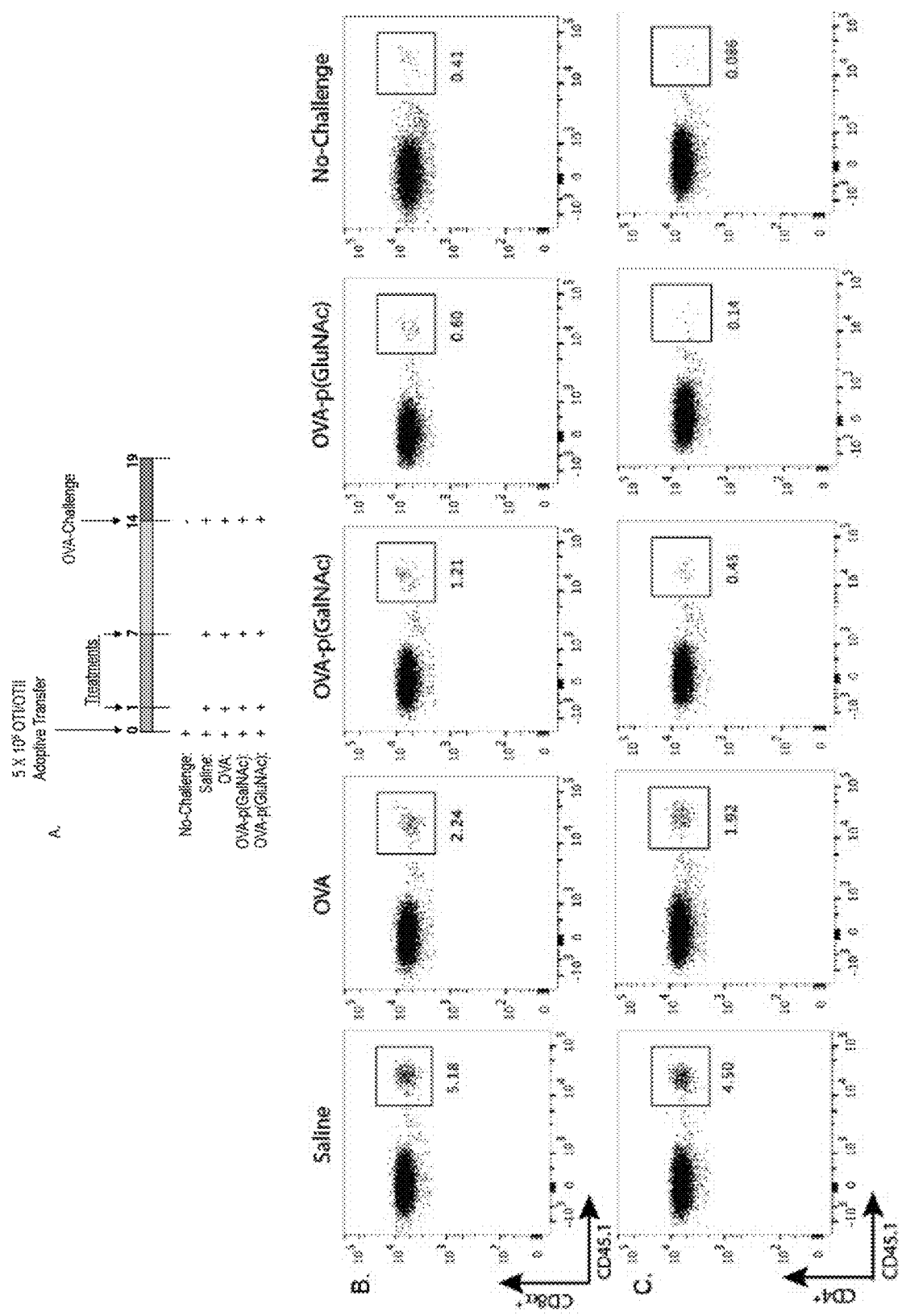
Fig. 15A-C

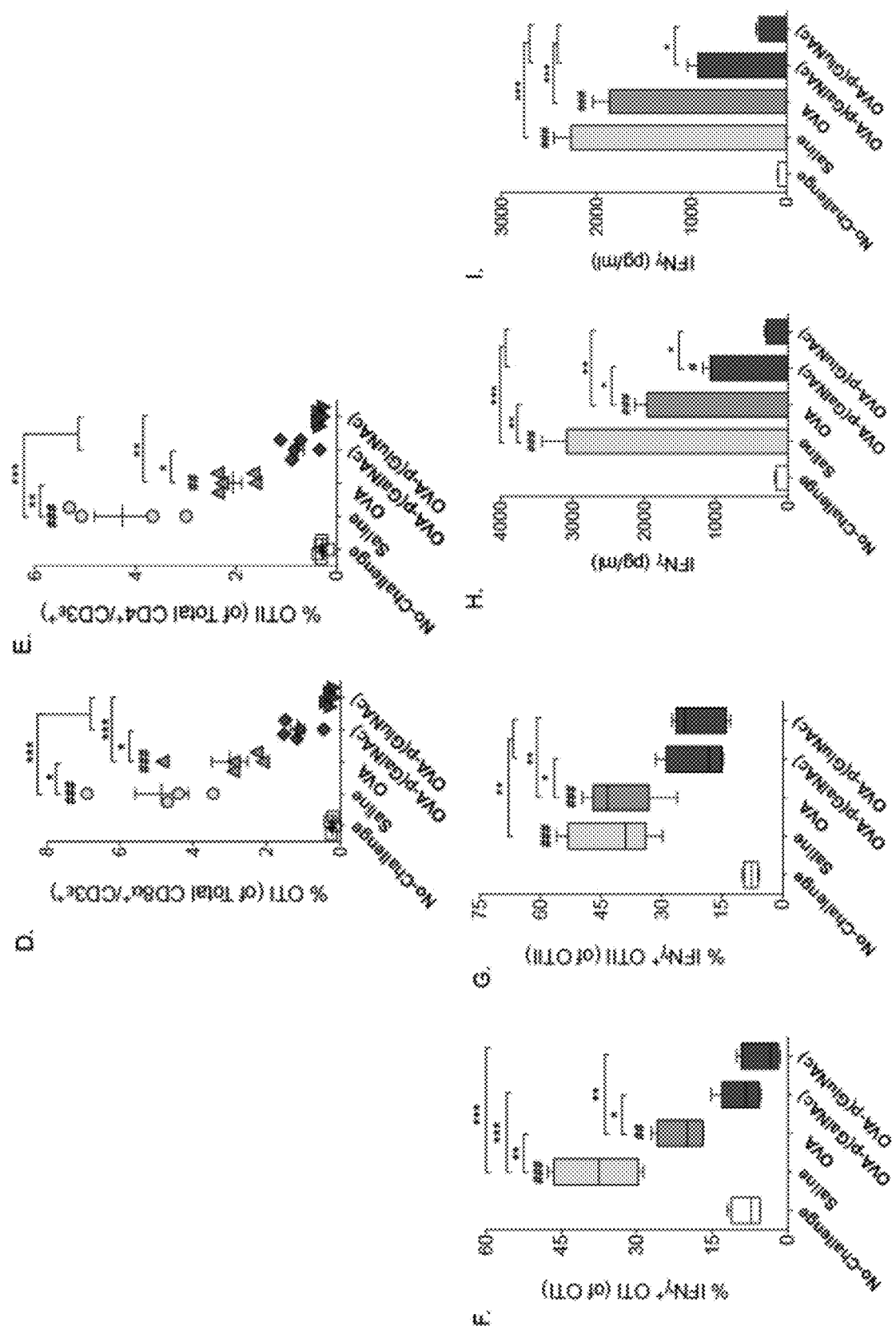
Fig. 15D-I

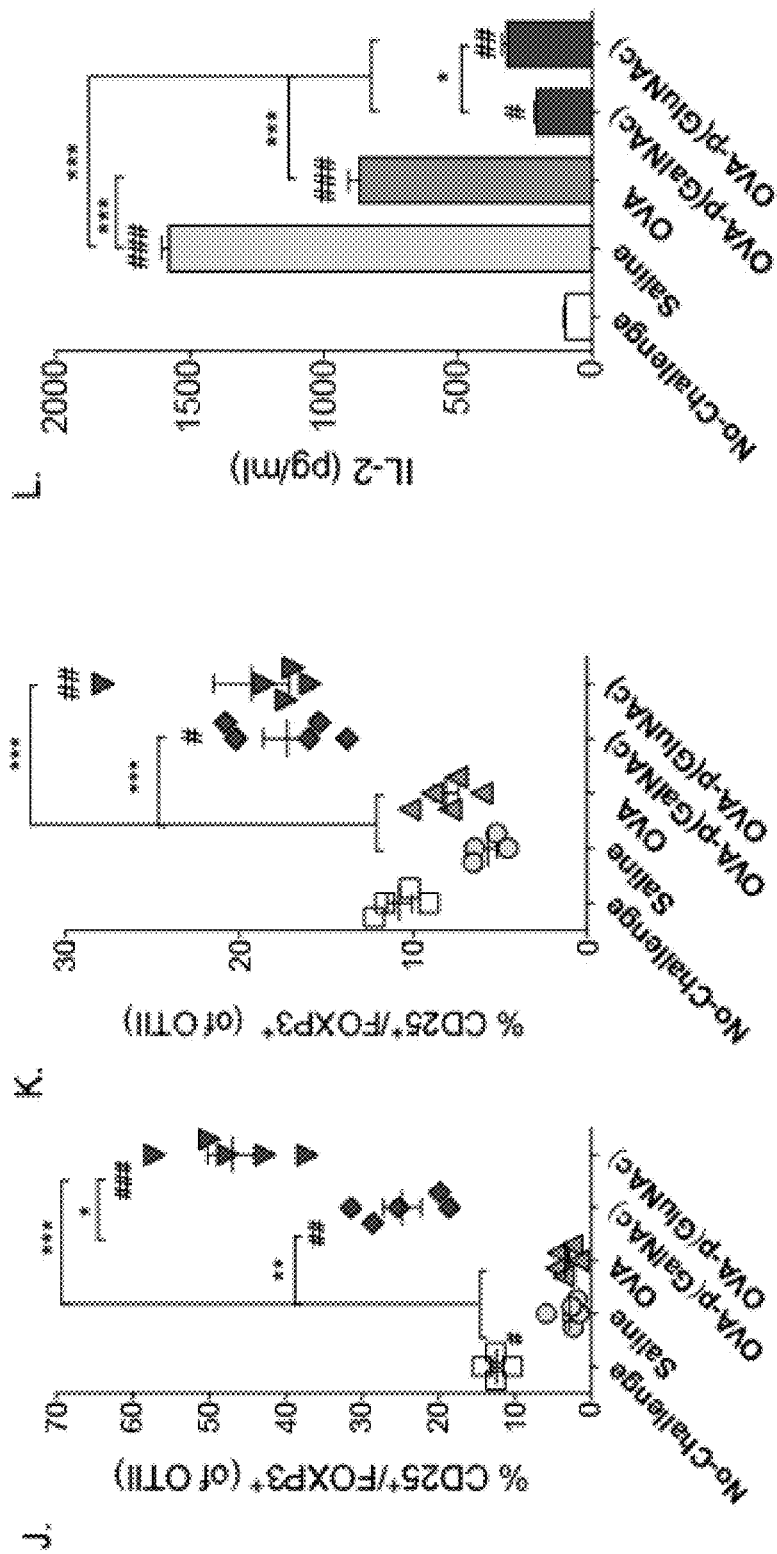
Fig. 15J-L

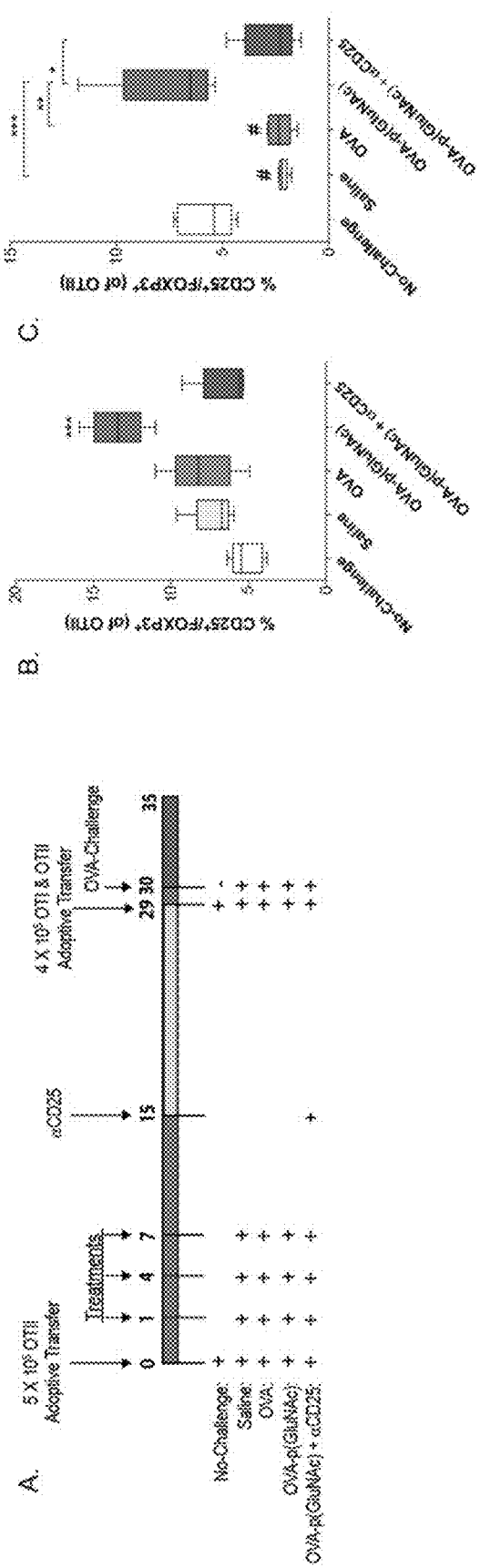
Fig. 16A-C

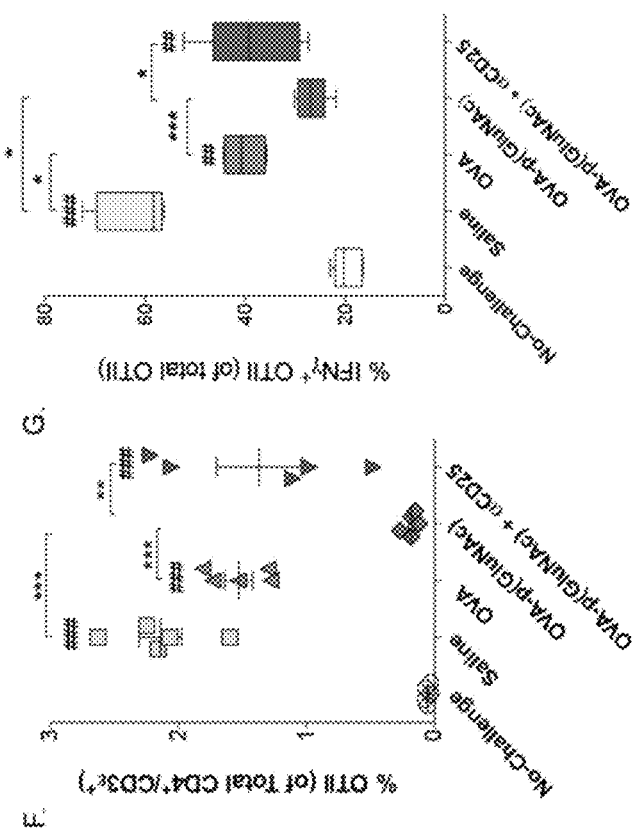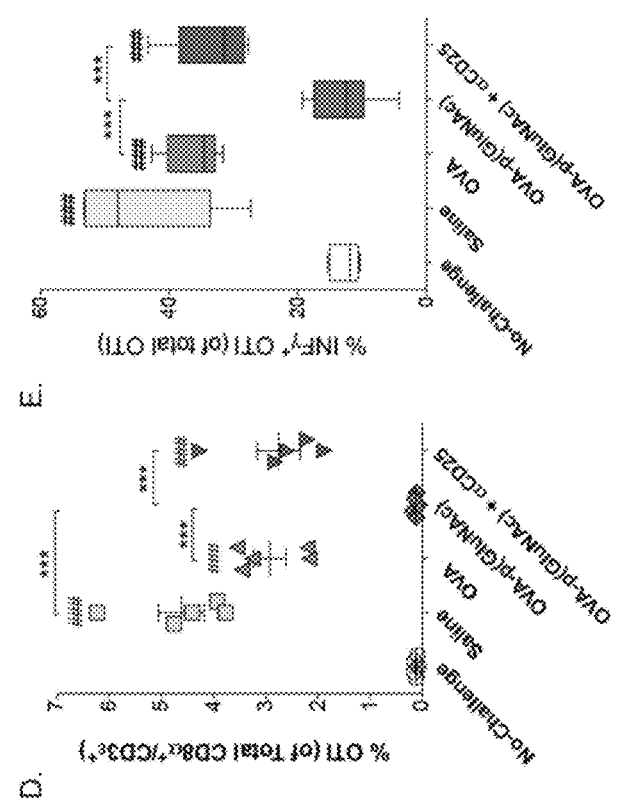
Fig. 16D-G

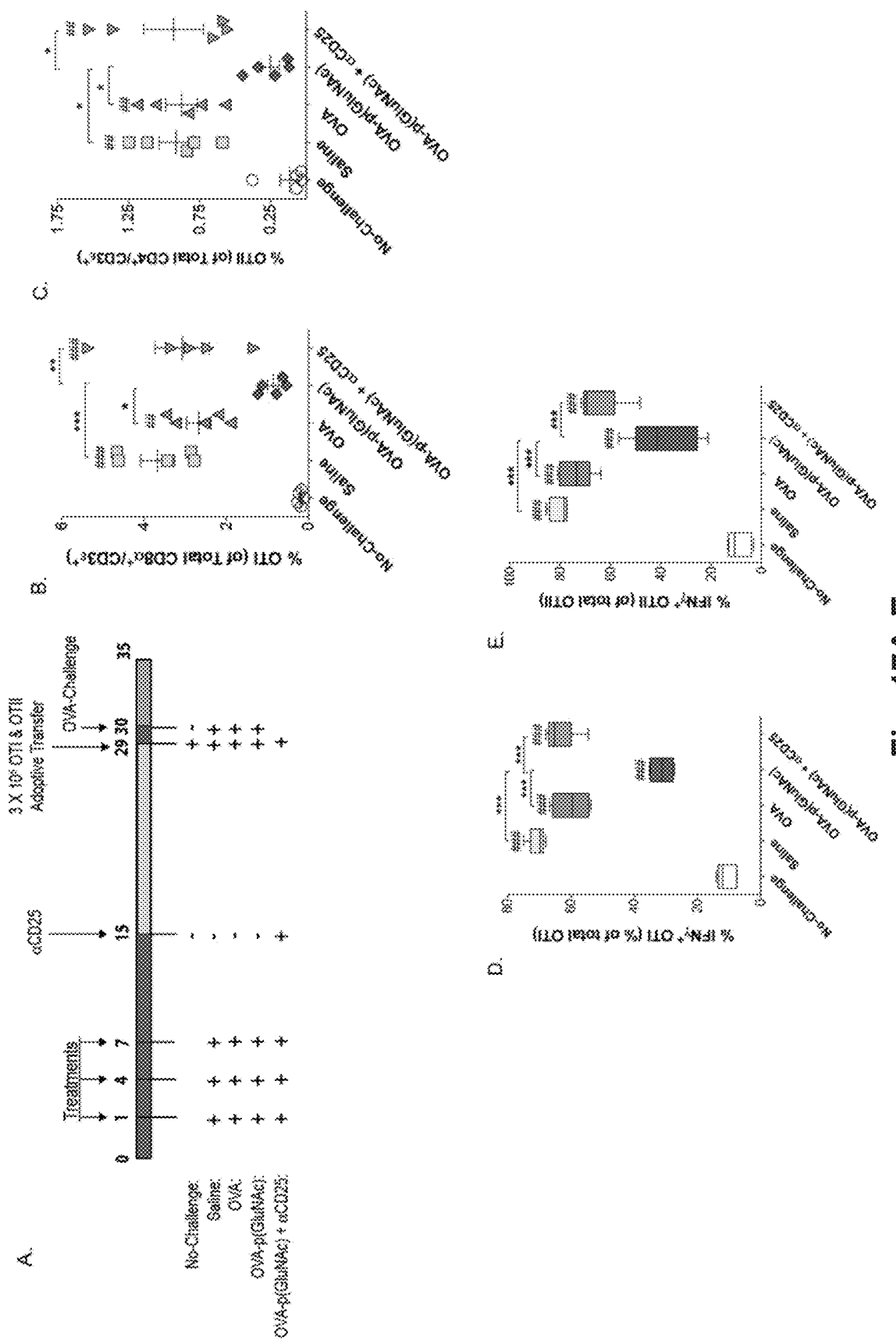
Fig. 17A-E

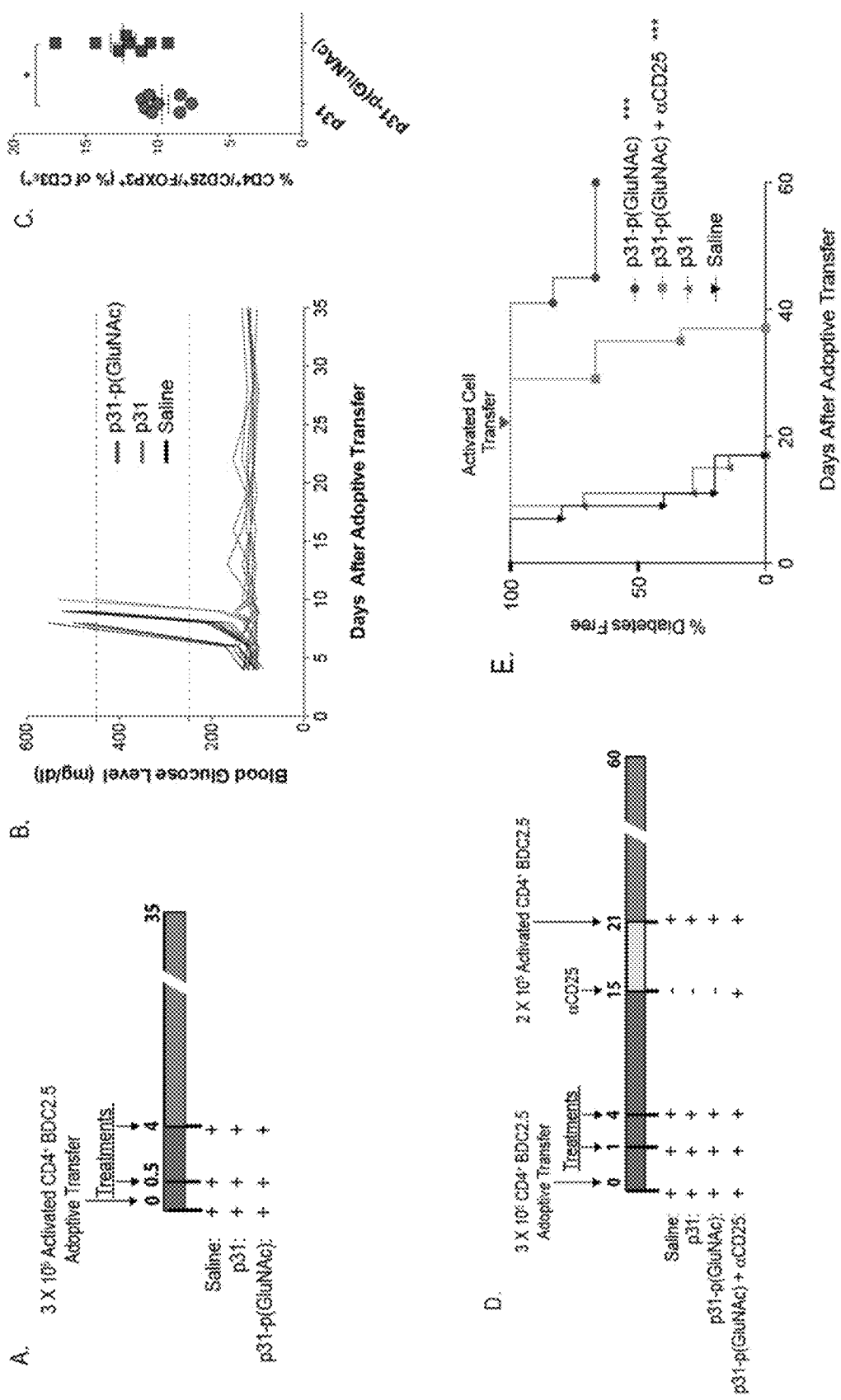
Fig. 18A-E

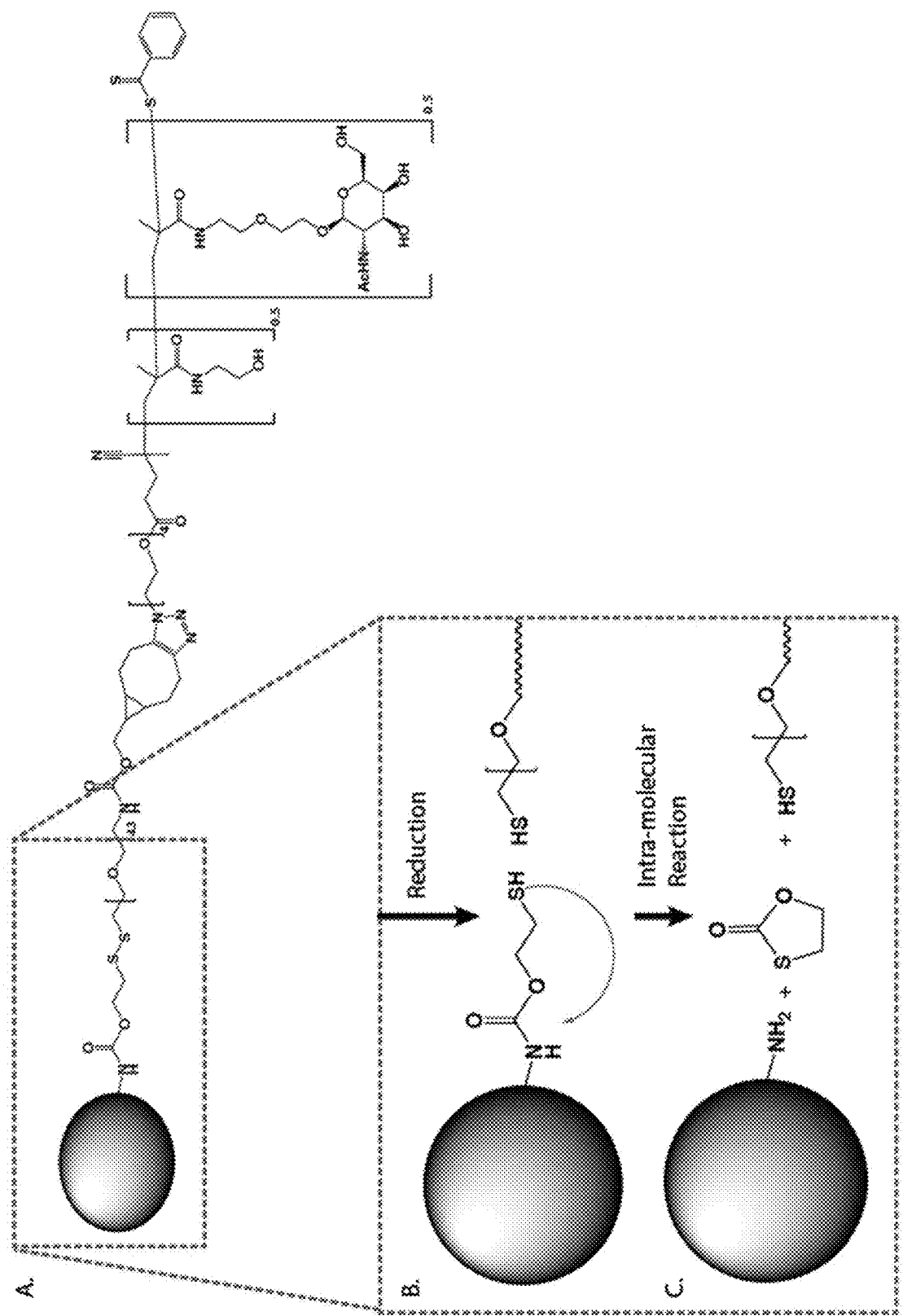
Fig. 19A-C

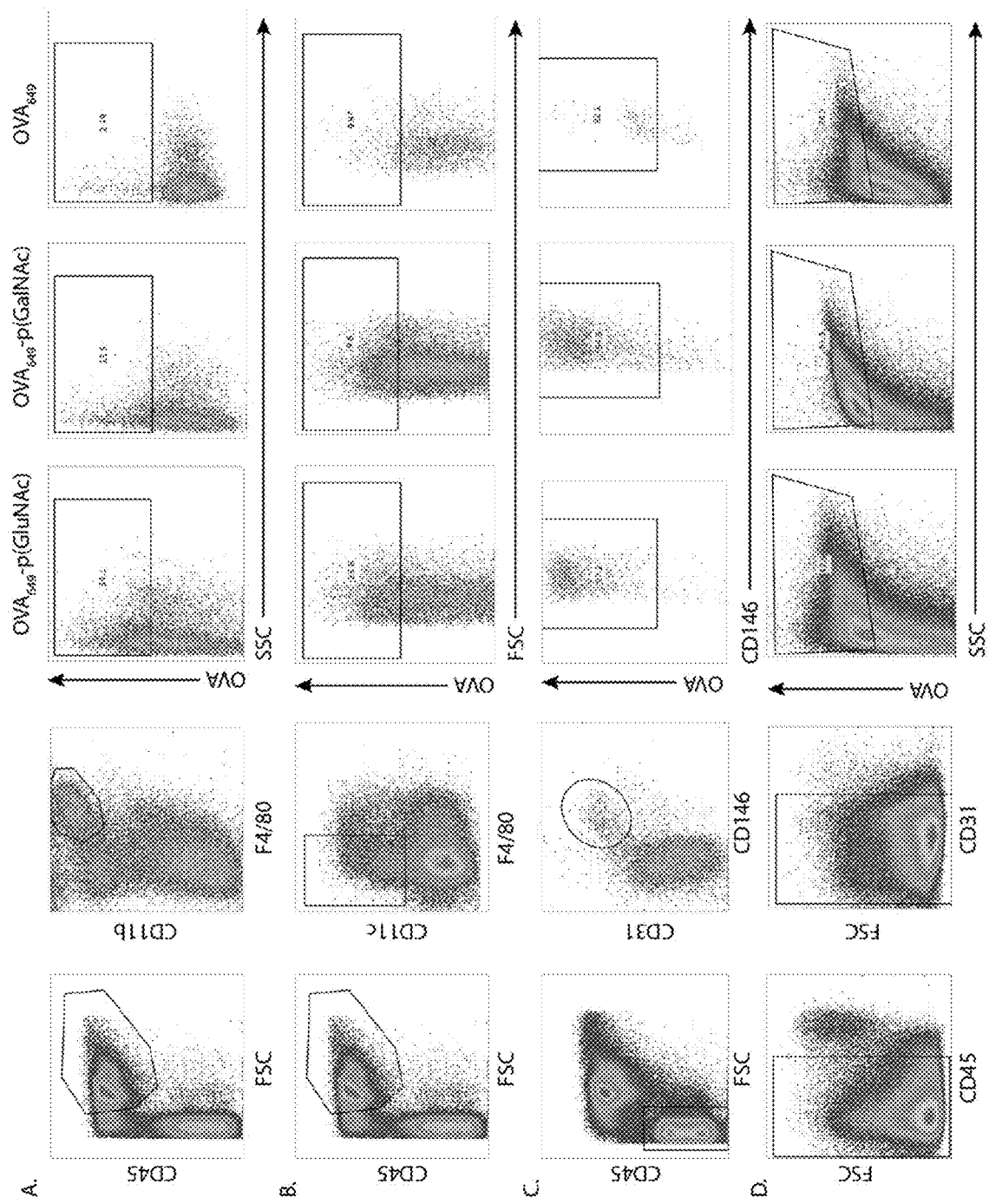
Fig. 20A-D

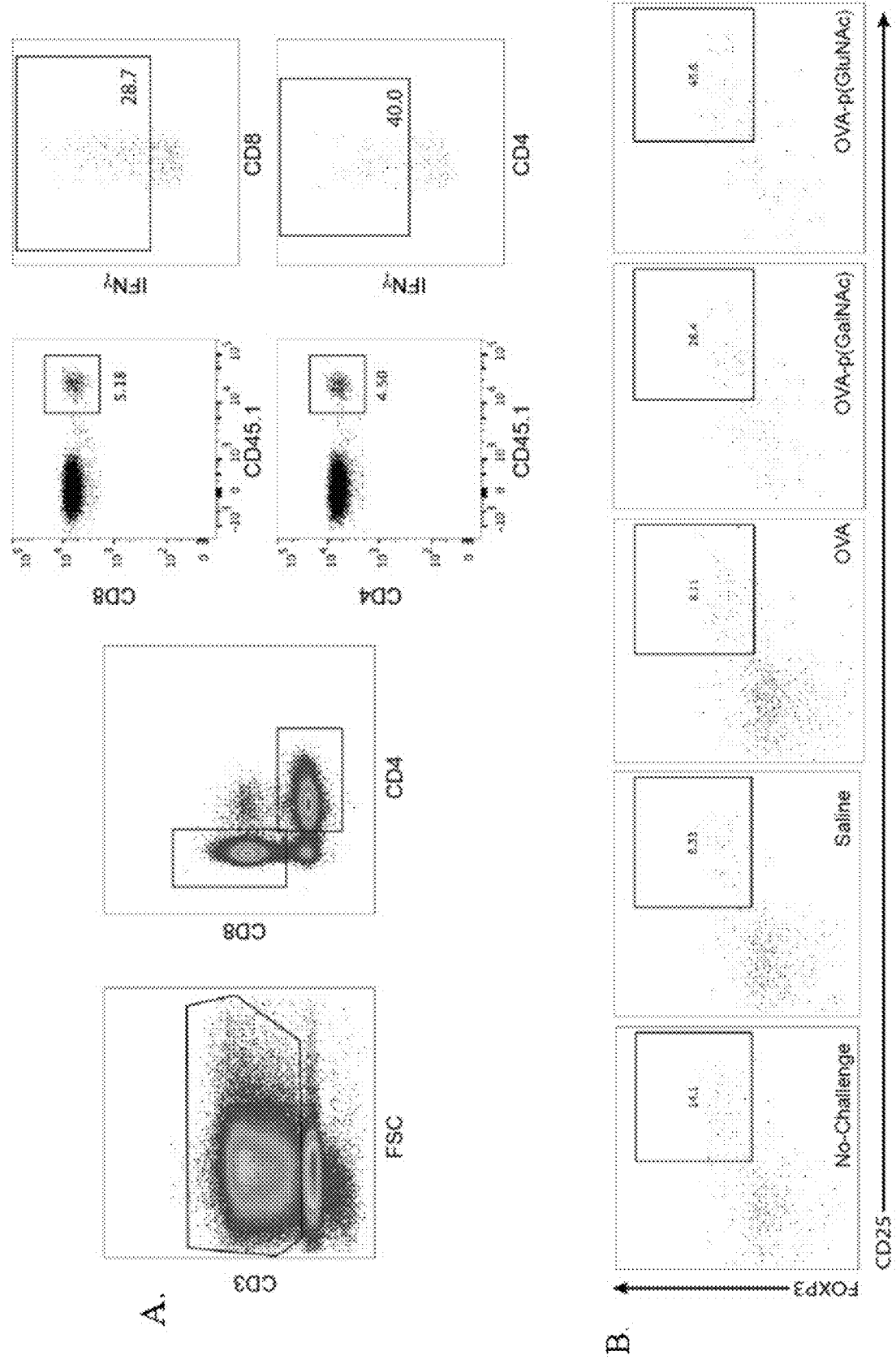
Fig. 22A-B

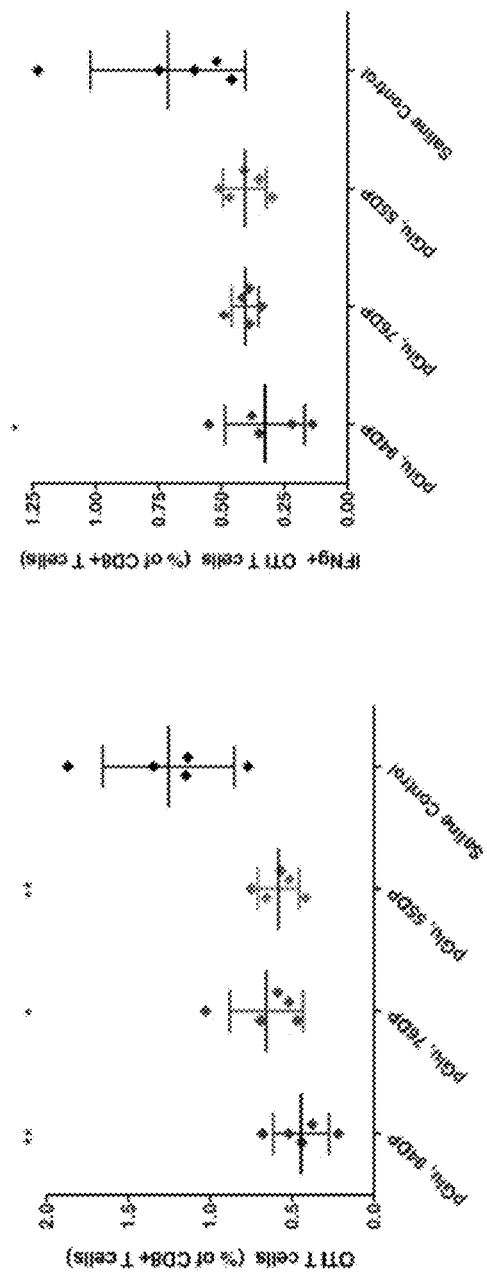
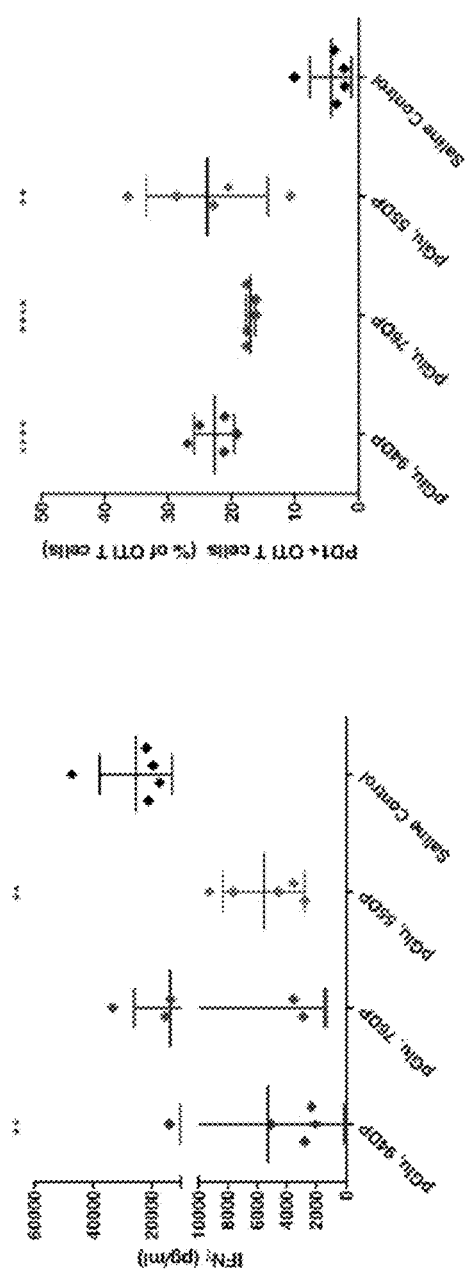
Fig. 32A
Fig. 32B
Fig. 32C
Fig. 32D

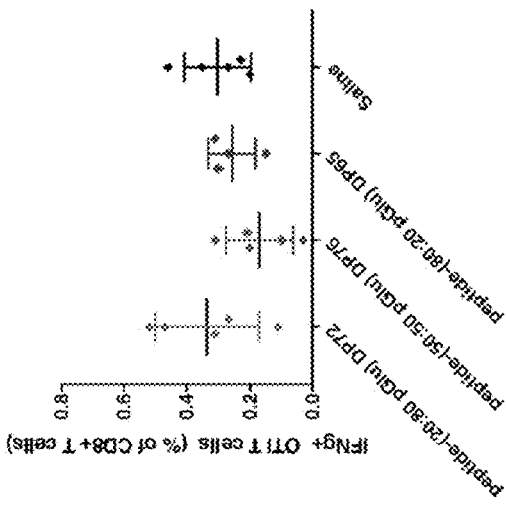
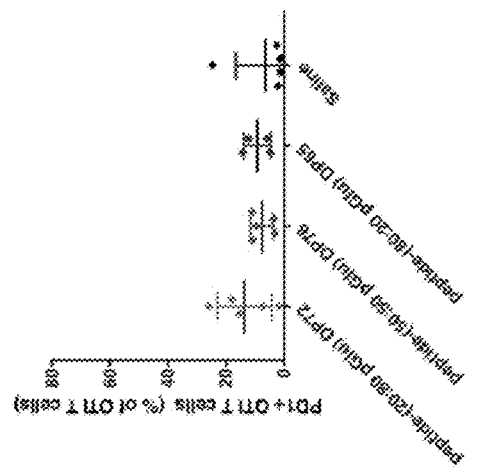
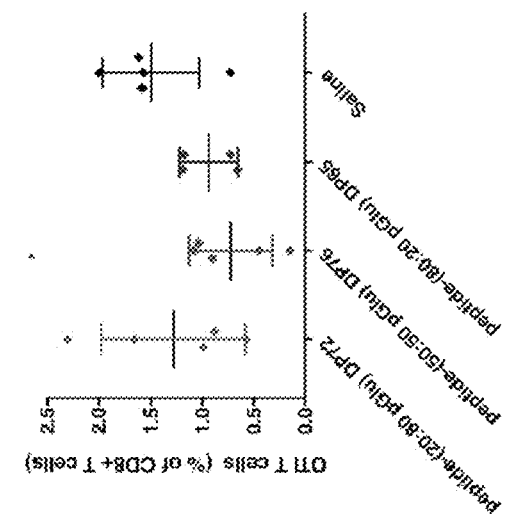
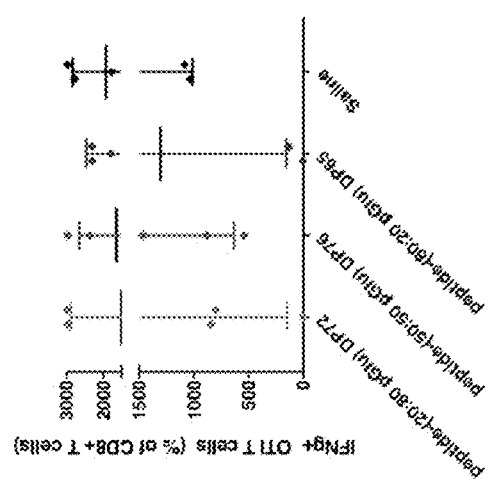

COMPOSITIONS AND METHODS FOR INDUCING IMMUNE TOLERANCE

CROSS REFERENCE TO RELATED APPLICATIONS

The present application is the United States National Phase under 35 U.S.C. § 371 of International Patent Application No. PCT/US2018/037631, filed on Jun. 14, 2018, which claims the benefit of priority to U.S. Provisional Patent Application No. 62/521,270, filed Jun. 16, 2017, the entirety of each of which is hereby incorporated by reference herein.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is ANOK019NP_ST25.TXT, the date of creation of the ASCII text file is Aug. 17, 2020, and the size of the ASCII text file is 86.4 KB.

BACKGROUND

Field

Several embodiments disclosed herein pertain generally to pharmaceutically acceptable compositions for use in inducing immune tolerance to specific antigens of interest, methods of generating such compositions, and methods/uses of same for induction of antigen specific tolerance.

Description of Related Art

The liver is involved in a variety of tolerogenic processes, for example development of tolerance to harmless non-self-antigens absorbed into the blood draining from the gut or to newly formed antigens resulting from hepatic metabolic activities, such antigens failing to induce an immune response in healthy individuals. Antigen-specific tolerance and cross-tolerance induction towards CD4+ and CD8+ T cells, respectively, has been attributed to liver sinusoidal endothelial cells (LSECs), which as MHC-I- and MHC-II-expressing blood vessel-lining cells represent the first cells to interact with peripheral lymphocytes entering the hepatic circulation. LSECs efficiently scavenge, process and present soluble antigens found in the bloodstream to circulating lymphocytes, typically resulting in the induction of CD4+ regulatory T cells or anergic CD8+ T cells.

SUMMARY

Some embodiments pertain to tolerogenic molecules and/or the use of tolerogenic molecules in methods of inducing immune tolerance in a patient. In some embodiments, the tolerogenic molecules comprise one or more antigens, fragments (e.g., immunogenic portions) thereof, mimotopes thereof, and the like. In some embodiments, the tolerogenic molecules comprise an antigen to which immune tolerance is desired. In some embodiments, the tolerogenic molecules comprise one or more liver targeting moieties. In some embodiments, the liver targeting moieties and antigens are bound to each other via a linking group. In several embodiments, the liver targeting moieties are covalently bound to the antigens to which tolerance is desired.

In several embodiments, the tolerogenic molecule comprises Formula 1:

Formula 1

In several embodiments, m is an integer from about 1 to 100. In several embodiments, X comprises an antigen, a mimetic thereof, a fragment thereof, or a tolerogenic portion thereof. In several embodiments, Y is of a linker moiety having a formula selected from the group consisting of:

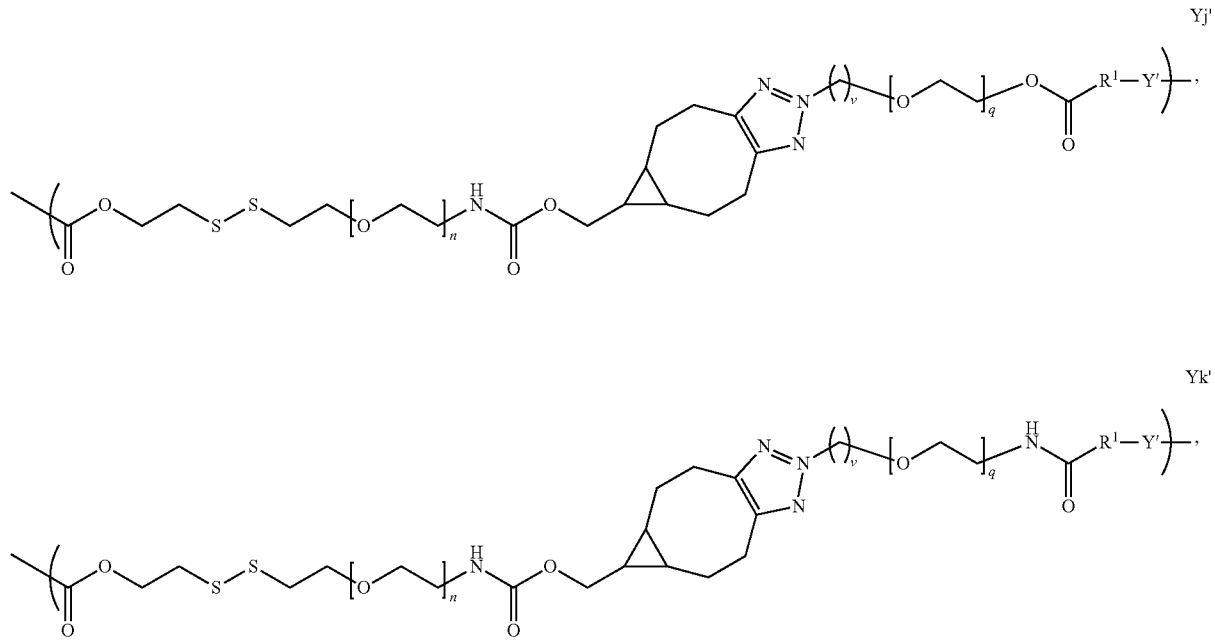

-continued
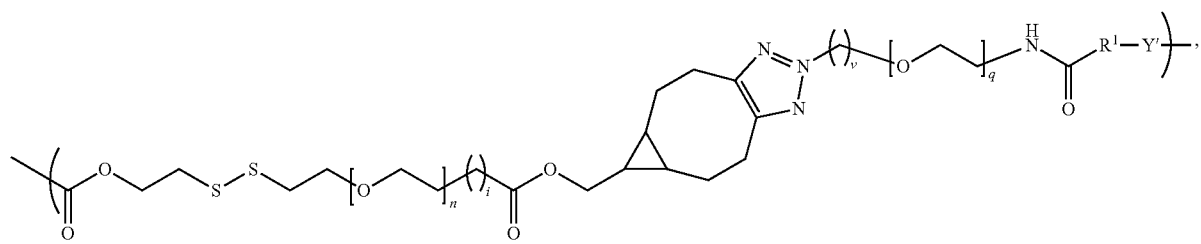
Yl'
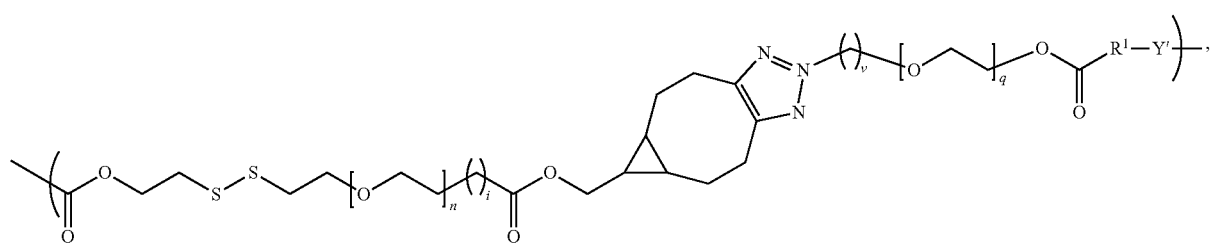
Ym'
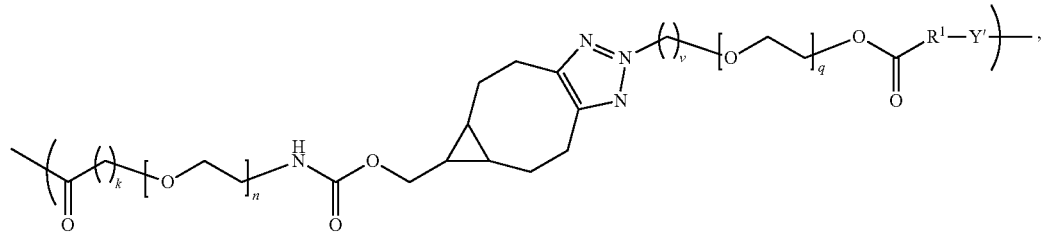
Yn'
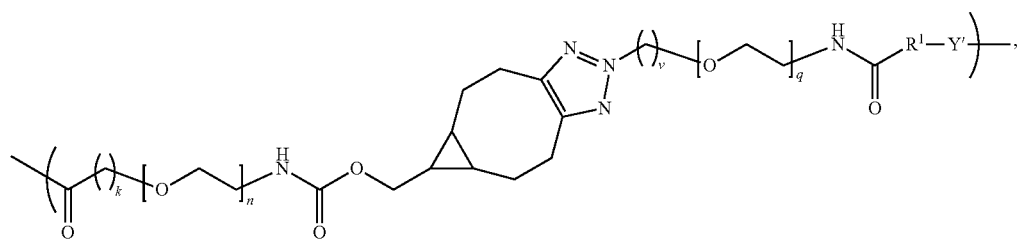
Yo'
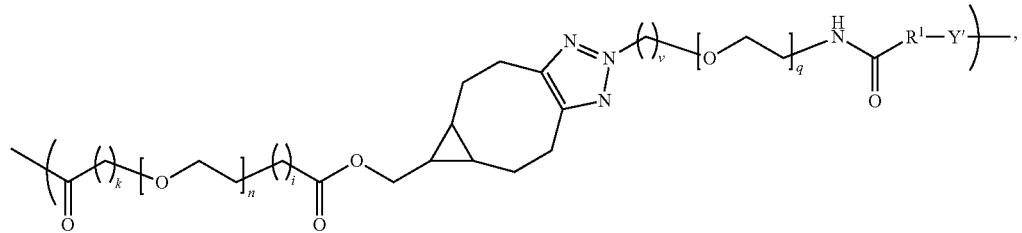
Yp'
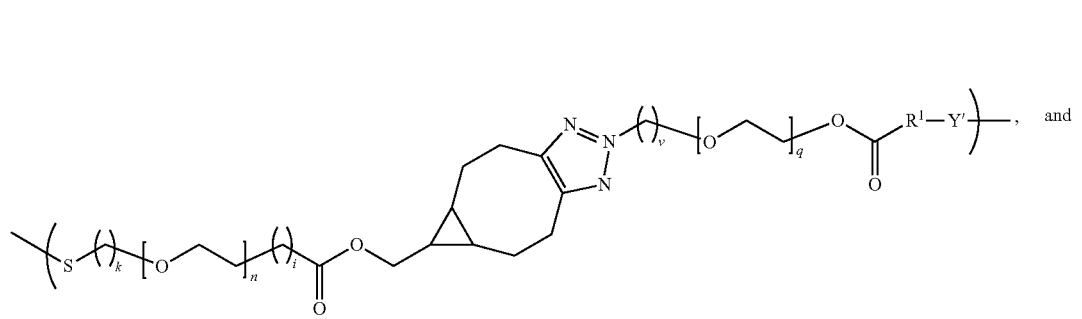
Yq', and

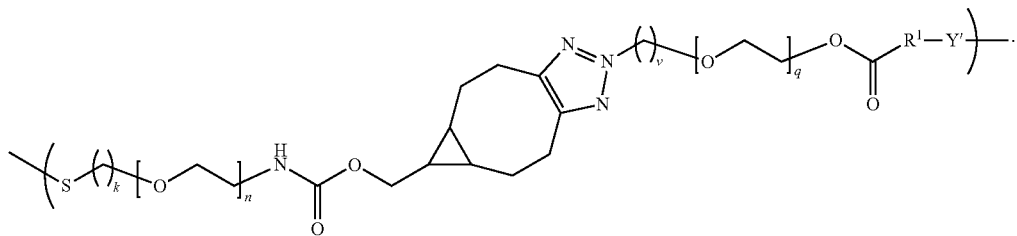

In several embodiments, n is an integer from about 1 to about 100. In several embodiments, q is an integer from about 1 to about 100. In several embodiments, k is an integer from about 1 to about 12. In several embodiments, i is an integer from about 0 to about 20. In several embodiments, v is an integer from about 1 to about 4.

In several embodiments, $R_1$ is selected from the group consisting of —$CH_2$—, —$(CH_2)_2$—$C(CH_3)(CN)$—, —$(CH_2)_2$—$C(CH_3)(CH_3)$—, —$(CH_2)_2$—$CH(CH_3)$—, and —$CH(CH_3)$—. In several embodiments, Y' is a random copolymer or block copolymer of $W^1$ and $W^2$. In several embodiments, $W^1$ and $W^2$ are as depicted below:

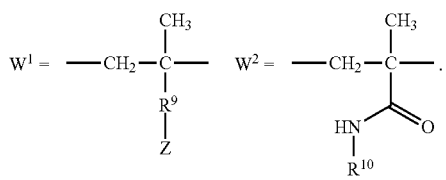

In several embodiments, the number of repeat units of $W^1$ is denoted as p and wherein p is an integer of at least about 1. In several embodiments, the number of repeat units of $W^2$ is denoted as r and wherein r is an integer of at least about 1. In several embodiments, $R^9$ is a direct bond, —C(O)—NH—$(CH_2)_2$—, or —C(O)—NH—$(CH_2)_2$—O—$CH_2$—$CH_2)_t$—.

In several embodiments, t is an integer from 1 to 5. In several embodiments, $R^2$ is selected from the group consisting of:

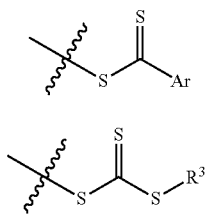

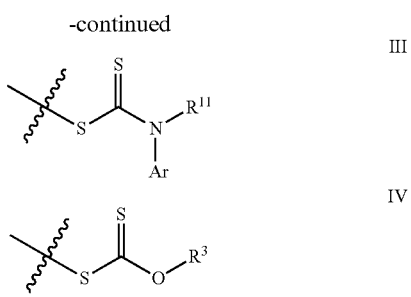

In several embodiments, Ar is a substituted or unsubstituted aromatic group. In several embodiments, $R^3$ is any carbon-containing linear or heterocyclic moiety (e.g., optionally substituted alkyl, optionally substituted heterocyclyl, optionally substituted aryl, optionally substituted heteroaryl, etc.), and $R^{11}$ is hydrogen or an optionally substituted alkyl.

In several embodiments, Z comprises a liver-targeting moiety. In several embodiments, Z is galactose, glucose, galactosamine, glucosamine, N-acetylgalactosamine, or N-acetylglucosamine. In several embodiments, Z is conjugated at its C1, C2 or C6 to Y.

In several embodiments, the ratio of p to r is about 1:1. In several embodiments, the ratio of p to r is about 4:1.

In several embodiments, Y is:

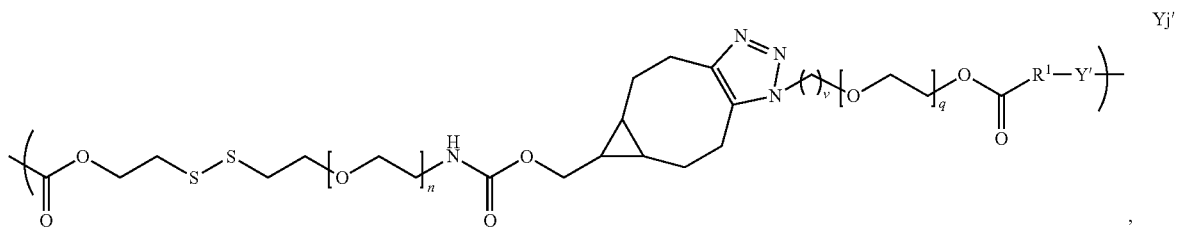

In several embodiments, n is 43 or 44. In several embodiments, v is 2. In several embodiments, q is 3. In several embodiments, $R^1$ is —$(CH_2)_2$—$C(CH_3)(CN)$—. In several embodiments, Z is one or more of galactose, glucose, galactosamine, glucosamine, N-acetylgalactosamine, or N-acetylglucosamine. In several embodiments, Z is N-acetylgalactosamine or N-acetylglucosamine.

In several embodiments, Y is prepared using N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol) ester linkers.

In several embodiments, X induces an unwanted immune response in a subject.

In several embodiments, X is associated with an autoimmune disease. In several embodiments, the autoimmune disease is selected from the group consisting of Type I diabetes, multiple sclerosis, rheumatoid arthritis, vitiligo, uveitis, pemphis vulgaris, neuromyelitis optica, and Parkinson's disease.

In several embodiments, X comprises a self antigen. In several embodiments, the self antigen is selected from insulin, proinsulin, preproinsulin, glutamic acid decarboxylase-65 (GAD-65), GAD-67, insulinomaassociated protein 2 (IA-2), and insulinoma-associated protein 213 (IA-213), ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestinepancreas/pancreatic associated protein, S1000, glial fibrillary acidic protein, regenerating gene II, pancreatic duodenal homeobox 1, dystrophia myotonica kinase, islet-specific glucose-6-phosphatase catalytic subunit-related protein, SST G-protein coupled receptors 1-5, and a portion of any of said antigens, and a mimetic of any of said antigens. In several embodiments, the self antigen is selected from myelin basic protein, myelin oligodendrocyte glycoprotein and proteolipid protein, a portion of any of said antigens, and a mimetic of any of said antigens.

In several embodiments, X comprises a food antigen. In several embodiments, the food antigen is selected from the group consisting of conarachin (Ara h 1), allergen II (Ara h 2), arachis agglutinin, conglutin (Ara h 6), 31 kda major allergen/disease resistance protein homolog (Mal d 2), lipid transfer protein precursor (Mal d 3), major allergen Mal d 1.03D (Mal d 1), a-lactalbumin (ALA), lactotransferrin, actinidin (Act c 1, Act d 1), phytocystatin, thaumatin-like protein (Act d 2), kiwellin (Act d 5), ovomucoid, ovalbumin, ovotransferrin, and lysozyme, livetin, apovitillin, vosvetin, 2S albumin (Sin a 1), 1 lS globulin (Sin a 2), lipid transfer protein (Sin a 3), profilin (Sin a 4), profilin (Api g 4), high molecular weight glycoprotein (Api g 5), Pen a 1 allergen (Pen a 1), allergen Pen m 2 (Pen m 2), tropomyosin fast isoform, high molecular weight glutenin, low molecular weight glutenin, alpha-, gamma- and omega-gliadin, hordein, secalin, avenin, major strawberry allergy Fra a 1-E (Fra a 1), profilin (Mus xp 1), a portion of any of said antigens, and a mimetic of any of said antigens. In several embodiments, the food antigen is selected from the group consisting of high molecular weight glutenin, low molecular weight glutenin, alpha-, gamma- and omega-gliadin, hordein, secalin, avenin, a portion of any of said antigens, and a mimetic of any of said antigens.

In several embodiments, X comprises a therapeutic agent. In several embodiments, the therapeutic agent is selected from Abciximab, Adalimumab, Agalsidase alfa, Agalsidase beta, Aldeslukin, Alglucosidase alfa, Factor VIII, Factor IX, Infliximab, L-asparaginase, Laronidase, Natalizumab, Octreotide, Phenylalanine ammonia-lyase (PAL), or Rasburicase (uricase), a portion of any of said antigens, and a mimetic of any of said antigens.

In several embodiments, X comprises a transplant antigen. In several embodiments, the transplant antigen is selected from the group consisting of subunits of the MHC class I and MHC class II haplotype proteins, and minor blood group antigens RhCE, Kell, Kidd, Duffy and Ss.

In several embodiments, Y is of a linker moiety having a formula selected from the group consisting of:

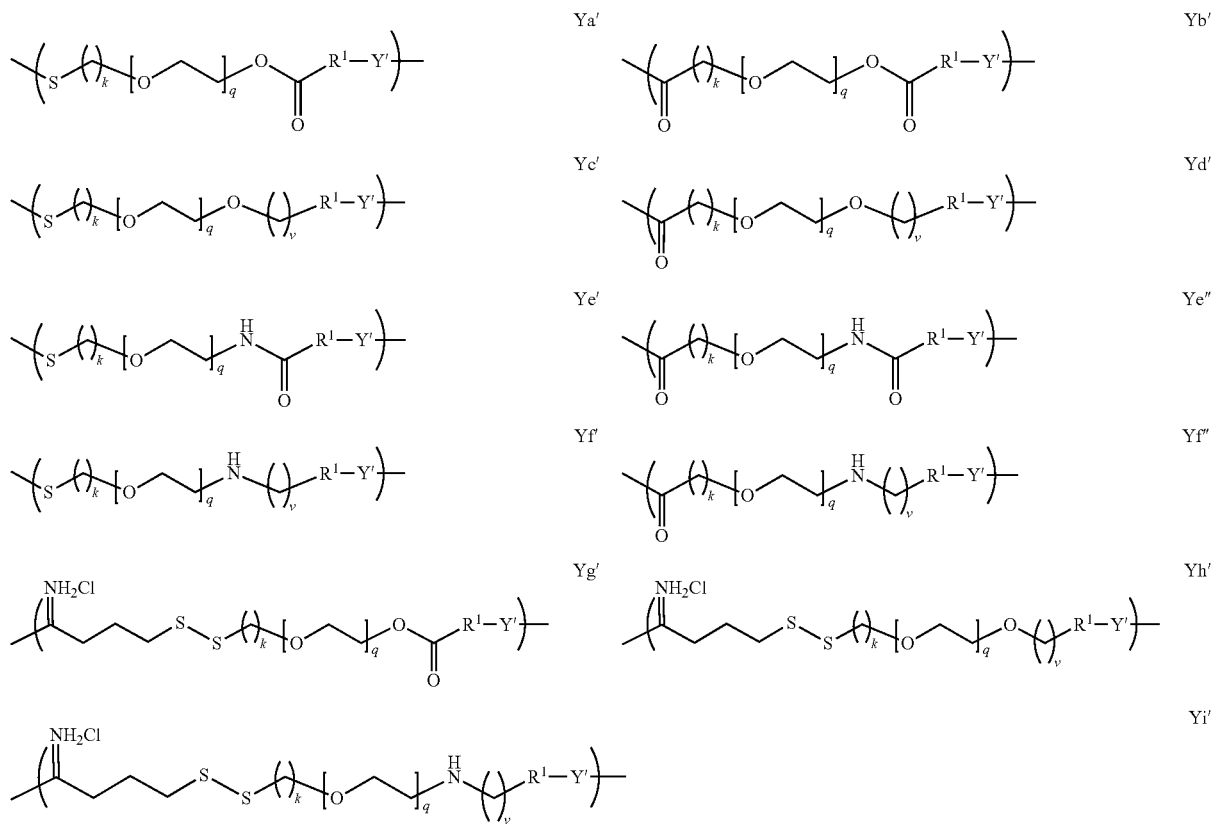

-continued
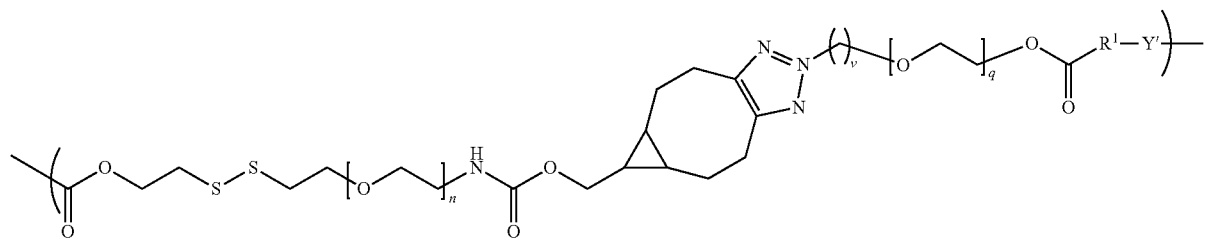
Yj′
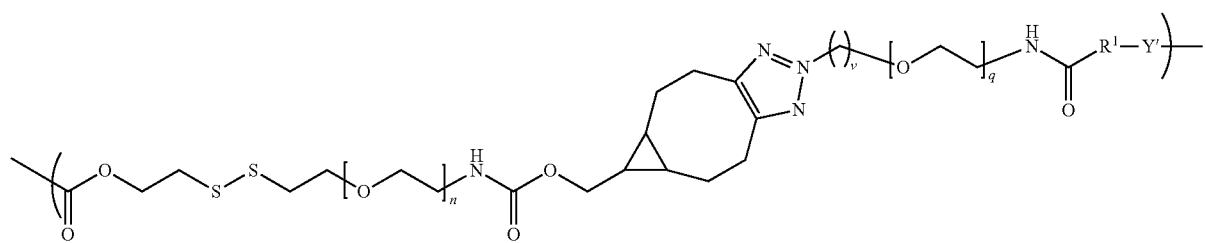
Yk′
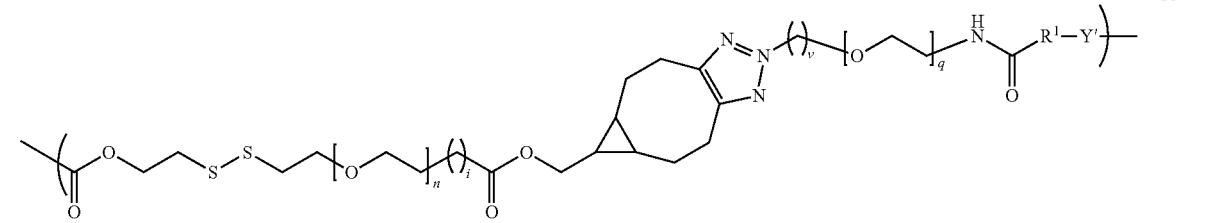
Yl′
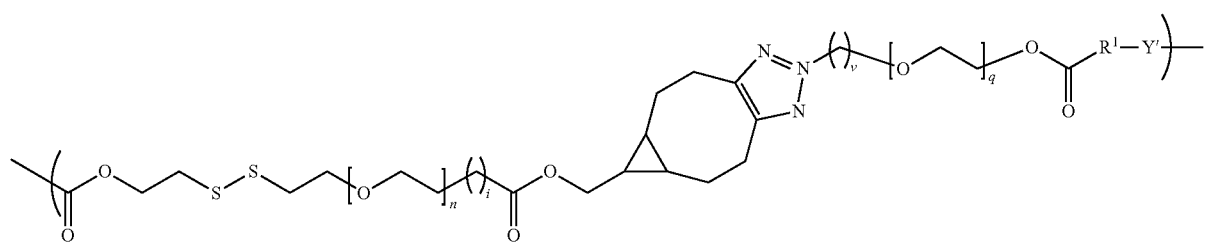
Ym′
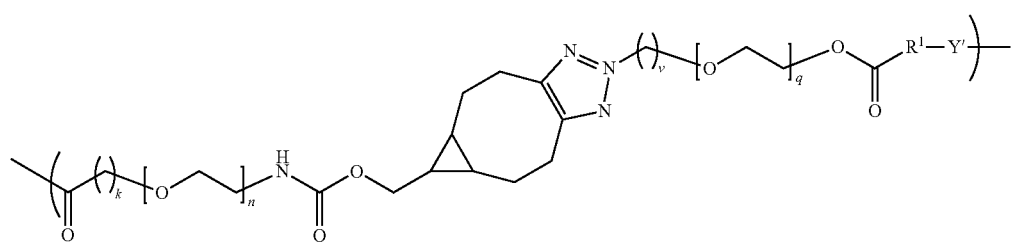
Yn′
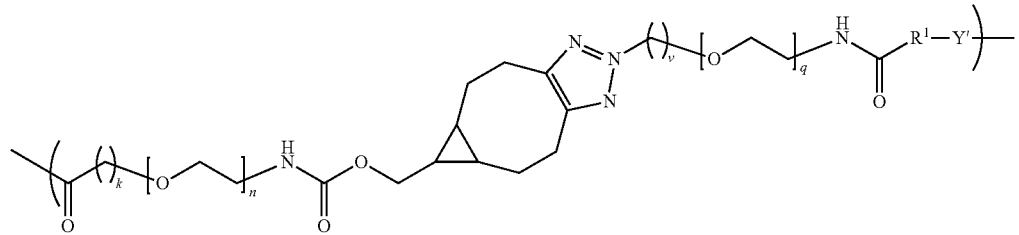
Yo′

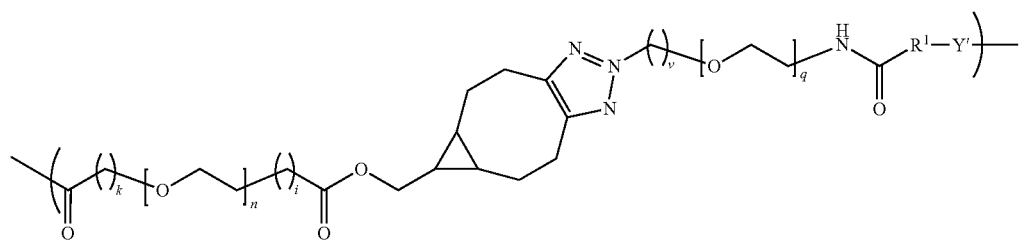
Yp'
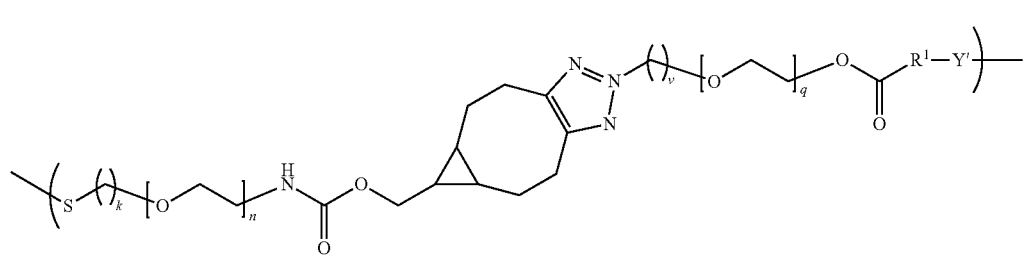
Yq'
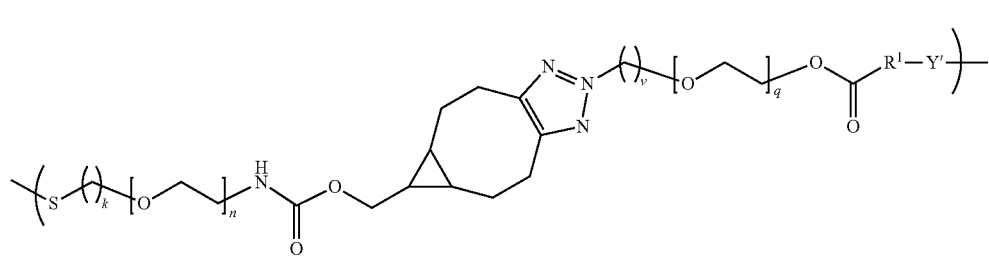
Yr'
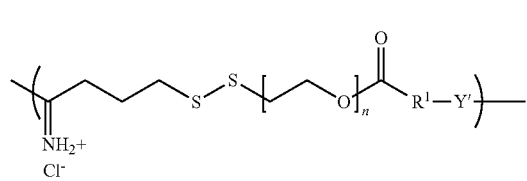
Yb1
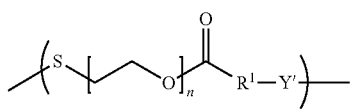
Yc1
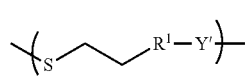
Yd1
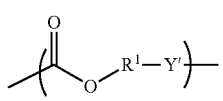
Ye1
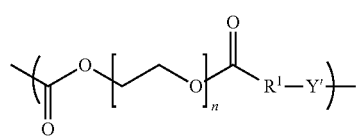
Yf1
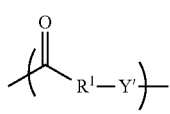
Yg1
Yh1
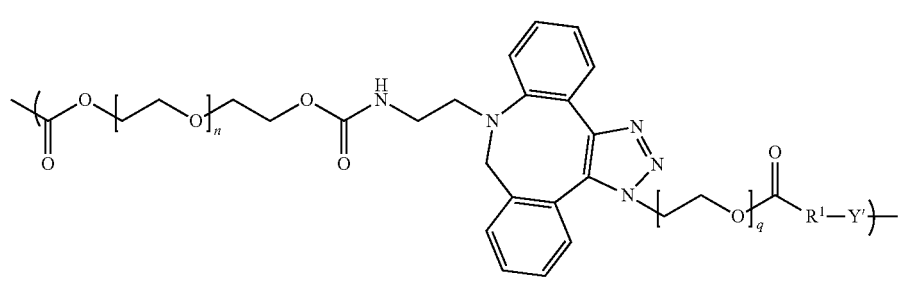

-continued
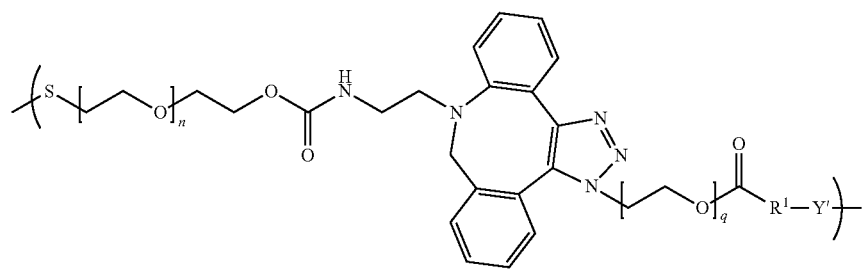
Yi1
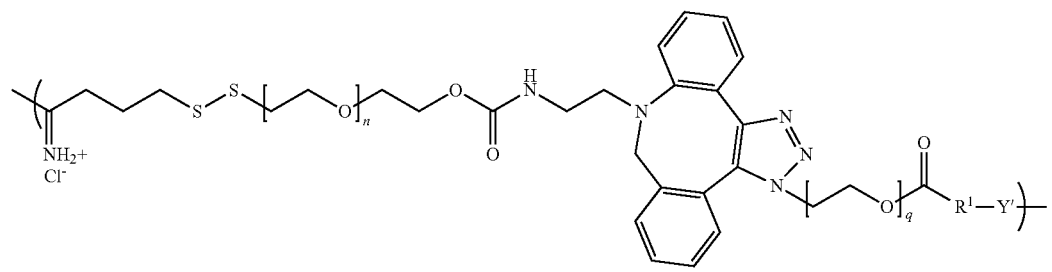
Yj1
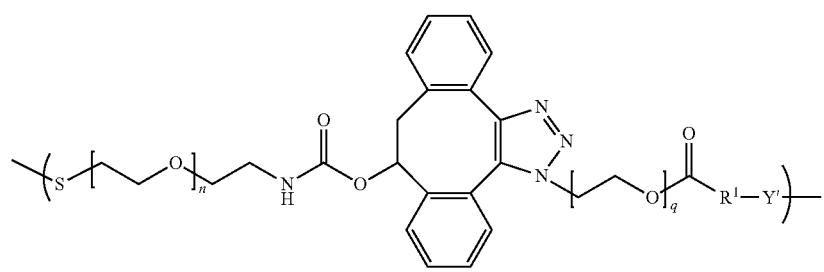
Yk1
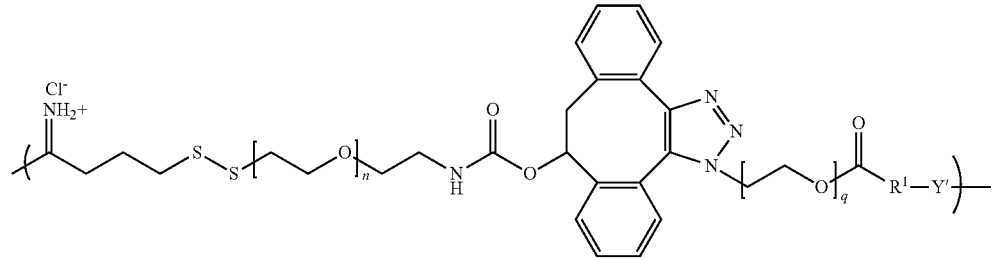
YL1
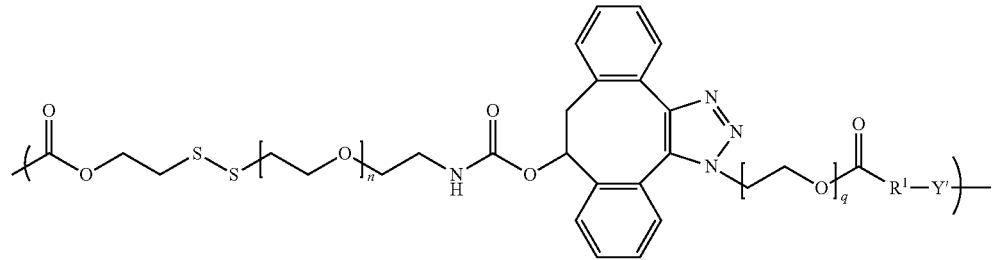
Ym1
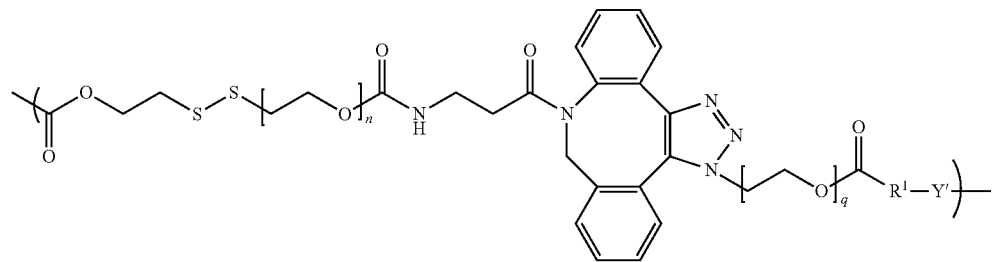
Yn1

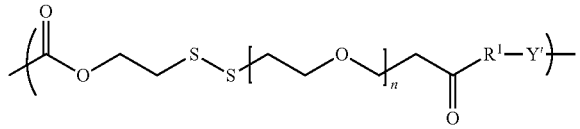
Yo1

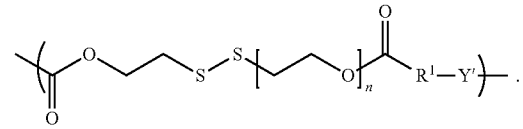
Yp1

In several embodiments, n is an integer from about 1 to about 100. In several embodiments, q is an integer from about 1 to about 100. In several embodiments, k is an integer from about 1 to about 20. In several embodiments, i is an integer from about 0 to about 20. In several embodiments, v is an integer from about 1 to about 20. In several embodiments, $R_1$ is selected from the group consisting of —$CH_2$—, —$(CH_2)_2$—$C(CH_3)(CN)$—, —$(CH_2)_2$—$C(CH_3)(CH_3)$—, —$(CH_2)_2$—$CH(CH_3)$—, and —$CH(CH_3)$—.

In several embodiments, Y' is a random copolymer or block copolymer of $W^1$ and $W^2$, where $W^1$ and $W^2$ are as depicted below:

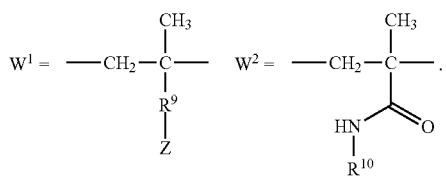

In several embodiments, the number of repeat units of $W^1$ in Y is denoted as p and wherein p is an integer of at least about 1. In several embodiments, the number of repeat units of $W^2$ in Y is denoted as r and wherein r is an integer of at least about 1. In several embodiments, the sum of p and r is greater than about 170.

In several embodiments, $R^9$ is a direct bond, —C(O)—NH—$(CH_2)_2$—, or —C(O)—NH—$(CH_2)_2$—(O—$CH_2$—$CH_2)_t$—. In several embodiments, t is an integer from 1 to 5.

In several embodiments, $R^2$ is selected from the group consisting of:

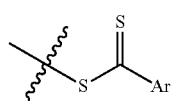
I

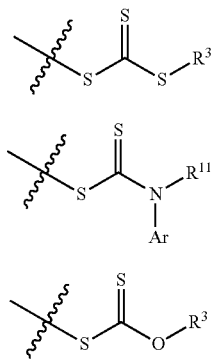
II

III

IV

In several embodiments, Ar is a substituted or unsubstituted aromatic group, $R^3$ is any carbon-containing linear or heterocyclic moiety (e.g., optionally substituted alkyl, optionally substituted heterocyclyl, optionally substituted aryl, optionally substituted heteroaryl, etc.), and $R^{11}$ is hydrogen or an optionally substituted alkyl.

In several embodiments, Z comprises a liver-targeting moiety. In several embodiments, Z is galactose, glucose, galactosamine, glucosamine, N-acetylgalactosamine, or N-acetylglucosamine. In several embodiments, Z is conjugated at its C1, C2 or C6 to Y.

In several embodiments, the ratio of p to r is about 1:1. In several embodiments, the ratio of p to r is about 4:1.

In several embodiments, Y is:

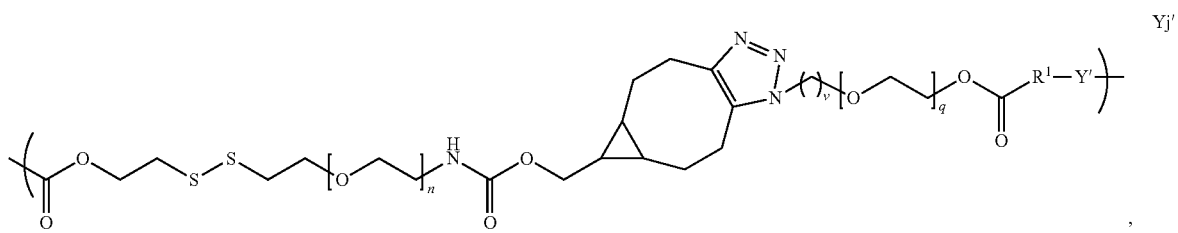
Yj' where n is about 43 or about 44, v is 2, q is 3, $R^1$ is —$(CH_2)_2$—$C(CH_3)(CN)$—, and Z is one or more of galactose, glucose, galactosamine, glucosamine, N-acetylgalactosamine, or N-acetylglucosamine. In several embodiments, Z is N-acetylgalactosamine or N-acetylglucosamine.

In several embodiments, Y is prepared using N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol) ester linkers.

In several embodiments, X induces an unwanted immune response in a subject.

In several embodiments, X is associated with an autoimmune disease. In several embodiments, the autoimmune disease is selected from the group consisting of Type I diabetes, multiple sclerosis, rheumatoid arthritis, vitiligo, uveitis, pemphis vulgaris, neuromyelitis optica, and Parkinson's disease.

In several embodiments, the autoimmune disease is Type I diabetes and X comprises insulin, a tolerogenic portion of thereof, or a mimetic thereof. In several embodiments, the autoimmune disease is Type I diabetes and X comprises proinsulin, a tolerogenic portion of thereof, or a mimetic thereof. In several embodiments, the autoimmune disease is Type I diabetes and X comprises preproinsulin, a tolerogenic portion of thereof, or a mimetic thereof. In several embodiments, the autoimmune disease is multiple sclerosis and X comprises myelin basic protein, a tolerogenic portion of thereof, or a mimetic thereof. In several embodiments, the autoimmune disease is multiple sclerosis and X comprises myelin oligodendrocyte glycoprotein, a tolerogenic portion of any of thereof, or a mimetic any of thereof. In several embodiments, the autoimmune disease is multiple sclerosis and X comprises myelin proteolipid protein, a tolerogenic portion of thereof, or a mimetic thereof.

In several embodiments, X comprises a self antigen. In several embodiments, the self antigen is selected from insulin, proinsulin, preproinsulin, glutamic acid decarboxylase-65 (GAD-65), GAD-67, insulinomaassociated protein 2 (IA-2), and insulinoma-associated protein 213 (IA-213), ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestinepancreas/pancreatic associated protein, S1000, glial fibrillary acidic protein, regenerating gene II, pancreatic duodenal homeobox 1, dystrophia myotonica kinase, islet-specific glucose-6-phosphatase catalytic subunit-related protein, SST G-protein coupled receptors 1-5, and a portion of any of said antigens, and a mimetic of any of said antigens. In several embodiments, the self antigen is selected from myelin basic protein, myelin oligodendrocyte glycoprotein and proteolipid protein, a portion of any of said antigens, and a mimetic of any of said antigens.

In several embodiments, X comprises a food antigen. In several embodiments, the food antigen is selected from the group consisting of conarachin (Ara h 1), allergen II (Ara h 2), arachis agglutinin, conglutin (Ara h 6), 31 kda major allergen/disease resistance protein homolog (Mal d 2), lipid transfer protein precursor (Mal d 3), major allergen Mal d 1.03D (Mal d 1), a-lactalbumin (ALA), lactotransferrin, actinidin (Act c 1, Act d 1), phytocystatin, thaumatin-like protein (Act d 2), kiwellin (Act d 5), ovomucoid, ovalbumin, ovotransferrin, and lysozyme, livetin, apovitillin, vosvetin, 2S albumin (Sin a 1), 1 1S globulin (Sin a 2), lipid transfer protein (Sin a 3), profilin (Sin a 4), profilin (Api g 4), high molecular weight glycoprotein (Api g 5), Pen a 1 allergen (Pen a 1), allergen Pen m 2 (Pen m 2), tropomyosin fast isoform, high molecular weight glutenin, low molecular weight glutenin, alpha-, gamma- and omega-gliadin, hordein, secalin, avenin, major strawberry allergy Fra a 1-E (Fra a 1), profilin (Mus xp 1), a portion of any of said antigens, and a mimetic of any of said antigens. In several embodiments, the food antigen is selected from the group consisting of high molecular weight glutenin, low molecular weight glutenin, alpha-, gamma- and omega-gliadin, hordein, secalin, avenin, a portion of any of said antigens, and a mimetic of any of said antigens. In several embodiments, food antigen is selected from the group consisting of gluten, gliadin, a portion of any of said antigens, and a mimetic of any of said antigens.

In several embodiments, X comprises a therapeutic agent. In several embodiments, therapeutic agent is selected from Abciximab, Adalimumab, Agalsidase alfa, Agalsidase beta, Aldeslukin, Alglucosidase alfa, Factor VII, Factor VIII, Factor IX, Infliximab, L-asparaginase, Laronidase, Natalizumab, Octreotide, Phenylalanine ammonia-lyase (PAL), or Rasburicase (uricase), a portion of any of said antigens, and a mimetic of any of said antigens. In several embodiments, therapeutic agent is selected from the group consisting of aspariginase, uricase, a portion of any of said antigens, and a mimetic of any of said antigens.

In several embodiments, X comprises a transplant antigen. In several embodiments, the transplant antigen is selected from the group consisting of subunits of the MHC class I and MHC class II haplotype proteins, and minor blood group antigens RhCE, Kell, Kidd, Duffy and Ss, a portion of any of said antigens, and a mimetic of any of said antigens.

Several embodiments pertain to a composition comprising a compound as disclosed elsewhere herein. Several embodiments pertain to the use of a compound as disclosed elsewhere herein for inducing tolerance to X.

Several embodiments pertain to a method of inducing tolerance to an antigen to which a subject is capable of developing an unwanted immune response, comprising administering a compound as disclosed elsewhere herein to the subject. In some embodiments, the compound is administered prior to the subject being exposed to the antigen. In several embodiments, the compound is administered after the subject has been exposed to the antigen. In several embodiments, the administration comprises at least one intravenous administration of the compound.

Several embodiments pertain to a use of the compound as disclosed herein for the preparation of a medicament for inducing tolerance to an antigen, a tolerogenic portion thereof, or a mimetic thereof to which a subject develops an unwanted immune response.

In several embodiments, X comprises a foreign transplant antigen, a tolerogenic portion thereof, or a mimetic thereof against which transplant recipients develop an unwanted immune response. In several embodiments, X comprises a foreign food, animal, plant or environmental antigen, a tolerogenic portion of any of thereof, or a mimetic of any of thereof against which induces patients develop an unwanted immune response. In several embodiments, X comprises a foreign therapeutic agent, a tolerogenic portion thereof, or a mimetic thereof against which patients develop an unwanted immune response. In several embodiments, X comprises a self-antigen, a tolerogenic portion thereof, or a mimetic thereof against the endogenous version of which patients develop an unwanted immune response or a tolerogenic portion thereof. In several embodiments, X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy.

Several embodiments pertain to a pharmaceutically acceptable composition for inducing tolerance to a therapeutic protein in a subject having a deficiency in production of a functional analogous native protein.

Several embodiments pertain to the use of a compound or composition as disclosed herein for treating an unwanted immune response against an antigen.

Several embodiments pertain to methods for manufacturing a medicament for use in treating an unwanted immune response against an antigen.

Several embodiments pertain to a composition comprising Formula 1:

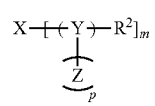

Formula 1

In several embodiments, m is an integer from about 1 to 50. X comprises an antigen, a fragment thereof, or a tolerogenic portion thereof.
In several embodiments, Y is of a linker moiety having a formula selected from the group consisting of:
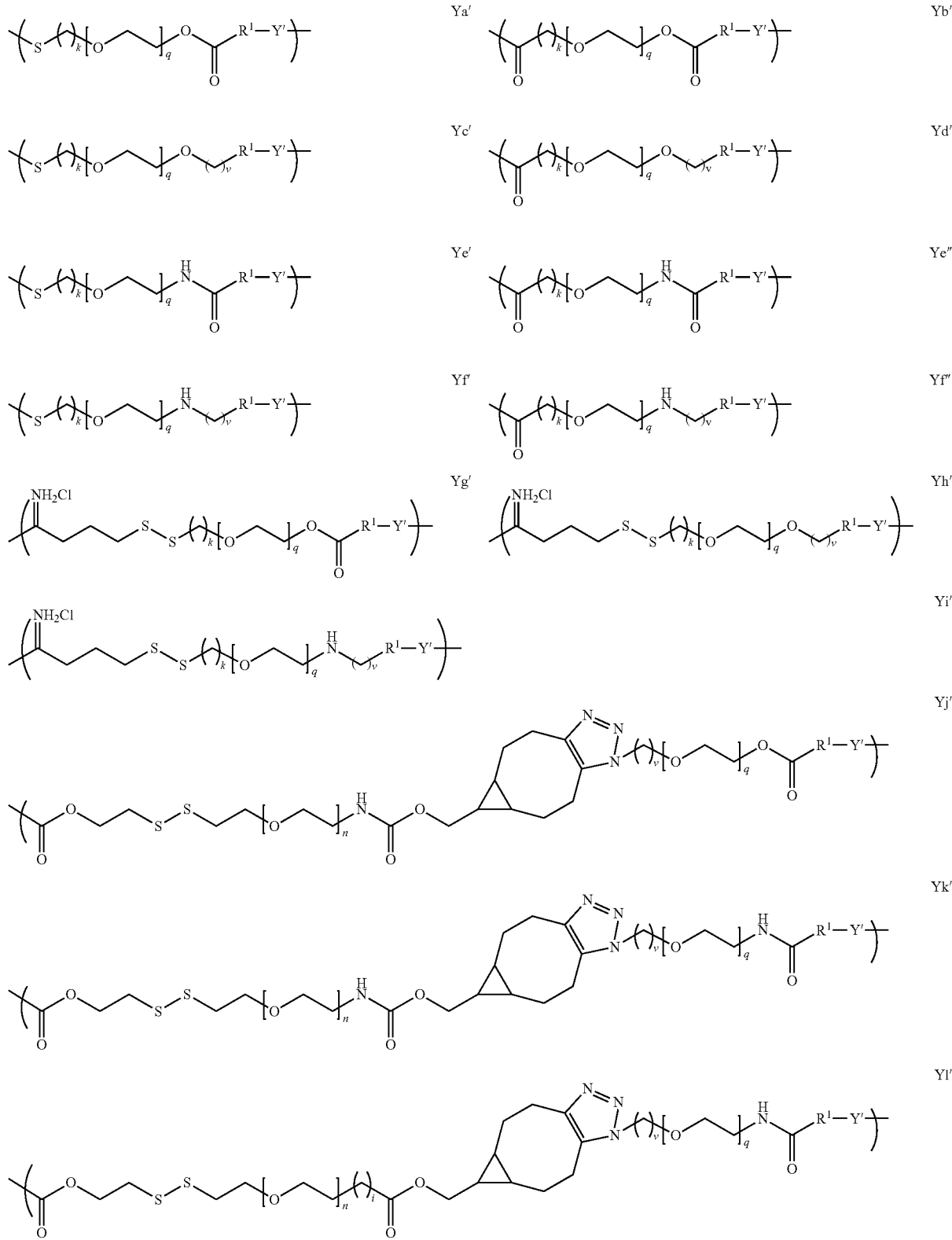

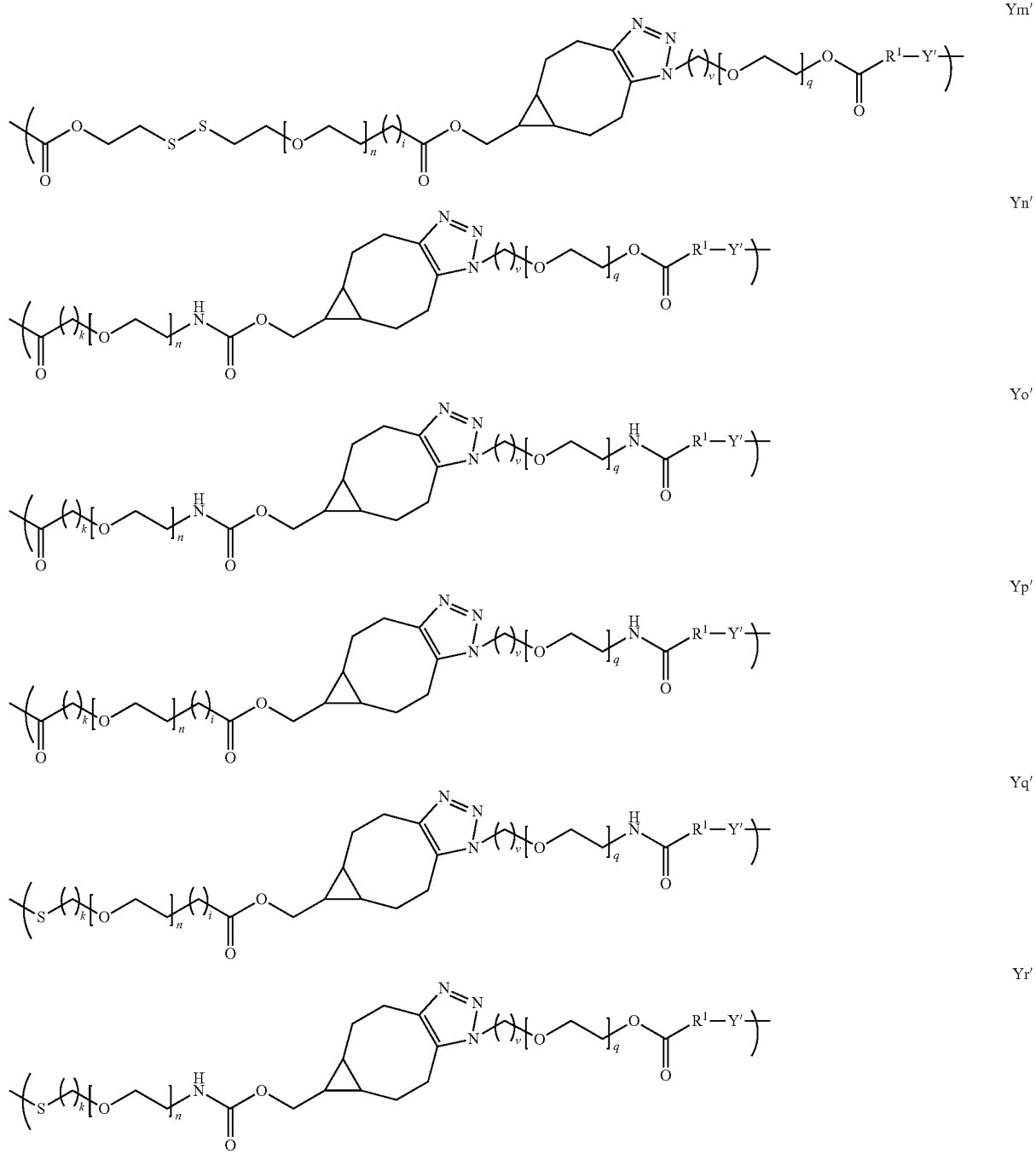

Ym'

Yn'

Yo'

Yp'

Yq'

Yr'

In several embodiments, n is an integer from about 1 to about 100. In several embodiments, q is an integer from about 1 to about 100. In several embodiments, k is an integer from about 1 to about 20. In several embodiments, i is an integer from about 0 to about 20. In several embodiments, v is an integer from about 1 to about 20. In several embodiments, $R_1$ is selected from the group consisting of —$CH_2$—, —$(CH_2)_2$—$C(CH_3)(CN)$—, —$(CH_2)_2$—$C(CH_3)(CH_3)$—, —$(CH_2)_2$—$CH(CH_3)$—, and —$CH(CH_3)$—.

In several embodiments, Y' is a random copolymer or block copolymer of $W^1$ and $W^2$, where $W^1$ and $W^2$ are as depicted below:

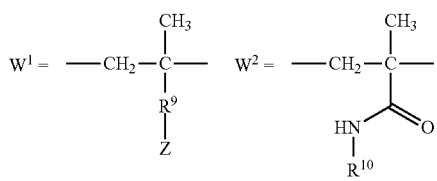

In several embodiments, the number of repeat units of $W^1$ in Y is denoted as p and wherein p is an integer of at least about 1. In several embodiments, the number of repeat units of $W^2$ in Y is denoted as r and wherein r is an integer of at least about 1. In several embodiments, sum of p and r is greater than about 170. In several embodiments, $R^9$ is a direct bond, —C(O)—NH—$(CH_2)_2$—, or —C(O)—NH—$(CH_2)_2$—(O—$CH_2$—$CH_2$)$_t$—. In several embodiments, t is an integer from 1 to 5.

In several embodiments, $R^2$ is selected from the group consisting of:

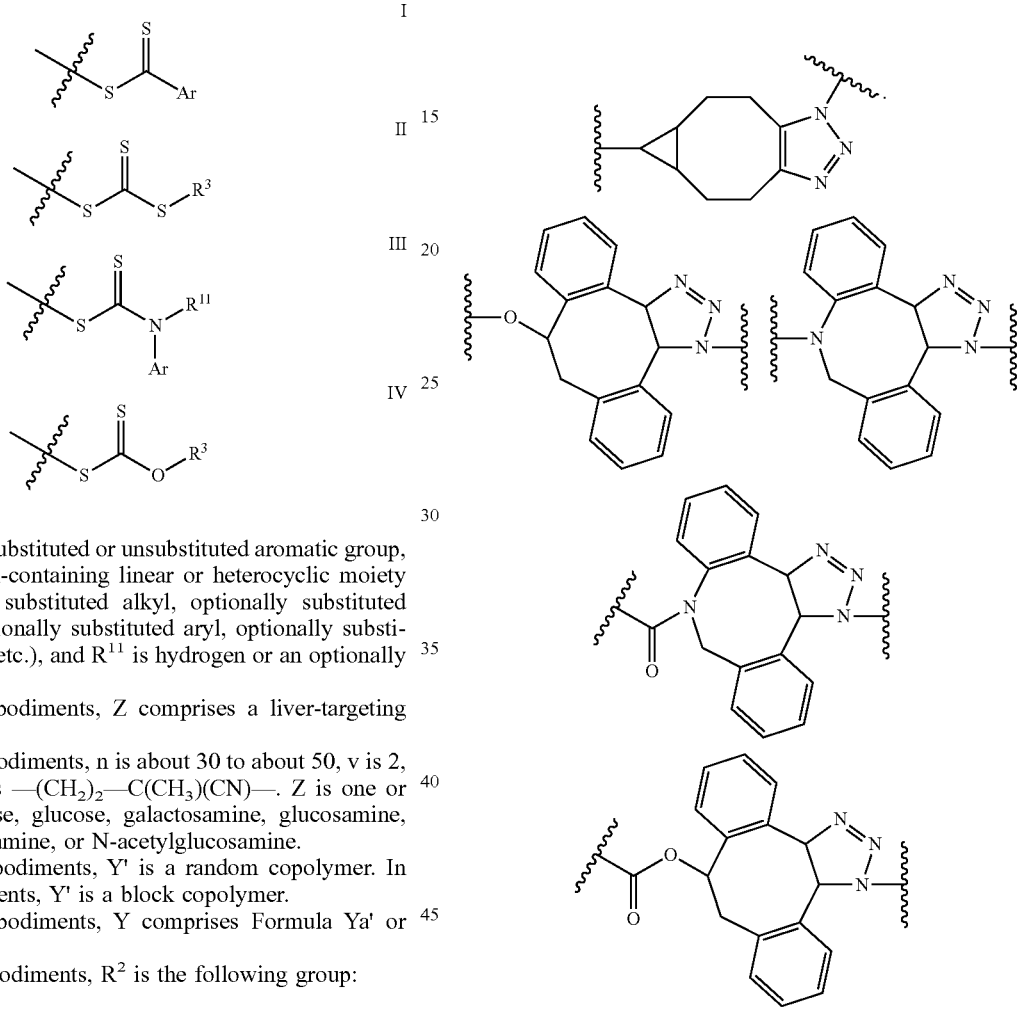

where Ar is a substituted or unsubstituted aromatic group, $R^3$ is any carbon-containing linear or heterocyclic moiety (e.g., optionally substituted alkyl, optionally substituted heterocyclyl, optionally substituted aryl, optionally substituted heteroaryl, etc.), and $R^{11}$ is hydrogen or an optionally substituted alkyl.

In several embodiments, Z comprises a liver-targeting moiety.

In several embodiments, n is about 30 to about 50, v is 2, q is 3, and $R^1$ is —$(CH_2)_2$—$C(CH_3)(CN)$—. Z is one or more of galactose, glucose, galactosamine, glucosamine, N-acetylgalactosamine, or N-acetylglucosamine.

In several embodiments, Y' is a random copolymer. In several embodiments, Y' is a block copolymer.

In several embodiments, Y comprises Formula Ya' or Formula Yj'.

In several embodiments, $R^2$ is the following group:

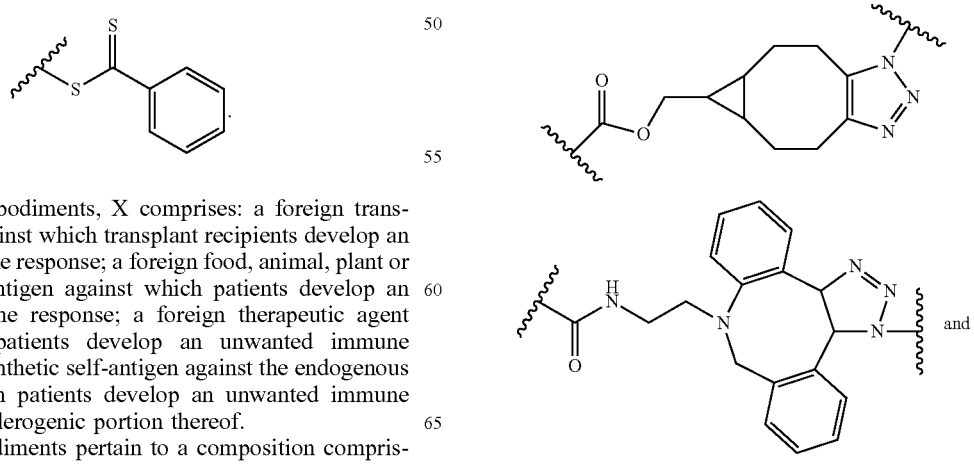

In several embodiments, X comprises: a foreign transplant antigen against which transplant recipients develop an unwanted immune response; a foreign food, animal, plant or environmental antigen against which patients develop an unwanted immune response; a foreign therapeutic agent against which patients develop an unwanted immune response; or a synthetic self-antigen against the endogenous version of which patients develop an unwanted immune response, or a tolerogenic portion thereof.

Several embodiments pertain to a composition comprising a pharmaceutically acceptable excipient and a compound as disclosed herein. Several embodiments pertain to the use of the composition as disclosed herein for treatment for an unwanted immune response.

Some embodiments pertain to a tolerogenic molecule comprising: an antigen, a mimetic of an antigen, or a tolerogenic portion of an antigen; a liver targeting moiety; and a linking group connecting the liver targeting moiety to the antigen. In several embodiments, the linking group comprising any one of the following functional units:

-continued

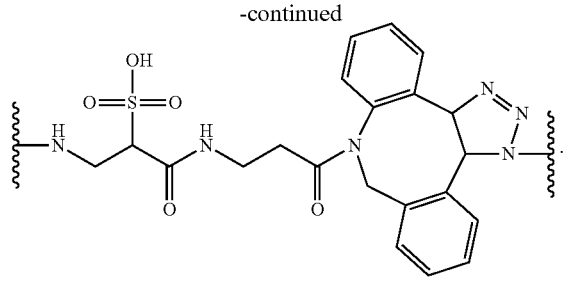

In several embodiments, the linking group comprises a disulfanyl ethyl ester or a sulfide of a disulfide bond.

In several embodiments, the liver targeting moiety is selected from the group consisting of galactose, galactosamine, N-acetylgalactosamine, glucose, glucoseamine and N-acetylglucosamine. In several embodiments, liver targeting moiety is conjugated to the linker at a C1, C2 or C6 position of the liver targeting moiety.

In several embodiments, the linking group further comprises a hydrophilic polymer chain. In several embodiments, the hydrophilic polymer chain comprises a polyethyleneglycol region.

In several embodiments, X induces an unwanted immune response in a subject.

In several embodiments, X is associated with an autoimmune disease. In several embodiments, the autoimmune disease is selected from the group consisting of Type I diabetes, multiple sclerosis, rheumatoid arthritis, vitiligo, uveitis, pemphis vulgaris, neuromyelitis optica, and Parkinson's disease.

In several embodiments, the autoimmune disease is Type I diabetes and X comprises insulin, a tolerogenic portion of thereof, or a mimetic thereof. In several embodiments, the autoimmune disease is Type I diabetes and X comprises proinsulin, a tolerogenic portion of thereof, or a mimetic thereof. In several embodiments, the autoimmune disease is Type I diabetes and X comprises preproinsulin, a tolerogenic portion of thereof, or a mimetic thereof. In several embodiments, the autoimmune disease is multiple sclerosis and X comprises myelin basic protein, a tolerogenic portion of thereof, or a mimetic thereof. In several embodiments, the autoimmune disease is multiple sclerosis and X comprises myelin oligodendrocyte glycoprotein, a tolerogenic portion of any of thereof, or a mimetic any of thereof. In several embodiments, the autoimmune disease is multiple sclerosis and X comprises myelin proteolipid protein, a tolerogenic portion of thereof, or a mimetic thereof.

In several embodiments, X comprises a self antigen. In several embodiments, the self antigen is selected from insulin, proinsulin, preproinsulin, glutamic acid decarboxylase-65 (GAD-65), GAD-67, insulinomaassociated protein 2 (IA-2), and insulinoma-associated protein 213 (IA-213), ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestinepancreas/pancreatic associated protein, S1000, glial fibrillary acidic protein, regenerating gene II, pancreatic duodenal homeobox 1, dystrophia myotonica kinase, islet-specific glucose-6-phosphatase catalytic subunit-related protein, SST G-protein coupled receptors 1-5, and a portion of any of said antigens, and a mimetic of any of said antigens. In several embodiments, the self antigen is selected from myelin basic protein, myelin oligodendrocyte glycoprotein and proteolipid protein, a portion of any of said antigens, and a mimetic of any of said antigens.

In several embodiments, X comprises a food antigen. In several embodiments, the food antigen is selected from the group consisting of conarachin (Ara h 1), allergen II (Ara h 2), arachis agglutinin, conglutin (Ara h 6), 31 kda major allergen/disease resistance protein homolog (Mal d 2), lipid transfer protein precursor (Mal d 3), major allergen Mal d 1.03D (Mal d 1), a-lactalbumin (ALA), lactotransferrin, actinidin (Act c 1, Act d 1), phytocystatin, thaumatin-like protein (Act d 2), kiwellin (Act d 5), ovomucoid, ovalbumin, ovotransferrin, and lysozyme, livetin, apovitillin, vosvetin, 2S albumin (Sin a 1), 1 lS globulin (Sin a 2), lipid transfer protein (Sin a 3), profilin (Sin a 4), profilin (Api g 4), high molecular weight glycoprotein (Api g 5), Pen a 1 allergen (Pen a 1), allergen Pen m 2 (Pen m 2), tropomyosin fast isoform, high molecular weight glutenin, low molecular weight glutenin, alpha-, gamma- and omega-gliadin, hordein, secalin, avenin, major strawberry allergy Fra a 1-E (Fra a 1), profilin (Mus xp 1), a portion of any of said antigens, and a mimetic of any of said antigens. In several embodiments, the food antigen is selected from the group consisting of high molecular weight glutenin, low molecular weight glutenin, alpha-, gamma- and omega-gliadin, hordein, secalin, avenin, a portion of any of said antigens, and a mimetic of any of said antigens. In several embodiments, food antigen is selected from the group consisting of gluten, gliadin, a portion of any of said antigens, and a mimetic of any of said antigens.

In several embodiments, X comprises a therapeutic agent. In several embodiments, therapeutic agent is selected from Abciximab, Adalimumab, Agalsidase alfa, Agalsidase beta, Aldeslukin, Alglucosidase alfa, Factor VII, Factor VIII, Factor IX, Infliximab, L-asparaginase, Laronidase, Natalizumab, Octreotide, Phenylalanine ammonia-lyase (PAL), or Rasburicase (uricase), a portion of any of said antigens, and a mimetic of any of said antigens. In several embodiments, therapeutic agent is selected from the group consisting of aspariginase, uricase, a portion of any of said antigens, and a mimetic of any of said antigens.

In several embodiments, X comprises a transplant antigen. In several embodiments, the transplant antigen is selected from the group consisting of subunits of the MHC class I and MHC class II haplotype proteins, and minor blood group antigens RhCE, Kell, Kidd, Duffy and Ss, a portion of any of said antigens, and a mimetic of any of said antigens.

Several embodiments pertain to a composition comprising a compound as disclosed elsewhere herein. Several embodiments pertain to the use of a compound as disclosed elsewhere herein for inducing tolerance to X.

Several embodiments pertain to a method of inducing tolerance to an antigen to which a subject is capable of developing an unwanted immune response, comprising administering a compound as disclosed elsewhere herein to the subject. In some embodiments, the compound is administered prior to the subject being exposed to the antigen. In several embodiments, the compound is administered after the subject has been exposed to the antigen. In several embodiments, the administration comprises at least one intravenous administration of the compound.

Several embodiments pertain to a use of the compound as disclosed herein for the preparation of a medicament for inducing tolerance to an antigen, a tolerogenic portion thereof, or a mimetic thereof to which a subject develops an unwanted immune response.

In several embodiments, X comprises a foreign transplant antigen, a tolerogenic portion thereof, or a mimetic thereof against which transplant recipients develop an unwanted immune response. In several embodiments, X comprises a foreign food, animal, plant or environmental antigen, a tolerogenic portion of any of thereof, or a mimetic of any of thereof against which induces patients develop an unwanted immune response. In several embodiments, X comprises a foreign therapeutic agent, a tolerogenic portion thereof, or a mimetic thereof against which patients develop an unwanted immune response. In several embodiments, X comprises a self-antigen, a tolerogenic portion thereof, or a mimetic thereof against the endogenous version of which patients develop an unwanted immune response or a tolerogenic portion thereof. In several embodiments, X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy.

Several embodiments pertain to a pharmaceutically acceptable composition for inducing tolerance to a therapeutic protein in a subject having a deficiency in production of a functional analogous native protein.

Several embodiments pertain to the use of a compound or composition as disclosed herein for treating an unwanted immune response against an antigen.

Several embodiments pertain to methods for manufacturing a medicament for use in treating an unwanted immune response against an antigen.

Several embodiments pertain to a tolerogenic molecule comprising an antigen, a liver targeting moiety, and a linking group connecting the liver targeting moiety to the antigen, wherein the linking group comprises the following functional unit:

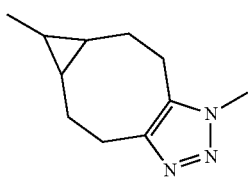

In several embodiments, the antigen is a self-antigen, a therapeutic agent, a food antigen, or a non-food foreign antigen. In several embodiments, the linking group comprises a disulfanyl ethyl ester or a sulfide of a disulfide bond. In several embodiments, the liver targeting moiety is selected from the group consisting of galactose, galactosamine, N-acetylgalactosamine, glucose, glucoseamine and N-acetylglucosamine. In several embodiments, the liver targeting moiety is conjugated to the linker at a C1, C2 or C6 position of the liver targeting moiety. In several embodiments, the antigen is selected from the group consisting of gliadin, glutenin, insulin, pro-insulin, pre-proinsulin, GAD65, IGRP, Factor VIII, uricase, and asparaginase. In several embodiments, the linking group further comprises a hydrophilic polymer chain. In several embodiments, hydrophilic polymer chain comprises a polyethyleneglycol region.

Several embodiments pertain to a method of inducing for inducing tolerance to an antigen, the method comprising: administering a tolerogenic molecule to a patient, the tolerogenic molecule comprising an antigen, a liver targeting moiety, and a linking group connecting the liver targeting moiety to the antigen, the linking group comprising the following functional unit:

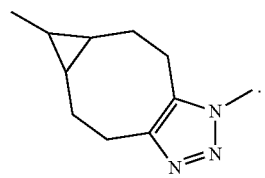

Several embodiments pertain to a use of a composition for induction of antigen-specific immune tolerance. In several embodiments, the composition for use comprises an antigen; a liver targeting moiety; and a linking group connecting the liver targeting moiety to the antigen, the linking group comprising the following functional unit:

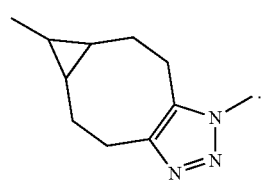

In several embodiments, the antigen is a self-antigen, a therapeutic agent, a food antigen, or a non-food foreign antigen.

In some embodiments, the linking group comprises all, or a portion of, the following functional unit:

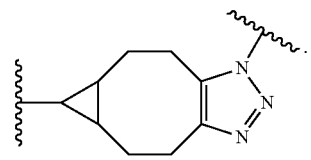 [SMILES: *C1C2CCc3nnn(*)c3CCC12]

In several embodiments, there is provided a composition comprising Formula 1:

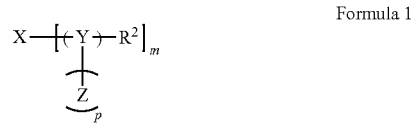

Formula 1 where: m is an integer from about 1 to 50; X comprises an antigen, a fragment thereof, or a tolerogenic portion thereof; Y is of a linker moiety having a formula selected from the group consisting of:

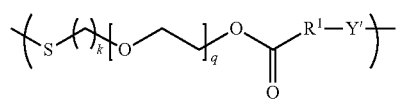
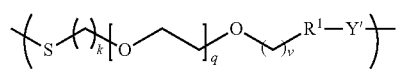
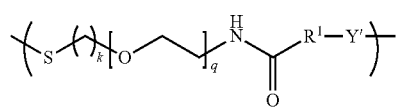
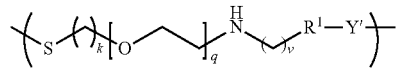
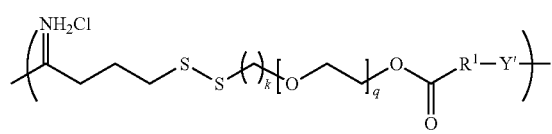
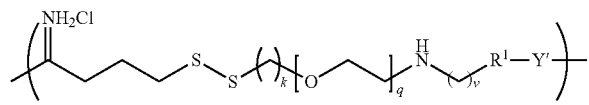
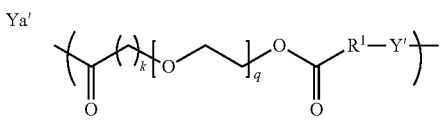
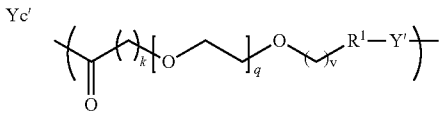
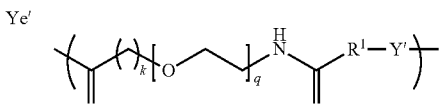
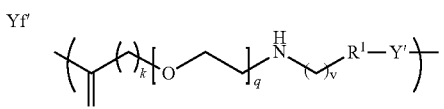
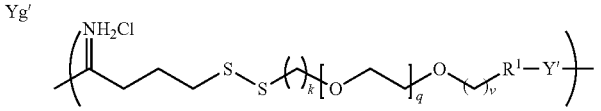
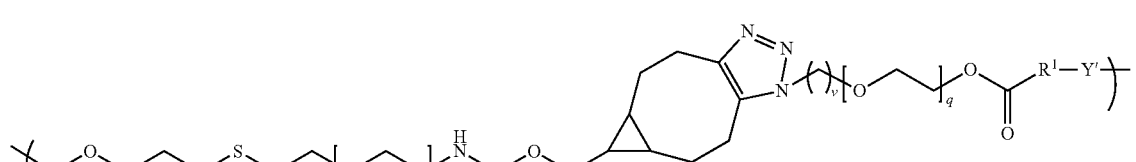
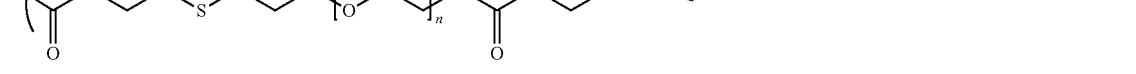

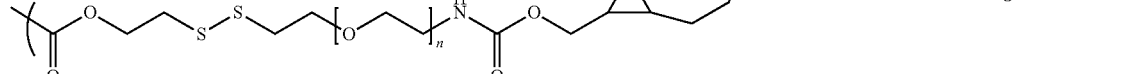
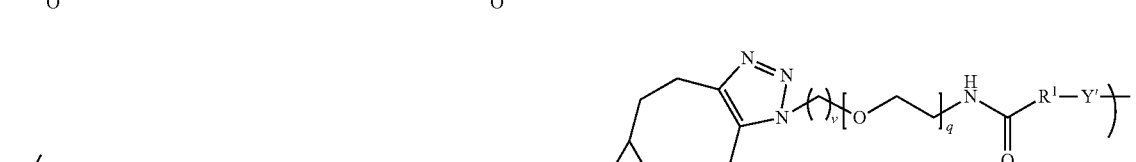
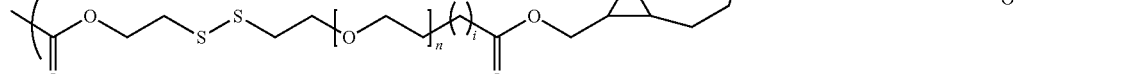
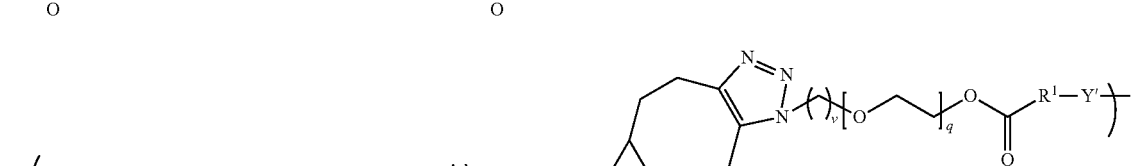
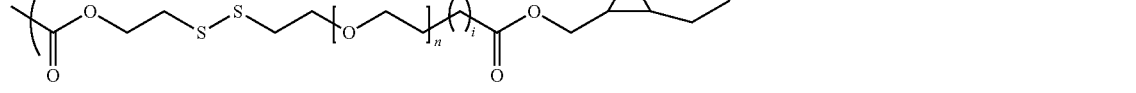

-continued

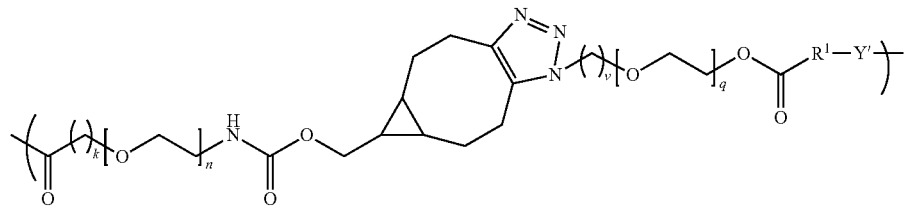
Yn'

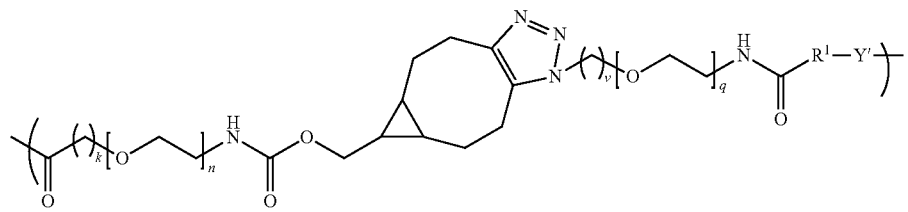
Yo'

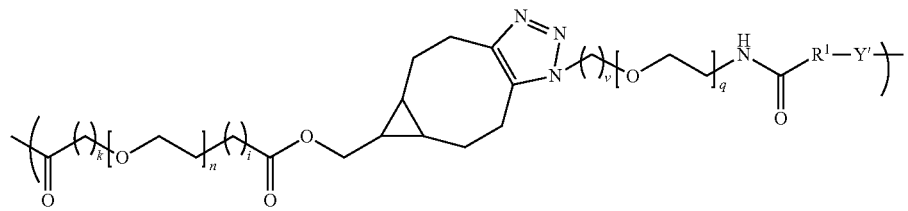
Yp'

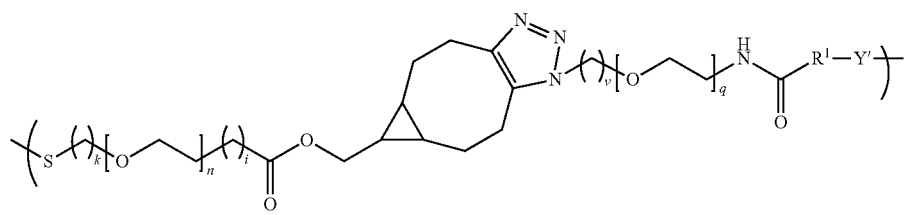
Yq'

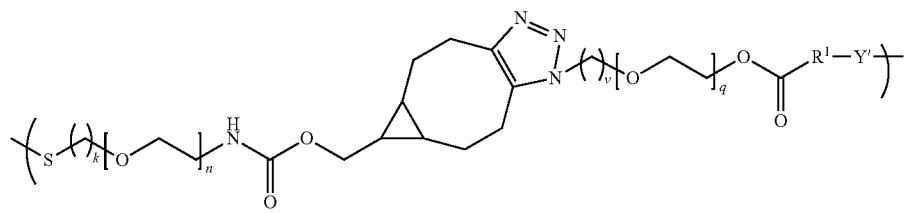
Yr' wherein: n is an integer from about 1 to about 100; q is an integer from about 1 to about 100; k is an integer from about 1 to about 20; i is an integer from about 0 to about 20; v is an integer from about 1 to about 20; $R_1$ is selected from the group consisting of —$CH_2$—, —$(CH_2)_2$—$C(CH_3)(CN)$—, —$(CH_2)_2$—$C(CH_3)(CH_3)$—, —$(CH_2)_2$—$CH(CH_3)$—, and —$CH(CH_3)$—; and Y' is a random copolymer or block copolymer of $W^1$ and $W^2$, where $W^1$ and $W^2$ are as depicted below:

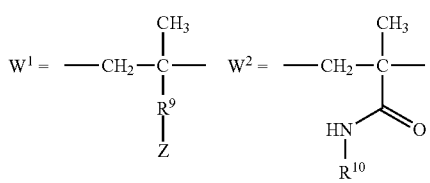

wherein the number of repeat units of $W^1$ in Y is denoted as p and wherein p is an integer of at least about 1; wherein the number of repeat units of $W^2$ in Y is denoted as r and wherein r is an integer of at least about 1; wherein the sum of p and r is greater than about 170; where, $R^9$ is a direct bond, —C(O)—NH—$(CH_2)_2$—, or —C(O)—NH—$(CH_2)_2$—(O—$CH_2$—$CH_2$)$_t$—; t is an integer from 1 to 5; and $R^2$ is selected from the group consisting of:

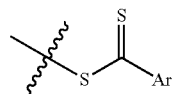
I

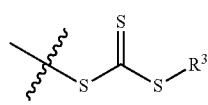
II

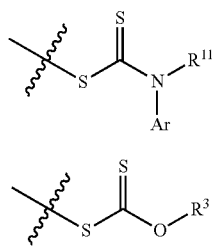

III

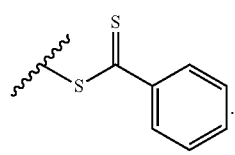 [SMILES: *SC(=S)c1ccccc1]

IV where Ar is a substituted or unsubstituted aromatic group, $R^3$ is any carbon-containing linear or heterocyclic moiety (e.g., optionally substituted alkyl, optionally substituted heterocyclyl, optionally substituted aryl, optionally substituted heteroaryl, etc.), and $R^{11}$ is hydrogen or an optionally substituted alkyl; and Z comprises a liver-targeting moiety.

In several embodiments, n is about 30 to about 50; v is 2; q is 3; R1 is —(CH$_2$)$_2$—C(CH$_3$)(CN)—; and Z is one or more of galactose, glucose, galactosamine, glucosamine, N-acetylgalactosamine, or N-acetylglucosamine.

In several embodiments, Y' is a random copolymer. In additional embodiments, Y' is a block copolymer. In several embodiments, Y comprises Formula Ya' or Formula Yj'.

In several embodiments, $R^2$ is the following group:

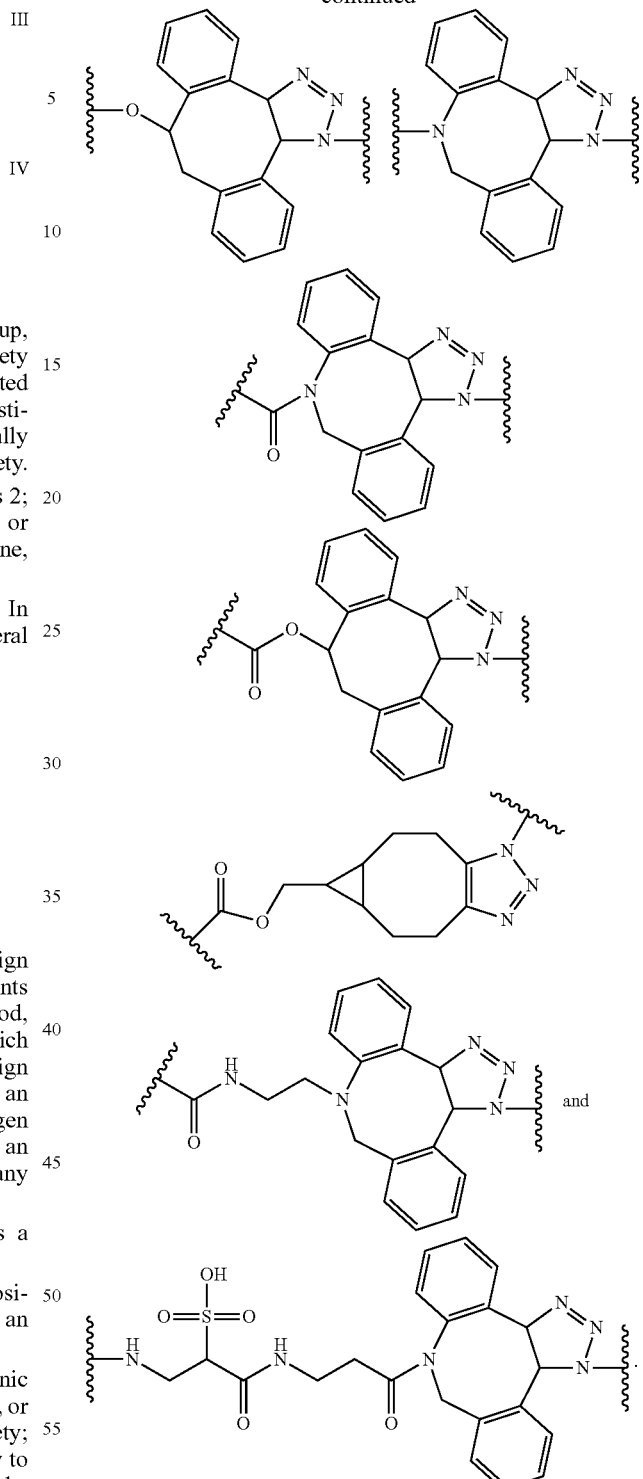

Depending on the embodiment, X can comprise a foreign transplant antigen against which transplant recipients develop an unwanted immune response; a foreign food, animal, plant or environmental antigen against which patients develop an unwanted immune response; a foreign therapeutic agent against which patients develop an unwanted immune response; or a synthetic self-antigen against the endogenous version of which patients develop an unwanted immune response, or a tolerogenic portion of any of such types of antigens.

In several embodiments, the composition comprises a pharmaceutically acceptable excipient.

In several embodiments, the compounds and compositions disclosed herein are for use in the treatment for an unwanted immune response.

In several embodiments, there is provided a tolerogenic molecule comprising: an antigen, a mimetic of an antigen, or a tolerogenic portion of an antigen; a liver targeting moiety; and a linking group connecting the liver targeting moiety to the antigen, the linking group comprising any one of the following functional units:

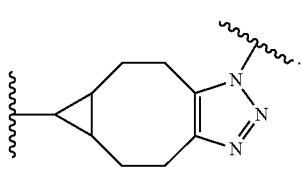

In several embodiments, the linking group comprises a disulfanyl ethyl ester or a sulfide of a disulfide bond. In several embodiments, the liver targeting moiety is selected from the group consisting of galactose, galactosamine, N-acetylgalactosamine, glucose, glucoseamine and N-acetylglucosamine. In some embodiments, the liver targeting moiety is conjugated to the linker at a C1, C2 or C6 position of the liver targeting moiety.

In several embodiments, the linking group further comprises a hydrophilic polymer chain. In one embodiment, the hydrophilic polymer chain comprises a polyethyleneglycol region.

In several embodiments, The compound of any one of claims 75 to 81, wherein the antigen, mimetic thereof, or tolerogenic portion thereof induces an unwanted immune response in a subject.

In several embodiments, the antigen, mimetic thereof, or tolerogenic portion thereof is associated with an autoimmune disease. In several embodiments, the autoimmune disease is selected from the group consisting of Type I diabetes, multiple sclerosis, rheumatoid arthritis, vitiligo, uveitis, pemphis vulgaris, neuromyelitis optica, and Parkinson's disease.

In several embodiments, the antigen, mimetic thereof, or tolerogenic portion thereof comprises a self antigen. In several embodiments, the self antigen is selected from insulin, proinsulin, preproinsulin, glutamic acid decarboxylase-65 (GAD-65), GAD-67, insulinomaassociated protein 2 (IA-2), and insulinoma-associated protein 213 (IA-213), ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestinepancreas/pancreatic associated protein, S1000, glial fibrillary acidic protein, regenerating gene II, pancreatic duodenal homeobox 1, dystrophia myotonica kinase, islet-specific glucose-6-phosphatase catalytic subunit-related protein, SST G-protein coupled receptors 1-5, a portion of any of said antigens, a mimetic of any of said antigens and combinations of any of the antigens, any of the portions and/or any of the mimetics of said antigens.

In several embodiments, the self antigen is selected from myelin basic protein, myelin oligodendrocyte glycoprotein and proteolipid protein, a portion of any of said antigens, a mimetic of any of said antigens, and combinations of any of the antigens, any of the portions and/or any of the mimetics of said antigens.

In several embodiments, the antigen, mimetic thereof, or tolerogenic portion thereof comprises a food antigen. In several embodiments, the the food antigen is selected from the group consisting of conarachin (Ara h 1), allergen II (Ara h 2), arachis agglutinin, conglutin (Ara h 6), 31 kda major allergen/disease resistance protein homolog (Mal d 2), lipid transfer protein precursor (Mal d 3), major allergen Mal d 1.03D (Mal d 1), a-lactalbumin (ALA), lactotransferrin, actinidin (Act c 1, Act d 1), phytocystatin, thaumatin-like protein (Act d 2), kiwellin (Act d 5), ovomucoid, ovalbumin, ovotransferrin, and lysozyme, livetin, apovitillin, vosvetin, 2S albumin (Sin a 1), 1 1S globulin (Sin a 2), lipid transfer protein (Sin a 3), profilin (Sin a 4), profilin (Api g 4), high molecular weight glycoprotein (Api g 5), Pen a 1 allergen (Pen a 1), allergen Pen m 2 (Pen m 2), tropomyosin fast isoform, high molecular weight glutenin, low molecular weight glutenin, alpha-, gamma- and omega-gliadin, hordein, secalin, avenin, major strawberry allergy Fra a 1-E (Fra a 1), profilin (Mus xp 1), a portion of any of said antigens, a mimetic of any of said antigens, and combinations of any of the antigens, any of the portions and/or any of the mimetics of said antigens.

In several embodiments, the food antigen is selected from the group consisting of gluten, gliadin, a portion of any of said antigens, a mimetic of any of said antigens, and combinations of any of the antigens, any of the portions and/or any of the mimetics of said antigens. In several embodiments, the food antigen is associated with celiac disease.

In several embodiments, the antigen, mimetic thereof, or tolerogenic portion thereof comprises a therapeutic agent. In several embodiments, the therapeutic agent is selected from Abciximab, Adalimumab, Agalsidase alfa, Agalsidase beta, Aldeslukin, Alglucosidase alfa, Factor VII, Factor VIII, Factor IX, Infliximab, L-asparaginase, Laronidase, Natalizumab, Octreotide, Phenylalanine ammonia-lyase (PAL), or Rasburicase (uricase), a portion of any of said agents, and a mimetic of any of said agents. In some embodiments, the therapeutic agent is selected from the group consisting of aspariginase, uricase, a portion of any of said agents, and a mimetic of any of said agents.

In several embodiments, the antigen, mimetic thereof, or tolerogenic portion thereof comprises a transplant antigen. In several embodiments, the transplant antigen is selected from the group consisting of subunits of the MHC class I and MHC class II haplotype proteins, and minor blood group antigens RhCE, Kell, Kidd, Duffy and Ss, a portion of any of said antigens, and a mimetic of any of said antigens.

In several embodiments, the autoimmune disease is Type I diabetes and the antigen is insulin, a tolerogenic portion of thereof, or a mimetic thereof. In several embodiments, the autoimmune disease is Type I diabetes and the antigen is proinsulin, a tolerogenic portion of thereof, or a mimetic thereof. In several embodiments, the autoimmune disease is Type I diabetes and the antigen is preproinsulin, a tolerogenic portion of thereof, or a mimetic thereof.

In several embodiments, the autoimmune disease is multiple sclerosis and the antigen is myelin basic protein, a tolerogenic portion of thereof, or a mimetic thereof. In several embodiments, the autoimmune disease is multiple sclerosis and the antigen is myelin oligodendrocyte glycoprotein, a tolerogenic portion of any of thereof, or a mimetic any of thereof. In several embodiments, the autoimmune disease is multiple sclerosis and the antigen is myelin proteolipid protein, a tolerogenic portion of thereof, or a mimetic thereof. In several embodiments, combinations of MBP, MOG and/or PLP (or fragments thereof) make up the antigen(s).

Also provided are pharmaceutical compositions comprising a compound according the embodiments described herein. Also provided are uses of the compounds disclosed herein inducing tolerance to antigen (or antigens) of interest.

Further, there are provided herein methods for inducing tolerance to an antigen to which a subject is capable of developing an unwanted immune response, comprising administering a compound (or compounds) as disclosed herein to the subject. In several embodiments, the compound is administered prior to the subject being exposed to the antigen, after the subject has been exposed to the antigen, or both. In several embodiments, the unwanted immune response is associated with Type I diabetes, multiple sclerosis, rheumatoid arthritis, vitiligo, uveitis, pemphis vulgaris, neuromyelitis optica, Parkinson's disease, or celiac disease. In several embodiments, the compounds disclosed herein are used in the preparation of a medicament for inducing tolerance to an antigen, a tolerogenic portion thereof, or a mimetic thereof to which a subject develops an unwanted immune response. Depending on the embodiment, the methods and compositions provided herein relate to when X comprises a foreign transplant antigen, a tolerogenic portion thereof, or a mimetic thereof against which transplant recipients develop an unwanted immune response. Depending on the embodiment, the methods and compositions provided relate to when X comprises a foreign food, animal, plant or environmental antigen, a tolerogenic portion of any of thereof, or a mimetic of any of thereof against which induces patients develop an unwanted immune response. Depending on the embodiment, the methods and compositions provided relate to when X comprises a foreign therapeutic agent, a tolerogenic portion thereof, or a mimetic thereof against which patients develop an unwanted immune response. Depending on the embodiment, the methods and compositions provided relate to when X comprises a self-antigen, a tolerogenic portion thereof, or a mimetic thereof against the endogenous version of which patients develop an unwanted immune response or a tolerogenic portion thereof. Depending on the embodiment, the methods and compositions provided relate to when X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy.

Several embodiments relate to a pharmaceutically acceptable composition for inducing tolerance to a therapeutic protein in a subject having a deficiency in production of a functional analogous native protein, comprising the compounds disclosed herein. Moreover, the compounds or compositions disclosed herein can be used for treating an unwanted immune response against an antigen and/or for manufacturing a medicament for use in treating an unwanted immune response against an antigen.

In several embodiments, there is provided a method of treating Type I diabetes, multiple sclerosis, rheumatoid arthritis, vitiligo, uveitis, pemphis vulgaris, neuromyelitis optica, Parkinson's disease, or celiac disease in a subject, comprising administering a therapeutically effective amount of the compounds and/or compositions disclosed herein to the subject.

In several embodiments, there is also provided a tolerogenic molecule comprising an antigen, a liver targeting moiety, and a linking group connecting the liver targeting moiety to the antigen, the linking group comprising the following functional unit:

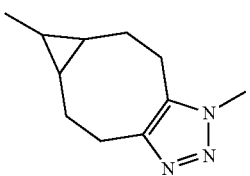

In several embodiments, the antigen is a self-antigen, a therapeutic agent, a food antigen, or a non-food foreign antigen. In several embodiments, the linking group comprises a disulfanyl ethyl ester or a sulfide of a disulfide bond. In several embodiments, the liver targeting moiety is selected from the group consisting of galactose, galactosamine, N-acetylgalactosamine, glucose, glucoseamine and N-acetylglucosamine. In several embodiments, the liver targeting moiety is conjugated to the linker at a C1, C2 or C6 position of the liver targeting moiety. In several embodiments, the antigen is selected from the group consisting of gliadin, glutenin, insulin, pro-insulin, pre-proinsulin, GAD65, IGRP, Factor VIII, uricase, and asparaginase. In several embodiments, the linking group further comprises a hydrophilic polymer chain. In one embodiment, the hydrophilic polymer chain comprises a polyethyleneglycol region.

In several embodiments, there is provided a method of inducing for inducing tolerance to an antigen, the method comprising administering a tolerogenic molecule to a patient, the tolerogenic molecule comprising an antigen, a liver targeting moiety, and a linking group connecting the liver targeting moiety to the antigen, the linking group comprising the following functional unit:

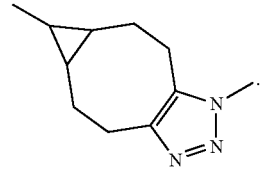

In several embodiments, there is provided for the use of a composition for induction of antigen-specific immune tolerance, the composition comprising an antigen; a liver targeting moiety; and a linking group connecting the liver targeting moiety to the antigen, the linking group comprising the following functional unit:

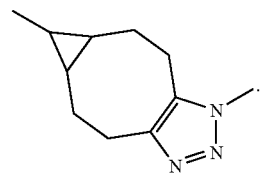

In several embodiments, the antigen is a self-antigen, a therapeutic agent, a food antigen, or a non-food foreign antigen.

BRIEF DESCRIPTION OF THE DRAWINGS

FIG. 1A-E. Hepatocytes take up and process extracellular antigens in cross-presentation-competent phagosomes. (A) Primary hepatocytes isolated from C57BL/6 mice contain subcellular organelles staining positive for MR, EEA1, LAMP-1, TAP1 and H-2 Kb, markers for antigen cross-presenting functions. Sorted CD11c$^+$CD8α$^+$ BMDCs from C57BL/6 mice were chosen as a positive control. Scale bar=10 μm. (B) The fluorescent signal originated from the intracellular degradation of DQ-OVA (a fluorogenic substrate for proteases) is detected by flow cytometric analysis of primary hepatocytes or BMDCs from C57BL/6 mice cultured for the indicated amount of time in the presence of 20 μg/ml DQ-OVA at 37° C. but not at 4° C. (C) In primary C57BL/6 hepatocytes, DQ-OVA fluorescent signal is localized in the proximity of or inside EEA1$^+$, LAMP-1$^+$, TAP1$^+$ and H-2 Kb$^+$ phagosomes. Scale bar=10 μm. (D) Quantification of signal co-localization of DQ-OVA with either EEA1, LAMP-1, TAP1 or H-2 Kb as detected by confocal microscopy in (C) indicates DQ-OVA degradation is mainly found in EEA1+ and TAP1$^+$ phagosomes. (E) EEA$^+$TAP1$^+$ phagosomes, typical of professional antigen cross-presenting cells as indicated by staining of CD11c$^+$CD8α$^+$ BMDCs, are found in the cytoplasm of primary hepatocytes. Scale bar=10 μm. *P<0.05, P<0.01 and *P<0.001 (unpaired Student's t-test in (B) and one-way ANOVA and Bonferroni post-hoc test correction in (D)). Data in (A,B,C,D) are representative of 3 independent experiments (mean and s.e.m. in (B,D)).

FIG. 5A-F. OVA cross-presenting hepatocytes induce CD8⁺ T cell tolerance in vivo via deletion and anergy. (A) Confocal microscopy of primary hepatocytes from C57BL/6 mice incubated ex vivo for 3 hr with 12.5 μM pGal-OVA and stained for H-2 Kb/SIINFEKL (SEQ ID NO: 104) and with DAPI. Scale bar=10 μm. (B) Experimental design. Hepatocytes are exposed to antigen ex vivo, prior to intravenous infusion. (C) Proliferation (measured as CFSE dilution) (top) and frequency or total cell counts (bottom) of viable CD3ε⁺CD8a⁺CD45.1⁺ OT-I cells were measured by flow cytometry after harvesting from the dLNs of recipient CD45.2⁺C57BL/6 mice treated as indicated in (B). Numbers in the representative dot plots indicate the frequency of CD45.1⁺ OT-I cells in the population of viable CD3ε⁺ CD8α⁺ cells. (D) Viable CD3ε⁺CD8α⁺CD45.1⁺ OT-I cells were stained with either Annexin V or for FasL, TRAIL or KLRG-1 and CD127 after harvesting from the dLNs of CD45.2⁺ C57BL/6 mice treated as in (B) and were analyzed by flow cytometry. (E) Upon ex vivo restimulation with $OVA_{257-264}$ (SIINFEKL, SEQ ID NO: 104), viable CD3ε⁺ CD8α⁺CD45.1⁺ OT-I cells harvested from the dLNs of CD45.2⁺ C57BL/6 mice treated as in (B) were stained intracellularly for IFN-γ (left) or IL-2 (right) and analyzed by flow cytometry. (F) IFN-γ secreted by total dLN cells harvested from treated CD45.2⁺ C57BL/6 mice and restimulated with SIINFEKL (SEQ ID NO: 104) was quantified by ELISA. *$P<0.05$, ****$P<0.0001$ and n.s.=not significant for comparisons of pGal-OVA hepatocyte-treated group with either vehicle (plus challenge)- or hepatocyte-treated group (one-way ANOVA and Bonferroni post-hoc test correction). Data are representative of 2 independent experiments (n=8; mean and s.e.m. in C—F).

FIG. 6A-F. PD-1/PD-L1 interactions are involved in the establishment of hepatocyte-dependent cross-tolerance. (A) After harvesting from the dLNs of recipient CD45.2⁺ C57BL/6 mice treated as in FIG. 5B, viable CD3ε⁺CD8α⁺ CD45.1⁺ OT-I cells were stained for PD-1 and with Annexin V and analyzed by flow cytometry. The frequencies of PD-1⁺ OT-I cells (top) and of Annexin V⁺PD-1⁺ OT-I cells (bottom) are indicated. Numbers in the representative dot plots indicate the frequency of Annexin V⁺ OT-I cells in the population of PD-1⁺ OT-I cells. (B) Liver sections were obtained from C57BL/6 mice and stained with DAPI and for either PD-L1 or PD-L2. Scale bar=50 μm. Pictures are representative of 3 different mice. (C) Proliferated ($CFSE^{low-neg}$) viable CD3ε⁺CD8α⁺CD45.1⁺ OT-I cells were measured by flow cytometry after harvesting from the dLNs of recipient CD45.2⁺ C57BL/6 mice infused with hepatocytes incubated ex vivo with pGal-OVA (12.5 μM) or with pGal-OVA (12.5 μM) and 100 μg/ml of either αPD-L1 antibody or isotype control antibody according to the schedule indicated in FIG. 5B. (D) The frequency (left) and total cell number (right) of viable CD3ε⁺CD8α⁺CD45.1⁺ OT-I cells harvested from the dLNs of recipient CD45.2⁺ C57BL/6 mice treated as indicated in (C) were measured by flow cytometry. (E) Viable CD3ε⁺CD8α⁺CD45.1⁺ OT-I cells were stained with either Annexin V or for FasL, TRAIL or KLRG-1 and CD127 after harvesting from the dLNs of CD45.2⁺C57BL/6 mice treated as in (C) and were analyzed by flow cytometry. (F) Upon ex vivo restimulation with $OVA_{257-264}$ (SIINFEKL, SEQ ID NO: 104), viable CD3ε⁺ CD8α⁺CD45.1⁺ OT-I cells harvested from the dLNs of CD45.2⁺ C57BL/6 mice treated as in (C) were stained intracellularly for IFN-γ (left) or IL-2 (right) and analyzed by flow cytometry. (G) IFN-γ secreted by total dLN cells harvested from recipient CD45.2⁺ C57BL/6 mice treated as in (C) and restimulated with SIINFEKL (SEQ ID NO: 104) was quantified by ELISA. *$P<0.05$, $P<0.01$, *$P<0.001$ and n.s.=not significant for comparisons of pGal-OVA hepatocyte-treated group with either vehicle (plus challenge)- or hepatocyte-treated group in (A) or for comparisons of pGal-OVA hepatocytes+αPD-L1 antibody hepatocyte-treated group with either pGal-OVA hepatocyte- or pGal-OVA+iso. ctrl. antibody hepatocyte-treated group in (c-g) (one-way ANOVA and Bonferroni post-hoc test correction). Data are representative of 2 independent experiments (n=8; mean and s.e.m. in A,C-G).

FIG. 7A-E. CD8⁺ T cell tolerance is the result of hepatocyte-dependent antigen cross-presentation. (A) Primary hepatocytes freshly isolated from wt, $TAP1^{-/-}$ or $β2m^{-/-}$ C57BL/6 mice stained for MHC-I (H-2 Kb) or with an isotype control antibody were analyzed by flow cytometry (left) or by confocal microscopy after 3 hr ex vivo incubation with 12.5 μM pGal-OVA and staining for H-2 Kb/SIINFEKL (SEQ ID NO: 104) and DAPI (right). Scale bar=10 μm. (B) Proliferation (CFSE dilution) (left), frequency (middle) and total cell number (right) of viable CD3ε⁺ CD8α⁺CD45.1⁺ OT-I cells were analyzed by flow cytometry after harvesting from the dLNs of recipient CD45.2⁺ C57BL/6 mice infused with either wt hepatocytes, $TAP1^{-/-}$ or $β2m^{-/-}$ hepatocytes ex vivo incubated with pGal-OVA (12.5 μM) according to the schedule described in FIG. 5B. (C) Viable CD3ε⁺CD8α⁺CD45.1⁺ OT-I cells harvested from the dLNs of recipient CD45.2⁺ C57BL/6 mice treated as described in (B) were stained for either FasL (left) or KLRG-1 and CD127 (right) and analyzed by flow cytometry. (D) Viable CD3ε⁺CD8α⁺CD45.1⁺ OT-I cells harvested from the dLNs of recipient CD45.2⁺ C57BL/6 mice treated as in (B) were stained intracellularly for IFN-γ after ex vivo restimulation with OVA$_{257-264}$ (SIINFEKL, SEQ ID NO: 104) and analyzed by flow cytometry. (E) Viable CD3ε$^+$CD8α$^+$CD45.1$^+$ OT-I cells were stained for PD-1 and with Annexin V after harvesting from the dLNs of recipient CD45.2$^+$ C57BL/6 mice treated as in (B) and analyzed by flow cytometry. The frequencies of PD-1$^+$ OT-I cells (left) and of Annexin V$^+$PD-1$^+$ OT-I cells (right) are indicated. (F) IFN-γ secreted by total dLN cells harvested from recipient CD45.2$^+$ C57BL/6 mice treated as in (B) and restimulated with SIINFEKL (SEQ ID NO: 104) was quantified by ELISA. *P<0.05, **P<0.01 (unpaired Student's t-test). Data are representative of 2 independent experiments (n=8; mean and s.e.m. in b-f).

FIG. 8A-G. OVA-specific hepatocyte-dependent cross-tolerance prevents acute rejection of skin grafts from OVA$^+$ mice. (A) Experimental design, in which hepatocytes are exposed to antigen ex vivo, prior to intravenous infusion. (B) Survival of the skin from a transgenic mouse expressing transmembrane OVA (OVA$^+$ skin) grafted onto wt C57BL/6 mice pre-treated with either pGal-OVA-incubated hepatocytes, untreated hepatocytes or vehicle according to the schedule indicated in (A). (C) The frequency of endogenous H-2 Kb/SIINFEKL (SEQ ID NO: 104)-specific CD3ε$^+$CD8α$^+$ cells in the blood or spleen of OVA$^+$ skin graft recipient mice on day 0 before transplantation (left), day 30 (middle) and day 60 (right) after transplantation was measured by flow cytometry. Dots outlined in black represent mice that retained skin grafts until day 60. (D) Frequency of endogenous H-2 Kb/SIINFEKL (SEQ ID NO: 104)-specific CD3ε$^+$CD8α$^+$ splenocytes in mice retaining or rejecting the OVA$^+$ skin graft as detected by flow cytometry on day 0 (before grafting) and on day 30 in the blood and day 60 in the spleen. (E) Viable CD3ε$^+$CD8α$^+$ splenocytes were analyzed by flow cytometry after harvesting on day 60 from skin-grafted C57BL/6 mice, ex vivo restimulation with OVA$_{257-264}$ (SIINFEKL, SEQ ID NO: 104) and intracellular staining for IFN-γ. (F) Viable CD3ε$^+$CD4$^+$ splenocytes were analyzed by flow cytometry after harvesting on day 60 from skin-grafted C57BL/6 mice, ex vivo restimulation with OVA$_{323-339}$ (ISQAVHAAHAEINEAGR; SEQ ID NO:105) and intracellular staining for IFN-γ. (G) The frequency of viable FoxP3$^+$CD25$^+$CD4$^+$ T cells was measured by flow cytometric analysis of splenocytes harvested on day 60 from skin-grafted C57BL/6 mice and restimulated with OVA$_{323-339}$. Dots outlined in black represent mice that retained skin grafts until day 60. ***P<0.001 in (B) (Log-rank Mantel-Cox test). *P<0.05, P<0.01, *P<0.001 and n.s.=not significant in (C, E-G) (one-way ANOVA and Bonferroni post-hoc test correction). *P<0.05, **P<0.01 and n.s.=not significant in (D) (Mann-Whitney test). Data are representative of one experiment (n=8; mean and s.e.m. in C-G).

FIG. 9A-D. OVA cross-presenting hepatocytes induce CD8$^+$ T cell tolerance in vivo via deletion and anergy. (A) Proliferation (CFSE dilution) (top), frequency (bottom left) and total number (bottom right) of viable CD3ε$^+$CD8α$^+$CD45.1$^+$ OT-I cells harvested from the spleen of recipient CD45.2$^+$ C57BL/6 mice treated as indicated in FIG. 5B were analyzed by flow cytometry. Numbers in the representative dot plots indicate the frequency of CD45.1$^+$ OT-I cells in the population of viable CD3ε$^+$CD8α$^+$ cells. (B) Viable CD3ε$^+$CD8α$^+$CD45.1$^±$ OT-I cells harvested from the spleen of CD45.2$^+$ C57BL/6 mice treated as in (A) and stained for either Annexin V or for FasL, TRAIL or KLRG-1 and CD127 were analyzed by flow cytometry. (C) Viable CD3ε$^+$CD8α$^+$CD45.1$^+$ OT-I cells were stained intracellularly for IFN-γ (left) or IL-2 (right) after harvesting from the spleen of CD45.2$^+$ C57BL/6 mice treated as in (A) and ex vivo restimulation with OVA$_{257-264}$ (SIINFEKL, SEQ ID NO: 104). (D) The frequency (left) and total cell counts (right) of viable CD3ε$^+$CD4$^+$CD45.1$^+$ OT-II cells harvested from the dLNs of recipient CD45.2$^+$ C57BL/6 mice treated as indicated in FIG. 5B were measured by flow cytometry. P<0.01, *P<0.001, ****P<0.0001 and n.s.=not significant for comparisons of pGal-OVA hepatocyte-treated group with either vehicle (plus challenge)- or hepatocyte-treated group (one-way ANOVA and Bonferroni post-hoc test correction). Data are representative of 2 independent experiments (n=8; mean and s.e.m. in A-D).

FIG. 10A-E. PD-1/PD-L1 interactions are involved in the establishment of hepatocyte-dependent cross-tolerance. (A) Viable CD3ε$^+$CD8α$^+$CD45.1$^+$ OT-I cells were stained for PD-1 and with Annexin V after harvesting from the spleen of recipient CD45.2$^+$ C57BL/6 mice treated as in FIG. 5B and analyzed by flow cytometry. The frequencies of PD-1$^+$ OT-I cells (left) and of Annexin V$^+$PD-1$^+$ OT-I cells (right) are indicated. (B) The expression of PD-L1 and PD-L2 was measured in primary hepatocytes from wt C57BL/6 mice by qPCR. Gene expression level relative to β-Actin is indicated. (C) The proliferation (CFSE dilution) (top), frequency (bottom left) and total cell number (bottom right) of viable CD45.1$^+$CD3ε$^+$CD8α$^+$ OT-I cells harvested from the spleen of recipient CD45.2$^+$C57BL/6 mice infused with hepatocytes incubated ex vivo with pGal-OVA (12.5 µM) or with pGal-OVA (12.5 µM) and 100 µg/ml of either αPD-L1 antibody or isotype control antibody according to the schedule indicated in FIG. 5B were measured by flow cytometry. (D) Flow cytometric analysis of viable CD3ε$^+$CD8α$^+$CD45.1$^+$ OT-I cells stained with either Annexin V or for FasL, TRAIL or KLRG-1 and CD127 after harvesting from the spleen of recipient CD45.2$^+$ C57BL/6 mice treated as in (C). (E) Viable CD3ε$^+$CD8α$^+$CD45.1$^+$ OT-I cells were stained intracellularly for IFN-γ (left) or IL-2 (right) after harvesting from the spleen of recipient CD45.2$^+$ C57BL/6 mice treated as indicated in (C) and ex vivo restimulation with OVA$_{257-264}$ (SIINFEKL, SEQ ID NO: 104). *P<0.05, P<0.01, *P<0.001, ****P<0.0001 and n.s.=not significant for comparisons of pGal-OVA hepatocyte-treated group with either vehicle (plus challenge)- or hepatocyte-treated group in (A) or for comparisons of pGal-OVA+αPD-L1 antibody hepatocyte-treated group with either pGal-OVA hepatocyte- or pGal-OVA+iso. ctrl. antibody hepatocyte-treated group in (C-E) (one-way ANOVA and Bonferroni post-hoc test correction). Data are representative of 2 independent experiments (n=8; mean and s.e.m. in A, C-E).

FIG. 11A-C. CD8$^+$ T cell tolerance is the result of hepatocyte-dependent antigen cross-presentation. (A) The proliferation (CFSE dilution) (left), frequency (middle) and total number (right) of viable CD3ε$^+$CD8α$^+$CD45.1$^+$ OT-I cells harvested from the spleen of recipient CD45.2$^+$ C57BL/6 mice infused with either wt hepatocytes, TAP1$^{-/-}$ or β2m$^{-/-}$ hepatocytes after ex vivo incubation with pGal-OVA (12.5 µM) and treated as described in FIG. 5B were measured by flow cytometry. (B) Viable CD3ε$^+$CD8α$^+$CD45.1$^+$ OT-I cells were stained for TRAIL after harvesting from the dLNs of recipient CD45.2$^+$C57BL/6 mice treated as in (A) and analyzed by flow cytometry. (C) Viable CD3ε$^+$CD8α$^+$CD45.1$^+$ OT-I cells were stained for either FasL (left), TRAIL (middle) or KLRG-1 and CD127 (right) after harvesting from the spleen of recipient CD45.2$^+$ C57BL/6 mice treated as in (A) and were analyzed by flow cytometry. (D) Viable CD3ε$^+$CD8α$^+$CD45.1$^+$ OT-I cells harvested from the spleen of recipient CD45.2$^+$ C57BL/6 mice treated as in (A) were stained intracellularly for IFN-γ after ex vivo restimulation with OVA$_{257-264}$ (SIINFEKL, SEQ ID NO: 104) and analyzed by flow cytometry. (E) Viable CD3ε⁺CD8α⁺CD45.1⁺ OT-I cells harvested from the dLNs (right) or spleen (left) of recipient CD45.2⁺ C57BL/6 mice treated as in (A) were stained intracellularly for IL-2 after ex vivo restimulation with SIINFEKL (SEQ ID NO: 104). (F) Viable CD3⁺CD8α⁺CD45.1⁺ OT-I cells were stained for PD-1 and with Annexin V and analyzed by flow cytometry after harvesting from the spleen of recipient CD45.2⁺ C57BL/6 mice treated as in (A). The frequencies of PD-1⁺ OT-I cells (left) and of Annexin V⁺PD-1⁺ OT-I cells (right) are indicated. *P<0.05, **P<0.01 and n.s.=not significant (unpaired t-test). Data are representative of 2 independent experiments (n=8; mean and s.e.m. in A-F).

FIG. 12A-B. Flow cytometry gating and examples. (A) Gating strategy utilized to identify CD45.1⁺ OT-I cells in CD45.2⁺ C57BL/6 mice in FIG. 5-7 and in FIG. S1-3. Briefly, lymphocytes were gated according to SSC and FSC from total spleen or dLN cells, followed by identification of viable cells, CD3ε⁺CD8α⁺ T cells and CD45.1⁺ OT-I cells. (B) Representative histograms of viable CD3ε⁺CD8α⁺ CD45.1⁺ OT-I cell counts positive for either Annexin V (top left), PD-1 (top right), FasL (bottom) or IFN-γ (bottom right) purified from the spleen of CD45.2⁺ C57BL/6 mice receiving either one of the treatments indicated in the legend following the experimental schedule described in FIG. 5B.

FIG. 13A-E: Antigen-p(GalNAc) and antigen-p(GluNAc) conjugates target hepatic tolerance-inducing antigen presenting and parenchymal cells. (A) Chemical structure of (i) antigen-p(GalNAc) and (ii) antigen-p(GluNAc) conjugates. Both whole protein and peptide antigens are tethered to glycopolymers via a self-immolative linkage that releases the antigen in its unmodified form (S1sup). (B) Gel electrophoresis analysis of (i) wt OVA, (ii) OVA-p(GalNAc), (iii) OVA-p(GalNAc)+β-mercaptoethanol, (iv) OVA-p(GluNAc), (v) OVA-p(GluNAc)+β-mercaptoethanol. (C) Whole organ florescent analysis of livers treated with fluorescently modified wt OVA and conjugates. Each symbol represents an individual mouse. Representative images of whole livers from mice treated with 10 μg of OVA as (i) OVA$_{750}$-p(GalNAc), (ii) OVA$_{750}$-p(GalNAc), (iii) OVA$_{750}$, 50 μg of OVA as (iv) OVA$_{750}$, or saline. (D) Biodistribution of fluorescently-labeled OVA in hepatic antigen presenting and parenchymal cells (KC: Kupffer Cells, LSECs: Liver sinusoidal endothelial cells) from animals treated with a single i.v. injection of OVA$_{649}$, OVA$_{649}$-p(GalNAc), or OVA$_{649}$-p(GluNAc). Percentage of OVA$_{649}$ positive cells in the parent population was determined via flow cytometry 3 h after administration and is depicted as mean±sem for n=4 mice per group. (C) Mean fluorescence intensity (MFI)±sem of LSECs taken from animals treated as described in D. Statistical differences in B and C were determined by one-way ANOVA using Bonferroni's post hoc test (*p≤0.05, ***p≤0.005).

FIG. 14A-H: Intravenously administered OVA-p(GalNAc) and OVA-p(GluNAc) conjugates enhance antigen presentation and OTI and OTII T cell deletional tolerance. (A) CD45.2⁺ mice that had received an adoptive transfer of CSFE-labeled OTI and OTII T cells were treated on day 1 with saline (vehicle) or 1 μg of OVA as wt OVA, OVA-p(GalNAc), or OVA-p(GluNAc). On day 5, the spleens of the mice were analyzed for OTI and OTII proliferation and phenotype. (A) Representative FACS plots showing proliferation of CFSE-labeled splenic OTI T cells (CD45.1⁺, CD3ε⁺, CD8α⁺) 5 days after receiving an i.v. injection of 1 μg of OVA as free OVA, OVA-p(GalNAc), or OVA-p(GluNAc). (B) Representative FACS plots showing proliferation of CFSE-labeled splenic OTII T cells (CD45.1⁺, CD3ε⁺, CD4⁺) treated as in A. Dose-dependent quantitative proliferative populations of (C) OTI T cells or (D) OTII T cells from the spleens mice treated as in A, as well as mice treated with a single 10 μg injection of OVA as wt OVA, OVA-p(GalNAc), or OVA-p(GluNAc). Percentage of apoptotic (annexin V⁺) (E) OTI or (F) OTII T cells from the spleens of mice treated as in A. Percentage of PD-1⁺ (G) OTI or (H) OTII T cells from the spleens of mice treated as in A. Each symbol represents an individual mouse and bars the mean±sem for n=4 mice per group. Statistical differences in C—H were determined by one-way ANOVA using Bonferroni's post hoc test (*p≤0.05, p≤0.01, *p≤0.005). Pound signs represent statistical significance with respect to vehicle treated mice.

FIG. 15A-L: Antigen-p(GalNAc) and antigen-p(GluNAc) conjugates induce CD8⁺ and CD4⁺ T cell tolerance to antigen challenge and increase the percentage of antigen-specific Tregs. (A) CD45.2⁺ mice that had received an adoptive transfer of both OTI and OTII T cells were treated on days 1 and 7 with saline or 10 μg of OVA as wt OVA, OVA-p(GalNAc), or OVA-p(GluNAc). On day 14, the mice in all treatment groups were given a challenge of OVA+LPS in the footpads, then 5 days later the dLNs and spleens were examined for an OVA-specific immune response. Representative FACS plots showing (B) OTI (CD45.1⁺, CD3ε⁺, CD8α⁺) and (C) OTII (CD45.1⁺, CD3⁺, CD4⁺) T cells in the dLNs 5 days following intradermal challenge with OVA+LPS. Quantification of the population of (D) OTI and (E) OTII T cells responding to antigen challenge in the dLNs. Percentage of Interferon-γ⁺ OTI and OTII cells in the dLNs after 6 h in vitro restimulation with the CD8-epitope (F) SIINFEKL (SEQ ID NO: 104) or (G) whole OVA, as measured by flow cytometry. Interferon-γ produced by dLN-resident cells after 4 days in vitro restimulation with (H) SIINFEKL (SEQ ID NO: 104) or (I) whole OVA, as measured by ELISA. (J) OTII Treg (CD45.1⁺, CD3ε⁺, CD4⁺, CD25⁺, FOXP3⁺) cell compartment in the dLNs on day 19. (K) OTII Treg (CD45.1⁺, CD3⁺, CD4⁺, CD25⁺, FOXP3⁺) cell compartment (FOXP3⁺, CD25⁺, CD4⁺, CD3ε⁺, CD45.2⁺) in the spleen on day 19. (L) IL-2 produced by cells taken from the dLN after 4 days in vitro restimulation with whole OVA, as measured by ELISA. Each symbol in graphs D, E, J, and K represents an individual mouse and all error bars signify mean±sem (n=4 for "No-Challenge" and "Saline" groups, n=5 for all other treatments). Statistical differences were determined by one-way ANOVA using Bonferroni's post hoc test (*p≤0.05, p≤0.01, *p≤0.005). Pound signs represent statistical significance respective to No-challenge group.

FIG. 16A-G: Antigen-p(GluNAc) conjugates induce tolerogenic memory via CD25+ regulatory T cells. (A) On day 0, OTII T cells (CD45.1⁺, CD4⁺) were adoptively transferred into C57BL/6 mice (CD45.2⁺) and then the mice were treated with either saline, or 5 μg of OVA as wt OVA (n=5) or OVA-p(GluNAc) on day 1, 4, and 7. On day 15, the OVA-p(GluNAc)+αCD25 group was given an i.p. injection of αCD25. Twenty-two days after the final treatment, all mice received a second adoptive transfer of both OTII (CD45.1⁺, CD4⁺) and OTI (CD45.1⁺, CD8⁺) T cells, and on the subsequent day, with the exception of the "No-Challenge" group, were challenged with intradermal injections of OVA+LPS in the foot pads. OTII Tregs (CD45.1⁺, CD3ε⁺, CD4⁺, CD25⁺, FOXP3⁺) in the (B) lymph nodes and (C) spleen 5 days after OVA challenge, on day 35. (D) Quantification of the relative number of OTI T cells in the lymph nodes 5 days after antigen challenge. (E) The percentage of INF-γ⁺ OTI cells in the lymph nodes after 6 hr restimulation with SIINFEKL (SEQ ID NO: 104). (F) The relative number of OTII cells in the lymph nodes 5 days after antigen challenge. (G) The percentage of INF-γ+ OTII cells in the lymph nodes after 6 hr restimulation with OVA. In D and F each symbol represents an individual mouse (n=4 for "No-Challenge" group, n=5 for all other treatments). All data represented as mean±sem. Statistical differences were determined by one-way ANOVA using Bonferroni's post hoc test (*p≤0.05, p≤0.01, *p≤0.005). Pound signs represent statistical significance respective to No-Challenge group.

FIG. 17A-E: Antigen-p(GluNAc) conjugates generate antigen-specific tolerogenic memory from endogenous T cell populations. (A) CD 45.2+ mice were treated with either saline, free OVA, or OVA-p(GluNAc) on days 1, 4, and 7. On day 15, the mice in the OVA-p(GluNAc)+αCD25 group were given an i.p. injection of αCD25. Twenty-two days after the final treatment, on day 29, all mice received an adoptive transfer of both OTII (CD45.1+, CD4+) and OTI (CD45.1+, CD8α+) T cells. On the subsequent day, all mice not in the no-challenge group were challenged with i.d. injections of OVA+ LPS in the foot pads. Quantification of the relative number of (B) OTI and (C) OTII T cells in the lymph nodes 5 days after challenge with OVA and LPS. The percentage of INF-γ+ OTI and INF-γ+ OTII T cells in the dLN after 6 hr restimulation with (D) SIINFEKL (SEQ ID NO: 104) or (E) OVA. In B and C each symbol represents an individual mouse (n=4 for "No-Challenge" group, n=5 for all other treatments). All data represented as mean±sem. Statistical differences were determined by one-way ANOVA using Bonferroni's post hoc test (*p≤0.05, p≤0.01, *p≤0.005). Pound signs represent statistical significance respective to No-Challenge group.

FIG. 18A-E: p31-p(GluNAc) conjugates protect mice from BDC2.5 T cell-induced diabetes, increase Tregs, and establish lasting protection against subsequent challenge. (A) Diabetes was induced in NOD/scid mice via an adoptive transfer of activated BDC2.5 splenocytes on day 0. Animals were then treated with saline, p31 peptide or p31-p(GalNAc) at 12 h and 4 d, and then the blood glucose was monitored for the next 31 days. (B) Blood glucose levels of animals treated as described in A. (C) Percentage of Tregs (CD3ε+, CD4+, CD25+, FOXP3+) on day 8 in the spleens of NOD/scid mice treated with p31 or p31-p(GalNAc) on day 1 and 4 after receiving an adoptive transfer of naïve CD4+ BDC2.5 T cells on day 0. Each symbol represents an individual mouse, and bars represent mean±sem. Statistical difference was determined by one-way ANOVA using Bonferroni's post hoc test (*p≤0.05). (D) Naive CD4+ BDC2.5 T cells were adoptively transferred into NOD/scid mice on day 0. On days 1 and 4, animals were treated with saline, free p31, or p31-p(GalNAc). Eleven days later, half the mice treated with p31-p(GalNAc) received an i.p. injection of αCD25. On day 21, all animals that had not developed hyperglycemia were given an adoptive transfer of activated BDC2.5 splenocytes. (E) Percentage of diabetes-free animals over the time course of the experiment depicted in D. Statistical significance between survival curves assessed with Log-rank (Mantel-Cox) test.

FIG. 19A-C. Antigen-p(GluNAc) and antigen-p(GalNAc) conjugates are designed to release antigens in their unmodified form after endocytosis. (A) Chemical structure of antigen-p(GalNAc) conjugates. (B) Upon endocytosis, the disulfide linkage in p(GalNAc) and p(GluNAc) linkage is reduced. (C) Reduction of the disulfide linkage releases a free-thiol, which undergoes and intro-molecular reaction that frees the antigen in its unmodified form.

FIG. 20A-C. OVA$_{649}$-p(GalNAc) and OVA$_{649}$-p(Gal-NAc) conjugates improve antigen targeting to hepatic antigen presenting cells. Representative flow cytometry plots of hepatic antigen presenting cells isolated via density gradient centrifugation then stained for viability and linage specific markers. Gates shown for live single-cell pollutions. Gating strategy for (A) Kupffer cells (CD11b+,F4/80+); (B) liver-resident CD11c+ (CD45+,CD11c+,F4/80−); (C) Sinusoidal endothelial cells (CD31+,CD146+); (D) Hepatocytes (CD45−,CD31−).

FIG. 22A-C. OVA-p(GluNAc) and OVA-p(GalNAc) abrogate an antigen specific immune response in the spleen and expand antigen-specific Tregs. Mice received an adoptive transfer of OTI and OTII T-cells on day zero. On day 1 and day 7, mice were treated with 10.0 µg of OVA as WT OVA, OVA-p(GalNAc), or OVA-p(GluNAc) via i.v. injection. On day 14, mice were challenged with OVA and LPS in all four foot pads. Five days after challenge, the spleens and lymph nodes of the animals were taken and analyzed for an antigen specific immune response. (A) Gating strategy used to determine the percentage of OTI and OTII T-cells in the draining lymph nodes and spleen, as well as the % of IFN-γ after restimulation of lymph node resident cells from animals treated as described in FIG. 3. (B) Representative flow cytometry plots of CD45.1+CD4+ CD25+FOXP3+ cells in the draining lymph nodes. (C) Percentage of OTI and OTII T-cells, of total CD8α+ and CD4+, respectively, in the spleen on day 19.

FIG. 32A-D. In vivo testing of embodiments (degree of polymerization). For BCN pGlu polymers, in vivo testing was performed with various degrees of polymerization of the targeting portion of the embodiments of the constructs disclosed herein.

FIG. 34A-D. In vivo testing of embodiments (repeat unit composition). For BCN pGlu polymers, induction of tolerance was tested with various ratios of sugar repeat units to spacer units.

DETAILED DESCRIPTION

Figure 1C:
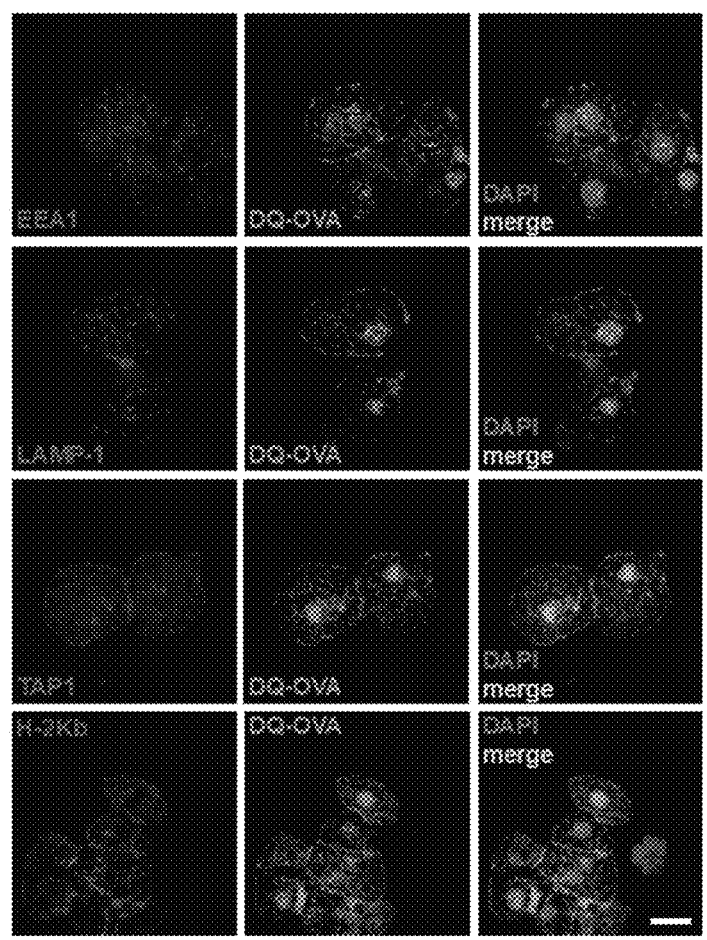

Immune reactions against various antigens can be a significant source of morbidity and mortality. Immune reactions can develop in an individual that lead to adverse impacts on the health and well-being of the individual, reduced efficacy of a treatment being received by an individual, and even reactions to endogenous molecules naturally occurring or existing in the individual. While broad immune suppression is utilized in certain scenarios to address certain types of immune responses, these can lead to generalized susceptibility to infection and sickness. Thus, a more tailored approach, such as those described herein, is advantageous in that antigen-specific responses can be targeted. Several embodiments disclosed herein leverage the role of the liver, and its various types of cells, in the development of tolerance to specific antigens. For example, in several embodiments, specific antigens are linked or coupled to a molecule that is configured to target the liver (or specific cells within or associated with the liver), thereby allowing the specific antigen to be processed and the immune system to be recalibrated to reduce, ameliorate, or otherwise eliminate an immune response against that antigen (or portion of an antigen, or a plurality of antigens). For example, in several embodiments, compositions provided herein are targeted for delivery to (and for uptake by) the liver, particularly hepatocytes, LSECs, Kupffer cells and/or stellate cells, or other cells with asialoglycoprotein receptors (ASGPR).

Some embodiments disclosed herein demonstrate that hepatocytes can be manipulated using synthetic constructs, such as those compositions disclosed herein, to actively induce immunologic tolerance of antigen-specific CD8$^+$ T cells, for example, by cross-presentation of extracellular antigens. Hepatocytes compose up to 80% of the total liver and are in direct contact with circulating T lymphocytes. Hepatocytes do not express immunological co-stimulatory molecules. For that reason, whether hepatocytes contribute to peripheral tolerogenesis by cross-presenting blood-borne antigens was tested. Demonstrated herein, and in accordance with several embodiments, hepatocytes can be manipulated (e.g., through targeting hepatocytes with constructs according to embodiments disclosed herein) to contribute to peripheral tolerogenesis by cross-presenting blood-borne antigens.

Unlike other organs, where circulating lymphocytes only extravasate and gain access to the parenchyma in the case of inflammation, the liver microvasculature has a peculiar fenestrated endothelium devoid of any basal membrane, allowing direct physical contact between circulating CD8+ T lymphocytes and the liver MHC-I+ parenchymal cells, the hepatocytes. Hepatocytes possess poor cross-presentation capacity in vitro as compared to other liver cells, especially LSECs. Nonetheless, direct antigen expression, obtained by transgenesis and/or viral vector transduction, and subsequent MHC-I-dependent antigen presentation in hepatocytes in vitro and in vivo can result in immune tolerance mainly by suboptimal activation of antigen-specific CD8+ T lymphocytes because of a lack of CD28 co-stimulation leading to clonal deletion of the T cells. The induction of CD4+ CD25+FoxP3+ Treg cells also occurs upon lentiviral-mediated hepatocyte-dependent antigen presentation, indicating a possible involvement of other antigen-presenting cells (APCs) in hepatocyte-driven tolerogenic mechanisms, since hepatocytes lack MHC-II expression to interact with CD4+ T cells directly.

Hepatocytes outnumber other cellular components of the liver and are in close contact with components of the blood. In some embodiments disclosed herein, hepatocytes are used to establish CD8+ T cell peripheral tolerance through mechanisms of extracellular antigen uptake and cross-presentation. In other embodiments, the compositions disclosed herein are used to induce tolerance through other mechanisms, alone or in conjunction with antigen cross-presentation. Hepatocytes possess lectin receptors (among others), including the asiaoglycoprotein receptor (ASGRP). Apoptotic processes activate neuraminidases that desialylate glycoproteins to expose terminal N-acetylgalactosamine residues, which bind to ASGPR. Given the peripheral tolerogenic nature of apoptotic debris, studies were designed (and are discussed herein) to determine whether hepatocytes might be involved in the collection of exogenous antigens (e.g., N-acetylgalactosaminylated antigens) and might process and present those antigens tolerogenically. Described herein are in vitro and in vivo results of an assessment of the cross-presentation capabilities of murine hepatocytes and the immunological consequences of hepatocyte-dependent antigen cross-presentation. While the studies herein involve murine models, some embodiments pertain to tolerogenesis in other mammals, including humans. The results demonstrate that, in several embodiments, hepatocyte-dependent antigen cross-presentation (among other mechanisms induced by administration of the constructs disclosed herein, and related methods) can be used in methods to induce CD8+ T cell deletion and anergy. In some embodiments, hepatocytes are useful as target cells for tolerogenic prophylactic or therapeutic interventions.

Generally, the compositions provided herein comprise an antigen of interest (e.g., one to which immune tolerance is desired, including antigenic fragments of a larger molecule, or in some embodiments, a plurality of antigens/fragments thereof), a targeting moiety (e.g., a molecule that specifically targets or is recognized by the liver, or a cell type within the liver), and a linker. As discussed in more detail below, the linkers may vary, depending on the embodiment, but in several embodiments are advantageously designed to release the antigen in vivo in its native, or substantially native form (e.g., the form in which it was conjugated to the linker). Thus, in several embodiments, the antigen of interest is liberated at, in or near the liver and is processed and presented to the immune system in a manner that allows the immune system to recognize the native antigen (or antigenic fragment thereof) as self, and reduce or eliminate an immune response against that antigen.

In several embodiments, the antigen can be endogenous (e.g., a self-antigen) or exogenous (e.g., a foreign antigen), including but not limited to: a foreign transplant antigen against which transplant recipients develop an unwanted immune response (e.g., transplant rejection), a foreign food, animal, plant or environmental antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease), or a tolerogenic portion (e.g., a fragment or an epitope) thereof; these compositions are useful for inducing tolerization to the antigen. Alternatively, the galactosylating or other liver-targeting moiety can be conjugated to an antibody, antibody fragment or ligand that specifically binds a circulating protein or peptide or antibody, which circulating protein or peptide or antibody is causatively involved in transplant rejection, immune response against a therapeutic agent, autoimmune disease, and/or allergy (as discussed above); these compositions are useful for clearing the circulating protein, peptide or antibody. Accordingly, the compositions of the present disclosure can be used for treating an unwanted immune response, e.g., transplant rejection, an immune response against a therapeutic agent, an autoimmune disease, and/or an allergy, depending on the embodiment. Also provided are pharmaceutical compositions containing a therapeutically effective amount of a composition of the disclosure admixed with at least one pharmaceutically acceptable excipient. In another aspect, the disclosure provides methods for the treatment of an unwanted immune response, such as transplant rejection, response against a therapeutic agent, autoimmune disease or allergy.

As will be discussed in more detail herein, in several embodiments, liver-targeting facilitates two possible mechanisms of tolerance induction: tolerization and clearance. Tolerization takes advantage of the liver's role in clearing apoptotic cells and processing their proteins to be recognized by the immune system as "self," as well as the liver's role in sampling peripheral proteins for immune tolerance. Clearance takes advantage of the liver's role in blood purification by rapidly removing and breaking down toxins, polypeptides and the like.

Accordingly, the compositions of the present disclosure (and related methods) can be used for treating an unwanted immune response, e.g., transplant rejection, an immune response against a therapeutic agent, an autoimmune disease, and/or an allergy, depending on the embodiment. Also provided are pharmaceutical compositions containing a therapeutically effective amount of a composition of the disclosure admixed with at least one pharmaceutically acceptable excipient. In another aspect, the disclosure provides methods for the treatment of an unwanted immune response, such as transplant rejection, response against a therapeutic agent, autoimmune disease or allergy.

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

As used herein, term "about" shall have its plain and ordinary meaning and, when referring to a measurable value such as an amount of a compound or agent of the current subject matter, dose, time, temperature, efficacy, and the like, is meant to encompass variations of ±20%, ±10%, ±5%, ±1%, ±0.5%, or even ±0.1% of the specified amount. Also included are any values within the disclosed range, including the listed endpoints.

As used herein, an "antigen" shall have its plain and ordinary meaning and shall refer to any substance that serves as a target for the receptors of an adaptive immune response, such as the T cell receptor, major histocompatibility complex class I and II, B cell receptor or an antibody. In some embodiments, an antigen may originate from within the body (e.g., "self," "auto" or "endogenous"). In additional embodiments, an antigen may originate from outside the body ("non-self," "foreign" or "exogenous"), having entered, for example, by inhalation, ingestion, injection, or transplantation, transdermally, etc. In some embodiments, an exogenous antigen may be biochemically modified in the body. Foreign antigens include, but are not limited to, food antigens, animal antigens, plant antigens, environmental antigens, therapeutic agents, as well as antigens present in an allograft transplant.

As used herein, the term "conservative changes" shall have its plain and ordinary meaning and refers to changes that can generally be made to an amino acid sequence without altering activity. These changes are termed "conservative substitutions" or mutations; that is, an amino acid belonging to a grouping of amino acids having a particular size or characteristic can be substituted for another amino acid. Substitutes for an amino acid sequence can be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such substitutions are not expected to substantially affect apparent molecular weight as determined by polyacrylamide gel electrophoresis or isoelectric point. Conservative substitutions also include substituting optical isomers of the sequences for other optical isomers, specifically d amino acids for 1 amino acids for one or more residues of a sequence. Moreover, all of the amino acids in a sequence can undergo a d to 1 isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free —NH$_2$. Yet another type of conservative substitution constitutes the case where amino acids with desired chemical reactivities are introduced to impart reactive sites for chemical conjugation reactions, if the need for chemical derivatization arises. Such amino acids include but are not limited to Cys (to insert a sulfhydryl group), Lys (to insert a primary amine), Asp and Glu (to insert a carboxylic acid group), or specialized noncanonical amino acids containing ketone, azide, alkyne, alkene, and tetrazine side-chains. Conservative substitutions or additions of free —NH$_2$ or —SH bearing amino acids can be particularly advantageous for chemical conjugation with the linkers and galactosylating moieties of Formula 1. Moreover, point mutations, deletions, and insertions of the polypeptide sequences or corresponding nucleic acid sequences can in some cases be made without a loss of function of the polypeptide or nucleic acid fragment. Substitutions can include, e.g., 1, 2, 3, 4, 5, 6, 7, 8, 9, 10, 15, 20, 25, 30, 35, 40, 45, 50 or more residues (including any number of substitutions between those listed). A variant usable in the present invention may exhibit a total number of up to 200 (e.g., up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200, including any number in between those listed) changes in the amino acid sequence (e.g., exchanges, insertions, deletions, N-terminal truncations, and/or C-terminal truncations). In several embodiments, the number of changes is greater than 200. Additionally, in several embodiments, the variants include polypeptide sequences or corresponding nucleic acid sequences that exhibit a degree of functional equivalence with a reference (e.g., unmodified or native sequence). In several embodiments, the variants exhibit about 80%, about 85%, about 90%, about 95%, about 97%, about 98%, about 99% functional equivalence to an unmodified or native reference sequence (and any degree of functional equivalence between those listed). The amino acid residues described herein employ either the single letter amino acid designator or the three-letter abbreviation in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

As used herein, the terms "effective amount" or "therapeutically effective amount" shall have its plain and ordinary meaning and shall refer to that amount of a recited compound that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, this amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art.

As used herein, the term "epitope", also known as antigenic determinant, shall have its plain and ordinary meaning and shall refer to a segment of a macromolecule, e.g. a protein, which is recognized by the adaptive immune system, such as by antibodies, B cells, major histocompatibility complex molecules, or T cells. An epitope is that part or segment of a macromolecule capable of binding to an antibody or antigen-binding fragment thereof. In this context, the term "binding" in particular relates to a specific binding. In the context of several embodiments of the present invention, it is preferred that the term "epitope" refers to a segment of protein or polyprotein that is recognized by the immune system. In several embodiments, the "antigen" used in the constructs disclosed herein may comprise a one or more epitopes. In some embodiments wherein more than one epitope is included, the additional epitopes may be from the same or a different antigen.

As used herein, the term galactose refers to a monosaccharide sugar that exists both in open-chain form and in cyclic form, having D- and L-isomers. In some embodiments, one or more of the cyclic forms are used, namely the alpha and/or beta anomer. In the alpha form, the C1 alcohol group is in the axial position, whereas in the beta form, the C1 alcohol group is in the equatorial position. In particular, "galactose" refers to the cyclic six-membered pyranose, more in particular the D-isomer and even more particularly the alpha-D-form (α-D-galactopyranose) the formal name for which is (2R,3R,4S,5R,6R)-6-(hydroxymethyl)tetrahydro-2H-pyran-2,3,4,5-tetraol. Glucose is an epimer of galactose; the formal name is (2R,3R,4S,5S,6R)-6-(hydroxymethyl)tetrahydro-2H-pyran-2,3,4,5-tetraol. The structure and numbering of galactose and glucose are shown giving two non-limiting examples of stereochemical illustration.

As used herein, the term glucose refers to a monosaccharide sugar that exists both in open-chain form and in cyclic form, having D- and L-isomers. In some embodiments, one or more of the cyclic forms are used, namely the alpha and/or beta anomer. In the alpha form, the C1 alcohol group is in the axial position, whereas in the beta form, the C1 alcohol group is in the equatorial position. The structure and numbering of galactose and glucose are shown giving two non-limiting examples of stereochemical illustration.

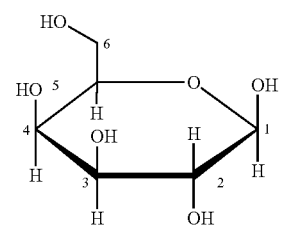

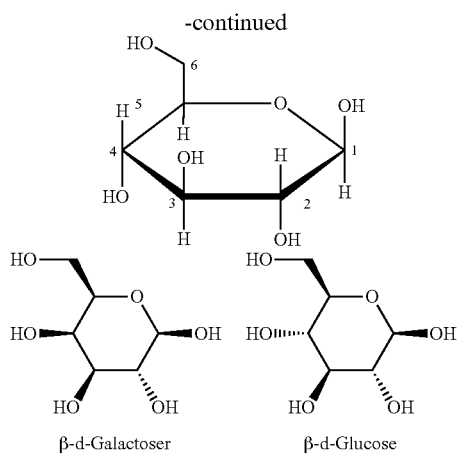

β-d-Galactoser   β-d-Glucose

As used herein, the term "galactosylating moiety" refers to a particular type of liver-targeting moiety. Galactosylating moieties include, but are not limited to a galactose, galactosamine and/or N-acetylgalactosamine residue. A "glucosylating moiety" refers to another particular type of liver-targeting moiety and includes, but is not limited to glucose, glucosamine and/or N-acetylglucosamine.

As used herein, the term "liver-targeting moiety" refers to moieties having the ability to direct an agent (e.g., an immune tolerance inducing construct, a polypeptide, etc.) to the liver. The liver comprises different cell types, including but not limited to hepatocytes, sinusoidal epithelial cells, Kupffer cells, stellate cells, and/or dendritic cells. Typically, a liver-targeting moiety directs a polypeptide to one or more of these cells. On the surface of the respective liver cells, receptors are present which recognize and specifically bind the liver-targeting moiety. Liver-targeting can be achieved by chemical conjugation of an antigen or ligand to a galactosylating or glucosylating moiety, desialylation of an antigen or ligand to expose underlying galactosyl or glucosyl moieties, or specific binding of an endogenous antibody to an antigen or ligand, where the antigen or ligand is: desialylated to expose underlying galactosyl or glucosyl moieties, conjugated to a galactosylating or a glucosylating moiety. Naturally occurring desialylated proteins are not encompassed within the scope of certain embodiments of the present disclosure.

The "numerical values" and "ranges" provided for the various substituents are intended to encompass all integers within the recited range. For example, when defining n as an integer representing a mixture including from about 1 to 100, particularly about 8 to 90 and more particularly about 40 to 80 ethylene glycol groups, where the mixture typically encompasses the integer specified as n±about 10% (or for smaller integers from 1 to about 25, ±3), it should be understood that n can be an integer from about 1 to 100 (e.g., 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110, or any between those listed, including the endpoints of the range) and that the disclosed mixture encompasses ranges such as 1-4, 2-4, 2-6, 3-8, 7-13, 6-14, 18-23, 26-30, 42-50, 46-57, 60-78, 85-90, 90-110 and 107-113 ethylene glycol groups. The combined terms "about" and "±10%" or "±3" should be understood to disclose and provide specific support for equivalent ranges wherever used.

As used herein, the term "optional" or "optionally" means that the subsequently described event or circumstance may or may not occur, and that the description includes instances where said event or circumstance occurs and instances in which it does not.

A peptide that specifically binds a particular target is referred to as a "ligand" for that target.

As used herein, a "polypeptide" is a term that refers to a chain of amino acid residues, regardless of post-translational modification (e.g., phosphorylation or glycosylation) and/or complexation with additional polypeptides, and/or synthesis into multisubunit complexes with nucleic acids and/or carbohydrates, or other molecules. Proteoglycans therefore also are referred to herein as polypeptides. A long polypeptide (having over about 50 amino acids) is referred to as a "protein." A short polypeptide (having fewer than about 50 amino acids) is referred to as a "peptide." Depending upon size, amino acid composition and three dimensional structure, certain polypeptides can be referred to as an "antigen-binding molecule," "antibody," an "antibody fragment" or a "ligand." Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide.

The term "purified" as used herein with reference to a polypeptide refers to a polypeptide that has been chemically synthesized and is thus substantially uncontaminated by other polypeptides, or has been separated or isolated from most other cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of a purified polypeptide therefore can be, for example, at least 70%, at least 75%, at least 80%, at least 90%, or at least 99%, by dry weight, the polypeptide. Polypeptides also can be engineered to contain a tag sequence (e.g., a polyhistidine tag, a myc tag, a FLAG® tag, or other affinity tag) that facilitates purification or marking (e.g., capture onto an affinity matrix, visualization under a microscope). Thus, a purified composition that comprises a polypeptide refers to a purified polypeptide unless otherwise indicated. The term "isolated" indicates that the polypeptides or nucleic acids of the disclosure are not in their natural environment. Isolated products of the disclosure can thus be contained in a culture supernatant, partially enriched, produced from heterologous sources, cloned in a vector or formulated with a vehicle, etc.

The term "random copolymer" refers to the product of simultaneous polymerization of two or more monomers in admixture, where the probability of finding a given monomeric unit at any given site in a polymer chain is independent of the nature of the neighboring units at that position (Bernoullian distribution). Thus, when the variable group identified as $W_p$ represents a random copolymer, the chain can comprise any sequence from 2 up to about 150 $W^1$ and $W^2$ groups, such as: —$W^1$—$W^2$—$W^1$—$W^2$; $W^2$—$W^1$—$W^2$—$W^1$; —$W^1$—$W^1$—$W^1$—$W^2$; $W^1$—$W^1$—$W^2$—$W^2$; $W^1$—$W^2$—$W^2$—$W^1$; $W^1$—$W^2$—$W^1$—$W^2$—$W^2$—$W^1$—$W^2$—$W^1$; —$W^1$—$W^1$—$W^2$—$W^2$—$W^1$—$W^2$—$W^2$—$W^1$; and $W^2$—$W^2$—$W^1$—$W^2$—$W^1$—$W^1$—$W^1$—$W^2$—$W^2$—$W^1$—$W^2$—$W^2$—$W^1$; ad infinitum, where Z attached to the various $W^1$ groups and the $W^1$ and $W^2$ groups themselves can be the same or different.

The term "sequence identity" is used with regard to polypeptide (or nucleic acid) sequence comparisons. This expression in particular refers to a percentage of sequence identity, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Particularly, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide. In addition, when a sequence is disclosed as "comprising" a nucleotide or amino acid sequence, such a reference shall also include, unless otherwise indicated, that the sequence "comprises", "consists of" or "consists essentially of" the recited sequence.

"Specific binding," as that term is commonly used in the biological arts, refers to a molecule that binds to a target with a relatively high affinity as compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and certain protein-receptor interactions; while such molecules might bind tissues besides their specific targets from time to time, to the extent that such non-target binding is inconsequential, the high-affinity binding pair can still fall within the definition of specific binding.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, the term "patient" or "subject" includes a human patient, although it is to be understood that the principles of the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects.

As used herein, the term "treat" or "treating" or "treatment" shall have its plain and ordinary meaning and refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc. In some embodiments, treating can include one or more of preventing or protecting against the disease or disorder, that is, causing the clinical symptoms not to develop; inhibiting the disease or disorder, that is, arresting or suppressing the development of clinical symptoms; and/or relieving the disease or disorder, that is, causing the regression of clinical symptoms. In certain embodiments, treatment of a subject achieves one, two, three, four, or more of the following effects, including, for example: (i) reduction or amelioration the severity of disease state or symptom associated therewith; (ii) reduction in the duration of a symptom associated with a disease or immune response; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalizations of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Administration can be by a variety of routes, including, without limitation, intravenous, intra-arterial, subcutaneous, intramuscular, intrahepatic, intraperitoneal and/or local delivery to an affected tissue.

As used herein, the term "operably linked," shall be given its ordinary meaning. In some embodiments, as an illustration, where two groups are operably linked, the groups are attached such that one or more of the linked groups is provided without substantial loss in its native reactivity or activity. In some embodiments, the antigens disclosed herein are operably linked to linking agents and targeting agents.

As used herein, the term "unwanted immune response" refers to a reaction by the immune system of a subject, which in the given situation is not desirable. The reaction of the immune system is unwanted if such reaction does not lead to the prevention, reduction, or healing of a disease or disorder but instead causes, enhances or worsens, or is otherwise associated with induction or worsening of a disorder or disease. Typically, a reaction of the immune system causes, enhances or worsens a disease if it is directed against an inappropriate target. For example, an unwanted immune response includes but is not limited to transplant rejection, immune response against a therapeutic agent, autoimmune disease, and allergy or hypersensitivity.

The term "variant" is to be understood as a protein (or nucleic acid) which differs in comparison to the protein from which it is derived by one or more changes in its length, sequence, or structure. The polypeptide from which a protein variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence or structure in comparison to the parent molecule. Also encompassed are modified molecules such as but not limited to post-translationally modified proteins (e.g. glycosylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Naturally occurring and artificially constructed variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, e.g., is functionally active. A variant can be characterized by a certain degree of sequence identity to the parent polypeptide from which it is derived. More precisely, a protein variant in the context of the present disclosure may exhibit at least 80% sequence identity to its parent polypeptide. Preferably, the sequence identity of protein variants is over a continuous stretch of 20, 30, 40, 45, 50, 60, 70, 80, 90, 100 or more amino acids. As discussed above, in several embodiments variants exhibit about 80%, about 85%, about 90%, about 95%, about 97%, about 98%, about 99% functional equivalence to an unmodified or native reference sequence (and any degree of functional equivalence between those listed).

Whenever a group is described as being "optionally substituted" that group may be unsubstituted or substituted with one or more of the indicated substituents. Likewise, when a group is described as being "unsubstituted or substituted" (or "substituted or unsubstituted") if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, C-amido, N-amido, S-sulfonamido, N-sulfonamido, C-carboxy, O-carboxy, haloalkyl, haloalkoxy, an amino, a mono-substituted amine group, a di-substituted amine group, a mono-substituted amine(alkyl), a di-substituted amine(alkyl), a diamino-group, a diether-, a polyamino-, and a polyether-.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by 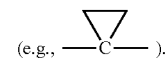, followed by the number of carbon atoms, followed by a "*". For example,

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 4 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "aryl" refers to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, the term "diamino-" denotes an a "—NR$_A$(R$_B$)N(R$_C$)—" group in which R$_B$ and R$_C$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein RA connects the two amino groups and can be (independently of R$_B$ and R$_C$) an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). RA, R$_B$, and R$_C$ can independently be substituted or unsubstituted.

As used herein, the term "diether-" denotes an a "—OR$_D$O—" group in which RD can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein RD connects the two 0 groups. RD can be optionally substituted or unsubstituted.

As used herein, the term "polyamino" denotes a repeating —N(R$_B$)alkyl-group. For illustration, the term polyamino can comprise —N(R$_B$)alkyl-N(R$_B$)alkyl-N(R$_B$)alkyl-N(R$_B$)alkyl-. In some embodiments, the alkyl of the polyamino is as disclosed elsewhere herein. While this example has only 4 repeat units, the term "polyamino" may consist of 1, 2, 3, 4, 5, 6, 7, 8, 9, or 10 repeat units, where R$_B$ and alkyl are as defined elsewhere herein. As noted here, the polyamino comprises amine groups with intervening alkyl groups (where alkyl is as defined elsewhere herein). A polyamino may terminate with an amine group or as an alkyl where the polyamino is a terminal group, or with as an —N(R$_C$)— where the polyamino bridges two atoms. For instance, any one of methylenediamino (—NHCH$_2$NH—), ethylenediamino (—NH(CH$_2$)$_2$NH—), etc. are considered a polyamino groups.

As used herein, the term "polyether" denotes a repeating —Oalkyl-group. For illustration, the term polyether can comprise —O-alkyl-O-alkyl—O-alkyl-O-alkyl. A polyether may have up to 10 repeat units, comprising —O— (ethers) with intervening alkyl groups (where alkyl is as defined elsewhere herein). The polyether may terminate with a hydroxy group or as an alkyl where the polyether is a terminal group, or with an —O— where the polyether bridges two atoms.

When a range of integers is given, the range includes any number falling within the range and the numbers defining ends of the range. For example, when an "integer from 1 to 20" is used, the integers disclosed in the range are 1, 2, 3, 4, 5, 6, 7, 8, 9, 10, etc., up to and including 20. When the terms "integer from 1 to 100" is used, the integers disclosed include, for example, 1, 2, 3, 4, 5, 6, 7, 8, 9, 10, 50, 51, 52, 53, etc., up to and including 100.

Compositions for Liver Targeting

One aspect of the disclosure relates to polymeric compositions or constructs for immune tolerance. Immune tolerance can be induced against a variety of antigens, based on the disclosure provided herein. For example, the antigen can be endogenous (e.g., a self-antigen) or exogenous (e.g., a foreign antigen), including but not limited to: a foreign transplant antigen against which transplant recipients develop an unwanted immune response (e.g., transplant rejection), a foreign food, animal, plant or environmental antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease), or a tolerogenic portion (e.g., a fragment or an epitope) of any such type of antigen.

In some embodiments, the construct comprises an antigen (or other antigenic molecule) linked via a linker to a targeting agent of the construct. Certain aspects of the disclosure are directed towards compositions comprising a compound of Formula 1:

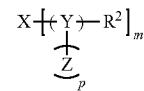

Formula 1 where X comprises an antigen or a tolerogenic portion thereof, Y comprises a linker moiety, Z comprises a liver targeting agent, p is an integer from 2 to 250, m is an integer from 1 to 100, R$^2$ is a terminal group or end-capping group, the left, opening parentheses "("signifies the location of the bond between X and Y, the right, closing parentheses")" signifies the location of the bond between Y and R$^2$, and the upper, opening parentheses " " signifies the location of the bond between Y and a Z unit (of which there are "p" Z units along Y).

As shown, each instance of Z can be moiety that is pendant from the Y linker moiety. Where a plurality of Z groups is present, together the pendant Z groups can provide a comb structure along the length of Y. In some embodiments, Formula 1 can be written as X—[Y(—Z)$_p$—R$^2$]$_m$. As shown, each antigen can have m units of —Y(—Z)$_p$—R$^2$. In several embodiments, m is an integer equal to or greater than about: 1, 2, 3, 4, 5, 10, 25, 50, 75, 100, or ranges including and/or spanning the aforementioned values.

In some embodiments, the construct comprises the following configuration, where the variables (e.g., X, Y, Z, R$^2$, m, p, etc.) are as disclosed elsewhere herein:

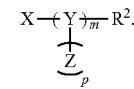

Formula 1'

In some embodiments, Formula 1' can be written as X—(Y(—Z)$_p$)$_m$—R$^2$.

Linking Groups

As disclosed in greater detail below, in several embodiments, linker moieties are used to join an antigen (against which tolerance is desired or an immunogenic fragment thereof) to a moiety configured to target the liver (or a specific liver cell subtype). In several embodiments, the antigen is joined with the linker (or linkers) in a manner that allows for the antigen to be liberated from the linker in vivo. In several embodiments, the linker (or linkers) is configured to release the antigen in substantially its native format (e.g., the form it was in when conjugated to the linker, though not necessarily a format found in nature, as the antigen could be a fragment, a recombinant antigen or the like).

In several embodiments, the linker comprises a polymeric chain with pendant liver targeting moieties decorating the polymeric chain. In some embodiments, the polymeric chain (or Y) comprises Y' as disclosed elsewhere herein. In several embodiments, the polymeric chain comprises an acrylate portion (e.g., acrylate-based polymers and/or acrylate-based copolymers). In several embodiments, the acrylate portion comprises one or more acrylate units (e.g., acrylate derivatives, including methacrylates and derivatives thereof) comprising a pendant liver targeting agent. In several embodiments, the polymeric chain comprises a hydrophilic portion and/or region. In several embodiments, the hydrophilic portion comprises a length of one or more regions having —$(CH_2CH_2O)_s$— where s is an integer from about 1 to about 44. In several embodiments, s is an integer greater than or equal to about: 1, 2, 3, 4, 5, 10, 15, 20, 30, 40, 50, 75, 100, 150, or ranges including and/or spanning the aforementioned values. In some embodiments, the hydrophilic portion comprises one or more polyethylene glycol (PEG) regions. In some embodiments, the PEG may have polydispersity as measured by the weight average molecular weight in g/mol (Mw) of the PEG divided by the number average molecular weight in g/mol (Mw) of the PEG (e.g., Mw/Mn). In some embodiments, the PEG chains have a number average or weight average molecular weight (g/mol) of equal to or at least about: 500, 1000, 2000, 5000, 10000, or ranges including and/or spanning the aforementioned values. In several embodiments, the polymeric chain is optionally substituted. In some embodiments, the polymeric chain comprises pendant hydrophilic groups such as a —OH, —$SO(OH)_2$, optionally substituted polyether, optionally substituted polyamino, and the like.

In several embodiments, the antigen and liver targeting portion of the compound are joined using click chemistry, for example, by functionalizing the antigen with a first linker arm comprising an alkynyl group (or an azide), functionalizing the liver targeting moiety with a second linker arm comprising an azide (or an alkynyl group), and clicking them together via "click" chemistry. In some embodiments, a alkynyl group that can be clicked in copper-free conditions is used. In some embodiments, —[Y(—Z)$_p$]— is a group represented by one or more of Formulae AI-AIV:

—(polymeric chain$^a$-Y'$\,$)—;      Formula AI

—(polymeric chain$^a$-CLICK-Y'$\,$)—;      Formula AII

—(CLICK-polymeric chain$^a$-Y'$\,$)—; and/or      Formula AIII

—(polymeric chain$^a$-CLICK-polymeric chain$^b$-Y'$\,$)—.      Formula AIV where the left, opening parentheses "(" signifies the location of the bond between X and Y, the right, closing parentheses ")" signifies the location of the bond between Y and $R^2$, Y' is a random copolymer or block copolymer of two or more different types of repeat units, wherein at least one type of repeat unit comprises a pendant Z group, (or plurality of pendant Z groups) where Z is galactose and/or glucose and/or a galactose and/or glucose receptor-targeting moiety.

In some embodiments, Y' is a random copolymer or block copolymer of $W^1$ and $W^2$, where $W^1$ and $W^2$ are as depicted below:

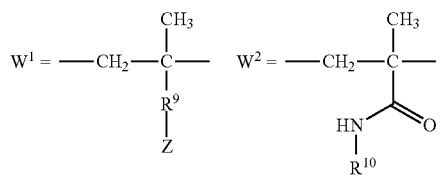

where Z is galactose and/or glucose and/or a galactose and/or glucose receptor-targeting moiety (including, but not limited to, one or more of galactosamine, glucosamine, N-acetylgalactosamine, or N-acetylglucosamine), $R^9$ is a direct bond, optionally substituted —C(O)—NH—$(CH_2)_2$— (an ethylaceetamido group or "EtAcN") or optionally substituted —C(O)—NH—$(CH_2)_2$—(O—$CH_2$—$CH_2)_t$— (a pegylated ethylacetamido group or "Et-PEGt-AcN"), t is an integer from 1 to 5. In some embodiments, t is an integer of equal to or at least about: 1, 2, 3, 4, 5, 10, 20, or ranges including and/or spanning the aforementioned values. In several embodiments, $R^{10}$ is an aliphatic group, an alcohol, an aliphatic amine-containing group, or an aliphatic alcohol. In some embodiments, $R^9$ or $R^{10}$ are independently optionally substituted alkyl, an optionally substituted polyether, or optionally substituted polyamino. In some embodiments, $R^{10}$ is an optionally substituted $C_f$alkyl, optionally substituted $C_f$alkylOH$_g$, or an optionally substituted —($C_f$alkylOH$_g$)—O)$_e$—H where f represents the number of carbons in the alkyl group and is an integer between 0 and 10, g represents the number of hydroxyl groups present on the alkyl group and is an integer between 0 and 10, and e represents the number of alkyl/ether repeat units and is an integer between 0 and 10. In some embodiments, e, f, and g are independently selected integers of equal to or at least about: 0, 1, 2, 3, 4, 5, 10, or ranges including and/or spanning the aforementioned values. In some embodiments, $R^{10}$ is a 2-hydroxyethyl (e.g., —$CH_2CH_2OH$). In some embodiments, $R^{10}$ is an optionally substituted 2-hydroxyethyl. In some embodiments, $R^{10}$ is an optionally substituted polyether.

In some embodiments, Y' is represented as —$W^1_p$—$W^2_r$—, where —$W^1_p$—$W^2_r$—represents a block copolymer or a random copolymer of $W^1$ and $W^2$ monomers having p repeat units of $W^1$ and r repeat units of $W^2$. In some embodiments, p is an integer equal to or greater than about: 1, 50, 85, 100, 150, 165, 200, 225, 250, 300, 400, or ranges including and/or spanning the aforementioned values. In some embodiments, r is an integer equal to or greater than about: 1, 50, 85, 100, 150, 165, 200, 225, 250, 300, 400, or ranges including and/or spanning the aforementioned values. In some embodiments, Y' is a homopolymer of $W^1$ or $W^2$. In some embodiments, r is 0. In some embodiments, the sum of p and r is an integer equal to or greater than about: 1, 50, 85, 100, 150, 165, 170, 200, 225, 250, 300, 400, 600, 800, or ranges including and/or spanning the aforementioned values.

In some embodiments, polymeric chain$^a$ and polymeric chain$^b$ are present or optionally not present. In some embodiments, where present, polymeric chain$^a$ and polymeric chain$^b$ can independently comprise hydrophilic polymers. In some embodiments, where present, polymeric chain$^a$ and polymeric chain$^b$ can independently comprise one or more optionally substituted —$(CH_2CH_2O)_s$—, optionally substituted —(CH$_2$)$_u$—, or optionally substituted alkylene. In several embodiments, u is an integer less than or equal to about: 1, 5, 10, 20, or ranges including and/or spanning the aforementioned values. In some embodiments, polymeric chain$^a$ and polymeric chain$^b$ comprise or consist of one or more of the following structures, or a portion thereof:

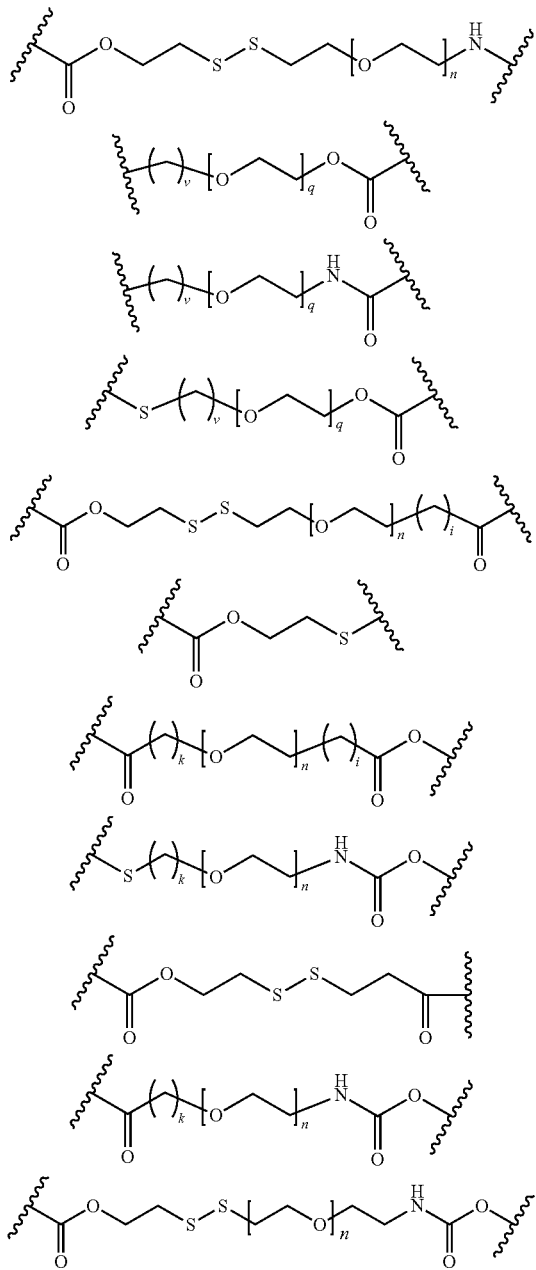

wherein the variables (e.g., i, k, n, q, v, etc.) are as disclosed elsewhere herein. In several embodiments, for example, n is an integer from about 1 to about 100, q is an integer from about 1 to about 100, k is an integer from about 1 to about 20, i is an integer from about 0 to about 20, and v is an integer from about 1 to about 20. In several embodiments, n or q represents the number of repeat units in a PEG chain. In some embodiments, the PEG chain may have some polydispersity. In some embodiments, n and q do not indicate a number of repeat units but instead independently indicate the presence of a PEG polymer chain having a Mn (in g/mol) or Mw (in g/mol) of equal to or at least about 500, 1000, 2000, 5000, 10000, or ranges including and/or spanning the aforementioned values. In some embodiments, k, i, and v can each independently comprise an optionally substituted alkylene.

In several embodiments, n is an integer greater than or equal to about: 1, 10, 20, 40, 50, 75, 100, 150 or ranges including and/or spanning the aforementioned values. In several embodiments, n is an integer greater than or equal to about: 1, 2, 3, 4, 5, 10, 15, 20, 30, 40, 50, or ranges including and/or spanning the aforementioned values. In several embodiments, q is an integer greater than or equal to about: 1, 10, 20, 40, 50, 75, 100, 150 or ranges including and/or spanning the aforementioned values. In several embodiments, q is an integer greater than or equal to about: 1, 2, 3, 4, 5, 10, 15, 20, 30, 40, 50, 75, 100, 150, or ranges including and/or spanning the aforementioned values. In several embodiments, k is an integer greater than or equal to about: 1, 2, 3, 4, 5, 10, 15, 20, or ranges including and/or spanning the aforementioned values. In several embodiments, v is an integer greater than or equal to about: 1, 2, 3, 4, 5, 10, 15, 20, or ranges including and/or spanning the aforementioned values. In several embodiments, k is 2. In several embodiments, v is 2. In several embodiments, n is 4. In several embodiments, n is 44. In several embodiments, q is 3. As used herein, variables disclosed as having structure, a value, or a range of values for one embodiment, may also have those values when the variable is used in another embodiment (even where the variable is not defined with respect to that other embodiment).

In several embodiments, the "CLICK" group and/or —[Y(—Z)$_p$]—, more generally, comprises the following functional unit:

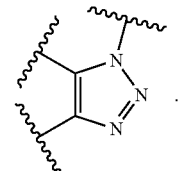 [SMILES: *c1nnn(*)c1*]

In several embodiments, the "CLICK" group and/or —[Y(—Z)$_p$]—, more generally, comprises one or more of the following units (each of which may be optionally substituted):

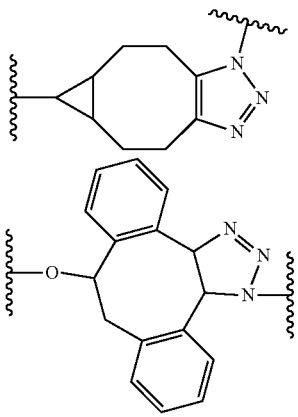

67
-continued
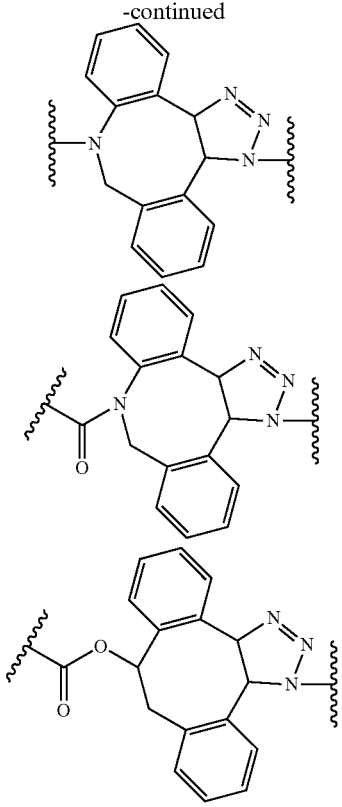
68
-continued
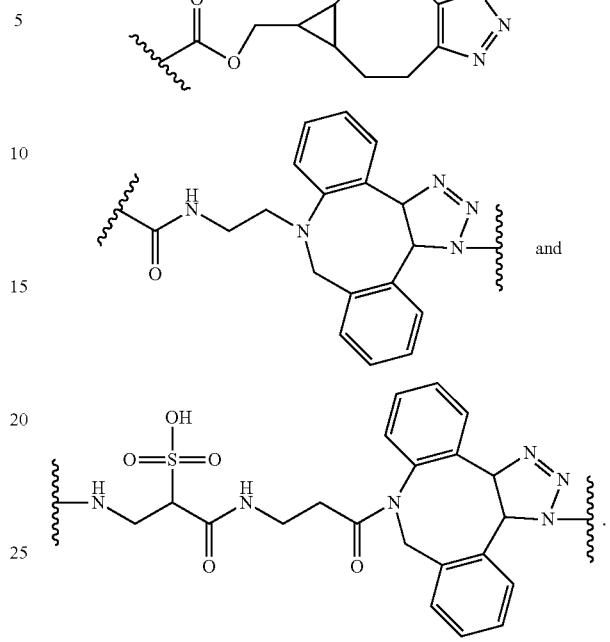
In several embodiments, —[Y(—Z)$_p$]— comprises the one or more of the following functional units:
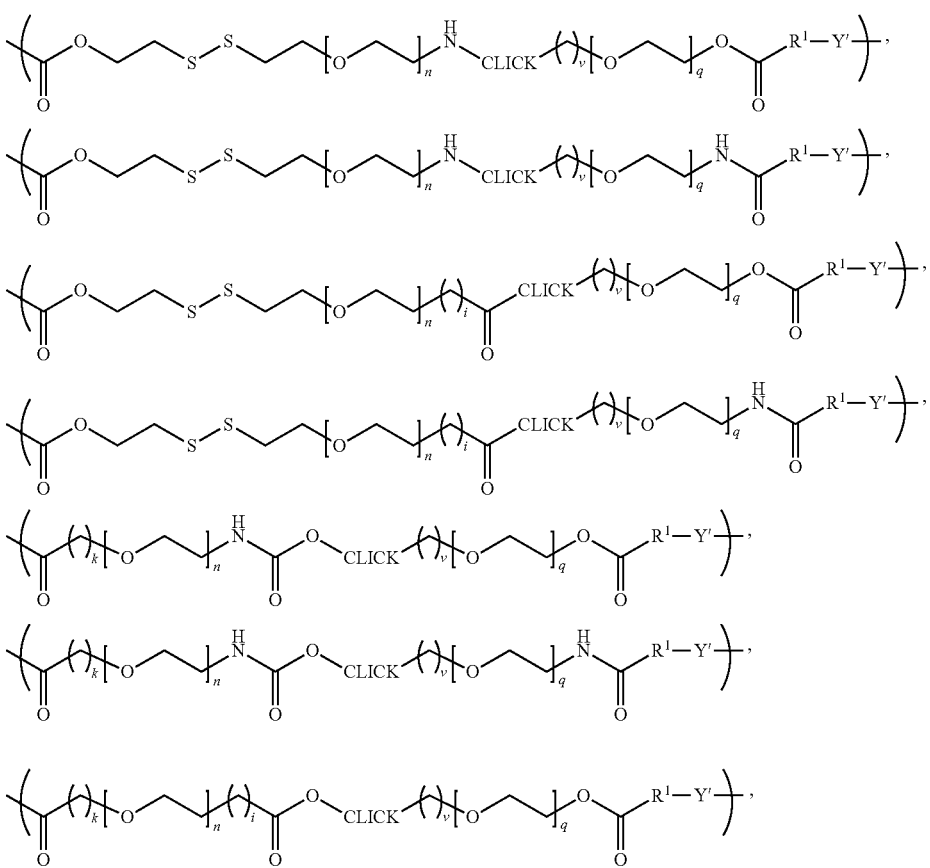

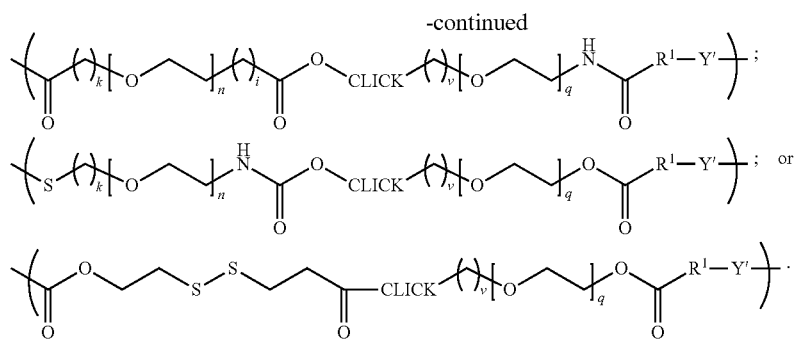

wherein each variable (e.g., i, k, n, q, v, CLICK, $R^1$, Y', etc.) is as disclosed elsewhere herein. In some embodiments, for example, n is an integer from about 1 to about 44, q is an integer from about 1 to about 44, k is an integer from about 1 to about 12, i is an integer from about 0 to about 20, v is an integer from about 1 to about 4, and $R_1$ is —$CH_2$—, —$(CH_2)_2$—$C(CH_3)(CN)$—, —$(CH_2)_2$—$C(CH_3)(CH_3)$—, —$(CH_2)_2$—$CH(CH_3)$—, —$CH(CH_3)$—, or is absent.

In several embodiments, —[Y(Z)$_p$]— is a group represented by any one or more of Formula Ya' to Yr':

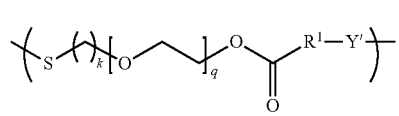
Ya'

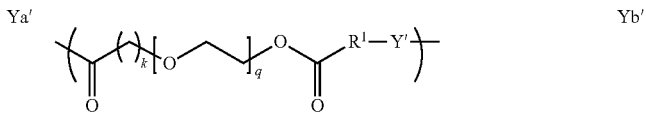
Yb'

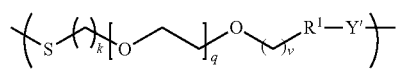
Yc'

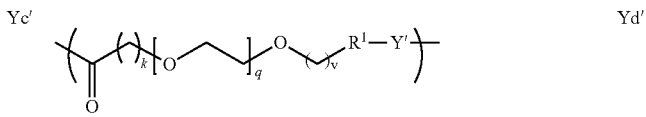
Yd'

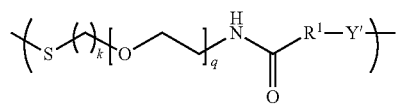
Ye'

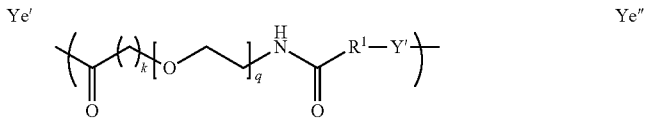
Ye''

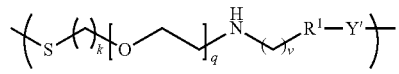
Yf'

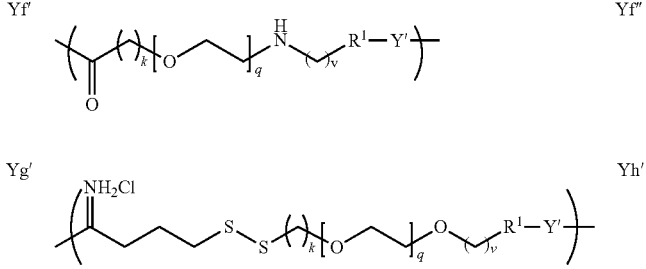
Yf''

Yg'

Yh'

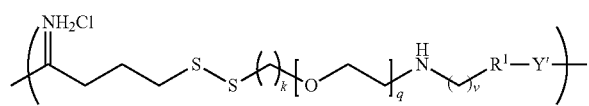

Yi'

Yj'

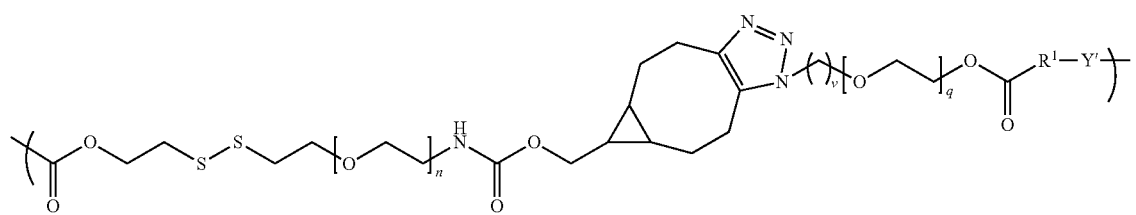

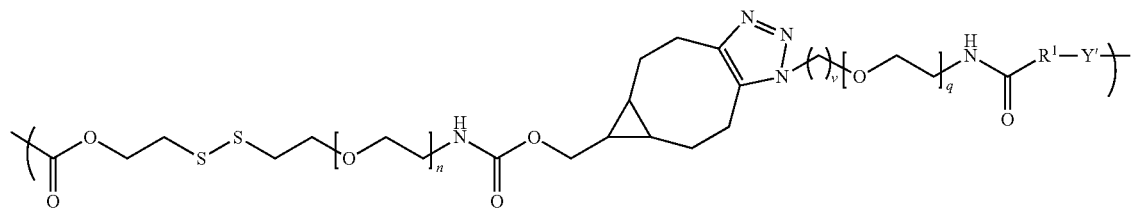
Yk'
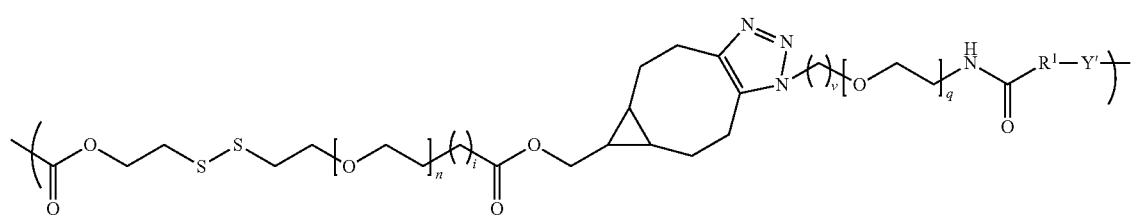
Yl'
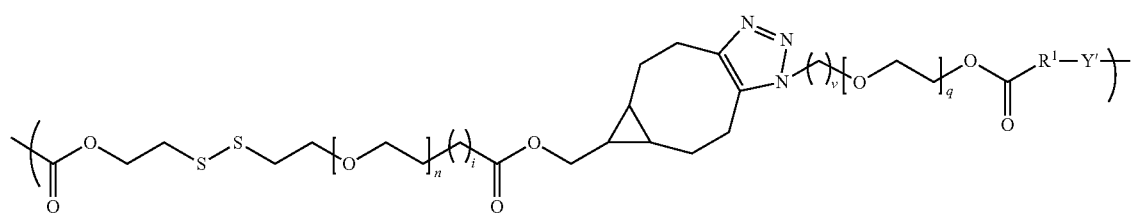
Ym'
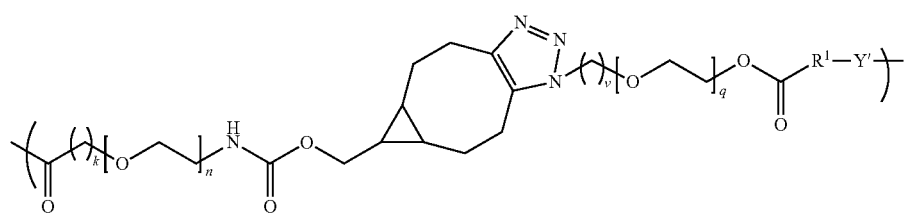
Yn'
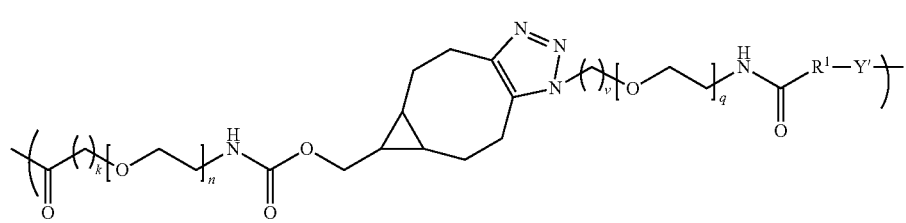
Yo'
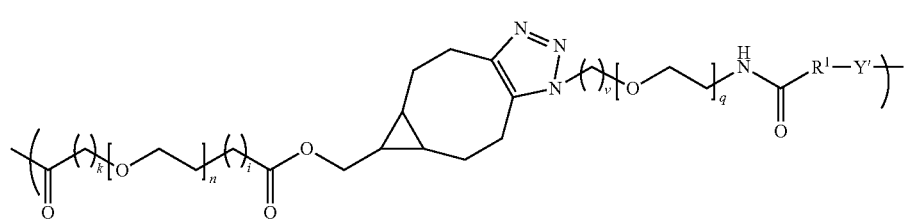
Yp'
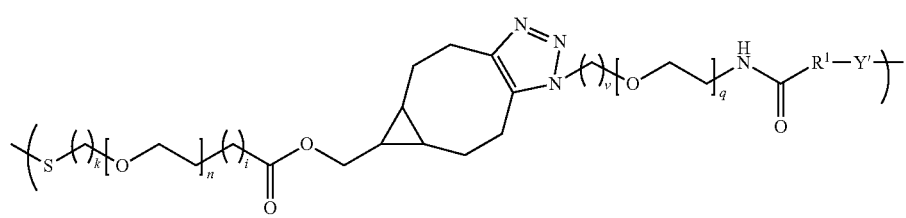
Yq'

Yr'
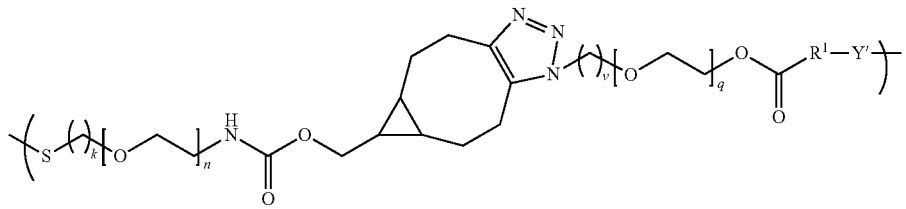

wherein the variables (e.g., i, k, n, q, v, $R^1$, Y', etc.) are as disclosed elsewhere herein. For example, in several embodiments, n is an integer greater than or equal to about: 1, 2, 3, 4, 5, 10, 15, 20, 30, 40, 50, or ranges including and/or spanning the aforementioned values. In several embodiments, q is an integer greater than or equal to about: 1, 2, 3, 4, 5, 10, 15, 20, 30, 40, 50, 75, 100, 150, or ranges including and/or spanning the aforementioned values. In several embodiments, k is an integer greater than or equal to about: 1, 2, 3, 4, 5, 10, 15, 20, or ranges including and/or spanning the aforementioned values. In several embodiments, v is an integer greater than or equal to about: 1, 2, 3, 4, 5, 10, 15, 20, or ranges including and/or spanning the aforementioned values. In several embodiments, k is 2. In several embodiments, v is 2. In several embodiments, n is 4. In several embodiments, n is 43 or 44. In several embodiments, q is 3. In several embodiments, $R_1$ is —$CH_2$—, —$(CH_2)_2$—C($CH_3$)(CN)—, —$(CH_2)_2$—C($CH_3$)($CH_3$)—, —$(CH_2)_2$—CH($CH_3$)— or —CH($CH_3$)—. In some embodiments, Y' is a random copolymer or block copolymer of $W^1$ and $W^2$ having p repeat units of $W^1$ and r repeat units of $W^2$.

In some embodiments, —[Y(Z)$_p$]— can be represented by any one or more of Formula Ya to Yr:

Ya
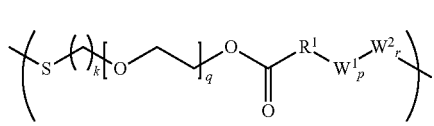

Yb
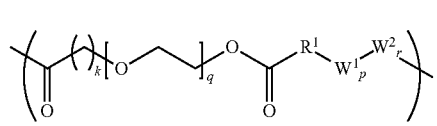

Yc
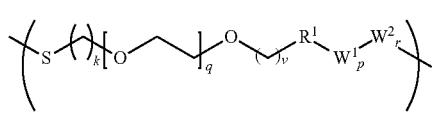

Yd
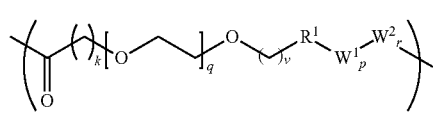

Ye
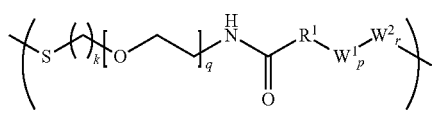

Yf
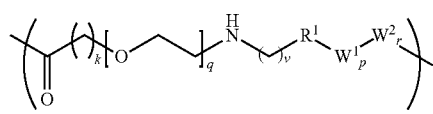

Yg
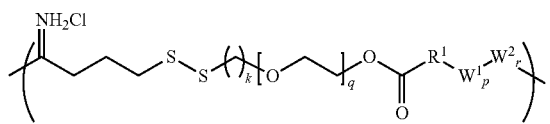

Yh
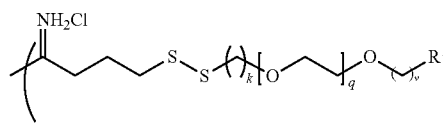

Yi
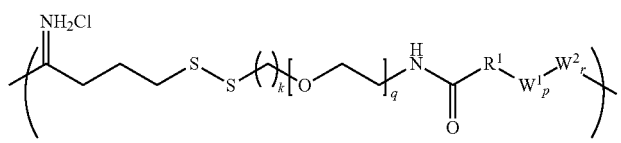

Yj
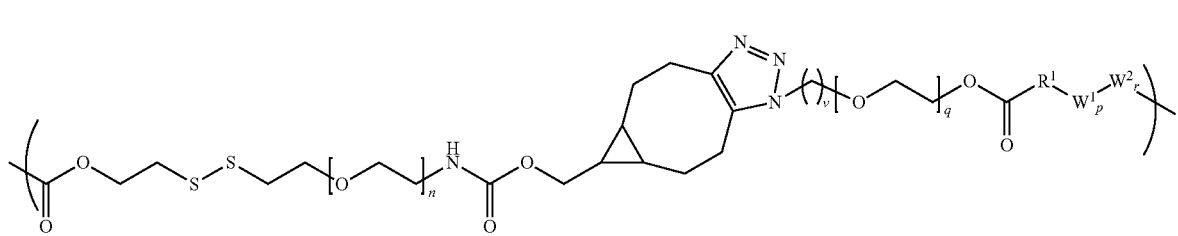

Yk
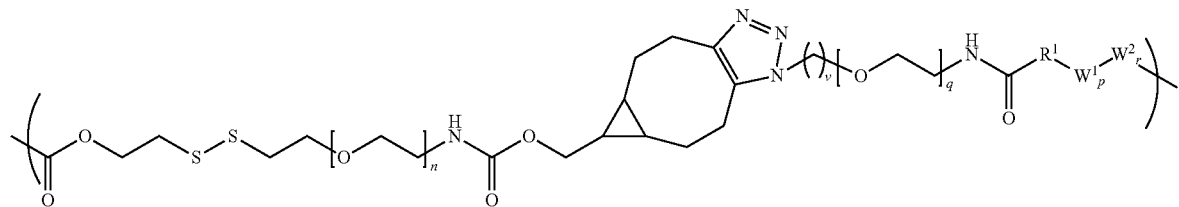
Yl
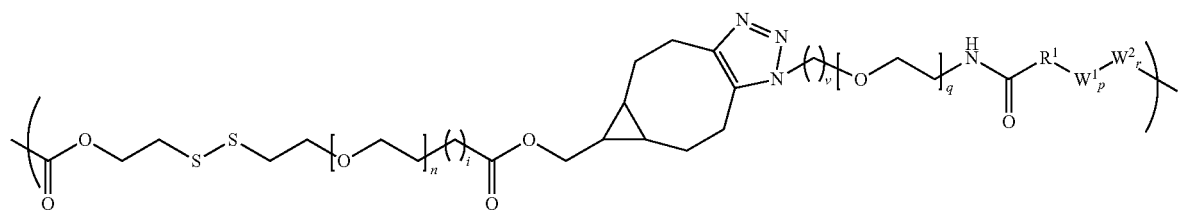
Ym
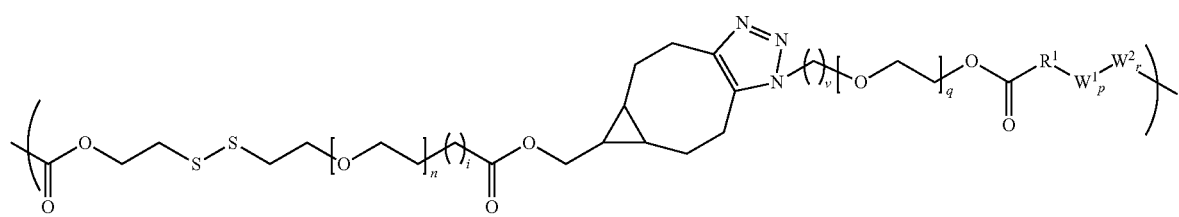
Yn
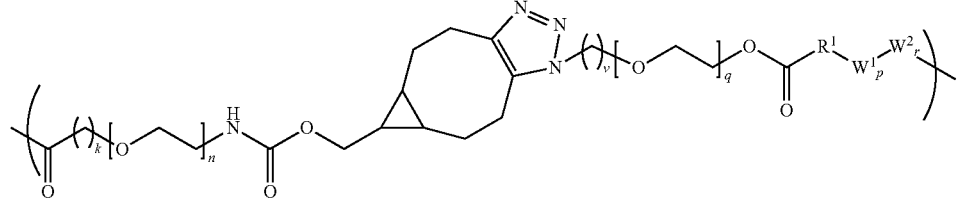
Yo
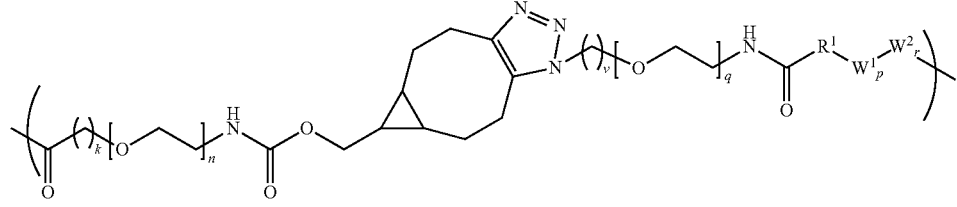
Yp
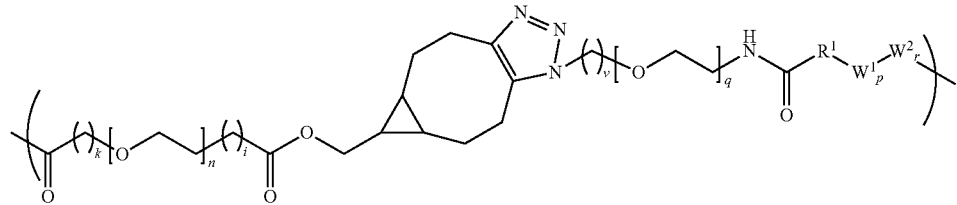
Yq
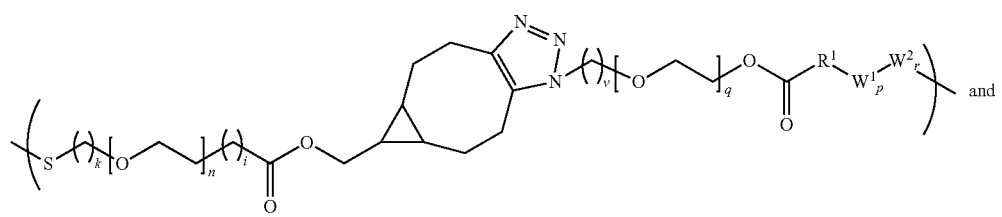
and

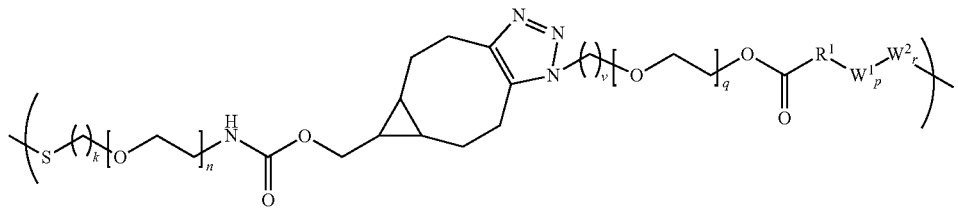

Yr where the variables (e.g., i, k, n, q, v, $R^1$, —$W^1$—, —$W^2$—, p, r, etc.) are as disclosed elsewhere herein. For instance, in some embodiments, the left, opening parentheses "("signifies the location of the bond between X and Y, the right, closing parentheses")" signifies the location of the bond between Y and $R^2$, n is an integer from 1 to 100, q is an integer from 1 to 44, k is an integer from 1 to 12, i is an integer from 0 to 20, v is an integer from 1 to 4, $R_1$ is —$CH_2$—, —$(CH_2)_2$—$C(CH_3)(CN)$—, —$(CH_2)_2$—$C(CH_3)(CH_3)$—, —$(CH_2)_2$—$CH(CH_3)$— or —$CH(CH_3)$—, $W^1$ and $W^2$ are as depicted below:

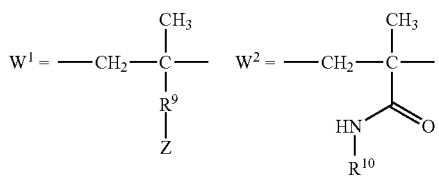

where Z is galactose and/or glucose and/or a galactose and/or glucose receptor-targeting moiety, $R^9$ is a direct bond, —C(O)—NH—$(CH_2)_2$—, or —C(O)—NH—$(CH_2)_2$—(O—$CH_2$—$CH_2)_t$—, t is an integer from 1 to 5, p is an integer from 2 to 250, $R^{10}$ is an aliphatic group, an alcohol, an aliphatic amine-containing group, or an aliphatic alcohol, and r is an integer from 0 to 250. In some embodiments, $R^{10}$ is a $C_f$alkyl or $C_f$alkyl$OH_g$, where f represents the number of carbons in the alkyl group and is an integer between 0 and 10, and g represents the number of hydroxyl groups present on the alkyl group and is an integer between 0 and 10. In some embodiments, $R^{10}$ is 2-hydroxyethyl. In some aspects —$W^1_p$—$W^2_r$— represents a block copolymer or a random copolymer of $W^1$ and $W^2$ monomers.

In several embodiments, as shown elsewhere herein, the targeting portion comprises one or more pendant liver targeting moieties decorating a portion of the linker. In several embodiments, the portion of the linker is a polymeric chain with pendant targeting agents attached randomly or in blocks along the chain. In some embodiments, the polymeric chain comprises an acrylate portion (e.g., acrylate polymers and/or acrylate copolymers). In several embodiments, the acrylate portion comprises an acrylate unit comprising a pendant liver targeting agent. In several embodiments, the acrylate portion further comprises an acrylate unit not comprising a pendant liver targeting agent.

In some embodiments, Y is a linker resulting from one or more reactions involving at least one of the following: N-hydroxysuccinamidyl (NHS) linker, NHS ester linker, PEG linker, maleimide linker, vinylsulfone linker, pyridyl di-thiol-poly(ethylene glycol) linker, pyridyl di-thiol linker, n-nitrophenyl carbonate linker, or a nitrophenoxy poly(ethylene glycol)ester linker. The linker may have one or more galactose and/or glucose moieties and/or galactose and/or glucose receptor-targeting moieties bound to it. In embodiments, Y comprises an antibody, an antibody fragment, a peptide, or a disulfanyl ethyl ester to which one or more galactose and/or glucose moieties and/or galactose and/or glucose receptor-targeting moieties are bound.

In some embodiments, —[Y(—Z)$_p$]— comprises one of the following structures:

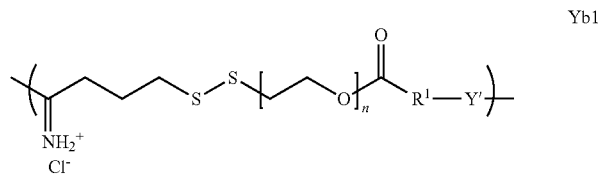

Yb1

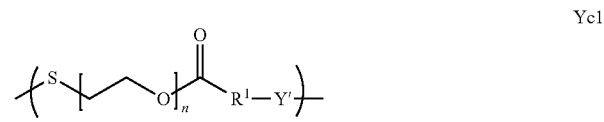

Yc1

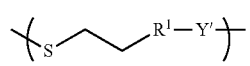

Yd1

Ye1

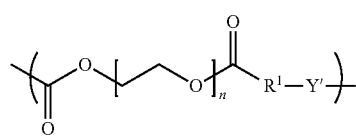

Yf1

Yg1

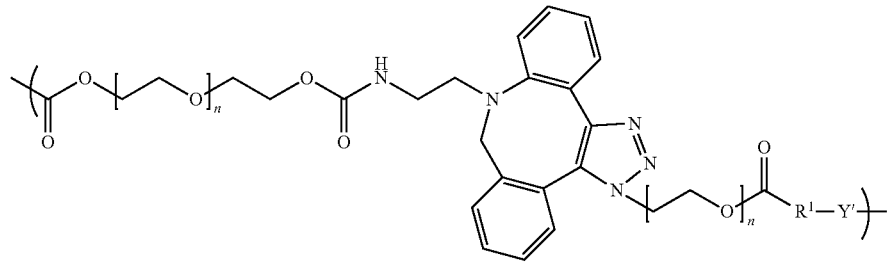
Yh1
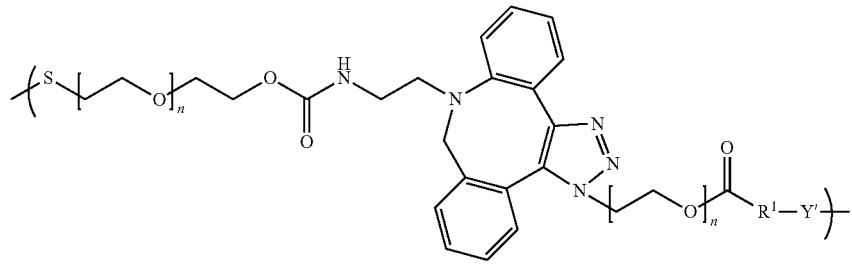
Yi1
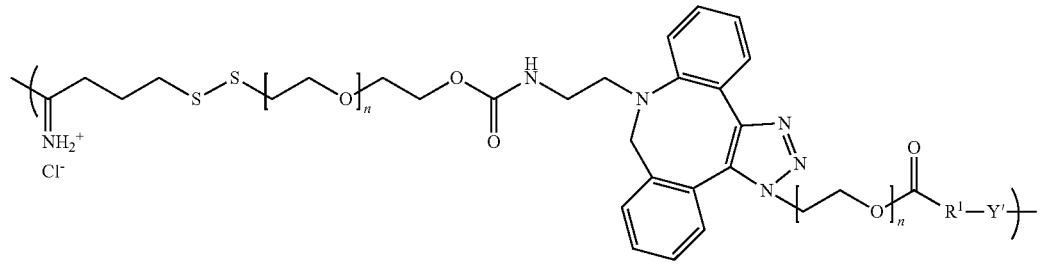
Yj1
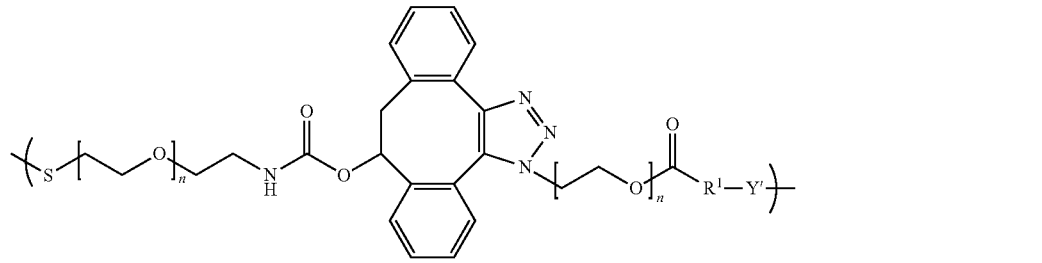
Yk1
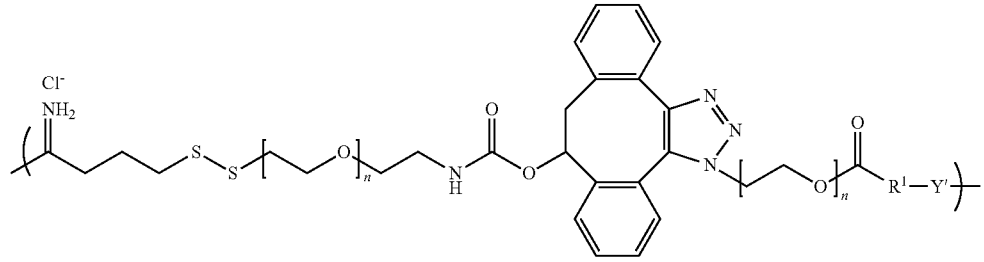
YL1
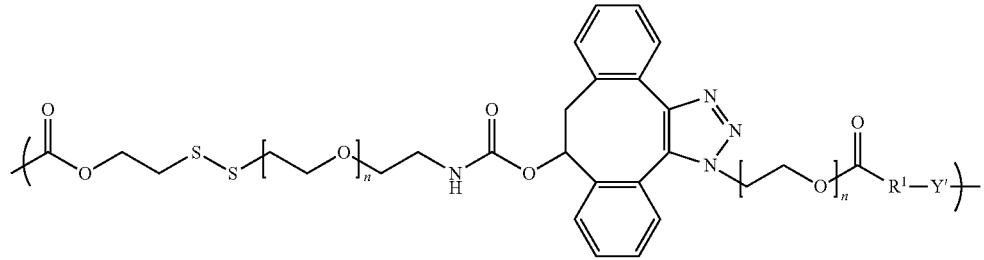
Ym1

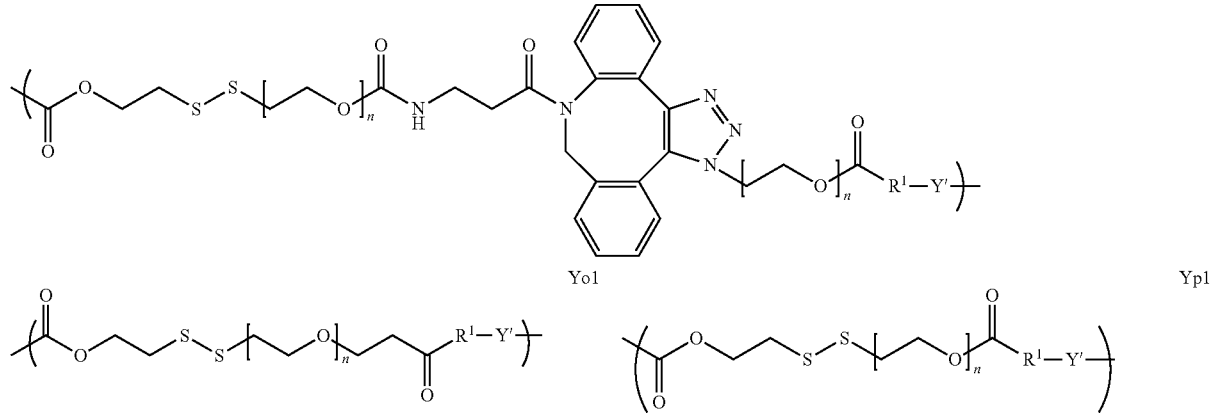

where the variables are as disclosed elsewhere herein.

In some embodiments, other linker structures can be found in U.S. application Publication Nos. U.S. 2017/0007708A1 and 2016/0243248A1 and International Publication No. WO 2017/046652, each of which is incorporated by reference in their entireties.

Targeting

According to several embodiments, targeting of compositions disclosed herein to the liver is accomplished by one or more types of moiety that binds to receptors on liver cells (or a subtype of liver cell). For example, in several embodiments, a galactosylating moiety (e.g., galactose, galactoseamine and N-acetylgalactosamine) is used. In several embodiments, such a moiety can be conjugated to a linker at any of the carbon molecules of the sugar. However, in several embodiments, conjugation at C1, C2 or C6 is preferred. For example, in several embodiments, a glucosylating moiety (e.g., glucose, glucoseamine and N-acetylglucosamine) is used. In several embodiments, such a moiety can be conjugated to a linker at any of the carbon molecules of the sugar. However, in several embodiments, conjugation at C1, C2 or C6 is preferred. Combinations of glucose and galactose-based moieties may also be used, depending on the embodiment. In several embodiments, specific ratios of glucose-based to galactose-based moieties are used, for example, about 500:1, about 250:1, about 100:1, about 50:1, about 25:1, about 10:1, about 5:1, about 2:1, about 1:1, about 1:2, about 1:5, about 1:10, about 1:25, about 1:50 about 1:100, about 1:250, about 1:500, and any ratio in between those listed, including endpoints. In additional embodiments, a polypeptide for which such liver-targeting is desired can be de-sialylated to facilitate targeting. Depending on the embodiment, the galactosylating or glucosylating moiety can be chemically conjugated or recombinantly fused to an antigen, whereas desialylation exposes a galactose-like moiety on an antigen polypeptide.

In several embodiments, various ratios of $W^1$ to $W^2$ are used. In some embodiments, a majority of Y' repeat units comprise $W^1$. In some embodiments, the ratio of $W^1$ to $W^2$ is equal to or greater than about about 50:1, about 25:1, about 10:1, about 5:1, about 4:1, about 2:1, about 1:1, about 1:2, about 1:4, about 1:5, about 1:10, about 1:25, about 1:50, and any ratio in between those listed, including endpoints. In some embodiments, the ratio of p to r is equal to or greater than about about 50:1, about 25:1, about 10:1, about 5:1, about 4:1, about 2:1, about 1:1, about 1:2, about 1:4, about 1:5, about 1:10, about 1:25, about 1:50, and any ratio in between those listed, including endpoints. In some embodiments, a homopolymer of $W^1$ is provided without a $W^2$ portion.

Antigens

In some embodiments, the antigen employed as X in the compositions of Formula 1 can be a protein or a peptide, e.g. the antigen may be a complete or partial therapeutic agent, a full-length transplant protein or peptide thereof, a full-length autoantigen or peptide thereof, a full-length allergen or peptide thereof, and/or a nucleic acid, or a mimetic of an aforementioned antigen. In some embodiments, one or more antigens employed as X are any one or more of the antigens as disclosed elsewhere herein. Combinations of multiple fragments may also be used, depending on the embodiment. For example, if a longer peptide identified as P has antigenic regions A, B, C, and D, compositions disclosed herein for induction of tolerance to P can comprise any combination of A, B, C, and D, and repeats of any of A, B, C, and D. Moreover, if several peptides are associated with an immune response, for example P2, P3, and P4, each comprising respective antigenic regions A, B, C, and D (e.g., P2A, P2B, P2C, and P2D), the compositions disclosed herein for induction of immune tolerance can comprise any combination of such regions, for example, P2A, P3B, P4C, P2D, etc. A listing of any particular antigen in a category or association with any particular disease or reaction does not preclude that antigen from being considered part of another category or associated with another disease or reaction. Immune tolerance can be induced against a variety of antigens, based on the disclosure provided herein. For example, the antigen can be endogenous (e.g., a self-antigen) or exogenous (e.g., a foreign antigen), including but not limited to: a foreign transplant antigen against which transplant recipients develop an unwanted immune response (e.g., transplant rejection), a foreign food, animal, plant or environmental antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease), or a tolerogenic portion (e.g., a fragment or an epitope) thereof.

Additional embodiments include antigens that are therapeutic proteins, such as asparaginase, uricase, rasburicase, and the like, and blood clotting factors, including but not limited to Factor VII, VIII, IX, etc. In several embodiments, the antigen is a self-antigen that is implicated in, for example, an auto-immune disease. For example, in several embodiments the antigen is selected from: insulin, proinsulin, preproinsulin, glutamic acid decarboxylase-65 (GAD-65 or glutamate decarboxylase 2), GAD-67, glucose-6 phosphatase 2 (IGRP or islet-specific glucose 6 phosphatase catalytic subunit related protein), insulinoma-associated protein 2 (IA-2), and insulinoma-associated protein 2β (IA-2β). Additional embodiments include use of antigens including myelin basic protein ("MBP"), myelin oligodendrocyte glycoprotein ("MOG") or myelin proteolipid protein ("PLP"). Additionally, in several embodiments, combinations of antigens may be used, depending on the embodiment, for example if multiple antigens are implicated in an immune response. Likewise, fragments (e.g., immunogenic portions) of any antigen listed can also be used in several embodiments as well as combinations of fragments, e.g., a fragment of a first, a fragment of a second, and a fragment of a third antigen of interest.

Antigens employed in the practice of the present disclosure can be one or more of the following. In several embodiments, the antigen comprises one or more therapeutic agents that are proteins, peptides, antibodies and antibody-like molecules, including antibody fragments and fusion proteins with antibodies and antibody fragments. These include human, non-human (such as mouse) and non-natural (e.g., engineered) proteins, antibodies, chimeric antibodies, humanized antibodies, and non-antibody binding scaffolds, such as fibronectins, DARPins, knottins, and the like. In several embodiments, human allograft transplantation antigens against which transplant recipients develop an unwanted immune response are used. In several embodiments, the antigen comprises one or more self-antigens that cause an unwanted autoimmune response. While self-antigens are of an endogenous origin in an autoimmune disease patient, according to several embodiments, the polypeptides employed in certain embodiments are synthesized exogenously (as opposed to being purified and concentrated from a source of origin).

In several embodiments, the antigen to which tolerance is desired comprises one or more foreign antigens, such as food, animal, plant and environmental antigens, against which a patient experiences an unwanted immune response. While a therapeutic protein can also be considered a foreign antigen due to its exogenous origin, for purposes of clarity in the description of the present disclosure such therapeutics are described as a separate group. Similarly, a plant or an animal antigen can be eaten and considered a food antigen, and an environmental antigen may originate from a plant. They are, however, all foreign antigens. In the interest of simplicity no attempt will be made to describe distinguish and define all of such potentially overlapping groups, as those skilled in the art can appreciate the antigens that can be employed in the compositions of the disclosure, particularly in light of the detailed description and examples.

In several embodiments, X is selected from the group consisting of insulin, proinsulin, preproinsulin, gluten, gliadin, myelin basic protein, myelin oligodendrocyte glycoprotein and proteolipid protein, Factor VIII, Factor IX, asparaginase, uricase and fragments of any of the preceding. In several embodiments, the antigen X is not a full length protein. For example, in some embodiments, the antigen is not full length gliadin, insulin, or proinsulin. In several embodiments, the antigen X is not a fragment of a protein. As discussed in more detail below, there exist a variety of antigens to which tolerance may be desired. These may include, but are not limited to, exogenous antigens that result in an adverse immune response when a subject is exposed to the antigen. In several embodiments, the adverse immune response could be a result of ingestion of the antigen, e.g., orally or nasally, or via some other mucosal route. These routes could be the case, for example, with food antigens. In some embodiments, the antigen may be purposefully administered to a subject, for example, with the administration of a therapeutic composition to treat a disease or condition that the subject is affected by. In still additional embodiments, the antigen may be produced by the subject, e.g., an auto-immune antigen. For example, in several embodiments, X comprises a foreign transplant antigen against which transplant recipients develop an unwanted immune response or a tolerogenic portion thereof. In several embodiments, X comprises a foreign food, animal, plant or environmental antigen against which patients develop an unwanted immune response or a tolerogenic portion thereof. In several embodiments, X comprises a foreign therapeutic agent against which patients develop an unwanted immune response or a tolerogenic portion thereof. In several embodiments, X comprises a synthetic self-antigen against the endogenous version of which patients develop an unwanted immune response or a tolerogenic portion thereof.

In further detail to the above, there are provided in several embodiments, compounds where X is a food antigen. In some such embodiments, X is one or more of conarachin (Ara h 1), allergen II (Ara h 2), arachis agglutinin, conglutin (Ara h 6), a-lactalbumin (ALA), lactotransferrin, Pen a 1 allergen (Pen a 1), allergen Pen m 2 (Pen m 2), tropomyosin fast isoform, high molecular weight glutenin, low molecular weight glutenin, alpha-gliadin, gamma-gliadin, omega-gliadin, hordein, seclain, and avenin. Fragments of any of these antigens and/or mimotopes of any of these antigens are also used, in several embodiments. In several embodiments, X is selected from the group consisting of gluten, high molecular weight glutenin, low molecular weight glutenin, alpha-gliadin, gamma-gliadin, omega-gliadin, hordein, seclain, and avenin and fragments thereof. In several embodiments, X is selected from the group consisting of gluten, high molecular weight glutenin, low molecular weight glutenin, alpha-gliadin, gamma-gliadin, and omega-gliadin and fragments thereof. In several embodiments, X is gluten or fragment thereof. In several embodiments, X is gliadin or fragment thereof. In several embodiments, X comprises LQLQPFPQPELPYPQPELPYPQPELPYPQPQPF (SEQ ID NO. 21). In one embodiment, X comprises PQPELPY (SEQ ID NO:47).

In several embodiments, there are provided compounds where X is a therapeutic agent. In several embodiments, there are provided compounds where X is a therapeutic protein, or immunogenic fragment thereof. In several embodiments, X is selected from the group consisting of Factor VII, Factor IX, asparaginase, and uricase, or fragments of any such therapeutic proteins. In several embodiments, X is a therapeutic agent selected from the group consisting of Factor VII and Factor IX and fragments thereof. In several embodiments, X is a therapeutic agent selected from the group consisting of Factor VIII or fragment thereof. In several embodiments, when X is a therapeutic agent, the compound can be used in the treatment, prevention, reduction, or otherwise amelioration of an immune response developed against a therapeutic agent for hemophilia. As discussed herein, mimotopes of any antigenic portion of the antigens above can be used in several embodiments.

In several embodiments, X comprises asparaginase or a fragment thereof. In several embodiments, X comprises uricase or a fragment thereof. In several such embodiments, the compound can be used in the treatment, prevention, reduction, or otherwise amelioration of an immune response developed against an anti-neoplastic agent. As discussed herein, mimotopes of any antigenic portion of the antigens above can be used in several embodiments.

In several embodiments, X is associated with an autoimmune disease. In several embodiments, the antigen is a self-antigen that is implicated in, for example, an autoimmune disease. For example, in several embodiments, the associated autoimmune disease is one or more of Type I diabetes, multiple sclerosis, rheumatoid arthritis, Parkinson's Disease, vitiligo, uveitis, pemphis vulgaris and neuromyelitis optica.

In several embodiments, the autoimmune disease is Type I diabetes and X comprises insulin or a fragment thereof. In several embodiments, the autoimmune disease is Type I diabetes and X comprises proinsulin or a fragment thereof. In several embodiments, X comprises FVNQHLCGSHLVEALYLVCGERGFFYTPKTRREAEDLQVGQVELGGGPGAGSLQPL ALEGSLQKRGIVEQCCTSICSLYQLENYCN (SEQ ID NO: 48). In several embodiments, X comprises FVNQHLCGSHLVEALYLVCGERGFFYTPKTRREAEDLQVGQVELGGGPGAGSLQPL ALEGSLQKRGIVEQ (SEQ ID NO: 49). In several embodiments, X comprises SHLVEALYLVCGERGFFYTPKTRREAEDLQVGQVELGGGPGAGSLQPLALEGSLQK RGIVEQ (SEQ ID NO: 50). In several embodiments, X comprises SHLVEALYLVCGERGFFYTPKTRREAEDLQ (SEQ ID NO. 51). In several embodiments, X comprises FVNQHLCGSHLVEALYLVCGERGFFYTPKTRREAEDLQ (SEQ ID NO: 52). In several embodiments, X comprises SHLVEALYLVCGERG (SEQ ID NO: 53). In several embodiments, X comprises GGGPGAGSLQPLALEGSLQKRGIVEQC (SEQ ID NO: XXX). In several embodiments, X comprises LALEGSLQKRG (SEQ ID NO: 55). In several embodiments, X comprises GSLQPLALEGSLQKRGIV (SEQ ID NO: 56). In several embodiments, X comprises GGGPGAGSLQPLALEGSLQK (SEQ ID NO: 57). In several embodiments, X comprises SHLVEALYLVCGERGFFYTPKTRREAED (SEQ ID NO: 58). In several embodiments, X comprises QPLALEGSLQKRGIVEQ (SEQ ID NO: 59). In several embodiments, X comprises MALWMRLLPLLALLALWGPDPAAAFVNQHLCGSHLVEALYLVCGERGFFYTPKTR REAEDLQVGQVELGGGPGAGSLQPLALEGSLQKRGIVEQCCTSICSLYQLENYCN (SEQ ID NO: 60). In several embodiments, the autoimmune disease is Type I diabetes and X comprises preproinsulin or a fragment thereof. In several embodiments, the autoimmune disease is Type I diabetes and X comprises glutamic acid decarboxylase-65 (GAD-65 or glutamate decarboxylase 2 or a fragment thereof. In several embodiments, the autoimmune disease is Type I diabetes and X comprises GAD-67 or a fragment thereof. In several embodiments, the autoimmune disease is Type I diabetes and X comprises glucose-6 phosphatase 2 (IGRP or islet-specific glucose 6 phosphatase catalytic subunit related protein) or a fragment thereof. In several embodiments, the autoimmune disease is Type I diabetes and X comprises insulinoma-associated protein 2 (IA-2), or a fragment thereof. In several embodiments, the autoimmune disease is Type I diabetes and X comprises insulinoma-associated protein 2P (IA-2β) or a fragment thereof. In several embodiments, X is selected from one or more of SEQ ID NOS: 61-66. In several embodiments, X is associated with Type 1 diabetes and is selected from one or more of SEQ ID NOS: 67-71. As discussed herein, mimotopes of any antigenic portion of the antigens above can be used in several embodiments. In several embodiments, combinations of these antigens can be incorporated into the tolerogenic compound which may aid in reducing immune responses to self-antigens at multiple points along the insulin pathway.

In several embodiments, the autoimmune disease is multiple sclerosis and X comprises myelin basic protein or a fragment thereof. In several embodiments, the autoimmune disease is multiple sclerosis and X comprises myelin oligodendrocyte glycoprotein or a fragment thereof. In several embodiments, the autoimmune disease is multiple sclerosis and X comprises proteolipid protein or a fragment thereof. As discussed herein, mimotopes of any antigenic portion of the antigens above can be used in several embodiments. In several embodiments, combinations of these antigens can be incorporated into the tolerogenic compound (e.g., a mixture of antigens or fragments of MOG, MBP and/or PLP) which may aid in reducing immune responses to self-antigens at multiple points along the enzymatic pathways that control myelination or myelin repair. In several embodiments, X comprises a portion of proteolipid protein comprising HCLGKWLGHPDKFVGI (SEQ ID NO: 24). In several embodiments, X comprises a polypeptide derived from myelin basic protein comprising GCRGQRHGSKYLATASTMDHARHGFLPRH (SEQ ID NO: 26). In several embodiments, X comprises a polypeptide derived from myelin basic protein comprising GCRGQRHGSKYLATASTMDHARHGFLPRHXXXX (SEQ ID NO: 27), wherein each X represents any amino acid, and each X optionally represents a plurality of amino acids. In several embodiments, X comprises a polypeptide derived from myelin basic protein comprising ENPVVHFFKNIVTPRTP (SEQ ID NO: 28). In several embodiments, X comprises a polypeptide derived from myelin basic protein comprising ENPVVHFFKNIVTPRTPPPSQGKCG (SEQ ID NO: 29). In several embodiments, X comprises a polypeptide derived from myelin basic protein comprising XXXXENPVVHFFKNIVTPRTPPPSQGKCG (SEQ ID NO: 30), wherein each X represents any amino acid, and each X optionally represents a plurality of amino acids. In several embodiments, X comprises a polypeptide derived from myelin basic protein comprising LSRFSWGAEGQRPGFGYGG (SEQ ID NO: 31). In several embodiments, X comprises a polypeptide derived from myelin basic protein comprising LSRFSWGAEGQRPGFGYGGRCG (SEQ ID NO: 32). In several embodiments, X comprises a polypeptide derived from myelin basic protein comprising SLSRFSWGAEGQRPGFGYGGRCG (SEQ ID NO: 33). In several embodiments, X comprises a polypeptide derived from myelin basic protein (or peptides in combination) comprising ENPVVHFFKNIVTPRTPPPSQGKGRGLSLSRF- SWGAEGQRPGFGYGGRCG (SEQ ID NO: 34). In several embodiments, X comprises a polypeptide derived from myelin basic protein (or peptides in combination) comprising GRTQDENPVVHFFKNIVTPR TPPPSQGKGRGLSLSRFSWGAEGQRPGFGYGGRCG (SEQ ID NO: 35). In several embodiments, X comprises a polypeptide derived from myelin basic protein (or peptides in combination) comprising GRTQDENPVVHFFKNIVTPRTPPPSQGKGRGLSLSRFSWG AEGQRPGFGYGGXXXXRCG (SEQ ID NO: 36), wherein each X represents any amino acid, and each X optionally represents a plurality of amino acids. In several embodiments, X comprises a polypeptide derived from myelin basic protein comprising AQGTLSKIFK LGGRDSRSGSPMARR (SEQ ID NO: 37). In several embodiments, X comprises a polypeptide derived from myelin basic protein comprising AQGTLSKIFKLG- GRDSRSGSPMARRCG (SEQ ID NO: 38). In several embodiments, X comprises a polypeptide derived from myelin basic protein comprising XXXXAQGTLSKIFKLG-GRDSRSGSPMARRCG (SEQ ID NO: 39), wherein each X represents any amino acid, and each X optionally represents a plurality of amino acids. In several embodiments, X comprises a polypeptide derived from myelin oligodendrocyte glycoprotein comprising GQFRVIGPRHPIRAL-VGDEV (SEQ ID NO: 40). In several embodiments, X comprises a polypeptide derived from myelin oligodendrocyte glycoprotein comprising GQFRVIGPRHPI-RALVGDEVELPCRIS (SEQ ID NO: 41). In several embodiments, X comprises a polypeptide derived from myelin oligodendrocyte glycoprotein comprising GCRGKNATGMEVGWYRPPFSRVVHLYRNGKXXXX (SEQ ID NO: 42), wherein each X represents any amino acid, and each X optionally represents a plurality of amino acids. In several embodiments, X comprises a polypeptide derived from myelin oligodendrocyte glycoprotein comprising XXXXGCRGKNATGMEVGWYRPPFSRVVH-LYRNGKXXXX (SEQ ID NO: 43), wherein each X represents any amino acid, and each X optionally represents a plurality of amino acids. In several embodiments, X comprises a polypeptide derived from myelin oligodendrocyte glycoprotein (or combination of polypeptides) comprising GQFRVIGPRHPIRALVGDEVELPCRISPGKNATG-MEVGWYRPPFSRVVHLYRNGK (SEQ ID NO: 44). In several embodiments, X comprises a polypeptide derived from myelin oligodendrocyte glycoprotein (or combination of polypeptides) comprising XXXXGQFRVIGPRHPI-RALVGDEVELPCRISPGKNATGMEVGWYRPPF-SRVVHLYR NGK (SEQ ID NO: 45) wherein each X represents any amino acid, and each X optionally represents a plurality of amino acids. In several embodiments, X comprises a polypeptide derived from myelin oligodendrocyte glycoprotein (or combination of polypeptides) comprising GQFRVIGPRHPIRALVGDEVELPCRISPGKNATG-MEVGWYRPPFSRVVHLYRNGKX XXX (SEQ ID NO: 46) wherein each X represents any amino acid, and each X optionally represents a plurality of amino acids.

In several embodiments, X can comprise a combination of any of the individual sequences provided for any antigen herein. For example, in several embodiments, X comprises GQFRVIGPRHPIRALVGDEVELPCRISPGKNATG-MEVGWYRPPFSRVVHL YRNGKDQDGDQA (SEQ ID NO: 72) and is for developing tolerance in multiple sclerosis. In several embodiments, X comprises QRHGSKY-LATASTMDHARHGFLPRHRDTGILD (SEQ ID NO: 73) and is for developing tolerance in multiple sclerosis. In several embodiments, X comprises SHGRTQDEN-PVVHFFKNIVTPRTPPPSQGKGRGLSLSRFSWGAE-GQRPGFGYGGRAS DYKSAHKGFKGVDAQGTL-SKIFKLGGRDSRSGSPMARR (SEQ ID NO: 74) and is for developing tolerance in multiple sclerosis. In several embodiments, X comprises HCLGKWLGHPDKFVGI (SEQ ID NO: 75) and is for developing tolerance in multiple sclerosis.

In several embodiments, compounds provided herein are configured to comprise multiple antigens relevant to a particular disease or antigen to which an immune tolerance response is desired. For example, in several embodiments, a plurality of antigens of interest, generically referred to as A, B, C, and D, can in several embodiments, be configured as a complex of antigens comprising A-B-C-D, A-C-D-B, C-D-B-A, or any other configuration of such antigens. In several embodiments, the antigens are separated, for example by a linker or a polymer, such that the compound comprises, for example, A-linker-B-linker-C-linker-D, or B-polymer-A-polymer-C-polymer-D, and the like. Additionally, in polymeric containing compounds, there may be a polymer that comprises various antigens at different positions along the polymeric backbone.

In several embodiments, the autoimmune disease is Parkinson's Disease and X comprises alpha synuclein or a fragment thereof. In several embodiments, X comprises MDVFMKGLSKAKEGVVAAAEKTKQGVAEAAGK-TKEGVLYV GSKTKEGVVHGVATVAEKTKEQVTN-VGGAVVTGVTAVAQKTVEGAGSIAAATGFV KKDQLGKNEEGAPQEGILEDMPVDPDNEAYEMPSE-EGYQDYEPEA (SEQ ID NO: 76). In several embodiments, X comprises GKTKEGVLYVGSKTKEGVVHGVAT-VAEKTKEQVTNVGGAVVTGVTAVAQKTVEG AGSIAAATGFVKKDQLGKNEEGAPQEGILEDMPVD-PDNEAYEMPSE EGYQDYEPEA (SEQ ID NO: 77). In several embodiments, X comprises KTKEGVLYVG-SKTKEGVVHGVATVAEKTKEQVTNVGGAV- VTGVT-AVAQKTVEGA GSIAAATGFVKKDQLGKNEEGAPQE-GILEDMPVDPDNEAYEMPSEEGYQDYEPEA (SEQ ID NO: 78). In several embodiments, X comprises TKEGVLY-VGSKTKEGVVHGVATVAEKTKEQVTNVGGAVVT-GVTAVAQKTVEGAG SIAAATGFVKKDQLGKNEEG-APQEGILEDMPVDPDNEAYEMPSEEGYQDYEPEA (SEQ ID NO: 79). In several embodiments, X comprises TKEGVVHGVATVAEKTKEQVTNVGGAVVTGVTA-VAQKTVEGAGSIAAATGFVKK DQLGKNEEGAPQEG-ILEDMPVDPDNEAYEMPSEEGYQDYEPEA (SEQ ID NO: 80). In several embodiments, X comprises QVTNVG-GAVVTGVTAVAQKTVEGAGS IAAATGFVKKDQLGK-NEEGAPQEGILEDM PVDPDNEAYEMPSEEGYQDYE-PEA (SEQ ID NO: 81). In several embodiments, X comprises VTNVGGAVVTGVTAVAQKTVEGAGS IAAATGFVKKDQLGKNEEGAPQEGILEDMP VDPD-NEAYEMPSEEGYQDYEPEA (SEQ ID NO: 82). In several embodiments, X comprises LGKNEEGAPQEG-ILEDMPVDPDNEAYEMPSEEGYQDYEPEA (SEQ ID NO: 83). In several embodiments, X comprises GGAVVTGVTAVAQKTVEGAGSIAAATGFVKKDQL (SEQ ID NO: 84). In several embodiments, X comprises MPVDPDNEAYEMPSEEGYQDYEPEA (SEQ ID NO: 85). In several embodiments, X comprises MPVDPD-NEAYEMPSE (SEQ ID NO: 86). In several embodiments, X comprises EMPSEEGYQDYEPEA (SEQ ID NO: 87). In several embodiments, X comprises DNEAYEMPSE-EGYQD (SEQ ID NO: 88). In several embodiments, X comprises GKTKEGVLYVGSKTKEGVVH (SEQ ID NO: 89). In several embodiments, X comprises GVLYVG-SKTKEGVVH (SEQ ID NO: 90). In several embodiments, X comprises GKTKEGVLYVGSKTK (SEQ ID NO: 91) or GKTKEGVLYVGSKT (SEQ ID NO:92). In several embodiments, X comprises KTKEGVLYVGSKTKE (SEQ ID NO: XXX). In several embodiments, X comprises KTKEGVLYVGSKTKE (SEQ ID NO: 93). In several embodiments, X comprises GVLYVGSKTK (SEQ ID NO: 94). In several embodiments, X comprises KTKEGVLYV (SEQ ID NO: 95). In several embodiments, X comprises VDPDNEAYE (SEQ ID NO: 96). In several embodiments, X comprises MDVFMKGLSKAKEGVVAAAEKTKQG-VAEAAGKTKEGVLYVGSKTKEGVVHGVA TVAEKT-KEQVTNVGGAVVTGVTAVAQKTVEGAGSIAAATG-FVKKDQLGKNEEGAP QEGILEDMPVDPDNEAYEMP-SEEGYQD (SEQ ID NO: 97). In several embodiments, X comprises MDVFMKGLSKAKEGVVAAAEKTKQGVA-EAAGKTKEGVLYVGSKTKEGVVHGVATVAEKTKE-QVTNVGGAVVTGVTAVAQKTVEGAGSIAAA- TGFVKKDQLGKNEEGAP QEGILEDMPVD (SEQ ID NO: 98). In several embodiments, X comprises MDVFMKGLSKAKEGVVAAAEKTKQGVAEAAGKTKEGVLYVGSKTKEGVVHGVA TVAEKTKEQVTNVGGAVVTGVTAVAQKTVEGAGSIAAATGFVKKDQLGKNEEGAP QEGILEDMPVDPDN (SEQ ID NO: 99). In several embodiments, X comprises MDVFMKGLSKAKEGVVAAAEKTKQGVAEAA (SEQ ID NO: 100). In several embodiments, X comprises MDVFMKGLSKAKEGVVAAAEKTKQGVAEAAGKTKEG (SEQ ID NO: 101). In several embodiments, X comprises TAVAQKTVEGAGSIAAATGFVKKDQLGKNEEGAPQE (SEQ ID NO: 102). In several embodiments, X comprises TAVAQKTVEGAGSIAAATGFVKKDQLGKNEEGAPQEGILEDMPVDPDNEAYEMPSE EGYQDYEPEA (SEQ ID NO: 103).

As discussed herein, mimotopes of any antigenic portion of the self-antigens above (or otherwise disclosed herein) can be used in several embodiments.

In several embodiments, the pharmaceutically acceptable composition consists of, or consists essentially of a compound wherein X is a food antigen, therapeutic agent, a self antigen, or fragment thereof, a linker Y, and a liver targeting moiety Z selected from glucose, galactose, glucosamine, galactosamine, N-acetylglucosamine, and N-acetylgalactosamine.

In the embodiments where the antigen is a therapeutic protein, peptide, antibody or antibody-like molecule, specific antigens can be selected from: Abatacept, Abciximab, Adalimumab, Adenosine deaminase, Ado-trastuzumab emtansine, Agalsidase alfa, Agalsidase beta, Aldeslukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin [including recombinant human insulin ("rHu insulin") and bovine insulin], Interferon-α2a, Interferon-α2b, Interferon-(β1a, Interferon-(β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Natalizumab, Octreotide, Ofatumumab, Oprelvekin, Pancreatic amylase, Pancreatic lipase, Papain, Peg-asparaginase, Peg-doxorubicin HCl, PEG-epoetin-β, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, vW factor. The therapeutic protein can be obtained from natural sources (e.g., concentrated and purified) or synthesized, e.g., recombinantly, and includes antibody therapeutics that are typically IgG monoclonal or fragments or fusions.

Particular therapeutic protein, peptide, antibody or antibody-like molecules include Abciximab, Adalimumab, Agalsidase alfa, Agalsidase beta, Aldeslukin, Alglucosidase alfa, Factor VIII, Factor IX, Infliximab, Insulin (including rHu Insulin), L-asparaginase, Laronidase, Natalizumab, Octreotide, Phenylalanine ammonia-lyase (PAL), or Rasburicase (uricase) and generally IgG monoclonal antibodies in their varying formats.

Another particular group includes the hemostatic agents (Factor VIII and IX), Insulin (including rHu Insulin), and the non-human therapeutics uricase, PAL and asparaginase.

Unwanted immune response in hematology and transplant includes autoimmune aplastic anemia, transplant rejection (generally), and Graft vs. Host Disease (bone marrow transplant rejection). In the embodiments where the antigen is a human allograft transplantation antigen, specific sequences can be selected from: subunits of the various MHC class I and MHC class II haplotype proteins (for example, donor/recipient differences identified in tissue cross-matching), and single-amino-acid polymorphisms on minor blood group antigens including RhCE, Kell, Kidd, Duffy and Ss. Such compositions can be prepared individually for a given donor/recipient pair.

In type 1 diabetes mellitus, several main antigens have been identified: insulin, proinsulin, preproinsulin, glutamic acid decarboxylase-65 (GAD-65 or glutamate decarboxylase 2), GAD-67, glucose-6 phosphatase (IGRP or islet-specific glucose 6 phosphatase catalytic subunit related protein), insulinoma-associated protein 2 (IA-2), and insulinoma-associated protein 2P (IA-2β); other antigens include ICA69, ICA12 (SOX-13), carboxypeptidase H, Imogen 38, GLIMA 38, chromogranin-A, HSP-60, carboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. It should be noted that insulin is an example of an antigen that can be characterized both as a self-antigen and a therapeutic protein antigen. For example, rHu Insulin and bovine insulin are therapeutic protein antigens (that are the subject of unwanted immune attack), whereas endogenous human insulin is a self-antigen (that is the subject of an unwanted immune attack). Because endogenous human insulin is not available to be employed in a pharmaceutical composition, a recombinant form is employed in certain embodiments of the compositions of the disclosure. Recombinant forms of certain of such self-antigens are used in several embodiments.

Human insulin, including an exogenously obtained form useful in the compositions of the disclosure, has the following sequence (UNIPROT P01308):

```
                                          (SEQ ID NO: 1)
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN.
```

GAD-65, including an exogenously obtained form useful in the compositions of the disclosure, has the following sequence (UNIPROT Q05329):

```
                                          (SEQ ID NO: 2)
MASPGSGFWS FGSEDGSGDS ENPGTARAWC QVAQKFTGGI

GNKLCALLYG DAEKPAESGG SQPPRAAARK AACACDQKPC

SCSKVDVNYA FLHATDLLPA CDGERPTLAF LQDVMNILLQ

YVVKSFDRST KVIDFHYPNE LLQEYNWELA DQPQNLEEIL

MHCQTTLKYA IKTGHPRYFN QLSTGLDMVG LAADWLTSTA
```

```
NTNMFTYEIA PVFVLLEYVT LKKMREIIGW PGGSGDGIFS

PGGAISNMYA MMIARFKMFP EVKEKGMAAL PRLIAFTSEH

SHFSLKKGAA ALGIGTDSVI LIKCDERGKM IPSDLERRIL

EAKQKGFVPF LVSATAGTTV YGAFDPLLAV ADICKKYKIW

MHVDAAWGGG LLMSRKHKWK LSGVERANSV TWNPHKMMGV

PLQCSALLVR EEGLMQNCNQ MHASYLFQQD KHYDLSYDTG

DKALQCGRHV DVFKLWLMWR AKGTTGFEAH VDKCLELAEY

LYNIIKNREG YEMVFDGKPQ HTNVCFWYIP PSLRTLEDNE

ERMSRLSKVA PVIKARMMEY GTTMVSYQPL GDKVNFFRMV

ISNPAATHQD IDFLIEEIER LGQDL.
```

IGRP, including an exogenously obtained form useful in the compositions of the disclosure, has the following sequence (UNIPROT QN9QR9):

```
                                      (SEQ ID NO: 3)
MDFLHRNGVLIIQHLQKDYRAYYTFLNFMSNVGDPRNIFFIYFPLCFQFN

QTVGTKMIWVAVIGDWLNLIFKWILFGHRPYWWVQETQIYPNHSSPCLEQ

FPTTCETGPGSPSGHAMGASCVWYVMVTAALSHTVCGMDKFSITLHRLTW

SFLWSVFWLIQISVCISRVFIATHFPHQVILGVIGGMLVAEAFEHTPGIQ

TASLGTYLKTNLFLFLFAVGFYLLLRVLNIDLLWSVPIAKKWCANPDWIH

IDTTPFAGLVRNLGVLFGLGFAINSEMFLLSCRGGNNYTLSFRLLCALTS

LTILQLYHFLQIPTHEEHLFYVLSFCKSASIPLTVVAFIPYSVHMLMKQS

GKKSQ.
```

In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor.

In Addison's Disease, main antigens include 21-hydroxylase, 17α-hydroxylase, and P450 side chain cleavage enzyme (P450scc); other antigens include ACTH receptor, P450c21 and P450c17.

In premature ovarian failure, main antigens include FSH receptor and α-enolase.

In autoimmune hypophysitis, or pituitary autoimmune disease, main antigens include pituitary gland-specific protein factor (PGSF) 1a and 2; another antigen is type 2 iodothyronine deiodinase.

In multiple sclerosis, main antigens include myelin basic protein ("MBP"), myelin oligodendrocyte glycoprotein ("MOG") and myelin proteolipid protein ("PLP").

MBP, including an exogenously obtained form useful in the compositions of the disclosure, has the following sequence (UNIPROT P02686):

```
                                      SEQ ID NO: 4)
MGNHAGKRELNAEKASTNSETNRGESEKKRNLGELSRTTSEDNEVFGEAD

ANQNNGTSSQDTAVTDSKRTADPKNAWQDAHPADPGSRPHLIRLFSRDAP

GREDNTFKDRPSESDELQTIQEDSAATSESILDVMASQKRPSQRHGSKYL

ATASTMDHARHGFLPRHRDTGILDSIGRFFGGDRGAPKRGSGKDSHHPAR

TAHYGSLPQKSHGRTQDENPVVHFFKNIVTPRTPPPSQGKGRGLSLSRFS

WGAEGQRPGFGYGGRASDYKSAHKGFKGVDAQGTLSKIFKLGGRDSRSGS

PMARR.
```

MOG, including an exogenously obtained form useful in the compositions of the disclosure, has the following sequence (UNIPROT Q16653):

```
                                      (SEQ ID NO: 5)
MASLSRPSLPSCLCSFLLLLLLQVSSSYAGQFRVIGPRHPIRALVGD

EVELPCRISPGKNATGMEVGWYRPPFSRVVHLYRNGKDQDGDQAPEYRGR

TELLKDAIGEGKVTLRIRNVRFSDEGGFTCFFRDHSYQEEAAMELKVEDP

FYWVSPGVLVLLAVLPVLLLQITVGLIFLCLQYRLRGKLRAEIENLHRTF

DPHFLRVPCWKITLFVIVPVLGPLVALIICYNWLHRRLAGQFLEELRNP

F.
```

PLP, including an exogenously obtained form useful in the compositions of the disclosure, has the following sequence (UNIPROT P60201):

```
                                      (SEQ ID NO: 6)
MGLLECCARCLVGAPFASLVATGLCFFGVALFCGCGHEALTGTEK

LIETYFSKNYQDYEYLINVIHAFQYVIYGTASFFFLYGALLLAEGFYTTG

AVRQIFGDYKTTICGKGLSATVTGGQKGRGSRGQHQAHSLERVCHCLGKW

LGHPDKFVGITYALTVVWLLVFACSAVPVYIYFNTWTTCQSIAFPSKTSA

SIGSLCADARMYGVLPWNAFPGKVCGSNLLSICKTAEFQMTFHLFIAAFV

GAAATLVSLLTFMIAATYNFAVLKLMGRGTKF.
```

Peptides/epitopes useful in the compositions of the disclosure for treating multiple sclerosis include some or all of the following sequences, individually in a composition of Formula 1 or together in a cocktail of compositions of Formula 1:

```
MBP13-32:
                                      (SEQ ID NO: 7)
    KYLATASTMDHARHGFLPRH;

MBP83-99:
                                      (SEQ ID NO: 8)
    ENPWHFFKNIVTPRTP;

MBP111-129:
                                      (SEQ ID NO: 9)
    LSRFSWGAEGQRPGFGYGG;

MBP146-170:
                                      (SEQ ID NO: 10)
    AQGTLSKIFKLGGRDSRSGSPMARR;

MOG1-20:
                                      (SEQ ID NO: 11)
    GQFRVIGPRHPIRALVGDEV;

MOG35-55:
                                      (SEQ ID NO: 12)
    MEVGWYRPPFSRWHLYRNGK;
``` and PLP139-154:

```
                                              (SEQ ID NO: 13)
HCLGKWLGHPDKFVGI.
```

In rheumatoid arthritis, main antigens include collagen II, immunoglobulin binding protein, the fragment crystallizable region of immunoglobulin G, double-stranded DNA, and the natural and cirtullinated forms of proteins implicated in rheumatoid arthritis pathology, including fibrin/fibrinogen, vimentin, collagen I and II, and alpha-enolase.

In autoimmune gastritis, a main antigen is H+,K+-ATPase.

In pernicious angemis, a main antigen is intrinsic factor.

In celiac disease, main antigens are tissue transglutaminase and the natural and deamidated forms of gluten or gluten-like proteins, such as alpha-, gamma-, and omega-gliadin, glutenin, hordein, secalin, and avenin. Those skilled in the art will appreciate, for example, that while the main antigen of celiac disease is alpha gliadin, alpha gliadin turns more immunogenic in the body through deamidation by tissue glutaminase converting alpha gliadin's glutamines to glutamic acid. Thus, while alpha gliadin is originally a foreign food antigen, once it has been modified in the body to become more immunogenic it can be characterized as a self-antigen.

In vitiligo, a main antigen is tyrosinase, and tyrosinase related protein 1 and 2.

MART1, Melanoma antigen recognized by T cells 1, Melan-A, including an exogenously obtained form useful in the compositions of the disclosure, has the following sequence (UNIPROT Q16655):

```
                                              (SEQ ID NO: 14)
MPREDAHFIYGYPKKGHGHSYTTAEEAAGIGILTVILGVLLLIGCWYCRR

RNGYRALMDKSLHVGTQCALTRRCPQEGFDHRDSKVSLQEKNCEPVVPNA

PPAYEKLSAEQSPPPYSP.
```

Tyrosinase, including an exogenously obtained form useful in the compositions of the disclosure, has the following sequence (UNIPROT P14679):

```
                                              (SEQ ID NO: 15)
MLLAVLYCLLWSFQTSAGHFPRACVSSKNLMEKECCPPWSGDRSPCGQLS

GRGSCQNILLSNAPLGPQFPFTGVDDRESWPSVFYNRTCQCSGNFMFFNC

GNCKFGFWGPNCTERRLLVRRNIFDLSAPEKDKFFAYLTLAKHTISSDYV

IPIGTYGQMKNGSTPMFNDINIYDLFVWMHYYVSMDALLGGSEIWRDIDF

AHEAPAFLPWHRLFLLRWEQEIQKLTGDENFTIPYWDWRDAEKCDICTDE

YMGGQHPTNPNLLSPASFFSSWQIVCSRLEEYNSHQSLCNGTPEGPLRRN

PGNHDKSRTPRLPSSADVEFCLSLTQYESGSMDKAANFSFRNTLEGFASP

LTGIADASQSSMHNALHIYMNGTMSQVQGSANDPIFLLHHAFVDSIFEQW

LRRHRPLQEVYPEANAPIGHNRESYMVPFIPLYRNGDFFISSKDLGYDYS

YLQDSDPDSFQDYIKSYLEQASRIWSWLLGAAMVGAVLTALLAGLVSLLC

RHKRKQLPEEKQPLLMEKEDYHSLYQSHL.
```

Melanocyte protein PMEL, gp100, including an exogenously obtained form useful in the compositions of the disclosure, has the following sequence (UNIPROT P40967):

```
                                              (SEQ ID NO: 16)
MDLVLKRCLLHLAVIGALLAVGATKVPRNQDWLGVSRQLRTKAWNRQLY

PEWTEAQRLDCWRGGQVSLKVSNDGPTLIGANASFSIALNFPGSQKVLP

DGQVIWVNNTIINGSQVWGGQPVYPQETDDACIFPDGGPCPSGSWSQKR

SFVYVWKTWGQYWQVLGGPVSGLSIGTGRAMLGTHTMEVTVYHRRGSRS

YVPLAHSSSAFTITDQVPFSVSVSQLRALDGGNKHFLRNQPLTFALQLH

DPSGYLAEADLSYTWDFGDSSGTLISRALVVTHTYLEPGPVTAQVVLQA

AIPLTSCGSSPVPGTTDGHRPTAEAPNTTAGQVPTTEVVGTTPGQAPTA

EPSGTTSVQVPTTEVISTAPVQMPTAESTGMTPEKVPVSENTMGTTLAE

MSTPEATGMTPAEVSIVVLSGTTAAQVTTTEWVETTARELPIPEPEGPD

ASSIMSTESITGSLGPLLDGTATLRLVKRQVPLDCVLYRYGSFSVTLDI

VQGIESAEILQAVPSGEGDAFELTVSCQGGLPKEACMEISSPGCQPPAQ

RLCQPVLPSPACQLVHQILKGGSGTYCLNVSLADTNSLAVVSTQLIMPG

QEAGLGQVPLIVGILLVLMAVVLASLIYRRRLMKQDFSVPQLPHSSSHW

LRLPRIFCSCPIGENSPLLSGQQV.
```

In myasthenia gravis, a main antigen is acetylcholine receptor.

In pemphigus vulgaris and variants, main antigens are desmoglein 3, 1 and 4; other antigens include pemphaxin, desmocollins, plakoglobin, perplakin, desmoplakins, and acetylcholine receptor.

In bullous pemphigoid, main antigens include BP180 and BP230; other antigens include plectin and laminin 5.

In dermatitis herpetiformis Duhring, main antigens include endomysium and tissue transglutaminase.

In epidermolysis bullosa acquisita, a main antigen is collagen VII.

In systemic sclerosis, main antigens include matrix metalloproteinase 1 and 3, the collagen-specific molecular chaperone heat-shock protein 47, fibrillin-1, and PDGF receptor; other antigens include Sc1-70, U1 RNP, Th/To, Ku, Jol, NAG-2, centromere proteins, topoisomerase I, nucleolar proteins, RNA polymerase I, II and III, PM-Slc, fibrillarin, and B23.

In mixed connective tissue disease, a main antigen is U1snRNP.

In Sjogren's syndrome, the main antigens are nuclear antigens SS-A and SS-B; other antigens include fodrin, poly(ADP-ribose) polymerase and topoisomerase, muscarinic receptors, and the Fc-gamma receptor Mb.

In systemic lupus erythematosus, main antigens include nuclear proteins including the "Smith antigen," SS-A, high mobility group box 1 (HMGB1), nucleosomes, histone proteins and double-stranded DNA (against which auto-antibodies are made in the disease process).

In Goodpasture's syndrome, main antigens include glomerular basement membrane proteins including collagen IV.

In rheumatic heart disease, a main antigen is cardiac myosin.

In autoimmune polyendocrine syndrome type 1 antigens include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega.

In neuromyelitis optica, a main antigen is AQP4.

Aquaporin-4, including an exogenously obtained form useful in the compositions of the disclosure, has the following sequence (UNIPROT P55087):

(SEQ ID NO: 17)
MSDRPTARRWGKCGPLCTRENIMVAFKGVWTQAFWKAVTAEFLAMLIFVL

LSLGSTINWGGTEKPLPVDMVLISLCFGLSIATMVQCFGHISGGHINPAV

TVAMVCTRKISIAKSVFYIAAQCLGAIIGAGILYLVTPPSVVGGLGVTMV

HGNLTAGHGLLVELIITFQLVFTIFASCDSKRTDVTGSIALAIGFSVAIG

HLFAINYTGASMNPARSFGPAVIMGNWENHWIYWVGPIIGAVLAGGLYEY

VFCPDVEFKRRFKEAFSKAAQQTKGSYMEVEDNRSQVETDDLIIKPGVVH

VIDVDRGEEKKGKDQSGEVLSSV.

In uveitis, main antigens include Retinal S-antigen or "S-arrestin" and interphotoreceptor retinoid binding protein (IRBP) or retinol-binding protein 3.

S-arrestin, including an exogenously obtained form useful in the compositions of the disclosure, has the following sequence (UNIPROT P10523):

(SEQ ID NO: 18)
MAASKGTSKS EPNHVIFKKI SRDKSVTIYL GNRDYIDHVS

QVQPVDGVVL VDPDLVKGKK VYVTLTCAFR YGQEDIDVIG

LTFRRDLYFS RVQVYPPVGA ASTPTKLQES LLKKLGSNTY

PFLLTFPDYL PCSVMLQPAP QDSGKSCGVD FEVKAFATDS

TDAEEDKIPK KSSVRLLIRK VQHAPLEMGP QPRAEAAWQF

FMSDKPLHLA VSLNKEIYFH GEPIPVTVTV TNNTEKTVKK

IKAFVEQVAN VVLYSSDYYV KPVAMEEAQE KVPPNSTLTK

TLTLLPLLAN NRERRGIALD GKIKHEDTNL ASSTIIKEGI

GRTVLGILVS YQIKVKLTVS GFLGELTSSE VATEVPFRLM

HPQPEDPAKE SYQDANLVFE EFARHNLKDA GEAEEGKRDK

NDVDE.

IRBP, including an exogenously obtained form useful in the compositions of the disclosure, has the following sequence (UNIPROT P10745):

(SEQ ID NO: 19)
MMREWVLLMSVLLCGLAGPTHLFQPSLVLDMAKVLLDNYCFPENLLGMQE

AIQQAIKSHEILSISDPQTLASVLTAGVQSSLNDRPLVISYEPSTPEPPP

QVPALTSLSEEELLAWLQRGLRHEVLEGNVGYLRVDSVPGQEVLSMMGEF

LVAHVWGNLMGTSALVLDLRHCTGGQVSGIPYIISYLHPGNTILHVDTIY

NRPSNTTTEIWTLPQVLGERYGADKDVVVLTSSQTRGVAEDIAHILKQMR

RAIVVGERTGGGALDLRKLRIGESDFFFTVPVSRSLGPLGGGSQTWEGSG

VLPCVGTPAEQALEKALAILTLRSALPGVVHCLQEVLKDYYTLVDRVPTL

LQHLASMDFSTVVSEEDLVTKLNAGLQAASEDPRLLVRAIGPTETPSWPA

PDAAAEDSPGVAPELPEDEAIRQALVDSVFQVSVLPGNVGYLRFDSFADA

SVLGVLAPYVLRQVWEPLQDTEHLIMDLRHNPGGPSSAVPLLLSYFQGPE

AGPVHLFTTYDRRTNITQEHFSHMELPGPRYSTQRGVYLLTSHRTATAAE

EFAFLMQSLGWATLVGEITAGNLLHTRTVPLLDTPEGSLALTVPVLTFID

NHGEAWLGGGVVPDAIVLAEEALDKAQEVLEFHQSLGALVEGTGHLLEAH

YARPEVVGQTSALLRAKLAQGAYRTAVDLESLASQLTADLQEVSGDHRLL

VFHSPGELVVEEAPPPPPAVPSPEELTYLIEALFKTEVLPGQLGYLRFDA

MAELETVKAVGPQLVRLVWQQLVDTAALVIDLRYNPGSYSTAIPLLCSYF

FEAEPRQHLYSVFDRATSKVTEVWTLPQVAGQRYGSHKDLYILMSHTSGS

AAEAFAHTMQDLQRATVIGEPTAGGALSVGIYQVGSSPLYASMPTQMAMS

ATTGKAWDLAGVEPDITVPMSEALSIAQDIVALRAKVPTVLQTAGKLVAD

NYASAELGAKMATKLSGLQSRYSRVTSEVALAEILGALQMLSGDPHLKAA

HIPENAKDRIPGIVPMQIPSPEVFEELIKFSFHTNVLEDNIGYLRFDMFG

DGELLTQVSRLLVEHIWKKIMHTDAMIIDMRFNIGGPTSSIPILCSYFFD

EGPPVLLDKIYSRPDDSVELWTHAQVVGERYGSKKSMVILTSSVTAGTAE

EFTYIMKRLGRALVIGEVTSGGCQPPQTYHVDDTNLYLTIPTARSVGASD

GSSWEGVGVTPHVVVPAEEALARAKEMLQHNQLRVKRSPGLQDHL.

In the embodiments where the antigen is a foreign antigen against which an unwanted immune response can be developed, such as food antigens, specific antigens can be:

from peanut: conarachin (Ara h 1), allergen II (Ara h 2), arachis agglutinin, conglutin (Ara h 6);

conarachin, for example has the sequence identified as UNIPROT Q6PSU6 from apple: 31 kda major allergen/disease resistance protein homolog (Mal d 2), lipid transfer protein precursor (Mal d 3), major allergen Mal d 1.03D (Mal d 1);

from milk: α-lactalbumin (ALA), lactotransferrin;

from kiwi: actinidin (Act c 1, Act d 1), phytocystatin, thaumatin-like protein (Act d 2), kiwellin (Act d 5);

from egg whites: ovomucoid, ovalbumin, ovotransferrin, and lysozyme;

from egg yolks: livetin, apovitillin, and vosvetin;

from mustard: 2S albumin (Sin a 1), 11S globulin (Sin a 2), lipid transfer protein (Sin a 3), profilin (Sin a 4);

from celery: profilin (Api g 4), high molecular weight glycoprotein (Api g 5);

from shrimp: Pen a 1 allergen (Pen a 1), allergen Pen m 2 (Pen m 2), tropomyosin fast isoform;

from wheat and/or other cereals: high molecular weight glutenin, low molecular weight glutenin, alpha-, gamma- and omega-gliadin, hordein, secalin and/or avenin;

peptides/epitopes useful in the compositions of the disclosure for treating Celiac Disease include some or all of the following sequences, individually in a composition of Formula 1 or together in a cocktail of compositions of Formula 1:

DQ-2 relevant, Alpha-gliadin "33-mer" native: LQLQPFPQPQLPYPQPQLPYPQPQLPYPQPQPF (SEQ ID NO:20)

DQ-2 relevant, Alpha-gliadin "33-mer" deamidated: LQLQPFPQPELPYPQPELPYPQPELPYPQPQPF (SEQ ID NO:21)

DQ-8 relevant, Alpha-gliadin: QQYPSGQGSFQPSQQNPQ (SEQ ID NO:22)

DQ-8 relevant, Omega-gliadin (wheat, U5UA46): QPFPQPEQPFPW (SEQ ID NO:23)

from strawberry: major strawberry allergy Fra a 1-E (Fra a 1); and from banana: profilin (Mus xp 1).

In the embodiments where the antigen is a foreign antigen against which an unwanted immune response is developed, such as to animal, plant and environmental antigens, specific antigens can, for example, be: cat, mouse, dog, horse, bee, dust, tree and goldenrod, including the following proteins or peptides derived from:

weeds, (including ragweed allergens amb a 1, 2, 3, 5, and 6, and Amb t 5; pigweed Che a 2 and 5; and other weed allergens Par j 1, 2, and 3, and Par o 1);

grass (including major allergens Cyn d 1, 7, and 12; Dac g 1, 2, and 5; Hol I 1.01203; Lol p 1, 2, 3, 5, and 11; Mer a 1; Pha a 1; Poa p 1 and 5);

pollen from ragweed and other weeds (including curly dock, lambs quarters, pigweed, plantain, sheep sorrel, and sagebrush), grass (including Bermuda, Johnson, Kentucky, Orchard, Sweet vernal, and Timothy grass), and trees (including *catalpa*, elm, hickory, olive, pecan, sycamore, and walnut);

dust (including major allergens from species *Dermatophagoides pteronyssinus*, such as Der p 1, 2, 3, 4, 5, 6, 7, 8, 9, 10, 11, 14, 15, 18, 20, 21, and 23; from species *Dermatophagoides* farina, such as Der f 1, 2, 3, 6, 7, 10, 11, 13, 14, 15, 16, 18, 22, and 24; from species *Blomia tropicalis* such as Blo t 1, 2, 3, 4, 5, 6, 10, 11, 12, 13, 19, and 21; also allergens Eur m 2 from Euroglyphus maynei, Tyr p 13 from Tyrophagus putrescentiae, and allergens Bla g 1, 2, and 4; Per a 1, 3, and 7 from cockroach);

pets (including cats, dogs, rodents, and farm animals; major cat allergens include Fel d 1 through 8, cat IgA, BLa g 2, and cat albumin; major dog allergens include Can f 1 through 6, and dog albumin);

bee stings, including major allergens Api m 1 through 12; and fungus, including allergens derived from, species of *Aspergillus* and *Penicillium*, as well as the species *Alternaria* alternate, *Davidiella tassiana*, and *Trichophyton rubrum*.

The antigen can be a complete protein, a portion of a complete protein, a peptide, or the like, and can be derivatized (as discussed above) for attachment to a linker and/or galactosylating moiety (or glucosylating moiety), can be a variant and/or can contain conservative substitutions, particularly maintaining sequence identity, and/or can be desialylated.

Certain embodiments, employ antigens that are included in (or result from) ingested food items.

Capping Group

As disclosed elsewhere herein, in some embodiments, $R^2$ comprises an end-capping group. In some embodiments, $R^2$ when disconnected from the construct, forms a stable or substantially stable free radical. In some embodiments, $R^2$ is a reversible addition-fragmentation chain transfer (RAFT) agent for a living polymerization. In some embodiments, $R^2$ can be reversibly added and removed to the construct to lengthen the linker region. In some embodiments, $R^2$ is a RAFT agent. In some embodiments, $R^2$ is an optionally substituted dithiobenzoate, a trithiocarobnate, or a xanthate.

In some embodiments, $R^2$ is any of functional groups I-IV:

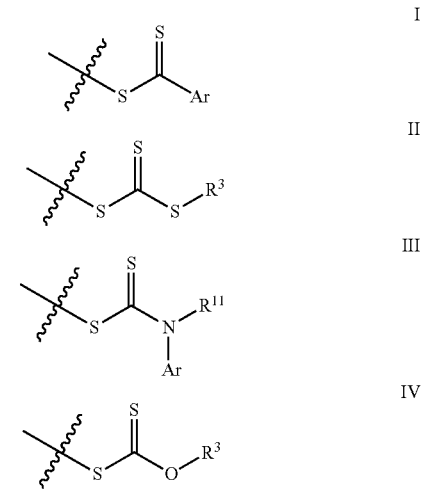

where Ar is a substituted or unsubstituted aromatic group, $R^3$ is any carbon-containing linear or heterocyclic moiety. In some embodiments, $R^3$ is an optionally substituted alkyl, optionally substituted cycloalkyl, optionally substituted aryl, or optionally substituted heteroaryl. In some embodiments, any one of Ar, $R^3$, or $R^{11}$ is optionally substituted. In some embodiments, any one of Ar, $R^3$, or $R^{11}$ is optionally substituted with an optionally substituted alkyl, optionally substituted heterocyclyl, optionally substituted aryl, optionally substituted heteroaryl. In some embodiments, $R^{11}$ is hydrogen or an optionally substituted alkyl. In some embodiments, $R^2$ is one of the functional groups:

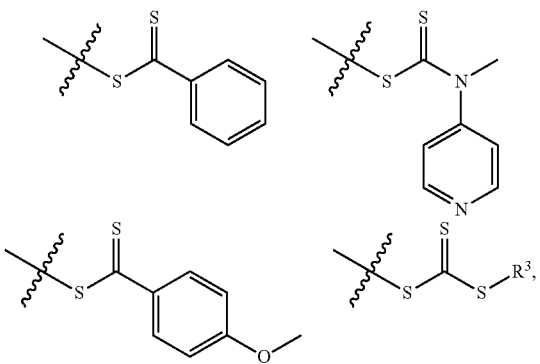

where $R^3$ is as defined above.

In some embodiments, $R^2$ is not a RAFT agent. In some embodiments, $R^2$ is H or is absent.

In some embodiments, multiple (2, 3, 4, 5, or more) antigens (and/or a plurality of tolerogenic portions thereof, fragments thereof, or mimetics thereof; e.g., X groups) are provided on a single construct. In some embodiments, the capping agent is an X unit. In some embodiments, for example, a construct of Formula 2 is provided, where X and X' are separate antigens (and/or tolerogenic portions thereof, fragments thereof, or mimetics thereof) that can be the same or different. In some embodiments, the other variables of Formula 2 are as disclosed elsewhere herein.

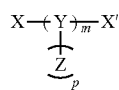

Formula 2

In some embodiments, multiple X groups can be provided along the Y' chain. In some embodiments, for example, one or more $W^1$ or $W^2$ units can be functionalized with one or more X units, as disclosed elsewhere herein. The following formulae demonstrate alternative configurations for tolerogenic compounds:

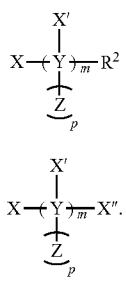

Formula 3

Formula 4

In some embodiments, the other variables of Formula 3 or Formula 4 are as disclosed elsewhere herein.

Methods

Also provided herein are methods of inducing tolerance to antigens which, when administered alone (e.g., without the presently disclosed compositions) would result in an adverse immune response. In several embodiments, the compositions provided for herein are used in the treatment, prevention, reduction or otherwise alter an immune response to an antigen. In several embodiments, the immune response has, or is occurring in an ongoing manner, while in some embodiments, the treatment and use of the compositions is in a prophylactic manner. For instance, in some embodiments, the is performed administration before, after, or before and after exposure to the antigen. In several embodiments, administration prior to exposure serves a prophylactic effect, which in several embodiments essentially avoids or significantly reduces in the immune response. Administration of the compositions can be via a variety of methods, including, but not limited to intravenous, intramuscular, oral, transdermal, or other infusion route. In several embodiments, the compositions are delivered in a therapeutically effective amount, for example, by a systemic or local route (e.g., intravenous, intraarterially, locally, intramuscular, subcutaneous, etc.). Administration can be daily, weekly, multiple times per day, or on an as needed basis (e.g., prior to an anticipated exposure).

In some embodiments, uses of compositions according to Formula 1 are provided for the treatment or prevention of unwanted effects due to exposure to a antigens. In some embodiments, the method involve administration of one or more compounds according to Formula 1 comprising one or more antigens, tolerogenic portions thereof, fragments thereof, or mimetics thereof. The compositions disclosed herein are suitable for administration to a subject in conjunction with such use, for example by oral, IV, IM, or other suitable route. Uses of the compositions disclosed herein, in several embodiments, unexpectedly result in the reduction, elimination or amelioration of adverse immune responses to antigens of interest.

In several embodiments, the amount of the composition administered is an amount sufficient to result in induction of clonal deletion and/or anergy of T cells that are specific to the antigen of interest. In several embodiments, the composition is configured to target primarily LSEC and/or hepatocytes. In several embodiments, the composition is configured to induce expansion of certain populations, or subpopulations, of regulatory T cells. For example, in several embodiments, $CD4^+CD25^+FOXP3^+$ regulatory T cells are induced.

In some embodiments, the method of treatment of an unwanted immune response against an antigen is accomplished by administering to a mammal in need of such treatment an effective amount of a composition comprising a compound of Formula 1 as disclosed herein. In some such methods the composition can be administered for clearance of a circulating protein or peptide or antibody that specifically binds to antigen moiety X, which circulating protein or peptide or antibody is causatively involved in transplant rejection, immune response against a therapeutic agent, autoimmune disease, hypersensitivity and/or allergy. The composition can be administered in an amount effective to reduce a concentration of the antibodies that are causatively involved in transplant rejection, immune response against a therapeutic agent, autoimmune disease, hypersensitivity and/or allergy in blood of the patient by at least 50% w/w, as measured at a time between about 12 to about 48 hours after the administration. The composition can administered for tolerization of a patient with respect to antigen moiety X.

Some embodiments pertain to a method of manufacturing compounds of Formula 1-4. In some embodiments, one or more of monomers are polymerized to provide a block copolymer or random copolymer of $W^1$ and $W^2$. In some embodiments, $W^1$ is used to make a homopolymer. In some embodiments, is $[Y(\text{---}Z)_p]_m\text{---}R^2$ is synthesized and coupled to X via a disulfide bond. In some embodiments, X is functionalized with an alkyne containing substitutent and is coupled to $[Y(\text{---}Z)_p]_m\text{---}R^2$ via a pendant azide linkage of Y. In some embodiments, X is functionalized with a reactive group and the $W^1$ and/or $W^2$ polymer or copolymer is grown from the reactive group of X. In some embodiments, various degrees of polymerization of $W^1$ and $W^2$ are provided. In some embodiments, the degree of polymerization (e.g., the number of $W^1$ and/or $W^2$ units) is equal to or at least about 10, 30, 50, 100, 150, 200, 250, 300, or ranges including and/or spanning the aforementioned values. In several embodiments, degree of polymerization unexpectedly increases the tolerogenic effect of the constructs disclosed herein.

In several embodiments, increased degree of polymerization unexpectedly increases the tolerogenic effect of the constructs disclosed herein. In several embodiments, increased degree of polymerization increases induction of T-cell anergy and binding to target cells. In several embodiments, one or more properties of the constructs disclosed herein unexpectedly increases the tolerogenic effect, induction of T-cell anergy, binding to target cells, and/or other properties.

In several embodiments, a 1 mg/ml weight of a construct as disclosed herein in reducing conditions (10 mM reduced glutathione) in a solution of PBS (pH 7.2) at a 60° C. show less than a 10% loss in stability (e.g., degradation) after a period of greater than or equal to about: 48 hours, 1 week, one month, 2 months, 6 months, 9 months, 12 months, or ranges including and/or spanning the aforementioned values. In several embodiments, a 1 mg/ml dry weight of a construct as disclosed herein in reducing conditions (10 mM reduced glutathione) in a solution of HEPES (pH 8.04) at a 60° C. show less than a 10% loss in stability (e.g., degradation) after a period of greater than or equal to about: 48 hours, 1 week, one month, 2 months, 6 months, 9 months, 12 months, or ranges including and/or spanning the aforementioned values. In several embodiments, a 1 mg/ml dry weight of a construct as disclosed herein in a solution of PBS (pH 7.2) at a room temperature show less than a 10% loss in stability (e.g., degradation) after a period of greater than or equal to about: 48 hours, 1 week, one month, 2 months, 6 months, 9 months, 12 months, or ranges including and/or spanning the aforementioned values. In several embodiments, a 1 mg/ml dry weight of a construct as disclosed herein in a solution of HEPES (pH 8.04) show less than a 10% loss in stability (e.g., degradation) after a period of greater than or equal to about: 48 hours, 1 week, one month, 2 months, 6 months, 9 months, 12 months, or ranges including and/or spanning the aforementioned values.

The various studies described in more detail below provide additional evidence that the compositions and methods disclosed herein are useful for the induction of antigen-specific immune tolerance, in accordance with several embodiments herein.

EXAMPLES

Additional embodiments are disclosed in further detail in the following examples, which are not in any way intended to limit the scope of the claims.

Materials and Instrumentation.

Exemplary vendors and instrumentation are disclosed here. Unless otherwise indicated reagents were purchased from Sigma-Aldrich. Methylene chloride (reagent grade) and N,N-dimethylformamide (reagent grade) were obtained from Fisher Scientific. Acetone (reagent grade) was obtained from BDH. Methanol (reagent grade) was obtained from EMD Millipore. Methylene chloride (anhydrous) was obtained from Acros Organics. Pyridine was obtained from VWR. N,N-dimethylformamide (HPLC grade) and ethyl acetate (HPLC grade) were obtained from Honeywell. N,N-dimethylformamide (anhydrous) was obtained from Millipore. D-Galactosamine HCl was obtained from Carbosynth. Methacryloyl chloride was obtained from BTC. Acetic anhydride, 4-dimethylaminopyridine, Diglycolamine, Dithiodipyridine, NaOMe (30% wt/wt in MeOH), Potassium thioacetate, Triethylamine, Tetraethylene glycol, and Lithium Bromide (anhydrous) were obtained from Alpha Aesar. 1,2-DCE, Molecular Sieves, Amberlite IR120 (H+) resin, D-Glucosamine HCl, N,N'-dicyclohexylcarbodiimide, Ethanolamine, 4-ethylbenzene-1-sulfonyl chloride, Potassium carbonate, Trimethylsilyl trifluoromethanesulfonate (TMSOTf), 2,2'-azobis(2-methylpropionitrile) (AIBN, recrystallized, 99% purity), N,N'-disuccinimidyl carbonate, 2-mercaptoethanol, 4-nitrophenyl chlorofomate, BCN—NHS, and human insulin protein were obtained from Sigma Aldrich. 4-cyano-4-(thiobenzoylthio)pentanoic acid was obtained from Strem Chemical. 11-Azido-3,6,9-trioxaundecanol, NHS-DTP (SPDP) and S-DBCO-Amine were obtained from BroadPharm. DIBO—OH was obtained from AstaTech, Inc. HS-PEG2K—$NH_2$ HCl was obtained from Jenchem. 2-(Pyridin-2-yldisulfanyl)ethanol was obtained from Synnovator, Inc. Ovalbumin protein (Endo-Grade) was obtained from Worthington Biochemical Corporation. Unless otherwise specified, all reagents were used directly, without further purification. All reactions were performed under an atmosphere of nitrogen, unless otherwise stated.

Instrumentation. $^1$H and $^{13}$C NMR spectra were obtained using a Varian 400 spectrometer energized to 399.85 MHz or a Varian 500 spectrometer energized to 499.9 MHz. All NMR spectra were analyzed at 25° C. and evaluated against residual solvent peaks. Gel permeation chromatography (GPC) was performed on a Shimadzu Prominence i-Series Plus instrument equipped with a Shimadzu RID20A differential refractometer detector maintained at 50° C. GPC stationary phase was a single Shodex KD-804 size exclusion column packed with styrene-divinylbenzene resin maintained at 50° C. GPC mobile phase was HPLC-grade N,N-dimethylformamide (Honeywell) containing 25 mM Lithium Bromide (Alpha Aesar) at a flow rate of 1.0 mL/min. Liquid chromatography-mass spectrometry (LC-MS) was performed on a Waters single quadrupole TOF spectrometer equipped with a Phenomenex Luna C-8 3µ30× 2.0 mm column. LC-MS mobile phase was a water-acetonitrile gradient containing 0.1% formic acid at a flow rate of 0.7 mL/min. Cation exchange chromatography (CEX) and size exclusion chromatography (SEC) were performed on an ÄKTA pure 25 L chromatography system. For CEX, the stationary phase was a single GE Healthcare 1.0 mL HiTrap Sp High Performance column. CEX mobile phase was 20 mM sodium acetate at pH 4.2 with a gradient of 0-100% of 20 mM sodium acetate pH 4.2 with 1.0 M NaCl at a flow rate of 1.0 mL/min. For SEC, the stationary phase was a single GE Healthcare HiLoad 16/600 Superdex 200 pg (16 mm×600 mm) column. SEC mobile phase was 1.0 M PBS buffer (pH 7.4) at a flow rate of 1.0 mL/min. SDS polyacrylamide gel electrophoresis (PAGE) was performed on Bolt 12% Bis-Tris protein gels (Invitrogen, 1.0 mm×12-well) (23 minutes, 180 V, 20× Bolt MES SDS PAGE running buffer, pH 7.0). Gels were stained with Coomassie SimplyBlue SafeStain (Life Technologies). Matrix-assisted laser desorption-ionization time-of-flight mass spectrometry (MALDI-TOF-MS) spectra were obtained on an Applied Biosystems Voyager-DE Pro instrument in linear positive mode. All MALDI samples were analyzed via 2,5-Dihydroxybenzoic acid (DHB) matrix. Size-exclusion chromatography (SEC) was done on a GE Healthcare life sciences ÄKTA pure 25 L system, using PBS as the mobile phase and a GE HiLoad 16/600 Superdex 200 prep grade column.

Example 1: Exemplary Chemical Synthesis of Monomers

The following provides exemplary procedures for the syntheses of various monomers for preparing certain embodiments as disclosed herein.

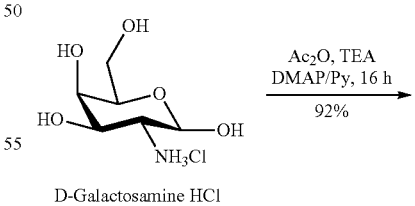

D-Galactosamine HCl

Compound 3

Galactosamine pentaacetate (3). D-Galactosamine HCl (6.73 g, 31.2 mmol) was suspended in pyridine (30 mL) and acetic anhydride (22 mL, 0.23 mol). The flask was cooled to 0° C. in an ice bath and DMAP and triethylamine were charged into the mixture. The contents of the flask were allowed to warm to room temperature under $N_2$ atmosphere. After stirring for 16 hours, the reaction mixture was diluted with EtOAc at which point additional solids were evident. The solid product 3 was collected by filtration on a fritted glass filter and placed on high-vacuum (11.23 g, 92%). This material was sufficiently pure by NMR and used directly in the next procedural step.

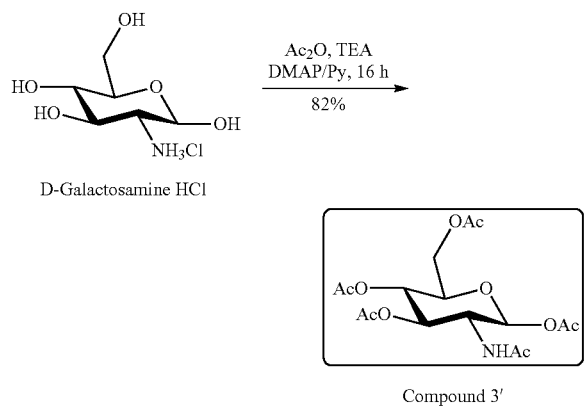

Glucosamine pentaacetate (3'). D-Glucosamine HCl (20 g, 92.7 mmol) was suspended in pyridine (125 mL). Acetic anhydride (123 mL, 1.3 mol) was added followed by a catalytic amount of DMAP and triethylamine (13 mL, 93 mmol, 1 eq.). The reaction mixture turned a pale-yellow color with minimal white solid precipitate. Stirring continued at room temperature under $N_2$ atmosphere. TLC analysis showed reaction completion and the mixture was filtered through a glass filter to remove some white solids (presumably a salt). The filtrate was diluted with ethyl acetate, washed with saturated $NaHCO_3$ and brine, dried over $Na_2SO_4$, filtered and concentrated. The crude material was dissolved in boiling absolute EtOH (350 mL) cooled to room temperature and placed in freezer for 16 hours. The white solids were collected on a Buchner funnel and washed with cold EtOH. The mother liquor was concentrated, recrystallized and dried on high-vacuum (29.2 mg, 82%).

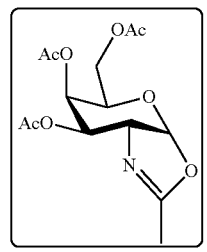

Compound 4

Triacetyl D-Galactose Oxazoline (4). Galactosamine pentaacetate 3 (21.86 g, 56 mmol) was dissolved in anhydrous dichloromethane (40 mL) under $N_2$ atmosphere in a flask equipped with a stir bar. 12.2 mL (1.2 eq., 67 mmol) of TMSOTf was added to the reaction mixture and stirring continued for 16 hours at room temperature. Reaction completion was confirmed by TLC analysis (70% EtOAc: Hex). The reaction solution was quenched by pouring into a saturated aqueous $NaHCO_3$/ice mixture followed by stirring for 30 minutes. The reaction mixture was then separated and the aqueous layer was extracted twice with DCM. The combined organic layers were dried over anhydrous $Na_2SO_4$, filtered and concentrated under vacuum resulting in 4 as a crude oil (18.4 g). Compound 4 was used without further purification in the next step.

Alternatively, the following procedures were used to provide 4 (e.g., 2-Methyl-(3,4,6-tri-O-acetyl-1,2-dideoxy-α-D-galactopyrano) [1,2-d]-1,3-oxazoline). D-galactosamine penta-acetate 15 (2.0 g, 5.15 mmol) was dissolved in dichloroethane (DCE) (20 mL). Then trimethylsilyl trifluoromethanesulfonate (TMSOTf) (1 ml, 5.53 mmol) was added, and the mixture was stirred at 50° C. for 9 h. The mixture was then removed from the heat and stirred for 7 h. Triethylamine (2 ml) was added to the mixture at room temperature. The mixture was then washed with a saturated solution of $NaHCO_3$ and then dried with sodium sulfate. The organic phase was then filtered and the solvent was removed via rotary evaporation and the residue was loaded onto silica gel. The product was purified via column chromatography on silica gel with EtOAc (100) to yield 16 as a yellow viscus solid. (Yield: 64%) 1H NMR: (400 MHz, CDCl3-d6): δ (ppm), 5.97 (d, J=6.9 Hz, 1H, H-4); 5.45 (t, J=3.0 Hz, 1H, H-5); 4.92 (dd, J=7.6 Hz, 3.4 Hz, 1H, H-4); 4.26 (td, J=6.7 Hz, 2.8 Hz, 1H); 4.25-4.13 (m, 1H, H-3); 3.99 (s, 1H); 2.13 (s, 3H); 2.07 (s, 6H); 2.05 (s, 3H). 13C NMR: (125 MHz, DMSO-d6): δ (ppm), 170.0; 169.55; 168.11; 165.21; 100.9; 70.66; 68.2; 65.02, 63.00, 61.8, 20.5, 20.44, 20.42, 13.91. MS m/z: [M+H]+ 330.12.

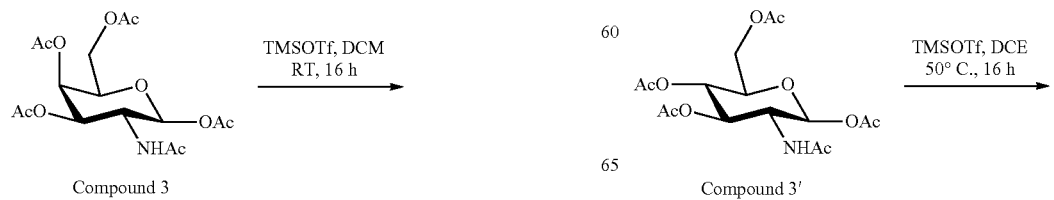

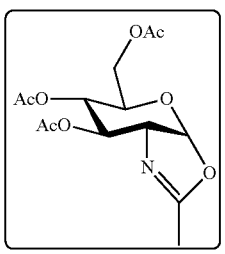

Compound 4'

Triacetyl D-Glucose Oxazoline (4'). Glucosamine pentaacetate 3' (19.64 g, 50.44 mmol) was dissolved in anhydrous dichloroethane (500 mL) under $N_2$ atmosphere. 17.0 g of activated AW-300 molecular sieves were added and the solution heated to 50° C. while stirring. TMSOTf (1.1 eq., 55.5 mmol, 10 mL) was slowly added to the reaction mixture and heating and stirring continued for 16 hours. TLC analysis showed the reaction was complete and the mixture was quenched by pouring into ice-cold saturated $NaHCO_3$. The reaction mixture was filtered through a glass frit and the layers of filtrate separated. The aqueous layer was extracted twice with DCM and the combined organic layers were dried over $Na_2SO_4$, filtered and concentrated under vacuum resulting in crude 4' as a yellow oil (16.09 g). $^1$H NMR showed a 5:1 ratio of product 4' and starting material 3'. This material was used directly without purification in the next step.

Alternatively, the following procedures were used to provide 4' (e.g., 2-Methyl-(3,4,6-tri-O-acetyl-1,2-dideoxy-α-D-glucopyrano)[1,2-d]-1,3-oxazoline). D-glucosamine penta-acetate (10 g, 25.6 mmol) was dissolved in dichloroethane (DCE) (150 mL). Then trimethylsilyl trifluoromethanesulfonate (TMSOTf) (5.5 ml, 30 mmol) was added, and the mixture was stirred at 50° C. for 1 h. The mixture was then removed from the heat and stirred for 16 h. Triethylamine (4 ml) was added to the mixture at room temperature. The mixture was then stirred for 10 min then the solvent was removed via rotary evaporation. The crude material was loaded onto silica gel and purified via flash chromatography, EtOAC (100) to give 14 as a pink oil (Yield: 61%). 1H NMR: (400 MHz, CDCl3-d6): δ (ppm), 5.86 (d, J=7.4 Hz, 1H, H-4); 5.22 (t, J=2.1 Hz, 1H, H-5); 4.87 (d, J=9.3 Hz, 1H, H-4); 4.12-4.05 (m, 3H, H-2, H-6, H-6'); 3.54-3.57 (m, 1H, H-3); 2.06 (s, 3H); 2.03 (s, 6H); 2.01 (s, 3H). 13C NMR: (125 MHz, CDCl3-d6): δ (ppm), 170.41; 169.55; 169.18; 166.34; 99.27; 70.04; 68.17; 67.43; 64.98; 63.12; 20.55, 20.34, 20.42, 13.91. MS m/z: [M+H]+ 330.12.

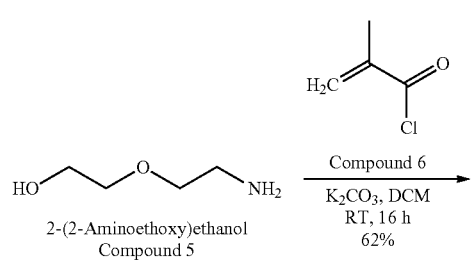

2-(2-Aminoethoxy)ethanol
Compound 5

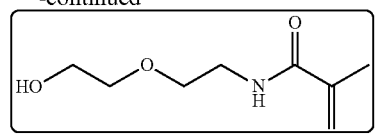

Compound 7

N-(2-(2-hydroxyethoxy)ethyl)methacrylamide (7). 2-(2-aminoethoxy)ethanol 5 (5.0 g, 47.6 mmol) was dissolved in 200 mL of anhydrous dichloromethane and 30 g of $K_2CO_3$ (217 mmol) was added. The suspension was stirred at 0° C. for 30 minutes followed by dropwise addition of methacryloyl chloride 6 (5.6 mL, 57.1 mmol). After stirring at room temperature for 16 hours, the reaction mixture was filtered through a pad of Celite to remove potassium carbonate and the filtrate concentrated below 30° C. providing a crude oil. Purification was conducted on a silica gel pad using 0-5% MeOH:DCM as an eluent. Fractions containing product were combined and evaporated under vacuum below 30° C. resulting in a pale yellow oil 7 (5.08 g, 62%). Compound 7 was stored under nitrogen at −20° C. before use.

Alternatively, the following procedures were also performed to provide Compound 7. To 200 ml of an ice-cold solution of 5 2-(2-aminoethoxy ethanol) (24 ml, 240 mmol) and potassium carbonate (15 g) in DCM was slowly added a solution of methacryloyl chloride 6 (24 ml, 250 mmol) in DCM (50 ml). The reaction was allowed to come to room temperature and stirred for another 4 h. After 4 h the reaction mixture was filtered through celite and the solvent was removed via rotary evaporation. The crude product was loaded onto silica gel and purified via flash chromatography, Ethyl Acetate (EtOAc):Hexanes (90:10), to give 7 as a colorless oil. (Yield: 72%) 1H NMR: (400 MHz, CDCl3-d6): δ (ppm), 6.53 (s, 1H); 5.66 (m, 1H); 5.29 (m, 1H); 3.71 (s, 2H); 3.56 (m, 4H); 3.48 (m, 2H); 1.91 (m, 3H). 13C NMR: (75 MHz, CDCl3-d6): δ (ppm), 169.34; 141.72; 120.37; 72.43; 69.82; 61.63; 39.81; 18.86. MS m/z: [M+H]+ 174.11.

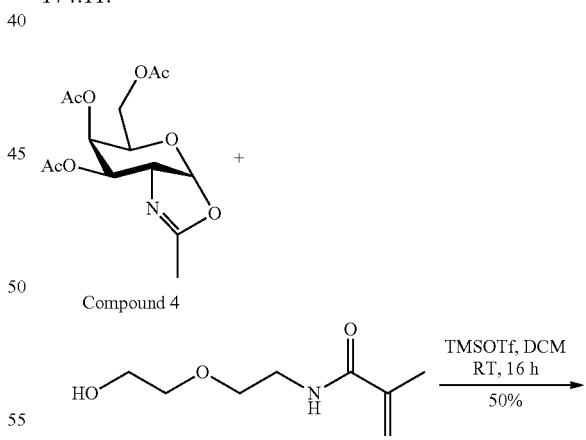

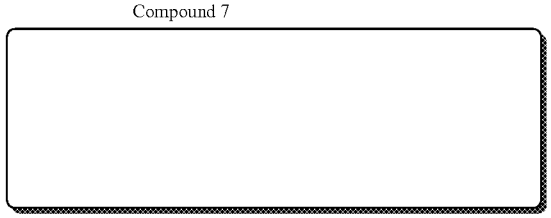

Compound 8

(2-(2-hydroxyethoxy)ethyl)methacrolyl 2-acetamido-3,4, 6-O-acetyl D-galactoside (8). Donor 4 (15.1 g, 46.1 mmol) and acceptor 7 (12.5 g, 72.2 mmol, 1.5 eq.) were combined and placed under high vacuum for 30 minutes and subsequently solubilized in anhydrous DCM (180 mL) under $N_2$ atmosphere. Flame dried AW-300 molecular sieves (15.0 g) were added and the mixture was stirred at room temperature for 30 minutes. The flask was then cooled to 0° C. and TMSOTf (6.3 mL, 34.6 mmol, 0.75 eq.) was slowly added to the reaction mixture over 10 minutes. The reaction was stirred for 16 hours and allowed to warm to room temperature. TLC analysis (60% acetone:hexane) showed minimal donor remaining and the reaction was filtered through a pad of Celite. The resulting filtrate was extracted with saturated $NaHCO_3$, water, and brine, and dried over anhydrous $Na_2SO_4$. The crude was purified on a 120 g silica flash cartridge using a 0-100% acetone:hexane gradient. Less pure fractions were combined, concentrated, and re-purified. Fractions containing pure product were combined and evaporated under vacuum providing 8 as an off-white foam (11.44 g, 50%).

Alternatively, the following procedures were also used to prepare 8 (e.g., 2-(2-Hydroxyethoxy)ethyl methacrylamide-2-acetamido-3,4,6-tri-O-acetyl-2-deoxy-α-D-galactopyranoside). A flask was charged with compound 4 (2.0 g, 6.0 mmol), 2-(2-Aminoethoxyethanol) methacrylamide 7 (1.1 g, 6.6 mmol), 4 Å molecular sieves (2.5 g), and DCE (20 ml). The solution was stirred for 30 min. TMSOTf (464 μL, 2.6 mmol) was added and the mixture was stirred at room temperature for 19 h, then TMSOTf (464 μL, 2.6 mmol) was added again and the reaction was allowed to stir for an additional 8 h. Triethylamine was then added to the reaction and the reaction was stirred for another 10 min. The solvents were removed via rotary evaporation and the crude product was loaded onto silica gel and purified via column chromatography, hexanes: EtOAc (80:20), to yield 8 as a viscous solid (Yield: 43%). 1H NMR: (500 MHz, CD3OD): δ (ppm), 5.72 (s, 1H), 5.35 (s, 1H), 4.67 (m, 1H), 4.65 (m, 1H), 4.32 (d, J=8.5 Hz, 1H), 4.27 (dd, J=5.0, 10.5 Hz, 1H), 4.17-3.69 (m, 6H), 2.01 (s, 3H), 1.99 (s, 3H), 1.97 (s, 3H), 1.89 (s×2, 6H). MS m/z: [M+H]+ 503.22.

(2-(2-hydroxyethoxy)ethyl)methacrolyl 2-acetamido-3,4, 6-O-acetyl D-glucoside (8'). Compound 4' (13.33 g, 40.5 mmol) and acceptor 7 (8.2 g, 47.3 mmol, 1.2 eq.) were combined and dried under high vacuum for one hour. The starting materials were solubilized in anhydrous DCM (125 mL) under nitrogen overlay and the contents of the flask stirred with flame-dried AW-300 molecular sieves (15 g) for 30 minutes. The reaction mixture was then cooled to 0° C. on an ice bath and TMSOTf (5.5 mL, 0.75 eq.) was added dropwise over a period of 15 minutes. After 4 hours and with equilibration to room temperature, a large amount of starting materials were observed by TLC. 1.0 mL of additional TMSOTf (0.14 eq.) was added. The reaction was complete by TLC analysis (50% acetone:hexane) after stirring for 16 hours at room temperature. The mixture was filtered through a pad of Celite, the filtrate washed with saturated $NaHCO_3$ and brine, dried over $Na_2SO_4$, filtered and concentrated. The crude oil was purified on a 120 g HP silica gel column using a 0-100% acetone:hexane gradient. Less pure fractions by TLC were combined, concentrated then re-purified. All fractions containing pure product by TLC were combined and evaporated under vacuum to providing product 8' as an oil (12.2 g, 59%).

Alternatively, the following procedures were also used to prepare 8' (e.g., 2-(2-Hydroxyethoxy)ethyl methacrylamide-2-acetamido-3,4,6-tri-O-acetyl-2-deoxy-α-D-glucopyranoside). A flask was charged with compound 4' (2.0 g, 6.0 mmol), 7 (1.1 g, 6.6 mmol), 4 Å molecular sieves (2.5 g), and DCE (20 ml). The solution was stirred for 30 min. TMSOTf (464 μL, 2.6 mmol) was added and the mixture was stirred at room temperature for 19 h, then TMSOTf (464 μL, 2.6 mmol) was added again and the reaction was allowed to stir for an additional 8 h. Triethylamine was then added to the reaction and the reaction was stirred for another 1 h. The solvents were removed via rotary evaporation and the crude product was loaded onto silica gel and purified via column chromatography, hexane: EtOAc (80:20), to yield 8' as a viscous solid (Yield: 51%). 1H NMR: (500 MHz, CD3OD): δ (ppm), 5.7 (s, 1H), 5.45 (s, 1H), 4.97 (dd, J=10.5, 10.5 Hz, 1H), 4.65 (d, J=8.5 Hz, 1H), 4.32 (d, J=8.5 Hz, 1H), 4.27 (dd, J=5.0, 10.5 Hz, 1H), 4.17-3.69 (m, 6H), 2.01 (s, 3H), 1.99 (s, 3H), 1.97 (s, 3H), 1.89 (s×2, 6H). MS m/z: [M+H]+ 503.31.

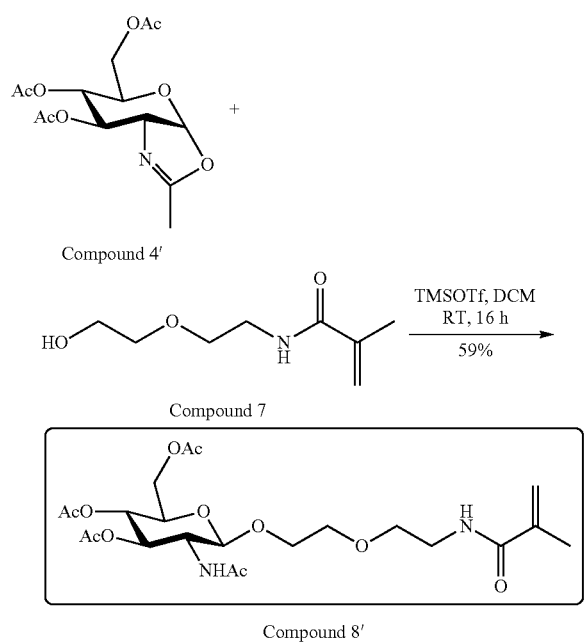

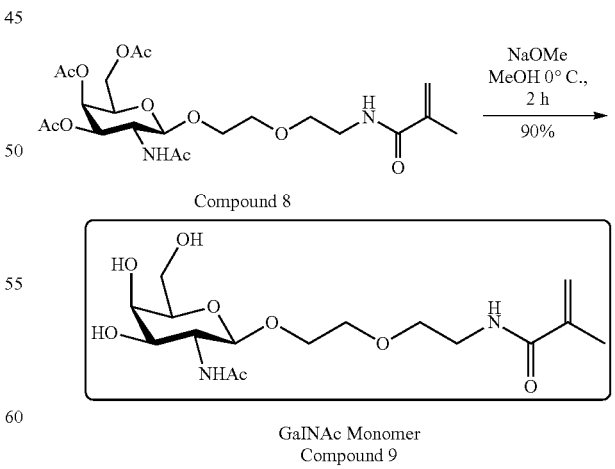

GalNAc Monomer (9). To a solution of compound 8 (14.13 g, 28.2 mmol) in anhydrous MeOH (160 mL) at 0° C. under $N_2$ was added a solution of NaOMe (4.5 M in MeOH, 6.8 mL). The reaction was warmed to room temperature and monitored by TLC (10% MeOH/DCM). After 2 hours, the reaction was complete and neutralized with Amberlite IR-120 (H+) resin. The reaction mixture was filtered, the resin washed with MeOH, and the combined filtrates evaporated providing a yellow syrup. The crude oil was purified by flash chromatography (0-25% MeOH:DCM) resulting in GalNAc monomer 9 (9.3 g, 90%) as a pale-yellow syrup. The GalNAc monomer 9 was stored in DMF at 40% wt/wt concentration, under nitrogen overlay at −20° C. 1H-NMR (499.9 MHz, D20, 25° C., ppm): δ=5.69 (s, 1H), 5.44 (s, 1H), 4.46 (d, J=8.5 Hz, 1H), 3.92 (d, J=3.2 Hz, 1H), 3.90-3.63 (m, 10H), 3.45 (J=10.1 Hz, J=6.5 Hz), 2.01 (s, 3H), 1.91 (s, 3H). 13C NMR: (125 MHz, D20, 25° C., ppm): δ=176.2; 169.34; 141.72; 120.37; 103.0; 76.5; 73.6; 72.43; 72.5; 69.82; 69.3; 61.63; 62.4; 53.9; 39.81; 23.5; 18.86; 11.0. MS m/z: [M+H]+ 377.19.

Alternatively, the following procedures were used to provide 9 (e.g., 2-(2-ethoxy)ethyl methacrylamide 2-acetamido-2-deoxy-β-D-galactopyranoside). Compound 8 (2.0 g, 3.98 mmol) was dissolved in 10 ml of MeOH and stirred at room temperature. Sodium methoxide (4 mmol) was added to the reaction and the reaction was stirred at room temperature. After 6 h, the solution was neutralized with Amberlite IR120 and then filtered. The solvent was removed via rotary evaporation and loaded on to silica gel. The products was purified via column chromatography using DCM:MeOH (83:17) to give 9 as a clear solid. (Yield: 78%) 1H NMR: (400 MHz, D20): δ (ppm), 5.69 (s, 1H), 5.44 (s, 1H), 4.46 (d, J=8.5 Hz, 1H), 3.92 (d, J=3.2 Hz, 1H), 3.90-3.63 (m, 10H), 3.45 (J=10.1 Hz, J=6.5 Hz), 2.01 (s, 3H), 1.91 (s, 3H). 13C NMR: (125 MHz, D20): δ (ppm), 176.2; 169.34; 141.72; 120.37; 103.0; 76.5; 73.6; 72.43; 72.5; 69.82; 69.3; 61.63; 62.4; 53.9; 39.81; 23.5; 18.86; 11.0. MS m/z: [M+H]+ 377.19.

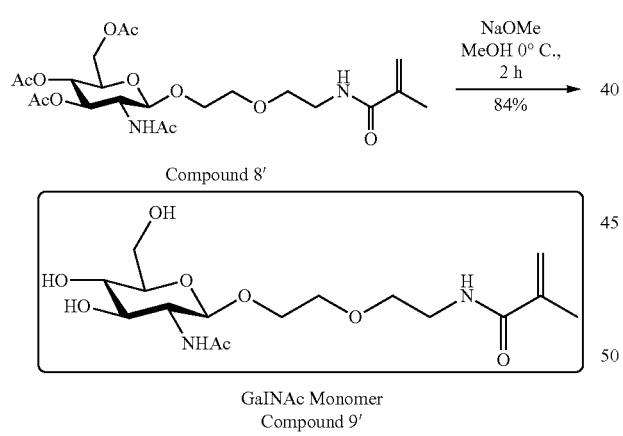

Compound 8'

GalNAc Monomer
Compound 9'

GlcNAc Monomer (9'). To a solution of compound 8' (12.2 g, 24.3 mmol) in anhydrous MeOH (160 mL) at 0° C. under $N_2$ was added a solution of NaOMe (4.5 M in MeOH, 6.5 mL). The reaction was warmed to room temperature and monitored by TLC (20% MeOH/DCM). After 2 hours, the reaction was complete and neutralized with Amberlite IR-120 (H+) resin. The resin was removed by filtration, washed with MeOH and the combined filtrate was evaporated and purified by flash chromatography (0-25% MeOH:DCM) to obtain GlcNAc monomer 9' as a pale-yellow syrup (7.5 g, 84%). The GlcNAc monomer 9' was stored in DMF at 58% wt/wt concentration, under nitrogen overlay at −20° C. $^1$H-NMR (499.9 MHz, D20, 25° C., ppm): δ=5.7 (s, 1H), 5.45 (s, 1H), 4.44 (d, J=8.5 Hz, 1H), 3.83-3.66 (m, 5H), 3.60-3.36 (m, 6H), 2.01 (s, 3H), 1.91 (s, 3H). $^{13}$C NMR: (125 MHz, D20, 25° C., ppm): δ=176.2; 169.34; 141.72; 120.37; 103.0; 76.5; 72.43; 72.5; 69.82; 69.3; 61.63; 62.4; 53.9; 39.81; 18.86; 11.0. MS m/z: [M+H]+ 377.18.

Alternatively, the following procedures were used to provide 9' (e.g., 2-(2-ethoxy)ethyl methacrylamide 2-acetamido-2-deoxy-β-D-glucopyranoside). Compound 8' (2.0 g, 3.98 mmol) was dissolved in 10 ml of MeOH and stirred at room temperature. Sodium methoxide (4 mmol) was added to the reaction and the reaction was stirred at room temperature. After 6 h, the solution was neutralized with Amberlite IR120 and then filtered. The solvent was removed via rotary evaporation and loaded on to silica gel. The products was purified via column chromatography using DCM:MeOH (83:17) to give 9' as a clear solid. 1H NMR: (400 MHz, D20): δ (ppm), 5.7 (s, 1H), 5.45 (s, 1H), 4.44 (d, J=8.5 Hz, 1H), 3.83-3.66 (m, 5H), 3.60-3.36 (m, 6H), 2.01 (s, 3H), 1.91 (s, 3H). 13C NMR: (125 MHz, D20): δ (ppm), 176.2; 169.34; 141.72; 120.37; 103.0; 76.5; 72.43; 72.5; 69.82; 69.3; 61.63; 62.4; 53.9; 39.81; 18.86; 11.0. MS m/z: [M+H]+ 377.18.

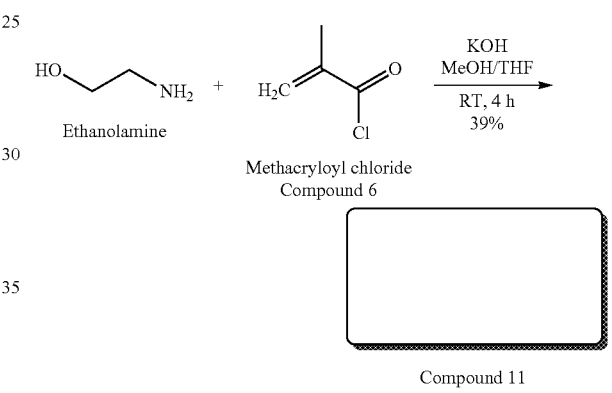

Compound 11

N-(2-hydroxyethyl)methacrylamide (HEMA) (11). To an ice-cold solution of ethanolamine (5.0 g, 82 mmol) in 70 mL of methanol was slowly added methacryloyl chloride (9.4 g, 90 mmol, 1.1 eq.) in THF (75 mL) under $N_2$ overlay. Potassium hydroxide (1.0 M, aqueous) was added to maintain a pH of 8-9 throughout the reaction. The mixture was warmed to room temperature over a period of 4 hours. The pH was adjusted to 5.0 with 1.0 M hydrochloric acid and the product was concentrated to minimum volume in the absence of light. The crude material was diluted with EtOAc, the layers separated, the aqueous layer was extracted with EtOAc three times. The combined organics were dried over $Na_2SO_4$, filtered and concentrated at room temperature. Purification was done on 120 g silica gel column using a gradient of acetone:hexane (0-60%). Fractions containing pure product were combined and concentrated in the absence of light resulting in pale yellow oil 11 (4.0 g, 39%). Compound 11 was diluted 72% wt/wt in DMF and stored under nitrogen at −20° C. $^1$H-NMR (499.9 MHz, CDCl$_3$, 25° C., ppm): δ=6.87 (m, 1H), 5.7 (m, 1H), 5.3 (m, 1H), 4.29 (s, 1H), 3.66 (t, J=5.1 Hz, 2H), 3.4 (dt, J=5.3, 5.1 Hz, H2), 1.96 (s, H3). $^{13}$C NMR: (125 MHz, CDCl3-d6, 25° C., ppm): δ=166.5, 139.2, 120.1, 61.2, 42.3, 18.4. MS m/z: [M+H]+ 130.08.

Alternatively, the following procedures were used to prepare compound 11 (N-(2-Hydroxyethyl) methacrylamide). To 200 ml of an ice-cold solution of ethanolamine (12 ml) and potassium carbonate (15 g) in DCM was slowly added a solution of methacryloyl chloride (6) (9 ml) in DCM (50 ml). The reaction was allowed to come to room temperature and stirred for another 4 h. After 4 h the reaction mixture was filtered through celite and the solvent was removed via rotary evaporation. The crude product was loaded onto silica gel and purified via flash chromatography, Ethyl Acetate (EtOAc):Hexanes (90:10), to give 11 as a colorless oil. (Yield: 75%) 1H NMR: (400 MHz, CDCl3-d6): 6.87 (m, 1H), 5.7 (m, 1H), 5.3 (m, 1H), 4.29 (s, 1H), 3.66 (t, J=5.1 Hz, 2H), 3.4 (dt, J=5.3, 5.1 Hz, H2), 1.96 (s, H3). 13C NMR: (125 MHz, CDCl3-d6): δ (ppm), 166.5, 139.2, 120.1, 61.2, 42.3, 18.4. MS m/z: [M+H]+ 130.08.

Example 2: RAFT Reagent Synthesis

The following provides exemplary procedures for the synthesis of certain RAFT reagents.

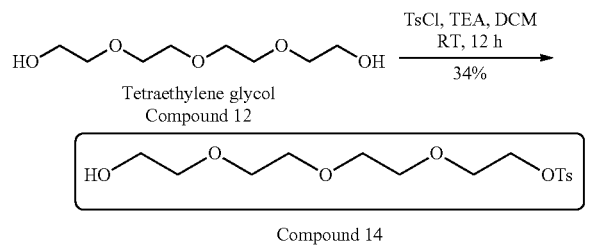

Tetra (ethylene glycol) mono p-toluenesulfonate (14). To a solution of tetraethylene glycol 12 (26.6 g, 137 mmol) in CH$_2$Cl2 (400 mL) was added 29.0 mL of triethylamine. The reaction was cooled to 0° C. and 4-methylbenzene-1-sulfonyl chloride (24.8 g, 130 mmol, 0.95 eq.) was added. The reaction was allowed to warm to room temperature and stirred for an additional 12 hours. The reaction mixture was washed with saturated NaHCO$_3$, brine, dried over Na$_2$SO$_4$, filtered and concentrated in vacuo. The crude material was purified on silica gel column, eluent 0-60% acetone:hexane system. Pure product 14 was collected as a light-yellow oil (16.3 g, 34%).

Tetra (ethylene glycol) monothioacetate (16). To a suspension of potassium thioacetate (10.7 g, 93.6 mmol, 2 eq.) in 680 mL of acetone was added a solution of mono p-toluenesulfonate 14 (16.3 g, 46.8 mmol) in 100 mL of acetone. The mixture was stirred at room temperature for 1 hour and then refluxed at 68° C. for 4 hours under a stream of nitrogen and a condenser. The reaction mixture was cooled to room temperature and filtered through a pad of Celite. The filtrate was concentrated to minimum volume, diluted with EtOAc (300 mL), washed with saturated NaHCO$_3$, brine, dried over Na$_2$SO$_4$ and evaporated under reduced pressure. The crude material was purified on a 120 g silica gel cartridge using an acetone:hexane gradient (0-35%), affording the desired product 16 as a brown syrup (8.65 g, 73%).

2-(2-(2-(2-(pyridin-2-yldisulfanyl)ethoxy)ethoxy)ethoxy)ethan-1-ol (18). Under nitrogen overlay, sodium methoxide (100 mL of 0.5 M in methanol) was slowly added into a stirred methanolic solution of monothioacetate 16 (5.2 g, 20.6 mmol) and 2,2-dithiodipyridine (5.44 g, 24.7 mmol, 1.2 eq.). After 2 hours, the reaction was concentrated and loaded onto a 120 g HP silica flash column and eluted with a gradient of acetone:hexane (0-50%) to afford desired product 18 as a dark yellow oil (3.15 g, 48%).

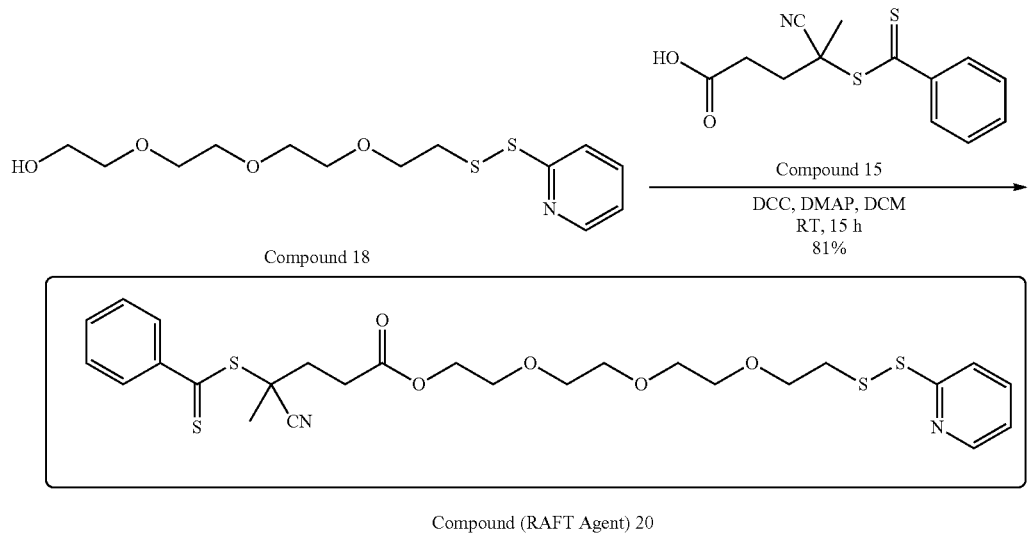

Thiol-Reactive μRAFT Agent (20). Disulfide compound 18 (355 mg, 1.11 mmol) and 4-cyano-4-(thiobenzoylthio)pentanoic acid 19 (345 mg, 1.24 mmol, 1.1 equivalents) were dissolved in anhydrous DCM (7.0 mL), resulting in a pink solution. 5.0 mol % of 4-dimethylaminopyridine (DMAP) was added into solution and the flask cooled to 0° C. and stirred for 30 minutes. N,N'-dicyclohexylcarbodiimide (DCC, 230 mg, 1.1 mmol, 1 eq.) in 5.0 mL of DCM was added slowly. The reaction was stirred and allowed to equilibrate to room temperature over 5 hours. The reaction was complete by TLC but was allowed to stir for 16 hours before work-up. The pink suspension was filtered through a pad of Celite, and the filtrate concentrated. Purification was done on a 25 g HP silica gel flash column using a 0-40% acetone:hexane gradient. The fractions containing pure product were combined and concentrated resulting in RAFT agent 20 (0.53 g, 81%) as a pink oil. RAFT agent 20 was diluted to 100 mg/mL in DMF for direct use in polymerization. $^1$H-NMR (499.9 MHz, D20, 25° C., ppm): δ=1.60 (br. S, 2H), 1.93 (s, 3H, methyl), 2.99 (t, 2H, methylene), 3.66 (m, 12H, PEG methylene), 4.27 (t, 2H, methylene), 7.08 (t, 1H, aromatic), 7.39 (t, 2H, aromatic), 7.57 (t, 1H, aromatic), 7.65 (t, 1H, aromatic), 7.77 (d, 1H, aromatic), 7.90 (d, 2H, aromatic), 8.45 (d, 1H, aromatic).

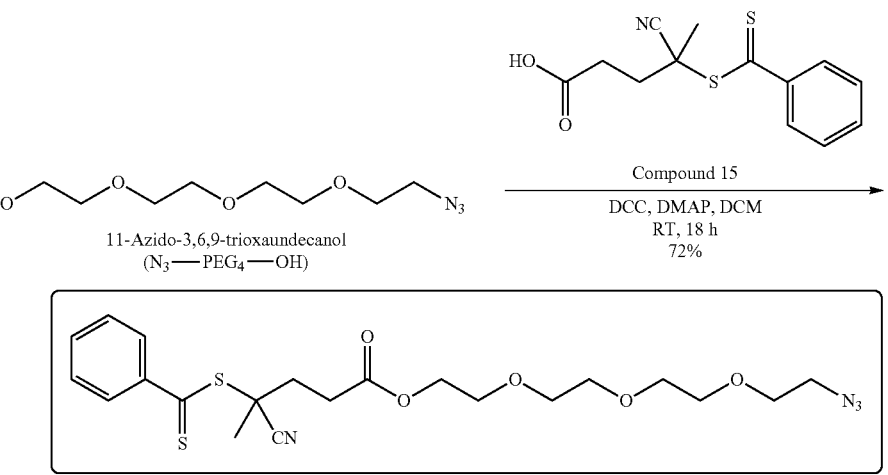

Alkyne-Reactive μRAFT Agent (21). To 4-cyano-4-(phenylcarbonothioylthio)pentanoic acid (505.1 mg, 1.81 mmol) and 4-dimethylaminopyridine (16.4 mg, 0.13 mmol) was added anhydrous dichloromethane (7.0 mL) under and atmosphere of dry $N_2$ gas with stirring, giving a red solution. To the flask was added a solution of 11-Azido-3,6,9-trioxaundecanol (358.4 mg, 1.64 mmol) in anhydrous dichloromethane (7.0 mL). The mixture was cooled in a water/ice bath under an atmosphere of dry $N_2$ gas for 20 minutes. Using a gas-tight syringe, a solution of dicyclohexyl carbodiimide (374 mg, 1.81 mmol) in anhydrous dichloromethane (7.0 mL) was slowly added to the reaction mixture over 15 minutes. A precipitate was observed to slowly form turning the reaction mixture dark pink in color. The mixture was maintained in a water/ice bath for 3 hours and then allowed to come to ambient temperature over 18 hours. The reaction mixture was then filtered through a Celite pad and the pad was rinsed with dichloromethane (3×15.0 mL) when all the red color was removed from the Celite. The solution was concentrated under vacuum at 20° C. to 1.0 mL and chromatographed on a silica gel column (12.0 g) using a gradient of acetone:hexane (0-40%). TLC (hexane:acetone 2:1 v/v) showed a major product with $R_f$=0.30. Fractions containing the product $R_f$=0.30 were pooled and concentrated to a red oil. The sample was then dried under vacuum for 30 hours to yield a dark red oil (563.0 mg, 72%). The final product and was then stored at 2° C. in a light resistant container. $^1$H-NMR (499.9 MHz, $CDCl_3$, 25° C., ppm): δ=1.93 (s, 3H, $CH_3$—C—(CN)—S); 3.37 (t, 2H, C$\underline{H}_2$—$CH_2$—C(O)—O); 3.6-3.75 (m, 16H, —C(O)—O—[$CH_2$—$CH_2$—O]3-$CH_2$—$CH_2$—N3); 4.26 (t, 2H, —C$\underline{H}_2$—($CH_3$)—CN); 7.39 (m, 2H); 7.56 (m, 1H); 7.90 (m, 2H).

Alternatively, the following procedures were used to provide 21 (N3TEG-RAFT). Azido-tetraethylene glycol 11 (219 mg, 1.0 mmol), DMAP (12 mg, 0.1 mmol) and RAFT agent 15 (279.0 mg, 1.0 mmol) were added to 10 ml of DCM and stirred on ice for 30 min. A solution of DCC (206 mg, 1.0 mmol) in DCM was added dropwise to the reaction mixture. The reaction mixture was allowed to come to room temperature and stirred for another 3 hours. The reaction was filtered and the solvent was removed via rotary evaporation. The product was loaded onto silica gel and separated via column chromatography using EtOAC to yield 21 as a pink liquid. (Yield: 23%) 1H NMR: (400 MHz, CDCl3-d6): δ (ppm), 7.76 (m, 2H), 7.43 (m, 1H), 7.28 (m, 2H), 4.11 (m, 2H), 3.57 (m, 2H), 3.51 (m, 12H), 3.23 (m, 2H), 2.75-2.45 (m, 4H), 1.79 (s, 3H). 13C NMR: (125 MHz, CDCl3-d6): δ (ppm), 221.2; 171.34; 144.72; 135.37; 129.0; 126.5; 119.6; 68.43; 65.5; 44.82; 31.3; 29.64; 24.5; 12.4. MS m/z: [M+H]+ 481.17.

Example 3: Thiol-Reactive Polymer Synthesis

The following provides exemplary procedures for the synthesis of certain thiol-terminated Y(Z)—$R^2$ units.

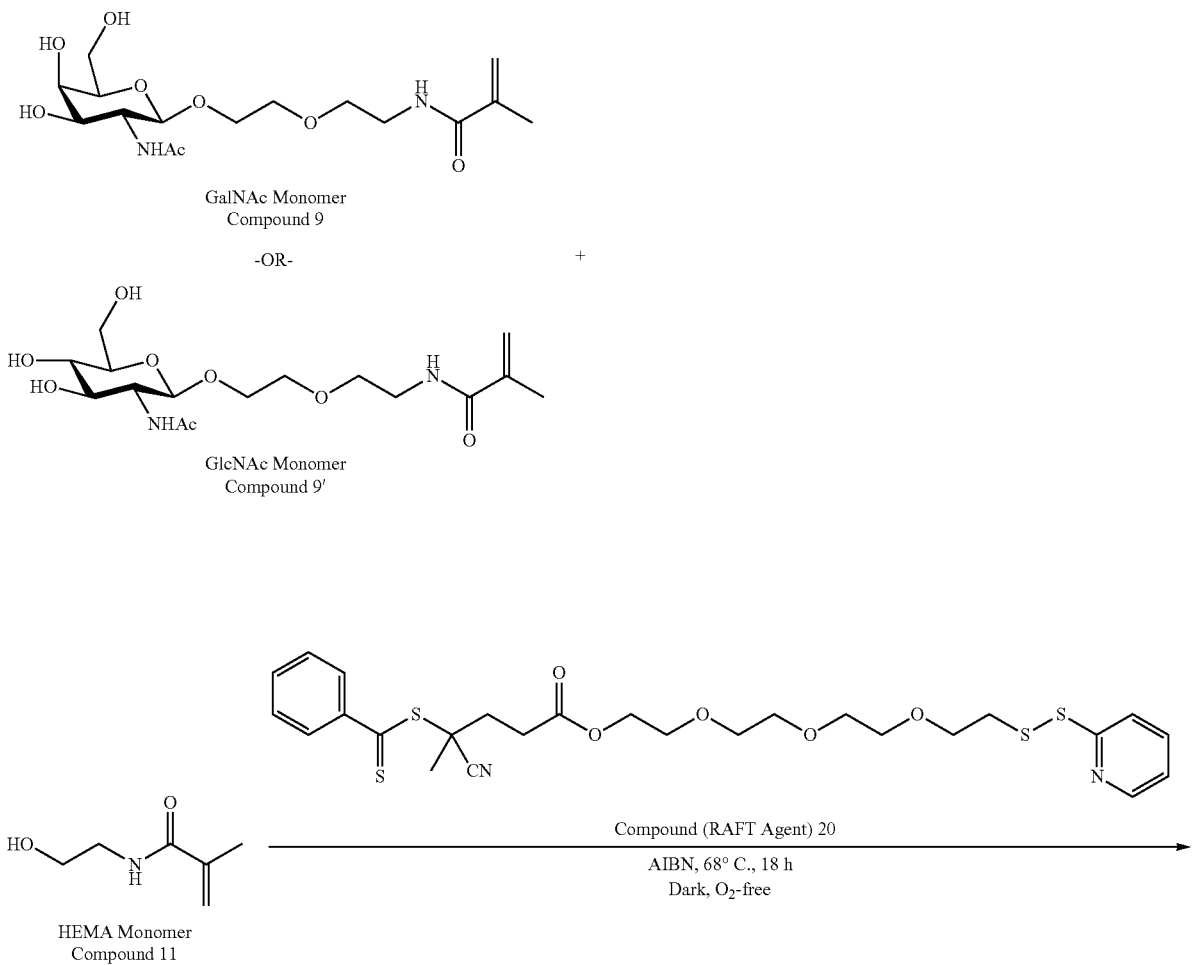

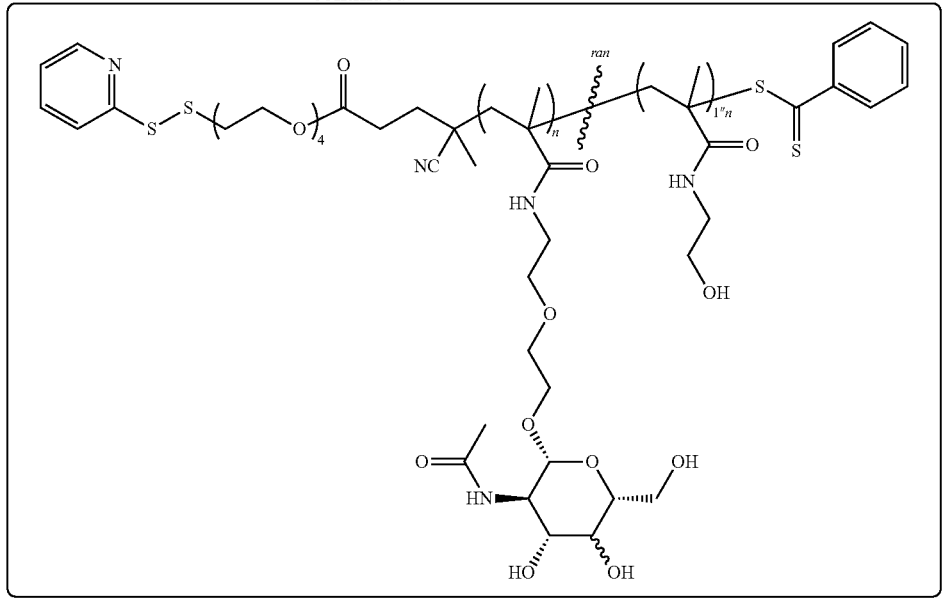

p(GalNAc-co-HEMA)-DTP -OR- p(GlcNAc-co-HEMA)-DTP p(GalNAc-co-HEMA)-DTP or p(GlcNAc-co-HEMA)-DTP. A typical example synthesis of a p(GalNAc-co-HEMA)-DTP with a target molecular weight of 21.0 kDa, a target degree of polymerization of 100 monomers, and a target GalNAc:HEMA monomer composition of 30:70 is as follows: A 10 mL single-neck Schlenk flask equipped with a PTFE valve and situated in a low-light area was purged with ultra-high-purity Argon (Grade 5), placed in an ice bath, and charged with a magnetic stir bar, compound 9 (300 mg, 0.80 mmol, solid), compound 11 (240 mg, 1.86 mmol, added as 240 μL neat oil), compound 20 (15.4 mg, 30 μmol added as 283 μL of stock solution at 54.53 mg/mL), 2,2′-azobis(2-methylpropionitrile) (1.09 mg, 6.6 μmol, added as 270 μL of stock solution at 4.04 mg/mL), and N,N-dimethylformamide (827 μL). The flask was sealed with a rubber septum, the septum reinforced with parafilm, and the solution was sparged on ice with ultra-high-purity (Grade 5) Argon for 2 hours. Following sparging, the solution was subjected to five freeze-pump-thaw cycles over liquid Nitrogen, each cycle consisted of a 3-minute freeze step, a 15-minute pump step, and a 2-minute thaw step. The solution was then overlaid with ultra-high-purity (Grade 5) Argon and allowed to stir at 800 rpm in a pre-heated oil bath at 68° C. for 18 hours. The RAFT polymerization was quenched by submerging the flask in an ice bath, exposing the solution to air, and allowing the solution to stir on ice at 500 rpm for 15 minutes. The crude polymer solution was then precipitated dropwise into 45 mL anhydrous ethyl acetate at room temperature and the resultant precipitate was pelleted via centrifugation at 4300-G for 10 minutes. The supernatant was then decanted, replaced with fresh anhydrous ethyl acetate, the pellet was re-suspended via vortex, re-pelleted via centrifugation, and the supernatant decanted again, affording a resultant pellet which was dried under high vacuum at room temperature for 2 hours affording a pink powder. The dried crude polymer was re-dissolved in 8.0 mL Milli-Q water, charged into a Slide-α-Lyzer dialysis cassette (3.5 kDa MWCO) and dialyzed against 500 volumes of Milli-Q water for 24 hours during which solvent exchanges were performed at t=4 hours and t=20 hours. The dialyzed aqueous solution was then dried via lyophilization for 4 days to yield p(GalNAc-co-HEMA)-DTP as a flaky light-pink solid (222.7 mg, 40.1%). GPC: $M_n$=22.2 kDa, $M_w$=24.7 kDa, $M_p$=21.9 kDa, Đ=1.11. $^1$H-NMR (499.9 MHz, D20, 25° C., ppm): δ=0.8-1.6 (m, 3H, backbone methyl), 1.6-2.3 (m, 2H, backbone methylene), 3.2-3.45 (br. s, 4H, ethoxy methylene), 3.5-4.1 (m, sugar ring protons), 4.45-4.6 (br. s, 1H, anomeric), 7.0-8.6 (m, 9H, end-group aromatic).

The same procedure was used to produce p(GlcNAc-co-HEMA)-DTP. All thiol-reactive polymers produced with the above procedure are described in Table 1. Structures and molecular weight was confirmed by NMR and GPC, respectively.

TABLE 1

Thiol-reactive polymers produced using procedures as disclosed in Example 3 using different monomer ratios.

| Polymer | Sugar:HEMA Ratio | $M_n$ | PDI |
|---|---|---|---|
| p(GalNAc-co-HEMA)-DTP | 4:1 | 14.9 | 1.10 |
| p(GalNAc-co-HEMA)-DTP | 3:7 | 21.9 | 1.11 |
| p(GalNAc-co-HEMA)-DTP | 1:4 | 13.2 | 1.10 |
| p(GlcNAc-co-HEMA)-DTP | 4:1 | 21.5 | 1.09 |
| p(GlcNAc-co-HEMA)-DTP | 1:1 | 19.3 | 1.11 |
| p(GlcNAc-co-HEMA)-DTP | 1:4 | 14.5 | 1.12 |

Example 4: Alkyne Reactive Polymer Synthesis
The following provides exemplary procedures for the synthesis of portions of Y(Z)—R² units.
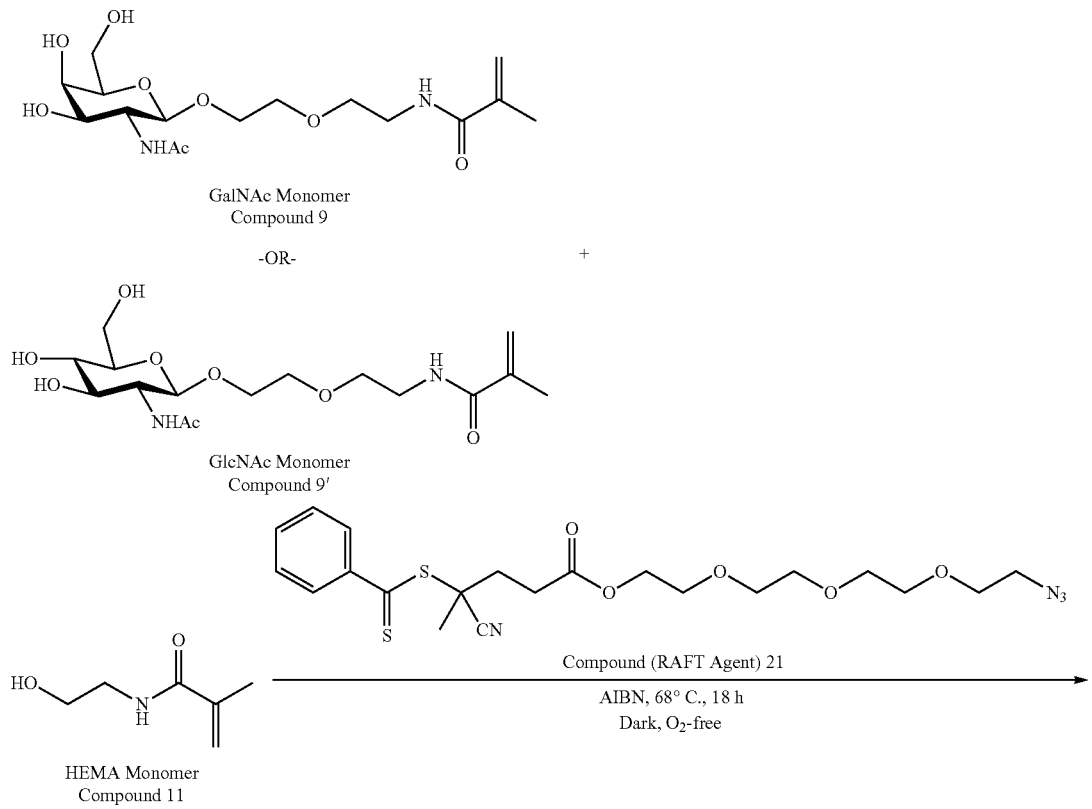
GalNAc Monomer
Compound 9
-OR-
GlcNAc Monomer
Compound 9'
HEMA Monomer
Compound 11
Compound (RAFT Agent) 21
AIBN, 68° C., 18 h
Dark, O₂-free
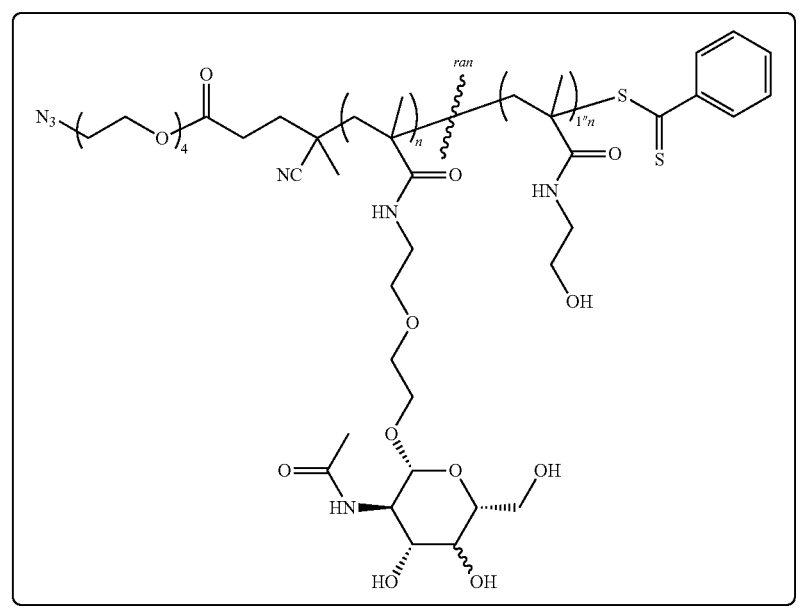
p(GalNAc-co-HEMA)-N₃  -OR-  p(GlcNAc-co-HEMA)-N₃ p(GalNAc-co-HEMA)-N3 or p(GlcNAc-co-HEMA)-N3. A typical example synthesis of a p(GalNAc-co-HEMA)-N3 with a target molecular weight of 18.1 kDa, a target degree of polymerization of 70 monomers, and a target GalNAc:HEMA monomer composition of 50:50 is as follows: A 10 mL single-neck Schlenk flask equipped with a PTFE valve and situated in a low-light area was purged with ultra-high-purity Argon (Grade 5), placed in an ice bath, and charged with a magnetic stir bar, compound 9 (600 mg, 1.59 mmol, solid), compound 11 (206 mg, 1.59 mmol, added as 206 µL neat oil), compound 21 (25.54 mg, 50 µmol added as 521 µL of stock solution at 49.0 mg/mL), 2,2'-azobis(2-methylpropionitrile) (2.18 mg, 13.3 µmol, added as 538 µL of stock solution at 4.05 mg/mL), and N,N-dimethylformamide (1153 µL). The flask was sealed with a rubber septum, the septum reinforced with parafilm, and the solution was sparged on ice with ultra-high-purity (Grade 5) Argon for 2 hours. Following sparging, the solution was subjected to five freeze-pump-thaw cycles over liquid Nitrogen, each cycle consisted of a 3-minute freeze step, a 15-minute pump step, and a 2-minute thaw step. The solution was then overlaid with ultra-high-purity (Grade 5) Argon and allowed to stir at 800 rpm in a pre-heated oil bath at 68° C. for 18 hours. The RAFT polymerization was quenched by submerging the flask in an ice bath, exposing the solution to air, and allowing the solution to stir on ice at 500 rpm for 15 minutes. The crude polymer solution was then precipitated dropwise into 45 mL anhydrous ethyl acetate at room temperature and the resultant precipitate was pelleted via centrifugation at 4300-G for 10 minutes. The supernatant was then decanted, replaced with fresh anhydrous ethyl acetate, the pellet was re-suspended via vortex, re-pelleted via centrifugation, and the supernatant decanted again, affording a resultant pellet which was dried under high vacuum at room temperature for 2 hours affording a pink powder. The dried crude polymer was re-dissolved in 8.0 mL Milli-Q water, charged into a Slide-a-Lyzer dialysis cassette (3.5 kDa MWCO) and dialyzed against 500 volumes of Milli-Q water for 24 hours during which solvent exchanges were performed at t=4 hours and t=20 hours. The dialyzed aqueous solution was then dried via lyophilization for 4 days to yield p(GalNAc-co-HEMA)-N3 as a flaky light-pink solid (210.4 mg, 25.3%). GPC: Mn=15.9 kDa, Mw=17.2 kDa, Mp=18.1 kDa, Đ=1.08. 1H-NMR (499.9 MHz, D20, 25° C., ppm): δ=0.8-1.6 (m, 3H, backbone methyl), 1.6-2.3 (m, 2H, backbone methylene), 3.2-3.5 (br. s, 4H, ethoxy methylene), 3.5-4.1 (m, sugar ring protons), 4.45-4.6 (br. s, 1H, anomeric), 7.45-8.0 (m, 5H, end-group aromatic).

The same procedure was used to produce p(GlcNAc-co-HEMA)-N3. All alkyne-reactive polymers produced with the above procedure are described in Table 2. Structures and molecular weight was confirmed by NMR and GPC, respectively.

TABLE 2

Alkyne-reactive polymers produced using procedure in section 5B.

| Polymer | Sugar:HEMA Ratio | Mn | PDI |
|---|---|---|---|
| p(GalNAc-co-HEMA)-N3 | 1:1 | 18.1 | 1.08 |
| p(GalNAc-co-HEMA)-N3 | 1:1 | 31.6 | 1.11 |
| p(GlcNAc-co-HEMA)-N3 | 1:1 | 16.7 | 1.08 |
| p(GlcNAc-co-HEMA)-N3 | 1:1 | 31.1 | 1.08 |

Alternatively, the following procedure was used to prepare the above azide-terminated polymers.

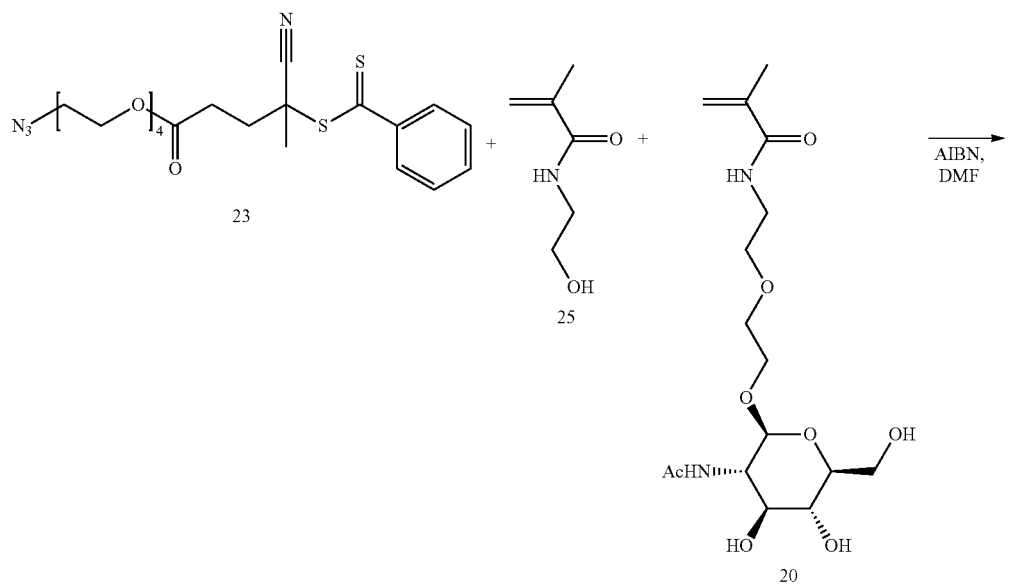

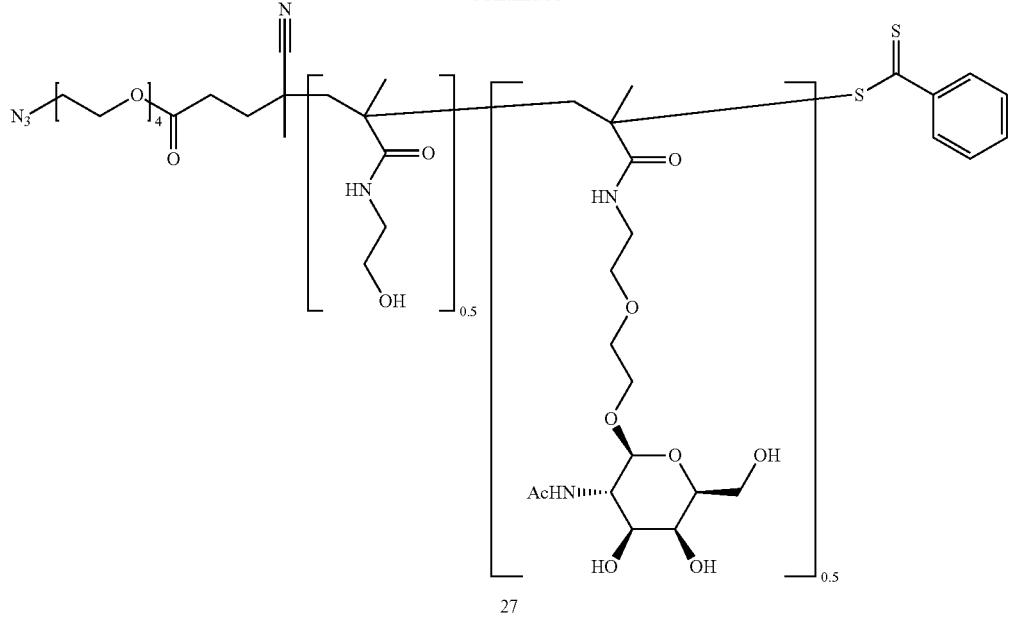

27 p(GalNAc) (27). Compound (25) (129 mg, 1.0 mmol), compound 20 (377 mg, 1.0 mmol), compound 23 (9.62 mg, 0.02 mmol), and AIBN (0.656 mg, 0.004 mmol) were added to dimethylformamide (DMF) (2.0 ml) were added to a schlenk flask and subjected to 4 freeze-thaw degassing cycles. The reaction mixture was then headed to 65° C. for 12 h. After 12 h 0.328 mg of AIBN were added to the reaction, and the mixture was allowed to stir at 65° C. for another 8 h. The reaction mixture was then cooled to room temperature and then precipitated in acetone. The polymer product rapidly crashed out of the mixture and the solvent was decanted. Residual solvent was then removed from the product under vacuum.

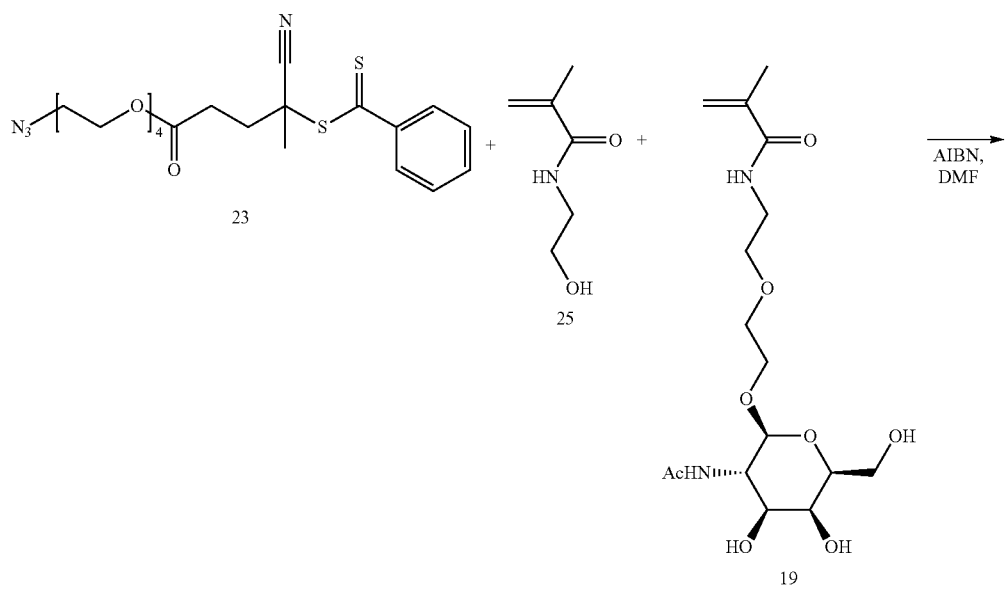

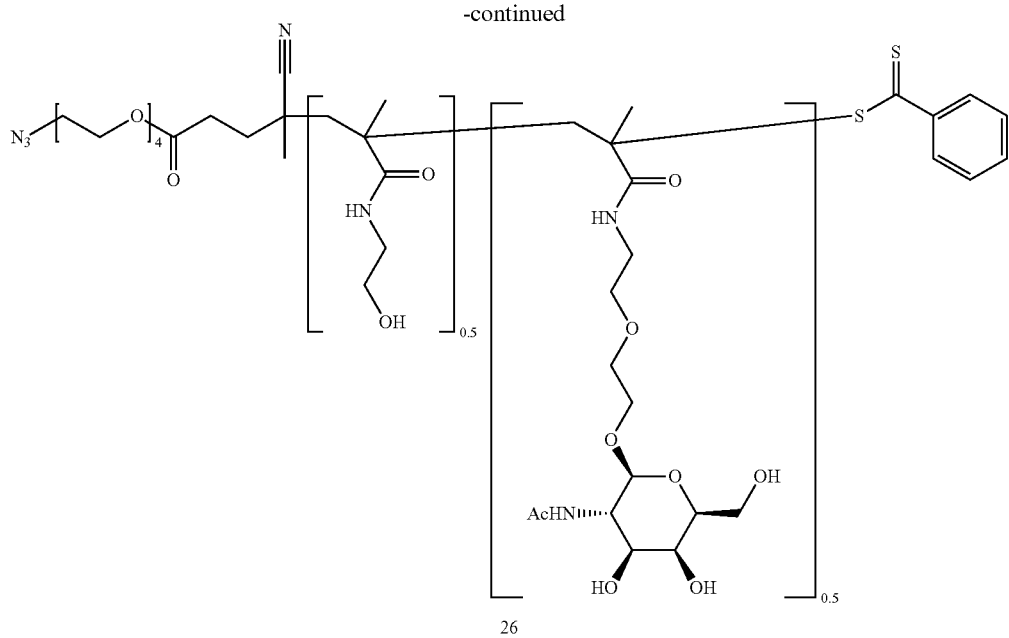

26 p(GluNAc) (26). Compound (25) (129 mg, 1.0 mmol), compound 19 (377 mg, 1.0 mmol), compound 23 (9.62 mg, 0.02 mmol), and AIBN (0.656 mg, 0.004 mmol) were added to dimethylformamide (DMF) (2.0 ml) were added to a schlenk flask and subjected to 4 freeze-thaw degassing cycles. The reaction mixture was then headed to 65° C. for 12 h. After 12 h 0.328 mg of AIBN were added to the reaction, and the mixture was allowed to stir at 65° C. for another 8 h. The reaction mixture was then cooled to room temperature and then precipitated in acetone. The polymer product rapidly crashed out of the mixture and the solvent was decanted. Residual solvent was then removed from the product under vacuum.

Example 5: Synthesis of DIBO Linkers

The following provides exemplary procedures for the synthesis of a DIBO-PEG2K-NHS linkers.

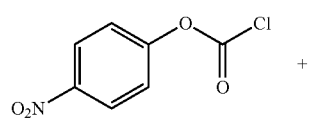 +

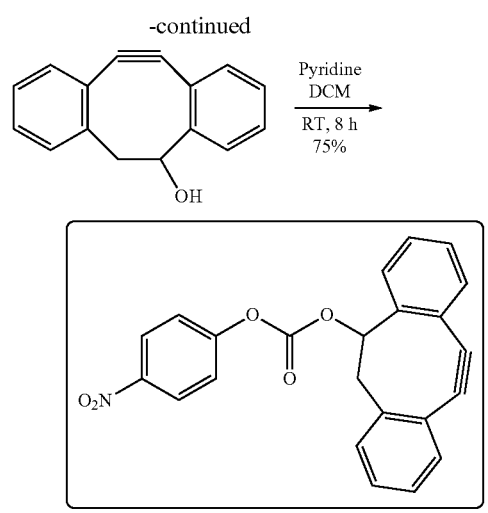

DIBO-NPC

DIBO—NPC. To a solution of DIBO—OH (110 mg, 0.5 mmol) in anhydrous dichloromethane (DCM) (10 mL) was added pyridine (20 μL, 2.5 mmol) and 4-nitrophenyl chloroformate (200 mg, 1.0 mmol) and stirred at room temperature for 8 hours. The reaction mixture was diluted with dichloromethane (5.0 mL) and washed with brine (2×5.0 mL). The organic layer was dried over sodium sulfate and solvent was evaporated in vacuo. The residue was chromatographed over silica gel eluting a gradient of hexane/ethyl acetate (0-100% in 30 minutes) giving DIBO—NPC as a white solid (145 mg, 75%). $^1$H NMR analysis were consistent with reported data.

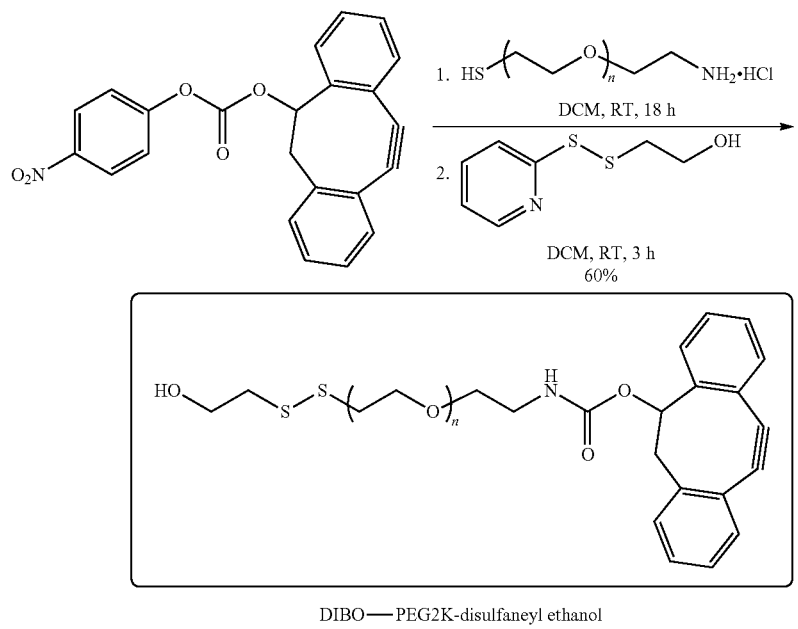

DIBO—PEG2K-disulfaneyl ethanol

DIBO-PEG2K-disulfaneyl ethanol. To a solution of DIBO—NPC (26 mg, 68 μmol) in anhydrous dichloromethane (DCM) (1.0 mL) was added N, N-diisopropylethylamine (35 μL, 204 μmol) and HS-PEG2K—NH$_2$ HCl (146 mg, 73 μmol). The reaction mixture was degassed with N2 for 5 minutes and stirred at room temperature for 18 hours. 2-(Pyridin-2-yldisulfanyl)ethanol (14.0 mg, 75 μmol) in dichloromethane (1.0 mL) was then added and stirred at room temperature for another 3 hours. The crude reaction mixture was concentrated under reduced pressure and purified via silica gel flash chromatography eluting dichloromethane/methanol (0-20% in 30 min) giving DIBO-PEG2K-disulfaneyl ethanol as yellow solid (90.0 mg, 60%).

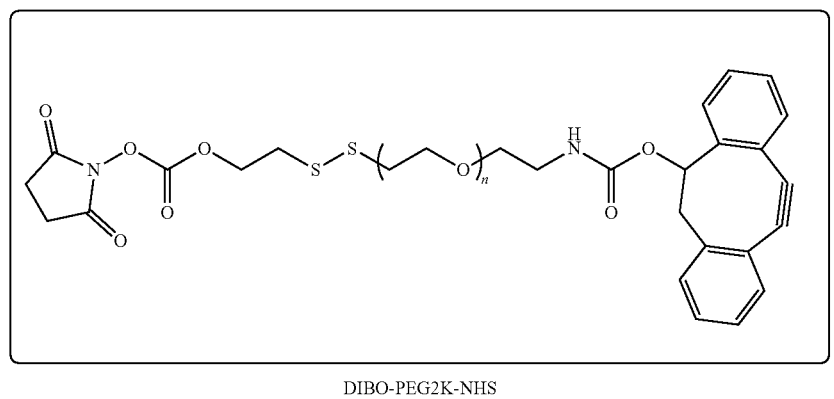

DIBO-PEG2K-NHS

DIBO-PEG2K—NHS. To a solution of DIBO-PEG2K-disulfaneyl ethanol (100 mg, 41 µmol) in acetonitrile (ACN) (2.0 mL) at 0° C. was added N,N'-disuccinimidyl carbonate (16.0 mg, 61.5 µmol) and N, N-diisopropylethylamine (21 µL, 123 µmol). The reaction mixture was degassed with nitrogen for 5 minutes, warmed to room temperature and stirred for 18 hours. The reaction mixture was concentrated under reduced pressure. The crude product was purified via silica gel flash chromatography eluting dichloromethane (containing 0.05% NEt$_3$):methanol (0-20% in 30 minutes) giving DIBO-PEG2K—NHS as yellow solid (40 mg, 38%). $^1$H-NMR (499.9 MHz, CDCl$_3$, 25° C., ppm): δ=7.52-7.49 (m, 1H), 7.37-7.27 (m, 7H), 5.80-5.45 (m, 2H), 3.90-3.55 (m, PEG methylene), 2.92-2.84 (m, 4H), 2.69 (s, 4H).

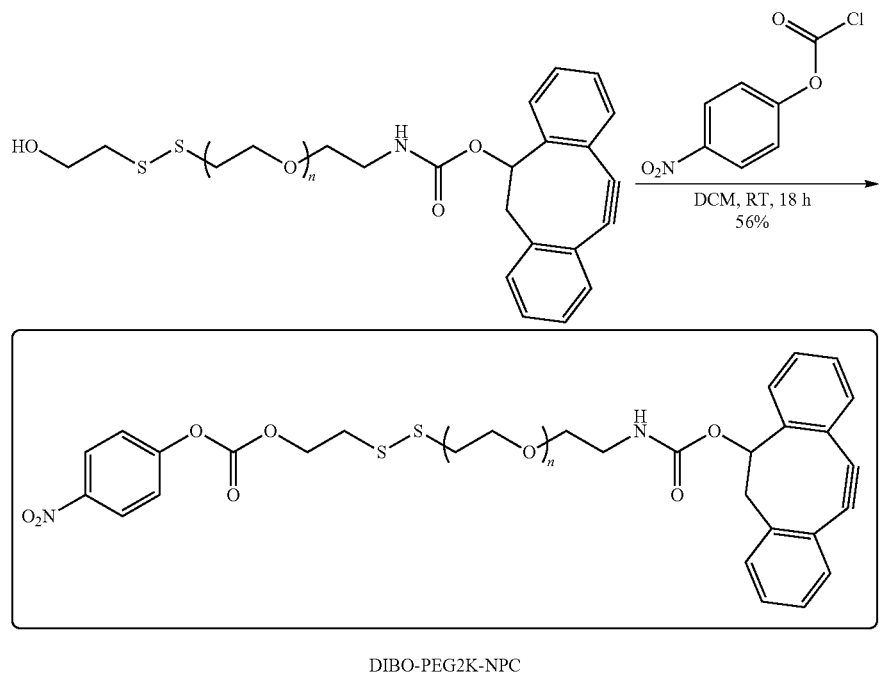

DIBO-PEG2K-NPC

DIBO-PEG2K—NPC. To a solution of DIBO-PEG2K-disulfaneyl ethanol (100 mg, 41 µmol) in dichloromethane (DCM) (2.0 mL) was added 4-nitrophenyl chloroformate (13 mg, 6.15 mmol) and pyridine (118 µL, 123 µmol). The reaction mixture was stirred at room temperature for 18 hours and concentrated under reduced pressure. The crude product was purified via silica gel flash chromatography eluting dichloromethane (containing 0.05% NEt$_3$):methanol (0-20% in 30 minutes) giving DIBO-PEG2K—NPC as yellow solid (60 mg, 56%). $^1$H-NMR (499.9 MHz, CDCl$_3$, 25° C., ppm): δ=8.30-8.25 (m, 2H), 7.52-7.27 (m, 10H), 5.80-5.50 (m, 2H), 3.83-3.47 (m, PEG H signals), 3.11-2.91 (m, 4H).

Example 6: Synthesis of DBCO Linkers

The following provides exemplary procedures for the synthesis of a DIBO-PEG2K—NHS linkers.

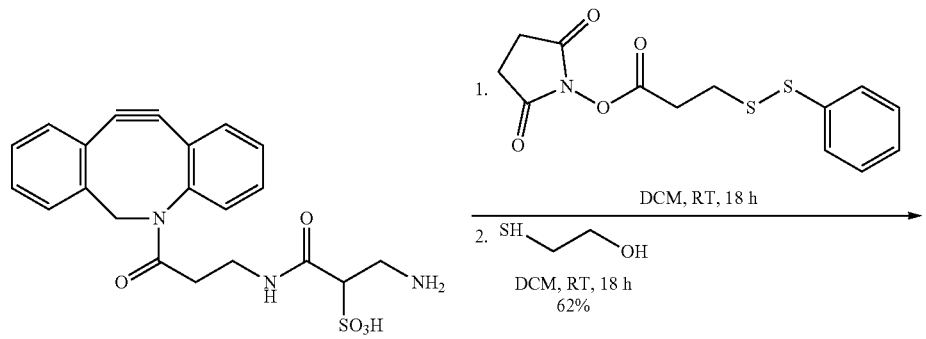

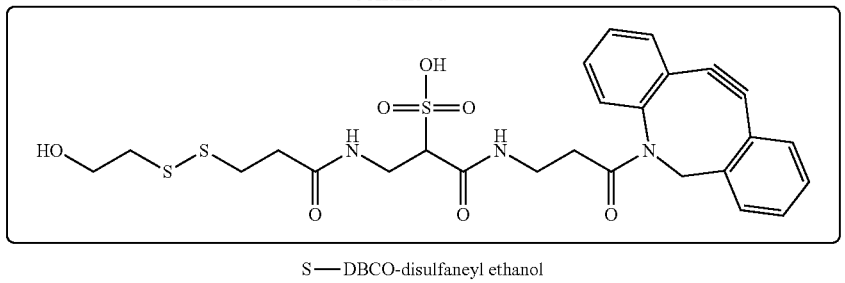

S—DBCO-disulfaneyl ethanol

S-DBCO-disulfaneyl ethanol. To a solution of s-DBCO-amine (100 mg, 234 µmol) in dichloromethane:methanol (1.0 mL: 300 µL) was added N, N-diisopropylethylamine (122 µL, 702 µmol) and NHS-DTP (SPDP, 110 mg, 352 µmol). The reaction mixture was degassed with nitrogen for 5 minutes and stirred at room temperature for 18 hours. The crude solution was precipitated dropwise into 45 mL diethyl ether and the resultant precipitate pelleted via centrifugation at 4300-G for 30 minutes. The supernatant was then decanted and the pellet was re-dissolved in dichloromethane (1 mL). To this crude reaction mixture was added N, N-diisopropylethylamine (122 µL, 702 µmol) and 2-mercaptoethanol (41 µL, 585 µmol) and stirred at room temperature for another 18 hours. The crude solution was precipitated dropwise into 45 mL diethyl ether and the resultant precipitate pelleted via centrifugation at 4300-G for 30 minutes. The supernatant was then decanted, the pellet was re-dissolved in dichloromethane, and purified via silica gel flash chromatography eluting dichloromethane (containing 0.05% NEt$_3$):methanol (0-20% in 30 minutes) affording S-DBCO-disulfaneyl ethanol as a yellow solid (85 mg, 62%).

NEt$_3$):methanol (0-20% in 30 minutes) giving S—DBCO—NHS as yellow solid (10.0 mg, 55%). $^1$H-NMR (499.9 MHz, CDCl$_3$, 25° C., ppm): δ=7.60-6.82 (m, 8H), 5.31-5.05 (m, 1H), 4.40-4.11 (m, 1H), 3.71-3.64 (m, 2H), 3.39-3.14 (m, 4H), 2.96-2.62 (m, 7H), 2.5 (s, 4H), 2.21-1.95 (m, 2H).

Example 7: Alkyne Synthesis

The following provides exemplary procedures for the synthesis of certain alkyne containing groups and their functionalization to antigens (or antigen mimics).

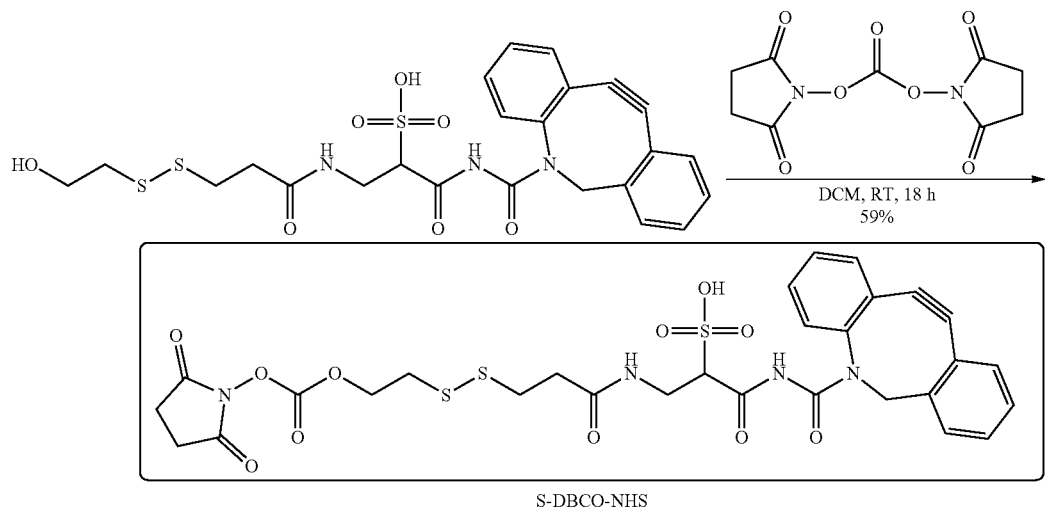

S—DBCO—NHS. To a solution of S-DBCO-disulfaneyl ethanol (15 mg, 25 µmol) in dichloromethane (DCM) (1.0 mL) at 0° C. was added N,N'-disuccinimidyl carbonate (13 mg, 51 µmol) and N, N-diisopropylethylamine (4.0 µL, 23 µmol). The reaction was warmed to room temperature, stirred for 18 hours and concentrated under reduced pressure. The crude product was purified via silica gel flash chromatography eluting dichloromethane (containing 0.05%

-continued

PEG2K—NH$_2$ disulfaneyl ethanol

PEG2K—NH₂-disulfaneyl ethanol. A solution of HS-PEG2K—NH₂ HCl (807.6 mg, 0.37 mmol) in dichloromethane (DCM, 5.0 mL) was added dropwise to a stirred solution of 2-(2-pyridinyldithio) ethanol (381.5 mg, 2.0 mmol) in methanol (3.0 mL). The solution was stirred at room temperature for 18 hours then concentrated to an oil and dissolved in 2-propanol (2.0 mL). The crude product was then precipitated dropwise into stirred ice-cold hexanes (40 mL) and placed at −20° C. for 4 hours. The precipitate and solvent mixture was centrifuged at 2000-G for 5 min with careful removal of supernatant. The sample was dried under vacuum for 20 minutes. The crude product was then used in the next step without further purification (crude yield 65%).

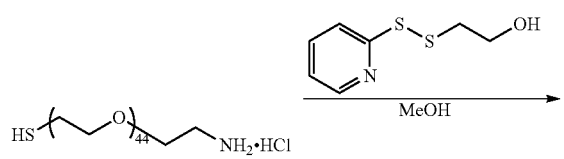

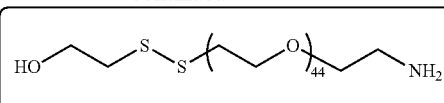

Ethanol disulfaneyl polyethylene glycol amine. A solution of thiol polyethylene glycol amine HCl 1 (JenKem Technology USA) (1.0 g, 0.5 mmol) in dichloromethane (DCM) (5 ml) was added dropwise to a stirred solution of 2-(2-pyridinyldithio)ethanol 2 (467.5 mg, 2.5 mmol) in isopropanol (IPA) (3 ml). The solution was stirred at room temperature for 10 h concentrated via rotary evaporation. An additional aliquot of IPA (3 ml) was added. The remaining crude product was then poured into ice cold diethyl ether (40 ml) and placed at −20° C. for 4 h. The precipitate and solvent mixture was centrifuged at 2000 g for 3 min. The solvent was then decanted and excess solvent was removed from the pelleted precipitate under reduced pressure. The crude product was then used in the next step without further purification (65% crude yield).

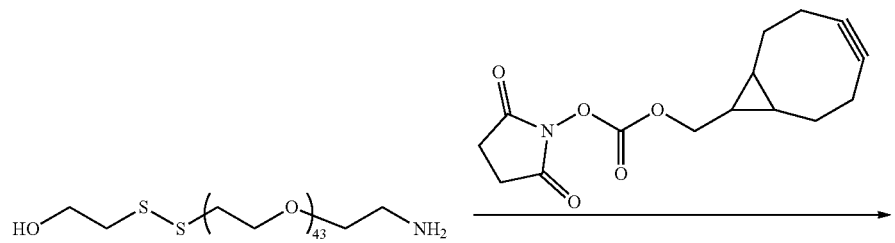

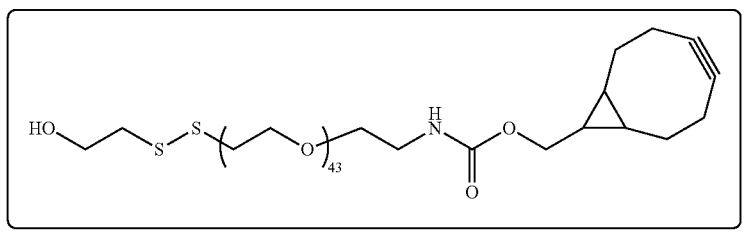

BCN PEG₄₃ disulfaneyl ethanol

Ethanol disulfaneyl polyethylene glycol (1R,8S,9s)-Bicyclo[6.1.0]non-4-yn-9-ylmethyl carbamate (5). A solution of (1R,8S,9s)-Bicyclo[6.1.0]non-4-yn-9-ylmethyl N-succinimidyl carbonate (4) (90 mg, 0.30 mmol) in DCM (0.5 ml) was added dropwise to an ice-cooled stirred solution of ethanol disulfaneyl polyethylene glycol amine (3) (0.5 g, 0.24 mmol) and triethylamine (48 mg, 0.48 mmol) in DCM (5 ml). After the addition of (4), the reaction was allowed to come to room temperature and stirred for another 6 h. The reaction mixture was then poured into ice-cold hexanes (40 ml) and placed at −20° C. for 4 h. The precipitate and solvent mixture was centrifuged at 2000 g for 3 min. The solvent was then decanted and excess solvent was removed from the pelleted precipitate under reduced pressure. The crude product was then used in the next step without further purification (75% crude yield).

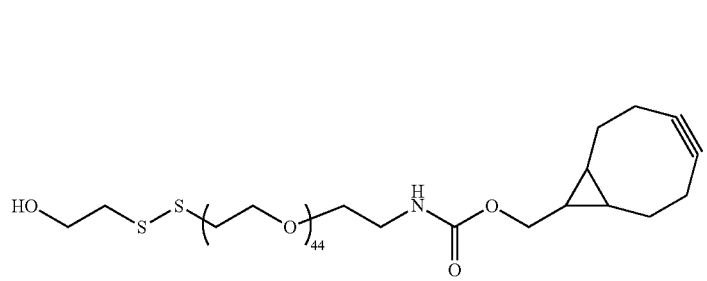 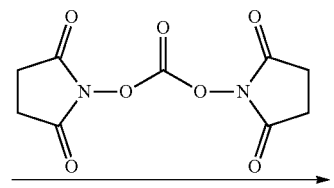

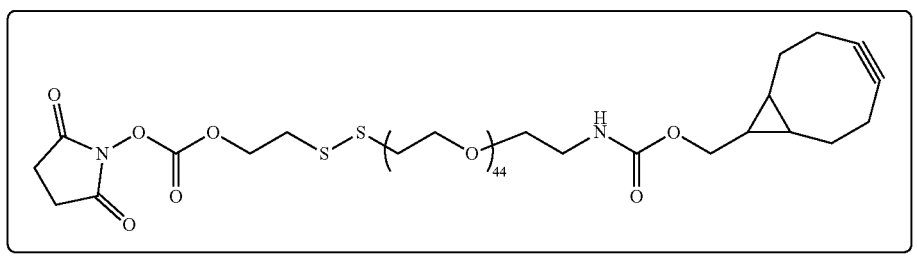

BCN—PEG-44-NHS

N-succinimidyl carbamate Ethanol disulfaneyl polyethylene glycol (1R,8S,9s)-Bicyclo[6.1.0]non-4-yn-9-ylmethyl carbamate (Self-immolative Linker) (7). A solution of Ethanol disulfaneyl polyethylene glycol (1R,8S,9s)-Bicyclo[6.1.0]non-4-yn-9-ylmethyl carbamate 5 (300 mg, 0.13 mmol) in anhydrous acetonitrile (ACN) (1.5 ml) was added dropwise to a stirred solution of N,N'-Disuccinimidyl carbonate (6) (61 mg, 0.24 mmol) and triethylamine (48 mg, 0.48 mmol) in anhydrous ACN (5 ml). The reaction mixture was stirred overnight and was then poured into ice-cold hexanes (40 ml) and placed at −20° C. for 4 h. The precipitate and solvent mixture was centrifuged at 2000 g for 3 min. The solvent was then decanted and excess solvent was removed from the pelleted precipitate under reduced pressure. The crude product was purified via silica gel flash chromatography DCM:MeOH (85:15) (yield: 43%, 129 mg).

The following alternative procedures can be used.

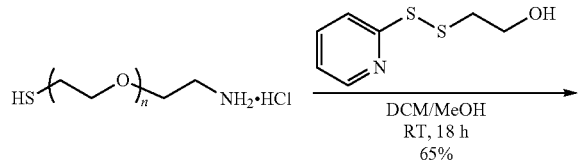

-continued

PEG2K—NH$_2$ disulfaneyl ethanol

PEG2K—NH$_2$-disulfaneyl ethanol. A solution of HS-PEG2K—NH$_2$ HCl (807.6 mg, 0.37 mmol) in dichloromethane (DCM, 5.0 mL) was added dropwise to a stirred solution of 2-(2-pyridinyldithio) ethanol (381.5 mg, 2.0 mmol) in methanol (3.0 mL). The solution was stirred at room temperature for 18 hours then concentrated to an oil and dissolved in 2-propanol (2.0 mL). The crude product was then precipitated dropwise into stirred ice-cold hexanes (40 mL) and placed at −20° C. for 4 hours. The precipitate and solvent mixture was centrifuged at 2000-G for 5 min with careful removal of supernatant. The sample was dried under vacuum for 20 minutes. The crude product was then used in the next step without further purification (crude yield 65%).

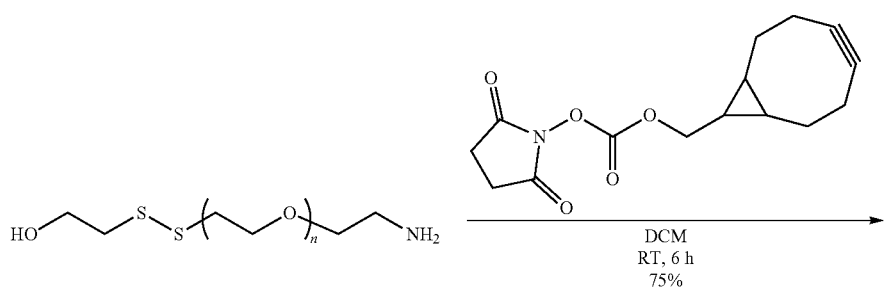

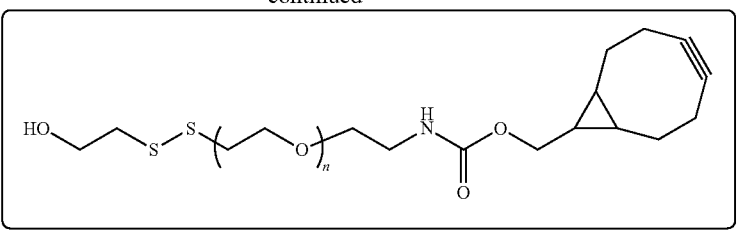

PEG2K—BCN disulfaneyl ethanol

BCN-PEG2K-disulfaneyl ethanol. A solution of BCN—NHS (902.0 mg, 0.30 mmol) in DCM (0.5 mL) was added dropwise to an ice-cold stirred solution of PEG2K—NH$_2$ disulfaneyl ethanol (520 mg, 0.24 mmol) and triethylamine (49.0 mg, 0.48 mmol) in DCM (5.0 mL). The reaction was allowed to come to room temperature and stirred for another 6 hours and concentrated to 2.0 mL. The reaction mixture was then precipitated dropwise into stirred ice-cold diethyl ether (40 mL) and placed at −20° C. for 4 hours. The precipitate and solvent mixture was centrifuged at 2000-G (3×, 10 minutes) with careful removal of supernatant after each round of centrifugation. The pellet was then dried under reduced pressure. The crude product was then used in the next step without further purification (75% crude yield).

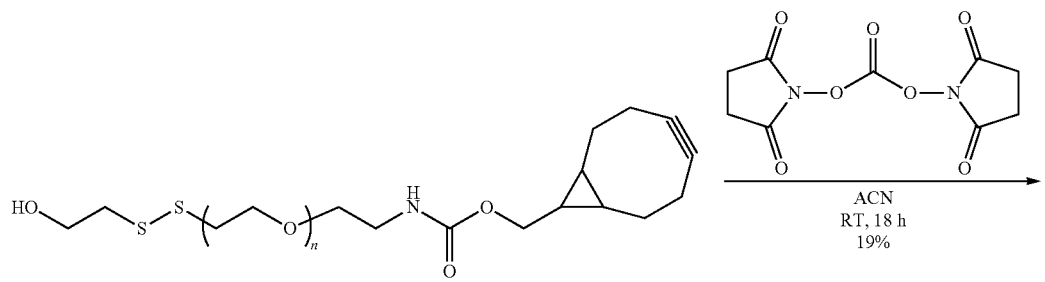

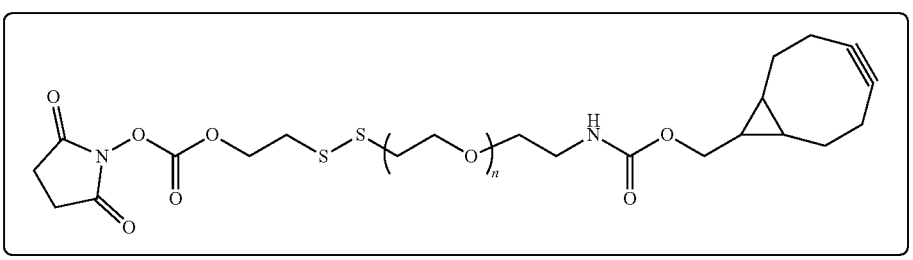

BCN—PEG2K—NHS

BCN-PEG2K—NHS. A solution of PEG2K—BCN disulfaneyl ethanol (642 mg, 0.18 mmol) in anhydrous acetonitrile (ACN) (1.5 mL) was added dropwise to a stirred solution of N,N'-disuccinimidyl carbonate (62.0 mg, 0.31 mmol) and triethylamine (48 mg, 0.48 mmol) in anhydrous ACN (5.0 mL). The reaction mixture was stirred for 16 hours and concentrated to 50% volume. It was then precipitated dropwise into stirred ice-cold diethyl ether (40 mL) and placed at −20° C. for 4 hours. The precipitate and solvent mixture was centrifuged at 2000-G (3×, 10 minutes) with careful removal of supernatant after each round of centrifugation. The pellet was then dried under reduced pressure. The crude product was purified via silica gel flash chromatography using a gradient of methanol:dichloromethane (0-15% v/v) affording BCN-PEG2K—NHS as a waxy oil (183 mg, 72 μmol, 19.4%). $^1$H-NMR (499.9 MHz, CDCl$_3$, 25° C., ppm): δ=0.76-2.36 (m. m., bicyclonon-4-yn-9-methyl), 2.84 (s, C(O)—CH$_2$—CH$_2$—C(O)), 3.89-3.35 (m, CH$_2$—CH$_2$—O).

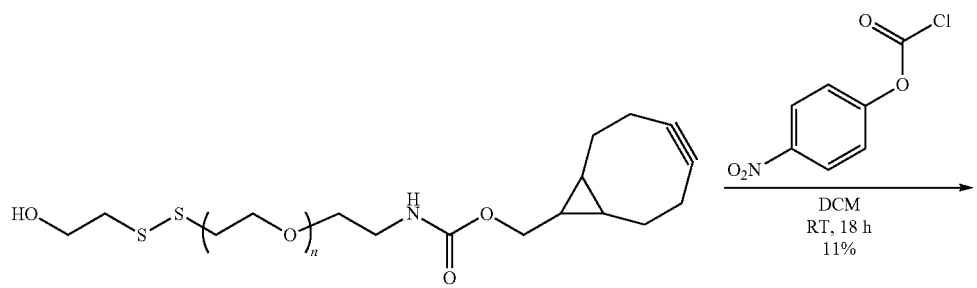

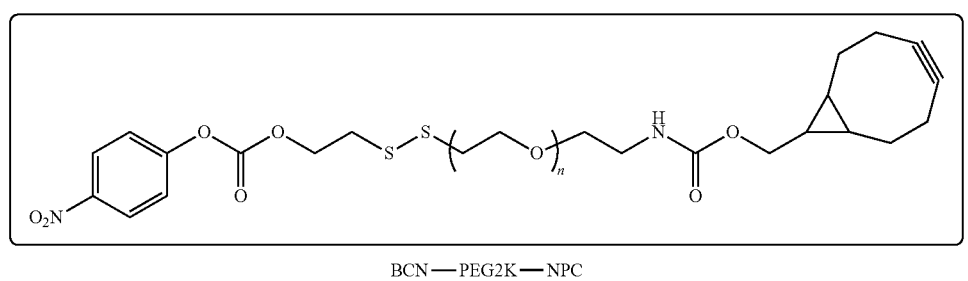

BCN—PEG2K—NPC

BCN-PEG2K—NPC. To PEG2K—BCN disulfaneyl ethanol (592 mg, 0.25 mmol) was added anhydrous dichloromethane (5.0 mL) and cooled in an ice bath for 10 minutes. To the solution was added anhydrous pyridine (50.0 μL mL, 0.6 mmol) and the solution was allowed to cool for an additional 5 minutes. A solution of 4-nitrophenyl chloroformate (75.0 mg, 0.37 mmol) in anhydrous dichloromethane (2.0 mL) was slowly added over 5 minutes using a gas-tight syringe. The solution was allowed to slowly come to ambient temperature. After storage for 18 hours the sample was concentrated to an oil and chromatographed on silica gel (4.0 g) using ethyl acetate 100% and then a gradient of methanol:dichloromethane (0-20% v/v), affording BCN-PEG2K—NPC as a waxy oil (72 mg, 28.0 μmol 11.2%). $^1$H-NMR (499.9 MHz, CDCl$_3$, 25° C., ppm): δ=3.4-3.9 (m, CH$_2$—CH$_2$—O), 7.41 (m, 2H, aromatic), 8.30 (m, 2H, aromatic).

Example 8: Conjugation of Alkyne to Biomolecule

The following provides exemplary procedures for the coupling of alkyne functionalized units to biomolecules.

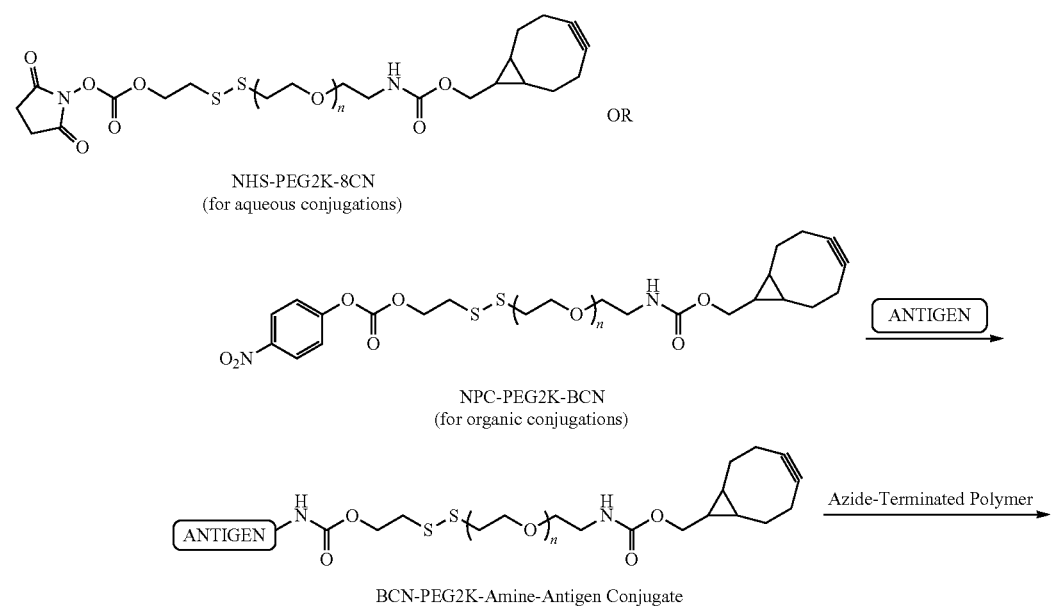

-continued
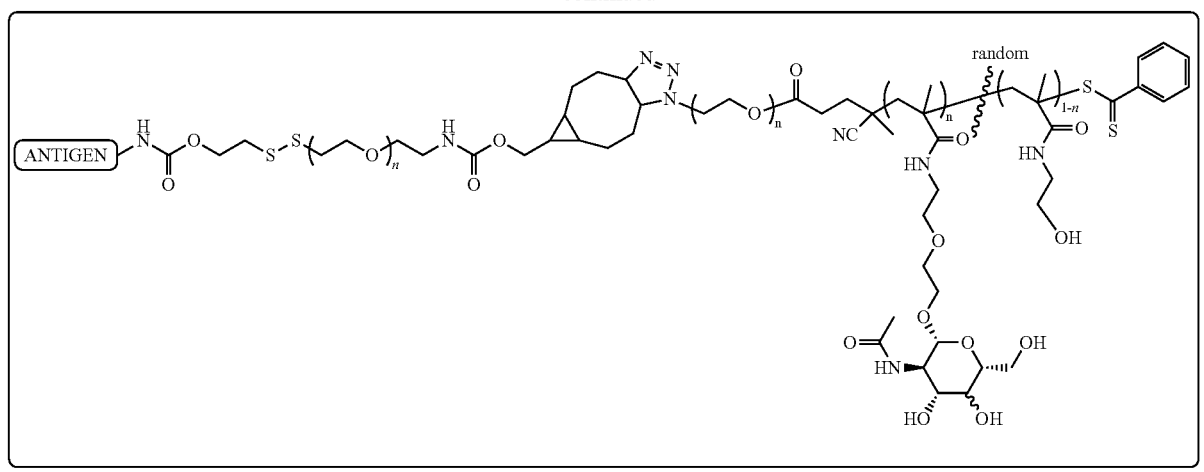
Antigen-NH-(BCN-PEG2K-p(GalNac-co-HEMA) Conjugate -OR- Antigen-NH-(BCN-PEG2K)-p(GlcNAc-co-HEMA) Conjugate
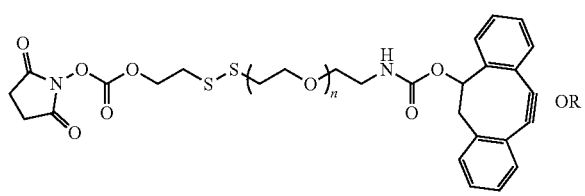
NHS-PEG2K-DIBO
(for aqueous conjugations)
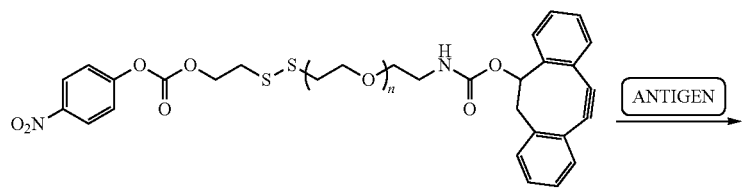
NPC-PEG2K-DIBO
(for organic conjugations)
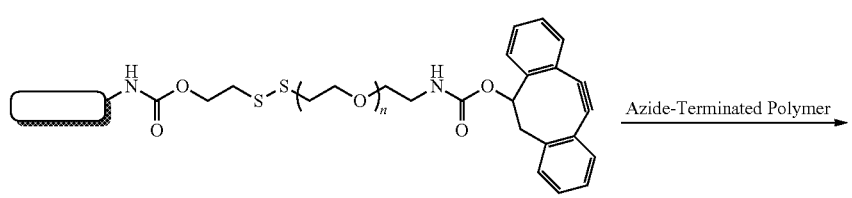
DIBO-PEG2K-Amine-Antigen Conjugate -continued
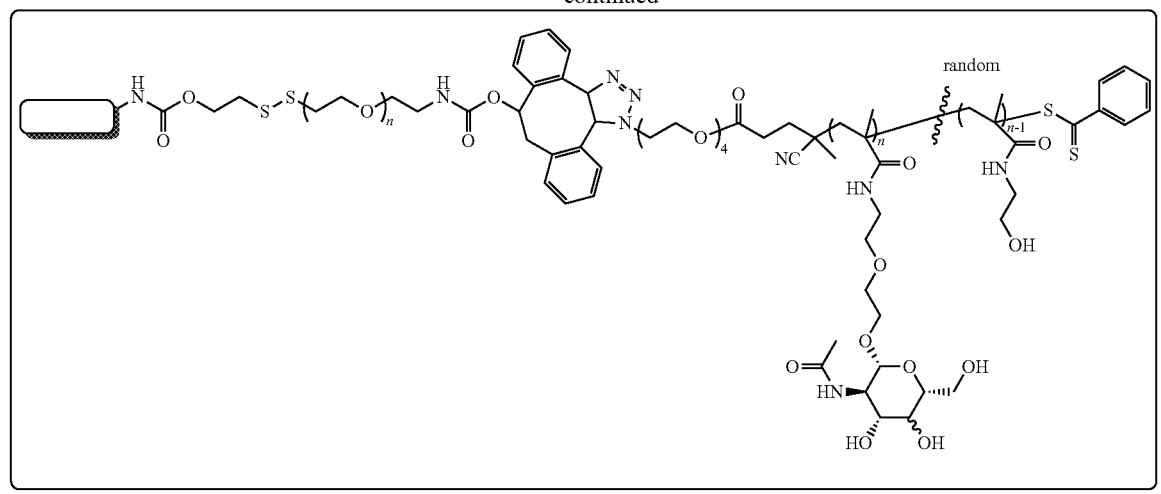
Antigen-NH-(BCN-PEG2K)-p(GalNAc-co-HEMA) Conjugate -OR- Antigen-NH-(BCN-PEG2K)-p(GlcNAc-co-HEMA) Conjugate
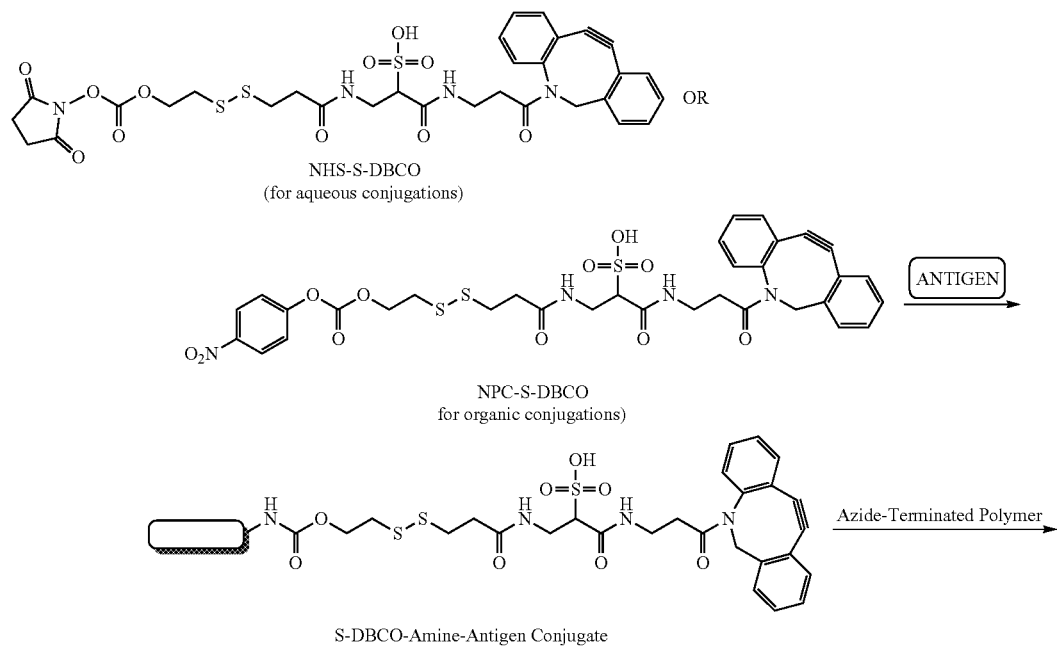
NHS-S-DBCO
(for aqueous conjugations)
NPC-S-DBCO
for organic conjugations)
S-DBCO-Amine-Antigen Conjugate
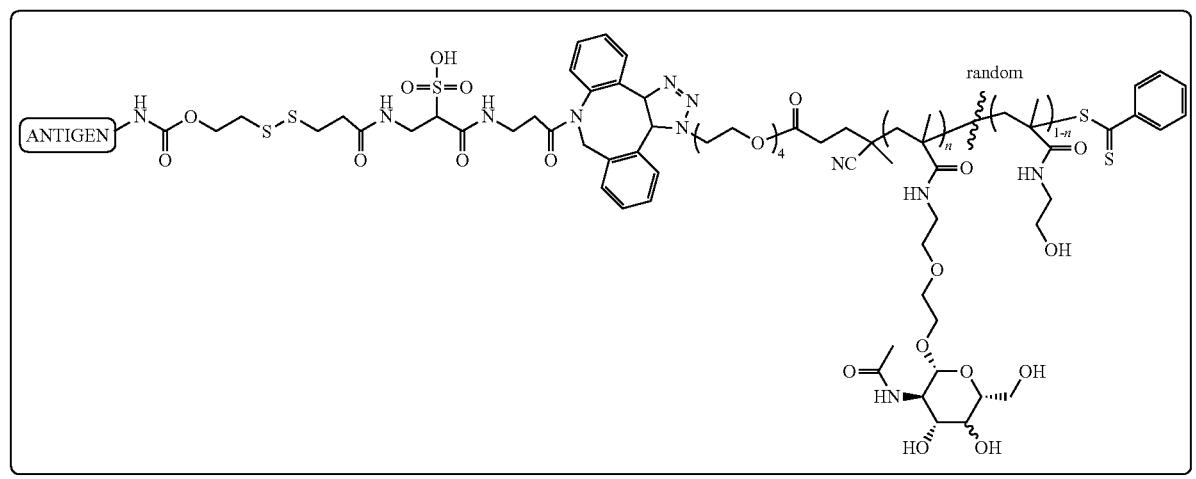
Antigen-NH-(S-DBCO)-P(GalNAc-co-HEMA) Conjugate -OR- Antigen-NH-(S-DBCO)-P(GlcNAc-co-HEMA) Conjugate Ovalbumin Ovalbumin-self-immolative linker-polymer conjugate. A typical example of a conjugation between Ovalbumin antigen, self-immolative linker BCN-PEG2K—NHS, and liver-targeting polymer p(GluNAc-co-HEMA)-N3 is as follows: EndoGrade Ovalbumin (OVA) (2.0 mg, 44.4 nmol) and BCN-PEG2K—NHS (0.44 µmol) in PBS pH 7.7 (40 µL) was added to an endotoxin free Eppendorf tube and placed on an orbital shaker at 60 rpm for 18 hours. The crude conjugate was diluted with Mili-Q water, charged into a Slide-a-Lyzer dialysis cassette (10 kDa MWCO) and dialyzed against 2000 volumes of Mili-Q water for 9 hours during which solvent exchanges were per formed at t=3 hours and t=6 hours. To the dialyzed aqueous solution was added p(GluNAc-co-HEMA)-N3 (31.1 kDa, 2.8 mg, 88.8 nmol) in Mili-Q water (100 µL) and the tube was placed on an orbital shaker (60 rpm) at room temperature for 18 hours. The conjugate was purified via cation exchange chromatography (CEX)/size-exclusion chromatography (SEC). The purified conjugate in PBS was buffer exchanged by charging into a Slide-a-Lyzer dialysis cassette (10 kDa MWCO) and dialyzed against 500 volumes of Mili-Q water for 10 hours during which solvent exchanges were per formed at t=3 hours and t=6 hours. The retentate was dried via lyophilization to yield Ovalbumin-NH—(BCN-PEG2K)-p(GluNAc-co-HEMA) as a white solid (26%).

The same procedure was used to produce Ovalbumin conjugates with DIBO-PEG2K and S-DBCO linkers and p(GalNAc-co-HEMA)-N3 liver-targeting polymers. All conjugates produced with the above procedure are described in Table 3.

TABLE 3

Ovalbumin-linker-polymer conjugates.

| Conjugate | Polymer MW | Yield (mg) | Yield (%) |
|---|---|---|---|
| Ovalbumin-NH-(BCN-PEG2K)-pGal | 31.6 kDa | 0.90 | 15% |
| Ovalbumin-NH-(BCN-PEG2K)-pGlu | 31.1 kDa | 0.54 | 15% |
| Ovalbumin-NH(DIBO-PEG2K)-pGal | 31.6 kDa | 0.63 | 18% |
| Ovalbumin-NH(DIBO-PEG2K)-pGlu | 31.1 kDa | 0.90 | 26% |
| Ovalbumin-NH-(S-DBCO)-pGal | 31.6 kDa | 2.63 | 30% |
| Ovalbumin-NH-(S-DBCO)-pGlu | 31.1 kDa | 2.18 | 25% |

Alternatively, the following procedures were used to provide OVA-self-immolative linker conjugate.

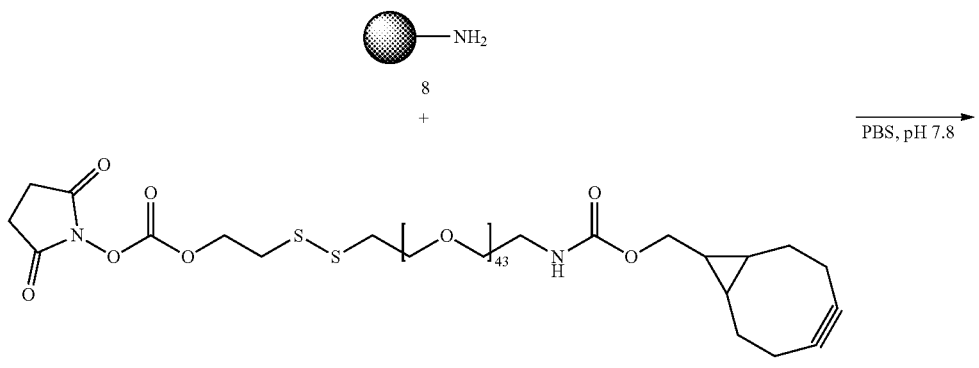

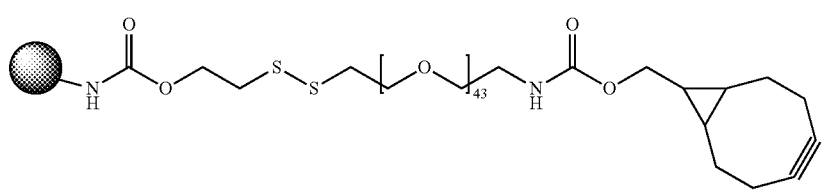

OVA-self-immolative linker conjugate. EndoGrade® Ovalbumin (OVA) (Hyglos) (10 mg, 222.2 nmol) and self-immolative Linker (5 mg, 2.2 µmol) 7 were added to an endotoxin free tube. PBS pH 7.6 (200 µL) was added to the tube and the tube was stirred at 6 h at room temperature. For fluorescent OVA formulations, 5 equivalents Dy-649-NHS-ester (Dyomics) to OVA, or 5 equivalents of DY-750-NHS-ester (Dyomics) to OVA was added to the reaction and the reaction was stirred for another 1 h at room temperature. The reaction mixture was then filtered (0.22 µM) and the conjugates were purified via size exclusion chromatography. The product was concentrated and used without further characterization.

p-31 p31-self-immolative linker conjugate. BDC2.5 mimotope 1040-31 (p31) YVRPLWVRME (AnaSpec) (0.29 mg, 222.2 nmol) and Self-immolative Linker (10 mg, 4.4 µmol) 7 were added to an endotoxin free tube. PBS pH 7.6 (200 µL) was added to the tube and the tube was stirred at 6 h at room temperature. The reaction mixture was then filtered (0.22 µM) and the conjugates were purified via size exclusion chromatography. The product was concentrated via centrifugal filtration and used without further characterization.

Insulin-Self-Immolative Linker-Polymer Conjugate

A typical example of a conjugation between Insulin antigen, self-immolative linker BCN-PEG2K—NPC, and liver-targeting polymer p(GluNAc-co-HEMA)-N3 is as follows:

Human Insulin (2.0 mg, 0.344 µmol), BCN-PEG2K—NPC (8.9 mg, 3.44 µmol) and triethyl amine (0.5 µL) in dimethyl sulfoxide (DMSO) (40 µL) was added to an endotoxin free Eppendorf tube. The tube was placed on a thermomixer at 400 rpm at 37° C. for 18 hours. The crude conjugate was diluted with Mili-Q water and charged into a Slide-a-Lyzer dialysis cassette (3.5 kDa MWCO) and dialyzed against 2000 volumes of Mili-Q water for 9 hours during which solvent exchanges were performed at t=3 hours and t=6 hours. To the dialyzed aqueous solution was added p(GluNAc-co-HEMA)-N3 (31.1 kDa, 22 mg, 0.688 µmol) in Mili-Q water (200 µL) and placed on an orbital shaker at 60 rpm for 18 hours. The conjugate was purified via cation exchange chromatography (CEX)/size-exclusion chromatography (SEC). The purified conjugate in PBS was buffer exchanged by charging into a Slide-a-Lyzer dialysis cassette (10 kDa MWCO) and dialyzed against 500 volumes of Mili-Q water for 18 hours during which solvent exchanges were performed at t=4 hours and t=8 hours. The retentate was dried via lyophilization to yield Insulin-NH—(BCN-PEG2K)-p(GluNAc-co-HEMA) as a white solid (50%).

The same procedure was used to produce Insulin conjugates with DIBO-PEG2K and S-DBCO linkers and p(GalNAc-co-HEMA)-N3 liver-targeting polymers. For all S-DBCO linker conjugates, the solvent was 1:1 DMSO:PBS buffer (10 mM, pH 7.7). All conjugates produced with the above procedure are described in Table 4.

TABLE 4

Insulin-linker-polymer conjugates.

| Conjugate | Polymer Molecular Weight | Yield (mg) | Yield (%) |
|---|---|---|---|
| Insulin-NH-(BCN-PEG2K)-pGal | 38.7 kDa | 10.0 | 63% |
| Insulin-NH-(BCN-PEG2K)-pGlu | 35.1 kDa | 0.50 | 10% |
| Insulin-NH-(DIBO-PEG2K)-pGal | 38.7 kDa | 11.3 | 75% |
| Insulin-NH-(DIBO-PEG2K)-pGlu | 31.1 kDa | 10.0 | 50% |
| Insulin-NH(S-DBCO)-pGal | 31.6 kDa | 2.40 | 18% |
| Insulin-NH-(S-DBCC)-pGlu | 31.1 kDa | 0.20 | 10% |

Example 9: Coupling of Alkyne and Azide

The following provides exemplary procedures for the coupling of alkyne functionalized biomolecules to alkyne reactive polymers.

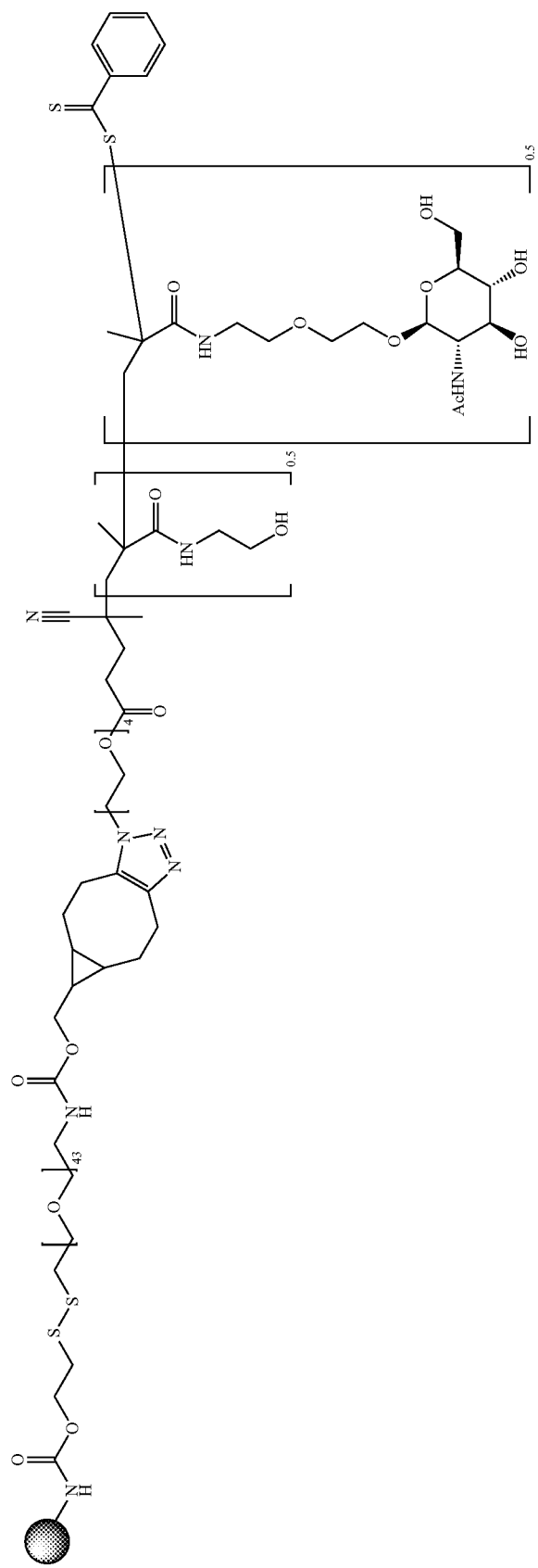

OVA-p(GluNAc) (28). Compound (9) (5.0 mg) was added to a solution of polymer 26 (15.0 mg) in PBS pH 7.4. The reaction was stirred at room temperature for 2 h. The reaction was then filtered (0.22 μM) and then the product 28 was isolated via SEC.

p31-p(GluNAc). p31-self-immolative linker conjugate (1.0 mg) was added to a solution of polymer (26) (15.0 mg) in PBS pH 7.4. The reaction was stirred at room temperature for 2 h. The reaction was then filtered (0.22 μM) and then the product, p31-p(GluNAc), was isolated via SEC.

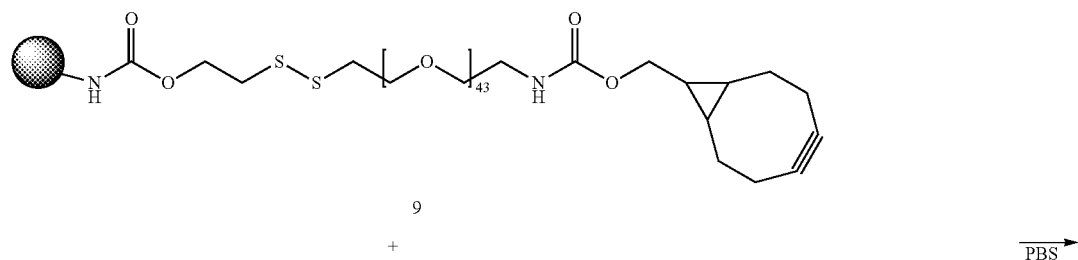

9

+

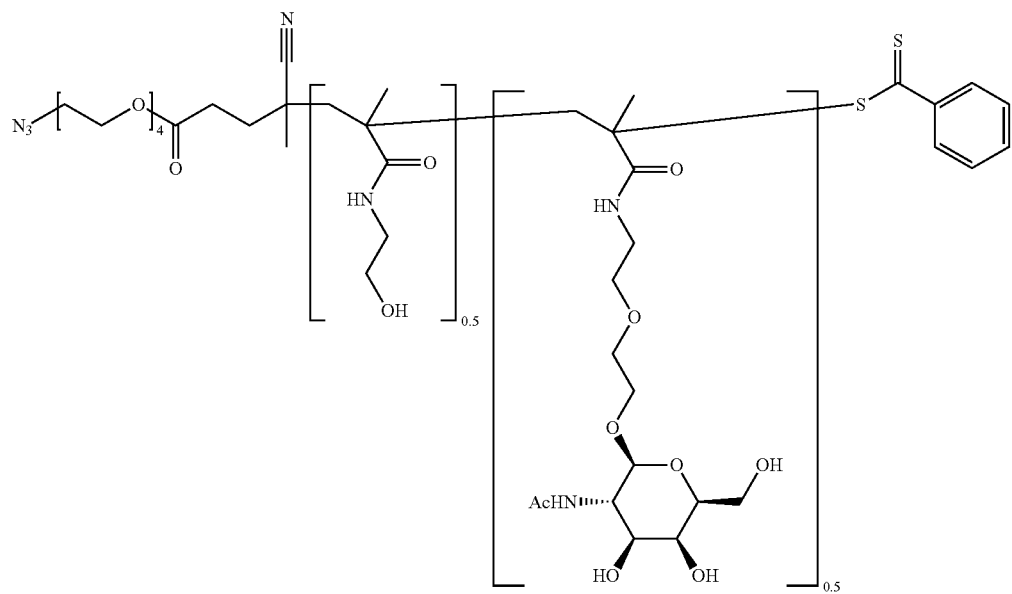

27

PBS

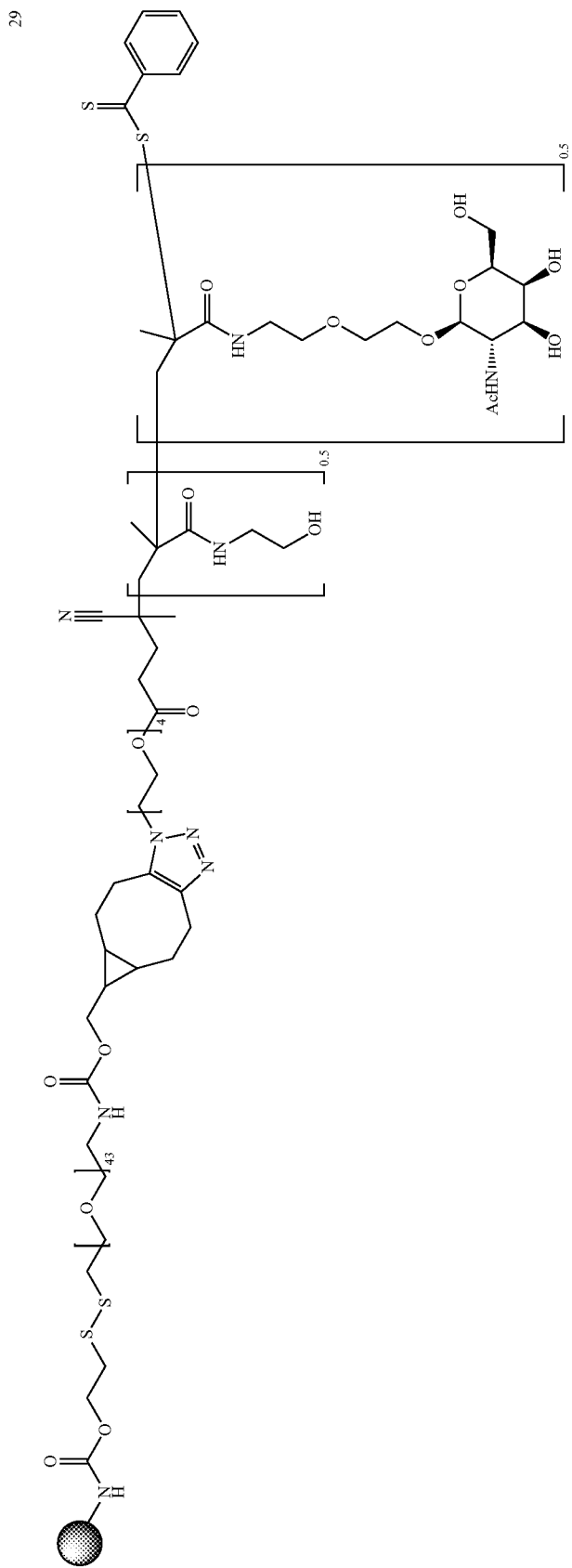

OVA-p(GluNAc) (29). Compound (9) (5.0 mg) was added to a solution of polymer 27 (15.0 mg) in PBS pH 7.4. The reaction was stirred at room temperature for 2 h. The reaction was then filtered (0.22 µM) and then the product 29 was isolated via SEC.

Example 10: Hepatocytes Efficiently Establish Cross-Tolerance

Flow cytometry. Flow cytometry measurements were performed using a LSRII flow cytometer (BD) and the data was analyzed using version 9.8.2 of FlowJo analysis software. Viable cells were determine using Fixable Viability Dye eFluor 780 (eBioscience). For staining of splenocytes, cells were exposed for 5 min at RT to 0.155 $NH_4Cl$ to lyse red blood cells. Cells were then washed with PBS, stained for 15 min on ice with LD stain, resuspended in PBS+2% FBS for surface staining for 30 min and finally fixed for 15 min in PBS+2% PFA. Intracellular staining of IFN-γ was carried out on ice in PBS supplemented with 2% FBS and 0.5% Saponin. Foxp3 staining was done using Transcription Factor Fixation/Permeabilization concentrate and diluent kit (ebioscience).

Data Anlaysis. Graphing and statistical analysis of data were performed using Prism (V5; GraphPad). Data was analyzed with 1 way ANOVA and Bonferonni test, α=5, was used for interpreting flow cytometry and ELISA results (*$p \leq 0.001$; $p \leq 0.01$; *$p \leq 0.05$). Statistical significance between survival curves assessed with Log-rank (Mantel-Cox) test.

Hepatocytes Efficiently Establish Cross-Tolerance by Deletion and Anergy of Antigen Specific CD8+ T Cells Via PD-1/PD-L1 Interactions Using a derivative of the model antigen ovalbumin (OVA) covalently modified with a polymer containing multiple N-acetylgalactosamine residues, pGalNAc-OVA, (as a non-limiting example—other agents such a galactose, galactosamine, glucose, glucosamine, and/or N-acetyl glucosamine can also be used in some embodiments) which enhances antigen uptake by mimicking the glycome of apoptotic debris, hepatocytes can be manipulated to induce tolerance of both adoptively transferred OT-I cells and endogenous OVA-specific $CD8^+$ T lymphocytes by clonal deletion and anergy. A non-limiting, but demonstrative example is shown herein, where, for example tolerance is induced to OVA-expressing skin transplants. In some embodiments, tolerance depends, at least in part, on hepatocyte antigen cross-presentation. However, in several embodiments, such cross-presentation is not required. In some embodiments, blockade of hepatocyte PD-L1 significantly reduced cross-tolerogenesis, suggesting that hepatocyte-dependent tolerance is not merely a consequence of abortive activation of $CD8^+$ T cells in the absence of co-stimulation. In some embodiments, hepatocytes can participate in peripheral tolerogenesis. In some embodiments, the manipulation of hepatocytes as described can be used in methods for targeted tolerogenic treatments.

Primary Hepatocytes Efficiently Used EEA1- and TAP1-Positive Cytoplasmic Compartments for the Processing of Extracellular Antigens Cross-presentation results from antigen uptake mediated by Fc or C-type lectin receptors (such as the mannose receptor), followed by antigen proteolytic degradation by proteasomes associated with early endosome antigen 1 (EEA1)-positive phagosomes (early endosomes), subsequent antigen transport and loading onto MHC-I molecules through transporters associated with antigen processing (TAP) and translocation of peptide/MHC-I complexes to the cell plasma membrane via the secretory pathway. Whether hepatocytes would employ cross-presentation-competent subcellular compartments to process soluble extracellular antigens was tested as described herein.

First, primary murine hepatocytes were characterized for their expression and distribution of markers associated with cross-presentation-competent phagosomes. Freshly isolated hepatocytes from C57BL/6 mice were stained for mannose receptor 1 (MR), EEA1, TAP1 and H-2 Kb and were analyzed by confocal microscopy. The expression and distribution of these markers indicated their localization to be either on the surface of hepatocytes (MR, H-2 Kb) or in subcellular compartments (MR, EEA1, TAP1 and H-2 Kb), with a similar pattern compared to sorted CD11c+CD8α+ bone marrow-derived dendritic cells (BMDCs), chosen as a positive reference for their professional antigen cross-presenting functions (FIG. 1A). The abundance of MR-, EEA1-, TAP1- and H-2 Kb-positive organelles is higher in professional cross-presenting CD11c+CD8α+ BMDCs, yet each of these markers was observed in primary hepatocytes (FIG. 1A).

Figure 1D:
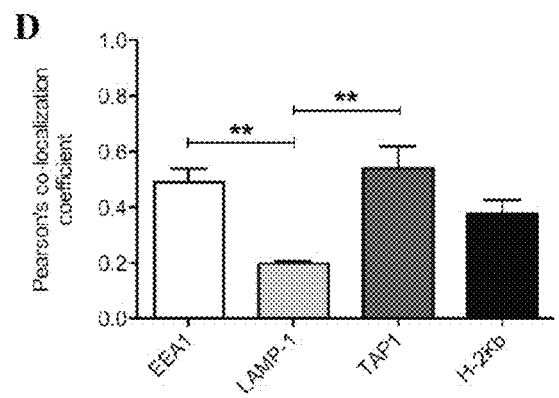
Figure 1E:
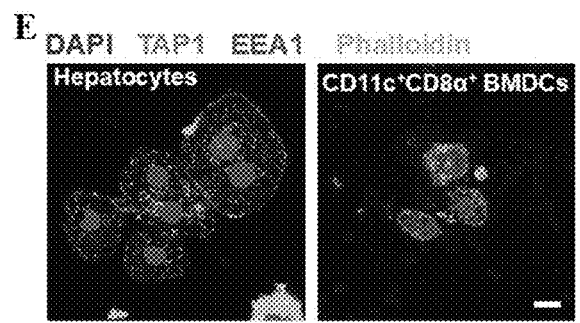

To test whether the subcellular compartments described in FIG. 1A are used by hepatocytes to process protein antigens found in the extracellular space, primary hepatocytes were cultured in the presence of DQ-Ovalbumin (DQ-OVA) and analyzed for mean fluorescent intensity (MFI) and localization of fluorescent signal derived from intracellular proteolytic degradation. The hepatocytes actively degrade proteins added to their supernatant, as DQ-OVA becomes fluorescent when cells are incubated at 37° C. but not at 4° C. (FIG. 1B). The magnitude of antigen processing in BMDCs was greater than in hepatocytes as indicated by the MFI of DQ-OVA, but the kinetics appeared similar between the two cell types, with DQ-OVA fluorescence peaking within the first 12 hr of culture and slowly decreasing over time until reaching background signal levels after 60 hr in culture without further addition of the antigen (FIG. 1B). By confocal microscopy, the fluorescent signal originating from the degradation of DQ-OVA in the proximity of or inside EEA1+, TAP1+ and H-2 Kb+ compartments was localized (FIG. 1C). DQ-OVA fluorescence was detected as associated with late endosomes, identified as LAMP-1+ organelles (FIG. 1C), even though quantification of co-localizing signals indicated that DQ-OVA degradation is mainly associated with EEA1+ and TAP1+ compartments (2.45 and 2.7 Pearson's co-localization coefficient fold increase over LAMP-1, respectively) (FIG. 1D). Whether hepatocytes contain phagosomes positive for both EEA1 and TAP, which are considered the hallmark of professional cross-presenting cells, was also investigated, as these phagosomes retain all the functions necessary for cross-presentation. EEA1+ TAP1+ subcellular compartments were found to be abundantly distributed in the cytoplasm of primary hepatocytes, and to a lesser extent as compared to sorted CD11c+CD8α+ BMDCs (FIG. 1E). These results are consistent with cross-presentation, according to which cross-presenting cells contain phagosomes (mainly recognized as EEA1+) equipped with the complete molecular machinery necessary to retro-translocate antigens to the cytoplasm for degradation into phagosome-associated proteasomes and to transport digested peptides into endosomal MHC-I-containing compartments, where peptides are loaded onto MHC-I complexes prior to their transportation to the cell membrane.

Figure 2:
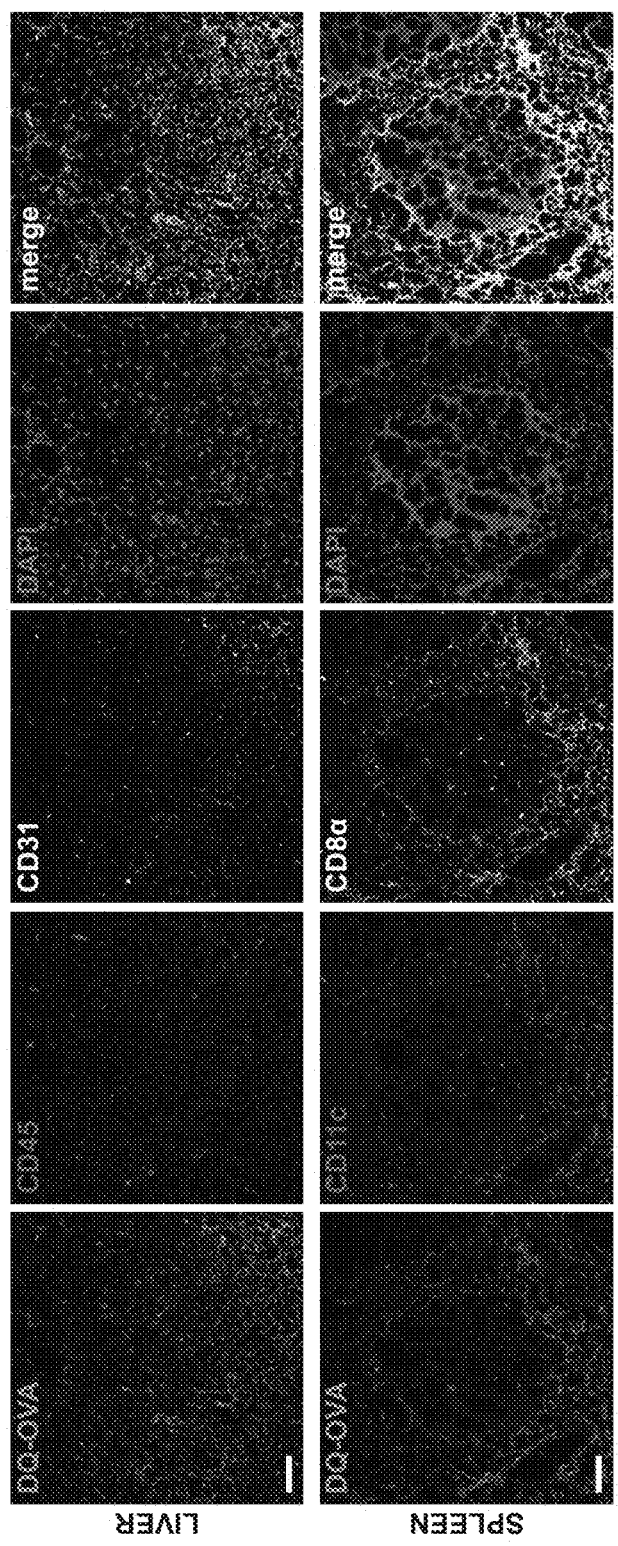
FIG. 2. Intravenously administered soluble antigens are processed by liver CD45$^-$CD31$^-$parenchymal cells and CD11c$^+$CD8α$^+$ splenocytes. 12 hr after i.v. administration to C57BL/6 mice, processed DQ-OVA is found within CD45⁻ CD31⁻ parenchymal cells of the liver (hepatocytes) (top row) and in CD11c⁺CD8α⁺ cells of the spleen (bottom row). Scale bar=50 μm. Pictures are representative of 5 different mice.

To confirm in vivo uptake and processing of blood-borne extracellular antigens by hepatocytes, 100 µg of DQ-OVA was injected intravenously (i.v.) into C57BL/6 mice and the animals were euthanized after 12 hr to harvest their livers and spleens, as they represent major blood-filtering organs. In the liver, DQ-OVA fluorescence was widely distributed in the parenchyma and, unlike other reports indicating LSECs as the major blood-filtering cells of the liver, mainly localized in hepatocytes, identified as non-hematopoietic (CD45-) non-endothelial (CD31-) parenchymal cells (FIG. 2, top panels). DQ-OVA processing in the spleen was mostly detected in cross-presenting DCs, identified as CD45+ CD11c+CD8α+ cells (FIG. 2, bottom panels).

It was concluded that murine hepatocytes phenotypically resemble antigen cross-presenting DCs, since actively processed extracellular antigens can be mostly detected in association with EEA1+, TAP1+ and H-2 Kb+ cytoplasmic compartments. It was also concluded that hepatocytes contain EEA1+TAP1+ phagosomes, which are considered a unique feature of professional cross-presenting cells. It was also concluded that scavenging and degradation of blood-borne antigens in vivo are main activities of hepatocytes in the liver and of cross-presenting CD45+CD11c+CD8α+ DCs in the spleen. The findings of this portion of the study are consistent with the compositions disclosed herein, which are configured to induce antigen-specific tolerance.

Polymer with Side-Chain N-Acetylgalactosamine (pGal) Covalently Conjugated to a Protein Antigen In some embodiments, a polymer with side-chain N-acetylgalactosamine (pGal) covalently conjugated to a protein antigen increased the efficiency of antigen cross-presentation in primary hepatocytes. As discussed, above, other side-chains can also be used, depending on the embodiment, such as glucose, glucosamine, N-acetlyglucosamine, galactose, galactosamine, or even combinations thereof.

Receptor-mediated endocytosis of extracellular antigens is the first step of the cross-presentation pathway. In some embodiments, antigen chemical modifications enhancing receptor binding can be exploited to improve either CD8+ T cell immunity or tolerance following antigen cross-presentation. Testing was performed to determine whether an antigen covalently modified with a water-soluble polymer functionalized with side-chain N-acetylgalactosamine residues (abbreviated pGal), which is recognized by several cross-presentation-related scavenger receptors including the MR, the fructose receptor and the liver-specific lectin ASGPR, could improve hepatocyte cross-presentation of the model antigen OVA.

Figure 3:
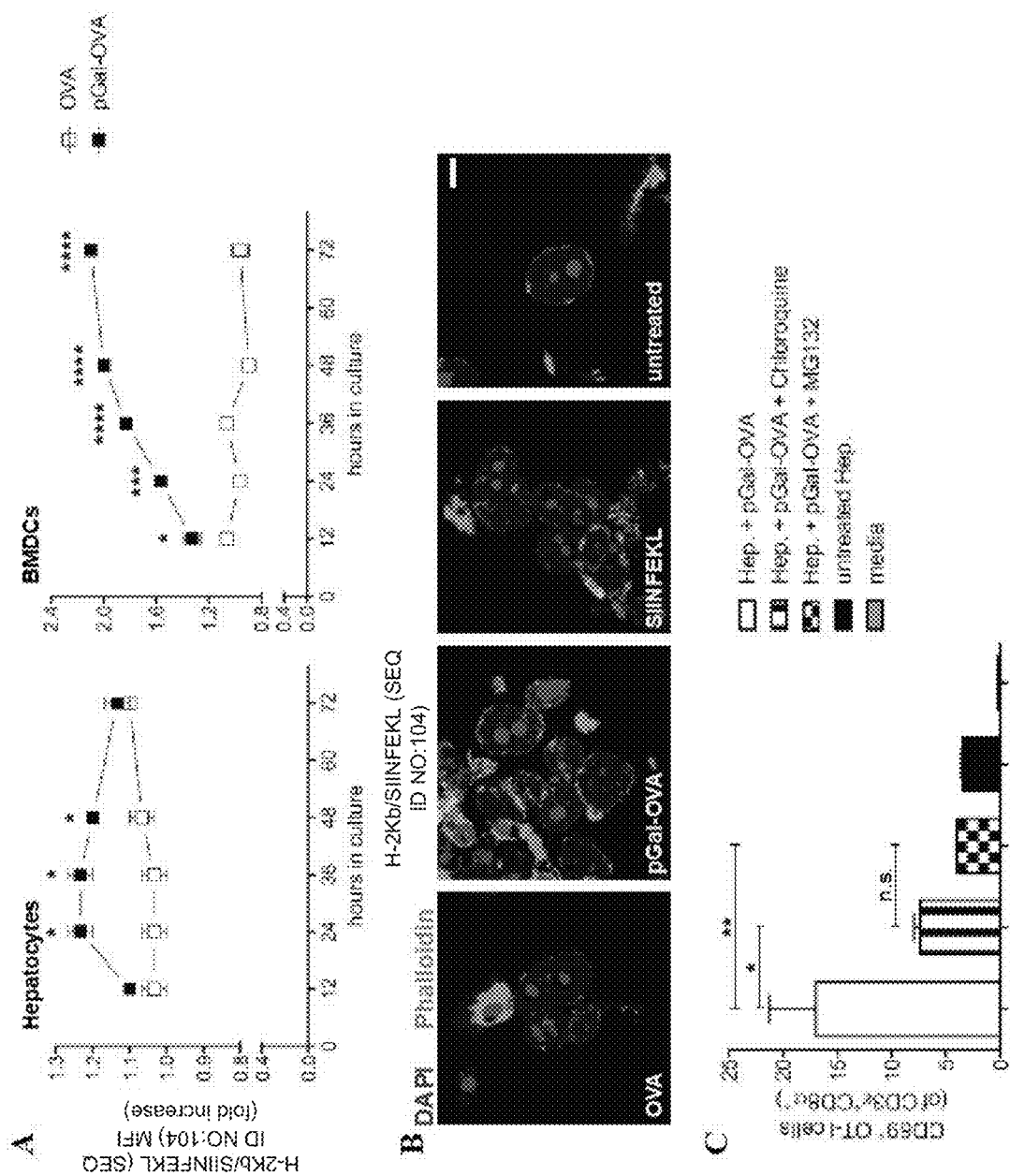
FIG. 3A-C. Polymer containing side-chain N-acetylgalactosamine (pGal) conjugate with OVA improves cross-presentation of extracellular OVA. (A) Culture of primary hepatocytes (left) or BMDCs (right) from C57BL/6 mice with pGal-OVA (black squares) increases the amount of H-2 Kb-bound SIINFEKL (SEQ ID NO: 104) detected by flow cytometric analysis as compared to culture with unmodified OVA (white squares). (B) H-2 Kb/SIINFEKL (SEQ ID NO: 104) staining of C57BL/6 primary hepatocytes after 24 hr culture in the presence of either 5 μM OVA, 5 μM pGal-OVA, 1 nM $OVA_{257-264}$ (i.e. SIINFEKL; SEQ ID NO: 104), or untreated confirms efficient cross-presentation of pGal-OVA. Scale bar=10 μm. (C) Treatment of primary hepatocytes with either chloroquine or MG132 significantly reduces the cross-presentation of pGal-OVA by primary hepatocytes to H-2 Kb/SIINFEKL (SEQ ID NO: 104)-specific OT-I cells, as indicated by staining for the early T cell antigen-sensing and activation marker CD69 on the surface of OT-I cells. *$P<0.05$, $P<0.01$, *$P<0.001$, ****$P<0.0001$ and n.s.=not significant (one-way ANOVA and Bonferroni post-hoc test correction). Data are representative of 3 independent experiments (n=3; mean and s.e.m. in (A,C)).
Figure 13A:
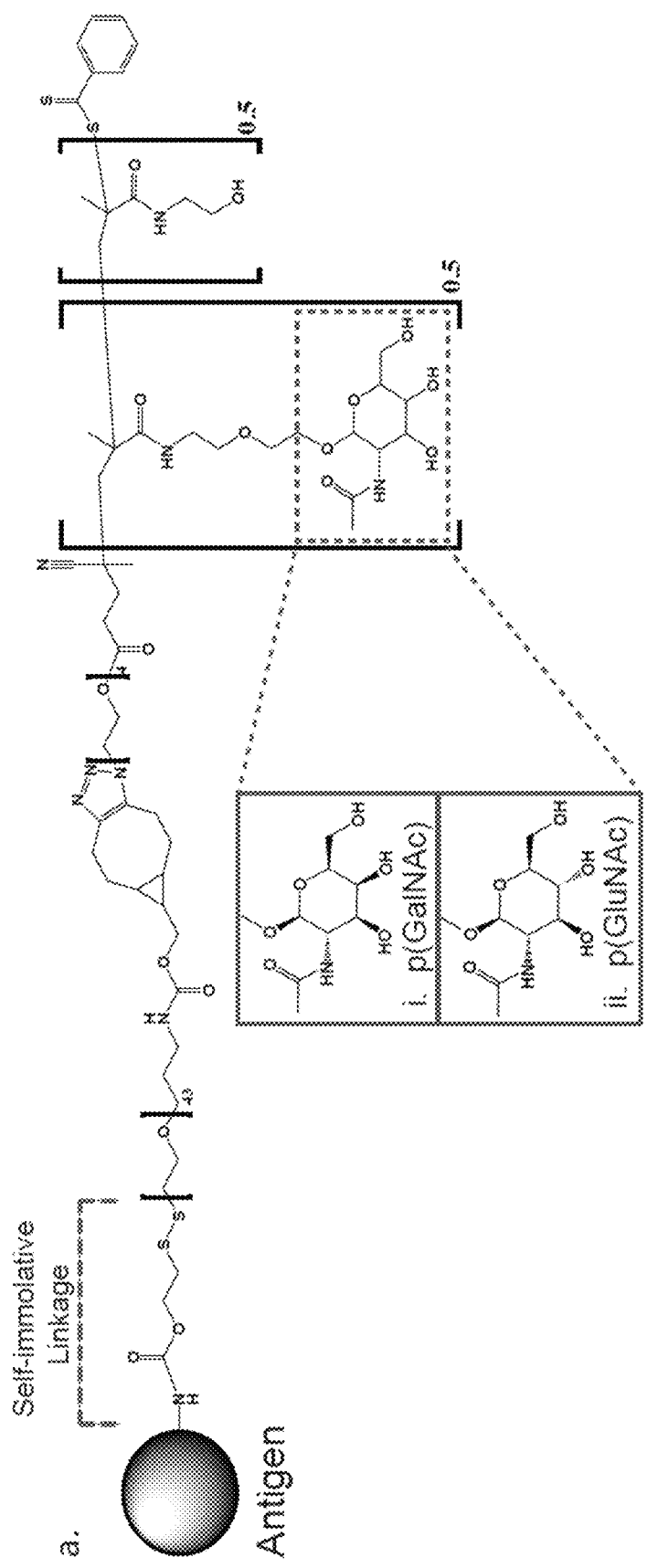
Figure 19D:
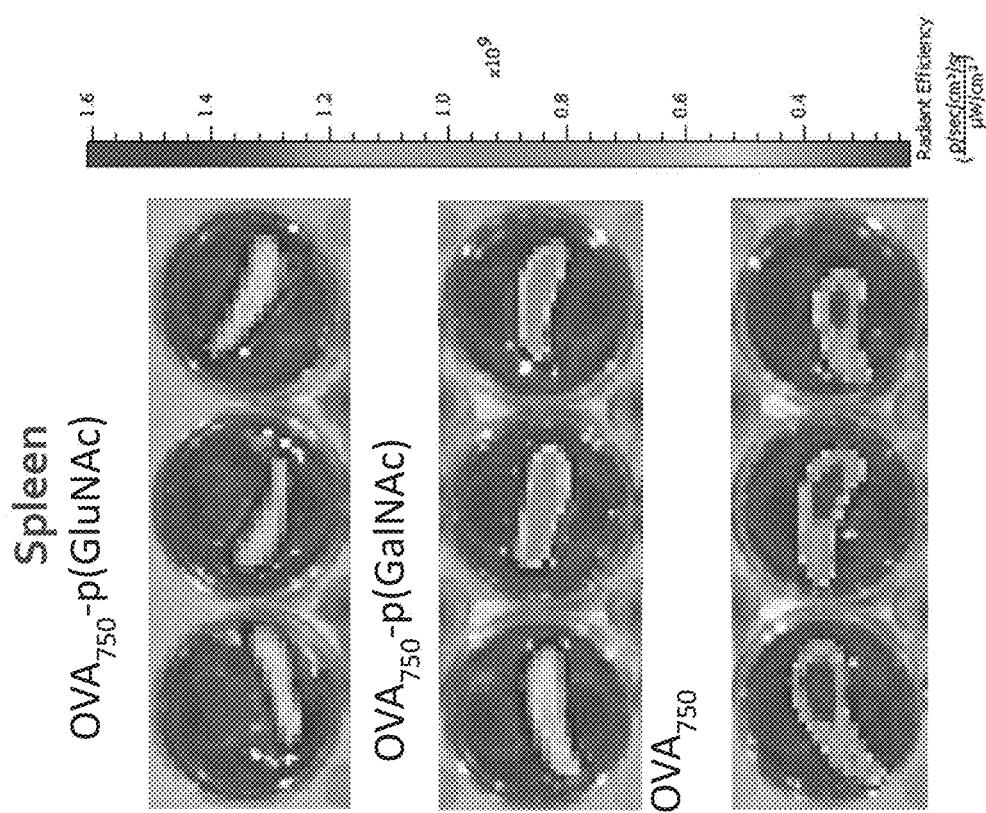
FIG. 19D. OVA$_{750}$-p(GluNAc) and OVA$_{750}$-p(GalNac) conjugates decrease OVA delivery to the spleen as compared to OVA$_{649}$. Spleens from animals treated with OVA$_{750}$-p (GalNAc) or OVA$_{750}$-p(GalNAc) had less fluorescence than spleens form animals treated with OVA$_{750}$.

OVA was modified with pGal (pGal-OVA) (see, e.g., FIG. 13A) and its cross-presentation was compared to that of unmodified OVA in hepatocytes or BMDCs incubated with equimolar doses of the unmodified OVA or pGal-OVA antigen (FIG. 3A). pGal-OVA resulted in a statistically significant 1.2- and 2.1-fold increase of cross-presentation of the OVA-derived CD8+ T cell immunodominant epitope SIINFEKL (SEQ ID NO: 104) in primary hepatocytes and BMDCs, respectively, as compared to OVA, as indicated by immunostaining for H-2 Kb/SIINFEKL (SEQ ID NO: 104) pMHC complexes and flow cytometric analysis (FIG. 3A). Confocal microscopy confirmed enhanced SIINFEKL (SEQ ID NO: 104) cross-presentation by pGal-OVA-treated hepatocytes as compared to OVA-treated hepatocytes (FIG. 3B). Thus, in accordance with several embodiments, linking of an antigen to which tolerance is desired to a liver targeting moiety increases delivery and/or cross-presentation of that antigen, and coordinately enhanced tolerogenic effects.

Whether cellular processes in hematopoietic and non-hematopoietic APCs for cross-presentation, such as endosome acidification and proteasomal degradation, were also employed by hepatocytes for pGal-OVA cross-presentation was then tested. Primary murine hepatocytes were treated with pGal-OVA alone or with pGal-OVA together with either chloroquine (an inhibitor of endosomal acidification) or MG132 (a proteasome inhibitor). The cells were cultured in vitro with OT-I cells, transgenic CD8+ T cells specific for H-2 Kb/SIINFEKL (SEQ ID NO: 104). After 24 hr of co-culture, flow cytometry was used to analyze the expression of CD69 by OT-I cells, as an early indicator of antigen sensing and TCR triggering. Blockade of either endosomal function or proteasomal protein degradation in hepatocytes resulted in statistically significant reduction of the frequency of OT-I cells able to experience antigen presentation by hepatocytes, as indicated by CD69 staining. After treatment of hepatocytes with pGal-OVA and either chloroquine or MG132, 7.38% and 3.98% of the OT-I cells were CD69+, respectively, as compared to 17% of CD69+ OT-I cells measured when hepatocytes were incubated with pGal-OVA alone (FIG. 3C).

These data indicate that pGal-OVA is processed in hepatocytes via the cellular pathway of antigen cross-presentation. Since the pGal modification of a protein antigen to which tolerance is desired results in more efficient scavenging and subsequent cross-presentation of the antigen itself, pGal-OVA was adopted as model antigen to characterize the antigen-specific immune response elicited by hepatocyte-dependent cross-presentation in vivo. As described herein, other antigens to which tolerance is desired are used, in several embodiments, such as, for example, therapeutic agents, self-antigens, food or other foreign antigens, transplant antigens, and the like. Likewise, other liver targeting agents are used in several embodiments.

Cross-Presentation of OVA by Hepatocytes

In some embodiments, cross-presentation of OVA by hepatocytes results in antigen-specific CD8+ T cell tolerance by induction of clonal deletion and anergy. In some embodiments, this tolerance is in the absence of effects on CD4+ T lymphocytes.

Figure 4:
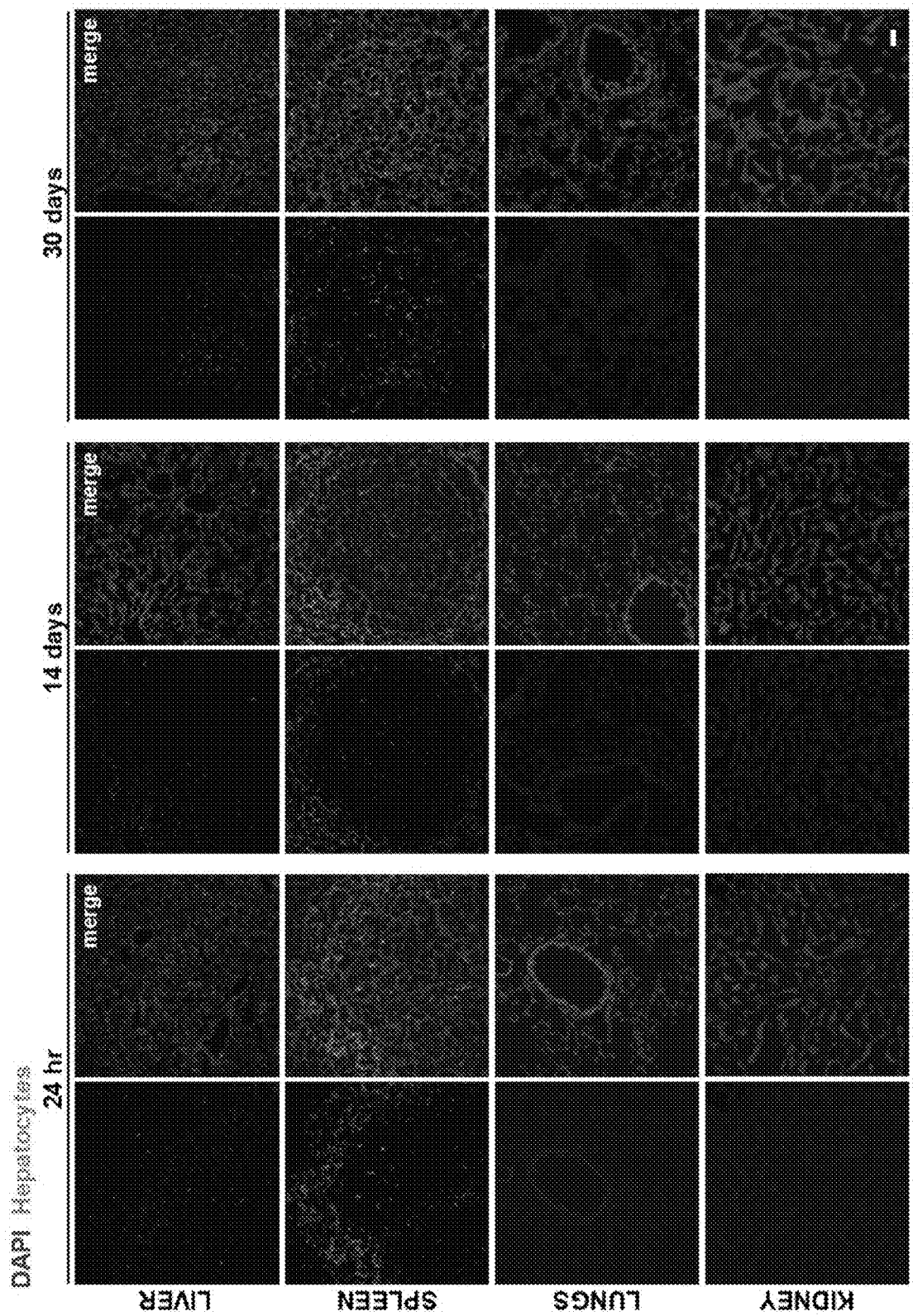
FIG. 4. Primary hepatocytes survive and home to liver and spleen after intravenous transfer. Liver, spleen, lung and kidney were harvested at either 24 hr, 14 days or 1 month from recipient C57BL/6 mice after i.v. transfer of CFSE-labelled C57BL/6 primary hepatocytes. Scale bar=50 μm. Data are representative of 5 different mice.

Scavenger receptors are expressed by a multitude of cells, especially in the liver and in the spleen, including DCs, macrophages and LSECs. To discriminate the role of hepatocytes in the establishment of cross-tolerance towards extracellular antigens using the pGal-OVA antigen construct, a model of i.v. adoptive transfer of freshly isolated and antigen-experienced hepatocytes was developed. When delivered i.v., CFSE-labeled primary hepatocytes appeared to home to the spleen and, to a lesser extent, the liver, and to survive in those sites for at least 1 month after infusion (FIG. 4).

To study the effects of hepatocyte cross-presentation on antigen-specific T cells in vivo, pGal-OVA were ex vivo incubated with hepatocytes isolated from C57BL/6 mice. After incubation with pGal-OVA and washing, OVA cross-presenting hepatocytes (FIG. 5A) were transferred i.v. into recipient CD45.2+ C57BL/6 mice, followed by i.v. administration of CFSE-labeled CD45.1+ OT-I cells 6 hr later. Two weeks after hepatocyte and OT-I cell transfer, recipient mice were vaccinated with an intradermal (i.d.) dose of OVA and LPS (antigen challenge) into the frontal footpads, and 4 days after challenge mice were euthanized to analyze the phenotype of adoptively transferred OT-I cells retrieved from the spleen and the LNs draining the vaccination site (dLNs) (FIG. 5B).

Figure 5C:
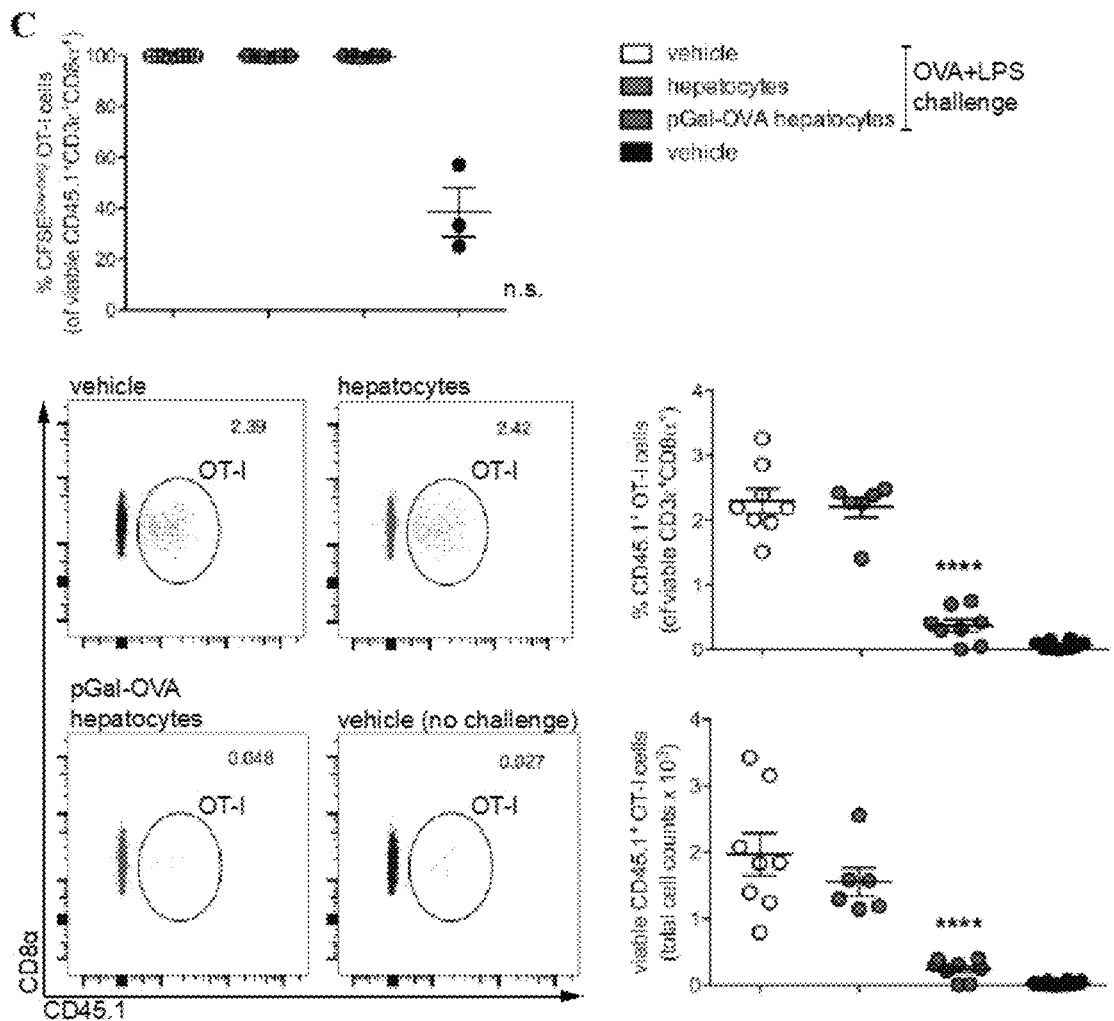
Figure 9A:
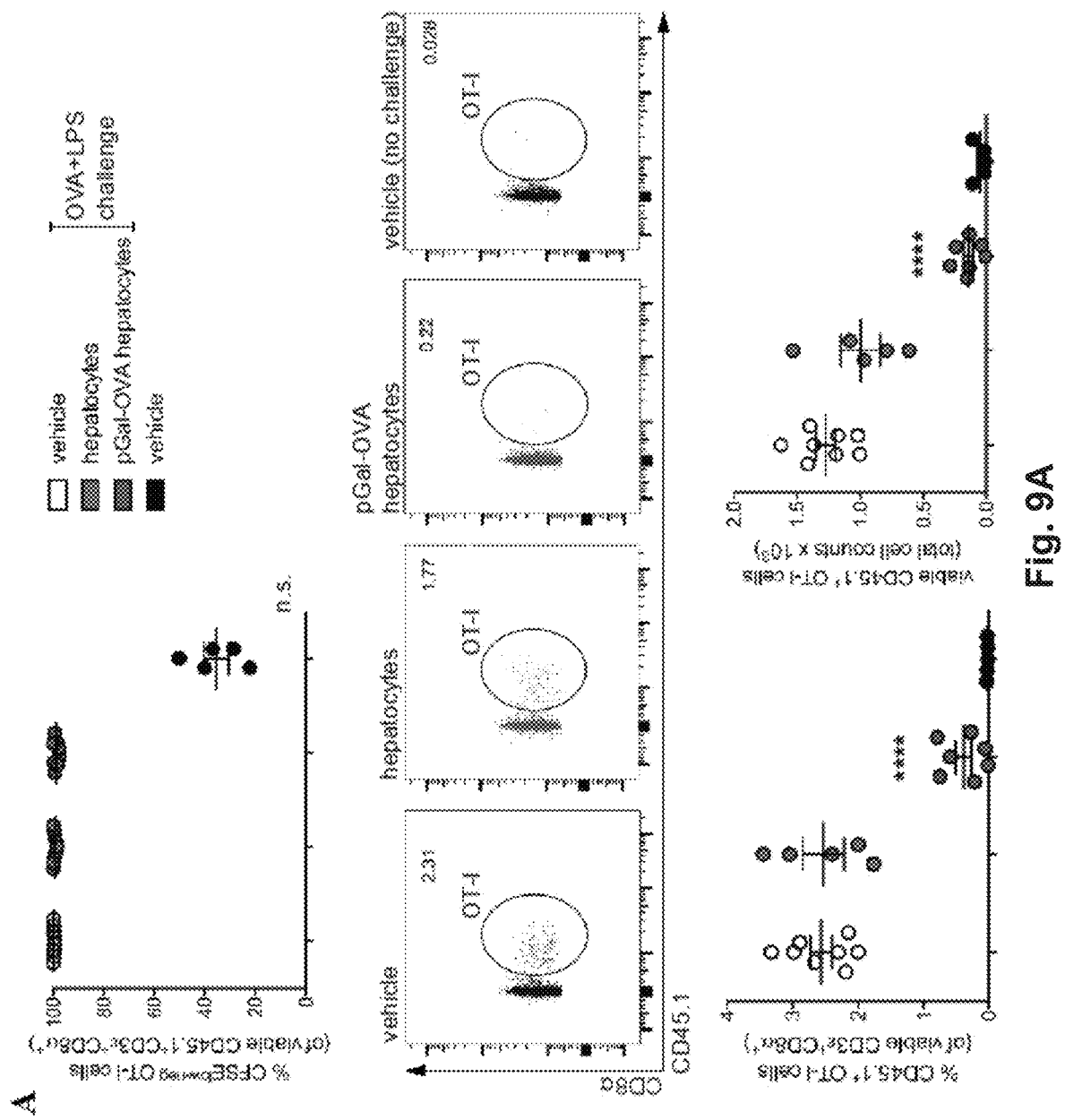

95% to 99.7% of the OT-I cells harvested from mice challenged with OVA/LPS on day 15 responded to vaccination by proliferating, as detected by flow cytometric analysis of CFSE dilution of viable $CD45.1^+CD3^+CD8^+$ cells in the dLNs and spleen of recipient mice (FIG. 5C and FIG. 9A, respectively, top panel). Even though no difference was detectable in the proliferative capacity of OT-I cells harvested from vaccinated mice administered on day 0 with either vehicle, untreated hepatocytes or OVA cross-presenting hepatocytes, the frequency of CD45.1$^+$ OT-I cells in the population of total viable CD3+CD8+ lymphocytes was significantly reduced to 0.4% in the dLNs of mice treated with OVA cross-presenting hepatocytes as compared to mice receiving either vehicle (2.3%) or untreated hepatocytes (2.2%) on day 0 (FIG. 5C, bottom panels). Reduced frequencies of CD45.1+ OT-I cells in mice pre-treated with OVA cross-presenting hepatocytes were paralleled by lower OT-I cell counts (FIG. 5C, bottom panels). Significantly reduced frequency and cell counts of CD45.1+ OT-I cells were also measured in the population of viable CD3+CD8+ lymphocytes isolated from the spleen of recipient mice (FIG. 9A, bottom panels).

Based on the significantly lower frequencies of CD45.1+ OT-I cells among total CD8+ T lymphocytes, whether non-deleted OT-I cells displayed signature markers of apoptosis or reduced survival was investigated. In the dLNs of mice administered with pGal-OVA-treated hepatocytes, significantly higher frequencies of Annexin-V$^+$ (38.6%), FasL$^+$ (2.6%), TRAIL$^+$ (5.77%) and KLRG1$^{hi}$CD127$^{low}$ (6.45%) OT-I cells were detected as compared to mice receiving on day 0 either vehicle (20.01%, 0.33%, 1.56% and 0.48%, respectively) or untreated hepatocytes (21.7%, 0.38%, 2.12% and 1.77%, respectively) (FIG. 5D). Similarly to the dLNs, the OT-I cells retrieved from the spleen of recipient mice also showed evidence of undergoing apoptosis and reduced survival capacity (FIG. 9B), indicating signs of induction of tolerance Moreover, administration of pGal-OVA-treated hepatocytes on day 0 also significantly affected the capacity of adoptively transferred OT-I cells to acquire effector functions following the vaccination challenge, as indicated by statistically lower frequencies of IFN-γ$^+$ and IL-2$^+$ viable CD45.1$^+$CD3$^+$CD8$^+$ OT-I cells in the dLNs (22.2% and 3.5%, respectively), as compared to mice administered on day 0 with either vehicle (61.8% and 10.4% of dLN IFN-γ$^+$ or IL-2$^+$ OT-I cells, respectively) or untreated hepatocytes (55.3% and 7.2% of dLN IFN-γ$^+$ or IL-2$^+$ OT-I cells, respectively) (FIG. 5E). Similar trends were also detected in the spleen of recipient mice (FIG. 9C). Interestingly, when total dLN cells were restimulated ex vivo with SIINFEKL (SEQ ID NO: 104), secreted IFN-γ was significantly reduced to 560 pg/mL in the supernatant of the cells harvested from mice receiving pGal-OVA-treated hepatocytes, as compared to 2540 pg/mL and 3250 pg/mL for mice receiving either vehicle or untreated hepatocytes on day 0, respectively (FIG. 5F).

In some embodiments, as shown, antigen cross-presenting hepatocytes significantly affect the phenotype of antigen-specific CD8+ T cells, inducing T cell deletion. In some embodiments, as shown, non-deleted OT-I cells isolated from mice receiving pGal-OVA pre-treated hepatocytes showed a phenotype reminiscent of anergic T cells, characterized by reduced responsiveness to vaccination antigen challenge. In some embodiments, as shown, total dLN cells, and not only OT-I cells, displayed impaired responsiveness to OVA vaccination as indicated by significantly reduced secretion of IFN-γ upon restimulation with SIINFEKL (SEQ ID NO: 104). From the lack of MHC-II expression by hepatocytes, no significant immune effect of pGal-OVA-treated hepatocytes could be detected on CD4+ OT-II cells adoptively transferred into recipient mice instead of OT-I cells (FIG. 9D).

CD8+ T Lymphocyte PD-1 Interactions with Hepatocyte PD-L1

In some embodiments, CD8+ T lymphocyte PD-1 interactions with hepatocyte PD-L1 participate in the establishment of hepatocyte-dependent cross-tolerance. PD-1 is a negative regulator of T cell responses and is associated with enhanced apoptosis and reduced secretion of pro-inflammatory cytokines of activated lymphocytes. Of note, expression of its receptor PD-L1 in the liver parenchyma is involved in hepatic retention and elimination of CD8+ T cells activated in the periphery. After observing induction of deletion and anergy of OT-I cells by antigen cross-presenting hepatocytes (FIG. 5 and FIG. 9), whether these effects could be ascribed to the PD-1/PD-L1 pathway was tested.

43.1% of the OT-I cells isolated from the dLNs of mice treated as in FIG. 5B and receiving OVA cross-presenting hepatocytes were PD-1+, significantly more frequent than in the dLNs of mice receiving either vehicle or untreated hepatocytes, where only 14.2% and 12.4% of the OT-I cells were PD-1+, respectively (FIG. 6A, top panel). Of note, the majority of the PD-1+ OT-I cells in mice administered on day 0 with pGal-OVA pre-treated hepatocytes were apoptotic, as shown by the significantly higher frequency of Annexin-V+PD-1+OT-I cells (70.6%) as compared to that observed in mice receiving either vehicle (45.4%) or untreated hepatocytes (44.8%) on day 0 (FIG. 6A, bottom panel). Similar results were also observed for the OT-I cells isolated from the spleen of vaccination challenged mice treated on day 0 with OVA cross-presenting hepatocytes (FIG. 10A).

PD-1 interacts with at least two receptors, PD-L1 and PD-L2. While expression of PD-L2 is restricted to activated lymphocytes and APCs, PD-L1 is widely expressed in lymphoid and non-lymphoid tissues. Hepatocytes express basal levels of PD-L1, which becomes overexpressed upon viral infection or treatment with type I and II interferons, leading to CD8+ T lymphocyte apoptosis. Under steady state conditions, high expression levels of PD-L1 were detected, but not PD-L2, on liver parenchymal cells from untreated C57BL/6 mice by both immunostaining followed by confocal microscopy and qPCR (FIG. 6B and FIG. 10B, respectively).

Figure 10C:
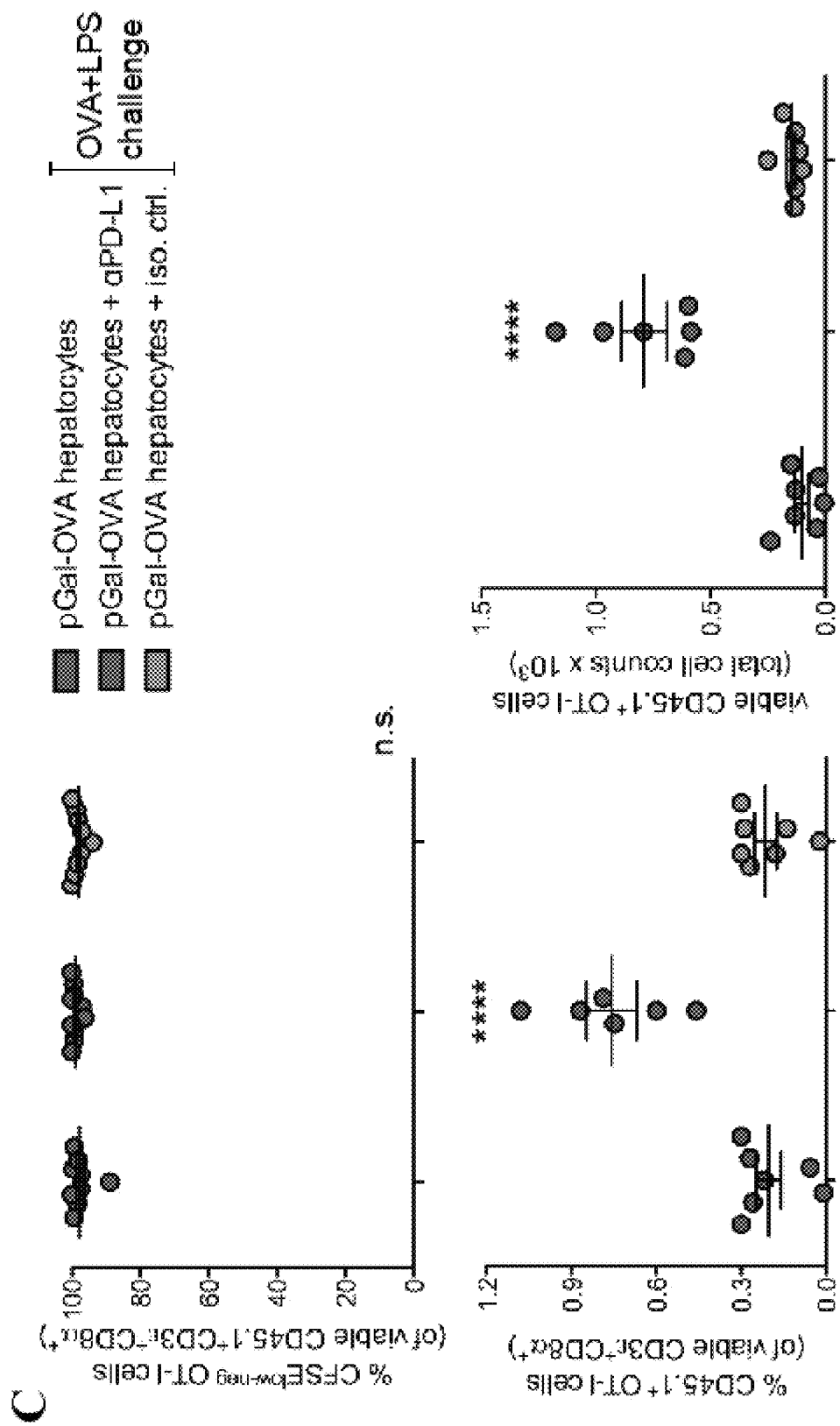

To test whether the interaction between PD-L1 expressed by OVA cross-presenting hepatocytes and PD-1 upregulated on the surface of hepatocyte-educated OT-I cells played a role in the establishment of the cross-tolerance effects observed in FIG. 5, the tolerogenic effects of pGal-OVA-treated hepatocytes were compared to those of pGal-OVA-treated hepatocytes incubated with a PD-L1 blocking antibody in the same experimental setting as shown in FIG. 5B (i.e., the antigen-experienced hepatocytes were exposed to PD-L1 blocking antibody, but the recipient animals were not). Vaccination challenge with OVA/LPS induced proliferation of the OT-I cells in the dLNs and spleen of recipient mice, with no significant differences among the treatment groups, as indicated by flow cytometric analysis of CFSE dilution of viable CD45.1+CD3+CD8+OT-I cells (FIG. 6C and FIG. 10C, top panel). Treatment of OVA cross-presenting hepatocytes with a PD-L1 blocking antibody prior to their infusion into recipient CD45.2+ C57BL/6 mice significantly reduced the induction of deletional tolerance by hepatocytes, since the frequency of CD45.1+ OT-I cells in the population of viable CD3+CD8+ lymphocytes was significantly increased in the dLNs of mice receiving on day 0 pGal-OVA- and αPD-L1-treated hepatocytes (0.45%) as compared to those receiving hepatocytes treated with either only pGal-OVA or with pGal-OVA and an isotype control antibody (0.22% and 0.20%, respectively) (FIG. 6D, left panel). Similar results were also observed for the OT-I cell counts (FIG. 6D, right panel) and were paralleled by the frequencies and counts of OT-I cells measured in the spleen of recipient mice (FIG. 10C, bottom panels).

Confirming reduced CD8+ T cell deletion, pre-treatment of OVA cross-presenting hepatocytes with αPD-L1 also significantly reduced the frequency of Annexin-V+, FasL+, TRAIL+ and KLRG1$^{hi}$CD127$^{low}$ OT-I cells isolated from the dLNs and spleen of recipient mice (FIG. 6E and FIG. 10D, respectively). In addition, blocking the interaction between OT-I-expressed PD-1 and hepatocyte-expressed PD-L1 also significantly prevented the induction of anergy and improved the acquisition of effector functions by non-deleted OT-I cells, resulting in increased frequencies of IFN-γ+ (47.11%) and IL-2+ (7.53%) OT-I cells isolated from dLNs and spleen of recipient mice after OVA/LPS challenge as compared to mice receiving either pGal-OVA-treated hepatocytes (24.53% and 3.19% of dLN IFN-γ+ and IL-2+ OT-I cells, respectively) or pGal-OVA and isotype control antibody-treated hepatocytes (29.16% and 4.21% of dLN IFN-γ+ and IL-2+ OT-I cells, respectively (FIG. 6F and FIG. 10E). Pretreatment of OVA cross-presenting hepatocytes with αPD-L1 also resulted in a trend for increased secretion of IFN-γ by total dLN cells harvested from recipient mice and restimulated ex vivo with SIINFEKL (SEQ ID NO: 104) (FIG. 6G).

Taken together, these data show that the interaction between PD-1, highly upregulated on the surface of CD8+ T cells experiencing antigen cross-presentation by hepatocytes, and PD-L1, strongly expressed by hepatocytes both at the mRNA and protein level, participates in the induction of hepatocyte-dependent cross-tolerance. In several embodiments, these mechanisms are leveraged to enhance the tolerance induced by the compositions and methods disclosed herein, for example enhancing the expression and/or interaction of PD-1 and PD-L1.

Cross-tolerance Effect of Hepatocyte-Dependent Antigen Presentation

In some embodiments, cross-tolerance is a direct effect of hepatocyte-dependent antigen presentation and/or does not require antigen presentation by host APCs. Altogether, the prolonged survival of hepatocytes after i.v. administration (FIG. 4), the lack of CD4+ T cell tolerance in the mice administered with pGal-OVA-treated hepatocytes (FIG. 9D), and the impaired tolerance after blocking PD-L1 specifically on OVA cross-presenting hepatocytes (FIG. 6) provide evidence that the establishment of tolerance following hepatocyte adoptive transfer is a consequence of hepatocyte cross-presentation. As discussed, herein, in several embodiments, these mechanisms are leveraged, at least in part, to enhance the induction of tolerance to an antigen of interest. Nevertheless, i.v. administered antigen-experienced hepatocytes could be phagocytosed and degraded, and their antigens, including OVA-derived epitopes, could be presented by host scavenger cells in the absence of co-stimulation, resulting in tolerance induction. For this reason, experiments were designed to elicit direct proof of hepatocyte-dependent cross-tolerance development in vivo.

The direct role of hepatocyte-dependent cross-presentation in the establishment of CD8+ T cell tolerance was confirmed by analyzing the development of cross-tolerance after administration of either pGal-OVA-treated TAP1$^{-/-}$ hepatocytes or of β-2 microglobulin (β2m)$^{-/-}$ hepatocytes into wild-type (wt) recipients as compared to administration of pGal-OVA-treated wt hepatocytes shown in FIG. 5, following the same experimental design indicated in FIG. 5B. Based at least in part on their genetic defects that lead to significant impairment of cross-presentation, ex vivo incubation of TAP1$^{-/-}$ or β2m$^{-/-}$ hepatocytes with pGal-OVA resulted in significant loss of cross-presentation of OVA-derived SIINFEKL (SEQ ID NO: 104) as compared to wt hepatocytes (FIG. 5A and FIG. 7A).

Upon vaccination challenge, OT-I cells retrieved from the dLNs and spleen of mice receiving either pGal-OVA-treated wt hepatocytes, pGal-OVA-treated TAP1$^{-/-}$ hepatocytes or pGal-OVA-treated β2m$^{-/-}$ hepatocytes responded by proliferation (FIG. 7B and FIG. 11A, left panel). Nonetheless, in the dLNs of mice administered on day 0 with pGal-OVA-experienced TAP1$^{-/-}$ or β2m$^{-/-}$ hepatocytes, the frequency of CD45.1+ OT-I cells in the population of viable CD3+ CD8+ lymphocytes was significantly greater than in mice infused with cross-presenting wt hepatocytes (0.14% and 0.13% as opposed to 0.04%, respectively) (FIG. 7B, middle panel). A similar trend was also observed for the counts of OT-I cells (FIG. 7B, left panel) and was paralleled by the frequencies and counts of OT-I cells measured in the spleen of recipient mice (FIG. 11A, middle and right panels). In parallel with increased frequency, the percentage of FasL+, TRAIL+ or KLRG1$^{hi}$CD127$^{low}$ OT-I cells retrieved from the dLNs or spleen of mice treated with pGal-OVA-experienced TAP1$^{-/-}$ hepatocytes was also significantly decreased as compared to mice receiving wt hepatocytes (FIG. 7C and FIGS. 11, B and C). Moreover, non-deleted OT-I cells from the dLNs or spleen of mice administered on day 0 with either TAP1$^{-/-}$ or (32m$^{-/-}$ pGal-OVA-treated hepatocytes responded to OVA/LPS challenge more efficiently, as indicated by the frequency of IFN-γ-expressing OT-I cells detected by flow cytometry (53.2% and 53.7% as compared to 33.8% in the dLNs) (FIG. 7D and FIG. 11D). The percentage of IL-2-producing OT-I cells was also significantly increased in both the spleen and dLNs of mice receiving pGal-OVA-experienced TAP1$^{-/-}$ or β2m$^{-/-}$ hepatocytes as compared to wt hepatocytes (15.5% and 11.5% as compared to 4.7% in the dLNs) (FIG. 11E). The frequency of PD-1+ and of Annexin-V+PD-1+ OT-I cells harvested from the dLNs or spleen of mice administered with TAP1$^{-/-}$ or 32m$^{-/-}$ hepatocytes pre-treated with pGal-OVA was significantly reduced as compared to mice administered with pGal-OVA-treated wt hepatocytes (21.2% and 16.4% as compared to 40.4% of PD-1+ OT-I cells and 41.2% and 31% as compared to 71.9% of PD-1+Annexin-V+ OT-I cells in the dLNs) (FIG. 7E and FIG. 11F). Lastly, impaired OVA cross-presentation by TAP$^{-/-}$ or β2m$^{-/-}$ hepatocytes also resulted in a generally stronger response to vaccination challenge with adjuvanted OVA, as suggested by a trend for increased secretion of IFN-γ by total dLN cells upon ex vivo restimulation with SIINFEKL (SEQ ID NO: 104) (FIG. 7F).

Altogether, these data confirm that the development of cross-tolerance in mice receiving pGal-OVA-treated hepatocytes depends at least in part on the direct interaction between OVA-specific CD8+ T lymphocytes and OVA cross-presenting hepatocytes and does not require processing of hepatocyte-derived or -associated antigens by host APCs. In fact, when cross-presentation defective TAP1$^{-/-}$ or β2m$^{-/-}$ hepatocytes were treated with pGal-OVA and infused into recipient mice, the induction of CD8+ T cell tolerance was significantly impaired as compared to that obtained by transfer of cross-presentation-competent wt hepatocytes. Therefore, in several embodiments, the methods disclosed herein are designed to maintain direct interaction between antigen-specific CD8$^+$ T lymphocytes and antigen-specific cross-presenting hepatocytes.

Antigen Cross Presenting Hepatocytes Tolerize Endogenous Antigen-Specific CD8+ T Lymphocytes and Prevent Acute Rejection of Skin Grafts In some embodiments, antigen cross-presenting hepatocytes tolerize endogenous antigen-specific CD8+ T lymphocytes and prevent acute rejection of skin grafts.

To test whether rare endogenous antigen-specific CD8+ T lymphocytes could be tolerized by antigen cross-presenting hepatocytes, wt C57BL/6 mice were infused with either pGal-OVA pre-treated hepatocytes, untreated (wt) hepatocytes or vehicle prior to grafting of skin derived from OVA-transgenic (OVA+/+) C57BL/6 mice (FIG. 8A). Acute rejection of a transplanted organ typically occurs within the first three weeks from grafting as a consequence of host alloreactive T cells recognizing and attacking donor tissues. This is consistent with what was observed in mice administered with either untreated hepatocytes or vehicle prior to grafting OVA+ skin, as all of these mice completely rejected the grafted skin by day 24 after transplantation (FIG. 8B). On the other hand, acute skin rejection could be delayed and in some cases even prevented in the mice pre-treated with OVA cross-presenting hepatocytes, as these mice only started to reject grafted OVA+ skin after 21 days from transplantation (FIG. 8B). Interestingly, 3 out of 8 mice receiving OVA cross-presenting hepatocytes as pre-tolerization treatment retained the OVA+ skin grafts until the end of the experimental timeline on day 60, resulting in a skin graft survival rate of 30% (FIG. 8B). The lack of acute skin rejection in the group of mice administered with pGal-OVA-treated hepatocytes was paralleled by lower frequencies of endogenous H-2 Kb/SIINFEKL (SEQ ID NO: 104)-specific CD8+ T lymphocytes as compared to those mice receiving either untreated hepatocytes or vehicle (FIG. 8C). After 30 days from skin transplantation, i.e. at the end of the acute rejection time window, H-2 Kb/SIINFEKL (SEQ ID NO: 104)-specific CD8+ T lymphocytes were 0.13% of viable circulating CD8+ T cells in mice that were pre-treated with OVA cross-presenting hepatocytes, as opposed to 0.43% and 0.34% in mice administered with either untreated hepatocytes or vehicle, respectively (FIG. 8C, middle). Similarly, at the end of the experimental timeline 60 days after skin transplantation, mice pre-treated with pGal-OVA-incubated hepatocytes still displayed a trend for a lower frequency of H-2 Kb/SIINFEKL (SEQ ID NO: 104)-specific CD3+CD8+ splenocytes (0.16%) compared to mice pre-treated with either wt hepatocytes or vehicle (0.25% and 0.27%, respectively), even though differences at this time point did not reach statistical significance (FIG. 8C, right). The 3 mice retaining the OVA+ skin graft until the end of the experimental time constantly showed significantly lower frequencies of H-2 Kb/SIINFEKL (SEQ ID NO: 104)-specific CD8+ T lymphocytes throughout the entire experimental time (0.047% on day 30 and 0.12% on day 60, in the blood and spleen, respectively) compared to the mice that rejected the OVA+ skin graft (0.34% on day 30 and 0.25% on day 60, in the blood and spleen, respectively) (FIG. 8D). Reduced frequency of endogenous SIINFEKL (SEQ ID NO: 104)-specific CD8+ T lymphocytes in mice pre-treated with OVA cross-presenting hepatocytes is consistent with antigen-specific CD8+ T cell clonal deletion as a mechanism of tolerance induction, similarly to what we observed with adoptively transferred OT-I cells (FIG. 5). Moreover, when splenocytes from skin-transplanted mice were re-stimulated ex vivo with SIINFEKL (SEQ ID NO: 104) after harvesting on day 60, a significant lower frequency of IFN-γ-expressing CD8$^+$ T cells was measured in the samples from mice administered with pGal-OVA-treated hepatocytes (0.043%) as compared to mice receiving either untreated hepatocytes (0.1%) or vehicle (0.09%), indicating anergy as an additional mechanism of tolerance (FIG. 8E). In several embodiments, these mechanisms are exploited by the administration of the compositions disclosed herein, and the clonal deletion and/or anergy of T cells specific to an antigen of interest allow for the develop of tolerance to that antigen, and the corresponding ability to reduce or eliminate adverse immune response to the antigen of interest.

Without being bound to a particular mechanism, clonal deletion and anergy of OVA-specific CD8$^+$ T lymphocytes can explain at least in part the lack of acute skin rejection in the mice pre-treated with OVA cross-presenting hepatocytes. The lack of chronic rejection in the 3 mice that retained the grafted skin until the end of the experimental time may require additional immune regulatory mechanisms, for example CD4$^+$ T cell tolerance and induction of Treg cells. To investigate whether either of these mechanisms occurred in this experimental setting, total splenocytes harvested from skin-grafted mice on day 60 were restimulated ex vivo with the CD4$^+$ T cell immunodominant epitope OVA$_{323-339}$ (ISQAVHAAHAEINEAGR; SEQ ID NO:105), and significantly lower frequencies of IFN-γ-expressing CD4$^+$ T lymphocytes were detected in the group of mice receiving OVA cross-presenting hepatocyte pre-treatment (0.28%) as compared to wt hepatocytes (0.58%) or vehicle (0.4%) (FIG. 8F). Mice administered with pGal-OVA-incubated hepatocytes had significantly higher frequencies of FoxP3$^+$CD25$^+$CD4$^+$ bona fide Treg cells (1.18%) as compared to the other treatment groups (0.53% and 0.83% for mice pre-treated with wt hepatocytes or vehicle, respectively), and the frequencies were especially higher in the 3 mice that did not reject the OVA$^+$ skin graft (FIG. 8G).

These data confirm that hepatocyte-dependent antigen cross-presentation is capable of inducing tolerance of rare endogenous antigen-specific CD8+ T cells by both clonal deletion and anergy, avoiding the early post-transplantation phase of antigen-specific cytotoxic T cell-dependent alloreactivity that would otherwise result in acute tissue graft rejection. The mice that were infused with OVA cross-presenting hepatocytes developed chronic rejection, starting to lose the grafted OVA+ skin after 3 weeks from the day of transplantation. Unexpectedly, 3 out of 8 mice pre-treated with OVA cross-presenting hepatocytes retained the OVA+ grafted skin until the end of the experimental timeline of 60 days post-grafting. Consistently with graft survival, these mice also showed the lowest frequencies of H-2 Kb/SIINFEKL (SEQ ID NO: 104)-specific CD8+ T lymphocytes throughout the entire experimental timeline and the highest frequency of FoxP3+CD25+CD4+ bona fide Treg cells, which are known for being involved in the prevention of chronic tissue rejection.

DISCUSSION

The results described herein shed light on the involvement of hepatocytes in the establishment of liver-mediated peripheral cross-tolerance towards soluble extracellular antigens. Because of its strategic location and microscopic anatomy, the liver has been associated with blood-filtering and immune tolerogenic functions. The hepatic structure is characterized by a complex network of enlarged capillaries, the sinusoids, which are lined by a fenestrated endothelium composed of LSECs and paralleled by plates of hepatocytes.

LSECs have been considered the major contributors to the immunomodulatory functions of the liver, as they are in direct contact with circulating lymphocytes, show efficient antigen scavenging capacity, express both MHC-I and MHC-II, and have low non-inducible levels of co-stimulatory molecules. On the other hand, hepatocytes only express MHC-I complexes and have been attributed poor antigen scavenging capacity in vitro, but efficient CD8+ T cell deletion ability in vivo upon direct antigen expression and MHC-I presentation in the absence of co-stimulation.

Given the direct contact that hepatocytes experience with T lymphocytes in the blood, it was reasoned that they could express and utilize the molecular machinery required for antigen processing and cross-presentation. Cross-presentation of extracellular antigens on MHC-I has been mainly attributed to specialized subsets of hematopoietic cells, in particular lymphoid organ-resident CD8c DCs. Nonetheless, as discussed herein, subsets of non-hematopoietic cells are also capable of cross-presentation, among which are stromal cells in the LNs and LSECs in the liver. Depending on the embodiment, one or more of these types of cells are targeted by the compositions disclosed herein.

The results described herein show that murine primary hepatocytes express high levels of the mannose scavenging receptor 1 (MR) found in other cross-presenting cells and contain abundant cellular compartments positive for markers associated with MHC-I presentation of extracellular antigens, in particular EEA1 and TAP1. Hepatocytes were found to contain $EEA1^+TAP1^+$ phagosomes, which are a peculiar characteristic of professional cross-presenting $CD11c^+CD8\alpha^+$ cells. Both in vitro and in vivo studies also demonstrated that hepatocytes actively process extracellular antigens, such as DQ-OVA, also in association with $EEA1^+$ and $TAP1^+$ compartments. The efficiency of antigen processing was less than that in $CD11c^+CD8\alpha^+$ DCs cells, probably due to the higher concentration of cross-presentation-competent phagosomes, mostly $EEA1^+TAP1^+$ compartments, in this DC subset as compared to hepatocytes.

To study the molecular mechanisms and the immunological outcomes of antigen cross-presentation by hepatocytes, a derivative of the model antigen OVA chemically modified with a polymer that is functionalized on its side chains with N-acetylgalactosamine (pGal-OVA) was utilized. This composition, as disclosed herein, is recognized by several scavenger receptors, including ASGPR on hepatocytes. Since receptor-mediated uptake of an antigen is the initial step of the cross-presentation pathway, improved uptake of pGal-OVA also led to enhanced cross-presentation of the OVA-derived immunodominant epitope SIINFEKL (SEQ ID NO: 104) by hepatocytes. Presentation of SIINFEKL (SEQ ID NO: 104) to antigen-specific OT-I cells by pGal-OVA-treated hepatocytes was significantly reduced when endosomal or proteasomal function was blocked using specific drug inhibitors. Reduction of the antigen presentation capacity of hepatocytes upon treatment with chloroquine or MG132 provides direct evidence that the cellular machinery of the antigen cross-presentation pathway is active in hepatocytes and further confirms that extracellular antigens enter this pathway after receptor-mediated endocytosis into hepatocytes. According to several embodiments, compositions disclosed herein are tailored to enhance the targeting, binding, and/or uptake of the compositions by the liver, through one or more of the scavenger receptors.

To characterize the effects of hepatocyte-dependent antigen cross-presentation, an ex vivo system was used where murine hepatocytes are first isolated from the liver of donor mice and incubated with the pGal-OVA antigen, then subsequently washed and infused i.v. into recipient mice. Surprisingly, adoptively transferred hepatocytes mainly home to the spleen and only to a lesser extent to the liver, while hepatocytes do not seed in other blood-filtering organs, including lungs and kidneys. Upon i.v. infusion, hepatocytes survive for at least 1 month in host animals, indicating that ex vivo manipulation of hepatocytes does not affect their viability.

When the phenotype of H-2 Kb/SIINFEKL (SEQ ID NO: 104)-specific OT-I cells was analyzed after an immunogenic challenge with OVA and LPS in mice receiving hepatocyte transfer, reduced frequencies and numbers of the OT-I cells that had previously experienced cognate antigen presentation by OVA cross-presenting hepatocytes were observed, suggesting an antigen-specific process of T cell deletion. Deletion of the OT-I cells could be attributed to T cell apoptosis, as the remaining non-deleted hepatocyte-educated OT-I cells showed a pro-apoptotic phenotype, indicated by staining with Annexin V and positivity for FasL and TRAIL, and reduced survival capacity, suggested by the increased frequency of OT-I cells displaying $KLRG1^{hi}CD127^{low}$ phenotypic signature of senescent cells. Not only did the non-deleted hepatocyte-educated OT-I cells show reduced survival, but they also responded poorly to vaccination antigen challenge, producing low levels of the pro-inflammatory cytokines IFN-γ and IL-2 upon ex vivo antigen-specific restimulation. Unresponsiveness to vaccination challenge indicated acquisition of an anergic phenotype by the OT-I cells, further indicating the establishment of tolerance. In some embodiments, hepatocyte-dependent anergy represents a terminally differentiated state leading to T cell deletion. In some embodiments, such a state can be reversed upon antigen re-encounter under pro-inflammatory conditions, similarly to LSEC-mediated CD8$^+$ T cell tolerance.

The significant reduction of IFN-γ secretion by total dLN cells harvested from mice receiving OVA cross-presenting hepatocytes as compared to the other treatment groups suggested establishment of hepatocyte-dependent cross-tolerance not only of adoptively transferred OT-I cells but also of endogenous OVA-specific CD8$^+$ T lymphocytes. Hepatocyte-dependent cross-tolerance by endogenous antigen-specific CD8$^+$ T lymphocytes was confirmed by infusion of pGal-OVA-treated hepatocytes prior to grafting OVA$^+$ skin into wt recipients, after which prevention of acute rejection of the OVA$^+$ skin was observed. The prolonged survival of OVA$^+$ grafted skin in mice receiving OVA cross-presenting hepatocytes as compared to mice receiving either vehicle or untreated hepatocytes prior to skin transplantation was associated with reduced frequencies of endogenous H-2 Kb/SIINFEKL (SEQ ID NO: 104)-specific CD8$^+$ T lymphocytes and poor pro-inflammatory cytokine expression in response to ex vivo restimulation with SIINFEKL (SEQ ID NO: 104). These findings confirmed the development of cross-tolerance in the compartment of endogenous OVA-specific CD8$^+$ T lymphocytes. Unexpectedly, 3 out of 8 mice receiving OVA cross-presenting hepatocytes prior to skin transplantation retained the OVA$^+$ skin until the end of the experimental timeline 60 days after grafting. Lack of skin graft rejection was associated with higher frequencies of bona fide CD4$^+$ Treg cells as compared to the mice that instead rejected the transplanted skin. In some embodiments, these results indicate that, together with hepatocyte-dependent cross-tolerogenesis, other mechanisms participated in the establishment of immune tolerance towards OVA in those mice that never rejected the OVA$^+$ skin grafts. In particular, the lack of acute skin rejection, made possible by hepatocyte-driven cross-tolerance, may create a window of time where graft-derived alloantigens, in this case OVA, could be drained to and presented by host APCs in the absence of danger signals, thus additionally resulting in the development of $CD4^+$ T cell tolerance, and enhanced graft survival.

The development of peripheral $CD4^+$ and $CD8^+$ T cell tolerance upon intravenous infusion of antigen-coupled cells depends on the apoptotic phenotype of the transferred cells causing them to be phagocytosed and their antigens to be presented by host APCs in non-inflammatory conditions. The prolonged in vivo survival of adoptively transferred hepatocytes indirectly rules out uptake of OVA cross-presenting hepatocytes by host APCs in the disclosed system. In order to provide a direct confirmation that the tolerogenic effects were the result of hepatocyte cross-presentation, pGal-OVA-treated $TAP1^{-/-}$ or $\beta 2m^{-/-}$ hepatocytes into were adoptively transferred into wt recipient mice together with OT-I cells. Impaired antigen cross-presentation by $TAP1^{-/-}$ and $\beta 2m^{-/-}$ hepatocytes resulted in significantly reduced OT-I cell tolerance, confirming the direct role of hepatocyte cross-presentation in tolerogenesis. Hepatocyte-dependent antigen presentation did not lead to direct $CD4^+$ T cell tolerance (with OT-II cells), further confirming that the tolerance effect here described is the result of antigen presentation on MHC-I molecules by hepatocytes. This is surprising considering evidence describing the induction of antigen-specific $CD4^+CD25^+FoxP3^+$ Treg cells upon hepatocyte-specific antigen expression through lentiviral transduction, which suggests that in the case of an antigen directly expressed by hepatocytes, tolerance could result from antigen spreading and MHC-II presentation by other host APCs.

The liver displays an unusual enrichment of $CD8^+$ T lymphocytes in its parenchyma as compared to other organs, and the majority of these cells have an activated phenotype. The liver acts as a T cell graveyard, where activated $CD8^+$ T lymphocytes accumulate and die by apoptosis, especially during the contraction phase of an immune response. Hepatic expression of PD-L1 is believed to be involved in the retention and deletion of activated $CD8^+$ T cells, in line with the negative effects of PD-1 on T cell functions. PD-1 is upregulated on activated T cells and is therefore considered one of the most important signals involved in the resolution phase of an immune response and associated with T cell exhaustion. PD-1 may play a role in the prevention of autoimmunity and maintenance of immune homeostasis, since PD-1-deficient mice develop spontaneous autoimmune manifestations during their lifetime. Increased frequencies of $PD-1^+$ and of apoptotic $Annexin-V^+PD-1^+$ OT-I cells in those mice administered with pGal-OVA-treated hepatocytes has been observed as compared to the other treatment groups. Hepatocytes have also been demonstrated to express PD-L1 at both the mRNA and protein level under steady-state conditions. The direct interaction between antigen-experienced PD-1-expressing OT-I cells and antigen cross-presenting $PD-L1^+$ hepatocytes may be one of the factors responsible for the induction of OT-I tolerance. When pGal-OVA-treated hepatocytes were incubated with a PD-L1 blocking antibody prior to their infusion into recipient mice, OT-I cells could be significantly, but potentially not completely, rescued from deletion and development of anergy. The data provided herein evidences that the PD-1/PD-L1 pathway is involved in the induction of hepatocyte-dependent cross-tolerance. Other interactions could be involved as well. For example, hepatocytes might express ligands of PD-1 different from PD-L1 and hepatocyte-educated T cells might bind to PD-L1 molecules expressed on other cells, since PD-L1 is widely expressed in both hematopoietic and non-hematopoietic tissues. Nonetheless, as is employed in several embodiments, specific abrogation of PD-L1 expression in hepatocytes or blockade of its activity may provide a novel targeted therapeutic strategy for patients affected by chronic hepatocyte infection as an alternative to unspecific systemic inhibition of PD-1/PD-L1, which can reverse the immune dysfunctional phenotype of hepatitis virus-specific $CD8^+$ T lymphocytes in pre-clinical and clinical trials.

The establishment of peripheral tolerance is associated with cellular apoptosis. Components derived from apoptotic cells are in fact phagocytosed and subsequently presented by APCs to adaptive immune cells in the absence of pro-inflammatory signals, therefore generating immune tolerance rather than immune activation. Apoptotic cells are characterized by peculiar morphological and molecular features, such as activation of neuraminidases. The enzymatic activity of neuraminidases, in turn, is responsible for the removal of terminal sialic acid moieties from cell membrane glycoproteins and glycolipids, leading to exposure of neo-terminal N-acetylgalacosylation on the surface of apoptotic cells and to their subsequent recognition by phagocytotic receptors. In this way, pGal-antigen conjugates molecularly mimic the glycated structures exposed on apoptotic debris. By taking advantage of such a chemical tool, according to several embodiments, the ability of hepatocytes to endocytose apoptotic debris is enhanced and while increasing the ability to induce tolerance, can also provide further insights on the immune tolerogenic outcomes (e.g., mechanisms) of such a phenomenon. It is also postulated that antigen glycation with different sugar residues can affect antigen processing and presentation by hepatocytes.

In summary, it has been shown in both in vitro and in vivo conditions that hepatocytes are efficient non-hematopoietic cross-presenting cells, which is exploited in several embodiments to induce antigen-specific tolerance. Hepatocyte-dependent cross-presentation was found to induce antigen-specific CD8+ T cell tolerance, mainly by clonal deletion and anergy of the T cells in a PD-1/PD-L1-dependent fashion. The data suggest that hepatocyte-dependent tolerogenesis via the PD-1/PD-L1 pathway could be at the origin of chronicity of hepatic viral infections. Because of their anatomical location, their abundance and their intense metabolic activities, hepatocytes have been shown to be potential key players in the establishment and maintenance of liver-mediated peripheral tolerance towards exogenous or endogenous extracellular antigens reaching the liver through the bloodstream. Moreover, the data support hepatocytes as interesting candidates for the targeted tolerogenic immunotherapies that are disclosed and/or referenced herein.

Materials and Methods

Mice

C57BL/6 mice were obtained from Harlan Laboratories (Gannat, France), C57BL/6 TAP1−/− mice (B6.129S2-Tapltm1Arp/J), C57BL/6 $P2m^{-/-}$ mice (B6.129P2-B2mtm1Unc/J) and C57BL/6 OVA+/+ mice (C57BL/6-Tg (CAG-OVA)916Jen/J) were purchased from The Jackson Laboratory (Farmington, Conn.), and CD45.1+ OT-I mice were generated by crossing C57BL/6-Tg(TcraTcrb)1100Mjb (OT-I) mice (The Jackson Laboratories) with CD45.1+ C57BL/6-Ly5.1 mice (Charles River, Saint-Germain-Nuelles, France). 8-12 week old female mice were used in all animal experiments. Animals were housed in pathogen-free conditions at the animal facility of the Ecole Polytechnique Fédërale de Lausanne and of the University of Chicago. All experiments were performed in accordance with Swiss and US law and with approval from the Cantonal Veterinary Office of Canton de Vaud, Switzerland, and of the Institutional Animal Care and Use Committee (IACUC) of the University of Chicago.

Cell Isolation and Antigen Loading

Hepatocytes were isolated from the liver of either wt, TAP1$^{-/-}$ or β2m$^{-/-}$ C57BL/6 mice and cultured on a feeder layer of 3T3 NIH fibroblasts in DMEM medium supplemented with 10% FBS and 100 IU/mL penicillin-streptomycin at 37° C. 5% $CO_2$. BMDCs were generated. To isolate CD11c+CD8α+ BMDCs, BMDCs were stained with Abs specific for CD11c (BioLegend) and CD8α (Life Technologies) and sorted with a FACSAria cell sorter (BD Biosciences). CD45.1+ OT-I cells were purified from the spleen and LNs of CD45.1+ OT-I mice by negative selection of CD8α+ T cells using the EasySep mouse CD8α T cell isolation kit (Stemcell Technologies) and labeled with CFSE (Life Technologies) following manufacturer's instructions. For in vitro analysis of OVA processing, hepatocytes and BMDCs were cultured in complete DMEM or complete RPMI 1640, respectively, supplemented with 20 μg/ml DQ-OVA (Life Technologies). For in vitro analysis of SIINFEKL (SEQ ID NO: 104)cross-presentation, hepatocytes and BMDCs were cultured in 5 μM OVA-, 5 μM pGal-OVA- or 1 nM SIINFEKL (SEQ ID NO: 104)-supplemented complete medium. For ex vivo loading with pGal-OVA prior to administration into mice, hepatocytes were isolated from donor mice and incubated for 3 hr at 37° C. 5% $CO_2$ with 12.5 μM pGal-OVA-supplemented complete DMEM (without feeder layer).

In Vitro Co-Culture of Hepatocytes and OT-I Cells

Freshly isolated wt C57BL/6 hepatocytes were cultured in 5 μM pGal-OVA-supplemented complete DMEM for 24 hr prior to washing and co-culture with $10^5$ OT-I cells for 24 hr. For drug inhibitors, chloroquine was used at 100 μM and MG132 at 10 μM and was added 1 hr after addition of the antigen. After co-culture, OT-I cells were harvested and stained with Abs specific for the markers CD3ε (eBioscience), CD8α (Life Technologies), and CD69 (BioLegend). Samples were acquired on an LSR II cytometer (BD Biosciences) and data analyzed with FlowJo software (Tree Star).

Confocal Microscopy and Flow Cytometry of Primary Hepatocytes and BMDCs

Primary hepatocytes were adhered onto 3T3 NIH fibroblast-coated glass coverslips and BMDCs were adhered onto poly-L-lysine-coated glass coverslips. At the end of the experimental procedures, cells were fixed in 4% paraformaldehyde solution, permeabilized in 3% BSA 0.1% saponin PBS and stained with primary Abs specific for MR-(AbD Serotec), EEA1 (BioConcept), LAMP-1 (Abcam), TAP1 (Santa Cruz Biotechnology), H-2 Kb (BioLegend) or H-2 Kb/SIINFEKL (SEQ ID NO: 104) (eBioscience) followed by fluorescently labeled secondary Abs (Life Technologies) and fluorochrome-conjugated phalloidin (Life Technologies). Liver, spleen, lungs and kidneys were harvested after perfusion of euthanized animals with HBSS (Life Technologies). Organs were fixed in 4% paraformaldehyde solution and frozen in OCT (Sakura). 10 μm-thick sections were sliced and stained with primary Abs specific for PD-L1 or PD-L2 (eBioscience) and fluorescently labeled secondary Abs (Life Technologies) or left unstained. Samples were mounted using ProLong Gold antifade reagent with DAPI (Life Technologies), imaged with a LSM 700 inverted confocal microscope (Zeiss) and data were analyzed with ImageJ software. For flow cytometry, at the end of the experimental procedures, hepatocytes or BMDCs were washed in 2% FBS PBS and acquired on an LSR II cytometer (BD Biosciences) and data analyzed with FlowJo software (Tree Star).

Hepatocyte Adoptive Transfer

For hepatocyte biodistribution studies, wt C57BL/6 mice were administered i.v. by tail vein injection with $10^6$ CFSE-labeled wt C57BL/6 hepatocytes in 100 μL DMEM. Mice were euthanized after 24 hr, 14 d and 1 month to collect liver, spleen, lungs and kidneys for confocal microscopy. For tolerance studies, on day 0 recipient wt C57BL/6 mice were administered i.v. by tail vein injection with either $10^6$ pGal-OVA-treated or untreated hepatocytes in 100 μL DMEM or with 100 μL DMEM (vehicle) followed by i.v. injection of $3*10^5$ CFSE-labeled CD45.1$^+$ OT-I cells 6 hr later. For PD-L1 blockade, 100 μg/ml αPD-L1 blocking Ab (BioxCell, clone 10F.9G2) or rat IgG isotype control Ab (Abcam) were added to the hepatocytes for 30 min prior to washing and administration into mice. On day 15, recipient mice were either vaccinated i.d. with 10 μg endo-grade chicken OVA (Hyglos)+50 ng ultra-pure LPS (InvivoGen) in 50 μL saline divided into the two frontal footpads or left untreated. On day 19, recipient mice were euthanized to collect spleen and brachial and axillary LNs (dLNs). Spleen and dLN single-cell suspensions were either cultured for 6 hr at 37° C. in the presence of 1 μg/mL SIINFEKL (SEQ ID NO: 104) (GenScript) with the addition of 5 μg/mL BFA for the last 3 hr of culture for antigen-specific restimulation and intracellular cytokine staining or directly stained for flow cytometry. For flow cytometry analysis, cells were first stained using Live/Dead fixable cell viability reagents (Life Technologies) followed by surface staining with Abs specific for the markers CD45.1 (eBioscience), CD3ε (eBioscience), CD8α (Life Technologies), FasL (BioLegend), TRAIL (BioLegend), KLRG-1 (BioLegend), CD127 (eBioscience) and PD-1 (BioLegend). Staining with biotinylated Annexin V and fluorescently labeled streptavidin (Life Technologies) was performed according to the manufacturer's instructions. For intracellular cytokine staining, cells were fixed in 2% paraformaldehyde solution, permeabilized in 0.5% saponin 2% FBS PBS solution, and incubated with Abs specific for IFN-γ (BioLegend) and IL-2 (eBioscience). Samples were acquired on an LSR II cytometer (BD Biosciences) and data analyzed with FlowJo software (Tree Star). dLN cells were restimulated for 4 days in the presence of 1 μg/mL SIINFEKL (SEQ ID NO: 104) for the measurement of IFN-γ by ELISA using the specific Ready-SET-go! ELISA kit from eBioscience.

RNA Extraction, RT-PCR and Gene Expression Analysis of PD-1 Ligands by qPCR

Total RNA was extracted from hepatocytes isolated from wt C57BL/6 mice using the RNeasy kit isolation protocol (Qiagen) according to manufacturer's instructions. cDNA was obtained by RT-PCR of total RNA performed using the SuperScript III First Strand Synthesis SuperMix (Life Technologies) following manufacturer's instructions. Gene expression analysis was performed by cDNA qPCR using TaqMan gene expression assays specific for PD-L1 (Mm00452054_ml) or PD-L2 (Mm00451734_ml) and β-Actin (Mm01268569_ml) (Life Technolgies) in a LightCycler 96 System (Roche). Relative gene expression was quantified using the formula (gene expression fold change)= $2^{(Cq\ Actin-Cq\ PD-L)}$ with β-Actin as reference gene.

Skin Transplantation Studies

On day −14 and −7 recipient wt C57BL/6 mice were administered i.v. by tail vein injection with either $10^6$ pGal-OVA-treated or untreated hepatocytes in 100 μL DMEM or with 100 μL DMEM (vehicle). On day 0, tail skin from donor OVA$^{+/+}$ C57BL/6 mice was grafted onto the back of recipient mice and the survival of the graft was monitored for the following 60 days. Blood was sampled on day 0 (before skin grafting) and on day 30 for flow cytometry analysis of circulating lymphocytes. On day 60, recipient mice were euthanized to collect the spleen. Single-cell suspensions of splenocytes were cultured for 6 hr at 37° C. in the presence of 1 μg/mL SIINFEKL (SEQ ID NO:104) or ISQAVHAAHAEINEAGR (SEQ ID NO:105) (GenScript) with the addition of 5 μg/mL BFA for the last 3 hr of culture for antigen-specific restimulation and intracellular cytokine staining or directly stained for flow cytometry. For flow cytometry analysis, cells were processed as indicated above.

Statistics

Statistically significant differences between experimental groups were determined by one-way ANOVA followed by either Bonferroni post-hoc test correction, unpaired Student's t-test, Log-rank Mantel-Cox test or Mann-Whitney test. *$P<0.05$, $P<0.01$, *$P<0.001$, ****$P<0.0001$ and n.s.=not significant. Statistical analyses were performed using Prism software (v6.0f, GraphPad Software).

FIG. 9. OVA cross-presenting hepatocytes induce CD8+ T cell tolerance in vivo via deletion and anergy. FIG. 10. PD-1/PD-L1 interactions are involved in the establishment of hepatocyte-dependent cross-tolerance. FIG. 11. CD8+ T cell tolerance is the result of hepatocyte-dependent antigen cross-presentation. FIG. 12. Flow cytometry raw data.

Example 11: Antigens Bearing Synthetic Glycosylations that Target Hepatic C-Type Lectins Induce Functional Regulatory T Cells and Lasting Protection from Autoimmunity in Mice In several embodiments, antigens modified with synthetic polymer glycosylations target the liver, induce tolerance and functional Tregs that persist and provide tolerogenic memory and lasting protection from experimental type-1 diabetes. Disclosed herein are experiments demonstrating that antigen presentation by hepatic antigen presenting cells (HAPCs) results in tolerogenic, and not effector, T cell education. For that reason, as disclosed herein, there are provided various strategies (e.g., development of compositions and uses thereof) that target antigens to HAPCs via innate tolerogenic pathways have the potential to induce antigen-specific immunological tolerance. Some embodiments disclosed herein demonstrate that exogenous- and auto-antigens modified with synthetic polymeric glycosylations composed of either NAc-β-galactosamine or NAc-β-glucosamine (or other moieties, such as galactose, glucose, galactosamine, glucosamine, or combinations there, including those in an α configuration) target HAPCs and/or induce antigen-specific tolerance as indicated, at least in part, by CD4$^+$ and CD8$^+$ T cell deletion and anergy and the induction of CD4$^+$CD25$^+$FOXP3$^+$ regulatory T cells (Tregs). Glycopolymer-modified antigens, but not antigens bearing native mannose residues, expanded Tregs, which are important, in several embodiments, for long-term suppression of antigen-specific immune responses. Using an adoptive transfer model of type 1 diabetes (T1D), it was demonstrated herein that treatment with auto-antigens modified with NAc-β-glucosamine-containing polymers prevented CD4+T cell-mediated diabetes, expanded antigen-specific Tregs, and/or imbued lasting tolerance to subsequent challenge with activated diabetogenic CD4$^+$ T cells. As discussed above, various other targeting moieties may be used, depending on the embodiment. These results demonstrate the efficacy of a clinically-viable tolerance-inducing strategy for the treatment of autoimmunity. Some embodiments described herein increase the understanding of the role of specific carbohydrate ligands and receptors in maintaining the liver's tolerance effect. In some embodiments, antigens modified with synthetic polymer glycosylations induce function Tregs that persist and provide tolerogenic memory and lasting protection from experimental type-1 diabetes.

Introduction To Study B

Aberrant activation of auto-reactive effector T cell responses is central to the etiology of autoimmune disorders. Many of the current gold-standard treatments for autoimmune diseases are non-specific and globally curb immune cell responses (including effector T cell responses). However, these non-specific treatments can result in an increased risk of opportunistic infections and malignancy. Additionally, it is unclear if these non-specific therapies are able to expand endogenous auto-antigen-specific Tregs, which are effective suppressors of effector T cell responses and are important for establishing lasting tolerance. Strategies that induce T cell deletion and senescence in specific T cell subsets while inducing antigen-specific Tregs in vivo via the body's intrinsic tolerogenic mechanisms would represent a major step forward in the development of a tolerance-inducing therapeutic. Some embodiments disclosed herein provide methods that induce T cell deletion and senescence in specific T cell subsets while inducing antigen-specific Tregs in vivo via the body's intrinsic tolerogenic mechanisms.

In some embodiments, the liver is used to exploit antigen-specific immune tolerance. Given its demonstrated ability to induce tolerance to auto- and food-derived antigens and its intimate contact with the blood, the liver microenvironment represents a physiological system useful in exploiting antigen-specific tolerance induction. The liver's tolerogenic effect is primarily maintained by populations of conventional and unconventional antigen presenting cells including immature liver-resident dendritic cells (DCs), liver sinusoidal endothelial cells (LSECs), Kuppfer cells (KCs), and even hepatocytes. In some embodiments, one or more of LSECs, KCs, and/or hepatocytes can be used (e.g., targeted by the compositions disclosed herein) to collect and tolerogenically cross-present exogenous antigens. In some embodiments, by secreting or promoting the production of anti-inflammatory cytokines and/or expressing the inhibitory molecule PD-L1, HAPCs can be used in methods to promote a tolerogenic milieu in which antigen presentation to CD4$^+$ and CD8$^+$ T cells results in anergy, deletion, and the induction of Tregs. Various combination therapies are provided for herein, with administration of a tolerance-inducing composition that targets the liver (one or more liver cell type) in combination with an enhancing agent that aids in the cross-presentation of the antigen to which tolerance is desired and/or other mechanisms that promote antigen-specific T cell deletion and/or anergy.

In some embodiments, to actively target antigens to HAPCs, C-type lectin receptors that play a central role in the inherently tolerogenic process of apoptotic cell debris clearance are exploited as potential pro-tolerogenic gateways for antigen delivery. Apoptosis results in increased desialyation of NAc-galactosamine (GalNAc) residues on membrane proteins and the release of intracellular proteins bearing NAc-glucosamine (GluNAc) residues. In some embodiments, these terminal GalNAc and GluNAc residues (or other glucose/galactose moieties disclosed herein) expedite the clearance of apoptotic debris via specific C-type lectins that are expressed by HAPCs. For this reason, in some embodiments, endowing antigens with synthetic glycosylations composed of either GalNAc or GluNAc can target these antigens to HAPCs through tolerogenic pathways resulting in the establishment of antigen-specific tolerance.

In some embodiments, i.v. administered antigens bearing synthetic polymeric GalNAc or GluNAc glycosylations, termed p(GalNAc) and p(GluNAc), respectively, generate persistent antigen-specific CD4$^+$ and CD8$^+$ T cell tolerance. In some embodiments, treatment with antigen-p(GalNAc) or antigen-p(GluNAc) conjugates induces antigen-specific Treg cells for the maintenance of lasting tolerance. In some embodiments, in an adoptive T cell transfer model of type-1 diabetes (T1D), treatment with auto-antigen-p(GluNAc) conjugates, but not the free antigen, protected mice from diabetes onset established long-term protection from autoimmune β cells destruction.

Results

Synthetic Glycosylations p(GalNAc) and p(GluNAc) Target Protein Antigens to HAPCs In some embodiments, to target HAPCs via innate tolerogenic pathways, the process by which apoptotic cell debris is taken up by HAPCs can be mimicked using the synthetic structures disclosed herein. Antigens were modified with synthetic polymeric glycosylations composed of random co-polymers of monomers bearing either β-linked NAc-galactosamine (p(GalNAc), FIG. 13A.i) or β-linked NAc-glucosamine (p(GluNAc), FIG. 13A.ii) residues and a biologically inert co-monomer. In some embodiments, as shown, p(GalNAc) and p(GluNAc) can be conjugated to antigens via surface amines. Thiol groups are used in other conjugation schemes disclosed herein. Given the possibility that covalent chemical modification of an antigen could block epitope loading onto MHC molecules, p(GalNAc) and p(GluNAc) polymers were attached to antigens via a reduction-sensitive self-immolating linkage that upon intracellular disulfide reduction initiates an intra-molecular reaction that liberates the antigen from the polymer, advantageously, with the antigen being released in its native form (FIG. 19A-C). In mechanistic studies, the model antigen ovalbumin (OVA) was modified with p(GalNAc) or p(GluNAc) (OVA-p(GalNAc), OVA-p(GluNAc)). As shown by gel electrophoretic analysis, OVA-p(GalNAc) and OVA-p(GluNAc) have effective molecular weights between 70 and 100 kDa (FIG. 12B (ii. & iv.)), and reduction of the self-immolating linker releases free OVA (FIGS. 12B.iii & 1B.iv).

To assess the ability of OVA-p(GalNAc) and OVA-p (GluNAc) conjugates to target HAPCs, fluorescently labeled OVA ($OVA_{750}$ or $OVA_{649}$) was conjugated to either p(GalNAc) or p(GluNAc) and then C57BL/6 mice were treated with the conjugates via tail vein injection with OVA in the form of $OVA_{750}$-p(GalNAc), $OVA_{750}$-p(GluNAc), $OVA_{750}$, $OVA_{649}$-p(GalNAc), $OVA_{649}$-p(GluNAc), or $OVA_{649}$. After 3 h, the livers of mice treated with formulations containing $OVA_{750}$ were perfused and imaged as whole organs for total fluoresce as a measure of hepatic antigen-load. At the same time point, the livers of animals treated with formulations containing $OVA_{649}$ were harvested and the HAPCs were isolated via density gradient centrifugation and analyzed for $OVA_{649}$ content via flow cytometry. Targeting was defined as a significant increase in antigen load or percentage of $OVA_{649}{}^+$ cells as compared to mice treated with $OVA_{750}$ or $OVA_{649}$. The results show that p(GalNAc) and p(GluNAc) (as well as other targeting moieties disclosed herein) enhance antigen delivery to the liver and target HAPCs. For example, whole liver imaging shows that while treating animals with $OVA_{750}$, $OVA_{750}$-p(GalNAc), or $OVA_{750}$-p (GluNAc) resulted in $OVA_{750}$ delivery to the liver, treatment with $OVA_{750}$-p(GalNAc), and $OVA_{750}$-p(GluNAc) produced a significantly greater hepatic antigen-load than treatment with $OVA_{750}$ (FIG. 13C). Notably, a five-fold greater does of $OVA_{750}$ (FIG. 13C: $OVA_{750}$ 5×) than $OVA_{750}$-p (GalNAc) or $OVA_{750}$-p(GluNAc) was required to achieve a comparable level of hepatic antigen-load (FIG. 13C). Additionally, whole organ fluorescence analysis of the spleens of animals treated with $OVA_{750}$-p(GalNAc), $OVA_{750}$-p(GluNAc), or $OVA_{750}$ showed considerably less fluorescence in the spleens of animals treated with $OVA_{750}$-p(GalNAc) and $OVA_{750}$-p(GluNAc) versus the spleens of mice treated with $OVA_{750}$ (FIG. 19D).

In several embodiments, increasing hepatic antigen-load is associated with increased antigen-presentation. Further each HAPC induces tolerance via one or another particular mechanism. Which HAPCs were targeted by $OVA_{649}$-p (GalNAc) and $OVA_{649}$-p(GluNAc) was analyzed. Flow cytometry analysis revealed that, in some embodiments, $OVA_{649}$-p(GalNAc) generates elevated percentages of $OVA_{649}{}^+$ DCs and KCs and specifically targets hepatocytes and LSECs (FIGS. 13D & E, FIG. 20) while $OVA_{649}$-p(GluNAc) targets DCs, KCs, hepatocytes and LSECs. Although the percentage of $OVA_{649^+}$ LSECs in animals treated with $OVA_{649}$-p(GalNAc), $OVA_{649}$-p(GluNAc), and $OVA_{649}$ were comparable (at nearly 100%), the mean fluorescence intensities of LSECs from mice treated with $OVA_{649}$-p(GalNAc) and $OVA_{649}$-p(GalNAc) were significantly greater than the LSECs of $OVA_{649}$ treated mice, indicating increased antigen load, with the greatest uptake being observed in the $OVA_{649}$-p(GluNAc) group. These results demonstrate the HAPC-targeting p(GalNAc) and p(GluNAc) and the clearance capabilities of hepatic GalNAc- and GluNAc-binding C-type lectins.

Conjugation to p(GalNAc) or p(GluNAc) Enhance Antigen Presentation and Tolerogenic T Cell Education Based on the ability of both p(GalNAc) and p(GluNAc) to target antigens to HAPCs, whether glycopolymer-mediated targeting of HAPCs resulted in increased antigen-presentation, T cell-priming, and antigen-specific T cell deletion was tested. Carboxyfluorescein succinimidyl ester (CFSE)-labeled OTI T cells ($CD45.1^+$, $CD8^+$) and CFSE-labeled OTII T cells ($CD45.1^+$, $CD4^+$) were adoptively transferred into recipient $CD45.2^+$ C57BL/6 mice. The next day, mice were treated via i.v. injection with either 1.0 or 10 μg of OVA as wt OVA, OVA-p(GalNAc), or OVA-p(GluNAc). Five days after treatment, the spleen resident OTI and OTII T cells of these animals were analyzed via flow cytometry for proliferation, activation, and apoptosis. Both OTI and OTII T cell proliferation, determined by dilution of CFSE, was markedly increased in mice treated with OVA-p(GalNAc) and OVA-p(GluNAc) with respect to mice treated with an equivalent dose of wt OVA (FIGS. 14A-D, FIG. 21). For example, mice treated with either 1 μg or 10 μg of OVA as OVA-p(GalNAc) or OVA-p(GluNAc) had a more than 2-fold increase in the percentage of proliferating OTI and OTII T cells compared to mice treated with an equivalent dose of free OVA, in accordance with the compositions disclosed herein providing for enhanced development of antigen-specific immune tolerance. Mice treated with 1 μg of OVA as OVA-p(GluNAc) had a 16% increase in OTI proliferation and a 18% increase in OTII proliferation relative to OVA-p(GalNAc)-treated mice (OTI: 66% vs. 49.9%; OTII: 91% vs. 73%) (FIGS. 14C & D). Notably, 1 μg of OVA-p(GalNAc) or OVA-p(GluNAc) elicited more OTI and OTII T cell proliferation than 10 μg of wt OVA.

Next, splenic OTI and OTII T cells were analyzed for annexin-V binding, a hallmark of apoptosis, and the surface expression of programmed cell death protein 1 (PD-1), a negative regulator of effector responses. OVA-p(GalNAc) or OVA-p(GluNAc) was found to significantly increase OTI and OTII deletional tolerance, as evidenced by the increased surface binding of annexin-V on both OTI and OTII T cells from mice treated with OVA-p(GalNAc) or OVA-p(GluNAc) in comparison to OVA-treated mice (OTI: 15.2%, 18.4%, and 10.3%, respectively; OTI: 17.6%, 47.3%, and 2.9%, respectively) (FIGS. 14E & F). OVA-p(GalNAc) and OVA-p(GluNAc) produced more PD-1$^+$ OTI T cells (24.5% and 45.7%, respectively) and OTII T cells (40.8% and 67.1%, respectively) than did wt OVA (OTI: 16.9%; OTII: 38.2%) (FIGS. 14G & H). It is notable that significantly more OTI and OTII T cells from mice treated with OVA-p(GluNAc) were positive for annexin-V and PD-1 than OTII and OTII cells from the spleens of mice treated with OVA-p(GalNAc). These results confirm that the endocytosis of antigens via p(GalNAc)- and p(GluNAc)-binding C-type lectins in the liver results in tolerogenic T cell education and suggest that p(GluNAc) conjugates induce a more exhausted and apoptotic T cell phenotype than p(GalNAc) modified antigens. Thus, in several embodiments, compositions comprising a glucose-based targeting moiety are preferred, for example use of glucose, glucosamine, or N-acetyl-glucosamine. In several embodiments, combinations of glucose-based and galactose-based moieties are used, resulting in synergistic effects with respect to induction of tolerance.

Figure 22C:
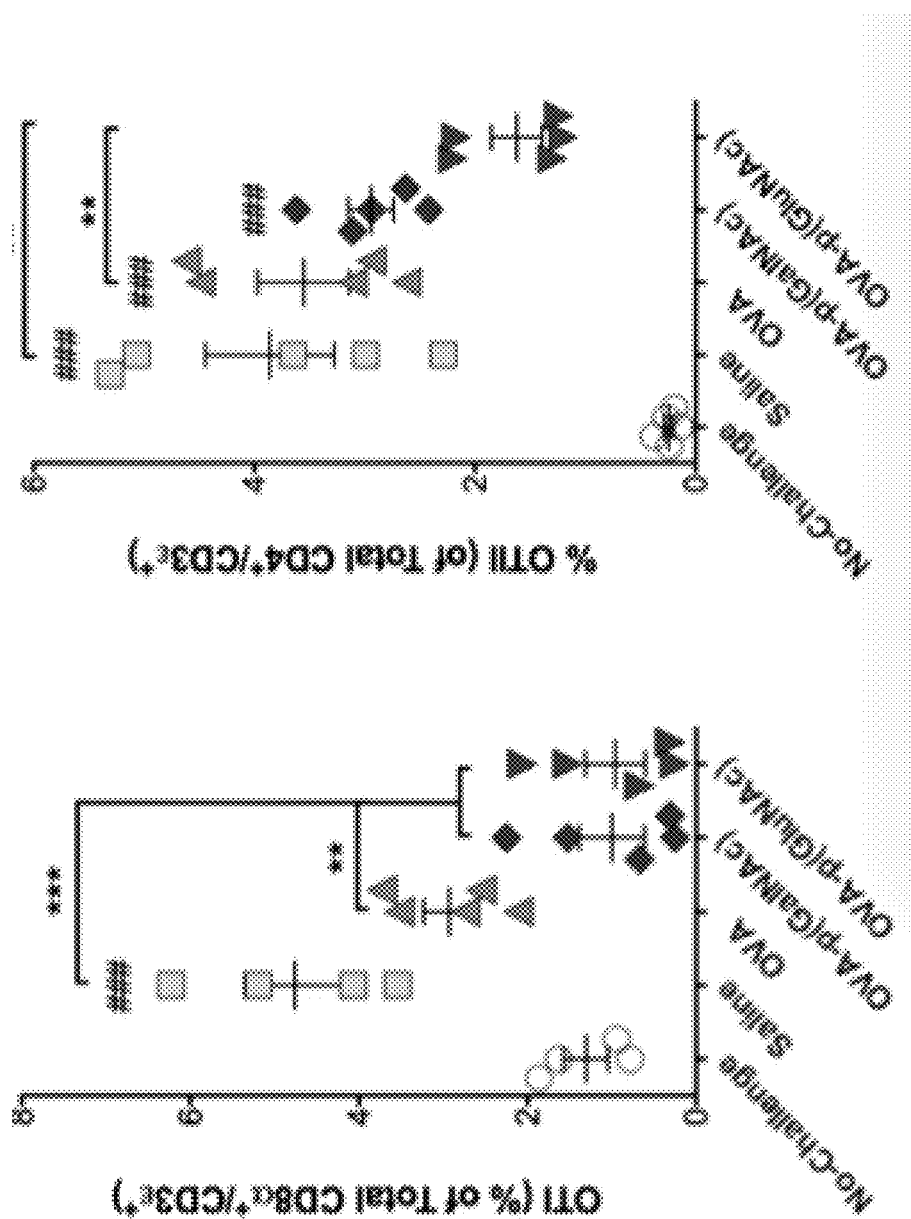

OVA-p(GalNAc) and OVA-p(GluNAc) Abrogate Antigen-Specific Immune Responses and Enrich Lymphoid Organs in Tregs In some embodiments, effective antigen-specific therapies capable of inducing lasting suppression of autoimmunity should induce tolerance in both the CD4$^+$ and CD8$^+$ T cell compartments as well as expand and maintain Tregs, which provide lasting protection. To determine the ability of OVA-glycopolymer conjugates to abrogate an antigen-specific immune response as well as augment the population of antigen-specific Tregs, OTI and OTII cells were adoptively transferred into C57BL/6 mice and then these animals were treated on day 1 and 7 with either saline, 10 μg of wt OVA, or 10 μg of OVA as OVA-p(GalNAc) or OVA-p(GluNAc) conjugates (FIG. 15A, FIG. 22). After 9 days, to allow for tolerization of the transferred T cells, the mice were challenged via an intradermal injection of OVA and lipopolysaccharide (LPS) into the footpads. Five days after antigen challenge, the immune response in the draining lymph nodes (dLNs) and spleen was analyzed to quantify the immune suppressive effects of each treatment. In this context, tolerance induction is marked by an attenuated T cell response and enrichment of antigen-specific Tregs.

Mice treated with OVA-p(GalNAc) and OVA-p(GluNAc) conjugates had dramatically fewer OTI and OTII T cells in the dLNs as compared to mice treated with saline or OVA (FIGS. 15B-E). For example, treatment with OVA-p(GalNAc) and OVA-p(GluNAc) resulted in a greater than 2- and 12-fold decrease in the percentage of OTI T cells, respectively, and a 2- and 6.5-fold decrease is OTII T cells, respectively, in the dLNs compared to OVA-treated mice. Furthermore, only mice treated with OVA-p(GalNAc) or OVA-p(GluNAc) conjugates had OTI and OTII T cell populations in the dLNs that were similar to mice that received the adoptive transfer of OTI and OTII cells, but were not challenged on day 14 (FIG. 15: "No-Challenge"). OVA-p(GalNAc) and OVA-p(GluNAc) conjugates were also able to decrease the percentage of OTI and OTII T cells in the spleen as compared to saline and OVA treated animals (FIG. 22). In addition to quantifying the percentage of OTI and OTII T cells in the dLNs, the effector function of lymph node-resident OTI and OTII T cells was accessed by characterizing the percentage of IFN-γ-producing cells. Mice treated with OVA-p(GalNAc) or OVA-p(GluNAc) had significantly fewer IFN-γ$^+$ OTI and IFN-γ$^+$ OTII T cells in the dLNs as a percentage of total OTI and OTII cells, respectively, versus animals treated with either OVA or saline (FIGS. 15F & G). Upon 4 days of in vitro restimulation with the CD8-dominant epitope SIINFEKL (SEQ ID NO: 104), lymphocytes isolated from the dLNs of mice treated with OVA-p(GalNAc) and OVA-p(GluNAc) produced 1.8- and 6-fold less INF-γ, respectively, compared to mice treated with OVA (FIG. 15H). Similarly, lymph node cells from mice treated with OVA-p(GalNAc) and OVA-p(GluNAc) that were restimulated with whole antigen produced 2- and 6.4-fold less INF-γ, respectively, as compared to restimulated cells from mice treated with OVA (FIG. 15I). Notably, lymphocytes from OVA-p(GluNAc)-treated animals that were restimulated with either SIINFEKL (SEQ ID NO: 104) or OVA produced significantly less IFN-γ than restimulated cells from OVA-p(GalNAc)-treated animals. Thus, not only did OVA-glycopolymer conjugates delete antigen-specific T cells, they also increased cellular inactivation in the remnant OTI and OTII T cell populations, a feature that is characteristic of several embodiments of the compositions disclosed herein.

Tregs are an immunosuppressive cell population that maintains immune homeostasis and are implicated in lasting suppression of autoimmunity. Five days after subcutaneous challenge, animals treated with OVA-p(GalNAc) and OVA-p(GluNAc) showed a more than 8- and 16-fold increase, respectively, in the percentage of OTII Tregs in the dLNs with respect to mice treated with saline (FIG. 15J). The percentage of antigen-specific Tregs were also elevated in spleens of animals treated with OVA-p(GalNAc) and OVA-p(GluNAc) with respect to animals treated with saline or OVA (FIG. 15K). Treatment with OVA-p(GluNAc) resulted in a significant increase in the percentage of OTII Tregs in the dLN compared to OVA-p(GalNAc)-treated animals. To elucidate the mechanism behind the increased Tregs in OVA-p(GalNAc) and OVA-p(GluNAc) treated animals, the IL-2 produced by splenocytes upon in vitro restimulation with whole antigen was measured. Low levels of IL-2 are necessary for the expansion and maintenance of functional Tregs. Treatment with both OVA-p(GalNAc) and OVA-p(GluNAc) resulted in splenocytes that produced a modicum of IL-2 that was significantly less than the IL-2 produced by splenocytes from mice treated with OVA or saline, but more than the IL-2 produced by splenocytes from mice that did not receive the antigen challenge (FIG. 15L). The elevated ratios of Tregs and lack of effector response generated by OVA-p(GalNAc) and OVA-p(GluNAc) suggests that these conjugates could provide lasting Treg-mediated immune regulation. In several embodiments, Treg-mediated immune regulation is characteristic of administration of the tolerance inducing compositions disclosed herein.

Modification of Antigens with Synthetic Glycosylations Induces Functional Tregs that are Necessary for Lasting Tolerance In the studies described above, treatment with either OVA-p(GalNAc) or OVA-p(GluNAc) resulted in antigen-specific tolerance. However, given the superior capacity of OVA-p(GluNAc) to limit pro-inflammatory cytokine production and augment Tregs in lymphoid tissues, the ability of antigen-p(GluNAc) conjugates to induce tolerogenic memory via functional Tregs that persist after treatment was tested. OTII T cells were adoptively transferred into mice on day 0, and then these mice were treated on days 1, 4, and 7 with either saline, 5.0 µg wt OVA, or 5.0 µg OVA as OVA-p(GluNAc) conjugate (FIG. 16A). To elucidate the role played by OVA-p(GluNAc)-induced Tregs in the establishment of lasting tolerance, half of the mice treated with OVA-p(GluNAc) were administered an i.p injection of 400 µg of αCD25 on day 15 (FIG. 16: "OVA-p(GluNAc)+ αCD25") to deplete or suppress the function of Tregs. On day 29, a second adoptive transfer of OTI and OTII T cells was performed on all mice. One day later, the mice were challenged with an intradermal injection of OVA and LPS and then analyzed 5 days later for an OVA-specific immune response in the dLNs and spleens. Given the absence of therapeutic intervention after the second adoptive transfer, any diminution in the immune response of the second set of adoptively transferred cells is the product of lasting tolerance produced by the treatments on days 1, 4, and 7.

Figure 23:
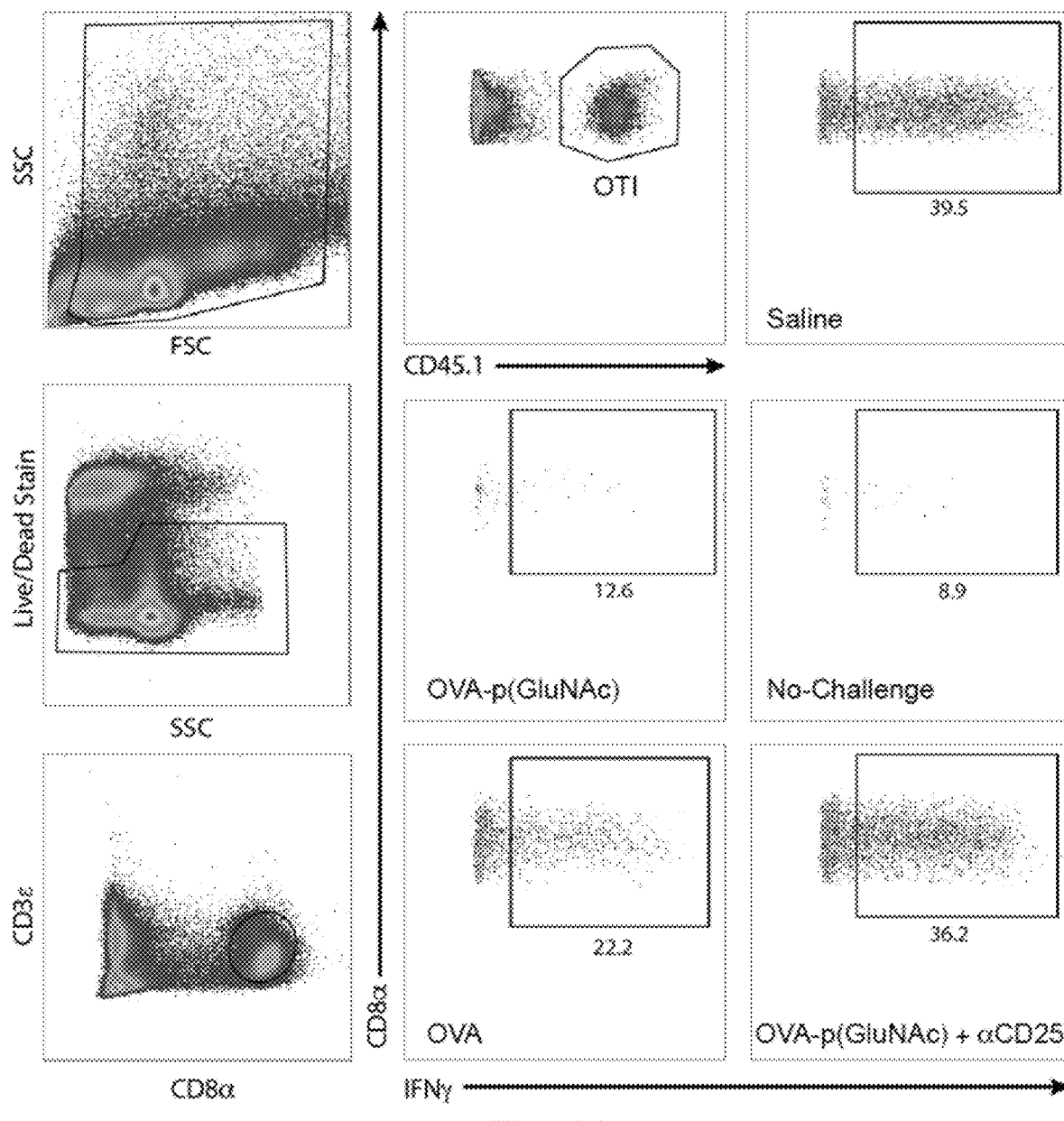
FIG. 23. OVA-p(GluNAc) induces tolerogenic memory in the CD8α+ T-cell compartment. Gating strategy used to determine the % of OTI T-cells in the draining lymph nodes of animals treated as described in FIG. 16 & FIG. 17. Representative plots of % IFN-γ+ OTII cells in the draining lymph nodes of animals treated as described in FIG. 4 after 6 h antigen-specific restimulation.
Figure 24:
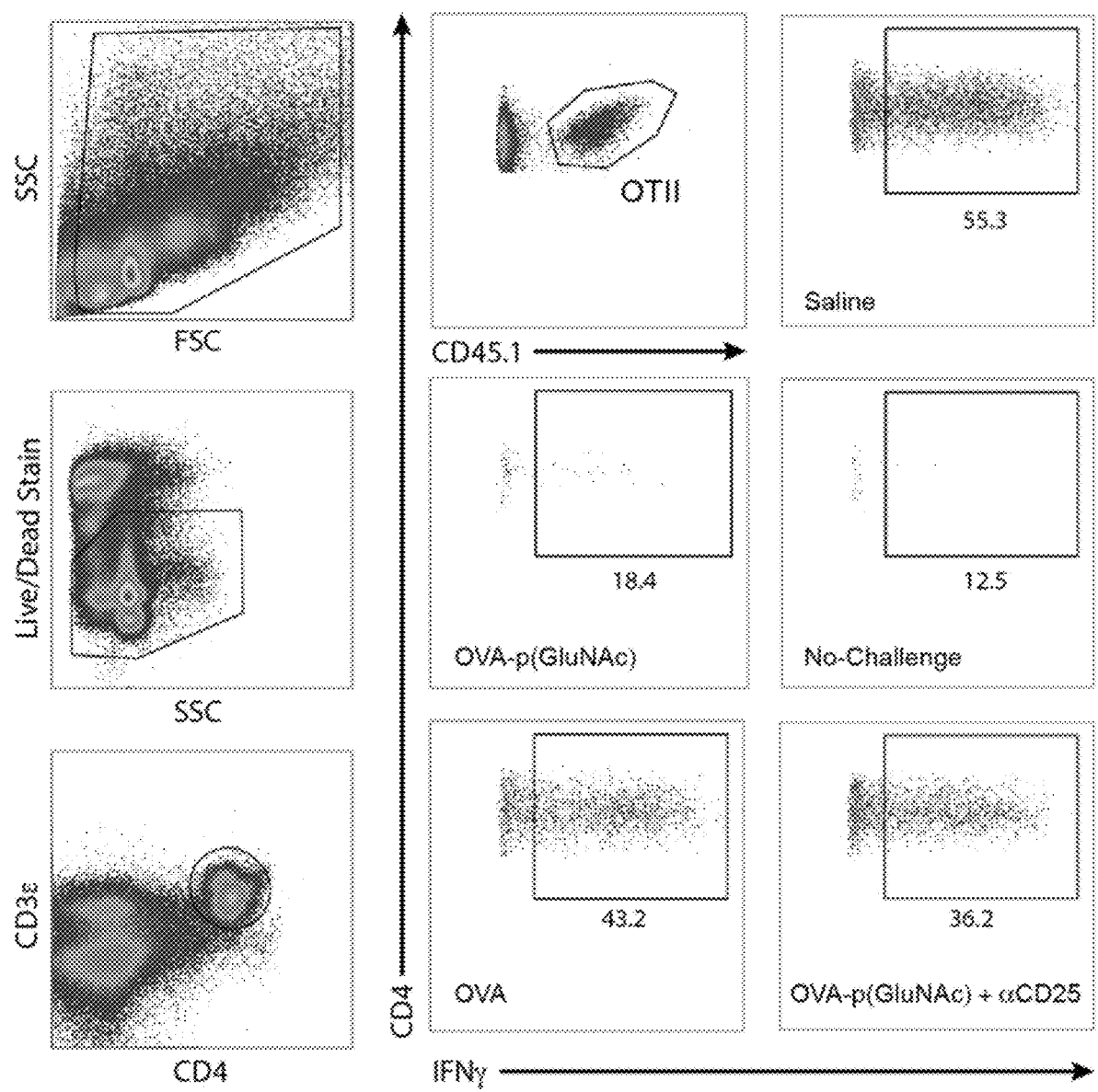
FIG. 24. OVA-p(GluNAc) induces tolerogenic memory in the CD4+ T-cell compartment. Gating strategy used to determine the % of OTII T-cells in the draining lymph nodes of animals treated as described in FIG. 16 & FIG. 17. Representative plots of % IFN-γ+ OTII cells in the draining lymph nodes of animals treated as described in FIG. 4 after 6 h antigen-specific restimulation.
Figure 25:
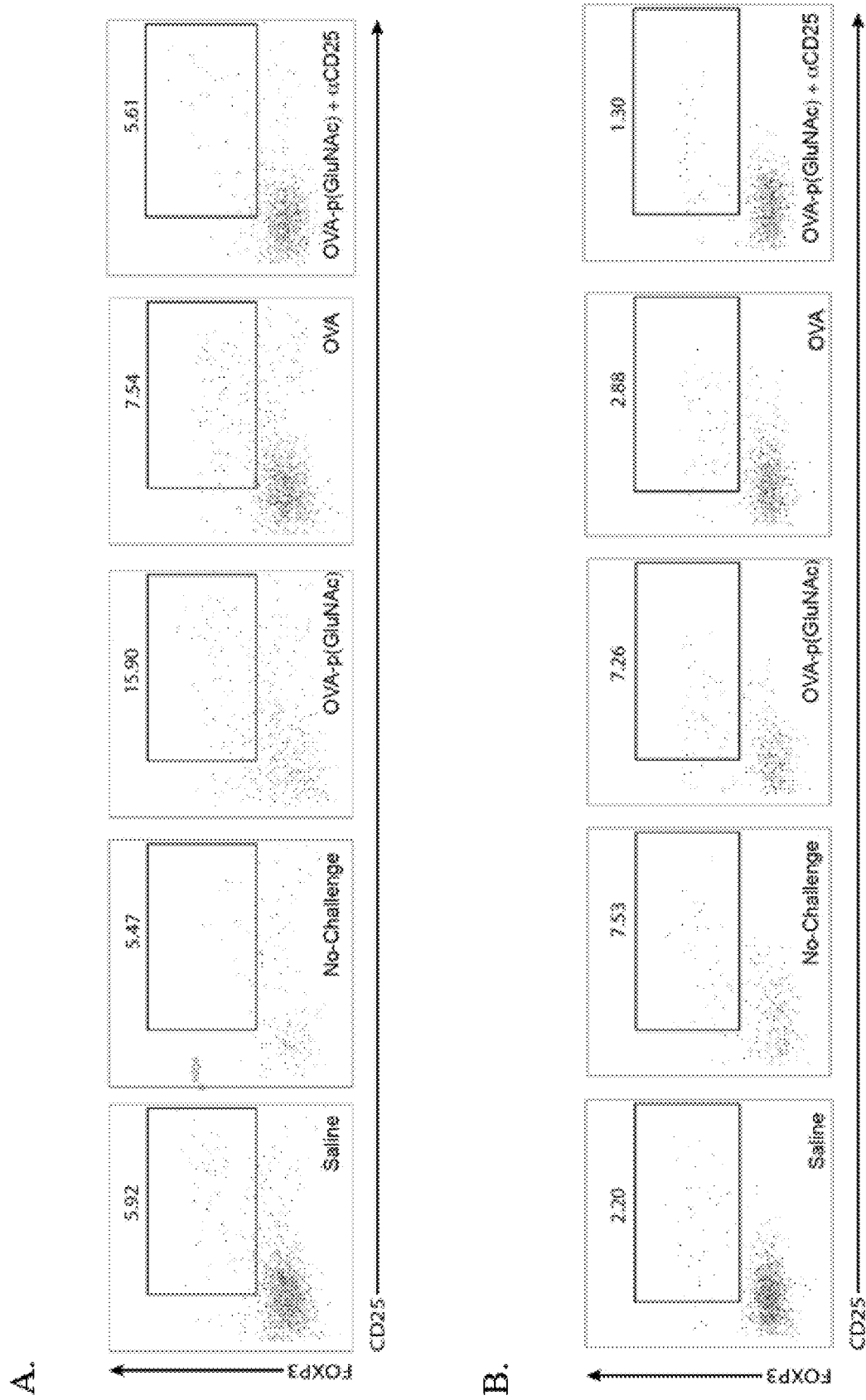
FIG. 25. OVA-p(GluNAc) enriches the draining lymph nodes in antigen specific Tregs. (A) Representative flow cytometry gating of CD25$^+$FOXP3$^+$ OTII T-cells in the draining lymph nodes of animals treated as described in FIG. 16A. (B) Representative flow cytometry gating of CD25$^+$ FOXP3$^+$ OTII T-cells in the draining lymph nodes of animals treated as described in FIG. 17.
Figure 26:
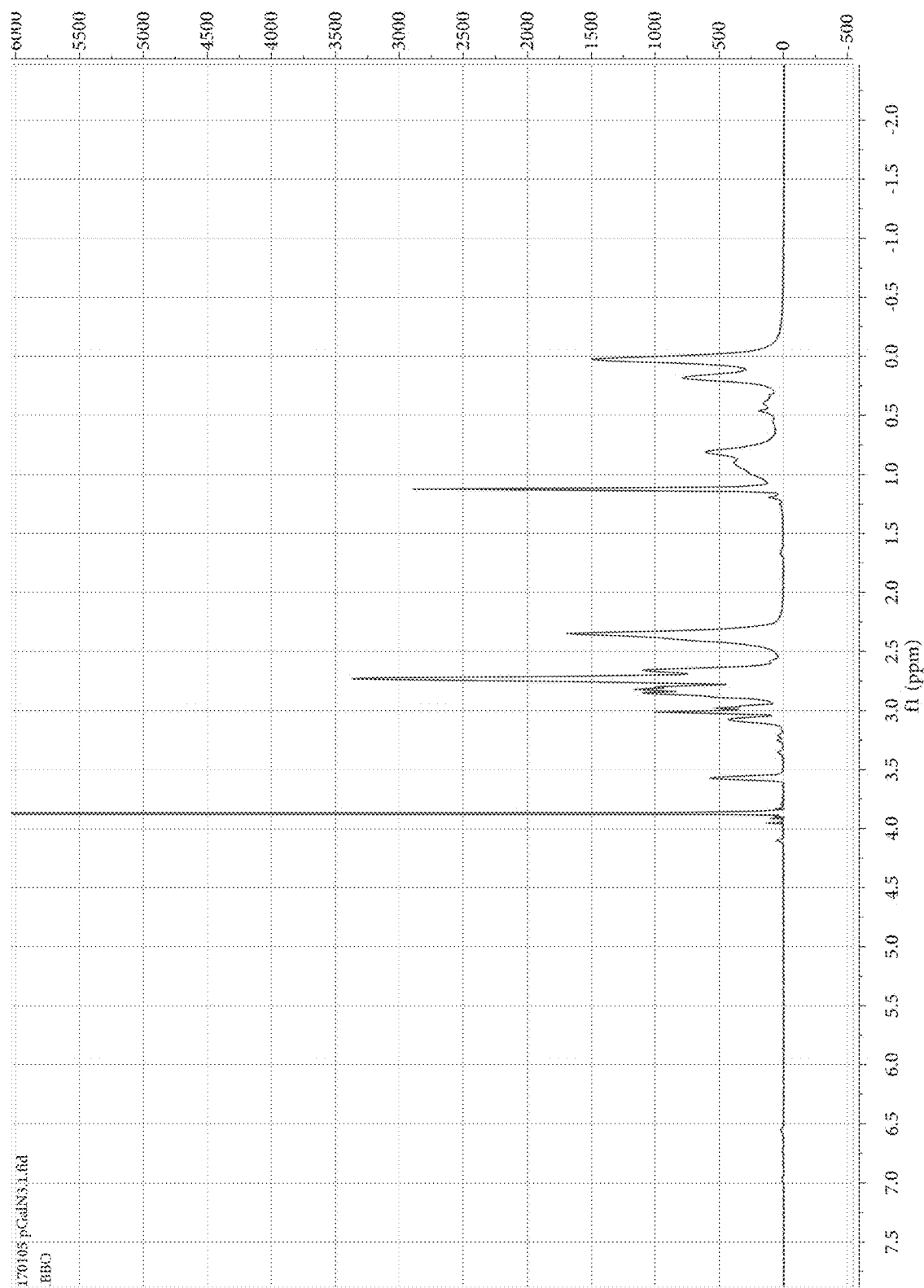
FIG. 26. Proton NMR spectra of p(GalNAc) as shown in FIG. 13A.
Figure 27:
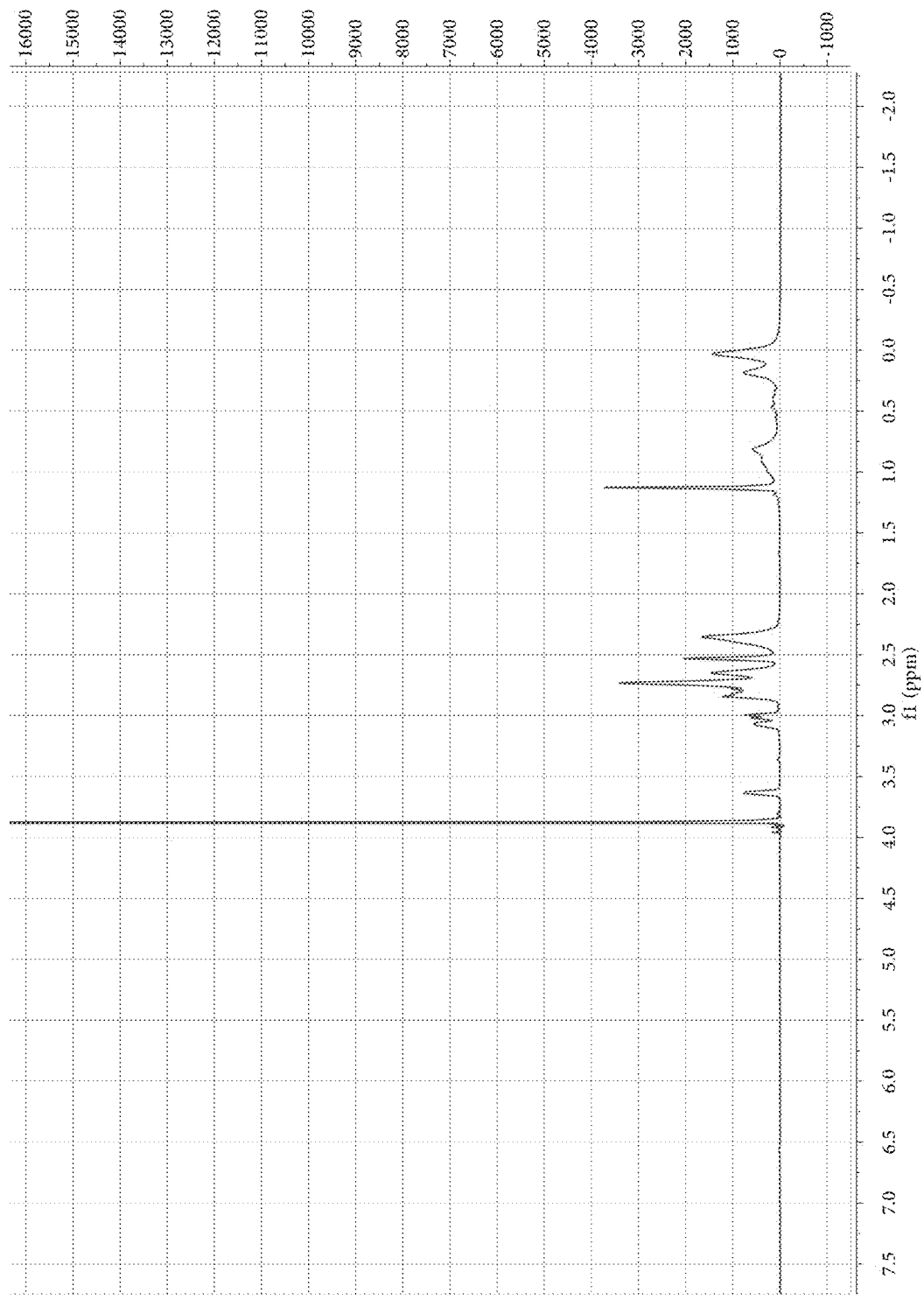
FIG. 27. Proton NMR spectra of p(GluNAc) as shown in FIG. 13A.
Figure 29:
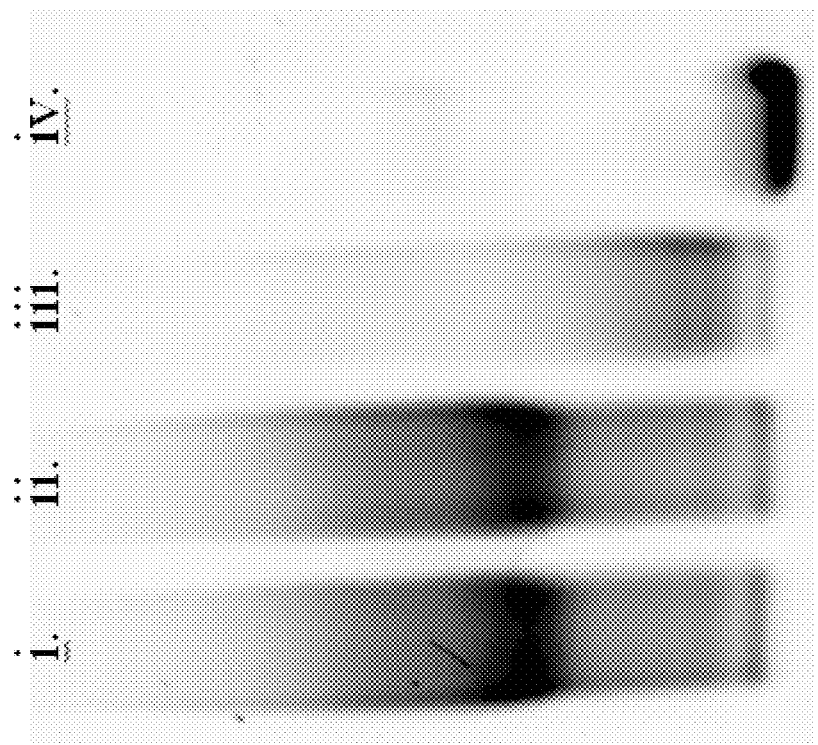
FIG. 29. Gel electrophoresis analysis of BCN OVA-p(GluNAc), BCN OVA-p(GalNAc), OVA-Linker, and OVA. i. OVA-p(GluNAc) before SEC, ii. OVA-p(GalNAc) (as shown in FIG. 13A) before SEC, iii. OVA-self-immolative linker conjugate, iv. OVA.

Analysis of OTII Tregs in the dLNs and spleen on day 35 showed that animals treated with OVA-p(GluNAc) on days 1, 4, and 7 had significantly higher percentages of OTII Tregs in the dLNs and spleens as compared to animals treated with saline, OVA, or OVA-p(GluNAc)+αCD25 (FIGS. 16B & C, FIG. 23-25). Given that no Treg-inducing therapies were administered after day 29, this increase in OTII Tregs in OVA-p(GluNAc)-treated mice as compared to OVA and saline treated mice is the result of OVA-p(GluNAc)-mediated Treg induction in the OTII T cell population that was transferred on day 0. Administering αCD25 subsequent to treatment with OVA-p(GluNAc) was sufficient to eliminate the increased percentage of Tregs in the lymphoid tissues achieved by OVA-p(GluNAc).

Analysis of the OTI and OTII-mediated immune response to antigen challenge demonstrated the functionality of OVA-p(GluNAc)-induced Tregs in the establishment of lasting tolerance. For example, five days after antigen challenge, mice treated with OVA-p(GluNAc) had 37- and 21-fold fewer OTI T cells in the dLNs as compared to animals treated with saline or OVA, respectively (FIG. 16D, FIG. 23). In addition to decreased numbers of OTI T cells in the dLNs, OVA-p(GluNAc) also resulted in an attenuation in the effector function of lymph node-resident OTI T cells, as evidenced by the contraction in IFN-γ$^+$ OTI T cells in the SIINFEKL(SEQ ID NO: 104)-restimulated lymph node cell population (FIG. 16E). Analogous results were also obtained in the CD4$^+$ T cell compartment, where animals treated with OVA-p(GluNAc) had a 9- and 6-fold decrease in the percentage of OTII T cells in the dLNs relative to animals treated with saline or OVA, respectively (FIG. 16F, FIG. 24). Upon restimulation with whole antigen, lymphocytes from the dLNs of mice treated with OVA-p(GluNAc) had fewer INF-γ$^+$ OTII T cells than the dLNs of mice treated with OVA or saline (FIG. 16G). Contrary to that observed in mice treated with OVA-p(GluNAc) alone, mice treated with OVA-p(GluNAc)+αCD25 experienced a robust OTI- and OTII-mediated immune response after antigen challenge. On day 35, mice treated with OVA-p(GluNAc)+αCD25 had OTI and OTII T cells populations in the dLNs that were comparable to those from animals treated with saline. Furthermore, αCD25 administration eradicated the suppression of OTI and OTII effector function generated by OVA-p(GluNAc) (FIGS. 16E & G). Indeed, depleting Tregs in OVA-p(GluNAc)-treated animals abrogated the lasting tolerance induced by OVA-p(GluNAc). OVA-p(GluNAc) produces CD25$^+$ regulatory T cells in the endogenous T cell compartment that mediate lasting tolerance To determine if OVA-p(GluNAc) could establish lasting tolerance via the induction of endogenous T cells with regulatory function, naïve mice were treated on days 1, 4, and 7 with saline, 5.0 µg wt OVA, or 5.0 µg OVA as OVA-p(GluNAc) conjugate (FIG. 17A). As in the previous study, half of the mice treated with OVA-p(GluNAc) were administered an i.p. injection of 400 µg of αCD25 on day 15 to mitigate the tolerance induced by CD25$^+$ cells. On day 29, all mice received an adoptive transfer of OTI and OTII cells, and then were challenged the following day with intradermal injections of OVA and LPS into the footpads. Five days after the challenge, the OVA-specific immune response in the dLNs of each animal was assessed via flow cytometry.

OVA-p(GluNAc) was able to institute lasting tolerance that was mediated by endogenous CD25$^+$ T cells with regulatory function. Treating animals with OVA-p(GluNAc) on days 1, 4, and 7 significantly reduced the percentage of OTI and OTII T cells in the dLNs 5 days after OVA+LPS challenge (FIGS. 17B & C, FIG. 23-25). Additionally, animals treated with OVA-p(GluNAc) had more than 4- and 2-fold fewer OTI T cells and more than 3-fold fewer OTII T cells in their dLNs as compared to animals treated with saline or OVA, respectively. Animals that were treated with OVA-p(GluNAc) and then αCD25 had significantly more OTI and OTII T cells compared to animals treated with OVA-p(GluNAc) alone. Upon restimulation with SIINFEKL (SEQ ID NO: 104) or whole antigen, lymphocytes from the dLNs of mice treated with OVA-p(GluNAc) had reduced percentages of INFγ$^+$ OTI T cells (FIG. 17D) and INFγ$^+$ OTII T cells (FIG. 17E) with respect to mice treated with saline, OVA, and OVA-p(GluNAc)+αCD25. These results demonstrate that OVA-p(GluNAc) treatment results in endogenous CD25$^+$ cells with regulatory function that persist in the face of antigen-specific challenge, and are necessary for lasting immune regulation.

Figure 28:
FIG. 28. Gel electrophoresis analysis of p31-p(GluNAc) and p31-p(GalNAc). i. p31, ii. p31-p(GluNAc), iii. p31-p(GluNAc)+β-mercaptoethanol, iv. p31-p(GalNAc) (as shown in FIG. 13A).

Engineering of Islet β-Cell Auto-Antigen with Tolerogenic Glycosylations Induces Protection from CD4$^+$ T Cell Mediated Diabetes To test if auto-antigen-p(GluNAc) conjugates could tolerize pathogenic T cells and thus prevent disease onset in a model of T cell mediated autoimmunity, the BDC2.5 T cell adoptive transfer model of type-1 diabetes was used. In this model, transgenic CD4$^+$ T cells that carry the BDC2.5 T cell receptor, which is reactive against islet β cells, are first activated ex vivo with the peptide mimotope p31, and then transferred into non-obese diabetic/severe combined immunodeficiency (NOD/scid) mice. NOD/scid mice that received an i.v. infusion of activated BDC2.5 splenocytes (3.0×10$^5$) were treated 12 h and 4 days later with either saline, 0.6 µg of p31 peptide, or 0.6 µg of p31 as p31-p(GluNAc) conjugate (FIG. 18A, FIG. 28). Activated BDC2.5 T cells are extremely diabetogenic in NOD/scid animals, and thus animals treated with either saline or p31 developed blood glucose concentrations indicative of diabetes (i.e. blood glucose >250 mg/dL) as soon as 7 days (FIG. 18B). After 10 d, all animals treated with p31 or saline had diabetes-indicative blood glucose levels; however, all animals treated with p31-p(GluNAc) maintained healthy blood glucose levels for the duration of the experiment. Thus, demonstrating the capability of antigen-p(GluNAc) conjugates to diminish the pathogenic effector function of activated auto-reactive T cells.

p31-p(GluNAc) Induces Tregs from Auto-Reactive T Cells that are Necessary for Lasting Protection from Autoimmunity To show that p31-p(GluNAc) could expand auto-reactive Tregs in vivo, an adoptive transfer of naïve BDC2.5 T cells into NOD/scid mice was performed, then subsequently these animals were treated 1 and 4 days later with either 0.6 µg of p31, or 0.6 µg of p31 as p31-p(GluNAc) conjugate (FIG. 18A). On day 8, the splenic population of BDC2.5 Tregs was determined by flow cytometry. Treatment with p31-p(GluNAc) conjugates resulted in a significant increase in the number of BDC2.5 Treg cells in the spleen with respect to animals treated with p31 (FIG. 18C).

Next, whether the increased population of Tregs produced by p31-p(GluNAc) conjugates was sufficient to induce lasting protection from autoimmunity was tested. An adoptive transfer of naïve CD4$^+$ BDC2.5 cells (3.0×10$^5$) into NOD/scid mice was performed and then these mice were treated with either saline, 0.6 µg of p31, or 0.6 µg of p31 as p31-p(GluNAc) conjugate at 1 and 4 days after T cell adoptive transfer (FIG. 18D). While not as diabetogenic as activated BDC2.5-T cells, naïve BDC2.5 T cells are activated in vivo as a result of pancreatic antigen, resulting in delayed diabetes onset. Only p31-p(GluNAc) treatment was able to protect against the diabetes caused by the adoptive transfer of naïve BDC2.5 T cells (FIG. 18E). All mice treated with saline or p31 (black and red lines in FIG. 18E) developed hyperglycemia by day 18 and were removed from the study. However, mice treated with p31-p(GluNAc) (blue and green lines in FIG. 18E) remained normoglycemic after day 18 and were subsequently used to examine the necessity of p31-p(GluNAc)-induced Tregs in the maintenance of tolerogenic memory.

On day 15, half of the mice that had been treated with p31-p(GluNAc) conjugates on days 1 and 4 were administered an i.p injection of 400 µg of αCD25 (FIG. 18E: "p31-p(GluNAc)+αCD25"). On day 21, 14 days after the final treatment, all remaining mice with normal blood glucose levels (i.e. all animals treated with p31-p(GluNAc) on days 1 and 4) were challenged with an adoptive transfer of in vitro p31-activated BDC2.5 T cells (2.0×10$^5$). Importantly, after the second adoptive transfer, the mice received no subsequent treatment. All mice treated with p31-p(GluNAc) alone remained diabetes-free for 20 days after being challenged with activated BDC2.5 T cells. Of note, 75% of the mice treated with p31-p(GluNAc) remained diabetes free on day 60 of the experiment, 39 days after being challenged with activated BDC2.5 T cells. However, mice treated with both p31-p(GluNAc) and then αCD25 on day 15 began to developing diabetes 10 days after receiving the infusion of activated BDC2.5 cells, and all mice in this group developed hyperglycemia by day 38. The inability of αCD25 treated animals to suppress the effector function of activated BDC2.5 T cells underscores the role played by p31-p(GluNAc)-induced Tregs in protection from autoimmunity.

DISCUSSION

A major obstacle in the development of a disease-modifying treatment for autoimmunity is the inability to ablate autoreactive effector T cells and generate functional regulatory T cells that persist after the initial treatment. Cell-based therapies using engineered Tregs are effective in treating various animal models of autoimmunity and are currently under clinical investigation. However, Treg-based therapies are limited by inadequate techniques for the ex vivo expansion of antigen-specific Tregs and the difficulty of isolating and manipulating Tregs in a clinical setting. An alternative approach would be the induction or expansion of functional Tregs in vivo via innate mechanisms. Other strategies for liver-mediated Treg induction based on lentiviral vectors or nanoparticle-mediated antigen delivery have recently emerged. Lentiviral-mediated expression of insulin B chain in hepatocytes protects mice from experimental T1D, for example. However, the inability to control antigen load in hepatocytes via lentiviral-mediated expression may limit the clinical viability of this approach, given that low levels of antigen presentation by hepatocytes may result in effector, not tolerogenic, T cell responses. Nanoparticle-based platforms, with either surface bound or encapsulated antigens, have been explored to induce Tregs by passively accumulating in either KCs or LSECs. However, by targeting only a subset of HAPCs, these platforms do not take full advantage of the liver's tolerogenic machinery. Furthermore, these nanoparticles are composed of non-biodegradable components or polymers that degrade into acidic products that could damage encapsulated antigens or activate targeted cells. Here, several embodiments of a clinically-viable strategy that harnesses the full capabilities of the liver's innate tolerogenic prowess for the induction of antigen-specific tolerance is demonstrated. By conjugating antigens to which tolerance is desired to linear polymeric glycosylations, the amount of biomaterial used to target HAPCs is lessened, and thus the potential for biomaterial-initiated cell activation or antigen-disruption is reduced. The small size (i.e. effectively on the same scale as a typical immunoglobulin) of antigen-p(GluNAc) and antigen-p(GalNAc), as opposed to antigen-loaded nanoparticles, allows the direct targeting of hepatocytes, which only have broad access to species that can pass through the ~100 nM diameter fenestrations in the sinusoidal endothelium. Thus, according to several embodiments the polymer-antigen compositions disclosed herein present an unexpectedly improved effect, in many cases with an overall reduced dose or load of the therapeutic composition being required.

Figure 21A:
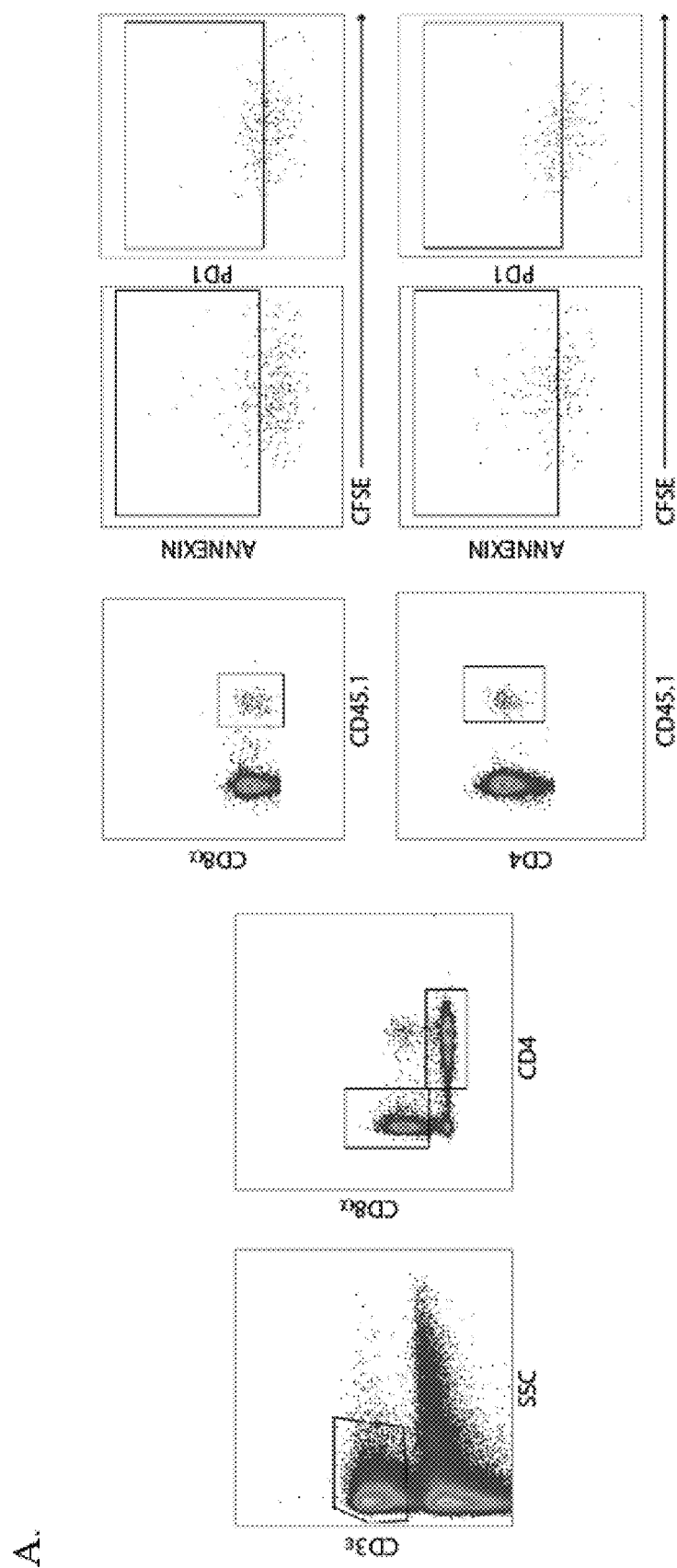
FIG. 21A-B. OVA-p(GluNAc) and OVA-p(GalNAc) conjugates improve antigen presentation by HAPCs and induce a tolerogenic phenotype in OTI and OTII T cells. CFSE-labeled OTI and OTII cells were transferred into mice, then mice were treated with wt OVA, OVA-p(GalNAc), or OVA-p(GluNAc) on the next day. 5 days after adoptive transfer of OTI and OTII cells, the spleens of animals were harvested and stained with antibodies for CD8α, CD45.1, CD3ε, PD-1, and CD4. Surface staining for annexin V was performed to capture early signals for apoptosis. (A) Gating strategy used to determine the % of OTI and OTII T-cells in the spleens of animals treated with WT OVA, OVA-p (GalNAc), or OVA-p(GluNAc). Representative plots of CSFE, annexin V, and PD-1 staining on lymphocytes taken from the spleens of mice treated with OVA-p(GluNAc) as described for FIG. 2 in the main text. Percentage of annexin V+ OTI and OTII T cells in the spleens of animals treated as in FIG. 2. (B) Data represented as mean±sem. Statistical differences were determined by one-way ANOVA using Bonferroni's post hoc test (*p≤0.05, p≤0.01, *p≤0.005). Pound signs represent statistical significance respective to No-Challenge group.
Figure 21B:
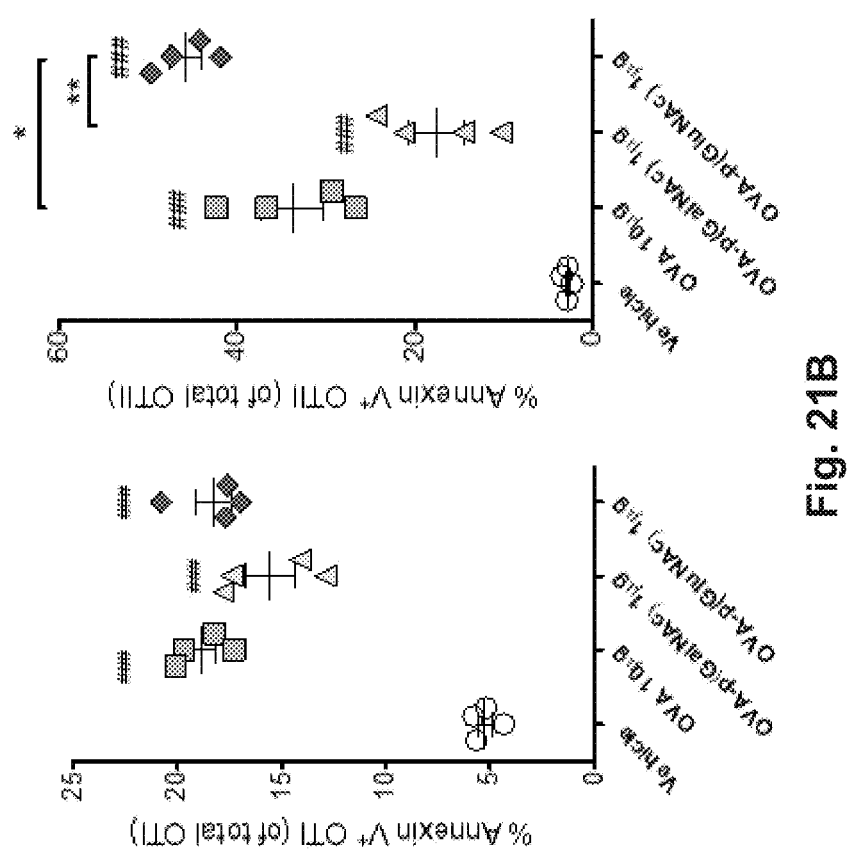

In some embodiments, a platform that targets antigens to HAPCs via tolerogenic pathways and thereby harness the un-tapped potential of the liver's tolerance effect is leveraged to achieve antigen-specific immune tolerance. Although antigen uptake via NAc-galactosamine- or NAc-glucosamine-binding C-type lectins on HAPCs has not be identified as an innate tolerogenic pathway for antigen uptake, antigen endocytosis via specific C-type lectins, and not others, by peripheral non-hepatic dendritic cells is believed to be naturally tolerogenic. The present disclosure demonstrates that OVA-conjugated to p(GalNAc) or p(GluNAc) elicits a more robust immune suppressive state than wt OVA, which bears native mannose residues. Hepatic mannose-binding receptors endocytose wt OVA and have been implicated in the removal of apoptotic debris. Accordingly, wt OVA was taken up by HAPCs (FIG. 13C), and did generate a mild tolerogenic effect on OTI and OTII T cells (FIG. 15), but did not expand Tregs or provided lasting tolerance (FIGS. 15-17). The superior ability of p(GalNAc) and p(GluNAc) (or other glucose/galactose-based moieties) to target the liver is one explanation for their enhanced tolerogenic effect. Indeed, a five-fold greater dose of wt OVA than OVA-p(GalNAc) or OVA-p(GluNAc) is required to generate a commensurate level of hepatic antigen-load (FIG. 1C). However, OVA-p(GalNAc) and OVA-p(GluNAc) induce more OTI and OTII T cell proliferation and an equivalent amount of apoptosis compared to a ten-fold greater dose of wt OVA, which would presumably produce an equivalent, if not greater, hepatic antigen-load (FIG. 14D, FIG. 21). These results strongly suggest that under steady-state conditions, antigen uptake via hepatic NAc-galactosamine- and NAc-glucosamine-binding lectins, versus mannose-binding receptors, results in more efficient hepatic antigen presentation via pathways that inherently induce tolerogenic T cell priming.

Given that, at an equivalent dose, p(GalNAc) and p(GluNAc) generate similar levels of hepatic antigen-load, the phenotypic differences observed between T cells from mice treated with OVA-p(GalNAc) and OVA-p(GluNAc) is likely a function of the specific HAPCs targeted by each conjugate. In several embodiments, the specific HAPCs are targeted depending, for example, on the type of antigen to which tolerance is desired, and/or the severity of an adverse reaction that a subject has had (or is expected to have) to an antigen. OVA-p(GluNAc) conjugates targeted LSECs, KCs, hepatocytes, and DCs, and OVA-p(GalNAc) conjugates targeted LSECs and hepatocytes. Due to their unencumbered contact with liver sinusoidal blood flow and expression of various C-type lectins, LSECs were the HAPC most efficiently targeted by both p(GalNAc) and p(GluNAc) conjugates. LSECs mediate $CD8^+$ and $CD4^+$ T cell suppression via LSEC-induced IL-10(46) and PD-1/PD-L1 signaling. Additionally, in the presence of KC-derived TGF-β, LSECs are efficient inducers of antigen-specific Tregs, which were elevated in the lymph nodes and spleens of mice treated with either OVA-p(GalNAc) or OVA-p(GluNAc) (FIGS. 15J & K). Hepatocytes express multiple NAc-galactosamine-binding receptors, including the asialoglycoprotein receptor (ASGPr), as well as various other receptors that bind NAc-glucosamine. For this reason, hepatocytes were also a major target for both p(GalNAc) and p(GluNAc) conjugates. Upon uptake of exogenous antigen, hepatocytes are capable of suppressing $CD8^+$ T cells via PD-1/PD-L1 signaling and thus prevent cytotoxic T cell responses against allogenic skin grafts. While p(GalNAc) is readily taken up by hepatic DCs, only p(GluNAc) was capable of targeting DCs relative to wt OVA. Hepatic DCs exhibit a suppressive phenotype with barely detectable levels of co-stimulatory molecules and elevated expression of IL-10. As a consequence, $CD8^+$ and $CD4^+$ T cells educated by non-activated hepatic DCs lack effector function. Like LSECs, murine KCs express the NAc-glucosamine-receptor LSECtin and are capable of Treg induction in response to exogenous antigen. Accordingly, the increased capacity of OVA-p(GluNAc) to target both LSECs and KCs correlated with an elevated percentage of antigen-specific Tregs in comparison to OVA-p(GalNAc). Thus, in several embodiments, compositions that favor the targeting of one or more of LSEC and/or KCs are preferred.

The capability of OVA-p(GalNAc) and OVA-p(GluNAc) to increase antigen-load in specific HAPCs is a contributing factor in their superior ability to induce antigen-specific tolerance. However, increased antigen presentation by some HAPCs does not necessarily correspond to enhanced tolerance. High levels of antigen presentation by LSECs results in elevated $CD8^+$ T cells IL-2 production that blocks LSEC-mediated $CD8^+$ T cell tolerance. Analysis of IL-2 production by antigen-restimulated splenocytes from OVA-p(GalNAc) and OVA-p(GluNAc) treated mice showed a slight increase in IL-2 compared to mice that did not receive an antigen challenge, but a multi-fold decrease in IL-2 production compared to restimulated splenocytes from OVA treated animals (FIG. 15L). Interestingly, low-dose IL-2 reverses diabetes in NOD mice via the expansion of endogenous Tregs and is currently being investigated clinically as a treatment for autoimmunity. The low levels of IL-2 produced by splenocytes from OVA-p(GalNAc)- and OVA-p(GluNAc)-treated mice coincided with an increase in the percentage of Tregs in these animals (FIGS. 15J-K), with the elevated IL-2 production mediate by OVA-p(GluNAc) corresponding to a greater percentage of Tregs than in OVA-p(GalNAc)-treated animals. Thus, antigen uptake by HAPCs via C-type lectins that bind p(GalNAc) and p(GluNAc) results in a population of T cells that maintain a goldilocks level of IL-2 production that is not too high, as to cause activation, and not too low, thus promoting Treg development.

Efficacy with p(GluNAc) conjugates was observed in the studies of deletion, anergy, and Treg augmentation (FIGS. 14 & 15), and thus the ability of p(GluNAc) to provide lasting tolerance and prevent autoimmunity was studied. Mice that received an adoptive transfer of OTII T cells and then treated with OVA-p(GluNAc), but not wt OVA, were able to eliminate an OTI and OTII T cell-mediated immune response that was initiated 23 days after the final treatment (FIG. 16A). Given that the half-life of antigens bearing GluNAc residues in the blood is less than an hour, it is unlikely that the lasting antigen-specific immune suppression generated by OVA-p(GluNAc) is a function of lingering antigen 23 days after the final treatment. On the contrary, the tolerogenic memory elicited by OVA-p(GluNAc) was correlated with an increase in the percentage of OTII Treg cells in the dLNs and spleen (FIGS. 16D & F). To support this interpretation, OVA-p(GluNAc) treated mice were administered αCD25, which has been widely used to examine the contribution of Treg cells in various autoimmunity models. Depletion or inactivation of Tregs via αCD25 in OVA-p(GluNAc)-treated mice nullified the ability of these mice to suppress an OVA-specific immune response, confirming the necessity of OVA-p(GluNAc)-induced Tregs in the establishment of lasting antigen-specific immune suppression. Importantly, the initial infusion of OTII T cells before the administration of OVA-p(GluNAc) was not necessary for the development of lasting tolerance. Again, inactivation of the $CD25^+$ T cell compartment of animals treated with OVA-p(GluNAc) abolished lasting tolerance in these mice, indicating that the tolerogenic memory generated by OVA-p(GluNAc) was a function of OVA-p(GluNAc)-induced endogenous $CD25^+$ T cells with regulatory function. In other words, while the possibility that OVA-p(GluNAc) also induces other subsets of endogenous $CD25^+FOXP3^-$ T cells that contribute to lasting immune regulation exists, functional $CD25^+$ T cells could be expanded with regulatory function from sparse subpopulations of endogenous antigen-specific T cells that mediated lasting tolerance.

The therapeutic potential of antigen-p(GluNAc) conjugates was then confirmed in an aggressive experimental model of T1D that mimics the auto-reactive T cell mediated β-cell destruction that is at the center of the etiology of human type T1D. Indeed, administration of p31-p(GluNAc) conjugates in mice that received an adoptive transfer of activated BDC2.5 splenocytes prevented diabetes onset, validating the functional immune suppression of antigen-experienced T cells by p(GluNAc) conjugates (FIG. 18B). Additionally, p31-p(GluNAc) treatment was able to induce BDC2.5 Tregs from naïve BDC2.5 $CD4^+$ T cells, which were necessary to suppress the effector function of ex vivo activated BDC2.5 splenocytes (FIGS. 18C & E).

In this study, a novel platform to target antigens to HAPCs for the induction of antigen-specific tolerance and Treg-mediated tolerogenic memory as a potential treatment for autoimmune disease is presented. Due to the versatility and mild conditions of the chemistry used to conjugate antigens to p(GalNAc) and p(GluNAc), this strategy can be used with any protein or peptide antigen that contains a native or engineered primary amine. It is believed that antigen-p(GalNAc) and especially antigen-p(GluNAc) conjugates, as disclosed herein, have the potential to be a disease-modifying treatment for a variety of T cell-mediated autoimmune disorders.

Materials and Methods:

Animals. All studies were carried out in accordance with procedures approved by the Swiss Veterinary Authority and the EPFL Centre d'Application du Vivant. Female CD45.2$^+$ mice (Harlan) aged 8-13 weeks were used for in vivo adoptive transfer studies. To generate CD45.1+ OTI and OTII mice, C57BL/6-Tg (TcraTcrb) 1100 Mjb (OTI) and C57BL/6-Tg(TcraTcrb)425Cbn/Crl (OTII) mice (Jackson Laboratories) were crossed with C57BL/6-Ly5.1 (Charles River) and bred in specific pathogen-free (SPF) conditions at EPFL. Diabetes studies were carried out on female NOD/scid mice (Charles River). NOD/BDC2.5 mice were bred in specific pathogen-free (SPF) conditions at EPFL.

Targeting hepatic antigen presenting cells. C57BL/6 mice were treated via tail vein injection with fluorescently labeled OVA in the form of free OVA (OVA$_{649}$), OVA$_{649}$-p(GalNAc), OVA$_{649}$-p(GluNAc), OVA$_{750}$, OVA$_{750}$-p(GalNAc), or OVA$_{750}$-p(GluNAc). After 3 h, the livers were perfused and the livers and spleens of animals treated with OVA$_{750}$, OVA$_{750}$-p(GalNAc), or OVA$_{750}$-p(GluNAc) were harvested and analyzed for total fluorescents using an IVIS® Spectrum in vivo imaging system (PerkinElmer). The livers from mice treated with OVA$_{649}$, OVA$_{649}$-p(GalNAc), OVA$_{649}$-p(GluNAc) were then enzymatically digested and processed into single cells suspensions. The hepatocytes were isolated from the cell suspensions by 3 successive centrifugations at 50 g for 5 min. The remaining hepatic cells were isolated via density gradient centrifugation using Percoll. The isolated cell subsets were stained for linage specific markers then analyzed via flow cytometry for the presence of OVA in the APC channel.

OTI and OTII T-cell isolation and adoptive transfer. CD8$^+$ and CD4$^+$ T-cells from the spleens and draining lymph nodes of female CD45.1$^+$ OTI and OTII mice were isolated using the appropriate CD8$^+$ or CD4$^+$ T-cell magnetic bead isolation kit (Miltenyi Biotec), per the manufacture's protocol. For proliferation studies, isolated OTI and OTII T-cells were resuspended in PBS and labeled with 1.0 µM CFSE (Invitrogen) for 6 minutes under constant agitation at room temperature. Labeled cells were washed with PBS. Both labeled and un-labeled OTI and OTII T-cells were resuspended in Isocove's modified Dulbecco's medium (IMDM) for i.v. administration. For adoptive transfer experiments, 150 µL of cell suspension containing OTI and OTII T-cells was injected via the tail vein into female CD45.2$^+$ C57BL/6 mice.

Short-term OTI and OTII T-cell phenotype study. 6.0×10$^5$ OTI and 6.0×10$^5$ OTII T-cells, isolated and CSFE-labeled as described above, were adoptively transferred into female CD45.2$^+$ C57BL/6 mice via tail vein injection. On the following day, the mice were treated with saline (n=4), or 1.0 µg OVA as wt OVA (n=4), OVA-p(GalNAc)(n=4), or OVA-p(GluNAc)(n=4) conjugates, or 10.0 µg OVA as wt OVA (n=4), OVA-p(GalNAc)(n=4), or OVA-p(GluNAc) (n=4) conjugates. After 5 days, the splenocytes from these animals were stained and assayed via flow cytometry.

OTI and OTII challenge model. A total of 5.0×10$^5$ OTI and 5.0×10$^5$ OTII T-cells were adoptively transferred into CD45.2$^+$ C57BL/6 mice via tail vein injection. On days 1 and 7, mice were administered saline (n=4) or 10.0 µg of OVA as wt OVA (n=5), OVA-p(GalNAc) (n=5), or OVA-p(GluNAc) (n=5) in 100 µl of saline via i.v. injection. Fourteen days after adoptive transfer, mice were challenged with 5.0 µg of OVA and 50.0 ng of ultrapure E. coli LPS (InvivoGen) in 25 µL of saline into each of the four footpads. 5 days later antigen-specific challenge, the spleen and dLN cells were harvested and analyzed via flow cytometry for antigen-specific immune response and the presence of Tregs. Additionally, dLN cells were restimulated in vitro in the presence of 1.0 mg/ml OVA (Sigma) or 1.0 µg/ml SIINFEKL (SEQ ID NO: 104) peptide (Genscript) for 6 h. After 3 h of in vitro restimulation, Brefeldin-A (5.0 µg/ml; Sigma) was added and intracellular cytokine expression was assessed by flow cytometry analysis. Restimulation was also carried out on dLN cells over 4 days for the measurement of secreted cytokines by ELISA using the Ready-Set-Go Kit (eBioscience).

OTII Treg-mediated tolerogenic memory. A total of 5.0× 10$^5$ OTII T-cells were adoptively transferred into female CD45.2$^+$ C57BL/6 mice via tail vein injection. On days 1, 4 and 7, mice were administered saline (n=9) or 5.0 µg of OVA as wt OVA (n=5), or OVA-p(GluNAc) (n=10) in 100 µl of saline via i.v. injection. Fifteen days after the adoptive transfer of OTII T-cells, 5 of the mice treated with OVA-p (GluNAc) were administered 400.0 µg of CD25-depeting antibody (BioXcell) via i.p. injection. Fourteen days later, on day 29, all mice received an adoptive transfer of 150.0 µL of IMDM containing 4.0×10$^5$ OTI and 4.0×10$^5$ OTII T-cells. The next day, day 30, the mice were challenged with 5.0 µg of OVA and 50.0 ng of ultrapure E. coli LPS in 25 µL of saline into each of the four footpads. Thirty-five days after the initial transfer of OTII T-cells, the spleen and dLN cells were harvested and analyzed for an OVA-specific immune response and the presence of Tregs. Additionally, dLN cells were restimulated as described above.

Tolerogenic memory for endogenous T-cells. On days 1, 4 and 7, CD57BL/6 mice were administered saline (n=9) or 5.0 µg of OVA as wt OVA (n=5), or OVA-p(GluNAc) (n=10) in 100 µl of saline via i.v. injection. Fifteen days after the adoptive transfer of OTII T-cells, 5 of the mice treated with OVA-p(GluNAc) were administered 400.0 µg of CD25-depeting antibody (BioXcell) via i.p. injection. Fourteen days later, on day 29, all mice received an adoptive transfer of 150.0 µL of IMDM containing 3.0×10$^5$ OTI and 3.0×10$^5$ OTII T-cells. The next day, day 30, each of the four footpads of the mice were challenged with 5.0 µg of OVA and 50.0 ng of ultrapure E. coli LPS in 25 µL of saline. Thirty-four days after the initial treatments, the spleen and dLN cells were harvested and analyzed for an OVA-specific immune response and the presence of Tregs. Additionally, dLN cells were restimulated as described above.

BDC2.5 Diabetes induction model. Splenocytes from female BDC2.5 transgenic mice were stimulated for 4 days in DMEM supplemented with 10% (vol/vol) FBS, 0.05 mM β-mercaptoethanol, 1% puromycin/streptomycin, and 0.50 µM p31 peptide, YVRPLWVRME, (GenScript). After stimulation, 3.0×10$^5$ splenocytes were i.v. injected into normalglycemic NOD/scid mice. At 8 h following adoptive transfer, mice were administered either saline (Vehicle) (n=5), or 0.6 µg of p31 as free p31 (n=8), or conjugated to p(GluNAc) (p31-p(GluNAc)) (n=8) via tail vein injection. Mice were given a subsequent dose of either saline or treatments on day 4. Diabetes onset was monitored every other day by measuring non-fasting blood glucose levels using an Accu-Check Aviva glucometer (Roche). Mice were considered diabetic upon two blood glucose readings above 250 mg/dL or a single blood glucose reading above 450 mg/dL. Mice deemed diabetic were euthanized.

Lasting protection from BDC2.5 T-cell-mediated diabetes. CD4$^+$ BDC2.5 T-cells were isolated from female NOD/BDC2.5 mice via a CD4$^+$ T-cell magnetic bead isolation kit (Miltenyi Biotec), per the manufactures instructions. After isolation, CD4+ BDC2.5+ T-cells were assayed for purity via flow cytometry. 3.0×10⁵ CD4+ BDC2.5 T-cells were injected into female NOD/scid mice via tail vein injection. After 8 h, the mice were then administered i.v. injections of either saline (n=8), or 0.6 µg of p31 as free p31 (n=17), or p31-p(GluNAc) conjugates (n=26). Mice were given a subsequent dose of either saline or the therapies on day 4. Starting on day 4, diabetes onset was monitored every other day by measuring non-fasting blood glucose levels. Mice were considered diabetic upon two blood glucose readings above 250 mg/dL or a single blood glucose reading above 450 mg/dL. Mice deemed diabetic were removed from the study and euthanized. On day 8, 8 p31-treated mice and 8 p31-p(GluNAc)-treated animals were euthanized and the spleens of these animals were analyzed via flow cytometry for the presence of CD4+CD25+FOXP3+ BDC2.5 T-cells. Fifteen days after adoptive transfer, 9 of the remaining 18 mice treated with p31-p(GluNAc) were administered 400.0 µg of CD25-depeting antibody (BioXcell) via i.p. injection. On day 21, all mice that retained non-diabetic blood glucose concentrations (i.e. those treated with p31-p(GluNAc) on days 1 and 4) were given an adoptive transfer of BDC2.5 splenocytes that had previously been stimulated in vitro for 4 days with p31 peptide as described above. The blood glucose concentrations of non-diabetic mice were measured until 60 days after the initial adoptive transfer of cells.

Example 12: Octet Results

For pGal polymers with similar % sugar monomer, the longer polymers (higher degrees of polymerization (DPs)) trended toward higher affinity (lower $K_D$ app) to human asialoglycoprotein receptor (ASGR), as measured by Octet. This was demonstrated with unconjugated pGal polymer (FIG. 30A) and polymer conjugated to ovalbumin peptide (pGal-OVA peptide conjugate, FIG. 30B).

Figures 30A, 30B:
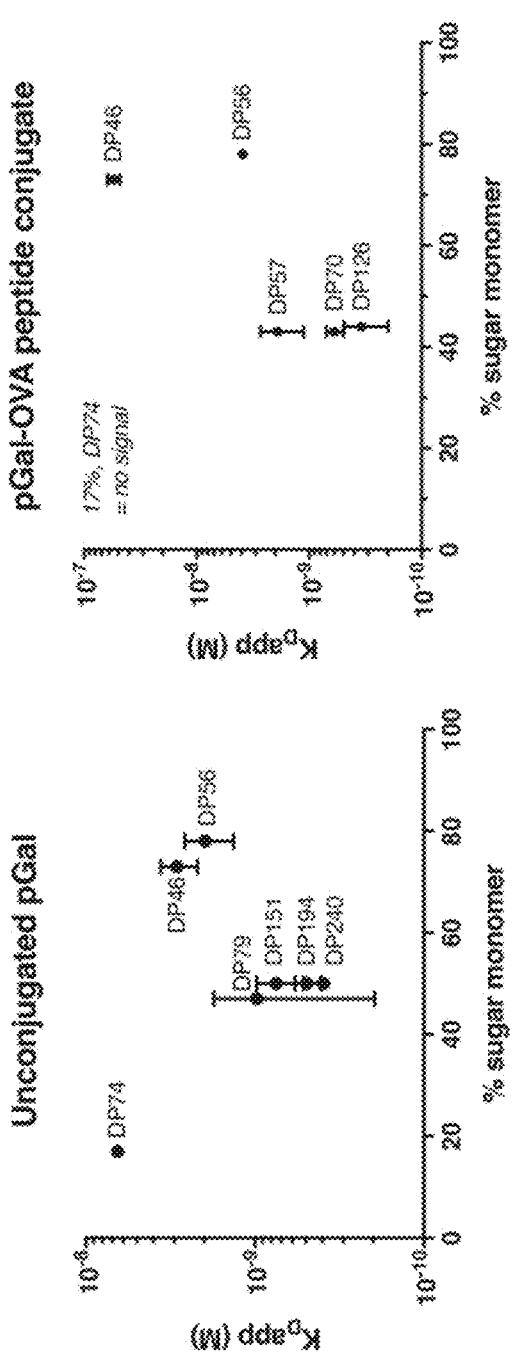
FIG. 30A-B. Octet testing of embodiments. For BCN pGal polymers, affinity was tested with various ratios of sugar repeat units to spacer units and various degrees of polymerization.

For pGal polymers with low % sugar monomer content, but similar DPs, an increase in % sugar monomer trended toward increase in affinity to human ASGR, as measured by Octet (FIGS. 30A and 30B). The pGal polymer with the lowest % sugar monomer demonstrated the poorest affinity to human ASGR by Octet as polymer alone. pGal polymers comprising 50% sugar monomer and 50% spacer monomer resulted in highest affinity to human ASGR by Octet. Of the polymers compared, further increase in % sugar monomer above 50% did not result in substantial increase in affinity to human ASGR by Octet.

Example 13: In Vivo OT Mouse Model (DP Study)

The effect of the polymer size (degree of polymerization, "DP") on induction of tolerance was investigated. Ya' pGal polymers (where k=2, q=3, the $W^1$ to $W^2$ ratio (e.g., the p to r ratio) was approximately 1:1, Z is N-acetylgalactosamine linked via the C-1 carbon, and $R^2$ is dithiobenzoate) of varying DPs were conjugated to ovalbumin peptide by way of thiol-reactive conjugation techniques. DP as used herein refers to the number of repeat units in the Y' portion of the conjugate. The ovalbumin peptide sequence included the MHCI dominant epitope, SIINFEKL (SEQ ID NO: 104), which is recognized by antigen-specific OTI T cells. Briefly, a total of 5.9×10⁵ unlabeled OTI CD8+ T cells and 5.9×10⁵ unlabeled OTll CD4+ T cells were injected into CD45.1+ recipient mice. At 1 day following adoptive transfer, mice were i.v. administered saline solutions containing pGal-OVA-peptide conjugates with degrees of polymerization (DP) of 57, 70, 126 kDa, or saline alone. Each mouse received 1.31 nmol of test article. At 15 d following adoptive transfer, mice were challenged with 2.5 µg of OVA and 12.5 ng of ultrapure E. coli LPS (InvivoGen) in 25 µL of saline injected intradermally into each rear and front leg pad (Hock method: total dose of 10 µg of OVA and 50 ng of LPS). Mice were sacrificed 4 days following challenge, and spleen and draining lymph node cells were isolated for phenotypic analysis and responses to antigen-specific restimulation. For ELISA analysis of cytokines, cells were restimulated in the presence of 0.1 mg/ml OVA or 1 µM SIINFEKL (SEQ ID NO: 104) peptide (Genscript). Supernatants were harvested after 3 days of culture and analyzed for cytokine production by ELISA. For flow cytometry analysis of intracellular cytokines, cells were restimulated in the presence of 1 mg/ml OVA or 1 µM SIINFEKL (SEQ ID NO: 104) peptide (Genscript) for 3 h. brefeldin-A (BD Biosciences) was added, and restimulation was resumed for an additional 2.5 h before staining and flow cytometry analysis.

Figure 31A:
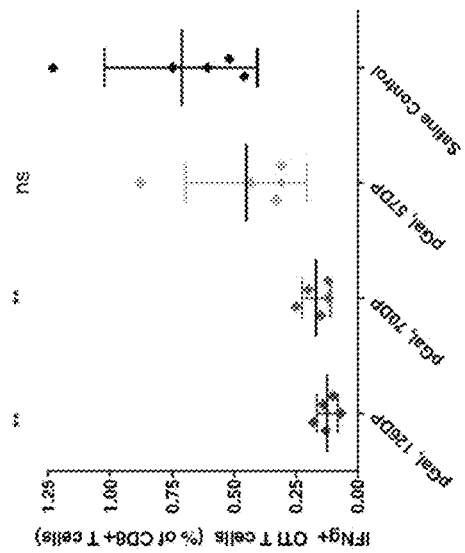
FIG. 31A-D. In vivo testing of embodiments (degree of polymerization). For BCN pGal polymers, in vivo testing was performed with various degrees of polymerization of the targeting portion of the embodiments of the constructs disclosed herein.
Figure 31B:
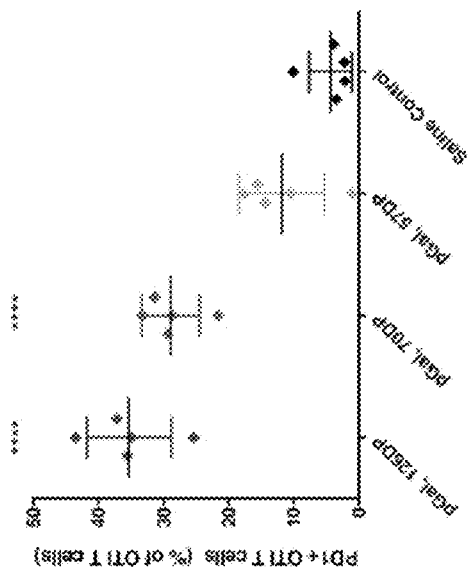
Figure 31C:
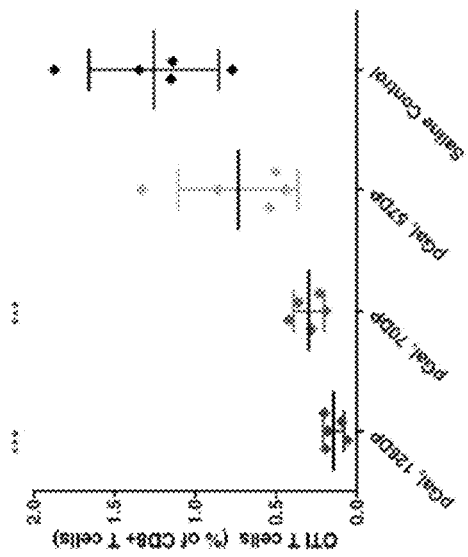

Profound tolerance was induced in the CD8+ T cell compartment by treatment with Ya' pGal polymers of varying DPs, as shown by data from spleen, in FIGS. 31A-D (* indicate $p<0.05$,  indicate $p<0.01$, * indicate $p<0.001$, **** indicate $p<0.0001$). In terms of total cell frequencies, increase in Ya' pGal polymer DP resulted in decreased levels of OTI cells after challenge, statistically lower than treatment by saline, as shown in FIG. 31A. When the cells that remained were analyzed by flow cytometry for expression of IFN-gamma after re-exposure to OVA antigen, the frequency of cells expressing this inflammatory cytokine were decreased most strongly in the groups receiving the treatment of Ya' pGal polymers with highest DP, as shown in FIG. 31B. Conversely, the treatment of Ya' pGal polymers with lowest DP resulted in the lowest reduction in frequency of IFN-gamma expressing cells. Furthermore, reduction in the quantity of the IFNgamma cytokine measured in cell culture supernatant (FIG. 31C) mirrored the flow cytometry trends.

Figure 31D:
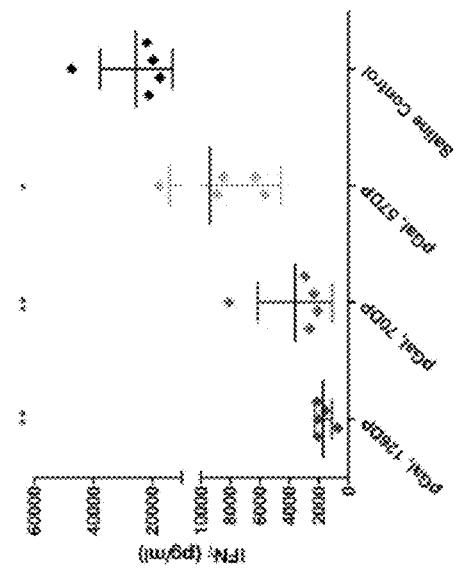
Figure 33A:
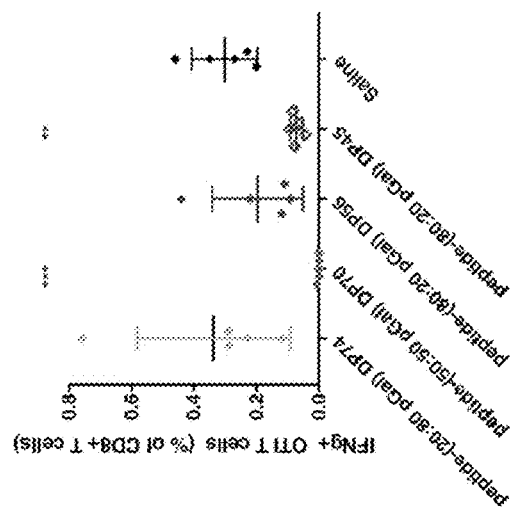
FIG. 33A-D. In vivo testing of embodiments (repeat unit composition). For BCN pGal polymers, induction of tolerance was tested with various ratios of sugar repeat units to spacer units.
Figure 33B:
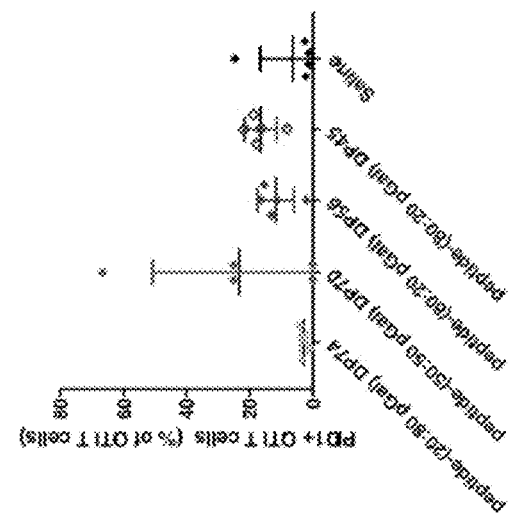
Figure 33C:
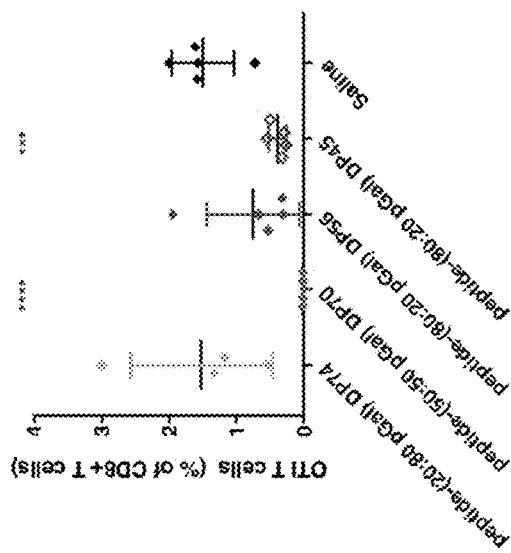
Figure 33D:
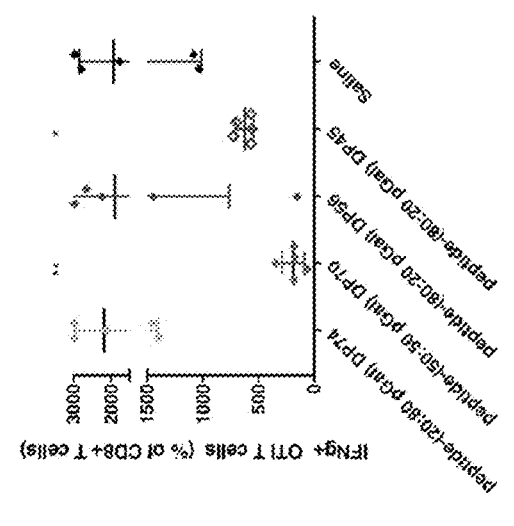

T cell phenotype was further assessed by measurement of T cell anergy and exhaustion marker Programmed Cell Death Protein-1 (PD-1) and was found to inversely correlate with inflammatory cytokine expression (FIG. 31D). Groups treated with Ya' pGal polymers with highest DP resulted in highest frequency of PD1+ OT IT cells.

Thus, increase in DP of Ya' pGal polymers resulted in increase in tolerization, as measured by reduction of inflammatory antigen-specific T cells and increase in tolerogenic T cell phenotype. Trends in the lymph nodes (data not shown) were consistent with the trends from the spleen.

Example 14: In Vivo OT Mouse Model (DP Study)

Effect of pGlu polymer size (degree of polymerization, DP) on induction of tolerance was investigated. Ya' pGlu polymers (where k=2, q=3, the $W^1$ to $W^2$ ratio (e.g., the p to r ratio) was approximately 1:1, Z is N-acetylglucosamine linked via the C-1 carbon, and $R^2$ is dithiobenzoate) of varying DPs were conjugated to ovalbumin peptide by way of thiol-reactive conjugation techniques. The ovalbumin peptide sequence included the MHCI dominant epitope, SIINFEKL (SEQ ID NO: 104), which is recognized by antigen-specific OTI T cells. Briefly, a total of 5.9×10⁵ unlabeled OTI CD8+ T cells and 5.9×10⁵ unlabeled OTll CD4+ T cells were injected into CD45.1+recipient mice. At 1 day following adoptive transfer, mice were i.v. administered saline solutions containing pGlu-OVA-peptide conjugates with DPs of 55, 76, or 94 kDa; or saline alone. Each mouse received 1.31 nmol of test article. At 15 d following adoptive transfer, mice were challenged with 2.5 μg of OVA and 12.5 ng of ultrapure *E. coli* LPS (InvivoGen) in 25 μL of saline injected intradermally into each rear and front leg pad (Hock method: total dose of 10 μg of OVA and 50 ng of LPS). Mice were sacrificed 4 days following challenge, and spleen and draining lymph node cells were isolated for phenotypic analysis and responses to antigen-specific restimulation. For ELISA analysis of cytokines, cells were restimulated in the presence of 0.1 mg/ml OVA or 1 μM SIINFEKL (SEQ ID NO: 104) peptide (Genscript). Supernatants were harvested after 3 days of culture and analyzed for cytokine production by ELISA. For flow cytometry analysis of intracellular cytokines, cells were restimulated in the presence of 1 mg/ml OVA or 1 μM SIINFEKL (SEQ ID NO: 104) peptide (Genscript) for 3 h. brefeldin-A (BD Biosciences) was added, and restimulation was resumed for an additional 2.5 h before staining and flow cytometry analysis.

Profound tolerance was induced in the CD8+ T cell compartment by treatment with Ya' pGlu polymers of varying DPs, as shown by data from spleen, in FIGS. 32A-D (* indicate $p<0.05$,  indicate $p<0.01$, * indicate $p<0.001$, ** indicate $p<0.0001$). In terms of total cell frequencies, treatment with Ya' pGlu constructs resulted in decreased levels of OTI cells after challenge, statistically lower than treatment by saline, as shown in FIG. 32A. When the cells that remained were analyzed by flow cytometry for expression of IFN-gamma after re-exposure to OVA antigen, the frequency of cells expressing this inflammatory cytokine were decreased in the groups receiving Ya' pGlu polymer treatment, as compared to saline treatment, as shown in FIG. 32B. Furthermore, reduction in the quantity of the IFN-gamma cytokine measured in cell culture supernatant (FIG. 32**C) mirrored the flow cytometry trends.

T cell phenotype was further assessed by measurement of T cell anergy and exhaustion marker Programmed Cell Death Protein-1 (PD-1) and was found to inversely correlate with inflammatory cytokine expression. Groups treated with Ya' pGlu polymer resulted in increased frequency of PD1+ OT IT cells, as compared to saline (FIG. 32D).

Thus, treatment with pGlu polymer of various DPs resulted in increase in tolerization, as measured by reduction of inflammatory antigen-specific T cells and increase in tolerogenic T cell phenotype. Trends in the lymph nodes (data not shown) were consistent with the trends from the spleen.

Example 15: In Vivo OT Mouse Model (Monomer Composition Study)

Effect of Ya' pGal (where k=2, q=3, Z is N-acetylgalactosamine linked via the C-1 carbon, and $R^2$ is dithiobenzoate) $W^1$ to $W^2$ ratio on induction of tolerance was investigated. Ya' pGal polymers of varying repeat unit compositions were conjugated to ovalbumin peptide by way of thiol-reactive conjugation techniques. The ovalbumin peptide sequence included the MHCI dominant epitope, SIINFEKL (SEQ ID NO: 104), which is recognized by antigen-specific OTI T cells. Polymers with % sugar monomer and % spacer monomer varied relative to each other were used; nomenclature indicates % sugar monomer: % spacer monomer. Briefly, A total of $6.9\times10^5$ unlabeled OTI CD8+ T cells and $6.9\times10^5$ unlabeled OTIl CD4+ T cells were injected into CD45.1+recipient mice. At 1 day following adoptive transfer, mice were i.v. administered saline solutions containing free OVA05 peptide; pGal-OVA peptide conjugate with % sugar monomer ratio (of total monomer, comprising sugar and spacer monomers) of 17%, 43%, 73%, 78%; or saline alone. Each mouse received 1.34 nmol of test article. At 15 d following adoptive transfer, mice were challenged with 2.5 μg of OVA and 12.5 ng of ultrapure *E. coli* LPS (InvivoGen) in 25 μL of saline injected intradermally into each rear and front leg pad (Hock method: total dose of 10 μg of OVA and 50 ng of LPS). Mice were sacrificed 4 days following challenge, and spleen and draining lymph node cells were isolated for phenotypic analysis and responses to antigen-specific restimulation. For ELISA analysis of cytokines, cells were restimulated in the presence of 0.1 mg/ml OVA or 1 μM SIINFEKL (SEQ ID NO: 104) peptide (Genscript). Supernatants were harvested after 3 days of culture and analyzed for cytokine production by ELISA. For flow cytometry analysis of intracellular cytokines, cells were restimulated in the presence of 1 mg/ml OVA or 1 μM SIINFEKL (SEQ ID NO: 104) peptide (Genscript) for 3 h. brefeldin-A (BD Biosciences) was added, and restimulation was resumed for an additional 2.5 h before staining and flow cytometry analysis.

Tolerance was induced in the CD8+ T cell compartment by treatment with Ya' pGal polymers of varying monomer compositions, when monomer incorporation was greater than 20% sugar monomer, as shown by data from spleen, in FIGS. 33A-D. In terms of total cell frequencies, Ya' pGal polymers with greater than 20% sugar monomer incorporation resulted in decreased levels of OTI cells after challenge, as shown in FIG. 33A. When the cells that remained were analyzed by flow cytometry for expression of IFN-gamma after re-exposure to OVA antigen, the frequency of cells expressing this inflammatory cytokine were decreased most strongly in the groups receiving the treatment of Ya' pGal polymers with greater than 20% sugar monomer incorporation, as shown in FIG. 33B. Furthermore, reduction in the quantity of the IFNgamma cytokine measured in cell culture supernatant (FIG. 33C) mirrored the flow cytometry trends.

T cell phenotype was further assessed by measurement of T cell anergy and exhaustion marker Programmed Cell Death Protein-1 (PD-1) and was found to inversely correlate with inflammatory cytokine expression. Groups treated with Ya' pGal polymers with greater than 20% sugar monomer incorporation resulted in an increase in frequency of PD1+ OT IT cells compared to saline (FIG. 33D). Trends in the lymph nodes (data not shown) were consistent with the trends from the spleen.

Example 16: In Vivo OT Mouse Model (Monomer Composition Study)

Effect of Ya' pGlu (where k=2, q=3, Z is N-acetylglucosamine linked via the C-1 carbon, and $R^2$ is dithiobenzoate) $W^1$ to $W^2$ ratio on induction of tolerance was investigated. Ya' pGlu polymers of varying monomer compositions were conjugated to ovalbumin peptide by way of thiol-reactive conjugation techniques. The ovalbumin peptide sequence included the MHCI dominant epitope, SIINFEKL (SEQ ID NO: 104), which is recognized by antigen-specific OTI T cells. Polymers with % sugar monomer and % spacer monomer varied relative to each other were used; nomenclature indicates % sugar monomer: % spacer monomer. Briefly, a total of $6.9\times10^5$ unlabeled OTI CD8+ T cells and $6.9\times10^5$ unlabeled OTIl CD4+ T cells were injected into CD45.1+recipient mice. At 1 day following adoptive transfer, mice were i.v. administered saline solutions containing free OVA05 peptide; pGlu-OVA peptide conjugates with % sugar monomer ratio of 18%, 48%, 78%; or saline alone.

Each mouse received 1.34 nmol of test article. At 15 d following adoptive transfer, mice were challenged with 2.5 µg of OVA and 12.5 ng of ultrapure *E. coli* LPS (InvivoGen) in 25 µL of saline injected intradermally into each rear and front leg pad (Hock method: total dose of 10 µg of OVA and 50 ng of LPS). Mice were sacrificed 4 days following challenge, and spleen and draining lymph node cells were isolated for phenotypic analysis and responses to antigen-specific restimulation. For ELISA analysis of cytokines, cells were restimulated in the presence of 0.1 mg/ml OVA or 1 µM SIINFEKL (SEQ ID NO: 104) peptide (Genscript). Supernatants were harvested after 3 days of culture and analyzed for cytokine production by ELISA. For flow cytometry analysis of intracellular cytokines, cells were restimulated in the presence of 1 mg/ml OVA or 1 µM SIINFEKL (SEQ ID NO: 104) peptide (Genscript) for 3 h. brefeldin-A (BD Biosciences) was added, and restimulation was resumed for an additional 2.5 h before staining and flow cytometry analysis.

Tolerance was induced in the CD8+ T cell compartment by treatment with Ya' pGlu polymers of varying monomer compositions, as shown by data from spleen, in FIGS. 34A-D. In terms of total cell frequencies, Ya' pGlu polymers resulted in decreased levels of OTI cells after challenge, as shown in FIG. 34A. When the cells that remained were analyzed by flow cytometry for expression of IFN-gamma after re-exposure to OVA antigen, the frequency of cells expressing this inflammatory cytokine were decreased in the groups receiving the treatment of pGlu polymers, as shown in FIG. 34B. Furthermore, reduction in the quantity of the IFNgamma cytokine measured in cell culture supernatant (FIG. 34C) mirrored the flow cytometry trends.

T cell phenotype was further assessed by measurement of T cell anergy and exhaustion marker Programmed Cell Death Protein-1 (PD-1) and was found to inversely correlate with inflammatory cytokine expression. Groups treated with Ya' pGlu polymers resulted in an increase in frequency of PD1+ OT IT cells compared to saline (FIG. 34D). Trends in the lymph nodes (data not shown) were consistent with the trends from the spleen.

Example 17: Stability Study

Purification of conjugates as synthesized in Example 8. 6 M urea was added to the crude conjugate to a final concentration of 10% (v/v). Conjugate was purified by cation exchange. Fractions containing conjugate were identified by SDS-PAGE, pooled, and concentrated by ultrafiltration on a 3 kDa MWCO regenerated cellulose membrane. Size exclusion chromatography in PBS pH 7.2 was used for further polishing, but at larger scales this will be replaced by tangential flow filtration. Conjugate fractions were identified, pooled, and concentrated as before then sterile filtered using a MILLEX GV 0.22 um filter unit.

HPLC Analysis. Conjugates were dissolved to 1 mg/ml (dry weight) in PBS pH 7.2 (ovalbumin) or HEPES, pH 8.04 (insulin) and assayed for stability to heat (60° C.), reducing conditions (10 mM reduced glutathione), and five freeze-thaw cycles. Samples were removed from incubation and assessed at time points by RP-HPLC, SEC-HPLC, and SDS-PAGE.

By Reverse Phase HPLC, 50 ul samples were were injected onto an XBridge C18 BEH C18 2.5 µm column and eluted with a gradient of 5-95% acetonitrile in water containing 0.1% TFA. On a 3 mm×75 mm column, a run is complete in 7 minutes. Peaks identified as polymer by absorbance at 302-340 nm, or as peptide by absorbance at 280 nm. Conjugate absorbed in both regions. HPLC peaks which began to appear during incubation which absorbed like free monomer or free peptide/protein were quantitated as area under the peak.

In SEC-HPLC, 50 ul samples were injected onto an Acquity UPLC protein BEH SEC 200 Å column (4.6 mm×150 mm) and eluted isocratically in PBS, pH 7.2. Peaks were similarly identified and quantitated.

For freeze-thaw samples, conjugates were dissolved to 1 mg/ml based on dry weight in PBS and put through five cycles of freezing at −20° C. followed by thawing at 20° C. The sample was then analyzed by the RP-HPLC method.

SDS-PAGE was performed by loading approximately 2 ug of conjugate in non-reducing loading buffer onto a 4-12% Bis Tris Bolt gel. Standards of ovalbumin or insulin were loaded to generate a standard curve on each gel from 0.1-2 ug. Gels were run according to manufacturers' directions, stained with InstantBlue coomassie blue, and imaged on a ChemiDoc MP by BioRad. The gel bands were quantitated using the Bio-Rad ImageLab 6.0 software and by ImageJ software for comparison. ImageJ was preferred because it deals better with baselines, but the findings do not change depending on which software is used to process the images.

Figure 35B:
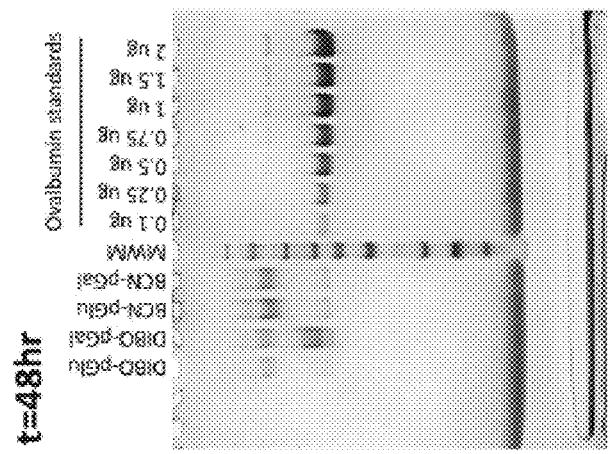
FIG. 35A-D. Stability Studies for Conjugates. For BCN and DIBO pGal polymers, conjugated to OVA (A) or insulin (C), stability studies were performed. The results for the OVA conjugates are shown in FIG. 35B and the results for the insulin conjugates are shown in FIG. 35D.
Figure 35A:
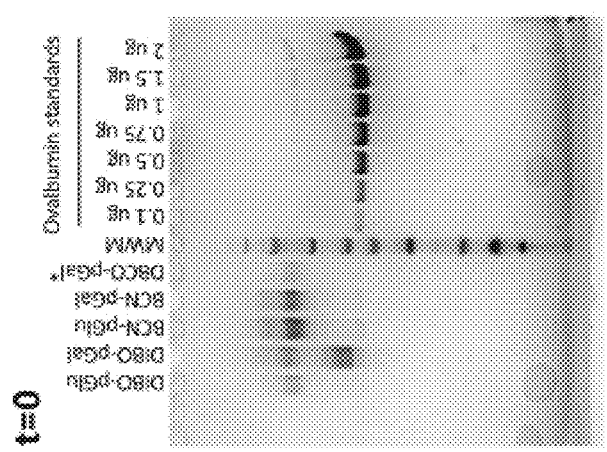
Figures 35C, 35D:
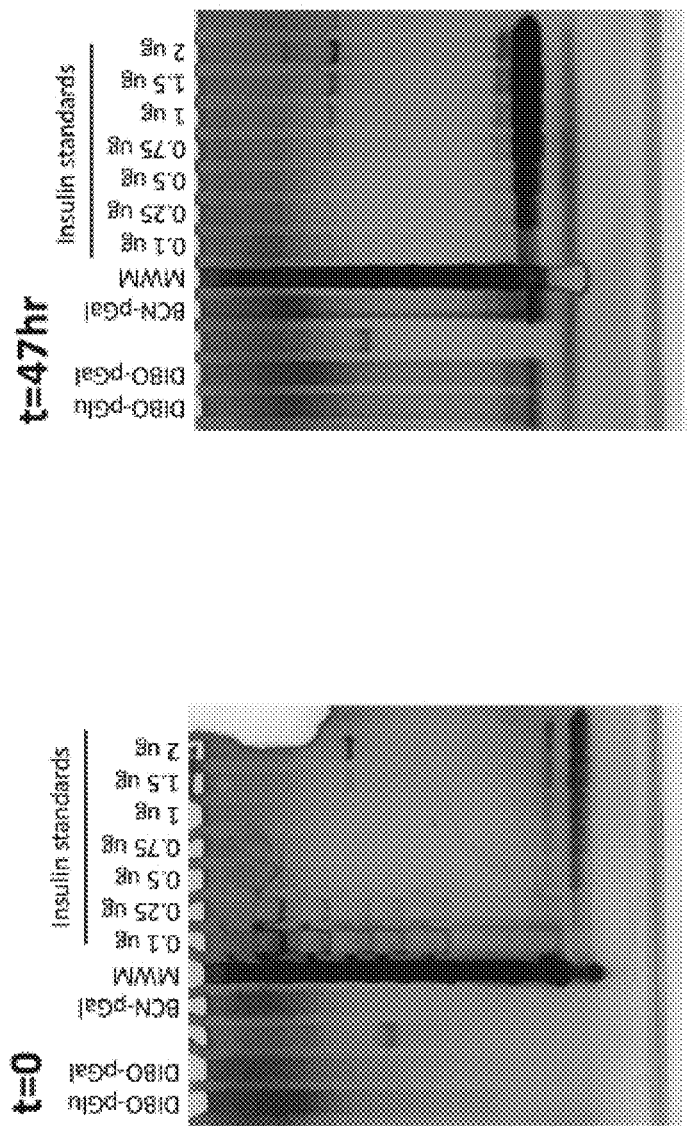

FIGS. 35B and 35D show the results of the testing.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention. The drawings are for the purpose of illustrating embodiments of the invention only, and not for the purpose of limiting it.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a tolerance inducing liver targeting composition" include "instructing the administration of a tolerance inducing liver targeting composition." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% homologous includes 96%, 97%, 98%, 99%, and 100% homologous to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

What is claimed is:

1. A compound comprising Formula 1:

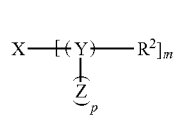

where:
- m is an integer from 1;
- X comprises an antigen or a tolerogenic portion thereof;
- Y is of a linker moiety having Formula Yj':

Y' is a random copolymer or block copolymer of $W^1$ and $W^2$, where $W^1$ and $W^2$ are as depicted below:

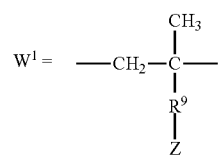 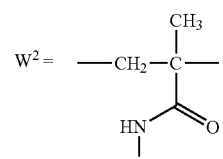

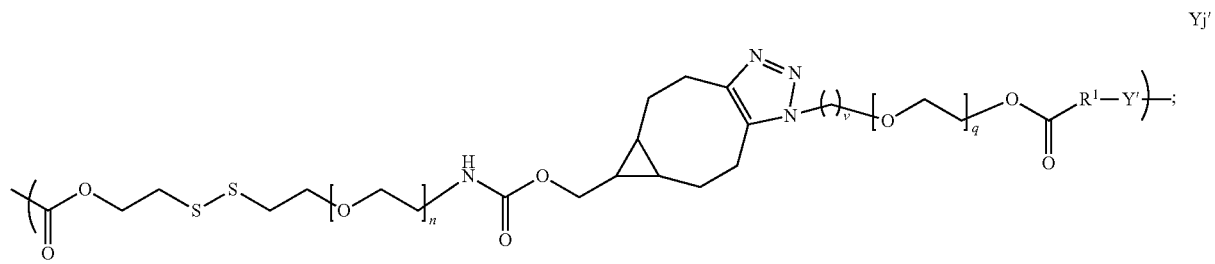

wherein:
- n is 43;
- q is 3;
- v is 2;
- $R_1$ is —$(CH_2)_2$—$C(CH_3)(CN)$—; and wherein the number of repeat units of $W^1$ is denoted as p and wherein p is an integer of at least 1;

wherein the number of repeat units of $W^2$ is denoted as r and wherein r is an integer of at least 1;

where, $R^9$ is —C(O)—NH—(CH$_2$)$_2$—(O—CH$_2$—CH$_2$)$_t$—;
t is 1;
where, $R^{10}$ is —CH$_2$—CH$_2$—OH; and
$R^2$ is:

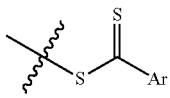

where Ar is an unsubstituted aromatic group; and
Z is N-acetylgalactosamine.

2. The compound of claim 1, where Z is conjugated at its C1, C2 or C6 to Y.

3. The compound of claim 1, wherein the ratio of p to r is 1:1.

4. The compound of claim 1, wherein the ratio of p to r is 4:1.

5. The compound of claim 1, where Y is prepared using N-hydroxysuccinamidyl linkers, maleimide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol)ester linkers.

6. The compound of claim 1, where X induces an unwanted immune response in a subject.

7. The compound of claim 1, wherein X comprises a self antigen.

8. The compound of claim 7, wherein the self antigen is selected from myelin oligodendrocyte glycoprotein (MOG), myelin basic protein (MBP), proteolipid protein (PLP), a portion of any of said antigens, and a mimetic of any of said antigens.

9. The compound of claim 7, wherein the self antigen is selected from insulin, proinsulin, preproinsulin, glutamic acid decarboxylase-65 (GAD-65), GAD-67, insulinomaassociated protein 2 (IA-2), a portion of any of said antigens, and a mimetic of any of said antigens.

10. The compound of claim 1, wherein X comprises a food antigen.

11. The compound of claim 10, wherein the food antigen is selected from the group consisting of high molecular weight glutenin, low molecular weight glutenin, alpha-, gamma- and omega-gliadin, hordein, secalin, avenin, a portion of any of said antigens, and a mimetic of any of said antigens.

12. A compound comprising Formula 1:

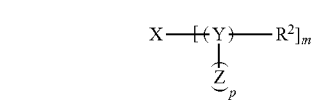

where:
m is an integer from 1 to 100;
X comprises an antigen or a tolerogenic portion thereof;
Y is of a linker moiety having Formula Yj':

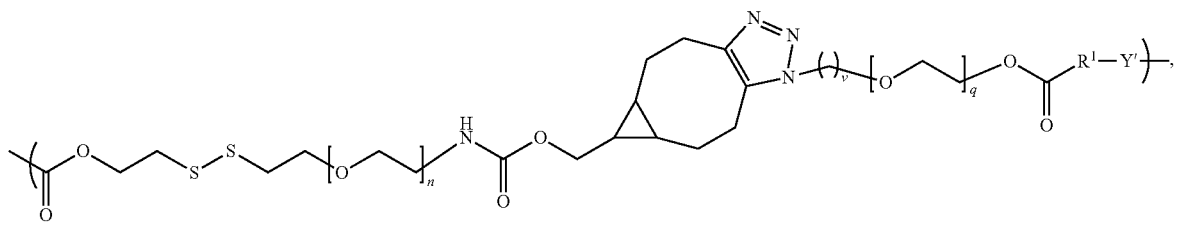

where
n is an integer from 1 to 100;
q is an integer from 1 to 100;
v is an integer from 1 to 4;
$R_1$ is —(CH$_2$)$_2$—C(CH$_3$)(CN); and
Y' is a random copolymer or block copolymer of $W^1$ and $W^2$, where $W^1$ and $W^2$ are as depicted below:

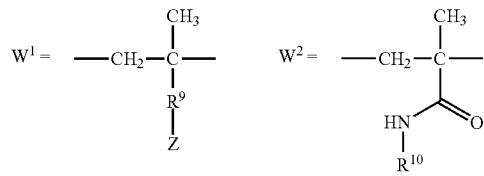

wherein the number of repeat units of $W^1$ is denoted as p and wherein p is an integer of at least 1;
wherein the number of repeat units of $W^2$ is denoted as r and wherein r is an integer of at least 1;
where, $R^9$ is C(O)—NH—(CH$_2$)$_2$—(O—CH$_2$—CH$_2$)$_t$—;
t is an integer from 1 to 5; and
$R^{10}$ is —CH$_2$—CH$_2$—OH;
$R^2$ is selected:

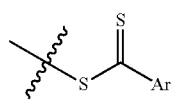

when Ar is an unsubstituted aromatic group; and
Z comprises a liver-targeting moiety.

13. The compound of claim 12, where Z is galactose, glucose, galactosamine, glucosamine, N-acetylgalactosamine, or N-acetylglucosamine.

14. The compound of claim 12, wherein X comprises a self antigen.

15. The compound of claim 14, wherein the self antigen is selected from myelin oligodendrocyte glycoprotein (MOG), myelin basic protein (MBP), proteolipid protein (PLP), a portion of any of said antigens, and a mimetic of any of said antigens.

16. The compound of claim 14, wherein the self antigen is selected from insulin, proinsulin, preproinsulin, glutamic acid decarboxylase-65 (GAD-65), GAD-67, insulinoma associated protein 2 (IA-2), a portion of any of said antigens, and a mimetic of any of said antigens.

17. The compound of claim 12, wherein X comprises a food antigen.

18. The compound of claim 17, wherein the food antigen is selected from the group consisting of high molecular weight glutenin, low molecular weight glutenin, alpha-, gamma- and omega-gliadin, hordein, secalin, avenin, a portion of any of said antigens, and a mimetic of any of said antigens.

* * * * *

SEQUENCE LISTING

```
<160> NUMBER OF SEQ ID NOS: 105

<210> SEQ ID NO 1
<211> LENGTH: 110
<212> TYPE: PRT
<213> ORGANISM: Homo sapiens
<220> FEATURE:
<221> NAME/KEY: MISC_FEATURE
<223> OTHER INFORMATION: Human insulin

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 585
<212> TYPE: PRT
<213> ORGANISM: Homo sapiens
<220> FEATURE:
<221> NAME/KEY: MISC_FEATURE
<223> OTHER INFORMATION: GAD65

<400> SEQUENCE: 2

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
            115                 120                 125
```

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540

-continued

```
Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 3
<211> LENGTH: 355
<212> TYPE: PRT
<213> ORGANISM: Homo sapiens
<220> FEATURE:
<221> NAME/KEY: MISC_FEATURE
<223> OTHER INFORMATION: IGRP

<400> SEQUENCE: 3

Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
                20                  25                  30

Gly Asp Pro Arg Asn Ile Phe Phe Ile Tyr Phe Pro Leu Cys Phe Gln
            35                  40                  45

Phe Asn Gln Thr Val Gly Thr Lys Met Ile Trp Val Ala Val Ile Gly
50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
            115                 120                 125

Ala Ala Leu Ser His Thr Val Cys Gly Met Asp Lys Phe Ser Ile Thr
            130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Ile Gln Thr Ala Ser Leu Gly Thr Tyr Leu
            195                 200                 205

Lys Thr Asn Leu Phe Leu Phe Leu Phe Ala Val Gly Phe Tyr Leu Leu
            210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Leu Ser Cys Arg Gly Gly Asn Asn Tyr
            275                 280                 285

Thr Leu Ser Phe Arg Leu Leu Cys Ala Leu Thr Ser Leu Thr Ile Leu
            290                 295                 300

Gln Leu Tyr His Phe Leu Gln Ile Pro Thr His Glu Glu His Leu Phe
305                 310                 315                 320
```

```
Tyr Val Leu Ser Phe Cys Lys Ser Ala Ser Ile Pro Leu Thr Val Val
                325                 330                 335

Ala Phe Ile Pro Tyr Ser Val His Met Leu Met Lys Gln Ser Gly Lys
            340                 345                 350

Lys Ser Gln
        355

<210> SEQ ID NO 4
<211> LENGTH: 304
<212> TYPE: PRT
<213> ORGANISM: Homo sapiens
<220> FEATURE:
<221> NAME/KEY: MISC_FEATURE
<223> OTHER INFORMATION: MBP

<400> SEQUENCE: 4

Met Gly Asn His Ala Gly Lys Arg Glu Leu Asn Ala Glu Lys Ala Ser
1               5                   10                  15

Thr Asn Ser Glu Thr Asn Arg Gly Glu Ser Lys Lys Arg Asn Leu
            20                  25                  30

Gly Glu Leu Ser Arg Thr Thr Ser Glu Asp Asn Glu Val Phe Gly Glu
            35                  40                  45

Ala Asp Ala Asn Gln Asn Asn Gly Thr Ser Ser Gln Asp Thr Ala Val
50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
            115                 120                 125

Glu Ser Leu Asp Val Met Ala Ser Gln Lys Arg Pro Ser Gln Arg His
            130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro Met Ala Arg Arg
290                 295                 300
```

<210> SEQ ID NO 5
<211> LENGTH: 247
<212> TYPE: PRT
<213> ORGANISM: Homo sapiens
<220> FEATURE:
<221> NAME/KEY: MISC_FEATURE
<223> OTHER INFORMATION: MOG

<400> SEQUENCE: 5

Met Ala Ser Leu Ser Arg Pro Ser Leu Pro Ser Cys Leu Cys Ser Phe
1               5                   10                  15

Leu Leu Leu Leu Leu Leu Gln Val Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 6
<211> LENGTH: 277
<212> TYPE: PRT
<213> ORGANISM: Homo sapiens
<220> FEATURE:
<221> NAME/KEY: MISC_FEATURE
<223> OTHER INFORMATION: PLP

<400> SEQUENCE: 6

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val

```
                    50                  55                  60
Ile His Ala Phe Gln Tyr Val Ile Tyr Gly Thr Ala Ser Phe Phe
 65                  70                  75                  80

Leu Tyr Gly Ala Leu Leu Ala Glu Gly Phe Tyr Thr Thr Gly Ala
                     85                  90                  95

Val Arg Gln Ile Phe Gly Asp Tyr Lys Thr Thr Ile Cys Gly Lys Gly
                    100                 105                 110

Leu Ser Ala Thr Val Thr Gly Gly Gln Lys Gly Arg Gly Ser Arg Gly
                    115                 120                 125

Gln His Gln Ala His Ser Leu Glu Arg Val Cys His Cys Leu Gly Lys
                    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                    165                 170                 175

Tyr Phe Asn Thr Trp Thr Thr Cys Gln Ser Ile Ala Phe Pro Ser Lys
                    180                 185                 190

Thr Ser Ala Ser Ile Gly Ser Leu Cys Ala Asp Ala Arg Met Tyr Gly
                    195                 200                 205

Val Leu Pro Trp Asn Ala Phe Pro Gly Lys Val Cys Gly Ser Asn Leu
                    210                 215                 220

Leu Ser Ile Cys Lys Thr Ala Glu Phe Gln Met Thr Phe His Leu Phe
225                 230                 235                 240

Ile Ala Ala Phe Val Gly Ala Ala Thr Leu Val Ser Leu Leu Thr
                    245                 250                 255

Phe Met Ile Ala Ala Thr Tyr Asn Phe Ala Val Leu Lys Leu Met Gly
                    260                 265                 270

Arg Gly Thr Lys Phe
                    275

<210> SEQ ID NO 7
<211> LENGTH: 20
<212> TYPE: PRT
<213> ORGANISM: Homo sapiens
<220> FEATURE:
<221> NAME/KEY: MISC_FEATURE
<223> OTHER INFORMATION: MBP13-32

<400> SEQUENCE: 7

Lys Tyr Leu Ala Thr Ala Ser Thr Met Asp His Ala Arg His Gly Phe
 1               5                  10                  15

Leu Pro Arg His
             20

<210> SEQ ID NO 8
<211> LENGTH: 16
<212> TYPE: PRT
<213> ORGANISM: Homo sapiens
<220> FEATURE:
<221> NAME/KEY: MISC_FEATURE
<223> OTHER INFORMATION: MBP83-99

<400> SEQUENCE: 8

Glu Asn Pro Trp His Phe Phe Lys Asn Ile Val Thr Pro Arg Thr Pro
 1               5                  10                  15

<210> SEQ ID NO 9
<211> LENGTH: 19
<212> TYPE: PRT
```

```
<213> ORGANISM: Homo sapiens
<220> FEATURE:
<221> NAME/KEY: MISC_FEATURE
<223> OTHER INFORMATION: MBP111-129

<400> SEQUENCE: 9

Leu Ser Arg Phe Ser Trp Gly Ala Glu Gly Gln Arg Pro Gly Phe Gly
1               5                   10                  15

Tyr Gly Gly

<210> SEQ ID NO 10
<211> LENGTH: 25
<212> TYPE: PRT
<213> ORGANISM: Homo sapiens
<220> FEATURE:
<221> NAME/KEY: MISC_FEATURE
<223> OTHER INFORMATION: MBP146-170

<400> SEQUENCE: 10

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 11
<211> LENGTH: 20
<212> TYPE: PRT
<213> ORGANISM: Homo sapiens
<220> FEATURE:
<221> NAME/KEY: MISC_FEATURE
<223> OTHER INFORMATION: MOG1-20

<400> SEQUENCE: 11

Gly Gln Phe Arg Val Ile Gly Pro Arg His Pro Ile Arg Ala Leu Val
1               5                   10                  15

Gly Asp Glu Val
            20

<210> SEQ ID NO 12
<211> LENGTH: 20
<212> TYPE: PRT
<213> ORGANISM: Homo sapiens
<220> FEATURE:
<221> NAME/KEY: MISC_FEATURE
<223> OTHER INFORMATION: MOG35-55

<400> SEQUENCE: 12

Met Glu Val Gly Trp Tyr Arg Pro Pro Phe Ser Arg Trp His Leu Tyr
1               5                   10                  15

Arg Asn Gly Lys
            20

<210> SEQ ID NO 13
<211> LENGTH: 16
<212> TYPE: PRT
<213> ORGANISM: Homo sapiens
<220> FEATURE:
<221> NAME/KEY: MISC_FEATURE
<223> OTHER INFORMATION: PLP139-154

<400> SEQUENCE: 13

His Cys Leu Gly Lys Trp Leu Gly His Pro Asp Lys Phe Val Gly Ile
1               5                   10                  15

<210> SEQ ID NO 14
```

```
<211> LENGTH: 118
<212> TYPE: PRT
<213> ORGANISM: Homo sapiens
<220> FEATURE:
<221> NAME/KEY: MISC_FEATURE
<223> OTHER INFORMATION: MART1

<400> SEQUENCE: 14
```

Met Pro Arg Glu Asp Ala His Phe Ile Tyr Gly Tyr Pro Lys Lys Gly
1               5                   10                  15

His Gly His Ser Tyr Thr Thr Ala Glu Ala Ala Gly Ile Gly Ile
            20                  25                  30

Leu Thr Val Ile Leu Gly Val Leu Leu Leu Ile Gly Cys Trp Tyr Cys
            35                  40                  45

Arg Arg Arg Asn Gly Tyr Arg Ala Leu Met Asp Lys Ser Leu His Val
        50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

```
<210> SEQ ID NO 15
<211> LENGTH: 529
<212> TYPE: PRT
<213> ORGANISM: Homo sapiens
<220> FEATURE:
<221> NAME/KEY: MISC_FEATURE
<223> OTHER INFORMATION: Tyrosinase

<400> SEQUENCE: 15
```

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
            20                  25                  30

Lys Glu Cys Cys Pro Pro Trp Ser Gly Asp Arg Ser Pro Cys Gly Gln
        35                  40                  45

Leu Ser Gly Arg Gly Ser Cys Gln Asn Ile Leu Leu Ser Asn Ala Pro
    50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190

Glu Ile Trp Arg Asp Ile Asp Phe Ala His Glu Ala Pro Ala Phe Leu
            195                 200                 205

Pro Trp His Arg Leu Phe Leu Leu Arg Trp Glu Gln Glu Ile Gln Lys
210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
            245                 250                 255

Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
            290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
            325                 330                 335

Asn Phe Ser Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
            370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
            405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
            435                 440                 445

Tyr Ser Tyr Leu Gln Asp Ser Asp Pro Asp Ser Phe Gln Asp Tyr Ile
            450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
            485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
            515                 520                 525

Leu

<210> SEQ ID NO 16
<211> LENGTH: 660
<212> TYPE: PRT
<213> ORGANISM: Homo sapiens
<220> FEATURE:
<221> NAME/KEY: MISC_FEATURE
<223> OTHER INFORMATION: Melanocyte protein PMEL, gp100

<400> SEQUENCE: 16

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gln Pro Val Tyr Pro Gln Glu Thr Asp Asp
            115                 120                 125

Ala Cys Ile Phe Pro Asp Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
            165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
    195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
            245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
            290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
            325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
            355                 360                 365

Ala Glu Ser Thr Gly Met Thr Pro Glu Lys Val Pro Val Ser Glu Val
            370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
            405                 410                 415

Gln Val Thr Thr Thr Glu Trp Val Glu Thr Thr Ala Arg Glu Leu Pro
            420                 425                 430

```
Ile Pro Glu Pro Gly Asp Ala Ser Ser Ile Met Ser Thr Glu
        435                 440                 445

Ser Ile Thr Gly Ser Leu Gly Pro Leu Leu Asp Gly Thr Ala Thr Leu
450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
                515                 520                 525

Ser Ser Pro Gly Cys Gln Pro Pro Ala Gln Arg Leu Cys Gln Pro Val
530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
                580                 585                 590

Leu Gly Gln Val Pro Leu Ile Val Gly Ile Leu Leu Val Leu Met Ala
                595                 600                 605

Val Val Leu Ala Ser Leu Ile Tyr Arg Arg Arg Leu Met Lys Gln Asp
                610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln
            660

<210> SEQ ID NO 17
<211> LENGTH: 323
<212> TYPE: PRT
<213> ORGANISM: Homo sapiens
<220> FEATURE:
<221> NAME/KEY: MISC_FEATURE
<223> OTHER INFORMATION: Aquaporin-4

<400> SEQUENCE: 17

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
                20                  25                  30

Ala Phe Trp Lys Ala Val Thr Ala Glu Phe Leu Ala Met Leu Ile Phe
            35                  40                  45

Val Leu Leu Ser Leu Gly Ser Thr Ile Asn Trp Gly Gly Thr Glu Lys
        50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
                100                 105                 110

Ala Lys Ser Val Phe Tyr Ile Ala Ala Gln Cys Leu Gly Ala Ile Ile
            115                 120                 125
```

```
Gly Ala Gly Ile Leu Tyr Leu Val Thr Pro Pro Ser Val Val Gly Gly
            130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
                180                 185                 190

Ile Gly Phe Ser Val Ala Ile Gly His Leu Phe Ala Ile Asn Tyr Thr
            195                 200                 205

Gly Ala Ser Met Asn Pro Ala Arg Ser Phe Gly Pro Ala Val Ile Met
        210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
                260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
        290                 295                 300

Asp Arg Gly Glu Glu Lys Lys Gly Lys Asp Gln Ser Gly Glu Val Leu
305                 310                 315                 320

Ser Ser Val

<210> SEQ ID NO 18
<211> LENGTH: 405
<212> TYPE: PRT
<213> ORGANISM: Homo sapiens
<220> FEATURE:
<221> NAME/KEY: MISC_FEATURE
<223> OTHER INFORMATION: S-arrestin

<400> SEQUENCE: 18

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
                20                  25                  30

Arg Asp Tyr Ile Asp His Val Ser Gln Val Gln Pro Val Asp Gly Val
            35                  40                  45

Val Leu Val Asp Pro Asp Leu Val Lys Gly Lys Lys Val Tyr Val Thr
50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160
```

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 19
<211> LENGTH: 1247
<212> TYPE: PRT
<213> ORGANISM: Homo sapiens
<220> FEATURE:
<221> NAME/KEY: MISC_FEATURE
<223> OTHER INFORMATION: IRBP

<400> SEQUENCE: 19

Met Met Arg Glu Trp Val Leu Leu Met Ser Val Leu Leu Cys Gly Leu
1               5                   10                  15

Ala Gly Pro Thr His Leu Phe Gln Pro Ser Leu Val Leu Asp Met Ala
            20                  25                  30

Lys Val Leu Leu Asp Asn Tyr Cys Phe Pro Glu Asn Leu Leu Gly Met
        35                  40                  45

Gln Glu Ala Ile Gln Gln Ala Ile Lys Ser His Glu Ile Leu Ser Ile
    50                  55                  60

Ser Asp Pro Gln Thr Leu Ala Ser Val Leu Thr Ala Gly Val Gln Ser
65                  70                  75                  80

Ser Leu Asn Asp Pro Arg Leu Val Ile Ser Tyr Glu Pro Ser Thr Pro
                85                  90                  95

Glu Pro Pro Pro Gln Val Pro Ala Leu Thr Ser Leu Ser Glu Glu Glu

```
                100             105                 110
Leu Leu Ala Trp Leu Gln Arg Gly Leu Arg His Glu Val Leu Glu Gly
            115                 120                 125
Asn Val Gly Tyr Leu Arg Val Asp Ser Val Pro Gly Gln Glu Val Leu
            130                 135             140
Ser Met Met Gly Glu Phe Leu Val Ala His Val Trp Gly Asn Leu Met
145                 150                 155                 160
Gly Thr Ser Ala Leu Val Leu Asp Leu Arg His Cys Thr Gly Gly Gln
                165                 170                 175
Val Ser Gly Ile Pro Tyr Ile Ile Ser Tyr Leu His Pro Gly Asn Thr
            180                 185                 190
Ile Leu His Val Asp Thr Ile Tyr Asn Arg Pro Ser Asn Thr Thr Thr
            195                 200                 205
Glu Ile Trp Thr Leu Pro Gln Val Leu Gly Arg Tyr Gly Ala Asp
            210                 215                 220
Lys Asp Val Val Leu Thr Ser Ser Gln Thr Arg Gly Val Ala Glu
225                 230                 235                 240
Asp Ile Ala His Ile Leu Lys Gln Met Arg Arg Ala Ile Val Val Gly
                245                 250                 255
Glu Arg Thr Gly Gly Ala Leu Asp Leu Arg Lys Leu Arg Ile Gly
                260                 265                 270
Glu Ser Asp Phe Phe Phe Thr Val Pro Val Ser Arg Ser Leu Gly Pro
            275                 280                 285
Leu Gly Gly Gly Ser Gln Thr Trp Glu Gly Ser Gly Val Leu Pro Cys
            290                 295                 300
Val Gly Thr Pro Ala Glu Gln Ala Leu Glu Lys Ala Leu Ala Ile Leu
305                 310                 315                 320
Thr Leu Arg Ser Ala Leu Pro Gly Val Val His Cys Leu Gln Glu Val
                325                 330                 335
Leu Lys Asp Tyr Tyr Thr Leu Val Asp Arg Val Pro Thr Leu Leu Gln
                340                 345                 350
His Leu Ala Ser Met Asp Phe Ser Thr Val Val Ser Glu Glu Asp Leu
                355                 360                 365
Val Thr Lys Leu Asn Ala Gly Leu Gln Ala Ala Ser Glu Asp Pro Arg
            370                 375             380
Leu Leu Val Arg Ala Ile Gly Pro Thr Glu Thr Pro Ser Trp Pro Ala
385                 390                 395                 400
Pro Asp Ala Ala Ala Glu Asp Ser Pro Gly Val Ala Pro Glu Leu Pro
                405                 410                 415
Glu Asp Glu Ala Ile Arg Gln Ala Leu Val Asp Ser Val Phe Gln Val
                420                 425             430
Ser Val Leu Pro Gly Asn Val Gly Tyr Leu Arg Phe Asp Ser Phe Ala
            435                 440                 445
Asp Ala Ser Val Leu Gly Val Leu Ala Pro Tyr Val Leu Arg Gln Val
            450                 455                 460
Trp Glu Pro Leu Gln Asp Thr Glu His Leu Ile Met Asp Leu Arg His
465                 470                 475                 480
Asn Pro Gly Gly Pro Ser Ser Ala Val Pro Leu Leu Leu Ser Tyr Phe
                485                 490                 495
Gln Gly Pro Glu Ala Gly Pro Val His Leu Phe Thr Thr Tyr Asp Arg
                500                 505                 510
Arg Thr Asn Ile Thr Gln Glu His Phe Ser His Met Glu Leu Pro Gly
            515                 520                 525
```

```
Pro Arg Tyr Ser Thr Gln Arg Gly Val Tyr Leu Leu Thr Ser His Arg
    530                 535                 540

Thr Ala Thr Ala Ala Glu Glu Phe Ala Phe Leu Met Gln Ser Leu Gly
545                 550                 555                 560

Trp Ala Thr Leu Val Gly Glu Ile Thr Ala Gly Asn Leu Leu His Thr
                565                 570                 575

Arg Thr Val Pro Leu Leu Asp Thr Pro Glu Gly Ser Leu Ala Leu Thr
            580                 585                 590

Val Pro Val Leu Thr Phe Ile Asp Asn His Gly Glu Ala Trp Leu Gly
        595                 600                 605

Gly Gly Val Val Pro Asp Ala Ile Val Leu Ala Glu Glu Ala Leu Asp
    610                 615                 620

Lys Ala Gln Glu Val Leu Glu Phe His Gln Ser Leu Gly Ala Leu Val
625                 630                 635                 640

Glu Gly Thr Gly His Leu Leu Glu Ala His Tyr Ala Arg Pro Glu Val
                645                 650                 655

Val Gly Gln Thr Ser Ala Leu Leu Arg Ala Lys Leu Ala Gln Gly Ala
            660                 665                 670

Tyr Arg Thr Ala Val Asp Leu Glu Ser Leu Ala Ser Gln Leu Thr Ala
        675                 680                 685

Asp Leu Gln Glu Val Ser Gly Asp His Arg Leu Leu Val Phe His Ser
    690                 695                 700

Pro Gly Glu Leu Val Val Glu Glu Ala Pro Pro Pro Pro Pro Ala Val
705                 710                 715                 720

Pro Ser Pro Glu Glu Leu Thr Tyr Leu Ile Glu Ala Leu Phe Lys Thr
                725                 730                 735

Glu Val Leu Pro Gly Gln Leu Gly Tyr Leu Arg Phe Asp Ala Met Ala
            740                 745                 750

Glu Leu Glu Thr Val Lys Ala Val Gly Pro Gln Leu Val Arg Leu Val
        755                 760                 765

Trp Gln Gln Leu Val Asp Thr Ala Ala Leu Val Ile Asp Leu Arg Tyr
    770                 775                 780

Asn Pro Gly Ser Tyr Ser Thr Ala Ile Pro Leu Leu Cys Ser Tyr Phe
785                 790                 795                 800

Phe Glu Ala Glu Pro Arg Gln His Leu Tyr Ser Val Phe Asp Arg Ala
                805                 810                 815

Thr Ser Lys Val Thr Glu Val Trp Thr Leu Pro Gln Val Ala Gly Gln
            820                 825                 830

Arg Tyr Gly Ser His Lys Asp Leu Tyr Ile Leu Met Ser His Thr Ser
        835                 840                 845

Gly Ser Ala Ala Glu Ala Phe Ala His Thr Met Gln Asp Leu Gln Arg
    850                 855                 860

Ala Thr Val Ile Gly Glu Pro Thr Ala Gly Ala Leu Ser Val Gly
865                 870                 875                 880

Ile Tyr Gln Val Gly Ser Ser Pro Leu Tyr Ala Ser Met Pro Thr Gln
                885                 890                 895

Met Ala Met Ser Ala Thr Thr Gly Lys Ala Trp Asp Leu Ala Gly Val
            900                 905                 910

Glu Pro Asp Ile Thr Val Pro Met Ser Glu Ala Leu Ser Ile Ala Gln
        915                 920                 925

Asp Ile Val Ala Leu Arg Ala Lys Val Pro Thr Val Leu Gln Thr Ala
    930                 935                 940
```

-continued

```
Gly Lys Leu Val Ala Asp Asn Tyr Ala Ser Ala Glu Leu Gly Ala Lys
            945                 950                 955                 960

Met Ala Thr Lys Leu Ser Gly Leu Gln Ser Arg Tyr Ser Arg Val Thr
                965                 970                 975

Ser Glu Val Ala Leu Ala Glu Ile Leu Gly Ala Asp Leu Gln Met Leu
                980                 985                 990

Ser Gly Asp Pro His Leu Lys Ala  Ala His Ile Pro Glu  Asn Ala Lys
                995                1000                1005

Asp Arg Ile Pro Gly Ile Val  Pro Met Gln Ile Pro  Ser Pro Glu
            1010                1015                1020

Val Phe Glu Glu Leu Ile Lys  Phe Ser Phe His Thr  Asn Val Leu
            1025                1030                1035

Glu Asp Asn Ile Gly Tyr Leu  Arg Phe Asp Met Phe  Gly Asp Gly
            1040                1045                1050

Glu Leu Leu Thr Gln Val Ser  Arg Leu Leu Val Glu  His Ile Trp
            1055                1060                1065

Lys Lys Ile Met His Thr Asp  Ala Met Ile Ile Asp  Met Arg Phe
            1070                1075                1080

Asn Ile Gly Gly Pro Thr Ser  Ser Ile Pro Ile Leu  Cys Ser Tyr
            1085                1090                1095

Phe Phe Asp Glu Gly Pro Pro  Val Leu Leu Asp Lys  Ile Tyr Ser
            1100                1105                1110

Arg Pro Asp Asp Ser Val Ser  Glu Leu Trp Thr His  Ala Gln Val
            1115                1120                1125

Val Gly Glu Arg Tyr Gly Ser  Lys Lys Ser Met Val  Ile Leu Thr
            1130                1135                1140

Ser Ser Val Thr Ala Gly Thr  Ala Glu Glu Phe Thr  Tyr Ile Met
            1145                1150                1155

Lys Arg Leu Gly Arg Ala Leu  Val Ile Gly Glu Val  Thr Ser Gly
            1160                1165                1170

Gly Cys Gln Pro Pro Gln Thr  Tyr His Val Asp Asp  Thr Asn Leu
            1175                1180                1185

Tyr Leu Thr Ile Pro Thr Ala  Arg Ser Val Gly Ala  Ser Asp Gly
            1190                1195                1200

Ser Ser Trp Glu Gly Val Gly  Val Thr Pro His Val  Val Val Pro
            1205                1210                1215

Ala Glu Glu Ala Leu Ala Arg  Ala Lys Glu Met Leu  Gln His Asn
            1220                1225                1230

Gln Leu Arg Val Lys Arg Ser  Pro Gly Leu Gln Asp  His Leu
            1235                1240                1245

<210> SEQ ID NO 20
<211> LENGTH: 33
<212> TYPE: PRT
<213> ORGANISM: Homo sapiens
<220> FEATURE:
<221> NAME/KEY: MISC_FEATURE
<223> OTHER INFORMATION: DQ2 Alpha-gliadin native

<400> SEQUENCE: 20

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe
```

<210> SEQ ID NO 21
<211> LENGTH: 33
<212> TYPE: PRT
<213> ORGANISM: Homo sapiens
<220> FEATURE:
<221> NAME/KEY: MISC_FEATURE
<223> OTHER INFORMATION: DQ-2 alpha-gliadin deamindated

<400> SEQUENCE: 21

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 22
<211> LENGTH: 18
<212> TYPE: PRT
<213> ORGANISM: Homo sapiens
<220> FEATURE:
<221> NAME/KEY: MISC_FEATURE
<223> OTHER INFORMATION: alpha-gliadin DQ8

<400> SEQUENCE: 22

Gln Gln Tyr Pro Ser Gly Gln Gly Ser Phe Gln Pro Ser Gln Gln Asn
1               5                   10                  15

Pro Gln

<210> SEQ ID NO 23
<211> LENGTH: 12
<212> TYPE: PRT
<213> ORGANISM: Homo sapiens
<220> FEATURE:
<221> NAME/KEY: MISC_FEATURE
<223> OTHER INFORMATION: DQ-8 Omega-gliadin

<400> SEQUENCE: 23

Gln Pro Phe Pro Gln Pro Glu Gln Pro Phe Pro Trp
1               5                   10

<210> SEQ ID NO 24
<211> LENGTH: 16
<212> TYPE: PRT
<213> ORGANISM: Homo sapiens
<220> FEATURE:
<221> NAME/KEY: MISC_FEATURE
<223> OTHER INFORMATION: PLP139-154

<400> SEQUENCE: 24

His Cys Leu Gly Lys Trp Leu Gly His Pro Asp Lys Phe Val Gly Ile
1               5                   10                  15

<210> SEQ ID NO 25
<211> LENGTH: 20
<212> TYPE: PRT
<213> ORGANISM: Homo sapiens
<220> FEATURE:
<221> NAME/KEY: MISC_FEATURE
<223> OTHER INFORMATION: MBP13-32

<400> SEQUENCE: 25

Lys Tyr Leu Ala Thr Ala Ser Thr Met Asp His Ala Arg His Gly Phe
1               5                   10                  15

Leu Pro Arg His
            20

<210> SEQ ID NO 26
<211> LENGTH: 29
<212> TYPE: PRT
<213> ORGANISM: Homo sapiens
<220> FEATURE:
<221> NAME/KEY: MISC_FEATURE
<223> OTHER INFORMATION: MBP2A conjugatable

<400> SEQUENCE: 26

Gly Cys Arg Gly Gln Arg His Gly Ser Lys Tyr Leu Ala Thr Ala Ser
1               5                   10                  15

Thr Met Asp His Ala Arg His Gly Phe Leu Pro Arg His
            20                  25

<210> SEQ ID NO 27
<211> LENGTH: 33
<212> TYPE: PRT
<213> ORGANISM: Homo sapiens
<220> FEATURE:
<221> NAME/KEY: MISC_FEATURE
<223> OTHER INFORMATION: MBP2b conjugatable
<220> FEATURE:
<221> NAME/KEY: MISC_FEATURE
<222> LOCATION: (30)..(33)
<223> OTHER INFORMATION: X is any amino acid

<400> SEQUENCE: 27

Gly Cys Arg Gly Gln Arg His Gly Ser Lys Tyr Leu Ala Thr Ala Ser
1               5                   10                  15

Thr Met Asp His Ala Arg His Gly Phe Leu Pro Arg His Xaa Xaa Xaa
            20                  25                  30

Xaa

<210> SEQ ID NO 28
<211> LENGTH: 17
<212> TYPE: PRT
<213> ORGANISM: Homo sapiens
<220> FEATURE:
<221> NAME/KEY: MISC_FEATURE
<223> OTHER INFORMATION: MBP83-99

<400> SEQUENCE: 28

Glu Asn Pro Val Val His Phe Phe Lys Asn Ile Val Thr Pro Arg Thr
1               5                   10                  15

Pro

<210> SEQ ID NO 29
<211> LENGTH: 25
<212> TYPE: PRT
<213> ORGANISM: Homo sapiens
<220> FEATURE:
<221> NAME/KEY: MISC_FEATURE
<223> OTHER INFORMATION: MBP3a conjugatable

<400> SEQUENCE: 29

Glu Asn Pro Val Val His Phe Phe Lys Asn Ile Val Thr Pro Arg Thr
1               5                   10                  15

Pro Pro Pro Ser Gln Gly Lys Cys Gly
            20                  25

<210> SEQ ID NO 30
<211> LENGTH: 29
<212> TYPE: PRT
<213> ORGANISM: Homo sapiens

```
<220> FEATURE:
<221> NAME/KEY: MISC_FEATURE
<223> OTHER INFORMATION: MBP3b conjugatable
<220> FEATURE:
<221> NAME/KEY: MISC_FEATURE
<222> LOCATION: (1)..(4)
<223> OTHER INFORMATION: X is any amino acid

<400> SEQUENCE: 30

Xaa Xaa Xaa Xaa Glu Asn Pro Val Val His Phe Phe Lys Asn Ile Val
1               5                   10                  15

Thr Pro Arg Thr Pro Pro Pro Ser Gln Gly Lys Cys Gly
            20                  25

<210> SEQ ID NO 31
<211> LENGTH: 19
<212> TYPE: PRT
<213> ORGANISM: Homo sapiens
<220> FEATURE:
<221> NAME/KEY: MISC_FEATURE
<223> OTHER INFORMATION: MBP111-129

<400> SEQUENCE: 31

Leu Ser Arg Phe Ser Trp Gly Ala Glu Gly Gln Arg Pro Gly Phe Gly
1               5                   10                  15

Tyr Gly Gly

<210> SEQ ID NO 32
<211> LENGTH: 22
<212> TYPE: PRT
<213> ORGANISM: Homo sapiens
<220> FEATURE:
<221> NAME/KEY: MISC_FEATURE
<223> OTHER INFORMATION: MBP4a conjugatable

<400> SEQUENCE: 32

Leu Ser Arg Phe Ser Trp Gly Ala Glu Gly Gln Arg Pro Gly Phe Gly
1               5                   10                  15

Tyr Gly Gly Arg Cys Gly
            20

<210> SEQ ID NO 33
<211> LENGTH: 23
<212> TYPE: PRT
<213> ORGANISM: Homo sapiens
<220> FEATURE:
<221> NAME/KEY: MISC_FEATURE
<223> OTHER INFORMATION: MBP4b conjugatable

<400> SEQUENCE: 33

Ser Leu Ser Arg Phe Ser Trp Gly Ala Glu Gly Gln Arg Pro Gly Phe
1               5                   10                  15

Gly Tyr Gly Gly Arg Cys Gly
            20

<210> SEQ ID NO 34
<211> LENGTH: 50
<212> TYPE: PRT
<213> ORGANISM: Homo sapiens
<220> FEATURE:
<221> NAME/KEY: MISC_FEATURE
<223> OTHER INFORMATION: MBP3+4 conjugatable

<400> SEQUENCE: 34

Glu Asn Pro Val Val His Phe Phe Lys Asn Ile Val Thr Pro Arg Thr
1               5                   10                  15
```

```
Pro Pro Pro Ser Gln Gly Lys Gly Arg Gly Leu Ser Leu Ser Arg Phe
            20                  25                  30

Ser Trp Gly Ala Glu Gly Gln Arg Pro Gly Phe Gly Tyr Gly Gly Arg
        35                  40                  45

Cys Gly
    50

<210> SEQ ID NO 35
<211> LENGTH: 55
<212> TYPE: PRT
<213> ORGANISM: Homo sapiens
<220> FEATURE:
<221> NAME/KEY: MISC_FEATURE
<223> OTHER INFORMATION: MBP dual 3-4

<400> SEQUENCE: 35

Gly Arg Thr Gln Asp Glu Asn Pro Val Val His Phe Phe Lys Asn Ile
1               5                   10                  15

Val Thr Pro Arg Thr Pro Pro Ser Gln Gly Lys Gly Arg Gly Leu
            20                  25                  30

Ser Leu Ser Arg Phe Ser Trp Gly Ala Glu Gly Gln Arg Pro Gly Phe
            35                  40                  45

Gly Tyr Gly Gly Arg Cys Gly
    50                  55

<210> SEQ ID NO 36
<211> LENGTH: 59
<212> TYPE: PRT
<213> ORGANISM: Homo sapiens
<220> FEATURE:
<221> NAME/KEY: MISC_FEATURE
<223> OTHER INFORMATION: MBP dual 3+4c conjugatable
<220> FEATURE:
<221> NAME/KEY: MISC_FEATURE
<222> LOCATION: (53)..(57)
<223> OTHER INFORMATION: X is any amino acid

<400> SEQUENCE: 36

Gly Arg Thr Gln Asp Glu Asn Pro Val Val His Phe Phe Lys Asn Ile
1               5                   10                  15

Val Thr Pro Arg Thr Pro Pro Ser Gln Gly Lys Gly Arg Gly Leu
            20                  25                  30

Ser Leu Ser Arg Phe Ser Trp Gly Ala Glu Gly Gln Arg Pro Gly Phe
            35                  40                  45

Gly Tyr Gly Gly Xaa Xaa Xaa Xaa Arg Cys Gly
    50                  55

<210> SEQ ID NO 37
<211> LENGTH: 25
<212> TYPE: PRT
<213> ORGANISM: Homo sapiens
<220> FEATURE:
<221> NAME/KEY: MISC_FEATURE
<223> OTHER INFORMATION: MBP146-170

<400> SEQUENCE: 37

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 38
```

```
<211> LENGTH: 27
<212> TYPE: PRT
<213> ORGANISM: Homo sapiens
<220> FEATURE:
<221> NAME/KEY: MISC_FEATURE
<223> OTHER INFORMATION: MBP5a conjuagatable

<400> SEQUENCE: 38

Ala Gln Gly Thr Leu Ser Lys Ile Phe Lys Leu Gly Gly Arg Asp Ser
1               5                   10                  15

Arg Ser Gly Ser Pro Met Ala Arg Arg Cys Gly
            20                  25

<210> SEQ ID NO 39
<211> LENGTH: 31
<212> TYPE: PRT
<213> ORGANISM: Homo sapiens
<220> FEATURE:
<221> NAME/KEY: MISC_FEATURE
<223> OTHER INFORMATION: MBP5b conjugatable
<220> FEATURE:
<221> NAME/KEY: MISC_FEATURE
<222> LOCATION: (1)..(4)
<223> OTHER INFORMATION: X is any amino acid

<400> SEQUENCE: 39

Xaa Xaa Xaa Xaa Ala Gln Gly Thr Leu Ser Lys Ile Phe Lys Leu Gly
1               5                   10                  15

Gly Arg Asp Ser Arg Ser Gly Ser Pro Met Ala Arg Arg Cys Gly
            20                  25                  30

<210> SEQ ID NO 40
<211> LENGTH: 20
<212> TYPE: PRT
<213> ORGANISM: Homo sapiens
<220> FEATURE:
<221> NAME/KEY: MISC_FEATURE
<223> OTHER INFORMATION: MOG1-20

<400> SEQUENCE: 40

Gly Gln Phe Arg Val Ile Gly Pro Arg His Pro Ile Arg Ala Leu Val
1               5                   10                  15

Gly Asp Glu Val
            20

<210> SEQ ID NO 41
<211> LENGTH: 27
<212> TYPE: PRT
<213> ORGANISM: Homo sapiens
<220> FEATURE:
<221> NAME/KEY: MISC_FEATURE
<223> OTHER INFORMATION: MOG6a conjugatable

<400> SEQUENCE: 41

Gly Gln Phe Arg Val Ile Gly Pro Arg His Pro Ile Arg Ala Leu Val
1               5                   10                  15

Gly Asp Glu Val Glu Leu Pro Cys Arg Ile Ser
            20                  25

<210> SEQ ID NO 42
<211> LENGTH: 34
<212> TYPE: PRT
<213> ORGANISM: Homo sapiens
<220> FEATURE:
<221> NAME/KEY: MISC_FEATURE
<223> OTHER INFORMATION: MOG 7b conjugatable
<220> FEATURE:
```

<221> NAME/KEY: MISC_FEATURE
<222> LOCATION: (31)..(34)
<223> OTHER INFORMATION: X is any amino acid

<400> SEQUENCE: 42

Gly Cys Arg Gly Lys Asn Ala Thr Gly Met Glu Val Gly Trp Tyr Arg
1               5                   10                  15

Pro Pro Phe Ser Arg Val Val His Leu Tyr Arg Asn Gly Lys Xaa Xaa
            20                  25                  30

Xaa Xaa

<210> SEQ ID NO 43
<211> LENGTH: 38
<212> TYPE: PRT
<213> ORGANISM: Homo sapiens
<220> FEATURE:
<221> NAME/KEY: MISC_FEATURE
<223> OTHER INFORMATION: MOG 7c Conjugatable
<220> FEATURE:
<221> NAME/KEY: MISC_FEATURE
<222> LOCATION: (1)..(4)
<223> OTHER INFORMATION: X is any amino acid
<220> FEATURE:
<221> NAME/KEY: MISC_FEATURE
<222> LOCATION: (35)..(38)
<223> OTHER INFORMATION: X is any amino acid

<400> SEQUENCE: 43

Xaa Xaa Xaa Xaa Gly Cys Arg Gly Lys Asn Ala Thr Gly Met Glu Val
1               5                   10                  15

Gly Trp Tyr Arg Pro Pro Phe Ser Arg Val Val His Leu Tyr Arg Asn
            20                  25                  30

Gly Lys Xaa Xaa Xaa Xaa
        35

<210> SEQ ID NO 44
<211> LENGTH: 55
<212> TYPE: PRT
<213> ORGANISM: Homo sapiens
<220> FEATURE:
<221> NAME/KEY: MISC_FEATURE
<223> OTHER INFORMATION: MOG6+7 conjugatable

<400> SEQUENCE: 44

Gly Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys
    50                  55

<210> SEQ ID NO 45
<211> LENGTH: 59
<212> TYPE: PRT
<213> ORGANISM: Homo sapiens
<220> FEATURE:
<221> NAME/KEY: MISC_FEATURE
<223> OTHER INFORMATION: MOG 6+7 inverted optional repeats
<220> FEATURE:
<221> NAME/KEY: MISC_FEATURE
<222> LOCATION: (1)..(4)
<223> OTHER INFORMATION: X is any amino acid

<400> SEQUENCE: 45

```
Xaa Xaa Xaa Xaa Gly Gln Phe Arg Val Ile Gly Pro Arg His Pro Ile
1               5                   10                  15

Arg Ala Leu Val Gly Asp Glu Val Glu Leu Pro Cys Arg Ile Ser Pro
                20                  25                  30

Gly Lys Asn Ala Thr Gly Met Glu Val Gly Trp Tyr Arg Pro Pro Phe
            35                  40                  45

Ser Arg Val Val His Leu Tyr Arg Asn Gly Lys
        50                  55
```

<210> SEQ ID NO 46
<211> LENGTH: 59
<212> TYPE: PRT
<213> ORGANISM: Homo sapiens
<220> FEATURE:
<221> NAME/KEY: MISC_FEATURE
<223> OTHER INFORMATION: MOG 6+7c conjugatable
<220> FEATURE:
<221> NAME/KEY: MISC_FEATURE
<223> OTHER INFORMATION: MOG 6+7b conjugatable
<220> FEATURE:
<221> NAME/KEY: MISC_FEATURE
<222> LOCATION: (56)..(59)
<223> OTHER INFORMATION: X is any amino acid

<400> SEQUENCE: 46

```
Gly Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
                20                  25                  30

Thr Gly Met Glu Val Gly Trp Tyr Arg Pro Pro Phe Ser Arg Val Val
            35                  40                  45

His Leu Tyr Arg Asn Gly Lys Xaa Xaa Xaa Xaa
        50                  55
```

<210> SEQ ID NO 47
<211> LENGTH: 7
<212> TYPE: PRT
<213> ORGANISM: Homo sapiens
<220> FEATURE:
<221> NAME/KEY: MISC_FEATURE
<223> OTHER INFORMATION: root gliadin

<400> SEQUENCE: 47

```
Pro Gln Pro Glu Leu Pro Tyr
1               5
```

<210> SEQ ID NO 48
<211> LENGTH: 86
<212> TYPE: PRT
<213> ORGANISM: Homo sapiens
<220> FEATURE:
<221> NAME/KEY: MISC_FEATURE
<223> OTHER INFORMATION: pro-insulin

<400> SEQUENCE: 48

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60
```

```
Arg Gly Ile Val Glu Gln Cys Cys Thr Ser Ile Cys Ser Leu Tyr Gln
 65                  70                  75                  80

Leu Glu Asn Tyr Cys Asn
                85

<210> SEQ ID NO 49
<211> LENGTH: 70
<212> TYPE: PRT
<213> ORGANISM: Homo sapiens
<220> FEATURE:
<221> NAME/KEY: MISC_FEATURE
<223> OTHER INFORMATION: human pro-insulin 1-70

<400> SEQUENCE: 49

Phe Val Asn Gln His Leu Cys Gly Ser His Leu Val Glu Ala Leu Tyr
  1               5                  10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln
 65                  70

<210> SEQ ID NO 50
<211> LENGTH: 62
<212> TYPE: PRT
<213> ORGANISM: Homo sapiens
<220> FEATURE:
<221> NAME/KEY: MISC_FEATURE
<223> OTHER INFORMATION: human proinsulin 1-70
<220> FEATURE:
<221> NAME/KEY: MISC_FEATURE
<223> OTHER INFORMATION: human proinsulin 9-70

<400> SEQUENCE: 50

Ser His Leu Val Glu Ala Leu Tyr Leu Val Cys Gly Glu Arg Gly Phe
  1               5                  10                  15

Phe Tyr Thr Pro Lys Thr Arg Arg Glu Ala Glu Asp Leu Gln Val Gly
                20                  25                  30

Gln Val Glu Leu Gly Gly Gly Pro Gly Ala Gly Ser Leu Gln Pro Leu
            35                  40                  45

Ala Leu Glu Gly Ser Leu Gln Lys Arg Gly Ile Val Glu Gln
        50                  55                  60

<210> SEQ ID NO 51
<211> LENGTH: 30
<212> TYPE: PRT
<213> ORGANISM: Homo sapiens
<220> FEATURE:
<221> NAME/KEY: MISC_FEATURE
<223> OTHER INFORMATION: Proinsulin 9-38

<400> SEQUENCE: 51

Ser His Leu Val Glu Ala Leu Tyr Leu Val Cys Gly Glu Arg Gly Phe
  1               5                  10                  15

Phe Tyr Thr Pro Lys Thr Arg Arg Glu Ala Glu Asp Leu Gln
                20                  25                  30

<210> SEQ ID NO 52
<211> LENGTH: 38
```

```
<212> TYPE: PRT
<213> ORGANISM: Homo sapiens
<220> FEATURE:
<221> NAME/KEY: MISC_FEATURE
<223> OTHER INFORMATION: prosinuslin 1-38

<400> SEQUENCE: 52

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln
        35

<210> SEQ ID NO 53
<211> LENGTH: 15
<212> TYPE: PRT
<213> ORGANISM: Homo sapiens
<220> FEATURE:
<221> NAME/KEY: MISC_FEATURE
<223> OTHER INFORMATION: proinsulin 9-23

<400> SEQUENCE: 53

Ser His Leu Val Glu Ala Leu Tyr Leu Val Cys Gly Glu Arg Gly
1               5                   10                  15

<210> SEQ ID NO 54
<211> LENGTH: 27
<212> TYPE: PRT
<213> ORGANISM: Homo sapiens
<220> FEATURE:
<221> NAME/KEY: MISC_FEATURE
<223> OTHER INFORMATION: Human proinsulin C13-A6)

<400> SEQUENCE: 54

Gly Gly Gly Pro Gly Ala Gly Ser Leu Gln Pro Leu Ala Leu Glu Gly
1               5                   10                  15

Ser Leu Gln Lys Arg Gly Ile Val Glu Gln Cys
            20                  25

<210> SEQ ID NO 55
<211> LENGTH: 11
<212> TYPE: PRT
<213> ORGANISM: Homo sapiens
<220> FEATURE:
<221> NAME/KEY: MISC_FEATURE
<223> OTHER INFORMATION: Human proinsulin C24-A1

<400> SEQUENCE: 55

Leu Ala Leu Glu Gly Ser Leu Gln Lys Arg Gly
1               5                   10

<210> SEQ ID NO 56
<211> LENGTH: 18
<212> TYPE: PRT
<213> ORGANISM: Homo sapiens
<220> FEATURE:
<221> NAME/KEY: MISC_FEATURE
<223> OTHER INFORMATION: Human proinsulin C19-A3

<400> SEQUENCE: 56

Gly Ser Leu Gln Pro Leu Ala Leu Glu Gly Ser Leu Gln Lys Arg Gly
1               5                   10                  15

Ile Val
```

```
<210> SEQ ID NO 57
<211> LENGTH: 20
<212> TYPE: PRT
<213> ORGANISM: Homo sapiens
<220> FEATURE:
<221> NAME/KEY: MISC_FEATURE
<223> OTHER INFORMATION: Human Proinsulin C13-32

<400> SEQUENCE: 57

Gly Gly Gly Pro Gly Ala Gly Ser Leu Gln Pro Leu Ala Leu Glu Gly
1               5                   10                  15

Ser Leu Gln Lys
            20

<210> SEQ ID NO 58
<211> LENGTH: 28
<212> TYPE: PRT
<213> ORGANISM: Homo sapiens
<220> FEATURE:
<221> NAME/KEY: MISC_FEATURE
<223> OTHER INFORMATION: Human proinsulin B9-C4

<400> SEQUENCE: 58

Ser His Leu Val Glu Ala Leu Tyr Leu Val Cys Gly Glu Arg Gly Phe
1               5                   10                  15

Phe Tyr Thr Pro Lys Thr Arg Arg Glu Ala Glu Asp
            20                  25

<210> SEQ ID NO 59
<211> LENGTH: 17
<212> TYPE: PRT
<213> ORGANISM: Homo sapiens
<220> FEATURE:
<221> NAME/KEY: MISC_FEATURE
<223> OTHER INFORMATION: Human Proinsulin C22-A5

<400> SEQUENCE: 59

Gln Pro Leu Ala Leu Glu Gly Ser Leu Gln Lys Arg Gly Ile Val Glu
1               5                   10                  15

Gln

<210> SEQ ID NO 60
<211> LENGTH: 110
<212> TYPE: PRT
<213> ORGANISM: Homo sapiens
<220> FEATURE:
<221> NAME/KEY: MISC_FEATURE
<223> OTHER INFORMATION: Pre-proinsulin

<400> SEQUENCE: 60

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
```

<210> SEQ ID NO 61
<211> LENGTH: 19
<212> TYPE: PRT
<213> ORGANISM: Homo sapiens
<220> FEATURE:
<221> NAME/KEY: MISC_FEATURE
<223> OTHER INFORMATION: IA2 sequence 1

<400> SEQUENCE: 61

Ala Tyr Gln Ala Glu Pro Asn Thr Cys Ala Thr Ala Gln Gly Glu Gly
1               5                   10                  15

Asn Ile Lys

<210> SEQ ID NO 62
<211> LENGTH: 24
<212> TYPE: PRT
<213> ORGANISM: Homo sapiens
<220> FEATURE:
<221> NAME/KEY: MISC_FEATURE
<223> OTHER INFORMATION: IA2 Seqeunce 2

<400> SEQUENCE: 62

Lys Leu Lys Val Glu Ser Ser Pro Ser Arg Ser Asp Tyr Ile Asn Ala
1               5                   10                  15

Ser Pro Ile Ile Glu His Asp Pro
            20

<210> SEQ ID NO 63
<211> LENGTH: 13
<212> TYPE: PRT
<213> ORGANISM: Homo sapiens
<220> FEATURE:
<221> NAME/KEY: MISC_FEATURE
<223> OTHER INFORMATION: IA2 sequence 3

<400> SEQUENCE: 63

Tyr Leu Lys Asn Val Gln Thr Gln Glu Thr Arg Thr Leu
1               5                   10

<210> SEQ ID NO 64
<211> LENGTH: 20
<212> TYPE: PRT
<213> ORGANISM: Homo sapiens
<220> FEATURE:
<221> NAME/KEY: MISC_FEATURE
<223> OTHER INFORMATION: IA2 sequence 4

<400> SEQUENCE: 64

Gly Gly Gly Pro Gly Ala Gly Ser Leu Gln Pro Leu Ala Leu Glu Gly
1               5                   10                  15

Ser Leu Gln Lys
            20

<210> SEQ ID NO 65
<211> LENGTH: 18
<212> TYPE: PRT
<213> ORGANISM: Homo sapiens
<220> FEATURE:
<221> NAME/KEY: MISC_FEATURE
<223> OTHER INFORMATION: IA2 sequence 5

<400> SEQUENCE: 65

Gly Ser Leu Gln Pro Leu Ala Leu Glu Gly Ser Leu Gln Lys Arg Gly
1               5                   10                  15

Ile Val

<210> SEQ ID NO 66
<211> LENGTH: 17
<212> TYPE: PRT
<213> ORGANISM: Homo sapiens
<220> FEATURE:
<221> NAME/KEY: MISC_FEATURE
<223> OTHER INFORMATION: IA2 sequence 6

<400> SEQUENCE: 66

Gln Pro Leu Ala Leu Glu Gly Ser Leu Gln Lys Arg Gly Ile Val Glu
1               5                   10                  15

Gln

<210> SEQ ID NO 67
<211> LENGTH: 20
<212> TYPE: PRT
<213> ORGANISM: Homo sapiens
<220> FEATURE:
<221> NAME/KEY: MISC_FEATURE
<223> OTHER INFORMATION: T1D related antigen 1

<400> SEQUENCE: 67

Gly Gly Gly Pro Gly Ala Gly Ser Leu Gln Pro Leu Ala Leu Glu Gly
1               5                   10                  15

Ser Leu Gln Lys
            20

<210> SEQ ID NO 68
<211> LENGTH: 18
<212> TYPE: PRT
<213> ORGANISM: Homo sapiens
<220> FEATURE:
<221> NAME/KEY: MISC_FEATURE
<223> OTHER INFORMATION: T1D related antigen 2

<400> SEQUENCE: 68

Gly Ser Leu Gln Pro Leu Ala Leu Glu Gly Ser Leu Gln Lys Arg Gly
1               5                   10                  15

Ile Val

<210> SEQ ID NO 69
<211> LENGTH: 17
<212> TYPE: PRT
<213> ORGANISM: Homo sapiens
<220> FEATURE:
<221> NAME/KEY: MISC_FEATURE
<223> OTHER INFORMATION: T1D related antigen #3

<400> SEQUENCE: 69

Gln Pro Leu Ala Leu Glu Gly Ser Leu Gln Lys Arg Gly Ile Val Glu
1               5                   10                  15

Gln

<210> SEQ ID NO 70
<211> LENGTH: 11
<212> TYPE: PRT
<213> ORGANISM: Homo sapiens
<220> FEATURE:
<221> NAME/KEY: MISC_FEATURE
<223> OTHER INFORMATION: T1D related antigen 4

<400> SEQUENCE: 70

```
Gln Pro Leu Ala Leu Glu Gly Ser Leu Gln Lys
1               5                   10
```

<210> SEQ ID NO 71
<211> LENGTH: 26
<212> TYPE: PRT
<213> ORGANISM: Homo sapiens
<220> FEATURE:
<221> NAME/KEY: MISC_FEATURE
<223> OTHER INFORMATION: T1D related antigen 5

<400> SEQUENCE: 71

```
Gly Gly Gly Pro Gly Ala Gly Ser Leu Gln Pro Leu Ala Leu Glu Gly
1               5                   10                  15

Ser Leu Gln Lys Arg Gly Ile Val Glu Gln
            20                  25
```

<210> SEQ ID NO 72
<211> LENGTH: 62
<212> TYPE: PRT
<213> ORGANISM: Homo sapiens
<220> FEATURE:
<221> NAME/KEY: MISC_FEATURE
<223> OTHER INFORMATION: MOG1-62 combined

<400> SEQUENCE: 72

```
Gly Gln Phe Arg Val Ile Gly Pro Arg His Pro Ile Arg Ala Leu Val
1               5                   10                  15

Gly Asp Glu Val Glu Leu Pro Cys Arg Ile Ser Pro Gly Lys Asn Ala
            20                  25                  30

Thr Gly Met Glu Val Gly Trp Tyr Arg Pro Pro Phe Ser Arg Val Val
        35                  40                  45

His Leu Tyr Arg Asn Gly Lys Asp Gln Asp Gly Asp Gln Ala
    50                  55                  60
```

<210> SEQ ID NO 73
<211> LENGTH: 32
<212> TYPE: PRT
<213> ORGANISM: Homo sapiens
<220> FEATURE:
<221> NAME/KEY: MISC_FEATURE
<223> OTHER INFORMATION: MBP7-39

<400> SEQUENCE: 73

```
Gln Arg His Gly Ser Lys Tyr Leu Ala Thr Ala Ser Thr Met Asp His
1               5                   10                  15

Ala Arg His Gly Phe Leu Pro Arg His Arg Asp Thr Gly Ile Leu Asp
            20                  25                  30
```

<210> SEQ ID NO 74
<211> LENGTH: 95
<212> TYPE: PRT
<213> ORGANISM: Homo sapiens
<220> FEATURE:
<221> NAME/KEY: MISC_FEATURE
<223> OTHER INFORMATION: MBP 76-170

<400> SEQUENCE: 74

```
Ser His Gly Arg Thr Gln Asp Glu Asn Pro Val Val His Phe Phe Lys
1               5                   10                  15

Asn Ile Val Thr Pro Arg Thr Pro Pro Ser Gln Gly Lys Gly Arg
            20                  25                  30

Gly Leu Ser Leu Ser Arg Phe Ser Trp Gly Ala Glu Gly Gln Arg Pro
        35                  40                  45
```

```
Gly Phe Gly Tyr Gly Gly Arg Ala Ser Asp Tyr Lys Ser Ala His Lys
    50                  55                  60

Gly Phe Lys Gly Val Asp Ala Gln Gly Thr Leu Ser Lys Ile Phe Lys
65                  70                  75                  80

Leu Gly Gly Arg Asp Ser Arg Ser Gly Ser Pro Met Ala Arg Arg
                85                  90                  95

<210> SEQ ID NO 75
<211> LENGTH: 16
<212> TYPE: PRT
<213> ORGANISM: Homo sapiens
<220> FEATURE:
<221> NAME/KEY: MISC_FEATURE
<223> OTHER INFORMATION: PLP 139-154

<400> SEQUENCE: 75

His Cys Leu Gly Lys Trp Leu Gly His Pro Asp Lys Phe Val Gly Ile
1               5                   10                  15

<210> SEQ ID NO 76
<211> LENGTH: 140
<212> TYPE: PRT
<213> ORGANISM: Homo sapiens
<220> FEATURE:
<221> NAME/KEY: MISC_FEATURE
<223> OTHER INFORMATION: alpha synuclein full

<400> SEQUENCE: 76

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 77
<211> LENGTH: 110
<212> TYPE: PRT
<213> ORGANISM: Homo sapiens
<220> FEATURE:
<221> NAME/KEY: MISC_FEATURE
<223> OTHER INFORMATION: alpha synuclein 31-140

<400> SEQUENCE: 77

Gly Lys Thr Lys Glu Gly Val Leu Tyr Val Gly Ser Lys Thr Lys Glu
1               5                   10                  15

Gly Val Val His Gly Val Ala Thr Val Ala Glu Lys Thr Lys Glu Gln
            20                  25                  30
```

Val Thr Asn Val Gly Gly Ala Val Thr Gly Val Thr Ala Val Ala
        35                  40                  45

Gln Lys Thr Val Glu Gly Ala Gly Ser Ile Ala Ala Thr Gly Phe
 50                  55                  60

Val Lys Lys Asp Gln Leu Gly Lys Asn Glu Glu Gly Ala Pro Gln Glu
 65                  70                  75                  80

Gly Ile Leu Glu Asp Met Pro Val Asp Pro Asp Asn Glu Ala Tyr Glu
                    85                  90                  95

Met Pro Ser Glu Glu Gly Tyr Gln Asp Tyr Glu Pro Glu Ala
                100                 105                 110

<210> SEQ ID NO 78
<211> LENGTH: 109
<212> TYPE: PRT
<213> ORGANISM: Homo sapiens
<220> FEATURE:
<221> NAME/KEY: MISC_FEATURE
<223> OTHER INFORMATION: alpha synuclein 32-140

<400> SEQUENCE: 78

Lys Thr Lys Glu Gly Val Leu Tyr Val Gly Ser Lys Thr Lys Glu Gly
 1                   5                  10                  15

Val Val His Gly Val Ala Thr Val Ala Glu Lys Thr Lys Glu Gln Val
                    20                  25                  30

Thr Asn Val Gly Gly Ala Val Val Thr Gly Val Thr Ala Val Ala Gln
                    35                  40                  45

Lys Thr Val Glu Gly Ala Gly Ser Ile Ala Ala Ala Thr Gly Phe Val
 50                  55                  60

Lys Lys Asp Gln Leu Gly Lys Asn Glu Glu Gly Ala Pro Gln Glu Gly
 65                  70                  75                  80

Ile Leu Glu Asp Met Pro Val Asp Pro Asp Asn Glu Ala Tyr Glu Met
                    85                  90                  95

Pro Ser Glu Glu Gly Tyr Gln Asp Tyr Glu Pro Glu Ala
                100                 105

<210> SEQ ID NO 79
<211> LENGTH: 108
<212> TYPE: PRT
<213> ORGANISM: Homo sapiens
<220> FEATURE:
<221> NAME/KEY: MISC_FEATURE
<223> OTHER INFORMATION: alpha synuclein 33-140

<400> SEQUENCE: 79

Thr Lys Glu Gly Val Leu Tyr Val Gly Ser Lys Thr Lys Glu Gly Val
 1                   5                  10                  15

Val His Gly Val Ala Thr Val Ala Glu Lys Thr Lys Glu Gln Val Thr
                    20                  25                  30

Asn Val Gly Gly Ala Val Val Thr Gly Val Thr Ala Val Ala Gln Lys
                    35                  40                  45

Thr Val Glu Gly Ala Gly Ser Ile Ala Ala Ala Thr Gly Phe Val Lys
                    50                  55                  60

Lys Asp Gln Leu Gly Lys Asn Glu Glu Gly Ala Pro Gln Glu Gly Ile
 65                  70                  75                  80

Leu Glu Asp Met Pro Val Asp Pro Asp Asn Glu Ala Tyr Glu Met Pro
                    85                  90                  95

Ser Glu Glu Gly Tyr Gln Asp Tyr Glu Pro Glu Ala
                100                 105

<210> SEQ ID NO 80
<211> LENGTH: 97
<212> TYPE: PRT
<213> ORGANISM: Homo sapiens
<220> FEATURE:
<221> NAME/KEY: MISC_FEATURE
<223> OTHER INFORMATION: alpha synuclein 44-140

<400> SEQUENCE: 80

Thr Lys Glu Gly Val Val His Gly Val Ala Thr Val Ala Glu Lys Thr
1               5                   10                  15

Lys Glu Gln Val Thr Asn Val Gly Gly Ala Val Val Thr Gly Val Thr
            20                  25                  30

Ala Val Ala Gln Lys Thr Val Glu Gly Ala Gly Ser Ile Ala Ala Ala
        35                  40                  45

Thr Gly Phe Val Lys Lys Asp Gln Leu Gly Lys Asn Glu Glu Gly Ala
    50                  55                  60

Pro Gln Glu Gly Ile Leu Glu Asp Met Pro Val Asp Pro Asp Asn Glu
65                  70                  75                  80

Ala Tyr Glu Met Pro Ser Glu Glu Gly Tyr Gln Asp Tyr Glu Pro Glu
                85                  90                  95

Ala

<210> SEQ ID NO 81
<211> LENGTH: 79
<212> TYPE: PRT
<213> ORGANISM: Homo sapiens
<220> FEATURE:
<221> NAME/KEY: MISC_FEATURE
<223> OTHER INFORMATION: alpha synuclein 62-140

<400> SEQUENCE: 81

Gln Val Thr Asn Val Gly Gly Ala Val Val Thr Gly Val Thr Ala Val
1               5                   10                  15

Ala Gln Lys Thr Val Glu Gly Ala Gly Ser Ile Ala Ala Ala Thr Gly
            20                  25                  30

Phe Val Lys Lys Asp Gln Leu Gly Lys Asn Glu Glu Gly Ala Pro Gln
        35                  40                  45

Glu Gly Ile Leu Glu Asp Met Pro Val Asp Pro Asp Asn Glu Ala Tyr
    50                  55                  60

Glu Met Pro Ser Glu Glu Gly Tyr Gln Asp Tyr Glu Pro Glu Ala
65                  70                  75

<210> SEQ ID NO 82
<211> LENGTH: 78
<212> TYPE: PRT
<213> ORGANISM: Homo sapiens
<220> FEATURE:
<221> NAME/KEY: MISC_FEATURE
<223> OTHER INFORMATION: alpha synuclein 63-140

<400> SEQUENCE: 82

Val Thr Asn Val Gly Gly Ala Val Val Thr Gly Val Thr Ala Val Ala
1               5                   10                  15

Gln Lys Thr Val Glu Gly Ala Gly Ser Ile Ala Ala Ala Thr Gly Phe
            20                  25                  30

Val Lys Lys Asp Gln Leu Gly Lys Asn Glu Glu Gly Ala Pro Gln Glu
        35                  40                  45

Gly Ile Leu Glu Asp Met Pro Val Asp Pro Asp Asn Glu Ala Tyr Glu
    50                  55                  60

```
Met Pro Ser Glu Glu Gly Tyr Gln Asp Tyr Glu Pro Glu Ala
 65                  70                  75
```

<210> SEQ ID NO 83
<211> LENGTH: 41
<212> TYPE: PRT
<213> ORGANISM: Homo sapiens
<220> FEATURE:
<221> NAME/KEY: MISC_FEATURE
<223> OTHER INFORMATION: alpha synuclein 100-140

<400> SEQUENCE: 83

```
Leu Gly Lys Asn Glu Glu Gly Ala Pro Gln Glu Gly Ile Leu Glu Asp
  1               5                  10                  15

Met Pro Val Asp Pro Asp Asn Glu Ala Tyr Glu Met Pro Ser Glu Glu
             20                  25                  30

Gly Tyr Gln Asp Tyr Glu Pro Glu Ala
             35                  40
```

<210> SEQ ID NO 84
<211> LENGTH: 34
<212> TYPE: PRT
<213> ORGANISM: Homo sapiens
<220> FEATURE:
<221> NAME/KEY: MISC_FEATURE
<223> OTHER INFORMATION: alpha synuclein 67-100

<400> SEQUENCE: 84

```
Gly Gly Ala Val Val Thr Gly Val Thr Ala Val Ala Gln Lys Thr Val
  1               5                  10                  15

Glu Gly Ala Gly Ser Ile Ala Ala Ala Thr Gly Phe Val Lys Lys Asp
             20                  25                  30

Gln Leu
```

<210> SEQ ID NO 85
<211> LENGTH: 25
<212> TYPE: PRT
<213> ORGANISM: Homo sapiens
<220> FEATURE:
<221> NAME/KEY: MISC_FEATURE
<223> OTHER INFORMATION: alpha synuclein 116-140

<400> SEQUENCE: 85

```
Met Pro Val Asp Pro Asp Asn Glu Ala Tyr Glu Met Pro Ser Glu Glu
  1               5                  10                  15

Gly Tyr Gln Asp Tyr Glu Pro Glu Ala
             20                  25
```

<210> SEQ ID NO 86
<211> LENGTH: 15
<212> TYPE: PRT
<213> ORGANISM: Homo sapiens
<220> FEATURE:
<221> NAME/KEY: MISC_FEATURE
<223> OTHER INFORMATION: alpha synuclein 116-130

<400> SEQUENCE: 86

```
Met Pro Val Asp Pro Asp Asn Glu Ala Tyr Glu Met Pro Ser Glu
  1               5                  10                  15
```

<210> SEQ ID NO 87
<211> LENGTH: 15
<212> TYPE: PRT
<213> ORGANISM: Homo sapiens

```
<220> FEATURE:
<221> NAME/KEY: MISC_FEATURE
<223> OTHER INFORMATION: alpha synuclein 126-140

<400> SEQUENCE: 87

Glu Met Pro Ser Glu Glu Gly Tyr Gln Asp Tyr Glu Pro Glu Ala
1               5                   10                  15

<210> SEQ ID NO 88
<211> LENGTH: 15
<212> TYPE: PRT
<213> ORGANISM: Homo sapiens
<220> FEATURE:
<221> NAME/KEY: MISC_FEATURE
<223> OTHER INFORMATION: alpha synuclein 119-133

<400> SEQUENCE: 88

Asp Asn Glu Ala Tyr Glu Met Pro Ser Glu Glu Gly Tyr Gln Asp
1               5                   10                  15

<210> SEQ ID NO 89
<211> LENGTH: 20
<212> TYPE: PRT
<213> ORGANISM: Homo sapiens
<220> FEATURE:
<221> NAME/KEY: MISC_FEATURE
<223> OTHER INFORMATION: alpha synuclein 31-50

<400> SEQUENCE: 89

Gly Lys Thr Lys Glu Gly Val Leu Tyr Val Gly Ser Lys Thr Lys Glu
1               5                   10                  15

Gly Val Val His
            20

<210> SEQ ID NO 90
<211> LENGTH: 15
<212> TYPE: PRT
<213> ORGANISM: Homo sapiens
<220> FEATURE:
<221> NAME/KEY: MISC_FEATURE
<223> OTHER INFORMATION: alpha synuclein 36-50

<400> SEQUENCE: 90

Gly Val Leu Tyr Val Gly Ser Lys Thr Lys Glu Gly Val Val His
1               5                   10                  15

<210> SEQ ID NO 91
<211> LENGTH: 15
<212> TYPE: PRT
<213> ORGANISM: Homo sapiens
<220> FEATURE:
<221> NAME/KEY: MISC_FEATURE
<223> OTHER INFORMATION: alpha synuclein 31-45

<400> SEQUENCE: 91

Gly Lys Thr Lys Glu Gly Val Leu Tyr Val Gly Ser Lys Thr Lys
1               5                   10                  15

<210> SEQ ID NO 92
<211> LENGTH: 14
<212> TYPE: PRT
<213> ORGANISM: Homo sapiens

<400> SEQUENCE: 92

Gly Lys Thr Lys Glu Gly Val Leu Tyr Val Gly Ser Lys Thr
1               5                   10
```

```
<210> SEQ ID NO 93
<211> LENGTH: 15
<212> TYPE: PRT
<213> ORGANISM: Homo sapiens
<220> FEATURE:
<221> NAME/KEY: MISC_FEATURE
<223> OTHER INFORMATION: alpha synuclein 32-46

<400> SEQUENCE: 93

Lys Thr Lys Glu Gly Val Leu Tyr Val Gly Ser Lys Thr Lys Glu
1               5                   10                  15

<210> SEQ ID NO 94
<211> LENGTH: 10
<212> TYPE: PRT
<213> ORGANISM: Homo sapiens
<220> FEATURE:
<221> NAME/KEY: MISC_FEATURE
<223> OTHER INFORMATION: alpha synuclein 36-45

<400> SEQUENCE: 94

Gly Val Leu Tyr Val Gly Ser Lys Thr Lys
1               5                   10

<210> SEQ ID NO 95
<211> LENGTH: 9
<212> TYPE: PRT
<213> ORGANISM: Homo sapiens
<220> FEATURE:
<221> NAME/KEY: MISC_FEATURE
<223> OTHER INFORMATION: alpha synuclein 32-40

<400> SEQUENCE: 95

Lys Thr Lys Glu Gly Val Leu Tyr Val
1               5

<210> SEQ ID NO 96
<211> LENGTH: 9
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 96

Val Asp Pro Asp Asn Glu Ala Tyr Glu
1               5

<210> SEQ ID NO 97
<211> LENGTH: 135
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 97

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60
```

```
Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp
        130                 135

<210> SEQ ID NO 98
<211> LENGTH: 119
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 98

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
                 20                  25                  30

Thr Lys Glu Gly Val Leu Tyr Val Gly Ser Lys Thr Lys Glu Gly Val
             35                  40                  45

Val His Gly Val Ala Thr Val Ala Glu Lys Thr Lys Glu Gln Val Thr
     50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp
            115

<210> SEQ ID NO 99
<211> LENGTH: 122
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 99

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
                 20                  25                  30

Thr Lys Glu Gly Val Leu Tyr Val Gly Ser Lys Thr Lys Glu Gly Val
             35                  40                  45

Val His Gly Val Ala Thr Val Ala Glu Lys Thr Lys Glu Gln Val Thr
     50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95
```

Lys Asp Gln Leu Gly Lys Asn Glu Glu Gly Ala Pro Gln Glu Gly Ile
            100                 105                 110

Leu Glu Asp Met Pro Val Asp Pro Asp Asn
        115                 120

<210> SEQ ID NO 100
<211> LENGTH: 30
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 100

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala
            20                  25                  30

<210> SEQ ID NO 101
<211> LENGTH: 36
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 101

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly
        35

<210> SEQ ID NO 102
<211> LENGTH: 36
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 102

Thr Ala Val Ala Gln Lys Thr Val Glu Gly Ala Gly Ser Ile Ala Ala
1               5                   10                  15

Ala Thr Gly Phe Val Lys Lys Asp Gln Leu Gly Lys Asn Glu Glu Gly
            20                  25                  30

Ala Pro Gln Glu
        35

<210> SEQ ID NO 103
<211> LENGTH: 66
<212> TYPE: PRT
<213> ORGANISM: Homo sapiens
<220> FEATURE:
<221> NAME/KEY: MISC_FEATURE
<223> OTHER INFORMATION: AS candidate

<400> SEQUENCE: 103

Thr Ala Val Ala Gln Lys Thr Val Glu Gly Ala Gly Ser Ile Ala Ala
1               5                   10                  15

Ala Thr Gly Phe Val Lys Lys Asp Gln Leu Gly Lys Asn Glu Glu Gly
            20                  25                  30

```
Ala Pro Gln Glu Gly Ile Leu Glu Asp Met Pro Val Asp Pro Asp Asn
            35                  40                  45

Glu Ala Tyr Glu Met Pro Ser Glu Glu Gly Tyr Gln Asp Tyr Glu Pro
 50                  55                  60

Glu Ala
 65

<210> SEQ ID NO 104
<211> LENGTH: 8
<212> TYPE: PRT
<213> ORGANISM: Homo sapiens
<220> FEATURE:
<221> NAME/KEY: MISC_FEATURE
<223> OTHER INFORMATION: Immunodominant Ovalbumin peptidem (OVA257-264)

<400> SEQUENCE: 104

Ser Ile Ile Asn Phe Glu Lys Leu
 1               5

<210> SEQ ID NO 105
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ovalbumin 323-339

<400> SEQUENCE: 105

Ile Ser Gln Ala Val His Ala Ala His Ala Glu Ile Asn Glu Ala Gly
 1               5                  10                  15

Arg
```